(12) United States Patent
Murata et al.

(10) Patent No.: US 9,695,118 B2
(45) Date of Patent: Jul. 4, 2017

(54) BENZAMIDE DERIVATIVE

(71) Applicant: Chugai Seiyaku Kabushiki Kaisha, Tokyo (JP)

(72) Inventors: Takeshi Murata, Kanagawa (JP); Satoshi Niizuma, Kanagawa (JP); Sousuke Hara, Kanagawa (JP); Hatsuo Kawada, Shizuoka (JP); Kihito Hada, Kanagawa (JP); Hideaki Shimada, Shizuoka (JP); Hiroshi Tanaka, Kanagawa (JP); Yoshito Nakanishi, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/396,678

(22) PCT Filed: Apr. 24, 2013

(86) PCT No.: PCT/JP2013/062003
§ 371 (c)(1),
(2) Date: Oct. 23, 2014

(87) PCT Pub. No.: WO2013/161851
PCT Pub. Date: Oct. 31, 2013

(65) Prior Publication Data
US 2015/0152047 A1 Jun. 4, 2015

(30) Foreign Application Priority Data
Apr. 24, 2012 (JP) .................................. 2012-098953

(51) Int. Cl.
*C07D 213/82* (2006.01)
*C07D 487/08* (2006.01)
(Continued)

(52) U.S. Cl.
CPC .......... *C07C 321/28* (2013.01); *C07C 317/14* (2013.01); *C07C 317/34* (2013.01);
(Continued)

(58) Field of Classification Search
CPC ... C07C 321/28; C07C 323/48; C07C 317/14; C07C 317/40; C07C 2101/02;
(Continued)

(56) References Cited

U.S. PATENT DOCUMENTS 4,943,583 A * 7/1990 Luthy .................. A01N 43/653
514/340
4,968,805 A * 11/1990 Okada et al. ................. 514/338
(Continued)

FOREIGN PATENT DOCUMENTS

| CA | 2 093 203 C | 10/1993 |
| CN | 101842368 A | 9/2010 |

(Continued)

OTHER PUBLICATIONS

Yamada; JP05255268, unverified machine translation obtained from EPO, published Oct. 1993.*
(Continued)

*Primary Examiner* — Noble Jarrell
*Assistant Examiner* — Daniel Carcanague
(74) *Attorney, Agent, or Firm* — Sterne, Kessler, Goldstein & Fox P.L.L.C.

(57) ABSTRACT

The present invention relates to benzamide derivatives represented by formula (I) or pharmaceutically acceptable salts thereof.

(Continued)

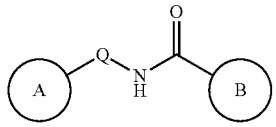

(I)

11 Claims, 19 Drawing Sheets

(51) Int. Cl.
| | |
|---|---|
| C07C 321/28 | (2006.01) |
| C07D 309/14 | (2006.01) |
| C07C 317/14 | (2006.01) |
| C07D 401/12 | (2006.01) |
| C07D 403/04 | (2006.01) |
| C07C 317/34 | (2006.01) |
| C07D 241/04 | (2006.01) |
| C07C 323/42 | (2006.01) |
| C07D 263/34 | (2006.01) |
| C07D 205/04 | (2006.01) |
| C07D 207/09 | (2006.01) |
| C07D 207/12 | (2006.01) |
| C07D 207/14 | (2006.01) |
| C07D 211/26 | (2006.01) |
| C07D 211/56 | (2006.01) |
| C07D 295/14 | (2006.01) |
| C07D 211/68 | (2006.01) |
| C07D 295/16 | (2006.01) |
| C07D 213/62 | (2006.01) |
| C07C 317/40 | (2006.01) |
| C07C 323/48 | (2006.01) |

(52) U.S. Cl.
CPC .......... *C07C 317/40* (2013.01); *C07C 323/42* (2013.01); *C07C 323/48* (2013.01); *C07D 205/04* (2013.01); *C07D 207/09* (2013.01); *C07D 207/12* (2013.01); *C07D 207/14* (2013.01); *C07D 211/26* (2013.01); *C07D 211/56* (2013.01); *C07D 211/68* (2013.01); *C07D 213/62* (2013.01); *C07D 213/82* (2013.01); *C07D 241/04* (2013.01); *C07D 263/34* (2013.01); *C07D 295/14* (2013.01); *C07D 295/16* (2013.01); *C07D 309/14* (2013.01); *C07D 401/12* (2013.01); *C07D 403/04* (2013.01); *C07D 487/08* (2013.01); *C07C 2101/02* (2013.01)

(58) Field of Classification Search
CPC ... C07C 317/34; C07C 323/42; C07D 309/14; C07D 487/08; C07D 213/82; C07D 207/12; C07D 211/56; C07D 295/16; C07D 211/68; C07D 263/34; C07D 213/62; C07D 211/26; C07D 205/04; C07D 295/14; C07D 207/09; C07D 403/04; C07D 207/14; C07D 401/12; C07D 241/04
USPC .. 514/210.16, 255.01, 254.1, 355, 622, 615, 514/252.12, 617; 544/400, 235, 391, 544/374; 564/149, 185, 176; 546/316
See application file for complete search history.

(56) References Cited

U.S. PATENT DOCUMENTS

| | | | |
|---|---|---|---|
| 9,090,568 B2 | 7/2015 | Liu et al. | |
| 9,102,631 B2 | 8/2015 | Cai et al. | |
| 9,290,460 B2 | 3/2016 | Cai et al. | |
| 9,567,304 B2* | 2/2017 | Murata | C07D 403/06 544/285 |
| 2005/0009894 A1* | 1/2005 | Babin | C07D 231/12 514/383 |
| 2006/0106062 A1* | 5/2006 | Kuang | C07D 401/04 514/314 |
| 2009/0099184 A1 | 4/2009 | Delombaert et al. | |
| 2010/0298298 A1 | 11/2010 | Clauss et al. | |
| 2011/0124670 A1* | 5/2011 | Buchdunger | A61K 31/41 514/275 |
| 2012/0094997 A1 | 4/2012 | England et al. | |
| 2015/0141400 A1* | 5/2015 | Murata | C07D 401/06 514/210.21 |
| 2016/0272595 A1* | 9/2016 | Murata | C07D 403/12 |

FOREIGN PATENT DOCUMENTS

| | | |
|---|---|---|
| CN | 102036990 A | 4/2011 |
| CN | 102099039 A | 6/2011 |
| EP | 0 329 020 A | 8/1989 |
| EP | 0 564 409 A1 | 10/1993 |
| EP | 1 702 917 A1 | 9/2006 |
| JP | H05-255268 | 10/1993 |
| JP | H07-133266 A | 5/1995 |
| JP | 2009-528992 A | 8/2009 |
| JP | 2010-523674 A | 7/2010 |
| JP | 2010-540602 A | 12/2010 |
| JP | 2011-515397 A | 5/2011 |
| JP | 2011-528015 A | 11/2011 |
| JP | 2012-505881 A | 3/2012 |
| WO | WO 03/053958 A1 | 7/2003 |
| WO | WO 2004/005281 A1 | 1/2004 |
| WO | WO 2004/085388 A2 | 10/2004 |
| WO | WO 2005/063709 A1 | 7/2005 |
| WO | WO 2007/098352 A2 | 8/2007 |
| WO | WO 2008/127615 A1 | 10/2008 |
| WO | WO 2009/117097 A1 | 9/2009 |
| WO | WO 2010/007034 A1 | 1/2010 |
| WO | WO 2010/056230 A1 | 5/2010 |
| WO | WO 2011/050120 A1 | 4/2011 |
| WO | WO 2011/062927 A1 | 5/2011 |
| WO | WO 2012/061926 A1 | 5/2012 |
| WO | WO 2013/161853 A1 | 10/2013 |
| WO | WO 2015/060373 A1 | 4/2015 |

OTHER PUBLICATIONS

Matsuo; Chem. Commun., 2012, 48, 9334-9342.*
Borza; Matrix Biology 34 (2014) 185-192.*
Deng, X., et al., "Discovery of 3,5-Diamino-1,2,4-triazole Ureas as Potent Anaplastic Lymphoma Kinase Inhibitors," *ACS Med. Chem. Lett.* 2:379-384, American Chemical Society, United States (2011).
Zubarev, A.A., et al., "3-Cyanopyridine-2(1H)-thiones and 3-cyano-2-(methylthio)pyridines in the synthesis of substituted 3-(aminomethyl)pyridines," *Russian Chemical Bulletin* 52(4):978-983, Springer, Germany (2003) (Abstract).
International Search Report for International Application No. PCT/JP2013/062003, Japanese Patent Office, Japan, mailed Jul. 23, 2013.
Co-pending Application, U.S. Appl. No. 14/396,498, inventors Murata, T., et al., Int'l Filing Date Apr. 24, 2013 (Not Yet Published).
Avivi-Green, C., et al., "Discoidin Domain Receptor 1-deficient Mice Are Resistant to Bleomycin-induced Lung Fibrosis," *Am. J. Respir. Crit. Care Med.* 174:420-427, American Thoracic Society, United States (2006).
Barker, K.T., et al., "Expression patterns of the novel receptor-like tyrosine kinase, DDR, in human breast tumours," *Oncogene* 10:569-575, Stockton Press, United States (1995).

(56) References Cited

OTHER PUBLICATIONS

Day, E., et al., "Inhibition of collagen-induced discoidin domain receptor 1 and 2 activation by imatinib, nilotinib and dasatinib," *European Journal of Pharmacology* 599:44-53, Elsevier B.V., Netherlands (2008).

Franco, C., et al., "Discoidin Domain Receptor 1 (Ddr1) Deletion Decreases Atherosclerosis by Accelerating Matrix Accumulation and Reducing Inflammation in Low-Density Lipoprotein Receptor-Deficient Mice," *Circ. Res.* 102:1202-1211, American Heart Association, United States (2008).

Gu, T-L., et al., "Survey of Tyrosine Kinase Signaling Reveals ROS Kinase Fusions in Human Cholangiocarcinoma," *PLoS One* 6(1):e15640, Public Library of Science, United States (2011).

Guerrot, D., et al., "Discoidin Domain Receptor 1 Is a Major Mediator of Inflammation and Fibrosis in Obstructive Nephropathy," *The American Journal of Pathology* 179(1):83-91, Elsevier Inc., United States (2011).

Kamohara, H., et al., "Discoidin domain receptor 1 isoform-a (DDR1a) promotes migration of leukocytes in three-dimensional collagen lattices," *The FASEB Journal* 15:2724-2726, Federation of American Societies for Experimental Biology, United States (2001).

Kim, H-G., et al., "DDR 1 Receptor Tyrosine Kinase Promotes Prosurvival Pathway through Notch1 Activation," *The Journal of Biological Chemistry* 286(20):17672-17681, The American Society for Biochemistry and Molecular Biology, Inc., United States (2011).

Rikova, K.., et al., "Global Survey of Phosphotyrosine Signaling Identifies Oncogenic Kinases in Lung Cancer," *Cell* 131:1190-1203, Elsevier Inc., United States (2007).

Rix, U., et al., "Chemical proteomic profiles of the BCR-ABL inhibitors imatinib, nilotinib, and dasatinib reveal novel kinase and nonkinase targets," *Blood* 110(12):4055-4063, The American Society of Hematology, United States (2007).

Rix, U., et al., "A comprehensive target selectivity survey of the BCR-ABL kinase inhibitor INNO-406 by kinase profiling and chemical proteomics in chronic myeloid leukemia cells," *Leukemia* 24:44-50, Macmillan Publishers Limited, United Kingdom (2010).

Song, S., et al., "Discoidin Domain Receptor 1 Isoform Expression and Potential Functions in Cirrhotic Human Liver," *The American Journal of Pathology* 178(3):1134-1144, Elsevier Inc., United States (2011).

Sun, X., et al., "LCB 03-0110, a Novel Pan-Discoidin Domain Receptor/c-Src Family Tyrosine Kinase Inhibitor, Suppresses Scar Formation by Inhibiting Fibroblast and Macrophage Activation," *The Journal of Pharmacology and Experimental Therapeutics* 340(3):510-519, American Society for Pharmacology and Experimental Therapeutics, United States (2012).

Valencia, K., et al., "Inhibition of Collagen Receptor Discoidin Domain Receptor-1 (DDR1) Reduces Cell Survival, Homing, and Colonization in Lung Cancer Bone Metastasis," *Clinical Cancer Research* 18(4):969-980, American Association for Cancer Research, United States (2012).

Valiathan, R.R., et al., "Discoidin domain receptor tyrosine kinases: new players in cancer progression," *Cancer Metastasis Rev.* 31:295-321, Springer Science, Germany (2012).

Vogel, W., et al., "The Discoidin Domain Receptor Tyrosine Kinases Are Activated by Collagen," *Molecular Cell* 1:13-23, Cell Press, United States (1997).

Vogel, W., "Discoidin domain receptors: structural relations and functional implications," *The FASEB Journal* 13:S77-S82, Federation of American Societies for Experimental Biology, United States (1999).

Yamanaka, R., et al., "Identification of expressed genes characterizing long-term survival in malignant glioma patients," *Oncogene* 25:5994-6002, Nature Publishing Group, United Kingdom (2006).

Yang, S.H., et al., "Discoidin domain receptor 1 is associated with poor prognosis of non-small cell lung carcinomas," *Oncology Reports* 24:311-319, Spandidos Publications, Greece (2010).

International Search Report for International Application No. PCT/JP2013/062006, Japanese Patent Office, Japan, mailed May 28, 2013.

Unverified English language machine translation of JP H05-255268.

McMahon, G., "VEGF Receptor Signaling in Tumor Angiogenesis," *The Oncologist* 5(*suppl 1*):3-10, AlphaMed Press, United States (2000).

Pinedo, H.M. and Slamon, D.J., "Translational Research: The Role of VEGF in Tumor Angiogenesis," *The Oncologist* 5 (*suppl 1*):1-2, AlphaMed Press, United States (2000).

Gao, M., et al., "Discovery and Optimization of 3-(2-(Pyrazolo[1,5-α]pyrimidin-6-γ10-ethynyl)benzamides as Novel Selective and Orally Bioavailable Discoidin Domain Receptor 1 (DDR1) Inhibitors," *Journal of Medicinal Chemistry* 56:3281-3295, American Chemical Society, United States (2013).

Kim, H.-G., et al., "Discovery of a Potent and Selective DDR1 Receptor Tyrosine Kinase Inhibitor," *ACS Chem. Biol.* 8:2145-2150, American Chemical Society, United States (2013).

Unverified English language translation of International Patent Publication No. WO 2013/161853 A1, WIPO, Switzerland (Listed on the accompanying form PTO/SB/O8A as document FP29).

Unverified English language translation of Japanese Patent Publication No. JP H07-133266A, Japanese Patent Office, Japan (Listed on the accompanying form PTO/SB/O8A as document FP23).

Co-Pending U.S. Appl. No. 15/030,804, inventors Murata, T., et al., 371 (c) date of Apr. 20, 2016 (Not Yet Published).

\* cited by examiner

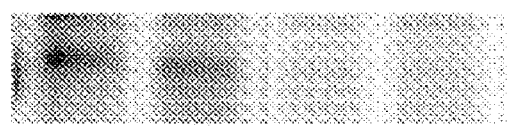
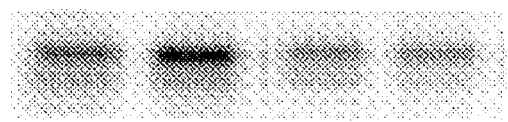
Fig. 2

Figure 3

| Example | Compound No. | Structure | Compound name | HPLC condition | Retention time (min) | m/z [M+H] |
|---|---|---|---|---|---|---|
| 9 | A-6 | 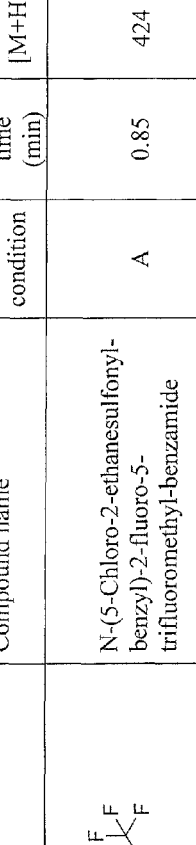 | N-(5-Chloro-2-ethanesulfonyl-benzyl)-2-fluoro-5-trifluoromethyl-benzamide | A | 0.85 | 424 |
| 10 | A-7 | 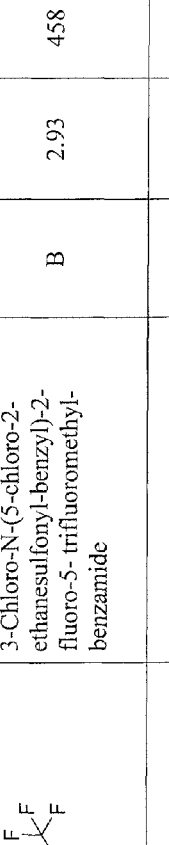 | 3-Chloro-N-(5-chloro-2-ethanesulfonyl-benzyl)-2-fluoro-5-trifluoromethyl-benzamide | B | 2.93 | 458 |
| 11 | A-8 | 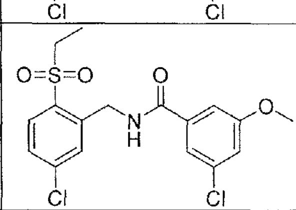 | 3-Chloro-N-(5-chloro-2-ethanesulfonyl-benzyl)-5-methoxy-benzamide | A | 0.83 | 402 |
| 12 | A-9 | 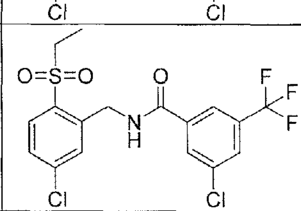 | 3-Chloro-N-(5-chloro-2-ethanesulfonyl-benzyl)-5-trifluoromethyl-benzamide | B | 2.95 | 440 |
| 13 | A-10 | 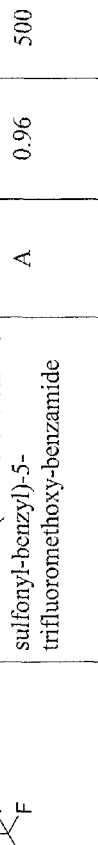 | 3-Bromo-N-(5-chloro-2-ethanesulfonyl-benzyl)-5-trifluoromethoxy-benzamide | A | 0.96 | 500 |

Figure 4

| Example | Compound No. | Structure | Compound name | HPLC condition | Retention time (min) | m/z [M+H] |
|---|---|---|---|---|---|---|
| 14 | A-11 | 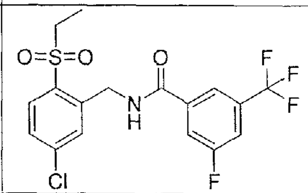 | N-(5-Chloro-2-ethanesulfonyl-benzyl)-3-fluoro-5-trifluoromethyl-benzamide | A | 0.88 | 424 |
| 15 | A-12 | 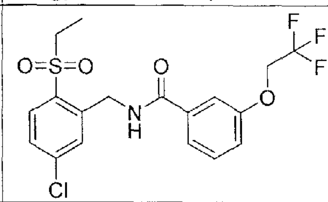 | N-(5-Chloro-2-ethanesulfonyl-benzyl)-3-(2,2,2-trifluoro-ethoxy)-benzamide | A | 0.83 | 436 |
| 16 | A-13 | 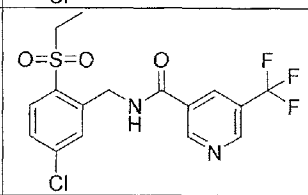 | N-(5-Chloro-2-ethanesulfonyl-benzyl)-5-trifluoromethyl-nicotineamide | A | 0.74 | 407 |
| 17 | A-15 | 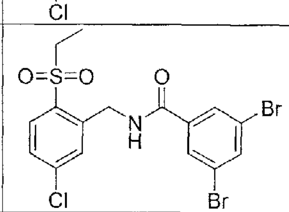 | 3,5-Dibromo-N-(5-chloro-2-ethane sulfonyl-benzyl)-benzamide | A | 0.95 | 494 |
| 18 | A-16 | 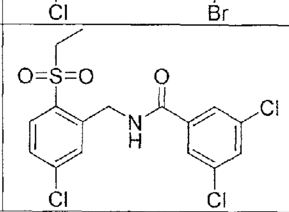 | 3,5-Dichloro-N-(5-chloro-2-ethane sulfonyl-benzyl)-benzamide | A | 0.92 | 406 |

Figure 5

| Example | Compound No. | Structure | Compound name | HPLC condition | Retention time (min) | m/z [M+H] |
|---|---|---|---|---|---|---|
| 83 | B-30 | 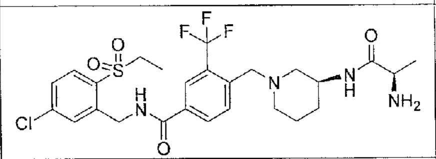 | 4-[(S)-3-((S)-2-Amino-propionylamino)-piperidin-1-ylmethyl]-N-(5-chloro-2-ethanesulfonyl-benzyl)-3-trifluoromethyl-benzamide | A | 0.43 | 589 |
| 84 | B-31 | 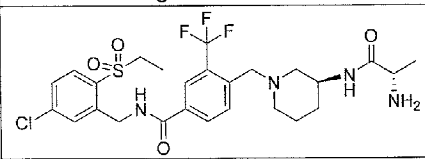 | 4-[(S)-3-((R)-2-Amino-propionylamino)-piperidin-1-ylmethyl]-N-(5-chloro-2-ethanesulfonyl-benzyl)-3-trifluoromethyl-benzamide | A | 0.43 | 589 |
| 85 | B-32 | 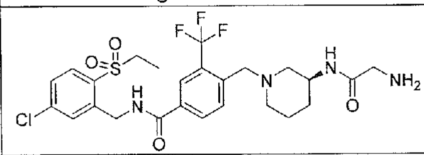 | 4-[(S)-3-(2-Amino-acetylamino)-piperidin-1-ylmethyl]-N-(5-chloro-2-ethanesulfonyl-benzyl)-3-trifluoro methyl-benzamide | A | 0.42 | 575 |
| 86 | B-34 | 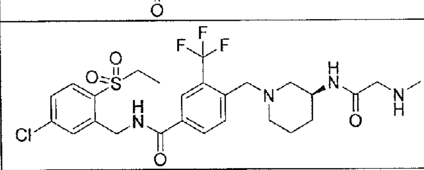 | N-(5-Chloro-2-ethanesulfonyl-benzyl)-4-[(S)-3-(2-methylamino-acetylamino)-piperidin-1-ylmethyl]-3-trifluoromethyl-benzamide | A | 0.44 | 589 |
| 87 | B-35 | 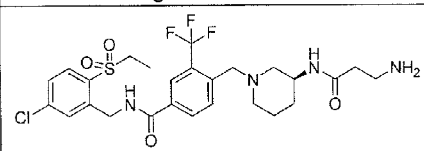 | 4-[(S)-3-(3-Amino-propionylamino)-piperidin-1-ylmethyl]-N-(5-chloro-2-ethanesulfonyl-benzyl)-3-trifluoromethyl-benzamide | A | 0.42 | 589 |
| 88 | B-36 | 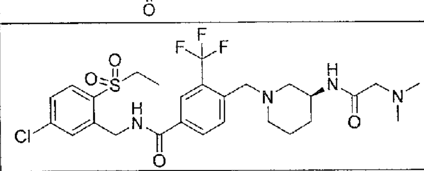 | N-(5-Chloro-2-ethanesulfonyl-benzyl)-4-[(S)-3-(2-dimethylamino-acetylamino)-piperidin-1-ylmethyl]-3-trifluoromethyl-benzamide | A | 0.43 | 603 |

Figure 6

| Example | Compound No. | Structure | Compound name | HPLC condition | Retention time (min) | m/z [M+H] |
|---|---|---|---|---|---|---|
| 123 | B-53 | 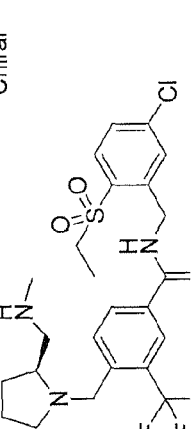 Chiral | N-(5-Chloro-2-ethanesulfonyl-benzyl)-4-((S)-2-methylaminomethyl-pyrrolidin-1-ylmethyl)-3-trifluoro methyl-benzamide | A | 0.52 | 532 |
| 124 | B-54 | 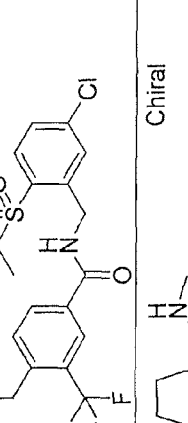 Chiral | 4-((R)-2-Aminomethyl-pyrrolidin-1-ylmethyl)-N-(5-chloro-2-ethanesulfonyl-benzyl)-3-trifluoromethyl-benzamide | A | 0.50 | 518 |
| 125 | B-56 | 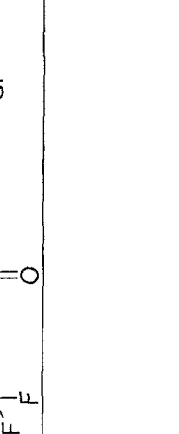 Chiral | N-(5-Chloro-2-ethanesulfonyl-benzyl)-4-((R)-2-methylamino methyl-pyrrolidin-1-ylmethyl)-3-trifluoromethyl-benzamide | A | 0.53 | 532 |

Figure 7

| Example | Compound No. | Structure | Compound name | HPLC condition | Retention time (min) | m/z [M+H] |
|---|---|---|---|---|---|---|
| 137 | B-62 | 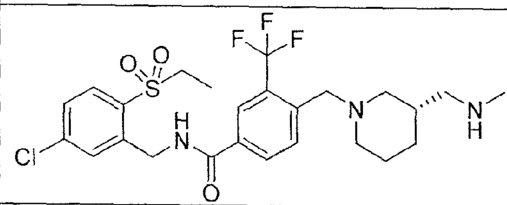 | N-(5-Chloro-2-ethanesulfonyl-benzyl)-4-((S)-3-methylaminomethyl-piperidin-1-ylmethyl)-3-trifluoromethyl-benzamide | A | 0.44 | 546 |
| 138 | B-63 | 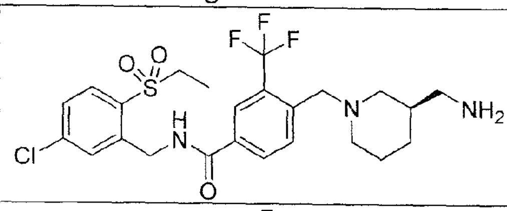 | 4-((R)-3-Aminomethyl-piperidin-1-ylmethyl)-N-(5-chloro-2-ethanesulfonyl-benzyl)-3-trifluoromethyl-benzamide | A | 0.42 | 532 |
| 139 | B-67 | 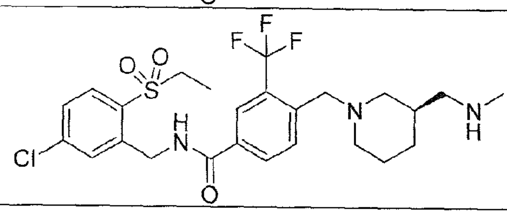 | N-(5-Chloro-2-ethanesulfonyl-benzyl)-4-((R)-3-methylaminomethyl-piperidin-1-ylmethyl)-3-trifluoromethyl-benzamide | A | 0.44 | 546 |

Figure 8

| Example | Compound No. | Structure | Compound name | HPLC condition | Retention time (min) | m/z [M+H] |
|---|---|---|---|---|---|---|
| 196 | D-10 | 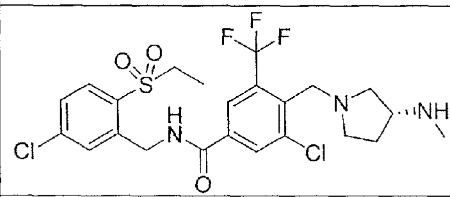 | 3-Chloro-N-(5-chloro-2-ethanesulfonyl-benzyl)-4-((R)-3-methylamino-pyrrolidin-1-ylmethyl)-5-trifluoromethyl-benzamide | A | 0.54 | 552 |
| 197 | D-11 | 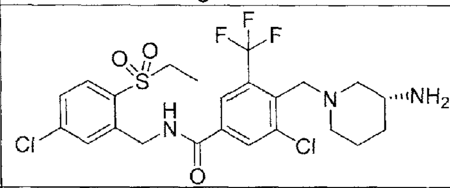 | 4-((R)-3-Amino-piperidin-1-ylmethyl)-3-chloro-N-(5-chloro-2-ethanesulfonyl-benzyl)-5-trifluoromethyl-benzamide | A | 0.57 | 552 |
| 198 | D-17 | 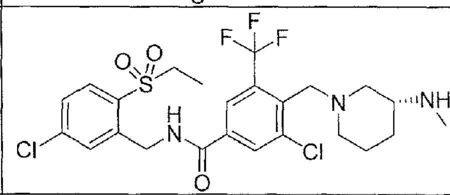 | 3-Chloro-N-(5-chloro-2-ethanesulfonyl-benzyl)-4-((R)-3-methylamino-piperidin-1-ylmethyl)-5-trifluoromethyl-benzamide | A | 0.60 | 566 |
| 199 | D-18 | 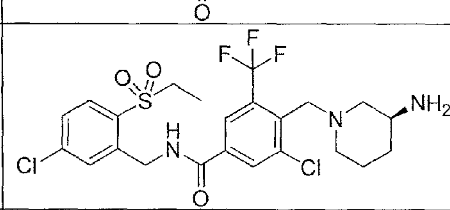 | 4-((S)-3-Amino-piperidin-1-ylmethyl)-3-chloro-N-(5-chloro-2-ethanesulfonyl-benzyl)-5-trifluoromethyl-benzamide | A | 0.56 | 552 |
| 200 | D-26 | 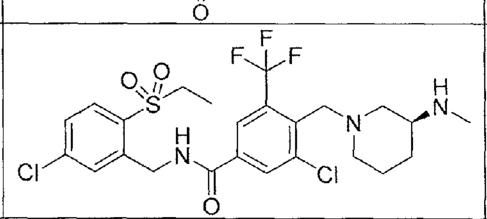 | 3-Chloro-N-(5-chloro-2-ethanesulfonyl-benzyl)-4-((S)-3-methylamino-piperidin-1-ylmethyl)-5-trifluoromethyl-benzamide | A | 0.58 | 566 |

Figure 9

| Example | Compound No. | Structure | Compound name | HPLC condition | Retention time (min) | m/z [M+H] |
|---|---|---|---|---|---|---|
| 201 | D-27 | 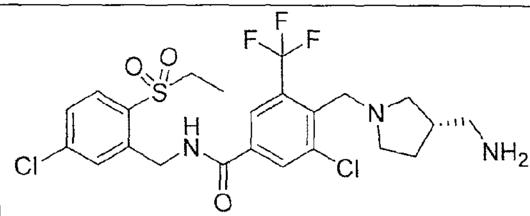 | 4-((S)-3-Aminomethyl-pyrrolidin-1-ylmethyl)-3-chloro-N-(5-chloro-2-ethanesulfonyl-benzyl)-5-trifluoromethyl-benzamide | A | 0.43 | 552 |
| 202 | D-28 | 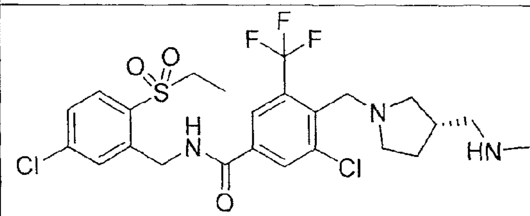 | 3-Chloro-N-(5-chloro-2-ethanesulfonyl-benzyl)-4-((S)-3-methylaminomethyl-pyrrolidin-1-ylmethyl)-5-trifluoromethyl-benzamide | A | 0.43 | 566 |

Figure 10

| Example | Compound No. | Structure | Compound name | HPLC condition | Retention time (min) | m/z [M+H] |
|---|---|---|---|---|---|---|
| 221 | E-2 | 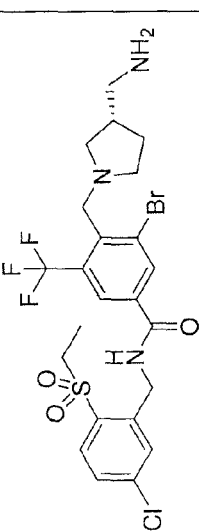 | 4-((R)-3-Amino-pyrrolidin-1-ylmethyl)-3-bromo-N-(5-chloro-2-ethanesulfonyl-benzyl)-5-trifluoromethyl-benzamide | A | 0.53 | 582 |
| 222 | E-3 | 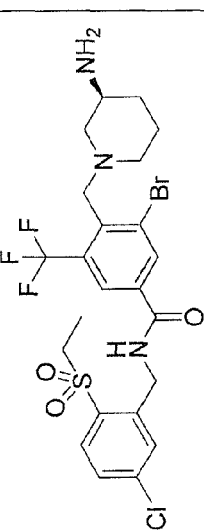 | 4-((S)-3-Amino-piperidin-1-ylmethyl)-3-bromo-N-(5-chloro-2-ethanesulfonyl-benzyl)-5-trifluoromethyl-benzamide | A | 0.59 | 596 |
| 223 | E-4 | 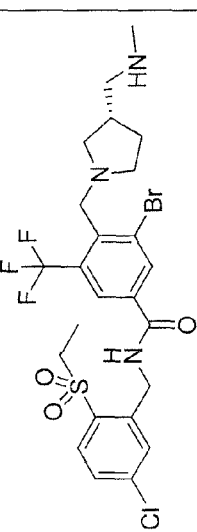 | 3-Bromo-N-(5-chloro-2-ethanesulfonyl-benzyl)-4-((S)-3-methylaminomethyl-pyrrolidin-1-ylmethyl)-5-trifluoromethyl-benzamide | A | 0.43 | 610 |

Figure 11

| Example | Compound No. | Structure | Compound name | HPLC condition | Retention time (min) | m/z [M+H] |
|---|---|---|---|---|---|---|
| 228 | E-6 | 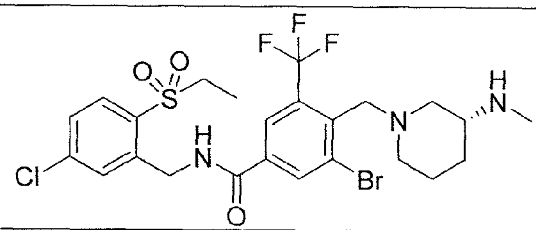 | 3-Bromo-N-(5-chloro-2-ethanesulfonyl-benzyl)-4-((R)-3-methylamino-piperidin-1-ylmethyl)-5-trifluoromethyl-benzamide | A | 0.60 | 610 |
| 229 | E-7 | 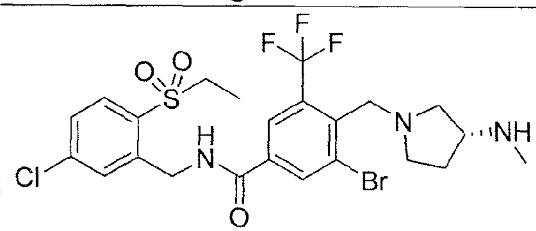 | 3-Bromo-N-(5-chloro-2-ethanesulfonyl-benzyl)-4-((R)-3-methylamino-pyrrolidin-1-ylmethyl)-5-trifluoromethyl-benzamide | A | 0.57 | 596 |
| 230 | E-8 | 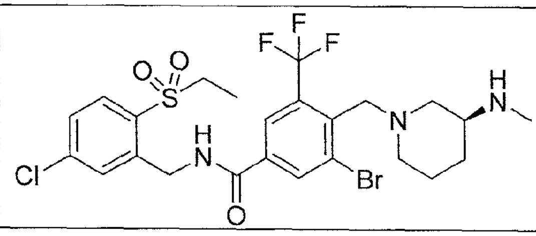 | 3-Bromo-N-(5-chloro-2-ethanesulfonyl-benzyl)-4-((S)-3-methylamino-piperidin-1-ylmethyl)-5-trifluoromethyl-benzamide | A | 0.60 | 610 |

Figure 12

| Example | Compound No. | Structure | Compound name | HPLC condition | Retention time (min) | m/z [M+H] |
|---|---|---|---|---|---|---|
| 255 | F-7 | 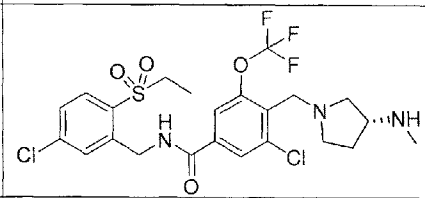 | 3-Chloro-N-(5-chloro-2-ethanesulfonyl-benzyl)-4-((R)-3-methylamino-pyrrolidin-1-ylmethyl)-5-trifluoromethoxy-benzamide | A | 0.54 | 568 |
| 256 | F-8 | 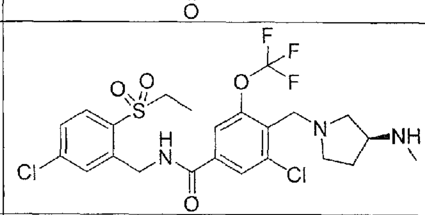 | 3-Chloro-N-(5-chloro-2-ethanesulfonyl-benzyl)-4-((S)-3-methylamino-pyrrolidin-1-ylmethyl)-5-trifluoromethoxy-benzamide | A | 0.53 | 568 |
| 257 | F-9 | 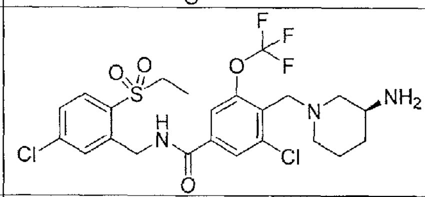 | 4-((S)-3-Amino-piperidin-1-ylmethyl)-3-chloro-N-(5-chloro-2-ethanesulfonyl-benzyl)-5-trifluoromethoxy-benzamide | A | 0.55 | 568 |
| 258 | F-15 | 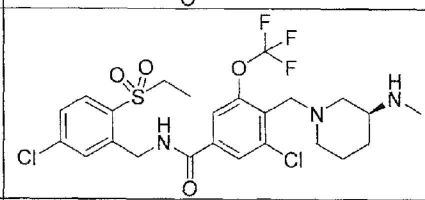 | 3-Chloro-N-(5-chloro-2-ethanesulfonyl-benzyl)-4-((S)-3-methylamino-piperidin-1-ylmethyl)-5-trifluoromethoxy-benzamide | A | 0.58 | 582 |
| 259 | F-16 | 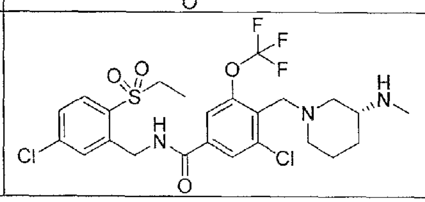 | 3-Chloro-N-(5-chloro-2-ethanesulfonyl-benzyl)-4-((R)-3-methylamino-piperidin-1-ylmethyl)-5-trifluoromethoxy-benzamide | A | 0.59 | 582 |

Figure 13

| Example | Compound No. | Structure | Compound name | HPLC condition | Retention time (min) | m/z [M+H] |
|---|---|---|---|---|---|---|
| 352 | I-25 | 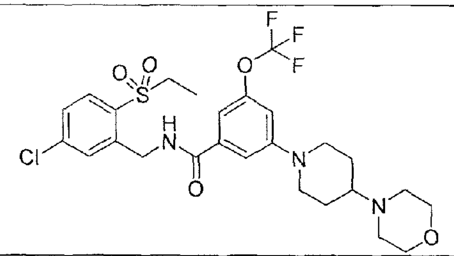 | N-(5-Chloro-2-ethanesulfonyl-benzyl)-3-(4-morpholin-4-yl-piperidin-1-yl)-5-trifluoromethoxy-benzamide | A | 0.56 | 590 |
| 353 | I-26 | 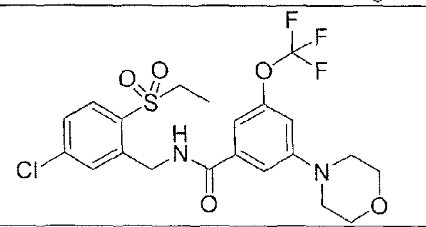 | N-(5-Chloro-2-ethanesulfonyl-benzyl)-3-morpholin-4-yl-5-trifluoromethoxy-benzamide | A | 0.86 | 507 |
| 354 | I-27 | 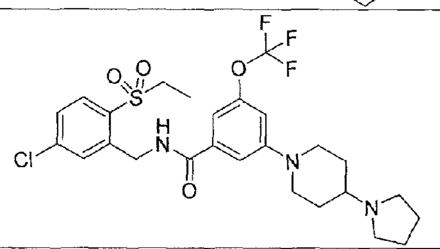 | N-(5-Chloro-2-ethanesulfonyl-benzyl)-3-(4-pyrrolidin-1-yl-piperidin-1-yl)-5-trifluoromethoxy-benzamide | A | 0.57 | 574 |
| 355 | I-28 | 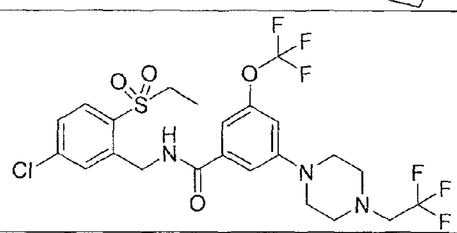 | N-(5-Chloro-2-ethanesulfonyl-benzyl)-3-[4-(2,2,2-trifluoro-ethyl)-piperazin-1-yl]-5-trifluoromethoxy-benzamide | A | 0.97 | 588 |

Figure 14

| Example | Compound No. | Structure | Compound name | HPLC condition | Retention Time (min) | m/z [M+H] |
|---|---|---|---|---|---|---|
| 385 | DD-2 | 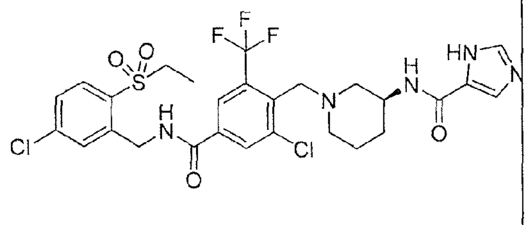 | N-[(3S)-1-[[2-chloro-4-[(5-chloro-2-ethylsulfonylphenyl)methylcarbamoyl]-6-(trifluoromethyl)phenyl]methyl]piperidin-3-yl]-1H-imidazole-5-carboxamide | F | 0.52 | 646 |
| 386 | DD-3 | 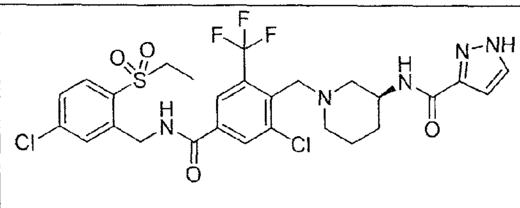 | N-[(3S)-1-[[2-chloro-4-[(5-chloro-2-ethylsulfonylphenyl)methylcarbamoyl]-6-(trifluoromethyl)phenyl]methyl]piperidin-3-yl]-1-methyl-1H-pyrazole-3-carboxamide | F | 0.58 | 646 |
| 387 | DD-4 | 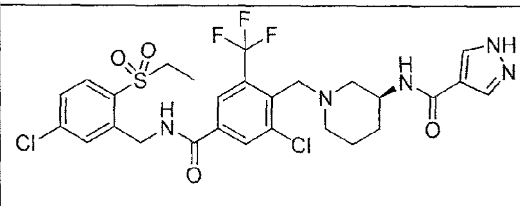 | N-[(3S)-1-[[2-chloro-4-[(5-chloro-2-ethylsulfonylphenyl)methylcarbamoyl]-6-(trifluoromethyl)phenyl]methyl]piperidin-3-yl]-1-methyl-1H-pyrazole-4-carboxamide | F | 0.54 | 646 |
| 402 | DD-18 | 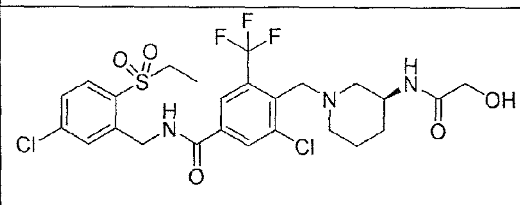 | 3-chloro-N-[(5-chloro-2-ethylsulfonylphenyl)methyl]-4-[[(3S)-3-[(2-hydroxyacetyl)amino]piperidin-1-yl]methyl]-5-(trifluoromethyl)benzamide | F | 0.54 | 610 |

Figure 15

| Example | Compound No. | Structure | Compound name | HPLC condition | Retention Time (min) | m/z [M+H] |
|---|---|---|---|---|---|---|
| 403 | DD-19 | 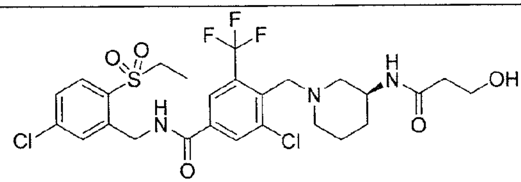 | 3-chloro-N-[(5-chloro-2-ethylsulfonylphenyl)methyl]-4-[[(3S)-3-(3-hydroxypropanoylamino)piperidin-1-yl]methyl]-5-(trifluoromethyl)benzamide | F | 0.51 | 624 |
| 404 | DD-20 | 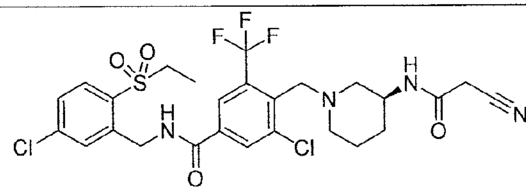 | 3-chloro-N-[(5-chloro-2-ethylsulfonylphenyl)methyl]-4-[[(3S)-3-[(2-cyanoacetyl)amino]piperidin-1-yl]methyl]-5-(trifluoromethyl)benzamide | F | 0.61 | 619 |

Figure 16

| Example | Compound No. | Structure | Compound name | HPLC condition | Retention Time (min) | m/z [M+H] |
|---|---|---|---|---|---|---|
| 390 | DD-6 | 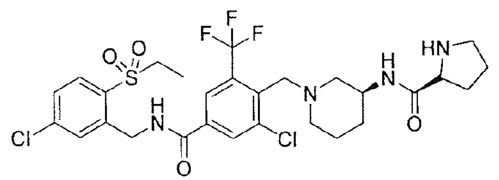 | (2R)-N-[(3S)-1-[[2-chloro-4-[(5-chloro-2-ethylsulfonyl)phenyl]methyl carbamoyl]-6-(trifluoromethyl)phenyl]methyl]piperidin-3-yl]pyrrolidine-2-carboxamide | F | 0.47 | 649 |
| 391 | DD-7 | 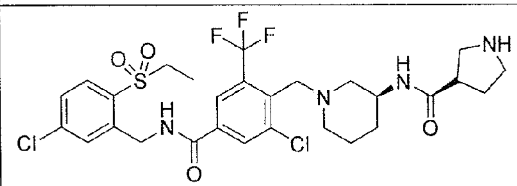 | (3S)-N-[(3S)-1-[[2-chloro-4-[(5-chloro-2-ethylsulfonyl)phenyl]methyl carbamoyl]-6-(trifluoromethyl)phenyl]methyl]piperidin-3-yl]pyrrolidine-3-carboxamide | F | 0.45 | 649 |
| 392 | DD-8 | 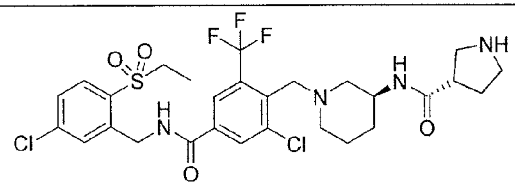 | (3R)-N-[(3S)-1-[[2-chloro-4-[(5-chloro-2-ethylsulfonyl)phenyl]methyl carbamoyl]-6-(trifluoromethyl)phenyl]methyl]piperidin-3-yl]pyrrolidine-3-carboxamide | F | 0.45 | 649 |
| 393 | DD-9 | 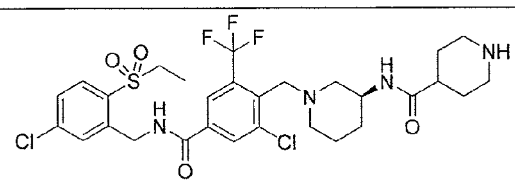 | N-[(3S)-1-[[2-chloro-4-[(5-chloro-2-ethylsulfonyl)phenyl]methyl(trifluoromethyl)phenyl]methylcarbamoyl]-6-(trifluoromethyl)phenyl]methyl]piperidin-3-yl]piperidin-4-carboxamide | F | 0.44 | 663 |

Figure 17

| Example | Compound No. | Structure | Compound name | HPLC condition | Retention Time (min) | m/z [M+H] |
|---|---|---|---|---|---|---|
| 394 | DD-10 | 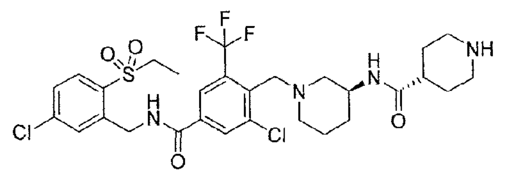 | (3R)-N-[(3S)-1-[[2-chloro-4-[(5-chloro-2-ethylsulfonylphenyl)methylcarbamoyl]-6-(trifluoromethyl)phenyl]methyl]piperidin-3-yl]piperidine-3-carboxamide | F | 0.46 | 663 |
| 395 | DD-11 | 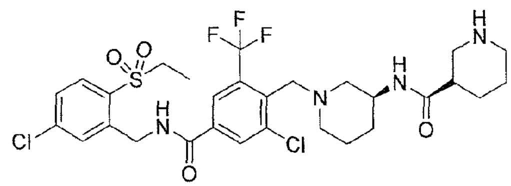 | (3S)-N-[(3S)-1-[[2-chloro-4-[(5-chloro-2-ethylsulfonylphenyl)methylcarbamoyl]-6-(trifluoromethyl)phenyl]methyl]piperidin-3-yl]piperidine-3-carboxamide | F | 0.46 | 663 |
| 396 | DD-12 | 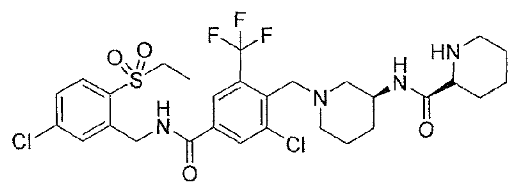 | (2S)-N-[(3S)-1-[[2-chloro-4-[(5-chloro-2-ethylsulfonylphenyl)methylcarbamoyl]-6-(trifluoromethyl)phenyl]methyl]piperidin-3-yl]piperidine-2-carboxamide | F | 0.48 | 663 |
| 397 | DD-13 | 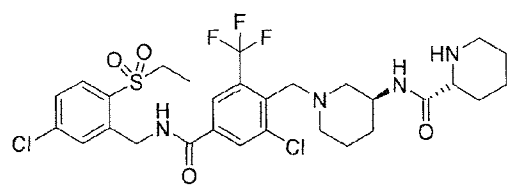 | (2R)-N-[(3S)-1-[[2-chloro-5-ethylsulfonylphenyl)methylcarbamoyl]-6-(trifluoromethyl)phenyl]methyl]piperidin-3-yl]piperidine-2-carboxamide | F | 0.47 | 663 |

Figure 18

| Example | Compound No. | Structure | Compound name | HPLC condition | Retention Time (min) | m/z [M+H] |
|---|---|---|---|---|---|---|
| 398 | DD-14 | 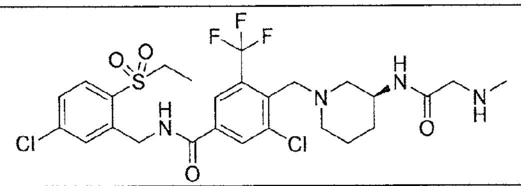 | 3-chloro-N-[(5-chloro-2-ethylsulfonyl phenyl)methyl]-4-[[(3S)-3-[[2-(methylamino)acetyl]amino]piperidin-1-yl]methyl]-5-(trifluoromethyl) benzamide | F | 0.45 | 623 |
| 399 | DD-15 | 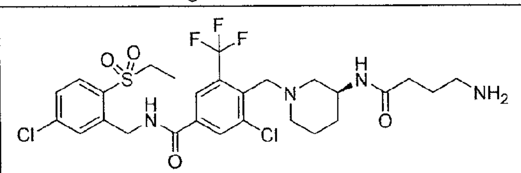 | 4-[[(3S)-3-(4-aminobutanoylamino)piperidin-1-yl]methyl]-3-chloro-N-[(5-chloro-2-ethylsulfonylphenyl) methyl]-5-(trifluoromethyl) benzamide | F | 0.44 | 637 |
| 400 | DD-16 | 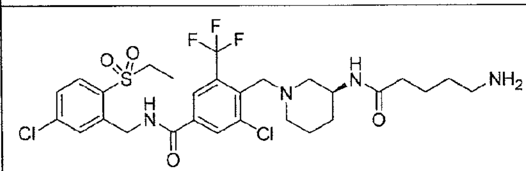 | 4-[[(3S)-3-(5-aminopentanoylamino) piperidin-1-yl]methyl]-3-chloro-N-[(5-chloro-2-ethylsulfonylphenyl) methyl]-5-(trifluoromethyl) benzamide | F | 0.44 | 651 |
| 401 | DD-17 | 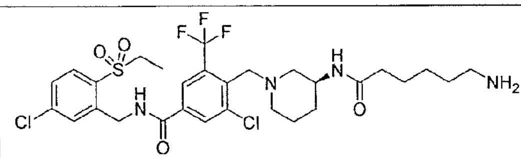 | 4-[[(3S)-3-(6-aminohexanoyl amino)piperidin-1-yl]methyl]-3-chloro-N-[(5-chloro-2-ethyl sulfonyl)phenyl)methyl]-5-(trifluoromethyl)benzamide | F | 0.45 | 665 |

Figure 19

| Example | Compound No. | Structure | Compound name | HPLC condition | Retention time (min) | m/z [M+H] |
|---|---|---|---|---|---|---|
| 426 | DD-34 | 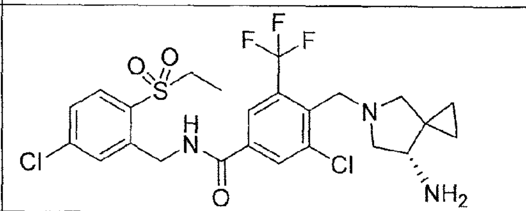 | 4-[[(7S)-7-amino-5-azaspiro[2.4]heptan-5-yl]methyl]-3-chloro-N-[(5-chloro-2-ethylsulfonyl)phenyl]methyl]-5-(trifluoromethyl)benzamide | F | 0.54 | 564 |
| 432 | DD-38 | 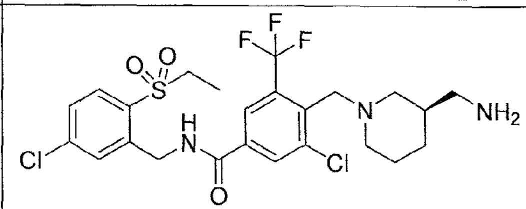 | 4-[[(2S)-2-(aminomethyl)piperidin-1-yl]methyl]-3-chloro-N-[(5-chloro-2-ethylsulfonyl)phenyl]methyl]-5-(trifluoromethyl)benzamide | A | 0.54 | 566 |
| 436 | DD-41 | 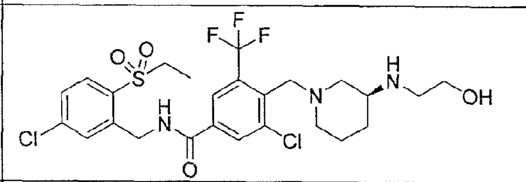 | 3-chloro-N-[(5-chloro-2-ethylsulfonyl)phenyl]methyl]-4-[[(3S)-3-(2-hydroxyethylamino)piperidin-1-yl]methyl]-5-(trifluoromethyl)benzamide | F | 0.56 | 596 |
| 437 | DD-42 | 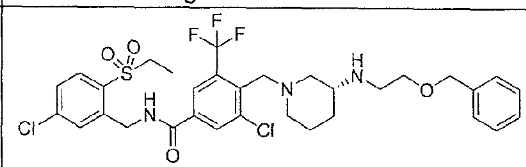 | 3-chloro-N-[(5-chloro-2-ethylsulfonyl)phenyl]methyl]-4-[[(3S)-3-(2-phenylmethoxyethylamino)piperidin-1-yl]methyl]-5-(trifluoromethyl)benzamide | F | 0.65 | 686 |

BENZAMIDE DERIVATIVE

TECHNICAL FIELD

The present invention relates to benzamide derivatives or salts thereof, or solvates thereof. More specifically, the present invention relates to benzamide derivatives, and provides pharmaceuticals, pharmaceutical compositions, and DDR1 inhibitors comprising the compounds, as well as pharmaceuticals comprising the above-mentioned compounds for treatment of diseases including cancer, cancer metastasis and invasion, fibrosis, and inflammation. The present invention also relates to methods for treating the above-mentioned diseases comprising administering effective doses of the compounds or salts thereof, or solvates thereof, and to use of the benzamide derivatives for the manufacture of the above-mentioned pharmaceutical compositions.

BACKGROUND ART

Discoidin Domain Receptor 1 (DDR1) is a receptor tyrosine kinase, and it is known that DDR1 is activated by collagen as a ligand to transduce signals into cells, and to promote invasion/metastasis or survival of the cells (Non-patent Documents 1, 2, and 3). DDR1 is considered to be an important factor that links extracellular matrix with malignant transformation of cancer, because high expression and activation of DDR1 is observed in various types of cancers.

For example, it is known that clinically DDR1 is highly expressed in non-small-cell lung cancer, glioma, breast cancer, and the like (Non-patent Documents 4, 5, 6, and 7), and it is reported that high expression correlates with poor prognosis in non-small-cell lung cancer and glioma. Further, in non-small-cell lung cancer and bile duct cancer, enhancement of DDR1 phosphorylation is observed, and its activation is strongly suggested (Non-patent Documents 8 and 9).

Studies using RNA interference reveal that DDR1 plays an important role in bone metastasis of lung cancer cells (Non-patent Document 5), and contributes to tumorigenicity of colon cancer or breast cancer cells as well as their survival in the presence of DNA-damaging agents (Non-patent Document 10). Accordingly, compounds having a DDR1 inhibitory effect are extremely useful for cancer treatment.

It is also reported that the DDR1 ligand, collagen, is abundantly present in fibrous tissues, and functions mediated through DDR1 activation are involved in various types of fibrosis. For example, DDR1 expression is enhanced in the liver of hepatic cirrhosis patients (Non-patent Document 11). It is reported that in DDR1 knockout mice, fibril formation in the kidney induced by unilateral ureteral ligation is suppressed (Non-patent Document 12), and fibril formation in a pulmonary fibrosis model induced by bleomycin is reduced (Non-patent Document 13). As it is clear from above, DDR1 inhibition is extremely useful for the prevention and treatment of organ fibrosis. DDR1 also enhances lymphocyte migration, and migration and inflammatory functions of macrophages (Non-patent Documents 14 and 15). For example, in DDR1 knockout mice, accumulation of macrophages is suppressed in an arteriosclerosis model (Non-patent Document 15). It is reported that lymphocytes and macrophages also accumulate and are activated in inflammatory diseases such as rheumatoid arthritis, Crohn's disease, ulcerative colitis, and multiple sclerosis. Accordingly, DDR1 inhibition is also extremely useful for the prevention and treatment of these diseases which originate from inflammation.

Examples of DDR1 inhibitory substances include multi-kinase inhibitors which have DDR1 inhibitory effect as one of their effects. Reported examples include Gleevec which has a 3-pyridylpyrimidine structure and serves as an inhibitor for bcr-abl, c-kit, CSF1R, PDGFRα, and the like (Patent Document 1, Non-patent Documents 16 and 17), and Tasigna which has a 3-pyridylpyrimidine structure and serves as an inhibitor for bcr-abl, c-kit, PDGFRα, Lck, Lyn, and the like (Patent Document 2, Non-patent Documents 16 and 17). Other reported examples include Sprycel which has a 2-methylpyrimidine structure and serves as an inhibitor for the Src family and the like (Patent Document 3, Non-patent Documents 16 and 17), INNO-406 which has a bipyrimidin-2-ylamino structure and serves as an inhibitor for bcr-abl, PDGFRα, Lyn, ZAK, and the like (Patent Document 4, Non-patent Document 18), and LCB03-0110 which has a thieno[3,2-b]pyridine structure and serves as an inhibitor for the Src family and the like (Non-patent Document 19).

However, compounds that selectively inhibit DDR1 are not yet known.

PRIOR ART DOCUMENTS

Non-Patent Documents

[Non-patent Document 1] European Patent No. 564409 specification
[Non-patent Document 2] WO 2004/005281
[Non-patent Document 3] WO 2004/085388
[Non-patent Document 4] WO 2005/063709

Non-Patent Documents

[Non-patent Document 1] FASEB J., 13: S77-S82, 1999
[Non-patent Document 2] Mol. Cell, 1: 13-23, 1997
[Non-patent Document 3] Cancer Metastasis Rev, electronic edition, Feb. 26, 2012
[Non-patent Document 4] Oncol. Rep., 24: 311-319, 2010
[Non-patent Document 5] Clin. Cancer Res., 18: 969-980, 2012
[Non-patent Document 6] Oncogene, 25: 5994-6002, 2006
[Non-patent Document 7] Oncogene, 10: 569-575, 1995
[Non-patent Document 8] Cell, 131: 1190-1203, 2007
[Non-patent Document 9] PloS One, 6: e15640, 2011
[Non-patent Document 10] J. Biol. Chem., 286: 17672-17681, 2011
[Non-patent Document 11] Am. J. Pathol., 178: 1134-44, 2011
[Non-patent Document 12] Am. J. Pathol., 179: 83-91, 2011
[Non-patent Document 13] Am. J. Respir. Crit. Care Med., 174: 420-427, 2006
[Non-patent Document 14] FASEB J., 15: 2724-2726, 2001
[Non-patent Document 15] Circ. Res., 102: 1202-1211, 2008
[Non-patent Document 16] Blood, 110: 4055-4063, 2007
[Non-patent Document 17] European Journal of Pharmacology, 599: 44-53, 2008
[Non-patent Document 18] Leukemia, 22: 44-50, 2010
[Non-patent Document 19] THE JOURNAL OF PHAMACOLOGY AND EXPERIMENTAL THERAPEUTICS, 340: 510-519, 2012

SUMMARY OF THE INVENTION

Problems to be Solved by the Invention

An objective of the present invention is to provide low molecular weight compounds that can selectively inhibit Discoidin Domain Receptor 1 (DDR1) and to provide pharmaceuticals effective for diseases associated with abnormalities of DDR1, such as cancer, cancer metastasis and invasion, fibrosis, and inflammation.

Means for Solving the Problems

Specifically, the present invention comprises:

[1]
A compound represented by general formula (I) below:

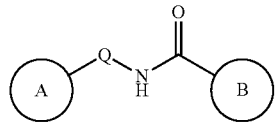
(I)

[wherein
Q represents $CH_2$ or NH;
Ring A represents formula (1) or (2) below:

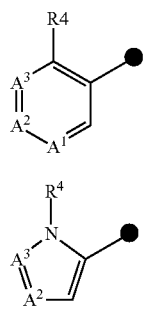

wherein $A^1$ represents N or $CR^1$;
$R^1$ represents a halogen atom, cyano group, $C_{1-3}$ alkyl group, or $C_{1-3}$ alkoxy group, wherein the $C_{1-3}$ alkyl group and $C_{1-3}$ alkoxy group may be substituted with 1 to 5 halogen atoms;
$R^1$ may be a hydrogen atom when $A^2$ and/or $A^3$ are N;
$A^2$ represents N or $CR^2$;
$R^2$ represents a hydrogen atom, halogen atom, $C_{1-3}$ alkyl group, or $C_{1-3}$ alkoxy group, wherein the $C_{1-3}$ alkyl group and $C_{1-3}$ alkoxy group may be substituted with 1 to 5 halogen atoms;
$A^3$ represents N or $CR^3$;
$R^3$ represents a hydrogen atom, a halogen atom, a $C_{1-3}$ alkyl group, or a $C_{1-3}$ alkoxy group, wherein the $C_{1-3}$ alkyl group and $C_{1-3}$ alkoxy group may be substituted with 1 to 5 halogen atoms; and
$R^4$ represents a $C_{1-6}$ alkylsulfonyl group, $C_{1-6}$ alkylsulfanyl group, $C_{1-6}$ alkylsulfinyl group, $C_{3-8}$ cycloalkylsulfonyl group, $C_{3-8}$ cycloalkylsulfanyl group, $C_{3-8}$ cycloalkylsulfinyl group, $C_{6-10}$ arylsulfonyl group, $C_{6-10}$ arylsulfanyl group, or $C_{6-10}$ arylsulfinyl group; and
Ring B represents any one of formulas (3) to (9) below:

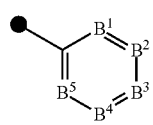
(3)

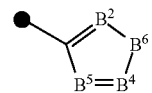
(4)

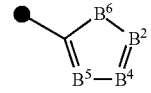
(5)

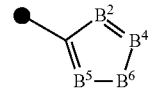
(6)

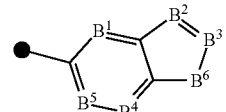
(7)

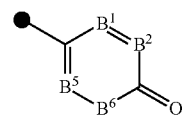
(8)

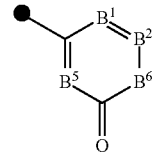
(9)

wherein $B^1$ represents N or CH;
$B^2$ represents N or $CR^5$;
$R^5$ represents a halogen atom, $C_{1-6}$ alkyl group, $C_{1-6}$ alkoxy group, $C_{2-6}$ alkenyl group, cyano group, nitro group, $C_{3-8}$ cycloalkyl group, 4- to 10-membered aromatic ring, 4- to 10-membered aromatic heterocycle, 3- to 12-membered heterocycle, or $C_{1-6}$ alkylsulfanyl group, wherein the $C_{1-6}$ alkyl group, $C_{1-6}$ alkoxy group, $C_{2-6}$ alkenyl group, or $C_{1-6}$ alkylsulfanyl group may be substituted with 1 to 5 halogen atoms;
$B^3$ represents N or $CR^6$;
$B^6$ represents O, S, or $NR^6$;
$R^6$ represents a hydrogen atom, $C_{1-3}$ alkyl group optionally substituted with a hydroxyl group, halogen atom, amino group, $OCOCH_3$ group, or group represented by following formula (i) below:

-X—Y—Z (i)

wherein in the formula (i),
X represents $—(CH_2)_n—$, —NH—, or —O—;
Y represents a $C_{3-8}$ cycloalkyl group, 4- to 10-membered aromatic ring, 3- to 12-membered heterocycle, 4- to 10-membered aromatic heterocycle, or $—(NH(CH_2)_q)_r—$, wherein the $C_{3-8}$ cycloalkyl group, 4- to 10-membered aromatic ring, 3- to 12-membered heterocycle, or 4- to 10-membered aromatic heterocycle may be substituted with 1 to 5 $C_{1-6}$ alkyl groups;
represents a hydrogen atom, a $C_{1-6}$ alkyl group, dimethylamine oxide, $—(CH_2)_mNRaRb$, $—NRiCOCH_2Rc$, $—(CH_2)_m$ $NRiCORc$, $—(CH_2)_mORd$, $—(CH_2)_mCORe$, $—(CH_2)_m$ $NRjSO_2Rk$, $—(CH_2)_mSO_2Rk$, $—(CH_2)_mCON$-RlRm, $C_{3-8}$ cycloalkyl group, 4- to 10-membered aromatic heterocycle, or 3- to 12-membered heterocycle, wherein the 4- to 10-membered aromatic heterocycle or 3- to 12-membered heterocycle may be substituted with 1 to 5 $C_{1-6}$ alkyl groups;

n represents 0, 1, 2, or 3;
m represents 0, 1, 2, or 3;
q represents 0, 1, 2, or 3;
r represents 0, 1, 2, or 3;
Ra and Rb are identical or different, each representing a hydrogen atom, $C_{1-6}$ alkyl group, $C_{2-6}$ alkynyl group, $C_{3-8}$ cycloalkyl group, 3- to 12-membered heterocycle, or —$SO_2CH_3$, wherein the $C_{1-6}$ alkyl group, $C_{3-8}$ cycloalkyl group, 3- to 12-membered heterocycle, or $C_{2-6}$ alkynyl group may be substituted with 1 to 5 halogen atoms, hydroxyl groups, $C_{1-6}$ alkoxy groups, amino groups, —$CONH_2$, mono-$C_{1-6}$ alkylamino groups, di-$C_{1-6}$ alkylamino groups, cyano groups, $OCH_2Ph$, and/or 3- to 12-membered heterocycles;
Rc represents a $C_{1-6}$ alkyl group, $C_{1-6}$ alkoxy group, $C_{3-8}$ cycloalkyl group, hydroxyl group, cyano group, 3- to 12-membered heterocycle, 4- to 10-membered aromatic heterocycle, or amino group, wherein the $C_{1-6}$ alkyl group may be independently substituted with 1 to 3 hydroxyl, amino, mono-$C_{1-6}$ alkylamino, and/or di-$C_{1-6}$ alkylamino groups;
Rd represents a hydrogen atom or a $C_{1-6}$ alkyl group, wherein the $C_{1-6}$ alkyl group may be substituted with 1 to 3 hydroxyl and/or amino groups;
Re represents a $C_{1-6}$ alkyl group, hydroxyl group, 3- to 12-membered heterocycle, or 4- to 10-membered aromatic heterocycle, wherein the $C_{1-6}$ alkyl group may be substituted with 1 to 3 hydroxyl and/or amino groups;
Ri represents a hydrogen atom or a $C_{1-6}$ alkyl group, wherein the $C_{1-6}$ alkyl group may be substituted with 1 to 5 halogen atoms;
Rj represents a hydrogen atom or $C_{1-6}$ alkyl group, wherein the $C_{1-6}$ alkyl group may be substituted with 1 to 5 halogen atoms;
Rk represents a hydrogen atom, $C_{1-6}$ alkyl group, amino group, mono-$C_{1-6}$ alkylamino group, or di-$C_{1-6}$ alkylamino group, wherein the $C_{1-6}$ alkyl group may be substituted with 1 to 3 hydroxyl, amino, mono-$C_{1-6}$ alkylamino, and/or di-$C_{1-6}$ alkylamino groups; and
Rl and Rm are identical or different, each representing a hydrogen atom, $C_{1-6}$ alkyl group, or 3- to 12-membered heterocycle, wherein the $C_{1-6}$ alkyl group may be independently substituted with 1 to 3 amino, mono-$C_{1-6}$ alkylamino, and/or di-$C_{1-6}$ alkylamino groups;
$B^4$ represents N or $CR^7$;
$R^7$ represents a hydrogen atom, halogen atom, cyano group, $C_{1-6}$ alkyl group, $C_{1-6}$ alkoxy group, $C_{2-6}$ alkenyl group, or $C_{3-8}$ cycloalkyl group (wherein the $C_{1-6}$ alkyl group, $C_{1-6}$ alkoxy group, $C_{2-6}$ alkenyl group, or $C_{3-8}$ cycloalkyl group may be substituted with 1 to 5 halogen atoms), or a group represented by formula (ii) below:

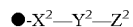—$X^2$—$Y^2$—$Z^2$ (ii)

wherein $X^2$ represents —$(CH_2)_p$—;
p represents 0, 1, 2, or 3;
$Y^2$ represents a 4- to 10-membered aromatic ring, 3- to 12-membered heterocycle, or 4- to 10-membered aromatic heterocycle, wherein the 4- to 10-membered aromatic ring, 3- to 12-membered heterocycle, or 4- to 10-membered aromatic heterocycle may be substituted with 1 to 5 $C_{1-6}$ alkyl groups;
$Z^2$ represents a hydrogen atom, a $C_{1-6}$ alkyl group, hydroxyl group, —$NRfRg$, 3- to 12-membered heterocycle, or 4- to 10-membered aromatic heterocycle, wherein the $C_{1-6}$ alkyl group may be substituted with 1 to 5 halogen atoms, and the 3- to 12-membered heterocycle or 4- to 10-membered aromatic heterocycle may be substituted with 1 to 5 $C_{1-6}$ alkyl groups; and
Rf and Rg are identical or different, each representing a hydrogen atom, $C_{1-6}$ alkyl group, —$COCH_3$, or —$SO_2CH_3$;
$B^5$ represents N or $CR^8$; and
$R^8$ represents a hydrogen atom, a $C_{1-6}$ alkyl group, or halogen atom, wherein the $C_{1-6}$ alkyl group may be substituted with 1 to 5 halogen atoms],
a pharmaceutically acceptable salt thereof, or a solvate thereof.

[2]
The compound, a pharmaceutically acceptable salt thereof, or a solvate thereof according to [1], wherein the compound is represented by the following general formula (II):

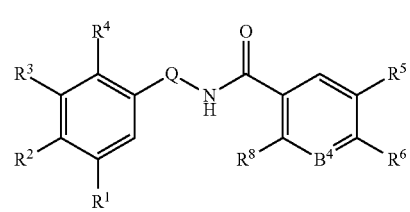

[wherein Q, $R^1$, $R^2$, $R^3$, $R^4$, $R^5$, $R^6$, $B^4$, and $R^8$ are as defined in [1], respectively].

[3]
The compound, a pharmaceutically acceptable salt thereof, or a solvate thereof according to [1] or [2], wherein Q is $CH_2$.

[4]
The compound, a pharmaceutically acceptable salt thereof, or a solvate thereof according to any one of [1] to [3], wherein $R^2$ represents a hydrogen atom or $C_{1-3}$ alkyl group, wherein the $C_{1-3}$ alkyl group and $C_{1-3}$ alkoxy group may be substituted with 1 to 5 halogen atoms.

[5]
The compound, a pharmaceutically acceptable salt thereof, or a solvate thereof according to any one of [1] to [4], wherein $R^3$ represents a hydrogen atom, chlorine atom, or $C_{1-3}$ alkyl group, wherein the $C_{1-3}$ alkyl group may be substituted with 1 to 5 halogen atoms.

[6]
The compound, a pharmaceutically acceptable salt thereof, or a solvate thereof according to any one of [1] to [5], wherein $R^5$ represents a halogen atom, $C_{1-3}$ alkyl group, $C_{2-3}$ alkenyl group, or $C_{1-3}$ alkoxy group, wherein the $C_{1-3}$ alkyl group, $C_{2-3}$ alkenyl group, or $C_{1-3}$ alkoxy group may be substituted with 1 to 5 halogen atoms.

[7]
The compound, a pharmaceutically acceptable salt thereof, or a solvate thereof according to any one of [1] to [6], wherein
$R^6$ represents a hydrogen atom or a group represented by formula (i) below:

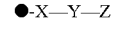—X—Y—Z (i)

wherein X represents $CH_2$;
Y represents piperazine, pyrrolidine, piperidine, morpholine, 3,3-dimethylpiperazine, 3,6-diazabicyclo[3.1.1]heptane, azaspiro[2.4]heptane, 2-oxo-1,3-diazinane, 1,2,5-oxadiazepane, 2-oxopiperidine, azetidine, 5-oxa-2,8-diazaspiro[3.5]nonane, 1,8-diazaspiro[5.5]undecane, imidazole, or benzene;

Z represents a hydrogen atom, $-(CH_2)_m NRaRb$, $-NHCOCH_2Rc$, $-(CH_2)_m NHCORc$, $-(CH_2)_m ORd$, $-(CH_2)_m CORe$, $-(CH_2)_m CONRlRm$, piperazine, pyrrolidine, piperidine, or tetrahydropyran; m represents 0, 1, 2, or 3;

Ra and Rb are identical or different, each representing a hydrogen atom, $C_{1-6}$ alkyl group, $C_{3-6}$ cycloalkyl group, or $-SO_2CH_3$, wherein the $C_{1-6}$ alkyl group or $C_{3-6}$ cycloalkyl group may be substituted with 1 to 5 halogen atoms, hydroxyl groups, $C_{1-6}$ alkoxy groups, amino groups, $-CONH_2$, mono-$C_{1-6}$ alkylamino groups, di-$C_{1-6}$ alkylamino groups, or cyano groups;

Rc represents a $C_{1-4}$ alkyl group, $C_{1-4}$ alkoxy group, 4- to 6-membered heterocycle, 4- to 6-membered aromatic heterocycle, or amino group, wherein the $C_{1-4}$ alkyl group may be independently substituted with 1 to 2 amino, mono-$C_{1-2}$ alkylamino, and/or di-$C_{1-2}$ alkylamino groups;

Rd represents a hydrogen atom or $C_{1-2}$ alkyl group, wherein the $C_{1-2}$ alkyl group may be substituted with an amino group or hydroxyl group;

Re represents a $C_{1-2}$ alkyl group or 4- to 6-membered heterocycle, wherein the $C_{1-2}$ alkyl group may be substituted with an amino group or hydroxyl group; and Rl and Rm are identical or different, each representing a hydrogen atom, $C_{1-3}$ alkyl group, or 4- to 6-membered heterocycle, wherein the $C_{1-3}$ alkyl group independently substituted with 1 to 3 amino, mono-$C_{1-3}$ alkylamino, and/or di-$C_{1-3}$ alkylamino groups.

[8]
The compound, a pharmaceutically acceptable salt thereof, or a solvate thereof according to any one of [1] to [7], wherein
$B^4$ represents $CR^7$, and
$R^7$ represents a chlorine atom, bromine atom, hydrogen atom, cyano group, $C_{1-3}$ alkyl group, $C_{1-3}$ alkoxy group, $C_{2-3}$ alkenyl group, $C_{3-6}$ cycloalkyl group (wherein the $C_{1-3}$ alkyl group, $C_{1-3}$ alkoxy group, $C_{2-3}$ alkenyl group, or $C_{3-6}$ cycloalkyl group may be substituted with 1 to 3 halogen atoms), or group represented by formula (ii) below:

●-$X^2$—$Y^2$—$Z^2$ (ii)

wherein $X^2$ represents $-(CH_2)_p-$, p represents 0 or 1;
$Y^2$ represents piperazine, pyrrolidine, piperidine, morpholine, or 3,3-dimethylpiperazine;
$Z^2$ represents a hydrogen atom, a $C_{1-3}$ alkyl group, $-NRfRg$, pyrrolidine, morpholine, or tetrahydropyran, wherein the $C_{1-3}$ alkyl group may be substituted with 1 to 3 halogen atoms; and
Rf and Rg are identical or different, each representing a hydrogen atom, $C_{1-3}$ alkyl group, $-COCH_3$, or $-SO_2CH_3$.

[9]
The compound, a pharmaceutically acceptable salt thereof, or a solvate thereof according to any one of [1] to [8], wherein $R^8$ represents a hydrogen atom.

[10]
A pharmaceuticals comprising the compound, a pharmaceutically acceptable salt thereof, or a solvate thereof according to any one of [1] to [9] as an active ingredient.

[11]
The pharmaceuticals according to [10], wherein the pharmaceuticals is used for treatment of cancer and/or cancer invasion/metastasis.

[12]
The pharmaceuticals according to [10], wherein the pharmaceuticals is used for treatment of fibrosis and/or inflammation.

[13]
A method for treating cancer, and/or cancer invasion/metastasis, comprising administering a pharmaceutically effective amount of a composition comprising the compound, a pharmaceutically acceptable salt thereof, or a solvate thereof according to any one of [1] to [9] to a patient in need thereof.

[14]
A method for treating fibrosis and/or inflammation, comprising administering a pharmaceutically effective amount of a composition comprising the compound, a pharmaceutically acceptable salt thereof, or a solvate thereof according to any one of [1] to [9] to a patient in need thereof.

[15]
Use of the compound, a pharmaceutically acceptable salt thereof, or a solvate thereof according to any one of [1] to [9] for the manufacture of an agent for treating cancer, and/or cancer invasion/metastasis.

[16]
Use of the compound, a pharmaceutically acceptable salt thereof, or a solvate thereof according to any one of [1] to [9] for the manufacture of an agent for treating fibrosis and/or inflammation.

[17]
The compound, a pharmaceutically acceptable salt thereof, or a solvate thereof according to any one of [1] to [9] for use in treating cancer, and/or cancer invasion/metastasis.

[18]
The compound, a pharmaceutically acceptable salt thereof, or a solvate thereof according to any one of [1] to [9] for use in treating fibrosis and/or inflammation.

Effects of the Invention

The compounds or pharmaceutically acceptable salts thereof, or solvates thereof according to the present invention have an effect of selectively inhibiting the Discoidin Domain Receptor 1 (DDR1). The compounds of the present application may be able to have efficacy for diseases associated with abnormalities of DDR1, such as cancer, cancer metastasis and invasion, fibrosis, and inflammation, and can prevent and/or treat diseases for which previous therapeutic agents are not sufficiently effective.

BRIEF DESCRIPTION OF THE DRAWINGS

FIG. 2 shows a DDR1 phosphorylation inhibitory effect of Compound B-2 in tumors.

FIG. 3 shows compounds synthesized from corresponding carboxylic acids under the same conditions as for Compound A-5. However, DMF was used as a solvent in the synthesis of Compound A-10.

FIG. 4 shows compounds synthesized from corresponding carboxylic acids under the same conditions as for Compound A-5. However, DMF was used as a solvent in the synthesis of Compound A-10.

FIG. 5 shows compounds synthesized using 4-((S)-3-amino-piperidin-1-ylmethyl)-N-(5-chloro-2-ethanesulfonyl-benzyl)-3-trifluoromethyl-benzamide (Compound B-25) and the corresponding amino acids under the same conditions as for Compound B-5.

FIG. 6 shows compounds synthesized using 4-formyl-3-trifluoromethyl-benzoic acid ethyl ester (Compound b31) and the corresponding cyclic amines under the same conditions as for Compounds b32, b33, b34, and B-51.

FIG. 7 shows compounds synthesized using N-(5-chloro-2-ethanesulfonyl-benzyl)-4-formyl-3-trifluoromethyl-benzamide (Compound b37) and the corresponding cyclic amines under the same conditions as for Compounds b38 and B-57.

FIG. 8 shows compounds synthesized from 3-chloro-4-formyl-5-trifluoromethyl-benzoic acid ethyl ester (Compound d7) and corresponding amines under the same conditions as for Compounds d8, d9, d10, and D-5. However, in the synthesis of D-11, chloroform was used in place of THF as a solvent under the conditions for d8.

FIG. 9 shows compounds synthesized from 3-chloro-4-formyl-5-trifluoromethyl-benzoic acid ethyl ester (Compound d7) and corresponding amines under the same conditions as for Compounds d8, d9, d10, and D-5. However, in the synthesis of D-11, chloroform was used in place of THF as a solvent under the conditions for d8.

FIG. 10 shows compounds synthesized from 3-bromo-4-formyl-5-trifluoromethyl-benzoic acid ethyl ester (Compound e2) using corresponding cyclic amines under the same conditions as for Compounds e3, e4, e5, and E-1.

FIG. 11 shows compounds synthesized from 3-bromo-N-(5-chloro-2-ethanesulfonyl-benzyl)-4-formyl-5-trifluoromethyl-benzamide (Compound e7) using corresponding cyclic amines under the same conditions as for Compounds e8 and E-5.

FIG. 12 shows compounds synthesized from 3-chloro-4-formyl-5-trifluoromethoxy-benzoic acid ethyl ester (Compound f15) and corresponding amines under the same conditions as for Compounds f16, f17, f18, and F-6. However, chloroform was used as a solvent under the conditions for Compound f16 in the synthesis of Compounds F-7 and F-8, and DCM was used as a solvent under the conditions for Compound f16 in the synthesis of Compounds F-9, F-15, and F-16. In addition, DCM was used as a solvent under the conditions for Compound f18 in the synthesis of Compounds F-16.

FIG. 13 shows compounds synthesized using 3-bromo-N-(5-chloro-2-ethanesulfonyl-benzyl)-5-trifluoromethoxy-benzamide (Compound A-10) and corresponding cyclic amines under the same conditions as for Compound i2.

FIG. 14 shows compounds synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compound DD-1.

FIG. 15 shows compounds synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compound DD-1.

FIG. 16 shows compounds synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compounds dd1 and DD-5.

FIG. 17 shows compounds synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compounds dd1 and DD-5.

FIG. 18 shows compounds synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compounds dd1 and DD-5.

FIG. 19 shows compounds synthesized using [2-chloro-4-[(5-chloro-2-ethylsulfonylphenyl)methylcarbamoyl]-6-(trifluoromethyl)phenyl]methyl methanesulfonate (Compound dd10) and corresponding amines under the same conditions as for Compounds dd11 and DD-31.

MODE FOR CARRYING OUT THE INVENTION

Figure 1:
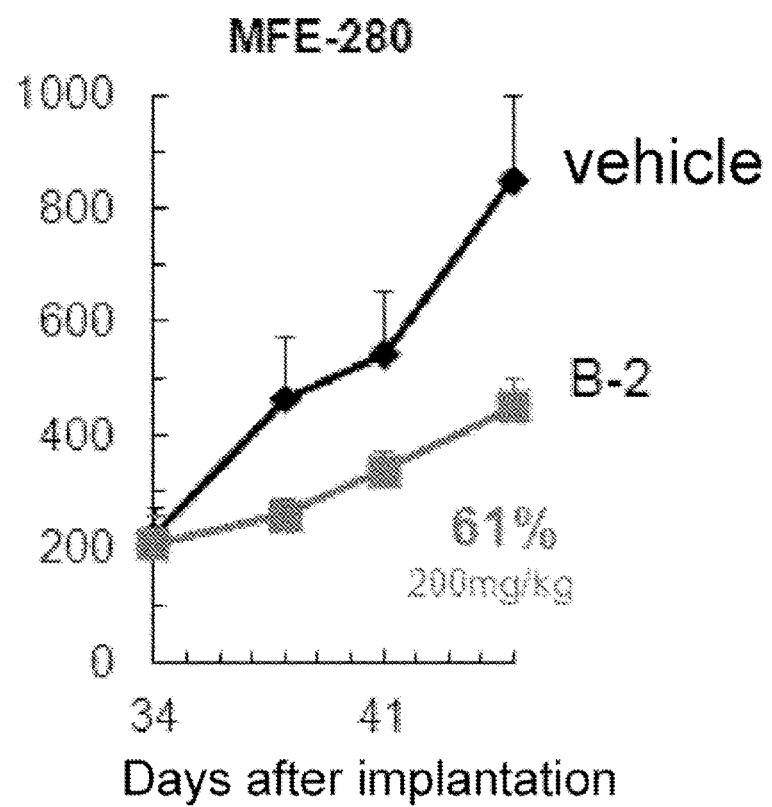
FIG. 1 is a graph showing an antitumor effect of Compound B-2.

The present invention relates to benzamide derivatives and uses thereof. The present inventors for the first time synthesized compounds represented by formula (I) shown above or pharmaceutically acceptable salts thereof and discovered that the compounds or salts thereof had the activity of inhibiting DDR1.

Herein, "alkyl" refers to a monovalent group derived from an aliphatic hydrocarbon by removing an arbitrary hydrogen atom. It contains no heteroatom or unsaturated carbon-carbon bond in the backbone, and has a subset of hydrocarbyl or hydrocarbon group structures which contain hydrogen and carbon atoms. The alkyl group includes linear and branched structures. Preferred alkyl groups include alkyl groups with one to six carbon atoms ($C_{1-6}$; hereinafter, "$C_{p-q}$" means that the number of carbon atoms is p to q), $C_{1-5}$ alkyl groups, $C_{1-4}$ alkyl groups, and $C_{1-3}$ alkyl groups.

Specifically, the alkyl includes, for example, methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group.

Herein, "alkenyl" refers to a monovalent hydrocarbon group having at least one double bond (two adjacent SP2 carbon atoms). The alkenyl group includes linear and branched structures. Depending on the configuration of the double bond and the substituent (if present), the geometry of the double bond can be an entgegen (E) or zuzammen (Z) configuration or a cis or trans configuration. Preferred examples of the alkenyl group include $C_{2-6}$ alkenyl groups.

Specific examples of the alkenyl include a vinyl group, allyl group, 1-propenyl group, 2-propenyl group, 1-butenyl group, 2-butenyl group (including cis and trans), 3-butenyl group, pentenyl group, and hexenyl group.

Herein, "alkynyl" refers to a monovalent hydrocarbon group having at least one triple bond (two adjacent SP carbon atoms). The alkynyl group includes linear and branched structures. Preferred examples include $C_{2-6}$ alkynyl groups.

Specific examples of the alkynyl include an ethynyl group, 1-propynyl group, propargyl group, 3-butynyl group, pentynyl group, and hexynyl group.

The alkenyl or alkynyl can have one or more double bonds or triple bonds, respectively.

Herein, "cycloalkyl" refers to a saturated or partially saturated cyclic monovalent aliphatic hydrocarbon group, and includes monocyclic groups, bicyclo rings, and spiro rings. Preferred cycloalkyl includes $C_{3-7}$ cycloalkyl groups. Specifically, the cycloalkyl group includes, for example, cyclopropyl group, cyclobutyl group, cyclopentyl group, cyclohexyl group, and cycloheptyl group.

Herein, "aryl" refers to a monovalent aromatic hydrocarbon ring. Preferred examples include $C_{6-10}$ aryl. Specific examples of the aryl include a phenyl group and naphthyl group (e.g., a 1-naphthyl group or 2-naphthyl group).

Herein, "halogen atom" refers to a fluorine atom, chlorine atom, bromine atom, or iodine atom.

Herein, "alkoxy" refers to an oxy group linked with an "alkyl" defined above. Preferred alkoxy includes $C_{1-6}$ alkoxy groups, $C_{1-4}$ alkoxy groups, and $C_{1-3}$ alkoxy groups. Specifically, alkoxy includes, for example, methoxy group, ethoxy group, 1-propoxy group, 2-propoxy group, n-butoxy group, i-butoxy group, sec-butoxy group, and tert-butoxy group.

Herein, "aromatic ring" refers to an aromatic monovalent or divalent hydrocarbon ring. The aromatic ring may be a single ring or a fused ring. The number of the ring-forming atoms is preferably 4 to 10 (4- to 10-membered aromatic ring).

Specific examples of the aromatic ring include benzene and naphthalene.

Herein, "heterocycle" refers to a non-aromatic monovalent or divalent heterocycle containing preferably 1 to 5 heteroatoms in the ring-forming atoms. The heterocycle may have a double and/or triple bond in the ring, carbon atoms in the ring may be oxidized to form carbonyl. The heterocycle may be a single ring, fused ring, or spiro ring. The number of the ring-forming atoms is preferably 3 to 12 (3- to 12-membered heterocycle), and more preferably 4 to 7 (4- to 7-membered heterocycle).

Specific examples of the heterocycle include piperazine, pyrrolidine, piperidine, morpholine, oxetane, dihydrofuran, tetrahydrofuran, dihydropyran, tetrahydropyran, tetrahydropyridine, thiomorpholine, pyrazolidine, imidazoline, imidazolidine, oxazolidine, isoxazolidine, thiazolidine, isothiazolidine, thiadiazolidine, azetidine, oxazolidone, benzodioxane, benzoxazoline, dioxolane, 3,6-diazabicyclo[3.1.1]heptane, azaspiro[2.4]heptane, 2-oxo-1,3-diazinane, 1,2,5-oxadiazepane, 2-oxopiperidine, azetidine, 5-oxa-2,8-diazaspiro[3.5]nonane, and 1,8-diazaspiro[5.5]undecane.

Herein, "aromatic heterocycle" refers to an aromatic monovalent or divalent heterocycle containing preferably 1 to 5 heteroatoms in the ring-forming atoms. The aromatic heterocycle may be partially saturated, and may be a single ring, fused ring (such as a bicyclic aromatic heterocycle in which a monocyclic aromatic heterocycle is fused with a benzene ring or monocyclic aromatic heterocycle), or spiro ring. The number of ring-forming atoms is preferably 4 to 10 (4- to 10-membered aromatic heterocycle).

Specific examples of the aromatic heterocycle include furan, thiophene, pyrrole, imidazole, pyrazole, thiazole, isothiazole, oxazole, isoxazole, oxadiazole, thiadiazole, triazole, tetrazole, pyridine, pyrimidine, pyridazine, pyrazine, triazine, benzofuran, benzothiophene, benzothiadiazole, benzothiazole, benzoxazole, benzoxadiazole, benzimidazole, indole, isoindole, indazole, quinoline, isoquinoline, cinnoline, quinazoline, quinoxaline, indolizine, and imidazopyridine.

Herein, "heteroatom" refers to a nitrogen atom (N), an oxygen atom (O) or a sulfur atom (S).

Herein, "monoalkylamino" refers to an amino group to which one of the above-defined "alkyl" groups is bonded. Preferred examples of the monoalkylamino include mono-$C_{1-6}$ alkylamino.

Herein, "dialkylamino" refers to an amino group linked with two "alkyls" defined above. The two alkyl groups may be the same or different. The dialkylamino preferably includes di$C_{1-6}$ alkylamino.

Herein, "alkylsulfonyl" refers to a sulfonyl group linked with an "alkyl" defined above (i.e., alkyl-$SO_2$—). The alkylsulfonyl preferably includes $C_{1-6}$ alkylsulfonyl and $C_{1-3}$ alkyl sulfonyl, specifically methylsulfonyl, ethylsulfonyl, n-propylsulfonyl, and i-propylsulfonyl.

Herein, "alkylsulfanyl" refers to a sulfanyl group to which the above-defined "alkyl" is bonded (i.e., alkyl-S—). Preferred examples of the alkylsulfanyl include $C_{1-6}$ alkylsulfanyl and $C_{1-3}$ alkylsulfanyl, specifically, methylsulfanyl, ethylsulfanyl, n-propylsulfanyl, and i-propylsulfanyl.

Herein, "alkylsulfinyl" refers to a sulfinyl group to which the above-defined "alkyl" is bonded (i.e., alkyl-SO—). Preferred examples of the alkylsulfinyl include $C_{1-6}$ alkylsulfinyl and $C_{1-3}$ alkylsulfinyl, specifically, methylsulfinyl, ethylsulfinyl, n-propylsulfinyl, and i-propylsulfinyl.

Herein, "arylsulfonyl" refers to a sulfonyl group to which the above-defined "aryl" is bounded (i.e., aryl-$SO_2$—). Preferred examples of the arylsulfonyl include $C_{6-10}$ arylsulfonyl, specifically, phenylsulfonyl, 1-naphthyl sulfonyl, and 2-naphthyl sulfonyl.

Herein, "arylsulfanyl" refers to a sulfanyl group to which the above-defined "aryl" is bounded (i.e., aryl-S—). Preferred examples of the arylsulfanyl include $C_{6-10}$ arylsulfanyl, specifically, phenylsulfanyl, 1-naphthylsulfanyl, and 2-naphthylsulfanyl.

Herein, "arylsulfinyl" refers to a sulfinyl group to which the above-defined "aryl" is bounded (i.e., aryl-SO—). Preferred examples of the arylsulfinyl include $C_{6-10}$ arylsulfinyl, specifically, phenylsulfinyl, 1-naphthylsulfinyl, and 2-naphthylsulfinyl.

Herein, "cycloalkylsulfonyl" refers to a sulfonyl group to which the above-defined "cycloalkyl" is bounded (i.e., cycloalkyl-$SO_2$—). Preferred examples of the cycloalkylsulfonyl include $C_{3-8}$ cycloalkylsulfonyl, specifically, cyclopentylsulfonyl, cyclohexylsulfonyl, and cycloheptylsulfonyl.

Herein, "cycloalkylsulfanyl" refers to a sulfanyl group to which the above-defined "cycloalkyl" is bounded (i.e., cycloalkyl-S—). Preferred examples of the cycloalkylsulfanyl include $C_{3-8}$ cycloalkylsulfanyl, specifically, cyclopentylsulfanyl, cyclohexylsulfanyl, cycloheptylsulfanyl.

Herein, "cycloalkylsulfinyl" refers to a sulfinyl group to which the above-defined "cycloalkyl" is bounded (i.e., cycloalkyl-SO—). Preferred examples of the cycloalkylsulfinyl include $C_{3-8}$ cycloalkylsulfinyl, specifically, cyclopentylsulfinyl, cyclohexylsulfinyl, cycloheptylsulfinyl.

The compounds of the present invention include free forms and pharmaceutically acceptable salts thereof. Such "salts" include, for example, inorganic acid salts, organic acid salts, inorganic base salts, organic base salts, and acidic or basic amino acid salts.

Preferred inorganic acid salts include, for example, hydrochloride, hydrobromide, sulfate, nitrate, and phosphate. Preferred organic salts include, for example, acetate, succinate, fumarate, maleate, tartrate, citrate, lactate, malate, stearate, benzoate, methanesulfonate, and p-toluenesulfonate.

Preferred inorganic base salts include, for example, alkali metal salts such as sodium salts and potassium salts; alkali earth metal salts such as calcium salts and magnesium salts; aluminum salts; and ammonium salts. Preferred organic base salts include, for example, diethylamine salts, diethanolamine salts, meglumine salts, and N,N-dibenzylethylenediamine salts.

Preferred acidic amino acid salts include, for example, aspartate and glutamate. Preferred basic amino acid salts include, for example, arginine salts, lysine salts, and ornithine salts.

When the compounds of the present invention are left standing under the atmosphere, they may absorb moisture to adsorb water or form hydrates. Such hydrates are also included in the salts of the present invention.

Furthermore, the compounds of the present invention may absorb other solvents to form solvates. Such solvates are also included in the salts of the present invention.

All structurally possible isomers (geometric isomers, optical isomers, stereoisomers, tautomers, etc.) of the compounds of the present invention and mixtures of such isomers are included in the present invention.

The compounds of the present invention may have polymorphic crystalline forms. Such polymorphs are all included in the present invention.

The compounds of the present invention include prodrugs thereof. The prodrugs refer to derivatives of the compounds of the present invention which have a chemically or metabolically degradable group, and upon administration to the living body, revert to the original compounds and exhibit the original drug efficacy. The prodrugs include non-covalent complexes and salts.

The compounds of the present invention include those in which one or more atoms within the molecule have been replaced with isotopes. Herein, the isotope refers to an atom which has the same atomic number (proton number) but is different in mass number (sum of protons and neutrons). The target atoms to be replaced with an isotope in the compounds of the present invention include, for example, hydrogen atom, carbon atom, nitrogen atom, oxygen atom, phosphorus atom, sulfur atom, fluorine atom, and chlorine atom. Their isotopes include $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$. In particular, radioisotopes such as $^3H$ and $^{14}C$, which decay emitting radiation, are useful in in vivo tissue distribution study, and such of pharmaceuticals or compounds. Stable isotopes do not decay, are almost constant in abundance, and emit no radiation. For this reason, stable isotopes can be used safely. The compounds of the present invention can be converted into isotope-substituted compounds according to conventional methods by replacing reagents used in synthesis with reagents containing corresponding isotopes.

Preferably, the compounds of the present invention represented by formula (I) shown above are as follows.

The above Q is preferably $CH_2$.

The above $A^1$ is preferably $CR^1$.

The above $R^1$ is preferably a chlorine atom, bromine atom, fluorine atom, methyl group, or cyano group, and more preferably a chlorine atom.

The above $A^2$ is preferably $CR^2$.

The above $R^2$ is preferably a hydrogen atom.

The above $A^3$ is preferably $CR^3$.

The above $R^3$ is preferably a hydrogen atom, methyl group, or chlorine atom.

The above $R^4$ is preferably a $C_{2-4}$ alkylsulfonyl group, $C_{2-4}$ alkylsulfanyl group, or $C_{2-4}$ alkylsulfinyl group, more preferably a $C_{2-4}$ alkylsulfonyl group, and still more preferably an ethylsulfonyl group.

The above $B^1$ is preferably CH.

The above $B^2$ is preferably $CR^5$.

Preferably, the above $R^5$ represents a halogen atom, $C_{1-3}$ alkyl group, $C_{2-3}$ alkenyl group, or $C_{1-3}$ alkoxy group, where the $C_{1-3}$ alkyl group or $C_{1-3}$ alkoxy group may be substituted with 1 to 5 halogen atoms. More preferably, the above $R^5$ represents a halogen atom, $C_{1-3}$ alkyl group, $C_2$ alkenyl group, or $C_1$ alkoxy group, where the $C_{1-3}$ alkyl group or $C_1$ alkoxy group may be substituted with 1 to 3 halogen atoms. The above $R^5$ is particularly preferably a trifluoromethyl group, trifluoromethoxy group, methyl group, ethyl group, vinyl group, chlorine atom, or bromine atom.

The above $B^3$ is preferably $CR^6$.

The above $B^6$ is preferably O or $NR^6$.

Preferably, the above $R^6$ represents a hydrogen atom or a group represented by formula (i) below.

(i)

The above X is preferably —$(CH_2)n$-, where n represents 1 or 2, and n is preferably 1.

The above Y preferably represents a 4- to 6-membered heterocycle, and is more preferably piperazine, pyrrolidine, piperidine, morpholine, 3,3-dimethylpiperazine, 3,6-diazabicyclo[3.1.1]heptane, azaspiro[2,4]heptane, 2-oxo-1,3-diazinane, 1,2,5-oxadiazepane, 2-oxopiperidine, azetidine, 5-oxa-2,8-diazaspiro[3.5]nonane, 1,8-diazaspiro[5.5]undecane, imidazole, or benzene. More preferably, the above Y is piperazine, pyrrolidine, piperidine, morpholine, or 3,3-dimethylpiperazine.

The above Z is preferably a hydrogen atom, a $C_{1-3}$ alkyl group, —$(CH_2)_m$—NRaRb, —$NHCOCH_2Rc$, —$(CH_2)_m$N-HCORc, —$(CH_2)_m$ORd, —$(CH_2)_m$CONRlRm, —$(CH_2)_m$ORd, —$(CH_2)_m$—CORe, or a 5- to 6-membered heterocycle, where m represents 0 or 1. The above Z is more preferably a hydrogen atom, —$(CH_2)_m$—NRaRb, —$NHCOCH_2Rc$, —$(CH_2)_m$NHCORc, —CORe, piperazine, pyrrolidine, piperidine, or tetrahydropyran.

Preferably, the above Ra and Rb are identical or different, each representing a hydrogen atom, a $C_{1-3}$ alkyl group, $C_{4-6}$ cycloalkyl group, or —$SO_2CH_3$, where the $C_{1-3}$ alkyl group or $C_{4-6}$ cycloalkyl group may be substituted with 1 to 3 halogen atoms, hydrogen atom, amino group, —$CONH_2$, methylamino group, dimethylamino group, cyano group. More preferably, the above Ra and Rb are identical or different, each representing a hydrogen atom, methyl group, ethyl group, isopropyl group, 2-aminoethyl group, 3-aminopropyl group, 2-methylaminoethyl group, or —$SO_2CH_3$.

Preferably, the above Rc represents a $C_{1-4}$ alkyl group, a $C_{1-2}$ alkoxy group, 4- to 6-membered heterocycle, 4- to 6-membered aromatic heterocycle, or an amino group, where the $C_{1-4}$ alkyl group may be independently substituted with 1 or 2 amino, mono-$C_{1-2}$ alkylamino, and/or di-$C_{1-2}$ alkylamino groups. More preferably, the above Rc represents a $C_{1-2}$ alkyl group, methoxy group, or amino group, where the $C_{1-2}$ alkyl group may be independently substituted with 1 to 2 amino, mono-$C_{1-2}$ alkylamino, and/or di-$C_{1-2}$ alkylamino groups.

Rd is preferably a hydrogen atom or $C_{1-2}$ alkyl group, where the $C_{1-2}$ alkyl group may be independently substituted with 1 or 2 amino group or hydroxyl group, and more preferably a hydrogen atom, methyl group, 2-aminoethyl group, or 2-hydroxyethyl group.

Preferably, the above Re represents a $C_{1-2}$ alkyl group or 4- to 6-membered heterocycle, where the $C_{1-2}$ alkyl group may be substituted with 1 to 3 amino groups. More preferably, the above Re represents a $C_{1-2}$ alkyl group, where the $C_{1-2}$ alkyl group may be substituted with 1 to 2 amino groups.

The above $B^4$ is preferably $CR^7$.

The above $R^7$ is preferably a hydrogen atom, halogen atom, cyano group, $C_{1-3}$ alkyl group, $C_{1-3}$ alkoxy group, $C_{2-3}$ alkenyl group, $C_{3-6}$ cycloalkyl group, or a group represented by —$X^2$—$Y^2$—$Z^2$, more preferably a hydrogen atom, chlorine atom, bromine atom, cyano group, methyl group, ethyl group, vinyl group, cyclopropyl group, or a group represented by —$X^2$—$Y^2$—$Z^2$.

The above $X^2$ is preferably —$(CH_2)_p$—, where p represents 0 or 1.

Preferably, the above $Y^2$ represents a 5- to 6-membered heterocycle, where the 5- to 6-membered heterocycle may be substituted with 1 to 5 $C_{1-6}$ alkyl groups. More preferably, the above Y² represents piperazine, pyrrolidine, piperidine, morpholine, or 3,3-dimethylpiperazine.

Preferably, the above $Z^2$ represents a hydrogen atom, a $C_{1-3}$ alkyl group, —NRfRg, or a 5- to 6-membered heterocycle, where the $C_{1-3}$ alkyl group may be substituted with 1 to 5 halogen atoms. More preferably, the above $Z^2$ represents a hydrogen atom, a $C_{1-3}$ alkyl group, —NRfRg, pyrrolidine, morpholine, or tetrahydropyran, where the $C_{1-3}$ alkyl group may be substituted with 1 to 3 halogen atoms.

Preferably, the above Rf and Rg each represents a hydrogen atom, a $C_{1-3}$ alkyl group, —COCH$_3$, or —SO$_2$CH$_3$.

The above $B^5$ is preferably $CR^8$.

The above $R^8$ is preferably a hydrogen atom or fluorine atom, and more preferably a hydrogen atom.

Compounds represented by formula (I) according to the present invention or pharmaceutically acceptable salts thereof are useful as compounds having an effect of selectively inhibiting Discoidin Domain Receptor 1 (DDR1), and are useful for the prevention and/or treatment of cancer, prevention and/or treatment of cancer invasion and metastasis, and prevention and/or treatment of fibrosis and inflammation.

Examples of the cancer include leukemia (such as acute myeloid leukemia, chronic myeloid leukemia, acute lymphocytic leukemia, and chronic lymphocytic leukemia), malignant lymphoma (such as Hodgkin's lymphoma and non-Hodgkin's lymphoma), brain tumor, neuroblastoma, glioma, thyroid cancer, myelodysplastic syndrome, head and neck cancer, esophageal cancer, gastric cancer, colon cancer, colorectal cancer, breast cancer, ovarian cancer, lung cancer, pancreatic cancer, liver cancer, gallbladder cancer, skin cancer, malignant melanoma, renal cancer, renal pelvic and ureteral cancer, bladder cancer, uterine cancer, testicular cancer, and prostatic cancer. Preferred examples include non-small-cell lung cancer, pancreatic cancer, endometrial cancer, brain tumor, bile duct cancer, colon cancer, breast cancer, ovarian cancer, and prostatic cancer.

Examples of the fibrosis and inflammation include hepatic fibrosis, renal fibrosis, pulmonary fibrosis, scleroderma/systemic sclerosis, myelofibrosis, endomyocardial fibrosis, hepatitis (non-alcoholic steatohepatitis, alcoholic hepatitis, drug-induced hepatitis, autoimmune hepatitis, and primary biliary cirrhosis), diabetic nephropathy, membranoproliferative glomerulonephritis, focal glomerulosclerosis, IgA nephropathy, membranous nephropathy, L chain deposition disease, lupus nephritis, cryoglobulinemic nephritis, HIV-associated nephritis, purpura nephritis, membranoproliferative nephritis, endocapillary proliferative nephritis, mesangial proliferative nephritis, crescentic nephritis, interstitial nephritis, hypertensive nephrosclerosis, anti-GBM nephritis (Goodpasture syndrome), HCV, HBV-associated nephropathy, ANCA nephritis, Alport's syndrome, chronic pancreatitis, rheumatoid arthritis, atherosclerosis, Crohn's disease, ulcerative colitis, and multiple sclerosis.

The compounds of the present invention and salts thereof can be formulated into tablets, powders, fine granules, granules, coated tablets capsules, syrups, troches, inhalants, suppositories, injections, ointments, eye ointments, eye drops, nasal drops, ear drops, cataplasms, lotions, and the like by conventional methods. For the formulation, conventional excipients, binding agents, lubricants, colorants, flavoring agents, and if needed, stabilizers, emulsifiers, absorbefacients, surfactants, pH adjusting agents, preservatives, antioxidants, and the like can be used. The compounds of the present invention are formulated by combining ingredients that are generally used as materials for pharmaceutical preparations, using conventional methods.

For example, to produce oral formulations, the compounds of the present invention or pharmaceutically acceptable salts thereof are combined with excipients, and if needed, binding agents, disintegrating agents, lubricants, colorants, flavoring agents, and the like; and then formulated into powders, fine granules, granules, tablets, coated tablets, capsules, and the like by conventional methods.

The ingredients include, for example, animal and vegetable oils such as soybean oils, beef tallow, and synthetic glycerides; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid esters, sorbitan fatty acid esters, glycerin fatty acid esters, polyoxyethylene sorbitan fatty acid esters, polyoxyethylene hydrogenated castor oils, and polyoxyethylene/polyoxypropylene block copolymers; water-soluble polymers such as hydroxyethyl cellulose, polyacrylic acids, carboxyvinyl polymers, polyethylene glycol, polyvinylpyrrolidone, and methyl cellulose; lower alcohols such as ethanol and isopropanol; polyalcohols such as glycerin, propylene glycol, dipropylene glycol, and sorbitol; saccharides such as glucose and sucrose; inorganic powders such as silicic anhydride, magnesium aluminum silicate, and aluminum silicate; and purified water.

Excipients include, for example, lactose, cornstarch, sucrose, glucose, mannitol, sorbit, crystalline cellulose, and silicon dioxide.

Binding agents include, for example, polyvinyl alcohol, polyvinyl ether, methyl cellulose, ethyl cellulose, Arabic gum, tragacanth, gelatin, shellac, hydroxypropylmethyl cellulose, hydroxypropyl cellulose, polyvinylpyrrolidone, polypropylene glycol/polyoxyethylene block polymer, and meglumine.

Disintegrating agents include, for example, starch, agar, gelatin powder, crystalline cellulose, calcium carbonate, sodium bicarbonate, calcium citrate, dextran, pectin, and calcium carboxymethyl cellulose.

Lubricants include, for example, magnesium stearate, talc, polyethylene glycol, silica, and hardened vegetable oil.

Colorants approved for use as additives for pharmaceuticals are used. Flavoring agents used include, for example, cacao powder, menthol, aromatic powder, peppermint oil, borneol, and cinnamon powder.

Of course, these tablets/granules may be coated with sugar, or if needed, other appropriate coatings. Alternatively, when liquid preparations such as syrups and injections are produced, the compounds of the present invention or pharmaceutically acceptable salts thereof are combined with pH adjusting agents, solubilizers, isotonizing agents, or such, and if needed, solubilizing agents, stabilizers, and such, and then formulated using conventional methods.

Methods for producing external preparations are not limited, and they can be produced by conventional methods. Various conventional materials for pharmaceuticals, quasi-drugs, cosmetics, and the like can be used as base materials in the production. Specifically, the base materials used include, for example, animal and vegetable oils, mineral oils, ester oils, waxes, higher alcohols, fatty acids, silicon oils, surfactants, phospholipids, alcohols, polyalcohols, water-soluble polymers, clay minerals, and purified water. Furthermore, as necessary, it is possible to add pH adjusting agents, antioxidants, chelating agents, preservatives, colorants, flavoring agents, and such. However, the base materials for external preparations of the present invention are not limited thereto.

Furthermore, if needed, the preparations may be combined with components that have an activity of inducing differentiation, or components such as blood flow-enhancing agents, antimicrobial agents, antiphlogistic agents, cell-activating agents, vitamins, amino acids, humectants, and keratolytic agents. The above-described base materials can be added at an amount that provides a concentration typically selected in the production of external preparations.

When the compounds of the present invention, salts, or solvates thereof are administered, their dosage forms are not particularly limited, and they may be administered orally or parenterally by conventionally used methods. They can be formulated and administered as tablets, powders, granules, capsules, syrups, troches, inhalants, suppositories, injections, ointments, eye ointments, eye drops, nasal drops, ear drops, cataplasms, lotions, and the like.

The dosage of pharmaceuticals of the present invention can be appropriately selected depending on the severity of symptom, age, sex, weight, administration method, type of salt, specific type of disease, and such.

The dosage considerably varies depending on the type of disease, severity of symptom, age, sex, sensitivity to the agent, and such of the patient. Typically, the agent is administered to an adult once or several times a day at a daily dose of about 0.03 to 1,000 mg, preferably 0.1 to 500 mg, and more preferably 0.1 to 100 mg. When an injection is used, the daily dose is typically about 1 µg/kg to 3,000 µg/kg, preferably about 3 µg/kg to 1,000 µg/kg.

When the compounds of the present invention are produced, material compounds and various reagents may form salts, hydrates, or solvates. The type varies depending on the starting material, solvent used, and such, and is not particularly limited as long as the reactions are not inhibited.

The solvents to be used vary depending on the starting material, reagent, and such, and as a matter of course, they are not particularly limited as long as they can dissolve starting materials to some extent without inhibiting the reactions.

Various isomers (for example, geometric isomers, optical isomers based on asymmetric carbons, rotational isomers, stereoisomers, and tautomers) can be purified and isolated by conventional separation methods such as recrystallization, diastereomer salt methods, enzyme-based resolution methods, various chromatographic methods (for example, thin-layer chromatography, column chromatography, high performance liquid chromatography, and gas chromatography).

When a compound of the present invention is obtained in a free form, it can be converted by conventional methods into a salt or solvate thereof that may be formed from the compound of the present invention. When a compound of the present invention is obtained as a salt or solvate thereof, it can be converted by conventional methods into a free form of the compound of the present invention.

The compounds of the present invention can be purified/isolated using conventional chemical methods such as extraction, concentration, distilling off, crystallization, filtration, recrystallization, and various chromatographic methods.

All the prior art documents cited in this specification are incorporated herein by reference.

General production methods for the compounds of the present invention and Examples will be shown below.

The compounds of the present invention can be synthesized by various methods, some of which will be described with reference to the following schemes. The schemes are illustrative, and the present invention is not limited only by the chemical reactions and conditions explicitly indicated. Although some substituents may be excluded in the following schemes for the sake of clarity, such exclusion is not intended to limit the disclosure of the schemes. Representative compounds of the present invention can be synthesized using appropriate intermediates, known compounds, and reagents.

The abbreviations generally used in the general production methods and Examples below, and the names of reagents and solvents corresponding to the chemical formulas will be described below.

AcOH Acetic acid
AD mix Asymmetric Dihydroxylation Mix
AIBN Azobisisobutyronitrile
BINAP 2,2'-Bis(diphenylphosphino)-1,1'-binaphthyl
Boc t-butoxycarbonyl
Boc$_2$O Di-t-butyl dicarbonate
BOP (Benzotriazol-1-yloxy)-tris(dimetylamino)phosphonium hexafluorophosphate and its derivatives
BPO Benzoyl peroxide
9-BBN 9-borabicyclo[3.3.1]nonane
CPME Cyclopentylmethyl ether
DBU 1,8-diazabicyclo[5.4.0]undec-7-ene
DCE Dichloroethane
DCC N,N'-Dicylohexylcarbodiimide
DCM Dichloromethane
DEAD Diethyl azodicarboxylate
DIPEA N,N-Diisopropylethylamine
DMF Dimethylformamide
DMA Dimethylacetamide
DMAP N,N-Dimethyl-4-aminopyridine
DMSO Dimethyl sulfoxide
DMT-MM 4-(4,6-Dimethoxy-1,3,5-triazin-2-yl)-4-methylmorpholinium Chloride
DPPA diphenylphosphorylazide
dppf Bis(diphenylphosphino)ferrocene
EtOH Ethanol
2-PrOH 2-Propanol
EtOAc Ethyl acetate
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HOBT 1-Hydroxybenzotriazole
LDA lithium diisopropylamide
LiHMDS Lithium bis(trimethylsilyl)amide(=Lithium hexamethyl disilazide)
m-CPBA m-Chloroperbenzoic acid
NMP N-Methylpyrolidone
NBS N-Bromosuccinimide
NCS N-Chlorosuccinimide
NIS N-Iodosuccinimide
nBupAd$_2$ Di(1-adamantyl)-n-butylphosphine
MeOH Methanol
S-Phos 2-Dicyclohexylphosphino-2',6'-dimethoxybiphenyl
TBME tert-Butylmethyl ether
TEA Triethylamine
TFA Trifluoroacetic acid
THF Tetrahydrofuran
WSCDI 1-Ethyl-3-(3-dimethylaminopropyl)carbodiimide hydrochloride
X-Phos 2',4',6'-Triisopropyl-2-(dicyclohexylphosphino)biphenyl Production Method I Method I is a method for forming a backbone of the formula (II), where Q is $CH_2$, $R^4$ is a sulfanyl group or sulfonyl group, and $R^6$ is H or halogen.

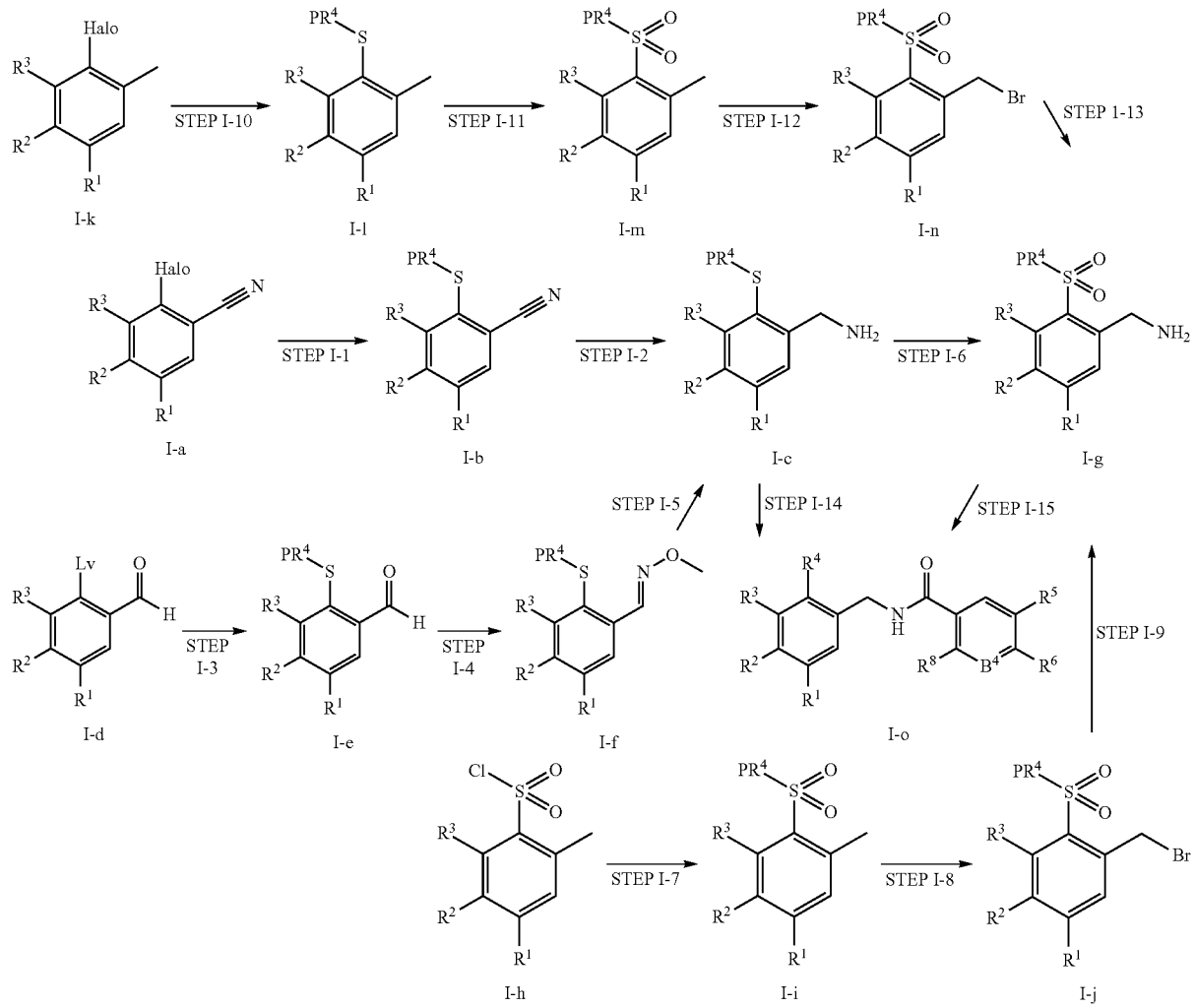

Lv: halogen or OTf

Step I-1

Step I-1 is a step of sulfanylating a halobenzonitrile derivative I-a by forming a carbon-sulfur bond. This step can be performed by reacting the halobenzonitrile derivative I-a with an alkylthiol or arylthiol reagent corresponding to $PR^4$ in the presence of a base. The thiol reagent includes acyclic alkylthiols such as methanethiol, ethanethiol, n-propylthiol, and i-propylthiol; cyclic alkylthiols such as cyclopentylthiol; and arylthiols such as phenylthiol. The base includes inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. Examples of the solvent include DMF, DMA, DMSO, dichloromethane, THF, acetonitrile, and mixtures thereof. DMF is preferred. The step can also be performed by reacting the halobenzonitrile derivative I-a with a metal alkyl/aryl thiolate corresponding to $PR^4$ under heating in a polar solvent such as DMF as in the method described in WO 2009/131245. Alternatively, the step can also be performed by reacting the halobenzonitrile derivative I-a with an acyclic alkylthiol corresponding to $PR^4$ under heating in a polar solvent such as 1,4-dioxane in the presence of a Pd catalyst, Pd catalyst ligand, and base as in the method described in WO 2006/038741. Here, the Pd catalyst is preferably $Pd_2(dba)_3$, the Pd catalyst ligand is preferably Xantphos, the base is preferably N,N-diisobutylethylamine, and the solvent is preferably 1,4-dioxane.

Step I-2

Step I-2 is a step of reducing a sulfanylbenzonitrile derivative I-b. This step can be performed by reducing the nitrile group of the sulfanylbenzonitrile derivative I-b by reaction with a reducing agent. The reducing agent includes metal reducing agents such as lithium aluminum hydride, diisobutylaluminum hydride, Selectride, Super-Hydride, and sodium borohydride-nickel chloride; and boron reducing agents such as a borane-THF complex and a borane-dimethyl sulfide complex. Lithium aluminum hydride and a borane-THF complex are preferred. The solvent includes THF, dimethyl ether, and dimethoxyethane, and is preferably THF.

Step I-3

Step I-3 is a step of sulfanylating an aldehyde derivative I-d by forming a carbon-sulfur bond. This step can be performed by reacting the aldehyde derivative I-d with a metal alkyl/aryl thiolate corresponding to $PR^4$ under heating, and for example, the method described in WO 2009/131245 can be used as a reference. Examples of the metal alkyl/aryl thiolate include sodium ethanethiolate, sodium methanethiolate, and potassium ethanethiolate. The solvent include DMF, DMA, DMSO, dichloromethane, THF, acetonitrile, and mixtures thereof, and is preferably DMF. The heating is preferably performed at 50° C. to 90° C. The step can also be performed by reacting the aldehyde I-d with an alkyl- or arylthiol reagent corresponding to $PR^4$ as in the method described in Step I-1. Alternatively, the step can also be performed by reacting the aldehyde derivative I-d with an acyclic alkylthiol corresponding to $PR^4$ under heating in a polar solvent such as 1,4-dioxane in the presence of a Pd catalyst, Pd catalyst ligand, and base as in the method described in WO 2006/038741.

Step I-4

Step I-4 is a step of oximating a sulfanylbenzaldehyde derivative I-e. This step can be performed by reacting the aldehyde I-e with O-methylhydroxylamine hydrochloride in the presence of a base. The base includes pyridine, triethylamine, N,N-diisobutylethylamine, and N,N-dimethyl-4-aminopyridine, and is preferably pyridine. The solvent used for the reaction includes dichloromethane, THF, acetonitrile, and CPME. The solvent need not be used when pyridine is used as a base.

Step I-5

Step I-5 is a step of reducing an O-methyl oxime derivative I-f. This step can be performed by reacting the O-methyl oxime derivative I-f with a boron reagent under heating and then treating with an acid. Examples of the boron reagent include boron reducing agents such as a borane-THF complex, a borane-dimethyl sulfide complex, thexylborane, and 9-BBN. A borane-THF complex is preferred. Examples of the acid include hydrochloric acid solutions. An aqueous hydrochloric acid solution is preferred. The solvent includes aprotic solvents, and is preferably THF. The heating can be performed at 50° C. to 90° C.

Step I-6

Step I-6 is a step of converting a sulfanylbenzylamine derivative I-c to a sulfoxide derivative. This step can be performed by protecting the free primary amine with a Boc group or the like, converting the derivative to a sulfoxide by oxidation with a peracid such as mCPBA, tBuOOH, $H_2O_2$, oxone, or potassium permanganate, and deprotecting the Boc group by treatment with hydrochloric acid, with reference to the method described in WO 2009/131245. The protecting group is preferably a Boc group, and the oxidizing agent is preferably mCPBA. The obtained sulfonylbenzylamine derivative I-g can be isolated as a hydrochloride.

Step I-7

Step I-7 is a step of alkylating a sulfonyl chloride derivative I-h. This step can be performed by converting the sulfonyl chloride derivative I-h to a sulfinate using a reducing agent under heating in situ, and then alkylating the sulfinate by treatment with an alkylating agent. The step can be performed, for example, by the method of Bioorg. Med. Chem. 13 (2005) 397-416. The reducing agent to a sulfinate is preferably sodium sulfite. The alkylating agent includes alkyl halides and 2-halocarboxylic acids, and is preferably alkyl iodides such as ethyl iodide.

Step I-8

Step I-8 is a step of brominating a sulfonyltoluene derivative I-i (Wohl-Ziegler reaction).

This step can be performed by reacting the sulfonyltoluene derivative I-i with a brominating agent under heating in the presence of a catalytic amount of a radical initiator. The brominating agent includes NBS and N-bromoimide, preferably, NBS. The radical initiator includes benzoyl peroxide and AIBN, and is preferably benzoyl peroxide. The solvent includes carbon tetrachloride, benzene, cyclohexane, and acetonitrile, and preferably, carbon tetrachloride. The heating temperature is preferably 80° C. or higher.

Step I-9

Step I-9 is a step of aminating a benzyl bromide derivative I-j. This step can be performed by reacting the benzyl bromide derivative I-j with an aminating agent. The aminating agent includes aqueous ammonia, liquid ammonia, and ammonia gas, and is preferably aqueous ammonia. Examples of the solvent include protic alcohol solvents, water, THF, and mixed solvents thereof. Ethanol is preferred.

Step I-10

Step I-10 is a step of sulfanylating a halobenzene derivative I-k by forming a carbon-sulfur bond. This step can be performed by reacting the halobenzene derivative I-k with a metal alkyl/aryl thiolate corresponding to $PR^4$ under heating, and for example, the method described in WO 2009/131245 can be used as a reference. The conditions to be selected in this step such as the reaction reagent and the solvent are the same as those in Step I-3.

Step I-11

Step I-11 is a step of oxidizing a sulfanyltoluene derivative I-1 to a sulfoxide. This step can be performed by reacting the sulfanyltoluene derivative I-1 with an oxidizing agent. The oxidizing agent includes peracids such as mCPBA, tBuOOH, $H_2O_2$, oxone, and potassium permanganate, and is preferably two or more equivalents of mCPBA. The solvent includes aprotic solvents, and is preferably dichloromethane or ethyl acetate.

Step I-12

Step I-12 is a step of brominating a sulfonyltoluene derivative I-m (Wohl-Ziegler reaction). This step can be performed by reacting the sulfonyltoluene derivative I-m with a brominating agent under heating in the presence of a catalytic amount of a radical initiator. The conditions to be selected in this step such as the reaction reagent and the solvent are the same as those in Step I-8.

Step I-13

Step I-13 is a step of aminating a benzyl bromide derivative I-n. This step can be performed by reacting the benzyl bromide derivative I-n with an aminating agent. The conditions to be selected in this step such as the reaction reagent and the solvent are the same as those in Step I-9.

Step I-14

Step I-14 is a step of amidating the sulfanylbenzylamine derivative I-c. This step can be performed by reacting the sulfanylbenzylamine derivative I-c with a corresponding carboxylic acid in the presence of a condensing agent and base. A condensing additive may be added as necessary. The condensing agent includes WSCDI, HBTU, HATU, BOP, DCC, DPPA, and DMT-MM, and is preferably WSCDI, HBTU, and HATU. The base includes tertiary amines, and is preferably N,N-diisobutylethylamine. The condensing additive under the above conditions includes HOBT and HOOBT, and is preferably HOBT. The solvent includes aprotic solvents, and is preferably Dichloromethane, THF, DMF, and the like.

Step I-15

Step I-15 is a step of amidating a sulfonylbenzylamine derivative I-g. This step can be performed by reacting the sulfonylbenzylamine derivative I-g with a corresponding carboxylic acid in the presence of a condensing agent and base. The conditions to be selected in this step such as the reaction reagent and the solvent are the same as those in Step I-14.

Production Method II

Method II is a method for forming a backbone of the formula (II), where Q is $CH_2$, $R^4$ is a sulfinyl group, and $R^6$ is H or halogen.

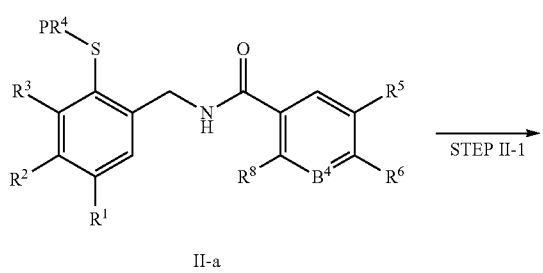

II-a

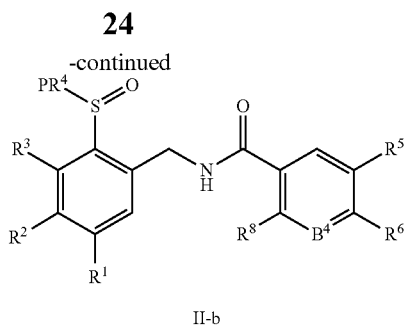

II-b

Step II-1

Step II-1 is a step of sulfinylating a sulfanyl derivative II-a. This step can be performed by reacting the sulfanyl derivative II-a with an oxidizing agent. The resulting sulfanyl derivative II-b is a racemate. The oxidizing agent includes peracids such as mCPBA, tBuOOH, $H_2O_2$, oxone, and potassium permanganate, and is preferably mCPBA. Preferred amount of the reagent is 0.9 to 1.0 equivalents. The solvent includes aprotic solvents, and is preferably dichloromethane or ethyl acetate.

Production Method III

Method III is a method for forming a backbone of the formula (II), where Q is NH, $R^4$ is a sulfanyl group or a sulfonyl group, and $R^6$ is H.

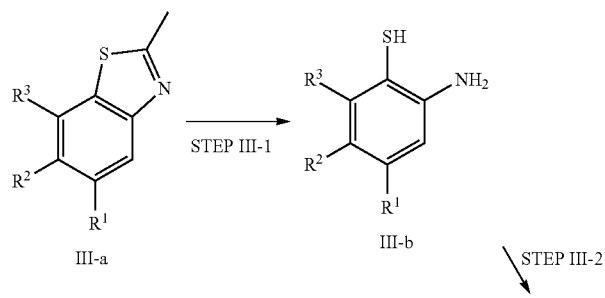

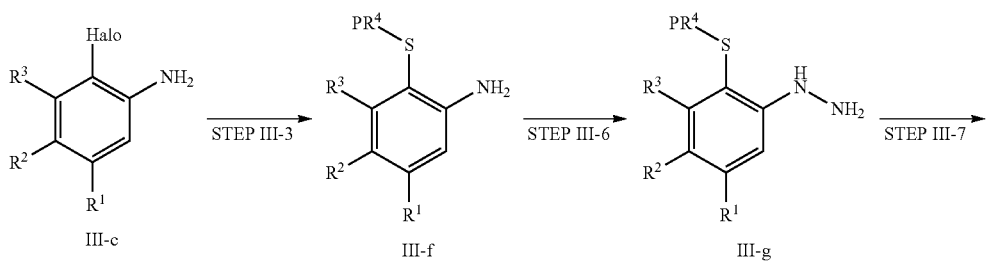

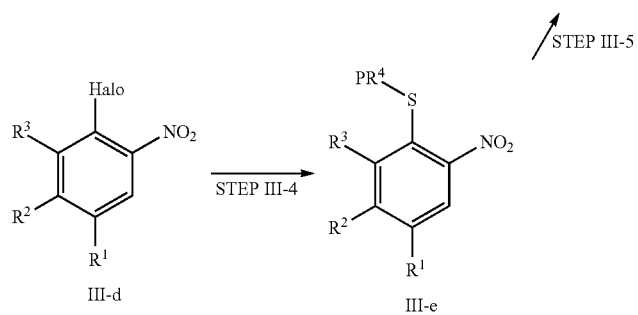

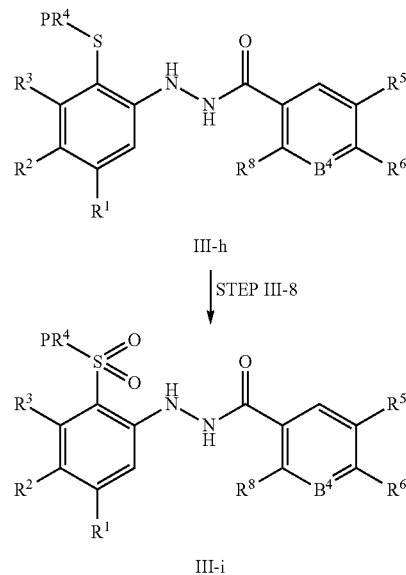

III-h

↓ STEP III-8

III-i

Step III-1

Step III-1 is a step of cleaving the thiazole ring of a benzothiazole derivative III-a by hydrolysis. This step can be performed by hydrolyzing the benzothiazole derivative III-a by reaction with an inorganic base under heating. The step can be performed, for example, by the method of J. Med. Chem. 2002, 45, 2229-2239. The inorganic base includes sodium hydroxide, lithium hydroxide, and potassium hydroxide, and is preferably sodium hydroxide. The solvent include ethylene glycol, water, dimethoxyethane, and mixed solvents thereof, and is preferably a mixed solvent of ethylene glycol and water. The heating is preferably performed at 100° C. or higher.

Step III-2

Step III-2 is a step of alkylating a thiophenol derivative III-b. This step can be performed by reacting the thiophenol derivative III-b with an alkylating agent corresponding to $PR^4$ in the presence of a base and phase transfer catalyst. The alkylating agent includes alkyl iodides, alkyl bromides, alkyl triflates, and alkyl mesylates, and is preferably alkyl iodides such as ethyl iodide. The base includes inorganic bases such as potassium carbonate, sodium carbonate, cesium carbonate, and lithium carbonate; and organic bases such as DBU, t-BuOK, LDA, LiHMDS, and N,N-dimethyl-4-aminopyridine. Cesium carbonate, potassium carbonate, and DBU are preferred. The phase transfer catalyst includes tetrabutylammonium iodide and tetrabutylammonium bromide. The solvent includes aprotic polar solvents and ether solvents, and is preferably DMF or THF.

Step III-3

Step III-3 is a step of sulfanylating a halobenzene derivative III-c. This step can be performed by reacting the halobenzene derivative III-c with a metal alkyl/aryl thiolate corresponding to $PR^4$ under heating, and for example, the method described in WO 2009/131245 can be used as a reference. The conditions to be selected in this step such as the reaction reagent and the solvent are the same as those in Step I-3.

Step III-4

Step III-4 is a step of sulfanylating a halonitrobenzene derivative III-d. This step can be performed by reacting the halonitrobenzene derivative III-d with an alkylthiol or arylthiol reagent corresponding to $PR^4$ in the presence of a base. The thiol reagent includes acyclic alkylthiols such as methanethiol, ethanethiol, n-propylthiol, and i-propylthiol; cyclic alkylthiols such as cyclopentylthiol; and arylthiols such as phenylthiol. The base includes inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. The solvent includes DMF, DMA, DMSO, dichloromethane, THF, acetonitrile, and mixtures thereof, and is preferably DMF.

Step III-5

Step III-5 is a step of aminating (reducing) a sulfanylnitrobenzene derivative III-e. This step can be performed by reacting the sulfanylnitrobenzene derivative III-e with a metal reducing agent under acidic conditions. The step can be performed, for example, with reference to the method described in a patent (EP 1065204). The reducing agent includes iron powder, zinc powder, and tin reagents, and is preferably iron powder. The acid to be added includes ammonium chloride, acetic acid, and hydrochloric acid, and is preferably ammonium chloride. The solvent includes protic alcohol solvents, water, and mixed solvents thereof, and is preferably a mixed solvent of ethanol and water.

Step III-6

Step III-6 is a step of converting a sulfanylaniline derivative III-f to a hydrazine. This step can be performed by converting the sulfanylaniline derivative III-f to a diazonium salt using a nitrite salt under strongly acidic conditions (Griess reaction) and then reacting it with a metal reducing agent without isolation. The nitrite salt used for the conversion to a diazonium salt is preferably sodium nitrite. The metal reducing agent used for the reduction of the diazonium salt to a phenylhydrazine is preferably tin(II) chloride. The solvent includes protic acidic solvents, and is preferably an aqueous hydrochloric acid solution.

Step III-7

Step III-7 is a step of amidating a sulfanylphenylhydrazine derivative III-g. This step can be performed by reacting the sulfanylphenylhydrazine derivative III-g with a corresponding carboxylic acid. The conditions to be selected in this step such as the reaction reagent and the solvent are the same as those in Step I-14.

Step III-8

Step III-8 is a step of oxidizing a sulfanylketohydrazine derivative III-h to a sulfoxide. This step can be performed by reacting the sulfanylketohydrazine derivative III-h with an oxidizing agent. The conditions to be selected in this step such as the reaction reagent and the solvent are the same as those in Step I-11.

Production Method IV

Method IV is a method for forming a backbone of the formula (II), where Q represents $CH_2$, $R^4$ represents a sulfonyl group, $B^4$ represents CH, and $R^6$ represents $X^1Y^1Z^1$.

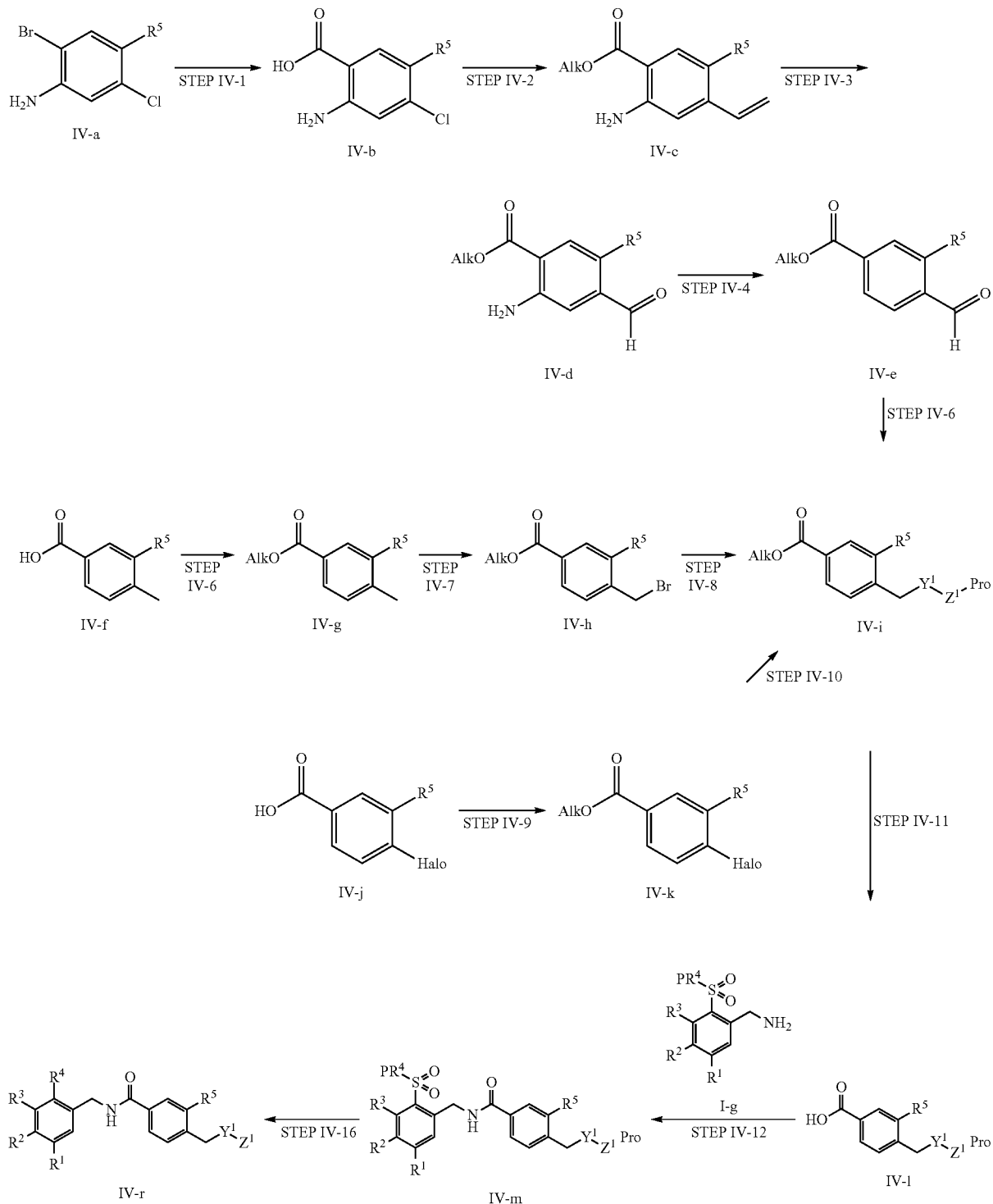

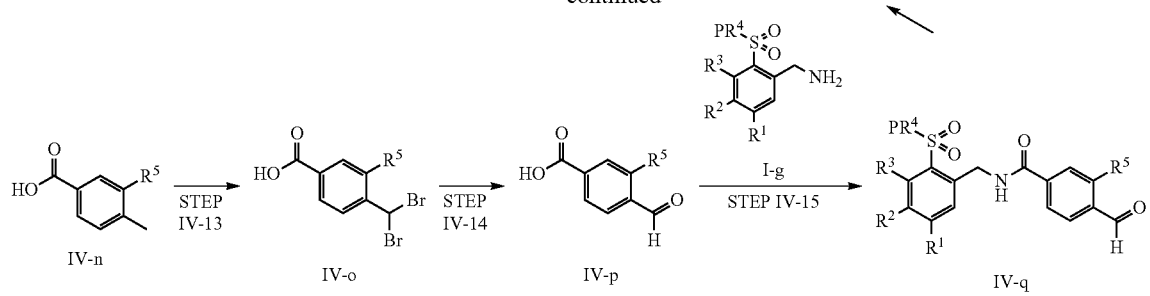

Step IV-1

Step IV-1 is a step of converting a bromoaniline derivative IV-a to a benzoic acid derivative IV-b in three steps. This step can be performed by protecting an amino group of the bromoaniline derivative IV-a with a diBoc group under basic conditions, and isolating and purifying the protected derivative; subsequently transferring the t-butoxycarbonyl group by treatment with n-butyllithium at −78° C.; and further deprotecting both the t-Bu group of the ester and the Boc group of the amine protecting group under acidic conditions. The step is performed with reference to the method of SYNLETT 20 (2005) 3107-3108. Under the diBoc protection conditions, preferably, a catalytic amount of 4-dimethylaminopyridine is added. The solvent includes an aprotic solvent such as a halomethane or ether solvent, and is preferably THF. In the t-butoxycarbonyl transfer, the solvent can be an aprotic solvent stable at strongly basic condition, and is preferably THF. In the deprotection of the t-Bu and Boc groups, the acid includes hydrochloric acid, sulfuric acid, TFA, or the like, and is preferably TFA, and the solvent is preferably dichloromethane.

Step IV-2

Step IV-2 is a step of converting the benzoic acid derivative IV-b to a vinylbenzoate IV-c in two steps. This step can be performed by esterification using an alkylating agent under basic conditions, isolation and purification, and subsequent reaction using a Pd catalyst in the presence of a base and vinylating agent under heating. The alkylating agent in the esterification includes alkyl halides, and is preferably alkyl iodides. The base includes inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. The solvent includes aprotic polar solvents and ether solvents, and is preferably DMF. The Pd catalyst in the vinylation includes zero-valent Pd complexes represented by tetrakistriphenylphosphine palladium. Palladium acetate using X-Phos or BuPAd2 as a ligand is preferred. The vinylating agent includes potassium vinyltrifluoroborate, vinylboronic acid, and vinylboronates, and is preferably potassium vinyltrifluoroborate. The base is preferably potassium carbonate or cesium carbonate. The solvent is preferably a mixed solvent of toluene and water.

Step IV-3

Step IV-3 is a step of converting a vinylbenzene derivative IV-c to a benzaldehyde derivative IV-d in two steps. This step can be performed by dihydroxylation of the vinylbenzene derivative IV-c using an osmium reagent, isolation and purification, and subsequent glycol cleavage. The step can be performed, for example, with reference to the method described in WO 2010/065760. In the dihydroxylation, the osmium reagent includes osmium tetroxide, AD-mix, or the like, and is preferably AD-mix-α or AD-mix-β. The solvent can be a mixed solvent of a water-soluble solvent and water, and is preferably a mixed solvent of t-BuOH and water. In the glycol cleavage, the oxidizing agent includes sodium metaperiodate, lead tetraacetate, or the like, and is preferably sodium metaperiodate. The solvent can be a mixed solvent of an organic solvent and water, an acetic acid solution, or the like, and is preferably a mixed solvent of TBME and water.

Step IV-4

Step IV-4 is a step of deaminating the aniline derivative IV-d. This step can be performed by converting the aniline derivative IV-d to a diazonium salt using a nitrite salt under acidic conditions (Griess reaction) and then reducing it without isolation. The nitrite salt used for the conversion to a diazonium salt is preferably sodium nitrite. The reducing agent in the reduction of the diazonium salt is preferably formic acid, and the formic acid can also be used as a solvent.

Step IV-5

Step IV-5 is a step of forming a C—N bond from a benzaldehyde derivative IV-e by reductive amination. This step can be performed by reacting the benzaldehyde derivative IV-e with a primary or secondary amine corresponding to Y1-Z1-Pro in the presence of a reducing agent. The reducing agent includes sodium triacetoxyborohydride, sodium cyanoborohydride, and 2-picoline-borane, and is preferably sodium triacetoxyborohydride. The solvent includes halomethane solvents and ether solvents, and is preferably chloroform, dichloromethane, or THF.

Step IV-6

Step IV-6 is a step of esterifying a benzoic acid derivative IV-f. This step can be performed by reacting the benzoic acid derivative IV-f with an alkylating agent in the presence of a base. The alkylating agent includes alkyl halides, and is preferably alkyl iodides. The base includes inorganic bases such as potassium carbonate, sodium carbonate, cesium carbonate, calcium carbonate, and sodium hydride; and organic bases such as t-BuOK, LDA, LiHMDS, N,N-dimethyl-4-aminopyridine, and DBU. Potassium carbonate and sodium carbonate are preferred. The solvent includes aprotic polar solvents, and is preferably DMF.

Step IV-7

Step IV-7 is a step of brominating a benzoate derivative IV-g (Wohl-Ziegler reaction). This step can be performed by reacting the benzoate derivative IV-g with a brominating agent under heating in the presence of a catalytic amount of a radical initiator. The conditions to be selected in this step such as the reaction reagent and the solvent are the same as those in Step I-8.

Step IV-8

Step IV-8 is a step of forming a C—N bond from a benzyl bromide derivative IV-h by substitution reaction. This step can be performed by reacting the benzyl bromide derivative IV-h with a primary or secondary amine corresponding to Y1-Z1-Pro in the presence of a base. The base includes inorganic bases such as potassium carbonate, sodium carbonate, cesium carbonate, calcium carbonate, and sodium hydride; and organic bases such as pyridine, triethylamine, N,N-diisobutylethylamine, N,N-dimethyl-4-aminopyridine, t-BuOK, LDA, LiHMDS, N,N-dimethyl-4-aminopyridine, and DBU. Triethylamine and potassium carbonate are preferred. The solvent includes halomethane solvents, ether solvents, and aprotic polar solvents, and is preferably dichloromethane, THF, and DMF.

Step IV-9

Step IV-9 is a step of esterifying a benzoic acid derivative IV j. This step can be performed by reacting the benzoic acid derivative IV-j with an alkylating agent in the presence of a base. The conditions to be selected in this step such as the reaction reagent and the solvent are the same as those in Step IV-6.

Step IV-10

Step IV-10 is a step of forming a C—C bond from a halobenzoate derivative IV-k by Suzuki-Molander coupling reaction. This step can be performed by reacting the halobenzoate derivative IV-k with a Molander reagent (potassium trifluoroborate derivative) corresponding to CH2-Y1-Z1-Pro under heating in the presence of a palladium reagent and base. Here, a reagent for palladium ligands is added as necessary. The step can be performed, for example, by the method of Acc. Chem. Res. 2007, 40, 275-286. Typical examples of the Pd reagent include palladium acetate, tetrakistriphenylphosphine palladium, and 1,1'-bis(diphenylphosphino)ferrocene-palladium(II) dichloride-dichloromethane complex. Palladium acetate is preferred. The reagent for palladium ligands includes X-Phos, S-Phos, triphenylphosphine, and tricyclohexylphosphine, and is preferably X-Phos, S-Phos, and nBuPAd$_2$. The base includes inorganic bases such as potassium carbonate, sodium carbonate, cesium carbonate, and tripotassium phosphate; and organic amines such as triethylamine, t-butylamine, N,N-diisobutylethylamine, and pyridine. Potassium carbonate and cesium carbonate are preferred. The solvent includes alcohols, toluene, THF, and mixed solvents of these solvents and water, and is preferably a mixed solvent of THF and water, toluene, or a mixed solvent of toluene and water.

Step IV-11

Step IV-11 is a step of saponifying (hydrolyzing) a benzoate derivative IV-i. This step can be performed by reacting the benzoate derivative IV-i with an inorganic base. Examples of the inorganic base include sodium hydroxide, lithium hydroxide, potassium hydroxide, calcium hydroxide, and barium hydroxide. Sodium hydroxide and potassium hydroxide are preferred. The solvent includes alcohols, water, and mixed solvents thereof, and is preferably an aqueous ethanol solution or an aqueous methanol solution.

When the reaction is slow, the reaction may be performed under heating at 40° C. to 60° C.

Step IV-12

Step IV-12 is a step of condensing (amidating) a benzoic acid derivative IV-1. This step can be performed by reacting the benzoic acid derivative IV-1 with a corresponding benzylamine derivative I-g in the presence of a condensing agent and base. A condensing additive may be added as necessary. The conditions to be selected in this step such as the reaction reagent and the solvent are the same as those in Step I-14.

Step IV-13

Step IV-13 is a step of dibrominating a toluene derivative IV-n (Wohl-Ziegler reaction). This step can be performed by reacting the toluene derivative IV-n with a brominating agent under heating in the presence of a catalytic amount of a radical initiator. The brominating agent includes NBS and N-bromoimide, and is preferably two equivalents or more of NBS. The radical initiator includes benzoyl peroxide and AIBN, and is preferably benzoyl peroxide. The solvent includes carbon tetrachloride, benzene, cyclohexane, and acetonitrile, and is preferably carbon tetrachloride. The heating temperature is preferably 80° C. or higher, and heating under reflux can be performed.

Step IV-14

Step IV-14 is a step of converting a dibromotoluene derivative IV-o to an aldehyde. This step can be performed by reacting the dibromotoluene derivative IV-o with silver nitrate under heating. The step can be performed, for example, by the method of J. Chem. Soc. (1939) 781. The solvent includes water, water-soluble solvents, and mixed solvents thereof, and is preferably an aqueous acetone solution. The heating temperature is preferably 60° C.

Step IV-15

Step IV-15 is a step of condensing (amidating) a benzaldehyde derivative IV-p. This step can be performed by reacting the benzaldehyde derivative IV-p with a corresponding benzylamine derivative I-g in the presence of a base. The conditions to be selected in this step such as the reaction reagent and the solvent are the same as those in Step I-14.

Step IV-16

Step IV-16 is a step of deprotecting the amine protecting group of a protected amine derivative IV-m. Here, the protecting group mainly refers to a Boc group. This step can be performed by reacting the protected amine derivative IV-m under strongly acidic conditions. The acid includes TFA, hydrochloric acid, sulfuric acid, mesylic acid, and Lewis acids, and is preferably TFA or hydrochloric acid. The solvent includes dichloromethane, ethyl acetate, 1,4-dioxane, acetonitrile, water, and mixed solvents thereof, and is preferably dichloromethane, ethyl acetate, or 1,4-dioxane.

Production Method V

Method V is a method for forming a backbone of the formula (II), where Q represents $CH_2$, $R^4$ represents a sulfonyl group, $B^4$ represents $CR^7$, $R^6$ represents $X^1Y^1Z^1$, and $R^7$ represents halogen.

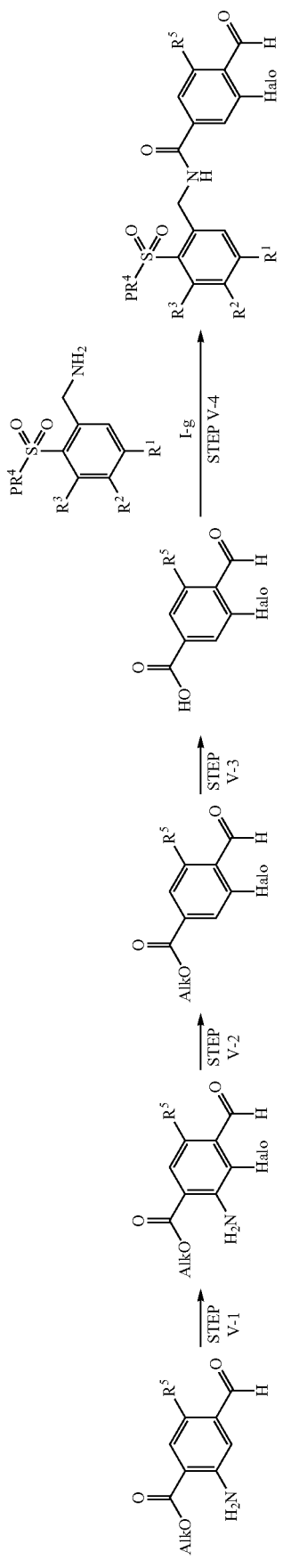
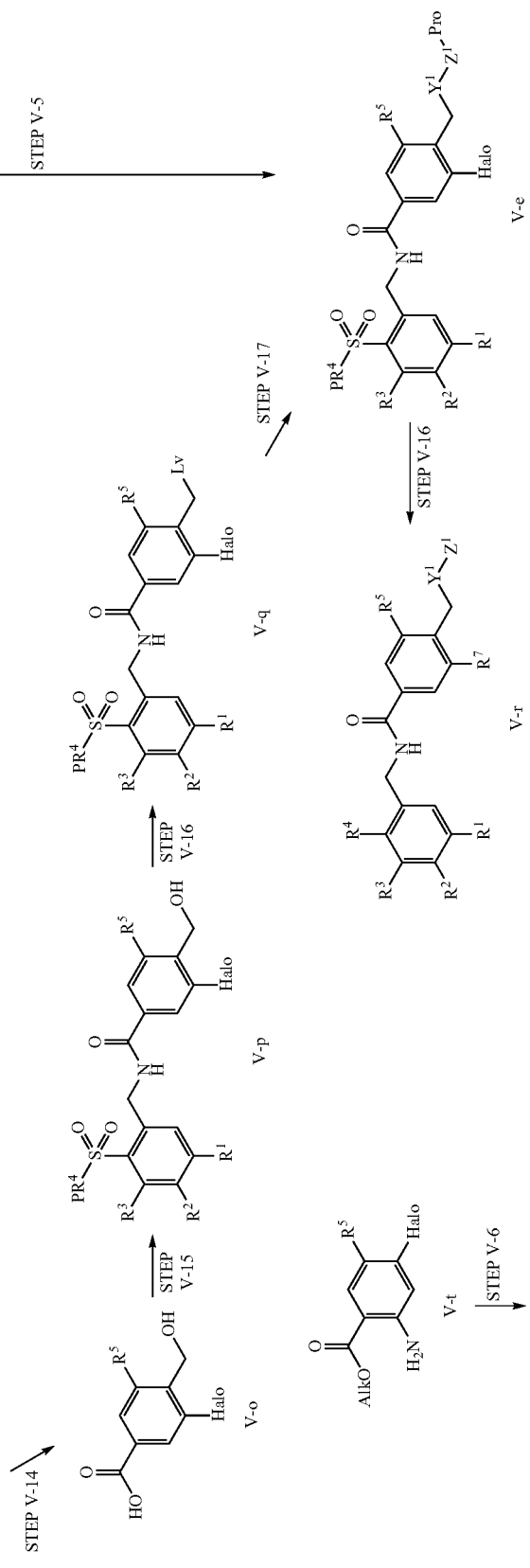

-continued
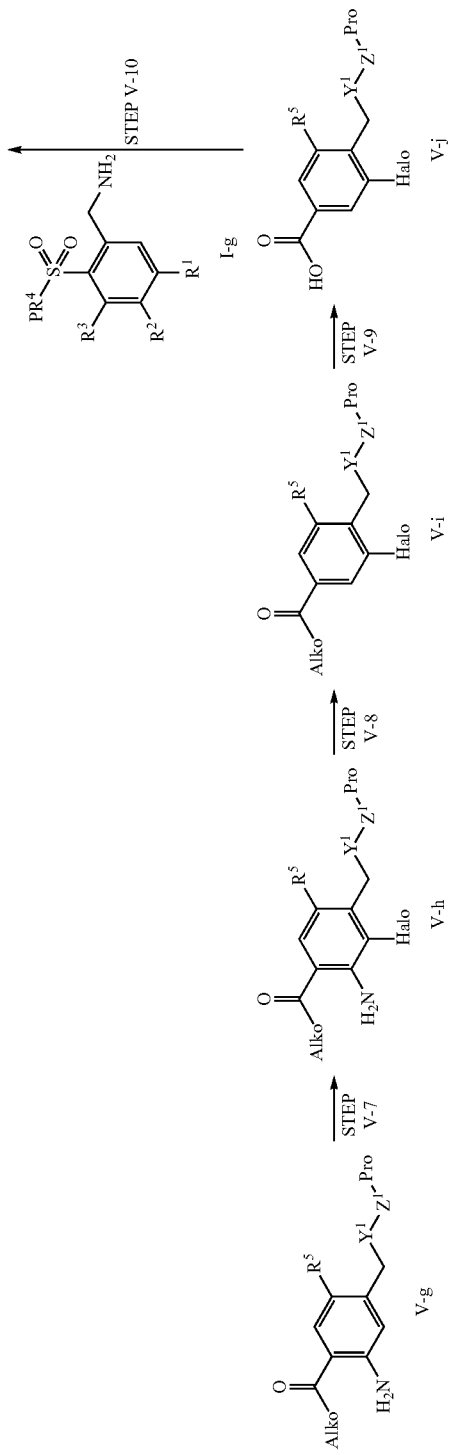

Step V-1

Step V-1 is a step of halogenating a benzaldehyde derivative IV-d. This step can be performed by reacting the benzaldehyde derivative IV-d with a halogenating agent under heating. An acid or a catalytic amount of a radical initiator can be added when the reaction slowly proceeds. The halogenating agent includes N-halosuccinimides, sulfuryl halides, and chlorine, bromine, and iodine under acidic conditions or in the presence of reduced iron powder, and is preferably N-halosuccinimides. The solvent includes aprotic polar solvents, halomethane solvents, ether solvents, alcohols, and water, and is preferably DMF.

Step V-2

Step V-2 is a step of deaminating an aniline derivative V-a. This step can be performed by converting the aniline derivative V-a to a diazonium salt using a nitrite salt under acidic conditions (Griess reaction) and then reducing it without isolation. The conditions to be selected in this step such as the reaction reagent and the solvent are the same as those in Step IV-4.

Step V-3

Step V-3 is a step of saponifying (hydrolyzing) a benzoate derivative V-b. This step can be performed by reacting the benzoate derivative V-b with an inorganic base. The conditions to be selected in this step such as the reaction reagent and the solvent are the same as those in Step IV-11.

Step V-4

Step V-4 is a step of condensing (amidating) a benzoic acid derivative V-c. This step can be performed by reacting the benzoic acid derivative V-c with a corresponding benzylamine derivative I-g in the presence of a condensing agent and base. A condensing additive may be added as necessary. The conditions to be selected in this step such as the reaction reagent and the solvent are the same as those in Step I-14.

Step V-5

Step V-5 is a step of forming a C—N bond from a benzaldehyde derivative V-d by reductive amination. This step can be performed by reacting the benzaldehyde derivative V-d with a primary or secondary amine corresponding to Y1-Z1-Pro in the presence of a reducing agent. The conditions to be selected in this step such as the reaction reagent and the solvent are the same as those in Step IV-5.

Step V-6

Step V-6 is a step of forming a C—C bond from a halobenzoate derivative V-f by Suzuki-Molander coupling reaction. This step can be performed by reacting the halobenzoate derivative V-f with a Molander reagent (potassium trifluoroborate derivative) corresponding to CH2-Y1-Z1-Pro under heating in the presence of a palladium reagent and base. Here, a reagent for palladium ligands is added as necessary. The step can be performed, for example, by the method of Acc. Chem. Res. 2007, 40, 275-286. The conditions to be selected in this step such as the reaction reagent and the solvent are the same as those in Step IV-10.

Step V-7

Step V-7 is a step of halogenating a benzoate derivative V-g. This step can be performed by reacting the benzoate derivative V-g with a halogenating agent. Heating can be performed, or an acid or a catalytic amount of a radical initiator can be added, when the reaction slowly proceeds. The conditions to be selected in this step such as the reaction reagent and the solvent are the same as those in Step V-1.

Step V-8

Step V-8 is a step of deaminating an aniline derivative V-h. This step can be performed by converting the aniline derivative V-h to a diazonium salt using a nitrite salt under acidic conditions (Griess reaction) and then reducing it without isolation. The conditions to be selected in this step such as the reaction reagent and the solvent are the same as those in Step IV-4.

Step V-9

Step V-9 is a step of saponifying (hydrolyzing) a benzoate derivative V-i. This step can be performed by reacting the benzoate derivative V-i with an inorganic base. The conditions to be selected in this step such as the reaction reagent and the solvent are the same as those in Step IV-11.

Step V-10

Step V-10 is a step of condensing (amidating) a benzoic acid derivative V-j. This step can be performed by reacting the benzoic acid derivative V-j with a corresponding benzylamine derivative I-g in the presence of a condensing agent and base. A condensing additive may be added as necessary. The conditions to be selected in this step such as the reaction reagent and the solvent are the same as those in Step I-14.

Step V-11

Step V-11 is a step of converting a benzoic acid derivative V-k by halogenation and esterification. The halogenating step can be performed by reacting the benzoic acid derivative V-k with a halogenating agent. Heating can be performed, or an acid or a catalytic amount of a radical initiator can be added, when the reaction slowly proceeds. The conditions to be selected in this step such as the reaction reagent and the solvent are the same as those in Step V-1. The esterifying step can be performed by reacting the halobenzoic acid derivative obtained in the above halogenating step with an alcohol corresponding to Alk by heating under acidic conditions. The alcohol includes lower alcohols, and is preferably methanol. The acid includes inorganic acids, and is preferably sulfuric acid.

Step V-12

Step V-12 is a step of iodinating an aniline derivative V-1. This step can be performed by converting the aniline derivative V-1 to a diazonium salt using a nitrite salt under acidic conditions (Griess reaction) and then reacting it with a metal iodide without isolation (Sandmeyer reaction). The nitrite salt used for the conversion to a diazonium salt is preferably sodium nitrite. The acid includes sulfuric acid, hydrochloric acid, and mesylic acid, and is preferably sulfuric acid. Here, the solvent includes polar solvents such as trifluoroethanol, DMF, and acetonitrile, and is preferably trifluoroethanol. The metal iodide includes potassium iodide, sodium iodide, and lithium iodide, and is preferably potassium iodide.

Step V-13

Step V-13 is a step of converting an iodobenzene derivative V-m by formylation and reduction. This step can be performed by converting the iodobenzene derivative V-m to a benzaldehyde derivative by metallization using an organometallic reagent and subsequent reaction with a formylating agent; and then reacting it with a hydride reducing agent without isolation. The metallizing agent includes Grignard reagents and other alkyl metals, and is preferaby isopropylmagnesium bromide. The formylating agent includes N-formylmorpholine, DMF, methyl formate, and N-methyl-N-pyridin-2-ylformamide, and is preferably N-formylmorpholine. The hydride reducing agent includes sodium borohydride, lithium borohydride, lithium aluminum hydride, diisobutylaluminum hydride, sodium triacetoxyborohydride, and Selectride, and is preferably sodium borohydride. The solvent includes ether solvents and aromatic solvents, and is preferably THF.

Step V-14

Step V-14 is a step of saponifying (hydrolyzing) a benzoate derivative V-n. This step can be performed by reacting the benzoate derivative V-n with an inorganic base. The conditions to be selected in this step such as the reaction reagent and the solvent are the same as those in Step IV-11.

Step V-15

Step V-15 is a step of condensing (amidating) a benzoic acid derivative V-o. This step can be performed by reacting the benzoic acid derivative V-o with a corresponding benzylamine derivative I-g in the presence of a condensing agent and base. A condensing additive may be added as necessary. The conditions to be selected in this step such as the reaction reagent and the solvent are the same as those in Step I-14.

Step V-16

Step V-16 is a step of introducing a leaving group into a benzyl alcohol derivative V-p (halogenation or sulfonation).

halomethane solvents. DMF is more preferred. It is preferred to add an inorganic salt such as potassium carbonate or sodium carbonate or to heat at 40° C. to 80° C. when the reaction is slow.

Step V-18

Step V-18 is a step of deprotecting the amine protecting group of a protected amine derivative V-e. Here, the protecting group mainly refers to a Boc group. This step can be performed by reacting the protected amine derivative V-e under strongly acidic conditions. The conditions to be selected in this step such as the reaction reagent and the solvent are the same as those in Step IV-16.

Production Method VI

Method VI is a method for forming a backbone of the formula (II), where Q represents $CH_2$, $R^4$ represents a sulfonyl group, $B^4$ represents $CR^7$, $R^6$ represents H, and $R^7$ represents $X^2Y^2Z^2$.

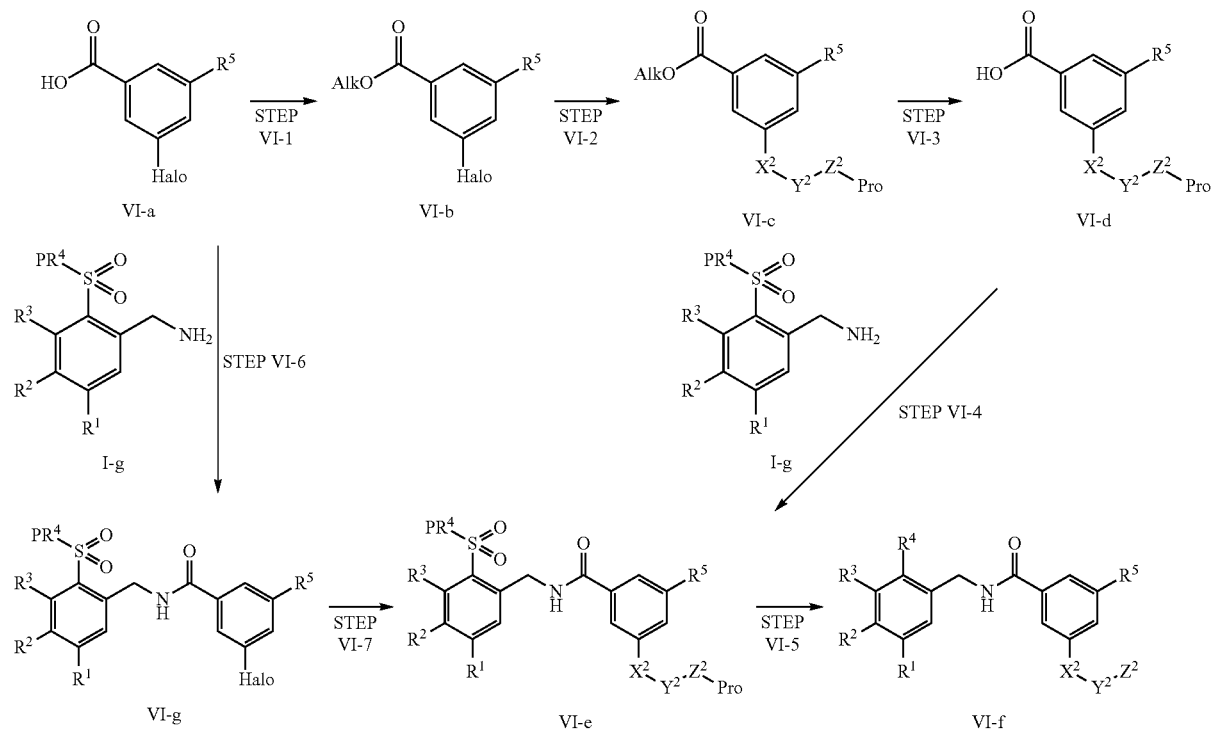

This step can be performed by reacting the benzyl alcohol derivative V-p with a halogenating reagent or a sulfonating reagent. The halogenation using a halogenating reagent is preferably bromination using carbon tetrabromide, N-bromosuccinimide, dibromoisocyanuric acid, or the like, and more preferably reaction with carbon tetrabromide in the presence of triphenylphosphine. The sulfonation using a sulfonating reagent includes methanesulfonylation, p-toluenesulfonylation, or triflation, and is preferably methanesulfonylation by reaction with methanesulfonyl chloride in the presence of a tertiary amine.

Step V-17

Step V-17 is a step of substitution reaction of an amide derivative V-q. This step can be performed by reacting the amide derivative V-q with a primary or secondary amine corresponding to Y1-Z1-Pro. Preferred examples of the solvent include aprotic polar solvents, ether solvents, and Step VI-1

Step VI-1 is a step of esterifying a benzoic acid derivative VI-a. This step can be performed by reacting the benzoic acid derivative VI-a with an alkylating agent in the presence of a base. The conditions to be selected in this step such as the reaction reagent and the solvent are the same as those in Step IV-6.

Step VI-2

Step VI-2 is a step of forming a C—N bond from a haloaryl derivative VI-b by Buchwald-Hartwig reaction. This step can be performed by reacting the haloaryl derivative VI-b with a secondary amine corresponding to $Y^2$—$Z^2$-Pro under heating in the presence of a palladium catalyst, reagent for palladium ligands, and base. The step can be performed, for example, by the method of Organic Syntheses, Coll. Vol. 10, p. 423 (2004); Vol. 78, p. 23 (2002); or Synlett 2006 (9): 1283. The palladium catalyst includes various palladium catalysts such as tris(dibenzylideneacetone)dipalladium(0), palladium acetate, and (Pd[P(o-Tolyl)3]2), and is preferably tris(dibenzylideneacetone)dipalladium(0). The reagent for palladium ligands includes various reagents for palladium ligands such as BINAP, dppf, Xantophos, and tri(t-butyl)phosphine, and is preferably BINAP. The base includes potassium carbonate, sodium carbonate, cesium carbonate, potassium hydroxide, sodium hydroxide, lithium bis(trimethylsilyl)amide, sodium bis(trimethylsilyl)amide, potassium tert-butoxide, and sodium tert-butoxide, and is preferably cesium carbonate. The solvent is preferably toluene.

Step VI-3

Step VI-3 is a step of saponifying (hydrolyzing) a benzoate derivative VI-c. This step can be performed by reacting the benzoate derivative VI-c with an inorganic base. The conditions to be selected in this step such as the reaction reagent and the solvent are the same as those in Step IV-11.

Step VI-4

Step VI-4 is a step of condensing (amidating) a benzoic acid derivative VI-d. This step can be performed by reacting the benzoic acid derivative VI-d with a corresponding benzylamine derivative I-g in the presence of a condensing agent and base. A condensing additive may be added as necessary. The conditions to be selected in this step such as the reaction reagent and the solvent are the same as those in Step I-14.

Step VI-5

Step VI-5 is a step of deprotecting the amine protecting group of a protected amine derivative VI-e. Here, the protecting group mainly refers to a Boc group. This step can be performed by reacting the protected amine derivative VI-e under strongly acidic conditions. The conditions to be selected in this step such as the reaction reagent and the solvent are the same as those in Step IV-16.

Step VI-6

Step VI-6 is a step of condensing (amidating) the benzoic acid derivative VI-a. This step can be performed by reacting the benzoic acid derivative VI-a with a corresponding benzylamine derivative I-g in the presence of a condensing agent and a base. A condensing additive may be added as necessary. The conditions to be selected in this step such as the reaction reagent and the solvent are the same as those in Step I-14.

Step VI-7

Step VI-7 is a step of forming a C—N bond from a haloaryl derivative VI-g by Buchwald-Hartwig reaction. This step can be performed by reacting the haloaryl derivative VI-g with a secondary amine corresponding to $Y^2$—$Z^2$-Pro under heating in the presence of a palladium catalyst, reagent for palladium ligands, and base. The step can be performed, for example, by the method of Organic Syntheses, Coll. Vol. 10, p. 423 (2004); Vol. 78, p. 23 (2002) or Synlett 2006 (9): 1283. The conditions to be selected in this step such as the reaction reagent and the solvent are the same as those in Step VI-2.

EXAMPLES

Herein below, the present invention will be specifically described with reference to the Examples, but it is not to be construed as being limited thereto.

NMR Analysis

NMR analysis was performed using ARX 300 (300 MHz) manufactured by Bruker Corporation, AVANCEIII600 (600 MHz) manufactured by Bruker Corporation, JNM-GSX 400 (400 MHz) manufactured by JEOL Corporation, JNM-EX 270 (270 MHz) manufactured by JEOL Corporation, ECA-400 (400 MHz) manufactured by JEOL Corporation, or 400 MR (400 MHz) manufactured by Varian Corporation. NMR data were reported in ppm (parts per million) (δ), and referenced to the deuterium lock signal from the sample solvent.

High Performance Liquid Chromatography (LC-MS) Mass Spectrometry Data

The data were obtained using the Micromass SQD Mass Spectrometer paired with Acquity Gradient Ultra High Performance Liquid Chromatography (manufactured by Waters Corporation), SQD2 Mass Spectrometer paired with Acquity Gradient Ultra High Performance Liquid Chromatography (manufactured by Waters Corporation), Micromass ZQ Mass Spectrometer paired with 2525 Gradient High Performance Liquid Chromatography (manufactured by Waters Corporation), or Micromass SQD Mass Spectrometer paired with 2524 Gradient High Performance Liquid Chromatography (manufactured by Waters Corporation).

Any of the conditions in Table 1 below was used for high performance liquid chromatography.

TABLE 1

| Analysis condition | Equipment | Column used | Column temperature | Mobile phase, gradient | Flow rate (mL/min) | Detection wavelength (PDA total) |
|---|---|---|---|---|---|---|
| A | Acquity SQD | Ascentis Express C18 HPLC column, 5 cm × 2.1 mm, 2.7 μm | 35° C. | A) 0.1% FA, CH3CN, B) 0.1% FA, H2O, A/B = 5/95 to 100/0 (1 min) → 100/0 (0.4 min) | 1 | 210-400 nm |
| B | ZQ | Wakosil-II 3C18 AR, 4.6 mm * 30 mm | Room Temp. | A) 0.05% TFA, CH3CN, B) 0.05% TFA, H2O, A/B = 10/90 → 10/90 (0.2 min) → 95/5 (3.1 min) → 95/5 (1.4 min) | 2 | 210-400 nm |
| C | SQD | Sunfire C18 (waters) 4.5 mm I.D. × 50 mm, 5 μm | Room Temp. | A) 0.05% TFA, CH3CN, B) 0.05% TFA, H2O, AB = 10/90 → 95/5 (3.5 min) → 10/90 (1 min) → 95/5 (0.5 min) | 4 | 210-370 nm |
| D | ZQ | Sunfire C18 (Waters) 4.6 mm I.D. × 50 mm, 5 μm | Room Temp. | A) 0.05% TFA, CH3CN, B) 0.05% TFA, H2O, | 4 | 210-400 nm |

TABLE 1-continued

| Analysis condition | Equipment | Column used | Column temperature | Mobile phase, gradient | Flow rate (mL/min) | Detection wavelength (PDA total) |
|---|---|---|---|---|---|---|
| E | SQD | ACE 5 C18 (4.5 mm I.D. × 50 mm, 5 µm) | Room Temp. | A/B = 10/90 → 95/5 (3.5 min) → 10/90 (1 min) → 95/5 (0.5 min) A) 0.05% TFA, CH3CN, B) 0.05% TFA, H2O, A/B = 10/90 → 95/5 (3.5 min) → 10/90 (1 min) → 95/5 (0.5 min) | 4 | 210-370 nm |
| F | Acquity I-Class SQD2 | Ascenis Express C18 HPLC column, 5 cm × 2.1 mm, 2.7 µm | 35° C. | A) 0.1% FA, CH3CN, B) 0.1% FA, H2O, A/B = 5/95 to 100/0 (1 min) → 100/0 (0.4 min) | 1 | 210-400 nm |

Microwave Reaction

The reaction was performed in Biotage Initiator using snap cap reaction vials. The maximum output setting includes air cooling of the reaction vessel to prevent a rise in temperature due to microwave irradiation.

Commercially available reagents were used without further purification. Room temperature refers to a temperature within the range of about 20-25° C.

All nonaqueous reactions were performed in anhydrous solvents. Concentration under reduced pressure or solvent evaporation was performed using a rotary evaporator. In HPLC fractionation, after an objective material was isolated, the material was obtained as a free form by performing neutralization as necessary.

In the preparation of a compound, when there was a possibility that an undesirable side reaction could occur, a functional group was protected by a protecting group as necessary, and the protecting group was removed after preparing the target molecule. Selection and removal of the protecting group was performed using, for example, a method described in Greene and Wuts, "Protective Groups in Organic Synthesis" (Fourth edition, John Wiley & Sons 2007).

Example 1

Compound a1

5-Chloro-2-ethylsulfanyl-benzonitrile

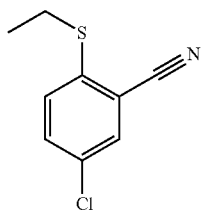

A solution of 5-chloro-2-fluoro-benzonitrile (3.60 g, 23.1 mmol) in DMF (46 ml) was cooled to 0° C. Potassium carbonate (9.60 g, 69.4 mmol) was added under a nitrogen atmosphere, and the mixture was stirred at room temperature for five minutes. Ethanethiol (2.05 ml, 27.8 mmol) was added, and the mixture was stirred at room temperature for three hours. Ethyl acetate was added to the reaction mixture. After washing with saturated saline, the organic layer was dried over anhydrous magnesium sulfate. The drying agent was removed by filtration, followed by concentration under reduced pressure. The resulting residue was purified by silica gel column chromatography (ethyl acetate/hexane) to yield the title compound (4.57 g, quant.) as a colorless solid.

HPLC retention time: 2.47 min (analysis condition D)

$^1$H-NMR (400 MHz, DMSO) δ: 8.01 (1H, d, J=2.2 Hz), 7.73 (1H, dd, J=2.2, 8.8 Hz), 7.58 (1H, d, J=8.8 Hz), 3.14 (2H, q, J=7.7 Hz), 1.27 (t, J=7.7 Hz).

Example 2

Compound a2

5-Chloro-2-ethylsulfanyl-benzylamine

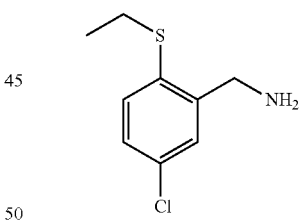

Lithium aluminum hydride (2.63 g, 69.4 mmol) was added to a solution of 5-chloro-2-ethylsulfanyl-benzonitrile (Compound a1, 4.57 g, 23.1 mmol) in THF (40 ml) while cooling at 0° C. The mixture was stirred at 0° C. for 30 minutes and then at room temperature for one hour. Water was added to the reaction mixture while cooling at 0° C., followed by filtration through celite. The filtrate was dried over anhydrous magnesium sulfate, and the drying agent was removed by filtration, followed by concentration under reduced pressure. The resulting residue was purified by silica gel column chromatography (ethyl acetate/hexane) to yield the title compound (4.00 g, 85%) as a yellow oily substance.

LCMS: m/z 202 [M+H]$^+$

HPLC retention time: 0.97 min (analysis condition D)

Example 3

Compound A-1

3-Bromo-N-(5-chloro-2-ethylsulfanyl-benzyl)-5-trifluoromethyl-benzamide

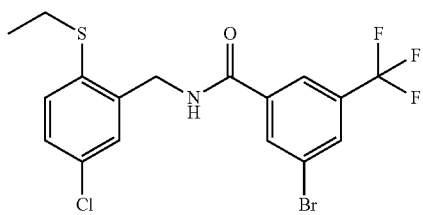 [SMILES: CCSc1ccc(Cl)cc1CNC(=O)c1cc(Br)cc(C(F)(F)F)c1]

HOBT (35.2 mg, 0.23 mmol) was added to a suspension of 5-chloro-2-ethylsulfanyl-benzylamine (Compound a2, 37.8 mg, 0.19 mmol), 3-bromo-5-(trifluoromethyl)benzoic acid (19.9 mg, 0.20 mmol), and WSCDI (43.1 mg, 0.23 mmol) in DCM (2 ml), followed by stirring for 20 hours. DCM was added to the reaction mixture. After washing with water, the organic layer was dried over anhydrous sodium sulfate. The drying agent was removed by filtration, followed by concentration under reduced pressure. The resulting residue was purified by silica gel column chromatography (ethyl acetate/hexane) to yield the title compound (78.0 mg, 92%) as a colorless solid.

LCMS: m/z 452 [M+H]$^+$

HPLC retention time: 1.06 min (analysis condition A)

Example 4

Compound A-2

3-Bromo-N-(5-chloro-2-ethanesulfonyl-benzyl)-5-trifluoromethyl-benzamide

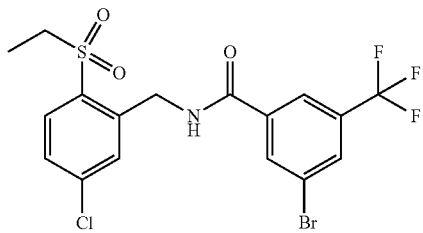 [SMILES: CCS(=O)(=O)c1ccc(Cl)cc1CNC(=O)c1cc(Br)cc(C(F)(F)F)c1]

m-CPBA (85.8 mg, 0.50 mmol) was added to a solution of 3-bromo-N-(5-chloro-2-ethylsulfanyl-benzyl)-5-trifluoromethyl-benzamide (Compound A-1, 72.8 mg, 0.16 mmol) in DCM (2.5 ml), followed by stirring for 20 hours. DCM was added to the reaction mixture. After washing with water, the organic layer was dried over anhydrous sodium sulfate. The drying agent was removed by filtration, followed by concentration under reduced pressure. The resulting residue was purified by amino silica gel column chromatography (ethyl acetate/hexane) to yield the title compound (69.6 mg, 89%) as a colorless solid.

LCMS: m/z 484 [M+H]$^+$

HPLC retention time: 0.94 min (analysis condition A)

Example 5

Compound A-3

3-Chloro-N-(5-chloro-2-ethylsulfanyl-benzyl)-5-trifluoromethoxy-benzamide

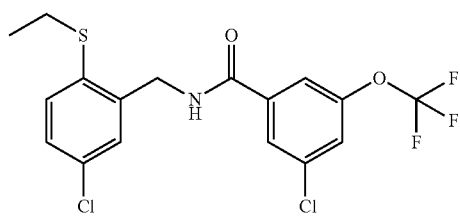 [SMILES: CCSc1ccc(Cl)cc1CNC(=O)c1cc(Cl)cc(OC(F)(F)F)c1]

The title compound was synthesized from 5-chloro-2-ethylsulfanyl-benzylamine (Compound a2) and 3-chloro-5-trifluoromethoxy-benzoic acid under the same conditions as for Compound A-1.

LCMS: m/z 424 [M+H]$^+$

HPLC retention time: 1.06 min (analysis condition A)

Example 6

Compound A-4

3-Chloro-N-(5-chloro-2-ethanesulfonyl-benzyl)-5-trifluoromethoxy-benzamide

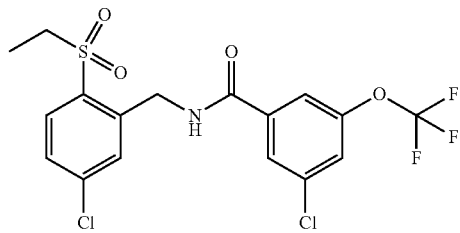 [SMILES: CCS(=O)(=O)c1ccc(Cl)cc1CNC(=O)c1cc(Cl)cc(OC(F)(F)F)c1]

The title compound was synthesized from 3-chloro-N-(5-chloro-2-ethylsulfanyl-benzyl)-5-trifluoromethoxy-benzamide (Compound A-3) under the same conditions as for Compound A-2.

LCMS: m/z 456 [M+H]$^+$

HPLC retention time: 0.94 min (analysis condition A)

Example 7

Compound a3

5-Chloro-2-ethanesulfonyl-benzylamine hydrochloride

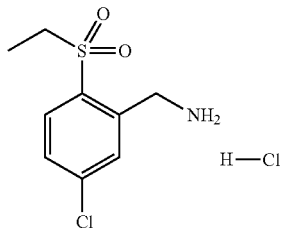

Compound a3 was synthesized from 5-chloro-2-ethylsulfanyl-benzylamine (Compound a2) according to the method described in Patent WO 2009131245.

Example 8

Compound A-5

N-(5-Chloro-2-ethanesulfonyl-benzyl)-3-trifluoromethyl-benzamide

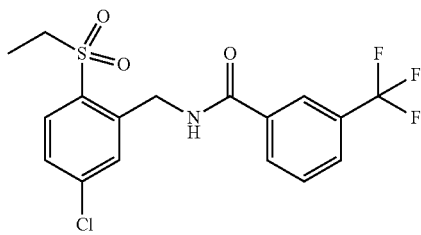 [SMILES: CCS(=O)(=O)c1ccc(Cl)cc1CNC(=O)c1cccc(C(F)(F)F)c1]

DIPEA (0.016 ml, 0.091 mmol) was added to a suspension of 5-chloro-2-ethanesulfonyl-benzylamine hydrochloride (Compound a3, 20.5 mg, 0.076 mmol), 3-(trifluoromethyl)benzoic acid (18.0 mg, 0.095 mmol), and WSCDI (18.9 mg, 0.099 mmol) in DCM (1.5 ml), followed by stirring for 20 hours. DCM was added to the reaction mixture. After washing with water, the organic layer was dried over anhydrous sodium sulfate. The drying agent was removed by filtration, followed by concentration under reduced pressure. The resulting residue was purified by silica gel column chromatography (ethyl acetate/hexane) to yield the title compound (26.9 mg, 87%) as a colorless solid.

LCMS: m/z 406 [M+H]$^+$

HPLC retention time: 0.83 min (analysis condition A)

Examples 9 to 18

Compounds in FIGS. 3-4 were synthesized from corresponding carboxylic acids under the same conditions as for Compound A-5. However, DMF was used as a solvent in the synthesis of Compound A-10.

Example 19

Compound A-14

4-Bromo-N-(5-chloro-2-ethanesulfonyl-benzyl)-3-trifluoromethyl-benzamide

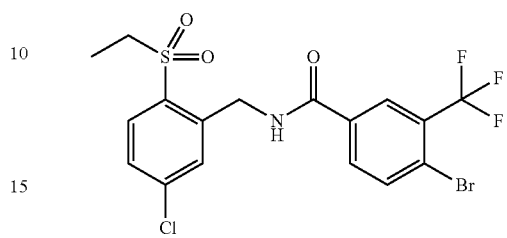

DIPEA (1.90 ml, 11 mmol) was added to a solution of 5-chloro-2-ethanesulfonyl-benzylamine hydrochloride (Compound a3, 1.00 g, 3.7 mmol), 4-bromo-3-trifluoromethyl-benzoic acid (1.1 g, 4.1 mmol), WSCDI (1.06 g, 5.6 mmol), and HOBT (0.75 g, 5.6 mmol) in DMF (18.5 ml); and the mixture was stirred at room temperature for 17 hours. The reaction mixture was diluted with ethyl acetate; and the organic layer was washed with water and saturated saline, and dried over anhydrous sodium sulfate. The drying agent was removed by filtration, followed by concentration under reduced pressure. The resulting residue was purified by silica gel column chromatography (ethyl acetate/DCM/hexane) to yield the title compound (1.56 g, 87%) as a colorless solid.

LCMS: m/z 484 [M+H]$^+$

HPLC retention time: 0.92 min (analysis condition A)

Example 20

Compound a4

2-Ethylsulfanyl-5-fluoro-phenylamine

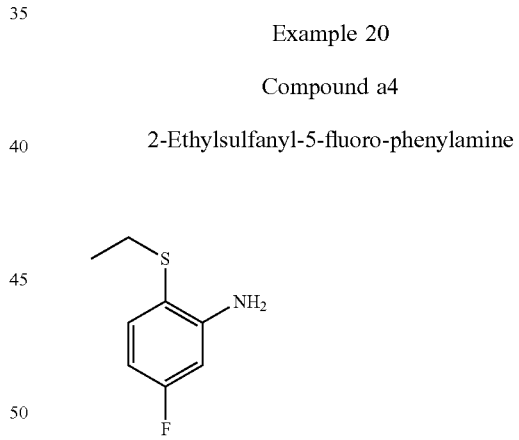

Ethyl iodide (0.66 ml, 8.3 mmol) was added to a suspension of 2-amino-4-fluoro-benzenethiol (1.13 g, 7.9 mmol), cesium carbonate (3.09 g, 9.5 mmol), and tetra-n-butylammonium iodide (3.21 g, 8.7 mmol) in DMF (10 ml) under a nitrogen atmosphere, followed by stirring for 2.5 hours. Ethyl acetate was added to the reaction mixture. After washing with a saturated aqueous sodium chloride solution, the organic layer was dried over anhydrous sodium sulfate. The drying agent was removed by filtration, followed by concentration under reduced pressure. The resulting residue was purified by silica gel column chromatography (ethyl acetate/hexane) to yield the title compound (1.19 g, 88%) as a colorless oily substance.

LCMS: m/z 172 [M+H]$^+$

HPLC retention time: 2.35 min (analysis condition D)

Example 21

Compound a5

(2-Ethylsulfanyl-5-fluoro-phenyl)-hydrazine

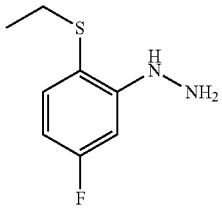

Concentrated hydrochloric acid (1.8 ml) and sodium nitrite (145 mg, 2.1 mmol) were added to a suspension of 2-ethylsulfanyl-5-fluoro-phenylamine (Compound a4, 300 mg, 1.8 mmol) in water (1.8 ml), and the mixture was stirred for two hours under ice cooling. A solution of stannic chloride dihydrate (909 mg, 4.0 mmol) in concentrated hydrochloric acid (1.8 ml) was added to this reaction solution, and the mixture was stirred for one hour under ice cooling. A 5N aqueous sodium hydroxide solution (9 ml) was added, followed by extraction with DCM. The extract was dried over anhydrous sodium sulfate. The drying agent was removed by filtration, followed by concentration under reduced pressure to yield the title compound (299 mg, 91%) as a pink oily substance.

HPLC retention time: 0.51 min (analysis condition A)

1H-NMR (400 MHz, CDCl$_3$) δ: 7.33 (1H, dd, J=8.2, 6.6 Hz), 6.79 (1H, dd, J=11.0, 2.7 Hz), 6.48 (1H, s), 6.40 (1H, td, J=8.2, 2.7 Hz), 3.58 (2H, brs), 2.65 (2H, q, J=7.3 Hz), 1.17 (3H, t, J=7.3 Hz).

Example 22

Compound A-17

3-Trifluoromethyl-benzoic acid N'-(2-ethylsulfanyl-5-fluoro-phenyl)-hydrazide

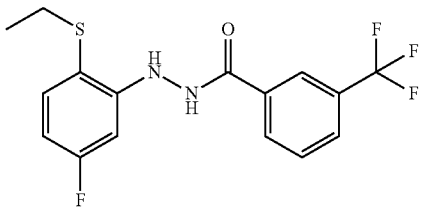 [SMILES: CCSc1ccc(F)cc1NNC(=O)c1cccc(C(F)(F)F)c1]

The title compound was synthesized from (2-ethylsulfanyl-5-fluoro-phenyl)-hydrazine (Compound a5) and 3-trifluoromethyl-benzoic acid under the same conditions as for Compound A-1.

LCMS: m/z 359 [M+H]$^+$

HPLC retention time: 0.93 min (analysis condition A)

Example 23

Compound A-18

3-Trifluoromethyl-benzoic acid N'-(2-ethanesulfonyl-5-fluoro-phenyl)-hydrazide

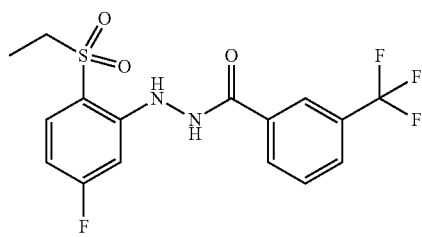 [SMILES: CCS(=O)(=O)c1ccc(F)cc1NNC(=O)c1cccc(C(F)(F)F)c1]

The title compound was synthesized from 3-trifluoromethyl-benzoic acid N'-(2-ethylsulfanyl-5-fluoro-phenyl)-hydrazide (Compound A-17) under the same conditions as for Compound A-2.

LCMS: m/z 391 [M+H]$^+$

HPLC retention time: 0.82 min (analysis condition A)

Example 24

Compound A-19

N-(2-Ethylsulfanyl-5-fluoro-benzyl)-3-trifluoromethyl-benzamide

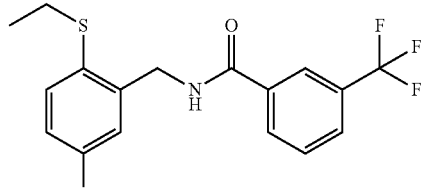

The title compound was synthesized from 2,5-difluorobenzonitrile under the same conditions as for Compounds a1, a2, and A-1. However, the reaction was performed using 3-trifluoromethyl-benzoic acid in place of 3-bromo-5-(trifluoromethyl)benzoic acid under the conditions for Compound A-1.

LCMS: m/z 358 [M+H]$^+$

HPLC retention time: 0.95 min (analysis condition A)

Example 25

Compound A-20

N-(2-Ethanesulfonyl-5-fluoro-benzyl)-3-trifluoromethyl-benzamide

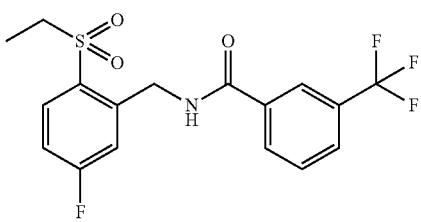 [SMILES: CCS(=O)(=O)c1ccc(F)cc1CNC(=O)c1cccc(C(F)(F)F)c1]

The title compound was synthesized from N-(2-ethylsulfanyl-5-fluoro-benzyl)-3-trifluoromethyl-benzamide (Compound A-19) under the same conditions as for Compound A-2.

LCMS: m/z 390 [M+H]$^+$

HPLC retention time: 0.81 min (analysis condition A)

Example 26

Compound a6

5-Bromo-2-ethylsulfanyl-benzaldehyde

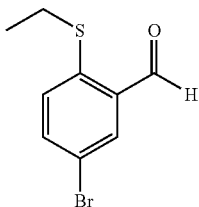

Sodium ethanethiolate (362 mg, 4.3 mmol) was added to a solution of 5-bromo-2-fluorobenzaldehyde (546 mg, 2.7 mmol) in DMF (1.08 ml), and the mixture was stirred at 60° C. After one hour, sodium ethanethiolate (123 mg, 1.5 mmol) was further added. The reaction solution was cooled to room temperature after 15 minutes, and a 1N aqueous hydrochloric acid solution was added, followed by extraction with ethyl acetate. The organic layer was sequentially washed with a saturated aqueous sodium bicarbonate solution and saturated saline, and dried over anhydrous sodium sulfate. The drying agent was removed by filtration, followed by concentration under reduced pressure. The resulting residue was purified by silica gel column chromatography (ethyl acetate/hexane) to yield the title compound (163 mg, 24%) as a yellow oily substance.

HPLC retention time: 0.91 min (analysis condition A)

$^1$H-NMR (400 MHz, CDCl$_3$) δ: 10.33 (1H, s), 7.95 (1H, d, J=2.2 Hz), 7.62 (1H, dd, J=2.2, 8.4 Hz), 7.30 (1H, d, J=8.4 Hz), 2.97 (2H, q, J=7.5 Hz), 1.36 (3H, t, J=7.5 Hz).

Example 27

Compound a7

5-Bromo-2-ethylsulfanyl-benzaldehyde O-methyl-oxime

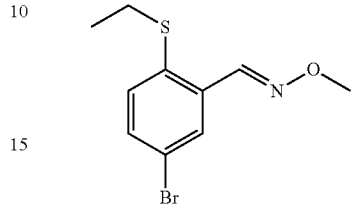

Hydroxylamine methyl ether hydrochloride (61 mg, 0.73 mmol) was added to a solution of 5-bromo-2-ethylsulfanyl-benzaldehyde (Compound a6, 163 mg, 0.66 mmol) in pyridine (0.42 ml), and the mixture was stirred at room temperature for two hours. Water was added to the reaction mixture, followed by extraction with ethyl acetate. The organic layer was washed with a 1N aqueous hydrochloric acid solution twice and then with saturated saline, and then dried over anhydrous sodium sulfate. The drying agent was removed by filtration, followed by concentration under reduced pressure to yield a crude product of the title compound.

LCMS: m/z 274 [M+H]$^+$

HPLC retention time: 1.10 min (analysis condition A)

Example 28

Compound a8

5-Bromo-2-ethylsulfanyl-benzylamine

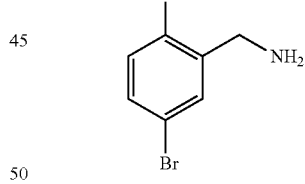

To a THF solution of the crude product of 5-bromo-2-ethylsulfanyl-benzaldehyde O-methyl-oxime (Compound a7, 182 mg, 0.66 mmol), a 1 mol/1 solution of borane-THF complex in THF (1.66 ml, 1.7 mmol) was added, and the mixture was stirred at 80° C. for 2.5 hours. The reaction mixture was cooled to 0° C., and crushed ice and a 1N aqueous hydrochloric acid solution (3 ml) were added, followed by stirring at 90° C. for one hour. The reaction solution was cooled to room temperature, and separated by adding water and ethyl acetate. The aqueous layer was made basic with a 5N aqueous sodium hydroxide solution, followed by three extractions with dichloromethane. The combined organic layers were dried over anhydrous sodium sulfate. The drying agent was removed by filtration, followed by concentration under reduced pressure to yield a crude product of the title compound.

HPLC retention time: 0.48 min (analysis condition D)
$^1$H-NMR (400 MHz, CDCl$_3$) δ: 7.48 (1H, d, J=2.2 Hz), 7.33 (1H, dd, J=2.2, 8.4 Hz), 7.17 (1H, d, J=8.4 Hz), 3.89 (2H, s), 2.93 (2H, q, J=7.5 Hz), 1.32 (3H, t, J=7.5 Hz).

Example 29

Compound a9

(5-Bromo-2-ethylsulfanyl-benzyl)-carbamic acid tert-butyl ester

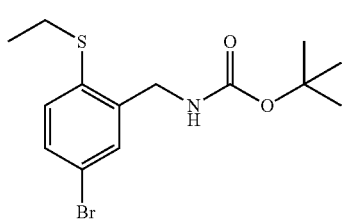 [SMILES: CCSc1ccc(Br)cc1CNC(=O)OC(C)(C)C]

Boc$_2$O (0.148 ml, 0.64 mmol) was added to a solution of the crude product of 5-bromo-2-ethylsulfanyl-benzylamine (Compound a8) in THF (2 ml), and the mixture was stirred at room temperature for one hour. Water was added to the reaction mixture, followed by extraction with ethyl acetate. The organic layer was washed with saturated saline, and then dried over anhydrous sodium sulfate. The drying agent was removed by filtration, followed by concentration under reduced pressure. The resulting residue was purified by silica gel column chromatography (ethyl acetate/hexane) to yield the title compound (168 mg, total yield from Compound a6 in three steps: 73%) as a yellow oily substance.

Example 30

Compound a10

(5-Bromo-2-ethanesulfonyl-benzyl)-carbamic acid tert-butyl ester

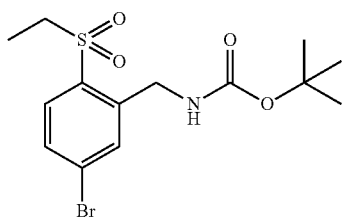 [SMILES: CCS(=O)(=O)c1ccc(Br)cc1CNC(=O)OC(C)(C)C]

mCPBA (234 mg, 1.02 mmol) was added to a solution of (5-bromo-2-ethylsulfanyl-benzyl)-carbamic acid tert-butyl ester (Compound a9, 168 mg, 0.49 mmol) in dichloromethane (2.4 ml) while cooling at 0° C. The mixture was then warmed to room temperature, and stirred for four hours. A saturated aqueous sodium bicarbonate solution was added to the reaction mixture, followed by extraction with ethyl acetate. The organic layer was washed with saturated saline, and then dried over anhydrous sodium sulfate. The drying agent was removed by filtration, followed by concentration under reduced pressure. The resulting residue was purified by silica gel column chromatography (ethyl acetate/hexane) to yield the title compound (180 mg, yield: 98%) as a yellow oily substance.

Example 31

Compound a11

5-Bromo-2-ethanesulfonyl-benzylamine hydrochloride

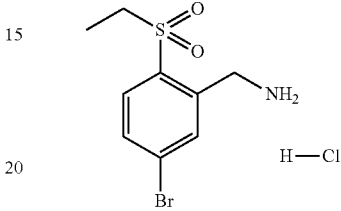

A 4N solution of hydrochloric acid in ethyl acetate (2.4 ml) was added to (5-bromo-2-ethanesulfonyl-benzyl)-carbamic acid tert-butyl ester (Compound a10, 180 mg, 0.48 mmol), and the mixture was stirred at room temperature for 1.5 hours. The reaction solution was concentrated under reduced pressure to yield the title compound (130 mg, yield: 87%) as a colorless solid.

Example 32

Compound A-21

N-(5-Bromo-2-ethanesulfonyl-benzyl)-3-trifluoromethyl-benzamide

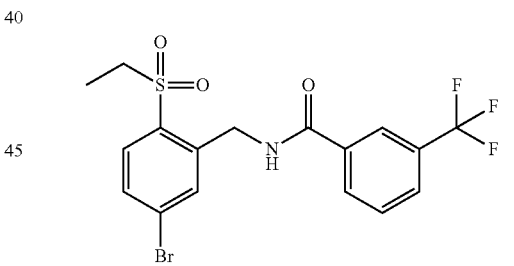

DIPEA (0.050 ml, 0.29 mmol) was added to a solution of 5-bromo-2-ethanesulfonyl-benzylamine hydrochloride (Compound a11, 30.0 mg, 0.095 mmol), 3-(trifluoromethyl) benzoic acid (19.9 mg, 0.11 mmol), and HBTU (39.8 mg, 0.11 mmol) in DCM (1 ml) under cooling in an ice water bath. The mixture was warmed to room temperature and stirred for 4.5 hours. Water was added to the reaction mixture, followed by extraction with ethyl acetate. The organic layer was then washed with saturated saline, and dried over anhydrous sodium sulfate. The drying agent was removed by filtration, followed by concentration under reduced pressure. The resulting residue was purified by silica gel column chromatography (ethyl acetate/hexane) to yield the title compound (42.5 mg, 99%) as a colorless solid.

LCMS: m/z 450 [M+H]$^+$
HPLC retention time: 0.87 min (analysis condition A)

Example 33

Compound A-22

N-(5-Bromo-2-ethanesulfonyl-benzyl)-3-chloro-5-trifluoromethyl-benzamide

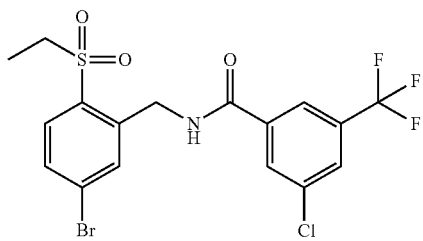 [SMILES: CCS(=O)(=O)c1ccc(Br)cc1CNC(=O)c1cc(Cl)cc(C(F)(F)F)c1]

The title compound was synthesized from 5-bromo-2-ethanesulfonyl-benzylamine hydrochloride (Compound a11) under the same conditions as for Compound A-21. However, 3-chloro-5-(trifluoromethyl)benzoic acid was used in place of 3-(trifluoromethyl)benzoic acid.

LCMS: m/z 484 [M+H]$^+$

HPLC retention time: 0.96 min (analysis condition A)

Example 34

Compound A-23

N-(5-Bromo-2-ethanesulfonyl-benzyl)-3-chloro-5-trifluoromethoxy-benzamide

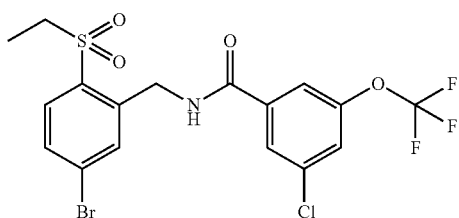 [SMILES: CCS(=O)(=O)c1ccc(Br)cc1CNC(=O)c1cc(Cl)cc(OC(F)(F)F)c1]

The title compound was synthesized from 5-bromo-2-ethanesulfonyl-benzylamine hydrochloride (Compound a11) under the same conditions as for Compound A-21. However, 3-chloro-5-(trifluoromethoxy)benzoic acid was used in place of 3-(trifluoromethyl)benzoic acid.

LCMS: m/z 500 [M+H]$^+$

HPLC retention time: 0.98 min (analysis condition A)

Example 35

Compound A-24

N-(5-Bromo-2-ethanesulfonyl-benzyl)-3-trifluoromethoxy-benzamide

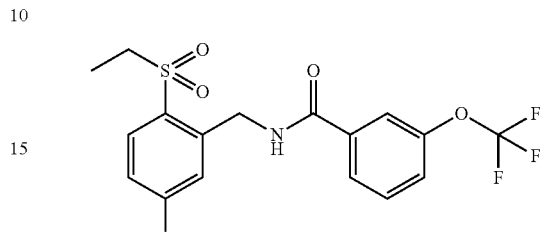

The title compound was synthesized from 5-bromo-2-ethanesulfonyl-benzylamine hydrochloride (Compound a11) under the same conditions as for Compound A-21. However, 3-(trifluoromethoxy)benzoic acid was used in place of 3-(trifluoromethyl)benzoic acid.

LCMS: m/z 466 [M+H]$^+$

HPLC retention time: 0.89 min (analysis condition A)

Example 36

Compound A-25

N-(5-Fluoro-2-methylsulfanyl-benzyl)-3-trifluoromethyl-benzamide

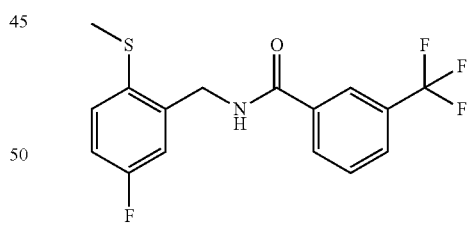

The title compound was synthesized from 2,5-difluoro-benzonitrile under the same conditions as for Compounds a1, a2, and A-1. However, the reaction was performed at 90° C. using sodium methanethiolate in place of ethanethiol and potassium carbonate under the conditions for Compound a1; and 3-trifluoromethyl-benzoic acid was used in place of 3-bromo-5-(trifluoromethyl)benzoic acid under the conditions for Compound A-1.

LCMS: m/z 344 [M+H]$^+$

HPLC retention time: 0.89 min (analysis condition A)

Example 37

Compound A-26

N-(5-Fluoro-2-methanesulfonyl-benzyl)-3-trifluoromethyl-benzamide

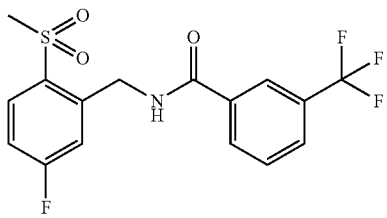 [SMILES: CS(=O)(=O)c1ccc(F)cc1CNC(=O)c1cccc(C(F)(F)F)c1]

The title compound was synthesized from N-(5-fluoro-2-methylsulfanyl-benzyl)-3-trifluoromethyl-benzamide (Compound A-25) under the same conditions as for Compound A-2.

LCMS: m/z 376 [M+H]$^+$

HPLC retention time: 0.78 min (analysis condition A)

Example 38

Compound b1

4-Bromo-3-trifluoromethyl-benzoic acid ethyl ester

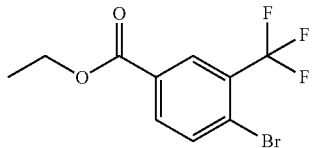 [SMILES: CCOC(=O)c1ccc(Br)c(C(F)(F)F)c1]

Potassium carbonate (1.5 g, 11.2 mmol) and ethyl iodide (1.2 g, 7.4 mmol) were added to a solution of 4-bromo-3-trifluoromethyl-benzoic acid (1.0 g, 3.7 mmol) in DMF (5 ml), and the mixture was stirred at room temperature for 24 hours. The reaction mixture was diluted with ethyl acetate, and the organic layer was washed with water and saturated saline, and dried over anhydrous sodium sulfate. The drying agent was removed by filtration. After concentration under reduced pressure, the resulting residue was purified by silica gel column chromatography (ethyl acetate/hexane) to yield the title compound (1.03 g, 94%) as a brown oily substance.

$^1$H-NMR (300 MHz, CDCl$_3$) δ: 8.34 (1H, d, J=1.9 Hz), 8.05 (1H, dd, J=8.4, 1.9 Hz), 7.82 (1H, d, J=8.4 Hz), 4.44 (2H, q, J=7.3 Hz), 1.43 (3H, t, J=7.3 Hz).

Example 39

Compound b2

4-(4-Ethoxycarbonyl-2-trifluoromethyl-benzyl)-piperazine-1-carboxylic acid tert-butyl ester

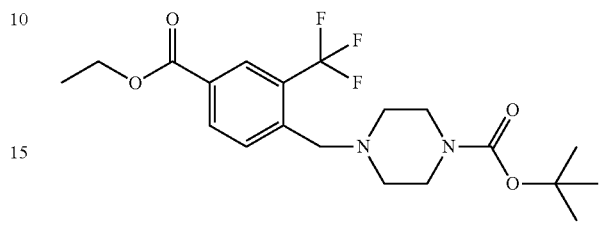

4-Bromo-3-trifluoromethyl-benzoic acid ethyl ester (Compound b1, 1.03 g, 3.5 mmol), potassium 4-trifluoroboratomethylpiperazine-1-carboxylic acid tert-butyl ester (1.06 g, 3.5 mmol), palladium acetate (40 mg, 0.17 mmol), X-phos (170 mg, 0.35 mmol), and cesium carbonate (3.39 g, 10.4 mmol) in a mixed solvent of THF/water (10/1) (35 mL) was stirred at 90° C. overnight. The reaction mixture was diluted with ethyl acetate, and the organic layer was washed with water and saturated saline, and dried over anhydrous sodium sulfate. The drying agent was removed by filtration. After concentration under reduced pressure, the resulting residue was purified by silica gel column chromatography (ethyl acetate/hexane) to yield the title compound (753 mg, 51%) as a colorless oily substance.

LCMS: m/z 417 [M+H]$^+$

HPLC retention time: 2.10 min (analysis condition C)

Example 40

Compound b3

4-(4-Carboxy-2-trifluoromethyl-benzyl)-piperazine-1-carboxylic acid tert-butyl ester

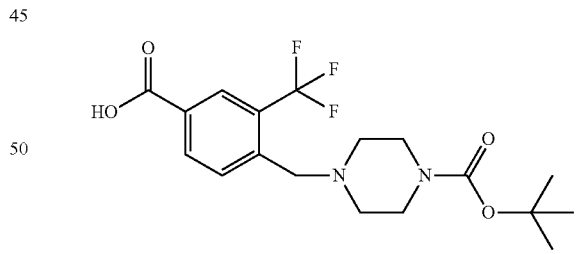

Potassium hydroxide (203 mg, 3.6 mmol) was added to a mixed solution of 4-(4-ethoxycarbonyl-2-trifluoromethyl-benzyl)-piperazine-1-carboxylic acid tert-butyl ester (Compound b2, 753 mg, 1.8 mmol) in EtOH (14.4 ml) and water (3.6 ml), and the mixture was stirred at 30-45° C. for six hours. The reaction mixture was neutralized to pH 5-6 by adding a 1N aqueous hydrochloric acid solution, and then diluted with ethyl acetate. The organic layer was washed with water and saturated saline, and dried over anhydrous sodium sulfate. The drying agent was removed by filtration. After concentration under reduced pressure, the resulting residue was purified by silica gel column chromatography (MeOH/DCM) to yield the title compound (652 mg, 93%) as a colorless foamy substance.

LCMS: m/z 389 [M+H]$^+$

HPLC retention time: 1.60 min (analysis condition C)

Example 41

Compound b4

4-[4-(5-Chloro-2-ethanesulfonyl-benzylcarbamoyl)-2-trifluoromethyl-benzyl]-piperazine-1-carboxylic acid tert-butyl ester

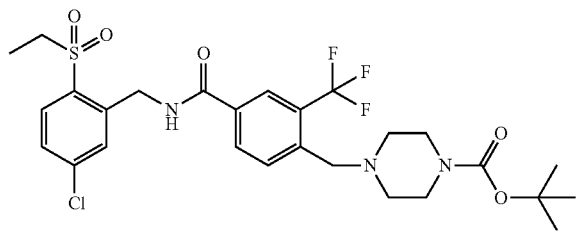 [SMILES: CCS(=O)(=O)c1ccc(Cl)cc1CNC(=O)c1ccc(CN2CCN(C(=O)OC(C)(C)C)CC2)c(C(F)(F)F)c1]

The title compound was synthesized from 4-(4-carboxy-2-trifluoromethyl-benzyl)-piperazine-1-carboxylic acid tert-butyl ester (Compound b3) under the same conditions as for Compound A-14.

Example 42

Compound B-1

N-(5-Chloro-2-ethanesulfonyl-benzyl)-4-piperazin-1-ylmethyl-3-trifluoromethyl-benzamide

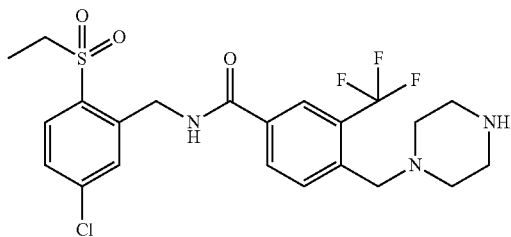 [SMILES: CCS(=O)(=O)c1ccc(Cl)cc1CNC(=O)c1ccc(CN2CCNCC2)c(C(F)(F)F)c1]

TFA (4 ml) was added to a solution of 4-[4-(5-chloro-2-ethanesulfonyl-benzylcarbamoyl)-2-trifluoromethyl-benzyl]-piperazine-1-carboxylic acid tert-butyl ester (Compound b4, 650 mg, 1.1 mmol) in DCM (12 ml), and the mixture was stirred at room temperature for three hours. The reaction mixture was concentrated under reduced pressure and then diluted with ethyl acetate. The organic layer was washed with a saturated aqueous sodium bicarbonate solution and saturated saline, and dried over anhydrous magnesium sulfate. The drying agent was removed by filtration, and the solvent was then concentrated under reduced pressure. The resulting residue was purified by amino silica gel column chromatography (MeOH/DCM) to yield the title compound (515 mg, 95%) as a colorless solid.

LCMS: m/z 504 [M+H]$^+$

HPLC retention time: 0.53 min (analysis condition A)

Example 43

Compound B-2

N-(5-Chloro-2-ethanesulfonyl-benzyl)-4-(4-methyl-piperazin-1-ylmethyl)-3-trifluoromethyl-benzamide

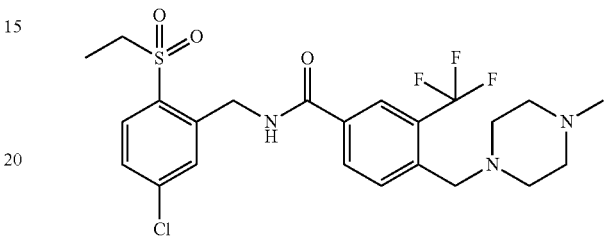

A suspension of N-(5-chloro-2-ethanesulfonyl-benzyl)-4-piperazin-1-ylmethyl-3-trifluoromethyl-benzamide (Compound B-1, 65 mg, 0.13 mmol) and paraformaldehyde (16 mg, 0.52 mmol) in formic acid (1 ml) was stirred at 80° C. for one hour. The reaction mixture was diluted with ethyl acetate, and the organic layer was washed with a saturated aqueous sodium bicarbonate solution and water, and saturated saline, respectively, and dried over anhydrous sodium sulfate. The drying agent was removed by filtration, and the solvent was then concentrated under reduced pressure. The resulting residue was purified by silica gel column chromatography (MeOH/DCM) and then by preparative TLC to yield the title compound (40 mg, 60%) as a colorless foamy substance.

LCMS: m/z 518 [M+H]$^+$

HPLC retention time: 0.53 min (analysis condition A)

Example 44

Compound B-3

N-(5-Chloro-2-ethanesulfonyl-benzyl)-4-(4-isopropyl-piperazin-1-ylmethyl)-3-trifluoromethyl-benzamide


Acetone (0.15 ml, 2.6 mmol) was added to a suspension of N-(5-chloro-2-ethanesulfonyl-benzyl)-4-piperazin-1-ylmethyl-3-trifluoromethyl-benzamide (Compound B-1, 65 mg, 0.13 mmol) and sodium triacetoxyborohydride (82 mg, 0.39 mmol) in THF (3.3 ml), and the mixture was stirred at 50-60° C. for three hours. The reaction mixture was diluted with ethyl acetate, and the organic layer was washed with a saturated aqueous sodium bicarbonate solution and water, and saturated saline, respectively, and dried over anhydrous sodium sulfate. The drying agent was removed by filtration, and the solvent was then concentrated under reduced pressure. The resulting residue was purified by silica gel column chromatography (MeOH/DCM) and then by amino silica gel column chromatography (ethyl acetate/hexane) to yield the title compound (46 mg, 66%) as a colorless foamy substance.

LCMS: m/z 546 [M+H]+

HPLC retention time: 0.55 min (analysis condition A)

Example 45

Compound B-4

N-(5-Chloro-2-ethanesulfonyl-benzyl)-4-[4-(tetrahydro-pyran-4-yl)-piperazin-1-ylmethyl]-3-trifluoromethyl-benzamide

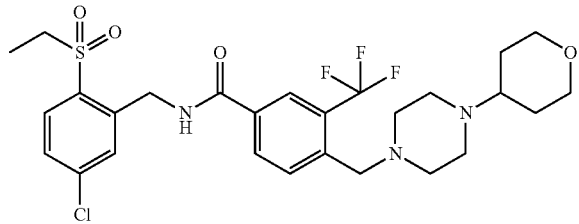 [SMILES: CCS(=O)(=O)c1ccc(Cl)cc1CNC(=O)c1ccc(CN2CCN(C3CCOCC3)CC2)c(C(F)(F)F)c1]

Tetrahydro-pyran-4-one (50 μl, 0.52 mmol) was added to a suspension of N-(5-chloro-2-ethanesulfonyl-benzyl)-4-piperazin-1-ylmethyl-3-trifluoromethyl-benzamide (Compound B-1, 65 mg, 0.13 mmol) and sodium triacetoxyborohydride (82 mg, 0.39 mmol) in THF (3.3 ml), and the mixture was stirred at 50-60° C. for three hours. The reaction mixture was diluted with ethyl acetate, and the organic layer was washed with a saturated aqueous sodium bicarbonate solution and water, and saturated saline, respectively, and dried over anhydrous sodium sulfate. The drying agent was removed by filtration, and the solvent was then concentrated under reduced pressure. The resulting residue was purified by silica gel column chromatography (MeOH/DCM) and then by preparative TLC to yield the title compound (47 mg, 62%) as a colorless foamy substance.

LCMS: m/z 588 [M+H]+

HPLC retention time: 0.54 min (analysis condition A)

Example 46

Compound B-5

4[4-(2-Amino-acetyl)-piperazin-1-ylmethyl]-N-(5-chloro-2-ethanesulfonyl-benzyl)-3-trifluoromethyl-benzamide

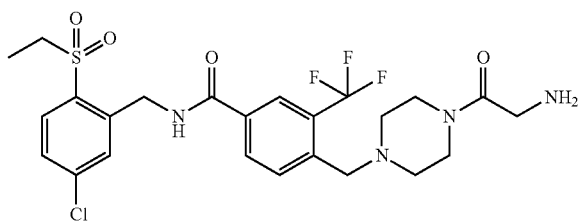 [SMILES: CCS(=O)(=O)c1ccc(Cl)cc1CNC(=O)c1ccc(CN2CCN(C(=O)CN)CC2)c(C(F)(F)F)c1]

HATU (63 mg, 0.16 mmol) and DIPEA (29 μL, 0.16 mmol) were added to a solution of N-(5-chloro-2-ethanesulfonyl-benzyl)-4-piperazin-1-ylmethyl-3-trifluoromethyl-benzamide (Compound B-1, 83 mg, 0.16 mmol) and tert-butoxycarbonylamino-acetic acid (32 mg, 0.18 mmol) in DMF (1.6 mL), and the mixture was stirred at room temperature for three hours. The reaction solution was diluted with ethyl acetate, and the organic layer was washed with water and saturated saline, and then dried over anhydrous sodium sulfate. The drying agent was removed by filtration. After concentration under reduced pressure, the resulting residue was purified by silica gel column chromatography (ethyl acetate/hexane) to yield (2-{4-[4-(5-chloro-2-ethanesulfonyl-benzylcarbamoyl)-2-trifluoromethyl-benzyl]-piperazin-1-yl}-2-oxo-ethyl)-carbamic acid tert-butyl ester (99 mg, 91%) as a colorless foamy substance.

TFA (0.5 ml) was added to a solution of (2-{4-[4-(5-chloro-2-ethanesulfonyl-benzylcarbamoyl)-2-trifluoromethyl-benzyl]-piperazin-1-yl}-2-oxo-ethyl)-carbamic acid tert-butyl ester (97 mg, 0.17 mmol) in DCM (1 ml), and the mixture was stirred at room temperature for one hour. The reaction mixture was concentrated under reduced pressure and then diluted with ethyl acetate. The organic layer was washed with a saturated aqueous sodium bicarbonate solution and saturated saline, and dried over anhydrous sodium sulfate. The drying agent was removed by filtration, and the solvent was then concentrated under reduced pressure. The resulting residue was purified by amino silica gel column chromatography (MeOH/DCM) to yield the title compound (54 mg, 66%) as a colorless foamy substance.

LCMS: m/z 561 [M+H]+

HPLC retention time: 0.47 min (analysis condition A)

Example 47

Compound b5

4-Methyl-3-trifluoromethyl-benzoic acid ethyl ester

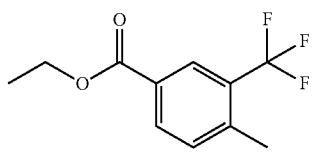 [SMILES: CCOC(=O)c1ccc(C)c(C(F)(F)F)c1]

The title compound was synthesized from 4-methyl-3-trifluoromethyl-benzoic acid under the same conditions as for Compound b1.

Example 48

Compound b6

4-Bromomethyl-3-trifluoromethyl-benzoic acid ethyl ester

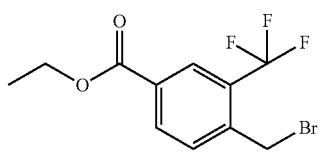 [SMILES: CCOC(=O)c1ccc(CBr)c(C(F)(F)F)c1]

A solution of 4-methyl-3-trifluoromethyl-benzoic acid ethyl ester (Compound b5, 1.11 g, 4.8 mmol), NBS (936 mg, 5.3 mmol), and 70% benzoyl peroxide (165 mg, 0.48 mmol) in carbon tetrachloride (24 ml) was stirred at 85° C. for four hours. The reaction mixture was filtered with celite, and the filtrate was concentrated under reduced pressure. The resulting residue was purified by silica gel column chromatography (DCM/hexane) to yield the title compound (900 mg, 60%) as a colorless solid.

$^1$H-NMR (300 MHz, CDCl$_3$) δ: 8.31 (1H, d, J=1.5 Hz), 8.21 (1H, dd, J=8.0, 1.5 Hz), 7.68 (1H, d, J=8.0 Hz), 4.65 (2H, s), 4.42 (2H, q, J=7.1 Hz), 1.41 (3H, t, J=7.1 Hz).

Example 49

Compound b7

4-((R)-3-tert-Butoxycarbonylamino-pyrrolidin-1-ylmethyl)-3-trifluoromethyl-benzoic acid ethyl ester

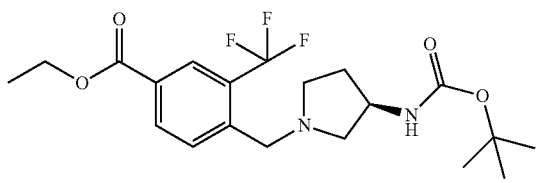 [SMILES: CCOC(=O)c1ccc(CN2CC[C@@H](NC(=O)OC(C)(C)C)C2)c(C(F)(F)F)c1]

(R)-Pyrrolidin-3-yl-carbamic acid tert-butyl ester (404 mg, 2.2 mmol) and TEA (605 μl, 4.3 mmol) were added to a solution of 4-bromomethyl-3-trifluoromethyl-benzoic acid ethyl ester (Compound b6, 450 mg, 1.4 mmol) in DCM (7 ml), and the mixture was stirred at room temperature for three hours. The reaction mixture was diluted with ethyl acetate, and the organic layer was washed with water and saturated saline, and dried over anhydrous sodium sulfate. The drying agent was removed by filtration, and the solvent was then concentrated under reduced pressure. The resulting residue was purified by silica gel column chromatography (ethyl acetate/hexane) to yield the title compound (590 mg, 98%) as a viscous oily substance.

$^1$H-NMR (300 MHz, CDCl$_3$) δ: 8.29 (1H, s), 8.18 (1H, d, J=8.2 Hz), 7.86 (1H, d, J=8.2 Hz), 4.83 (1H, brs), 4.41 (2H, q, J=7.2 Hz), 4.14-4.24 (1H, m), 3.82 (2H, s), 2.80-2.87 (1H, m), 2.65-2.70 (1H, m), 2.54-2.58 (1H, m), 2.22-2.41 (2H, m), 1.57-1.61 (1H, m), 1.44 (9H, s), 1.41 (3H, t, J=7.2 Hz).

Example 50

Compound b8

4-((R)-3-tert-Butoxycarbonylamino-pyrrolidin-1-ylmethyl)-3-trifluoromethyl-benzoic acid

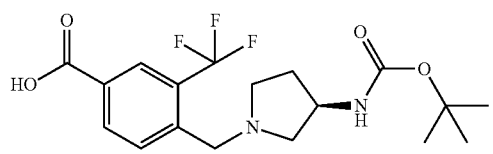 [SMILES: CC(C)(C)OC(=O)N[C@@H]1CCN(Cc2ccc(C(=O)O)cc2C(F)(F)F)C1]

A 1N aqueous sodium hydroxide solution (0.9 ml) was added to a solution of 4-((R)-3-tert-butoxycarbonylamino-pyrrolidin-1-ylmethyl)-3-trifluoromethyl-benzoic acid ethyl ester (Compound b7, 192 mg, 0.46 mmol) in EtOH (2 ml), and the mixture was stirred at 40-65° C. for one hour. The reaction mixture was neutralized by adding a 1N aqueous hydrochloric acid solution (0.9 ml), and the solvent was then concentrated under reduced pressure to yield a crude product of the title compound.

Example 51

Compound b9

{(R)-1-[4-(5-Chloro-2-ethanesulfonyl-benzylcarbamoyl)-2-trifluoromethyl-benzyl]-pyrrolidin-3-yl}-carbamic acid tert-butyl ester

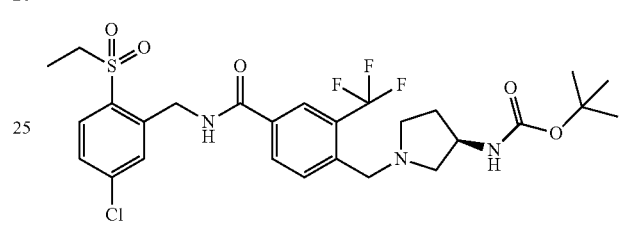

The title compound was synthesized from 4-((R)-3-tert-butoxycarbonylamino-pyrrolidin-1-ylmethyl)-3-trifluoromethyl-benzoic acid (Compound b8) under the same conditions as for Compound A-14.

Example 52

Compound B-6

4-((R)-3-Amino-pyrrolidin-1-ylmethyl)-N-(5-chloro-2-ethanesulfonyl-benzyl)-3-trifluoromethyl-benzamide

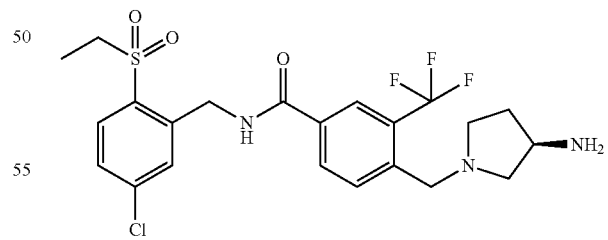

The title compound was synthesized from {(R)-1-[4-(5-chloro-2-ethanesulfonyl-benzylcarbamoyl)-2-trifluoromethyl-benzyl]-pyrrolidin-3-yl}-carbamic acid tert-butyl ester (Compound b9) under the same conditions as for Compound B-1.

LCMS: m/z 504 [M+H]$^+$

HPLC retention time: 0.41 min (analysis condition A)

Example 53

Compound B-7

4-((R)-3-Acetylamino-pyrrolidin-1-ylmethyl)-N-(5-chloro-2-ethanesulfonyl-benzyl)-3-trifluoromethyl-benzamide

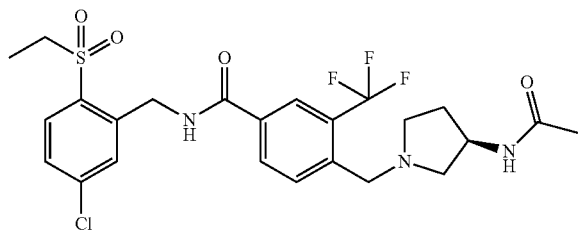 [SMILES: CCS(=O)(=O)c1ccc(Cl)cc1CNC(=O)c1ccc(CN2CC[C@@H](NC(C)=O)C2)c(C(F)(F)F)c1]

Acetyl chloride (8.5 μl, 0.12 mmol) and TEA (27.7 μl, 0.20 mmol) were added to a solution of 4-((R)-3-amino-pyrrolidin-1-ylmethyl)-N-(5-chloro-2-ethanesulfonyl-benzyl)-3-trifluoromethyl-benzamide (Compound B-6, 50 mg, 0.10 mmol) in DCM (1 ml), and the mixture was stirred at room temperature for one hour. The reaction mixture was diluted with ethyl acetate, and the organic layer was washed with water and saturated saline, and dried over anhydrous sodium sulfate. The drying agent was removed by filtration, and the solvent was then concentrated under reduced pressure. The resulting residue was purified by silica gel column chromatography (MeOH/DCM) and then by preparative TLC (MeOH/DCM) to yield the title compound (39 mg, 72%) as a colorless foamy substance.

LCMS: m/z 546 [M+H]$^+$

HPLC retention time: 0.48 min (analysis condition A)

Example 54

Compound B-8

N-(5-Chloro-2-ethanesulfonyl-benzyl)-4-((R)-3-dimethylamino-pyrrolidin-1-ylmethyl)-3-trifluoromethyl-benzamide

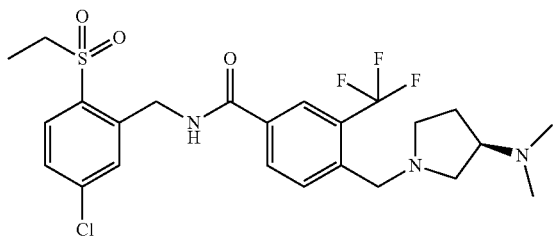 [SMILES: CCS(=O)(=O)c1ccc(Cl)cc1CNC(=O)c1ccc(CN2CC[C@@H](N(C)C)C2)c(C(F)(F)F)c1]

The title compound was synthesized from 4-((R)-3-amino-pyrrolidin-1-ylmethyl)-N-(5-chloro-2-ethanesulfonyl-benzyl)-3-trifluoromethyl-benzamide (Compound B-6) under the same conditions as for Compound B-2.

LCMS: m/z 532 [M+H]$^+$

HPLC retention time: 0.51 min (analysis condition A)

Example 55

Compound B-9

N-(5-Chloro-2-ethanesulfonyl-benzyl)-4-((R)-3-methanesulfonylamino-pyrrolidin-1-ylmethyl)-3-trifluoromethyl-benzamide

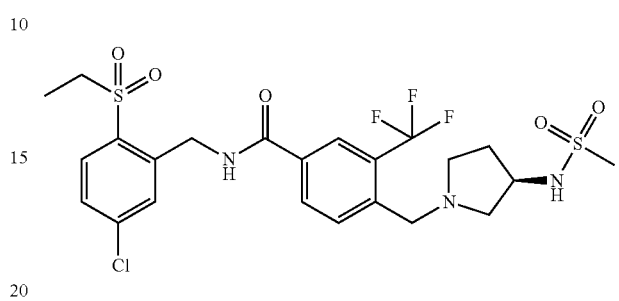

Mesylate chloride (10 μl, 0.13 mmol) was added to a solution of 4-((R)-3-amino-pyrrolidin-1-ylmethyl)-N-(5-chloro-2-ethanesulfonyl-benzyl)-3-trifluoromethyl-benzamide (Compound B-6, 60 mg, 0.12 mmol) and TEA (17 μl, 0.12 mmol) in DCM (2 ml) under ice-cooling, and the mixture was stirred at room temperature for eight hours. The reaction solution was diluted with DCM. The organic layer was washed with saturated saline, and then dried over anhydrous sodium sulfate. The drying agent was removed by filtration. After concentration under reduced pressure, the resulting residue was purified by silica gel column chromatography (methanol/DCM) to yield the title compound (49 mg, 82%) as a colorless solid.

LCMS: m/z 582 [M+H]$^+$

HPLC retention time: 0.51 min (analysis condition A)

Example 56

Compound B-10

{(R)-1-[4-(5-Chloro-2-ethanesulfonyl-benzylcarbamoyl)-2-trifluoromethyl-benzyl]-pyrrolidin-3-yl}-carbamic acid methyl ester

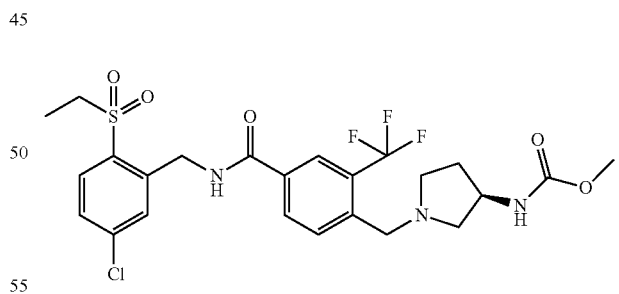

Methyl chloroformate (10 μl, 0.12 mmol) and TEA (30 μl, 0.22 mmol) were added to a solution of 4-((R)-3-amino-pyrrolidin-1-ylmethyl)-N-(5-chloro-2-ethanesulfonyl-benzyl)-3-trifluoromethyl-benzamide (Compound B-6, 55 mg, 0.11 mmol) in DCM (1 ml), and the mixture was stirred at room temperature for two hours. The reaction solution was diluted with ethyl acetate, and the organic layer was washed with water and saturated saline, and then dried over anhydrous sodium sulfate. The drying agent was removed by filtration. After concentration under reduced pressure, the resulting residue was purified by preparative TLC (methanol/DCM) to yield the title compound (37 mg, 60%) as a pale yellow foamy substance.

LCMS: m/z 562 [M+H]$^+$

HPLC retention time: 0.52 min (analysis condition A)

Example 57

Compound B-11

N-(5-Chloro-2-ethanesulfonyl-benzyl)-3-trifluoromethyl-4-((R)-3-ureido-pyrrolidin-1-ylmethyl)-benzamide

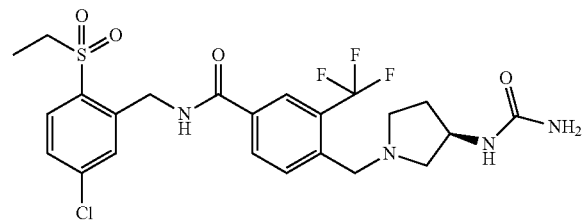 [SMILES: CCS(=O)(=O)c1ccc(Cl)cc1CNC(=O)c1ccc(CN2CC[C@@H](NC(N)=O)C2)c(C(F)(F)F)c1]

Acetic acid (0.8 ml) was added to a solution of 4-((R)-3-amino-pyrrolidin-1-ylmethyl)-N-(5-chloro-2-ethanesulfonyl-benzyl)-3-trifluoromethyl-benzamide (Compound B-6, 80 mg, 0.16 mmol) in DCM (0.8 ml), and this was cooled to 0° C. Sodium cyanate (20.6 mg, 0.32 mmol) was added thereto, and the mixture was stirred at room temperature for two hours. The reaction solution was diluted with ethyl acetate, and the organic layer was washed with a saturated aqueous sodium bicarbonate solution, water, and saturated saline, and then dried over anhydrous sodium sulfate. The drying agent was removed by filtration. After concentration under reduced pressure, the resulting residue was purified by preparative TLC (methanol/DCM) to yield the title compound (40.1 mg, 46%) as a pale colorless foamy substance.

LCMS: m/z 547 [M+H]$^+$

HPLC retention time: 0.48 min (analysis condition A)

Example 58

Compound B-12

4-[(R)-3-(2-Amino-acetylamino)-pyrrolidin-1-ylmethyl]-N-(5-chloro-2-ethanesulfonyl-benzyl)-3-trifluoromethyl-benzamide

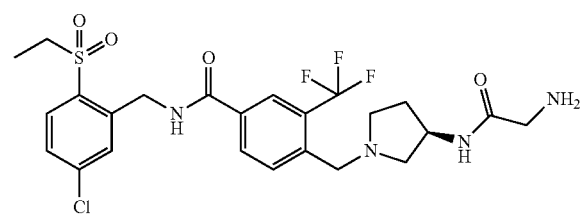 [SMILES: CCS(=O)(=O)c1ccc(Cl)cc1CNC(=O)c1ccc(CN2CC[C@@H](NC(=O)CN)C2)c(C(F)(F)F)c1]

The title compound was synthesized from 4-((R)-3-amino-pyrrolidin-1-ylmethyl)-N-(5-chloro-2-ethanesulfonyl-benzyl)-3-trifluoromethyl-benzamide (Compound B-6) under the same conditions as for Compound B-5.

LCMS: m/z 561 [M+H]$^+$

HPLC retention time: 0.44 min (analysis condition A)

Example 59

Compound b10

4-[(R)-3-(tert-Butoxycarbonyl-methyl-amino)-pyrrolidin-1-ylmethyl]-3-trifluoromethyl-benzoic acid ethyl ester

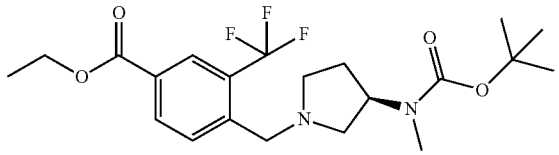 [SMILES: CCOC(=O)c1ccc(CN2CC[C@@H](N(C)C(=O)OC(C)(C)C)C2)c(C(F)(F)F)c1]

The title compound was synthesized from 4-bromomethyl-3-trifluoromethyl-benzoic acid ethyl ester (Compound b6) and methyl-(R)-pyrrolidin-3-yl-carbamic acid tert-butyl ester under the same conditions as for Compound b7.

Example 60

Compound b11

4-[(R)-3-(tert-Butoxycarbonyl-methyl-amino)-pyrrolidin-1-ylmethyl]-3-trifluoromethyl-benzoic acid

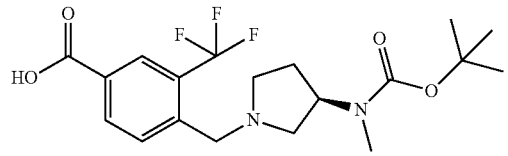 [SMILES: CN(C(=O)OC(C)(C)C)[C@@H]1CCN(Cc2ccc(C(=O)O)cc2C(F)(F)F)C1]

The title compound was synthesized from 4-[(R)-3-(tert-butoxycarbonyl-methyl-amino)-pyrrolidin-1-ylmethyl]-3-trifluoromethyl-benzoic acid ethyl ester (Compound b10) under the same conditions as for Compound b8.

Example 61

Compound b12

{(R)-1-[4-(5-Chloro-2-ethanesulfonyl-benzylcarbamoyl)-2-trifluoromethyl-benzyl]-pyrrolidin-3-yl}-methyl-carbamic acid tert-butyl ester

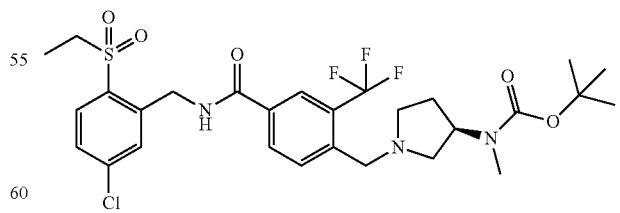

The title compound was synthesized from 4-[(R)-3-(tert-butoxycarbonyl-methyl-amino)-pyrrolidin-1-ylmethyl]-3-trifluoromethyl-benzoic acid (Compound b11) using DCM in place of DMF under the same conditions as for Compound A-14.

Example 62

Compound B-13

N-(5-Chloro-2-ethanesulfonyl-benzyl)-4-((R)-3-methylamino-pyrrolidin-1-ylmethyl)-3-trifluoromethyl-benzamide

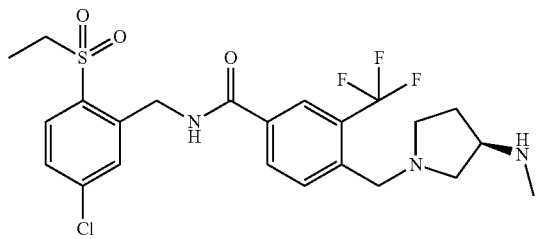 [SMILES: CCS(=O)(=O)c1ccc(Cl)cc1CNC(=O)c1ccc(CN2CC[C@@H](NC)C2)c(C(F)(F)F)c1]

The title compound was synthesized from {(R)-1-[4-(5-chloro-2-ethanesulfonyl-benzylcarbamoyl)-2-trifluoromethyl-benzyl]-pyrrolidin-3-yl}-methyl-carbamic acid tert-butyl ester (Compound b12) under the same conditions as for Compound B-1.

LCMS: m/z 518 [M+H]$^+$

HPLC retention time: 0.49 min (analysis condition A)

Example 63

Compound b13

4-((R)-3-Methylamino-pyrrolidin-1-ylmethyl)-3-trifluoromethyl-benzoic acid ethyl ester

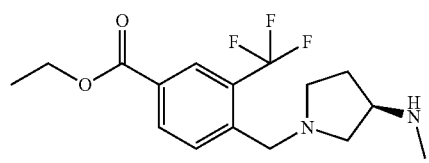 [SMILES: CCOC(=O)c1ccc(CN2CC[C@@H](NC)C2)c(C(F)(F)F)c1]

The title compound was synthesized from 4-[(R)-3-(tert-butoxycarbonyl-methyl-amino)-pyrrolidin-1-ylmethyl]-3-trifluoromethyl-benzoic acid ethyl ester (Compound b10) under the same conditions as for Compound B-1.

Example 64

Compound b14

4-[(R)-3-(Methanesulfonyl-methyl-amino)-pyrrolidin-1-ylmethyl]-3-trifluoromethyl-benzoic acid ethyl ester

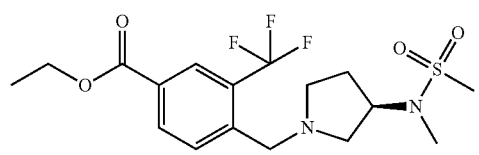 [SMILES: CCOC(=O)c1ccc(CN2CC[C@@H](N(C)S(C)(=O)=O)C2)c(C(F)(F)F)c1]

The title compound was synthesized from 4-((R)-3-methylamino-pyrrolidin-1-ylmethyl)-3-trifluoromethyl-benzoic acid ethyl ester (Compound b13) under the same conditions as for Compound B-9.

Example 65

Compound b15

4-[(R)-3-(Methanesulfonyl-methyl-amino)-pyrrolidin-1-ylmethyl]-3-trifluoromethyl-benzoic acid

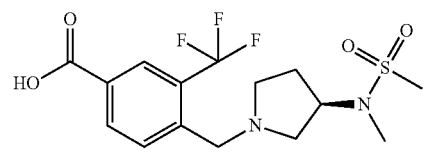 [SMILES: CN([C@@H]1CCN(Cc2ccc(C(=O)O)cc2C(F)(F)F)C1)S(C)(=O)=O]

The title compound was synthesized from 4-[(R)-3-(methanesulfonyl-methyl-amino)-pyrrolidin-1-ylmethyl]-3-trifluoromethyl-benzoic acid ethyl ester (Compound b14) under the same conditions as for Compound b3.

Example 66

Compound B-14

N-(5-Chloro-2-ethanesulfonyl-benzyl)-4-[(R)-3-(methanesulfonyl-methyl-amino)-pyrrolidin-1-ylmethyl]-3-trifluoromethyl-benzamide

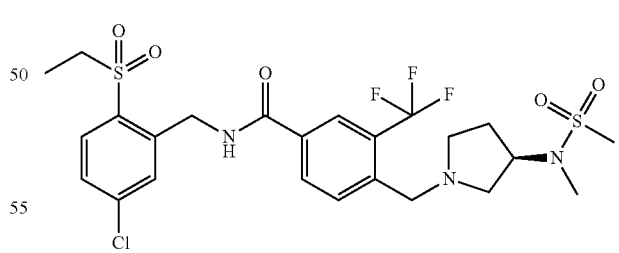

The title compound was synthesized from 4-[(R)-3-(methanesulfonyl-methyl-amino)-pyrrolidin-1-ylmethyl]-3-trifluoromethyl-benzoic acid (Compound b15) under the same conditions as for Compound A-14.

LCMS: m/z 596 [M+H]$^+$

HPLC retention time: 0.56 min (analysis condition A)

Example 67

Compound B-15

4-((S)-3-Amino-pyrrolidin-1-ylmethyl)-N-(5-chloro-2-ethanesulfonyl-benzyl)-3-trifluoromethyl-benzamide

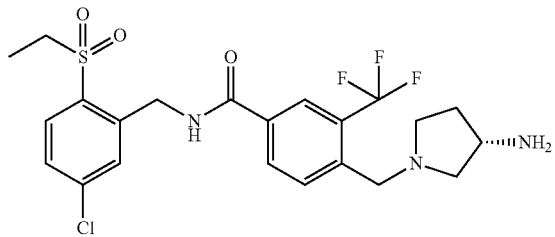 [SMILES: CCS(=O)(=O)c1ccc(Cl)cc1CNC(=O)c1ccc(CN2CC[C@H](N)C2)c(C(F)(F)F)c1]

The title compound was synthesized from 4-bromomethyl-3-trifluoromethyl-benzoic acid ethyl ester (Compound b6) and (S)-pyrrolidin-3-yl-carbamic acid tert-butyl ester under the same conditions as for Compounds b7, b8, b9, and B-6. However, potassium hydroxide was used in place of sodium hydroxide under the conditions for Compound b8.

LCMS: m/z 504 [M+H]$^+$

HPLC retention time: 0.41 min (analysis condition A)

Example 68

Compound B-16

4-((S)-3-Acetylamino-pyrrolidin-1-ylmethyl)-N-(5-chloro-2-ethanesulfonyl-benzyl)-3-trifluoromethyl-benzamide

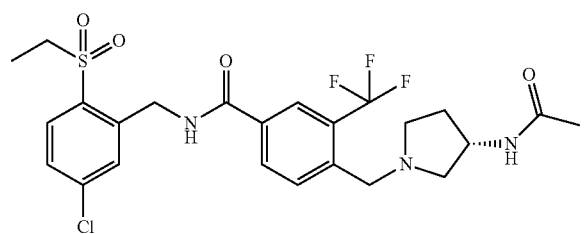 [SMILES: CCS(=O)(=O)c1ccc(Cl)cc1CNC(=O)c1ccc(CN2CC[C@H](NC(C)=O)C2)c(C(F)(F)F)c1]

The title compound was synthesized from 4-((S)-3-amino-pyrrolidin-1-ylmethyl)-N-(5-chloro-2-ethanesulfonyl-benzyl)-3-trifluoromethyl-benzamide (Compound B-15) under the same conditions as for Compound B-7.

LCMS: m/z 546 [M+H]$^+$

HPLC retention time: 0.49 min (analysis condition A)

Example 69

Compound B-17

N-(5-Chloro-2-ethanesulfonyl-benzyl)-4-((S)-3-dimethylamino-pyrrolidin-1-ylmethyl)-3-trifluoromethyl-benzamide

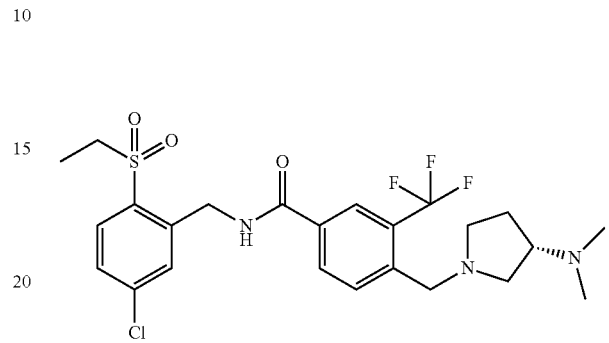

The title compound was synthesized from 4-((S)-3-amino-pyrrolidin-1-ylmethyl)-N-(5-chloro-2-ethanesulfonyl-benzyl)-3-trifluoromethyl-benzamide (Compound B-15) under the same conditions as for Compound B-2.

LCMS: m/z 532 [M+H]$^+$

HPLC retention time: 0.51 min (analysis condition A)

Example 70

Compound B-18

N-(5-Chloro-2-ethanesulfonyl-benzyl)-4-((S)-3-methanesulfonylamino-pyrrolidin-1-ylmethyl)-3-trifluoromethyl-benzamide

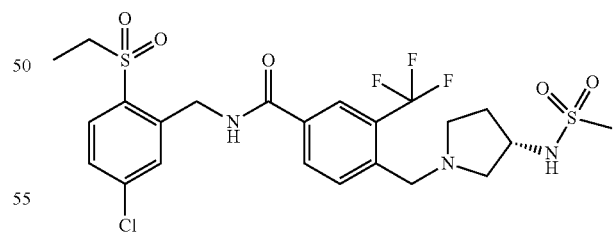

The title compound was synthesized from 4-((S)-3-amino-pyrrolidin-1-ylmethyl)-N-(5-chloro-2-ethanesulfonyl-benzyl)-3-trifluoromethyl-benzamide (Compound B-15) under the same conditions as for Compound B-9.

LCMS: m/z 582 [M+H]$^+$

HPLC retention time: 0.51 min (analysis condition A)

Example 71

Compound B-19

4-((R)-3-Amino-piperidin-1-ylmethyl)-N-(5-chloro-2-ethanesulfonyl-benzyl)-3-trifluoromethyl-benzamide

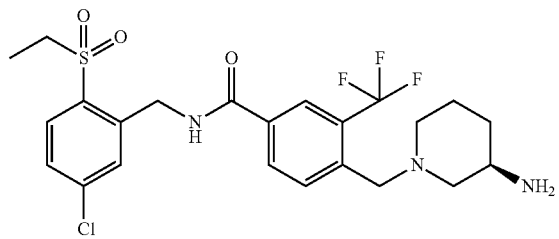 [SMILES: CCS(=O)(=O)c1ccc(Cl)cc1CNC(=O)c1ccc(CN2CCC[C@@H](N)C2)c(C(F)(F)F)c1]

The title compound was synthesized from 4-bromomethyl-3-trifluoromethyl-benzoic acid ethyl ester (Compound b6) and (R)-piperidin-3-yl-carbamic acid tert-butyl ester under the same conditions as for Compounds b7, b8, b9, and B-6. However, potassium hydroxide was used in place of sodium hydroxide under the conditions for Compound b8.

LCMS: m/z 518 [M+H]$^+$

HPLC retention time: 0.50 min (analysis condition A)

Example 72

Compound B-20

N-(5-Chloro-2-ethanesulfonyl-benzyl)-4-((R)-3-dimethylamino-piperidin-1-ylmethyl)-3-trifluoromethyl-benzamide

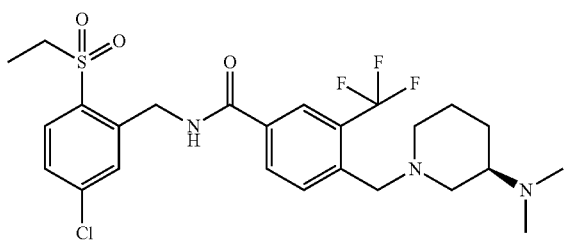 [SMILES: CCS(=O)(=O)c1ccc(Cl)cc1CNC(=O)c1ccc(CN2CCC[C@@H](N(C)C)C2)c(C(F)(F)F)c1]

The title compound was synthesized from 4-((R)-3-amino-piperidin-1-ylmethyl)-N-(5-chloro-2-ethanesulfonyl-benzyl)-3-trifluoromethyl-benzamide (Compound B-19) under the same conditions as for Compound B-2.

LCMS: m/z 546 [M+H]$^+$

HPLC retention time: 0.54 min (analysis condition A)

Example 73

Compound B-21

4-((R)-3-Acetylamino-piperidin-1-ylmethyl)-N-(5-chloro-2-ethanesulfonyl-benzyl)-3-trifluoromethyl-benzamide

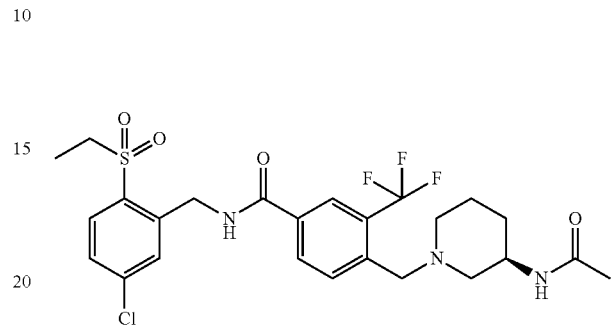

The title compound was synthesized from 4-((R)-3-amino-piperidin-1-ylmethyl)-N-(5-chloro-2-ethanesulfonyl-benzyl)-3-trifluoromethyl-benzamide (Compound B-19) under the same conditions as for Compound B-7.

LCMS: m/z 560 [M+H]$^+$

HPLC retention time: 0.51 min (analysis condition A)

Example 74

Compound B-22

N-(5-Chloro-2-ethanesulfonyl-benzyl)-4-((R)-3-methanesulfonylamino-piperidin-1-ylmethyl)-3-trifluoromethyl-benzamide

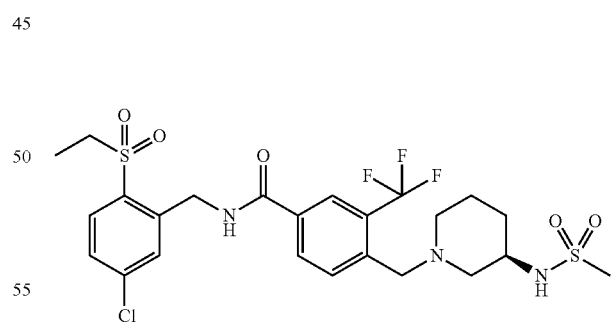

The title compound was synthesized from 4-((R)-3-amino-piperidin-1-ylmethyl)-N-(5-chloro-2-ethanesulfonyl-benzyl)-3-trifluoromethyl-benzamide (Compound B-19) under the same conditions as for Compound B-9.

LCMS: m/z 596 [M+H]$^+$

HPLC retention time: 0.54 min (analysis condition A)

Example 75

Compound B-23

N-(5-Chloro-2-ethanesulfonyl-benzyl)-3-trifluoromethyl-4-((R)-3-ureido-piperidin-1-ylmethyl)-benzamide

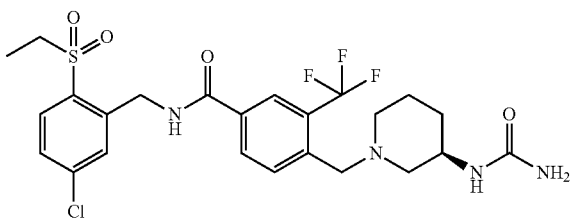 [SMILES: CCS(=O)(=O)c1ccc(Cl)cc1CNC(=O)c1ccc(CN2CCC[C@@H](NC(N)=O)C2)c(C(F)(F)F)c1]

The title compound was synthesized from 4-((R)-3-amino-piperidin-1-ylmethyl)-N-(5-chloro-2-ethanesulfonyl-benzyl)-3-trifluoromethyl-benzamide (Compound B-19) under the same conditions as for Compound B-11.

LCMS: m/z 561 [M+H]$^+$
HPLC retention time: 0.50 min (analysis condition A)

Example 76

Compound B-24

N-(5-Chloro-2-ethanesulfonyl-benzyl)-4-((R)-3-methylamino-piperidin-1-ylmethyl)-3-trifluoromethyl-benzamide

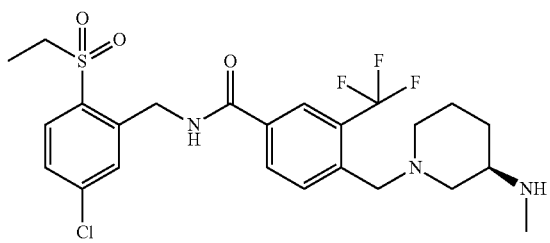 [SMILES: CCS(=O)(=O)c1ccc(Cl)cc1CNC(=O)c1ccc(CN2CCC[C@@H](NC)C2)c(C(F)(F)F)c1]

The title compound was synthesized from 4-bromomethyl-3-trifluoromethyl-benzoic acid ethyl ester (Compound b6) and methyl-(R)-piperidin-3-yl-carbamic acid tert-butyl ester under the same conditions as for Compounds b7, b8, b9, and B-6. However, the reaction was performed using DCM in place of DMF under the conditions for Compound b9.

LCMS: m/z 532 [M+H]$^+$
HPLC retention time: 0.52 min (analysis condition A)

Example 77

Compound b16

4-((S)-3-tert-Butoxycarbonylamino-piperidin-1-ylmethyl)-3-trifluoromethyl-benzoic acid ethyl ester

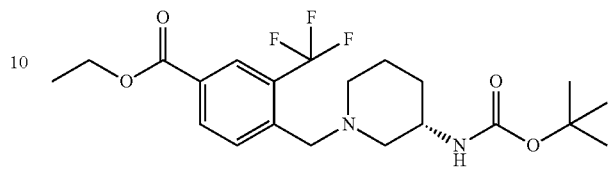

The title compound was synthesized from 4-bromomethyl-3-trifluoromethyl-benzoic acid ethyl ester (Compound b6) and (S)-piperidin-3-yl-carbamic acid tert-butyl ester under the same conditions as for Compound b7.

Example 78

Compound B-25

4-((S)-3-Amino-piperidin-1-ylmethyl)-N-(5-chloro-2-ethanesulfonyl-benzyl)-3-trifluoromethyl-benzamide

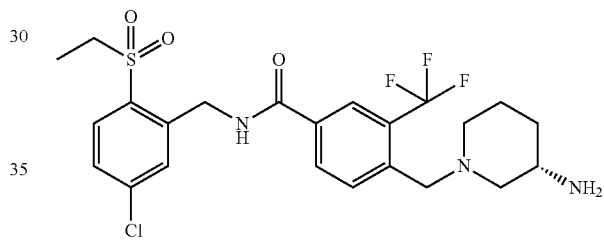

The title compound was synthesized from 4-((S)-3-tert-butoxycarbonylamino-piperidin-1-ylmethyl)-3-trifluoromethyl-benzoic acid ethyl ester (Compound b16) under the same conditions as for Compounds b8, b9, and B-6. However, the reaction was performed using DCM in place of DMF under the conditions for Compound b9.

LCMS: m/z 518 [M+H]$^+$
HPLC retention time: 0.51 min (analysis condition A)

Example 79

Compound B-26

N-(5-Chloro-2-ethanesulfonyl-benzyl)-4-((S)-3-dimethylamino-piperidin-1-ylmethyl)-3-trifluoromethyl-benzamide

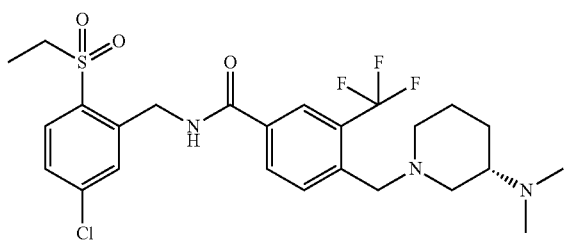 [SMILES: CCS(=O)(=O)c1ccc(Cl)cc1CNC(=O)c1ccc(CN2CCC[C@H](N(C)C)C2)c(C(F)(F)F)c1]

The title compound was synthesized from 4-((S)-3-amino-piperidin-1-ylmethyl)-N-(5-chloro-2-ethanesulfonyl-benzyl)-3-trifluoromethyl-benzamide (Compound B-25) under the same conditions as for Compound B-2.

LCMS: m/z 546 [M+H]$^+$

HPLC retention time: 0.55 min (analysis condition A)

Example 80

Compound B-27

4-((S)-3-Acetylamino-piperidin-1-ylmethyl)-N-(5-chloro-2-ethanesulfonyl-benzyl)-3-trifluoromethyl-benzamide

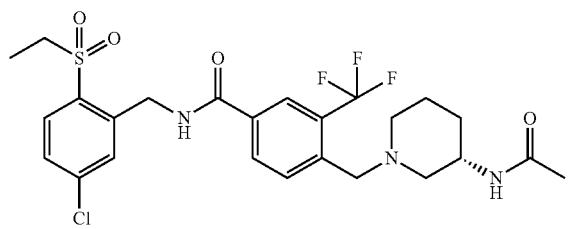 [SMILES: CCS(=O)(=O)c1ccc(Cl)cc1CNC(=O)c1ccc(CN2CCC[C@H](NC(C)=O)C2)c(C(F)(F)F)c1]

The title compound was synthesized from 4-((S)-3-amino-piperidin-1-ylmethyl)-N-(5-chloro-2-ethanesulfonyl-benzyl)-3-trifluoromethyl-benzamide (Compound B-25) under the same conditions as for Compound B-7.

LCMS: m/z 560 [M+H]$^+$

HPLC retention time: 0.51 min (analysis condition A)

Example 81

Compound B-28

N-(5-Chloro-2-ethanesulfonyl-benzyl)-4-((S)-3-methanesulfonylamino-piperidin-1-ylmethyl)-3-trifluoromethyl-benzamide

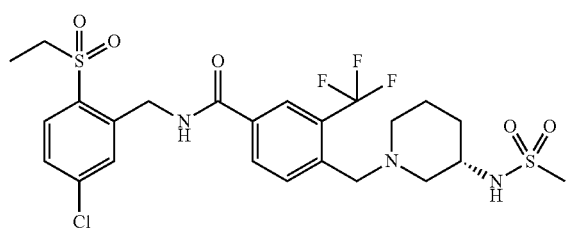 [SMILES: CCS(=O)(=O)c1ccc(Cl)cc1CNC(=O)c1ccc(CN2CCC[C@H](NS(C)(=O)=O)C2)c(C(F)(F)F)c1]

The title compound was synthesized from 4-((S)-3-amino-piperidin-1-ylmethyl)-N-(5-chloro-2-ethanesulfonyl-benzyl)-3-trifluoromethyl-benzamide (Compound B-25) under the same conditions as for Compound B-9.

LCMS: m/z 596 [M+H]$^+$

HPLC retention time: 0.54 min (analysis condition A)

Example 82

Compound B-29

N-(5-Chloro-2-ethanesulfonyl-benzyl)-3-trifluoromethyl-4-((S)-3-ureido-piperidin-1-ylmethyl)-benzamide

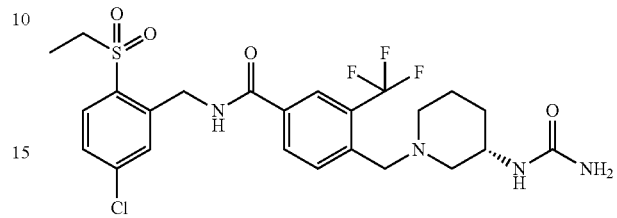

The title compound was synthesized from 4-((S)-3-amino-piperidin-1-ylmethyl)-N-(5-chloro-2-ethanesulfonyl-benzyl)-3-trifluoromethyl-benzamide (Compound B-25) under the same conditions as for Compound B-11.

LCMS: m/z 561 [M+H]$^+$

HPLC retention time: 0.49 min (analysis condition A)

Examples 83 to 88

The compounds of FIG. 5 were synthesized using 4-((S)-3-amino-piperidin-1-ylmethyl)-N-(5-chloro-2-ethanesulfonyl-benzyl)-3-trifluoromethyl-benzamide (Compound B-25) and the corresponding amino acids under the same conditions as for Compound B-5.

Example 89

Compound B-33

4-[(S)-3-(2-Amino-2-methyl-propionylamino)-piperidin-1-ylmethyl]-N-(5-chloro-2-ethanesulfonyl-benzyl)-3-trifluoromethyl-benzamide

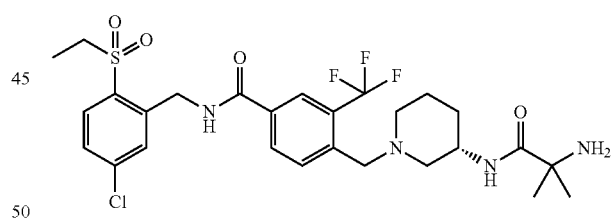

A solution of 2-(9H-fluoren-9-ylmethoxycarbonylamino)-2-methyl-propionic acid (38 mg, 0.12 mmol) and HATU (52 mg, 0.14 mmol) in DMF (1 ml) was stirred for five minutes. Then, 4-((S)-3-Amino-piperidin-1-ylmethyl)-N-(5-chloro-2-ethanesulfonyl-benzyl)-3-trifluoromethyl-benzamide (Compound B-25, 65 mg, 0.11 mmol) and DIPEA (55 μl, 0.32 mmol) were added thereto, and the mixture was stirred at room temperature for two hours. The reaction mixture was diluted with ethyl acetate, and the organic layer was washed with saturated saline and dried over anhydrous sodium sulfate. The drying agent was removed by filtration, and the solvent was then concentrated under reduced pressure. The resulting residue was purified by amino silica gel column chromatography (ethyl acetate/hexane) to yield (1-{(S)-1-[4-(5-chloro-2-ethanesulfonyl-benzylcarbamoyl)-2-trifluoromethyl-benzyl]-piperidin-3- ylcarbamoyl}-1-methyl-ethyl)-carbamic acid 9H-fluoren-9-ylmethyl ester (60 mg, 70%) as a colorless solid.

LCMS: m/z 825 [M+H]+

HPLC retention time: 3.17 min (analysis condition C)

Piperidine (0.14 ml, 0.14 mmol) was added to a solution of (1-{(S)-1-[4-(5-chloro-2-ethanesulfonyl-benzylcarbamoyl)-2-trifluoromethyl-benzyl]-piperidin-3-ylcarbamoyl}-1-methyl-ethyl)-carbamic acid 9H-fluoren-9-ylmethyl ester (60 mg, 0.073 mmol) in DCM (0.73 ml), and the mixture was stirred at room temperature for two hours. The reaction mixture was diluted with DCM, and the organic layer was washed with saturated saline and dried over anhydrous sodium sulfate. The drying agent was removed by filtration, and the solvent was then concentrated under reduced pressure. The resulting residue was purified by amino silica gel column chromatography (ethyl acetate/hexane) to yield the title compound (25 mg, 57%) as a colorless solid.

LCMS: m/z 603 [M+H]+

HPLC retention time: 0.44 min (analysis condition A)

Example 90

Compound b17

4-[(S)-3-(tert-Butoxycarbonyl-methyl-amino)-piperidin-1-ylmethyl]-3-trifluoromethyl-benzoic acid

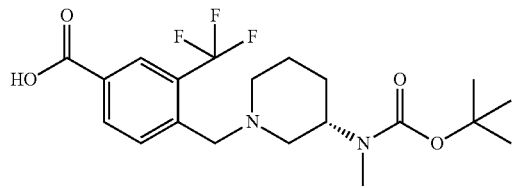 [SMILES: CN(C(=O)OC(C)(C)C)[C@H]1CCCN(Cc2ccc(C(=O)O)cc2C(F)(F)F)C1]

A 60% dispersion of sodium hydride in mineral oil (oil dispersion) (195 mg, 4.9 mmol) was added to a solution of 4-((S)-3-tert-butoxycarbonylamino-piperidin-1-ylmethyl)-3-trifluoromethyl-benzoic acid ethyl ester (Compound b16, 625 mg, 1.5 mmol) in THF (5.2 ml) under ice-cooling, and methyl iodide (0.3 ml, 4.9 mmol) was further added thereto. The reaction solution was stirred at room temperature overnight, and water was then added thereto. After extraction with ethyl acetate, the extract was washed with saturated saline and then dried over anhydrous magnesium sulfate. The drying agent was removed by filtration, and concentration was performed under reduced pressure to yield the title compound as a crude product.

Example 91

Compound b18

4-[(S)-3-(tert-Butoxycarbonyl-methyl-amino)-piperidin-1-ylmethyl]-3-trifluoromethyl-benzoic acid ethyl ester

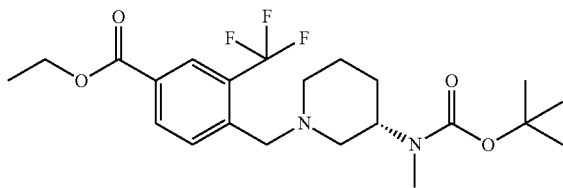 [SMILES: CCOC(=O)c1ccc(CN2CCC[C@H](N(C)C(=O)OC(C)(C)C)C2)c(C(F)(F)F)c1]

The title compound was synthesized from the crude product of 4-[(S)-3-(tert-butoxycarbonyl-methyl-amino)-piperidin-1-ylmethyl]-3-trifluoromethyl-benzoic acid (Compound b17) under the same conditions as for Compound b1.

Example 92

Compound B-37

N-(5-Chloro-2-ethanesulfonyl-benzyl)-4-((S)-3-methylamino-piperidin-1-ylmethyl)-3-trifluoromethyl-benzamide

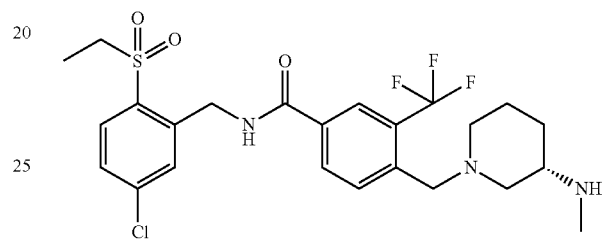

The title compound was synthesized from 4-[(S)-3-(tert-butoxycarbonyl-methyl-amino)-piperidin-1-ylmethyl]-3-trifluoromethyl-benzoic acid ethyl ester (Compound b18) under the same conditions as for Compounds b8, b9, and B-6. However, the reaction was performed using DCM in place of DMF under the conditions for Compound b9.

LCMS: m/z 532 [M+H]+

HPLC retention time: 0.53 min (analysis condition A)

Example 93

Compound b19

4-[(S)-3-(tert-Butoxycarbonylamino-methyl)-pyrrolidin-1-ylmethyl]-3-trifluoromethyl-benzoic acid ethyl ester

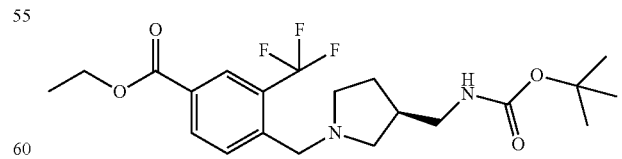

The title compound was synthesized from 4-bromomethyl-3-trifluoromethyl-benzoic acid ethyl ester (Compound b6) and (R)-1-pyrrolidin-3-ylmethyl-carbamic acid tert-butyl ester under the same conditions as for Compound b7.

Example 94

Compound B-38

4-((S)-3-Aminomethyl-pyrrolidin-1-ylmethyl)-N-(5-chloro-2-ethanesulfonyl-benzyl)-3-trifluoromethyl-benzamide

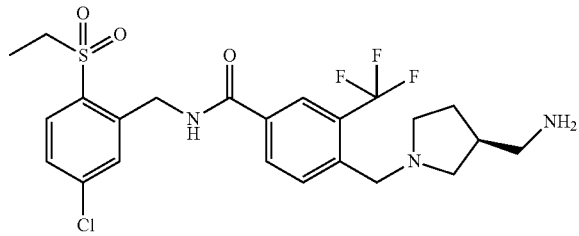 [SMILES: CCS(=O)(=O)c1ccc(Cl)cc1CNC(=O)c1ccc(CN2CC[C@@H](CN)C2)c(C(F)(F)F)c1]

The title compound was synthesized from 4-[(S)-3-(tert-butoxycarbonylamino-methyl)-pyrrolidin-1-ylmethyl]-3-trifluoromethyl-benzoic acid ethyl ester (Compound b19) under the same conditions as for Compounds b3, b4, and B-1. However, the reaction was performed using DCM in place of DMF under the conditions for Compound b4.

LCMS: m/z 518 [M+H]$^+$
HPLC retention time: 0.39 min (analysis condition A)

Example 95

Compound B-39

N-(5-Chloro-2-ethanesulfonyl-benzyl)-4-((S)-3-dimethylaminomethyl-pyrrolidin-1-ylmethyl)-3-trifluoromethyl-benzamide

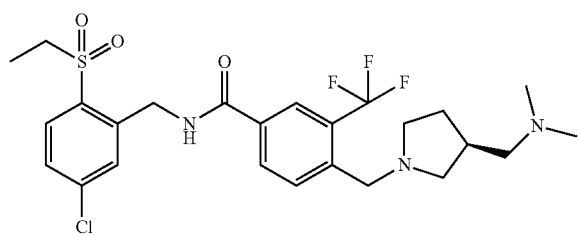 [SMILES: CCS(=O)(=O)c1ccc(Cl)cc1CNC(=O)c1ccc(CN2CC[C@@H](CN(C)C)C2)c(C(F)(F)F)c1]

The title compound was synthesized from 4-((S)-3-aminomethyl-pyrrolidin-1-ylmethyl)-N-(5-chloro-2-ethanesulfonyl-benzyl)-3-trifluoromethyl-benzamide (Compound B-38) under the same conditions as for Compound B-2.

LCMS: m/z 546 [M+H]$^+$
HPLC retention time: 0.41 min (analysis condition A)

Example 96

Compound B-40

4-[(S)-3-(Acetylamino-methyl)-pyrrolidin-1-ylmethyl]-N-(5-chloro-2-ethanesulfonyl-benzyl)-3-trifluoromethyl-benzamide

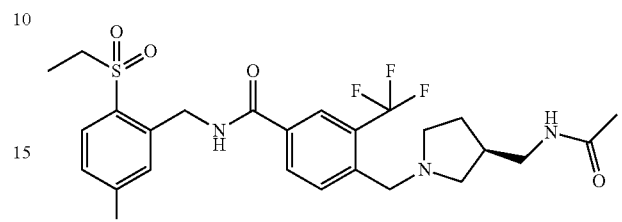

The title compound was synthesized from 4-((S)-3-aminomethyl-pyrrolidin-1-ylmethyl)-N-(5-chloro-2-ethanesulfonyl-benzyl)-3-trifluoromethyl-benzamide (Compound B-38) under the same conditions as for Compound B-7.

LCMS: m/z 560 [M+H]$^+$
HPLC retention time: 0.49 min (analysis condition A)

Example 97

Compound B-41

N-(5-Chloro-2-ethanesulfonyl-benzyl)-4-[(R)-3-(methanesulfonylamino-methyl)-pyrrolidin-1-ylmethyl]-3-trifluoromethyl-benzamide

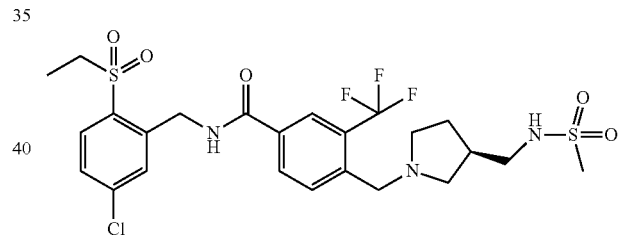

The title compound was synthesized from 4-((S)-3-aminomethyl-pyrrolidin-1-ylmethyl)-N-(5-chloro-2-ethanesulfonyl-benzyl)-3-trifluoromethyl-benzamide (Compound B-38) under the same conditions as for Compound B-9.

LCMS: m/z 596 [M+H]$^+$
HPLC retention time: 0.51 min (analysis condition A)

Example 98

Compound b20

4-[(S)-3-(tert-Butoxycarbonylamino-methyl)-pyrrolidin-1-ylmethyl]-3-trifluoromethyl-benzoic acid

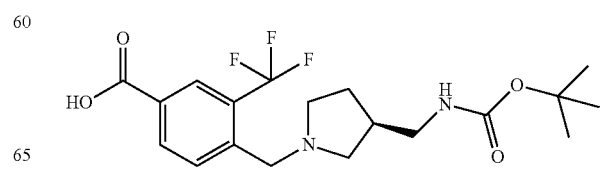

The title compound was synthesized from 4-[(S)-3-(tert-butoxycarbonylamino-methyl)-pyrrolidin-1-ylmethyl]-3-trifluoromethyl-benzoic acid ethyl ester (Compound b19) under the same conditions as for Compound b8. However, the reaction was performed at room temperature.

LCMS: m/z 403 [M+H]$^+$

HPLC retention time: 1.35 min (analysis condition E)

Example 99

Compound b21

4-{(R)-3-[(tert-Butoxycarbonyl-methyl-amino)-methyl]-pyrrolidin-1-ylmethyl}-3-trifluoromethyl-benzoic acid

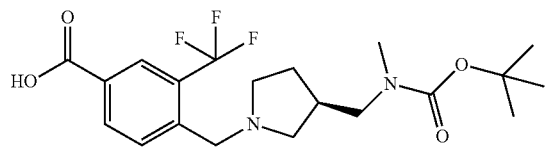 [SMILES: CN(C[C@@H]1CCN(Cc2ccc(C(=O)O)cc2C(F)(F)F)C1)C(=O)OC(C)(C)C]

A 60% dispersion of sodium hydride in mineral oil (oil dispersion) (36.5 mg, 0.91 mmol) was added to a solution of 4-[(S)-3-(tert-butoxycarbonylamino-methyl)-pyrrolidin-1-ylmethyl]-3-trifluoromethyl-benzoic acid (Compound b20, 92 mg, 0.23 mmol) in THF under ice-cooling, and the mixture was stirred at room temperature for 0.5 hour. Methyl iodide (57.8 µl, 0.93 mmol) was added thereto, and the mixture was stirred at room temperature for two hours. Water was added to the reaction solution. After extraction with ethyl acetate, the extract was dried over anhydrous sodium sulfate. The drying agent was removed by filtration, and concentration was performed under reduced pressure to yield the title compound as a crude product.

Example 100

Compound b22

{(R)-1-[4-(5-Chloro-2-ethanesulfonyl-benzylcarbamoyl)-2-trifluoromethyl-benzyl]-pyrrolidin-3-ylmethyl}-methyl-carbamic acid tert-butyl ester

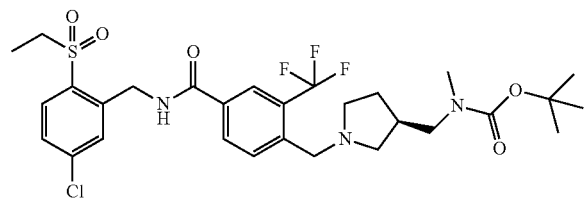 [SMILES: CCS(=O)(=O)c1ccc(Cl)cc1CNC(=O)c1ccc(CN2CC[C@@H](CN(C)C(=O)OC(C)(C)C)C2)c(C(F)(F)F)c1]

The title compound was synthesized from 4-{(R)-3-[(tert-butoxycarbonyl-methyl-amino)-methyl]-pyrrolidin-1-ylmethyl}-3-trifluoromethyl-benzoic acid (Compound b21) using DCM in place of DMF under the same conditions as for Compound A-14.

Example 101

Compound B-42

N-(5-Chloro-2-ethanesulfonyl-benzyl)-4-((S)-3-methylaminomethyl-pyrrolidin-1-ylmethyl)-3-trifluoromethyl-benzamide

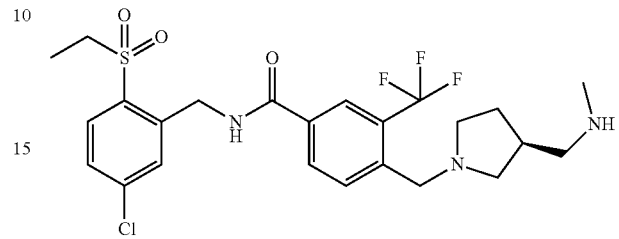

The title compound was synthesized from {(R)-1-[4-(5-chloro-2-ethanesulfonyl-benzylcarbamoyl)-2-trifluoromethyl-benzyl]-pyrrolidin-3-ylmethyl}-methyl-carbamic acid tert-butyl ester (Compound b22) under the same conditions as for Compound B-1.

LCMS: m/z 532 [M+H]$^+$

HPLC retention time: 0.40 min (analysis condition A)

Example 102

Compound b23

4-[(R)-3-(tert-Butoxycarbonylamino-methyl)-pyrrolidin-1-ylmethyl]-3-trifluoromethyl-benzoic acid ethyl ester

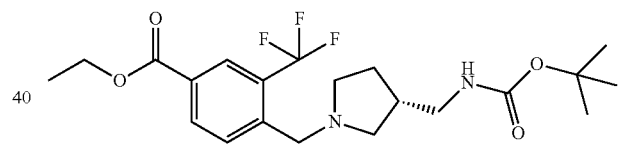

The title compound was synthesized from 4-bromomethyl-3-trifluoromethyl-benzoic acid ethyl ester (Compound b6) and (S)-1-pyrrolidin-3-ylmethyl-carbamic acid tert-butyl ester under the same conditions as for Compound b7.

Example 103

Compound B-43

4-((R)-3-Aminomethyl-pyrrolidin-1-ylmethyl)-N-(5-chloro-2-ethanesulfonyl-benzyl)-3-trifluoromethyl-benzamide

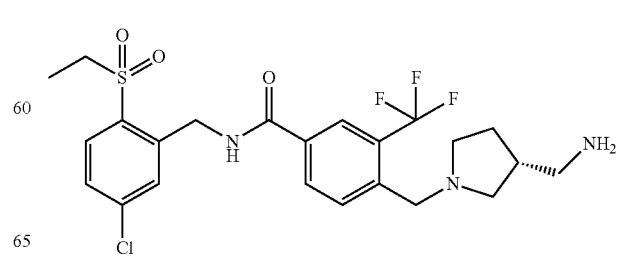

The title compound was synthesized from 4-[(R)-3-(tert-butoxycarbonylamino-methyl)-pyrrolidin-1-ylmethyl]-3-trifluoromethyl-benzoic acid ethyl ester (Compound b23) under the same conditions as for Compounds b3, b4, and B-1. However, the reaction was performed using DCM in place of DMF under the conditions for Compound b4.

LCMS: m/z 518 [M+H]$^+$

HPLC retention time: 0.40 min (analysis condition A)

Example 104

Compound B-44

N-(5-Chloro-2-ethanesulfonyl-benzyl)-4-((R)-3-dimethylaminomethyl-pyrrolidin-1-ylmethyl)-3-trifluoromethyl-benzamide

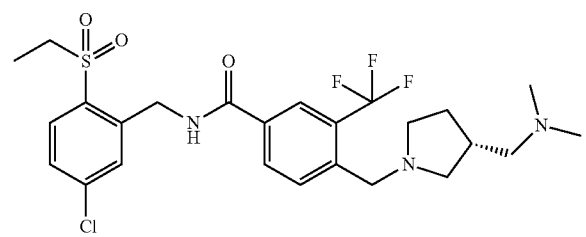 [SMILES: CCS(=O)(=O)c1ccc(Cl)cc1CNC(=O)c1ccc(CN2CC[C@H](CN(C)C)C2)c(C(F)(F)F)c1]

The title compound was synthesized from 4-((R)-3-aminomethyl-pyrrolidin-1-ylmethyl)-N-(5-chloro-2-ethanesulfonyl-benzyl)-3-trifluoromethyl-benzamide (Compound B-43) under the same conditions as for Compound B-2.

LCMS: m/z 546 [M+H]$^+$

HPLC retention time: 0.41 min (analysis condition A)

Example 105

Compound B-45

4-[(R)-3-(Acetylamino-methyl)-pyrrolidin-1-ylmethyl]-N-(5-chloro-2-ethanesulfonyl-benzyl)-3-trifluoromethyl-benzamide

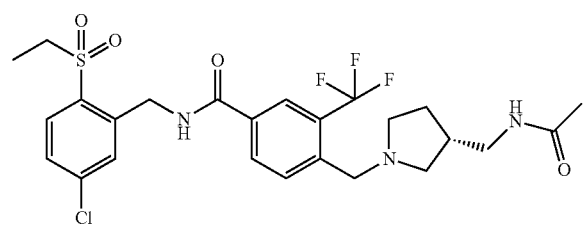 [SMILES: CCS(=O)(=O)c1ccc(Cl)cc1CNC(=O)c1ccc(CN2CC[C@H](CNC(C)=O)C2)c(C(F)(F)F)c1]

The title compound was synthesized from 4-((R)-3-aminomethyl-pyrrolidin-1-ylmethyl)-N-(5-chloro-2-ethanesulfonyl-benzyl)-3-trifluoromethyl-benzamide (Compound B-43) under the same conditions as for Compound B-7.

LCMS: m/z 560 [M+H]$^+$

HPLC retention time: 0.48 min (analysis condition A)

Example 106

Compound B-46

N-(5-Chloro-2-ethanesulfonyl-benzyl)-4-[(S)-3-(methanesulfonylamino-methyl)-pyrrolidin-1-ylmethyl]-3-trifluoromethyl-benzamide

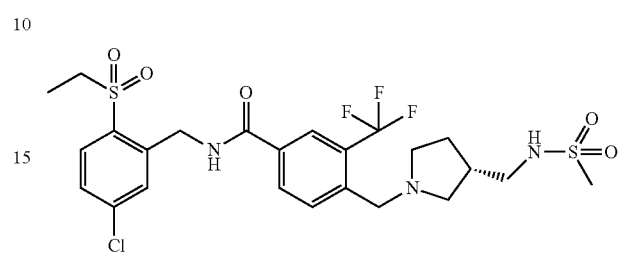

The title compound was synthesized from 4-((R)-3-aminomethyl-pyrrolidin-1-ylmethyl)-N-(5-chloro-2-ethanesulfonyl-benzyl)-3-trifluoromethyl-benzamide (Compound B-43) under the same conditions as for Compound B-9.

LCMS: m/z 596 [M+H]$^+$

HPLC retention time: 0.51 min (analysis condition A)

Example 107

Compound b24

4-{(S)-3-[(tert-Butoxycarbonyl-methyl-amino)-methyl]-pyrrolidin-1-ylmethyl}-3-trifluoromethyl-benzoic acid ethyl ester

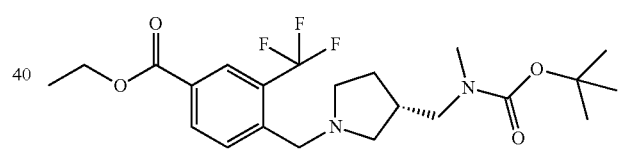

The title compound was obtained as a crude product from 4-[(R)-3-(tert-butoxycarbonylamino-methyl)-pyrrolidin-1-ylmethyl]-3-trifluoromethyl-benzoic acid ethyl ester (Compound b23) under the same conditions as for Compound b21.

Example 108

Compound b25

4-{(S)-3-[(tert-Butoxycarbonyl-methyl-amino)-methyl]-pyrrolidin-1-ylmethyl}-3-trifluoromethyl-benzoic acid

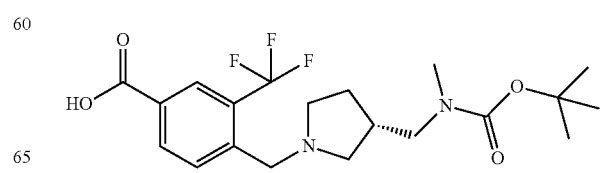

The title compound was obtained from the crude product of 4-{(S)-3-[(tert-butoxycarbonyl-methyl-amino)-methyl]-pyrrolidin-1-ylmethyl}-3-trifluoromethyl-benzoic acid ethyl ester (Compound b24) under the same conditions as for Compound b3.

Example 109

Compound b26

{(S)-1-[4-(5-Chloro-2-ethanesulfonyl-benzylcarbamoyl)-2-trifluoromethyl-benzyl]-pyrrolidin-3-ylmethyl}-methyl-carbamic acid tert-butyl ester

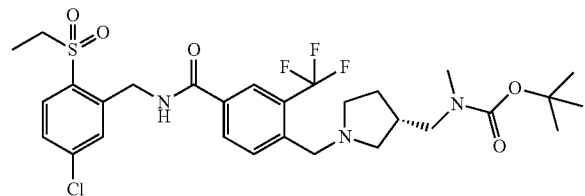 [SMILES: CCS(=O)(=O)c1ccc(Cl)cc1CNC(=O)c1ccc(CN2CC[C@H](CN(C)C(=O)OC(C)(C)C)C2)c(C(F)(F)F)c1]

The title compound was synthesized from 4-{(S)-3-[(tert-butoxycarbonyl-methyl-amino)-methyl]-pyrrolidin-1-ylmethyl}-3-trifluoromethyl-benzoic acid (Compound b25) under the same conditions as for Compound A-14.

Example 110

Compound B-47

N-(5-Chloro-2-ethanesulfonyl-benzyl)-4-((R)-3-methylaminomethyl-pyrrolidin-1-ylmethyl)-3-trifluoromethyl-benzamide

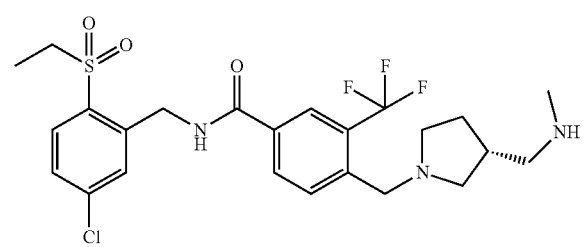 [SMILES: CCS(=O)(=O)c1ccc(Cl)cc1CNC(=O)c1ccc(CN2CC[C@H](CNC)C2)c(C(F)(F)F)c1]

The title compound was synthesized from {(S)-1-[4-(5-chloro-2-ethanesulfonyl-benzylcarbamoyl)-2-trifluoromethyl-benzyl]-pyrrolidin-3-ylmethyl}-methyl-carbamic acid tert-butyl ester (Compound b26) under the same conditions as for Compound B-1.

LCMS: m/z 532 [M+H]$^+$

HPLC retention time: 0.41 min (analysis condition A)

Example 111

Compound B-48

N-(5-Chloro-2-ethanesulfonyl-benzyl)-4-((R)-3-hydroxy-pyrrolidin-1-ylmethyl)-3-trifluoromethyl-benzamide

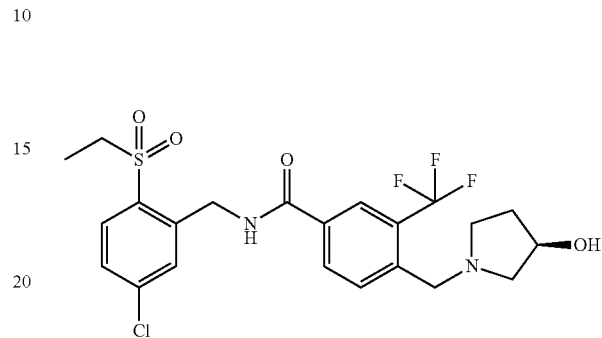

The title compound was synthesized from 4-bromomethyl-3-trifluoromethyl-benzoic acid ethyl ester (Compound b6) and (R)-pyrrolidin-3-ol under the same conditions as for Compounds b7, b8, and b9. However, potassium hydroxide was used in place of sodium hydroxide under the conditions for Compound b8.

LCMS: m/z 505 [M+H]$^+$

HPLC retention time: 0.49 min (analysis condition A)

Example 112

Compound B-49

N-(5-Chloro-2-ethanesulfonyl-benzyl)-4-((R)-3-methoxy-pyrrolidin-1-ylmethyl)-3-trifluoromethyl-benzamide

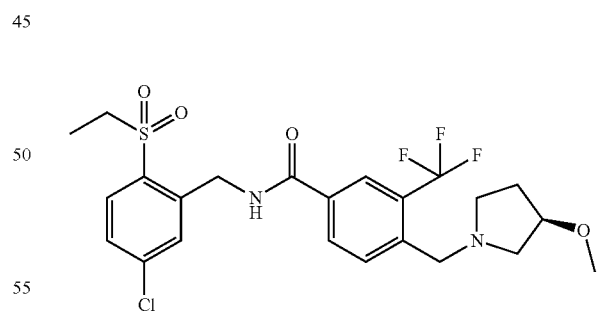

The title compound was synthesized from 4-bromomethyl-3-trifluoromethyl-benzoic acid ethyl ester (Compound b6) and (R)-3-methoxy-pyrrolidine under the same conditions as for Compounds b7, b8, and b9. However, potassium hydroxide was used in place of sodium hydroxide under the conditions for Compound b8.

LCMS: m/z 519 [M+H]$^+$

HPLC retention time: 0.53 min (analysis condition A)

Example 113

Compound B-50

N-(5-Chloro-2-ethanesulfonyl-benzyl)-4-pyrrolidin-1-ylmethyl-3-trifluoromethyl-benzamide

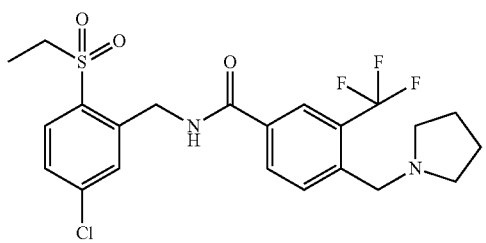 [SMILES: CCS(=O)(=O)c1ccc(Cl)cc1CNC(=O)c1ccc(CN2CCCC2)c(C(F)(F)F)c1]

The title compound was synthesized from 4-bromomethyl-3-trifluoromethyl-benzoic acid ethyl ester (Compound b6) and pyrrolidine under the same conditions as for Compounds b7, b8, and b9. However, potassium hydroxide was used in place of sodium hydroxide under the conditions for Compound b8.

LCMS: m/z 489 [M+H]$^+$
HPLC retention time: 0.51 min (analysis condition A)

Example 114

Compound b27

2-Amino-4-chloro-5-trifluoromethyl-benzoic acid ethyl ester

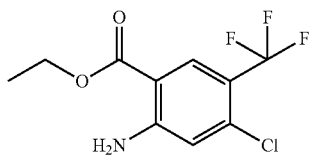 [SMILES: CCOC(=O)c1cc(C(F)(F)F)c(Cl)cc1N]

Boc$_2$O (53.3 ml, 240 mmol) was added to a suspension of 2-bromo-5-chloro-4-trifluoromethyl-phenylamine (26.8 g, 98 mmol) and DMAP (2.39 g, 20 mmol) in THF (500 ml), and the mixture was stirred at room temperature for 2.5 hours. The reaction solution was concentrated under reduced pressure, and the resulting residue was purified by silica gel column chromatography (ethyl acetate/hexane) to yield 4-(bis(tert-butoxycarbonyl)amino)-5-bromo-2-chloro-1-trifluoromethylbenzene (45.9 g, 99%) as a colorless solid.

HPLC retention time: 1.12 min (analysis condition A)
1H-NMR (400 MHz, CDCl$_3$) δ: 7.92 (1H, s), 7.40 (1H, s), 1.43 (18H, s).

A 1.57 M solution of n-BuLi in hexane (33 ml, 52 mmol) was added to a solution of 4-(bis(tert-butoxycarbonyl)amino)-5-bromo-2-chloro-1-trifluoromethylbenzene (20.5 g, 43 mmol) in THF (430 ml) over 10 minutes at −78° C., and then this was stirred for one hour. A saturated aqueous ammonium chloride solution (200 ml) was added thereto, and the mixture was then warmed to room temperature. Ethyl acetate (400 ml) was added thereto, and this was washed with a saturated aqueous sodium chloride solution. The organic layer was dried over anhydrous sodium sulfate. The drying agent was removed by filtration. After concentration under reduced pressure, the resulting residue was purified by silica gel column chromatography (ethyl acetate/hexane) to yield 2-tert-butoxycarbonylamino-4-chloro-5-trifluoromethyl-benzoic acid tert-butyl ester (13.9 g, 82%) as a colorless solid.

HPLC retention time: 1.29 min (analysis condition A)
1H-NMR (400 MHz, CDCl$_3$) δ: 10.55 (1H, s), 8.72 (1H, s), 8.22 (1H, s), 1.62 (9H, s), 1.55 (9H, s).

Trifluoroacetic acid (88 ml) was added to a solution of 2-tert-butoxycarbonylamino-4-chloro-5-trifluoromethyl-benzoic acid tert-butyl ester (13.9 g, 35 mmol) in DCM (350 ml), and the mixture was stirred at room temperature for 15 hours. The reaction solution was concentrated under reduced pressure to yield 2-amino-4-chloro-5-trifluoromethyl-benzoic acid as a crude product.

LCMS: m/z 240 [M+H]$^+$
HPLC retention time: 0.71 min (analysis condition A)

Potassium carbonate (19.4 g, 141 mmol) and ethyl iodide (4.22 ml, 53 mmol) were added to a solution of the crude product of 2-amino-4-chloro-5-trifluoromethyl-benzoic acid, which was obtained as mentioned above, in DMF (176 ml), and the mixture was stirred at room temperature for two hours. Water (170 ml) was added to the reaction solution. After extraction with ethyl acetate, the extract was washed with a saturated aqueous sodium chloride solution and dried over anhydrous sodium sulfate. The drying agent was removed by filtration. After concentration under reduced pressure, the resulting residue was purified by silica gel column chromatography (ethyl acetate/hexane) to yield 2-amino-4-chloro-5-trifluoromethyl-benzoic acid ethyl ester (5.89 g, 63%) as a yellow solid.

LCMS: m/z 268 [M+H]$^+$
HPLC retention time: 0.93 min (analysis condition A)

Example 115

Compound b28

2-Amino-5-trifluoromethyl-4-vinyl-benzoic acid ethyl ester

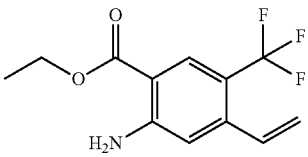 [SMILES: C=Cc1cc(N)c(C(=O)OCC)cc1C(F)(F)F]

Distilled water (112 ml) was added to a suspension of 2-amino-4-chloro-5-trifluoromethyl-benzoic acid ethyl ester (Compound b27, 9.00 g, 34 mmol), potassium vinyltrifluoroborate (6.31 g, 47 mmol), BuPAd2 (1.21 g, 3.4 mmol), palladium acetate (378 mg, 1.7 mmol), and potassium carbonate (13.9 g, 100 mmol) in toluene (336 ml), and the mixture was stirred at 90° C. under an argon atmosphere for 18 hours. The reaction solution was cooled to room temperature, and ethyl acetate was then added thereto, and this was washed with water. The organic layer was dried over anhydrous sodium sulfate. The drying agent was removed by filtration. After concentration under reduced pressure, the resulting residue was purified by silica gel column chromatography (ethyl acetate/hexane) to yield the title compound (7.93 g, 91%) as a yellow solid.

LCMS: m/z 260 [M+H]$^+$
HPLC retention time: 0.94 min (analysis condition A)

Example 116

Compound b29

2-Amino-4-(1,2-dihydroxy-ethyl)-5-trifluoromethyl-benzoic acid ethyl ester

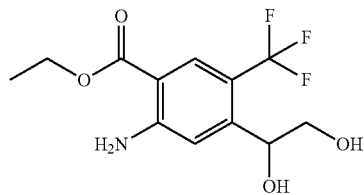 [SMILES: CCOC(=O)c1cc(C(F)(F)F)c(C(O)CO)cc1N]

A mixture of AD-mix-α (61.3 g) in t-BuOH/water (140 ml/140 ml) was stirred at room temperature for five minutes. A mixture of 2-amino-5-trifluoromethyl-4-vinyl-benzoic acid ethyl ester (Compound b28, 14.4 g, 56 mmol) in t-BuOH/water (140 ml/140 ml) was added to this reaction solution, and the mixture was stirred at room temperature for 0.5 hour. Sodium nitrite (35.1 g) was added to the reaction mixture, and the mixture was stirred at room temperature for one hour. Ethyl acetate was added to the reaction mixture. After washing with a saturated aqueous sodium chloride solution, the organic layer was dried over anhydrous sodium sulfate. The drying agent was removed by filtration. After concentration under reduced pressure, the resulting solid was washed with DCM to yield the title compound (12.9 g, 79%) as a colorless solid.

LCMS: m/z 294 [M+H]$^+$

HPLC retention time: 0.63 min (analysis condition A)

Example 117

Compound b30

2-Amino-4-formyl-5-trifluoromethyl-benzoic acid ethyl ester

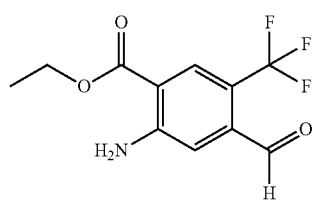 [SMILES: CCOC(=O)c1cc(C(F)(F)F)c(C=O)cc1N]

Water (273 ml) and sodium periodate (16.4 g, 76 mmol) were added to a solution of 2-amino-4-(1,2-dihydroxy-ethyl)-5-trifluoromethyl-benzoic acid ethyl ester (Compound b29, 16.0 g, 54 mmol) in TBME (546 ml), and the mixture was stirred at room temperature for seven hours. TBME was added to the reaction mixture. After washing with a saturated aqueous sodium chloride solution, the organic layer was dried over anhydrous sodium sulfate. The drying agent was removed by filtration, and concentration was performed under reduced pressure to yield the title compound (14.1 g, 99%) as a yellow solid.

LCMS: m/z 262 [M+H]$^+$

HPLC retention time: 0.87 min (analysis condition A)

Example 118

Compound b31

4-Formyl-3-trifluoromethyl-benzoic acid ethyl ester

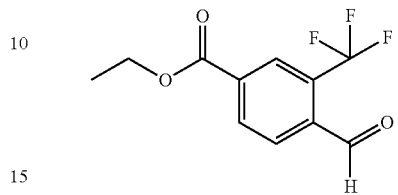

Sodium nitrite (2.6 g, 38.3 mmol) was added to a solution of 2-amino-4-formyl-5-trifluoromethyl-benzoic acid ethyl ester (Compound b30, 1.00 g, 3.83 mmol) in formic acid (12 mL) under ice-cooling, and the mixture was stirred under ice-cooling for 30 minutes. A saturated aqueous sodium bicarbonate solution was added thereto. After extraction with ethyl acetate, the extract was washed with saturated saline and then dried over anhydrous magnesium sulfate. The drying agent was removed by filtration. After concentration under reduced pressure, the resulting residue was purified by silica gel column chromatography (ethyl acetate/hexane) to yield the title compound (650 mg, 71%).

1H-NMR (300 MHz, CDCl$_3$) δ: 10.44 (1H, s), 8.44 (1H, s), 8.34 (1H, d, J=8.2 Hz), 8.20 (1H, d, J=8.2 Hz), 4.46 (2H, q, J=7.1 Hz), 1.44 (3H, t, J=7.1 Hz).

Example 119

Compound b32

4-[(S)-2-(tert-Butoxycarbonylamino-methyl)-pyrrolidin-1-ylmethyl]-3-trifluoromethyl-benzoic acid ethyl ester

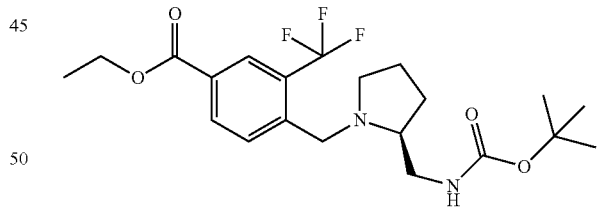

(S)-1-Pyrrolidin-2-ylmethyl-carbamic acid tert-butyl ester (488 mg, 2.4 mmol) and sodium triacetoxyborohydride (516 mg, 2.4 mmol) were added to a solution of 4-formyl-3-trifluoromethyl-benzoic acid ethyl ester (Compound b31, 200 mg, 0.81 mmol) in THF (8 ml), and the mixture was stirred at room temperature for one hour. The reaction solution was diluted with ethyl acetate, and the organic layer was washed with a saturated aqueous sodium bicarbonate solution, water, and saturated saline, and then dried over anhydrous sodium sulfate. The drying agent was removed by filtration. After concentration under reduced pressure, the resulting residue was purified by silica gel column chromatography (ethyl acetate/hexane) to yield the title compound (265 mg, 76%) as an oily substance.

1H-NMR (300 MHz, CDCl₃) δ: 8.29 (1H, s), 8.18 (1H, d, J=8.2 Hz), 7.85 (1H, d, J=8.2 Hz), 4.83 (1H, brs), 4.41 (2H, q, J=7.2 Hz), 4.11 (1H, d, J=14.8 Hz), 3.63 (1H, d, J=14.8 Hz), 3.37-3.26 (1H, m), 3.14-3.06 (1H, m), 2.95-2.89 (1H, m), 2.82-2.72 (1H, m), 2.23-2.14 (1H, m), 1.99-1.89 (1H, m), 1.78-1.62 (3H, m), 1.44 (9H, s), 1.41 (3H, t, J=7.2 Hz).

Example 120

Compound b33

4-[(S)-2-(tert-Butoxycarbonylamino-methyl)-pyrrolidin-1-ylmethyl]-3-trifluoromethyl-benzoic acid

The title compound was synthesized from 4-[(S)-2-(tert-butoxycarbonylamino-methyl)-pyrrolidin-1-ylmethyl]-3-trifluoromethyl-benzoic acid ethyl ester (Compound b32) under the same conditions as for Compound b8.

Example 121

Compound b34

{(S)-1-[4-(5-Chloro-2-ethanesulfonyl-benzylcarbamoyl)-2-trifluoromethyl-benzyl]-pyrrolidin-2-ylmethyl}-carbamic acid tert-butyl ester

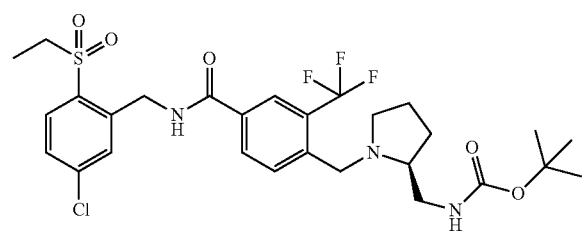 [SMILES: CCS(=O)(=O)c1ccc(Cl)cc1CNC(=O)c1ccc(CN2CCC[C@H]2CNC(=O)OC(C)(C)C)c(C(F)(F)F)c1]

The title compound was synthesized from 4-[(S)-2-(tert-butoxycarbonylamino-methyl)-pyrrolidin-1-ylmethyl]-3-trifluoromethyl-benzoic acid (Compound b33) under the same conditions as for Compound A-14.

Example 122

Compound B-51

4-((S)-2-Aminomethyl-pyrrolidin-1-ylmethyl)-N-(5-chloro-2-ethanesulfonyl-benzyl)-3-trifluoromethyl-benzamide

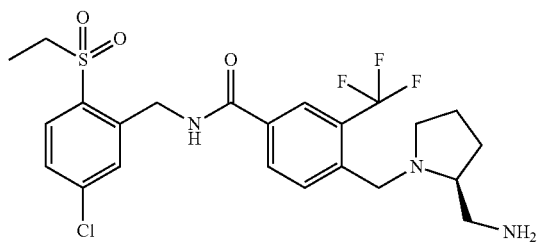 [SMILES: CCS(=O)(=O)c1ccc(Cl)cc1CNC(=O)c1ccc(CN2CCC[C@H]2CN)c(C(F)(F)F)c1]

The title compound was synthesized from {(S)-1-[4-(5-chloro-2-ethanesulfonyl-benzylcarbamoyl)-2-trifluoromethyl-benzyl]-pyrrolidin-2-ylmethyl}-carbamic acid tert-butyl ester (Compound b34) under the same conditions as for Compound B-1.

LCMS: m/z 518 [M+H]⁺

HPLC retention time: 0.50 min (analysis condition A)

Examples 123 to 125

The compounds of FIG. 6 were synthesized using 4-formyl-3-trifluoromethyl-benzoic acid ethyl ester (Compound b31) and the corresponding cyclic amines under the same conditions as for Compounds b32, b33, b34, and B-51.

Example 126

Compound B-52

N-(5-Chloro-2-ethanesulfonyl-benzyl)-4-((S)-2-dimethylaminomethyl-pyrrolidin-1-ylmethyl)-3-trifluoromethyl-benzamide

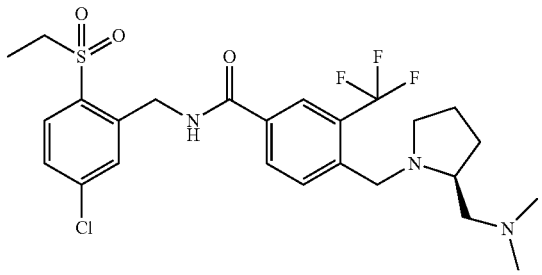 [SMILES: CCS(=O)(=O)c1ccc(Cl)cc1CNC(=O)c1ccc(CN2CCC[C@H]2CN(C)C)c(C(F)(F)F)c1]

The title compound was synthesized from 4-((S)-2-aminomethyl-pyrrolidin-1-ylmethyl)-N-(5-chloro-2-ethanesulfonyl-benzyl)-3-trifluoromethyl-benzamide (Compound B-51) under the same conditions as for Compound B-2.

LCMS: m/z 546 [M+H]$^+$

HPLC retention time: 0.53 min (analysis condition A)

Example 127

Compound B-55

N-(5-Chloro-2-ethanesulfonyl-benzyl)-4-((R)-2-dimethylaminomethyl-pyrrolidin-1-ylmethyl)-3-trifluoromethyl-benzamide

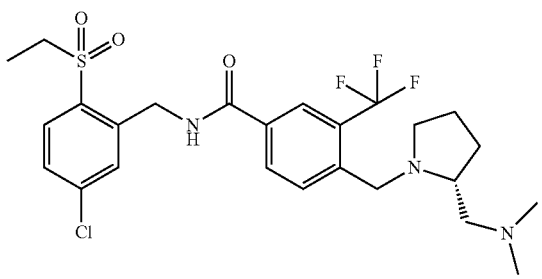 [SMILES: CCS(=O)(=O)c1ccc(Cl)cc1CNC(=O)c1ccc(CN2CCC[C@@H]2CN(C)C)c(C(F)(F)F)c1]

The title compound was synthesized from 4-((R)-2-aminomethyl-pyrrolidin-1-ylmethyl)-N-(5-chloro-2-ethanesulfonyl-benzyl)-3-trifluoromethyl-benzamide (Compound B-54) under the same conditions as for Compound B-2.

LCMS: m/z 546 [M+H]$^+$

HPLC retention time: 0.54 min (analysis condition A)

Example 128

Compound b35

4-Dibromomethyl-3-trifluoromethyl-benzoic acid

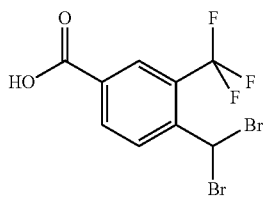 [SMILES: O=C(O)c1ccc(C(Br)Br)c(C(F)(F)F)c1]

NBS (2.18 g, 12 mmol) and BPO/H$_2$O (79.1 mg, 0.24 mmol) were added to a solution of 4-methyl-3-trifluoromethyl-benzoic acid (1.00 g, 4.9 mmol) in CC14 (20 ml), and the mixture was heated under reflux for 24 hours. Hexane was added to the reaction mixture, and extraction was performed with a 0.5N aqueous sodium hydroxide solution. A 0.5N aqueous hydrochloric acid solution was added thereto, and extraction was performed with isopropyl acetate and cyclopentylmethyl ether. The organic layer was then washed with saturated saline and dried over anhydrous sodium sulfate. The drying agent was removed by filtration, and concentration was performed under reduced pressure to yield the title compound (1.78 g, 100%) as a pale yellow powder.

LCMS: m/z 359 [M−H]$^-$

HPLC retention time: 0.81 min (analysis condition A)

Example 129

Compound b36

4-Formyl-3-trifluoromethyl-benzoic acid

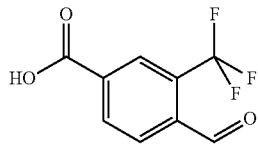 [SMILES: O=Cc1ccc(C(=O)O)cc1C(F)(F)F]

An aqueous solution (7 ml) of silver nitrate (2.04 g, 12 mmol) was added to a solution of 4-dibromomethyl-3-trifluoromethyl-benzoic acid (Compound b35, 1.74 g, 4.8 mmol) in acetone (35 ml), and the mixture was stirred at 60° C. for 26 hours. An aqueous solution (1 ml) of silver nitrate (407 mg, 2.4 mmol) was added thereto, and the mixture was stirred at 60° C. for further 16 hours. Isopropyl acetate and a 1N aqueous hydrochloric acid solution were added to the reaction mixture, and the solid was removed by filtration. The filtrate was extracted with isopropyl acetate twice, and the organic layer was then washed with saturated saline and dried over anhydrous sodium sulfate. The drying agent was removed by filtration, and concentration was performed under reduced pressure to yield the title compound as a crude product.

Example 130

Compound b37

N-(5-Chloro-2-ethanesulfonyl-benzyl)-4-formyl-3-trifluoromethyl-benzamide

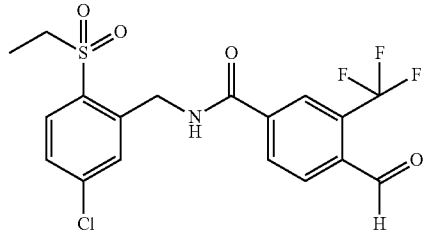 [SMILES: CCS(=O)(=O)c1ccc(Cl)cc1CNC(=O)c1ccc(C=O)c(C(F)(F)F)c1]

The title compound was synthesized from the crude product of 4-formyl-3-trifluoromethyl-benzoic acid (Compound b36) under the same conditions as for Compound A-14.

Example 131

Compound b38

{(S)-1-[4-(5-Chloro-2-ethanesulfonyl-benzylcarbamoyl)-2-trifluoromethyl-benzyl]-piperidin-3-ylmethyl}-carbamic acid tert-butyl ester

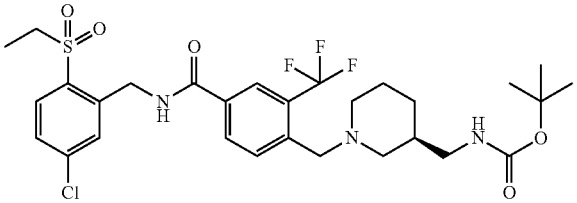 [SMILES: CCS(=O)(=O)c1ccc(Cl)cc1CNC(=O)c1ccc(CN2CCC[C@@H](CNC(=O)OC(C)(C)C)C2)c(C(F)(F)F)c1]

The title compound was synthesized from N-(5-chloro-2-ethanesulfonyl-benzyl)-4-formyl-3-trifluoromethyl-benzamide (Compound b37) under the same conditions as for Compound b32. However, the reaction was performed using chloroform in place of THF as a solvent, and (R)-1-piperidin-3-ylmethyl-carbamic acid tert-butyl ester in place of (S)-1-pyrrolidin-2-ylmethyl-carbamic acid tert-butyl ester.

Example 132

Compound B-57

4-((S)-3-Aminomethyl-piperidin-1-ylmethyl)-N-(5-chloro-2-ethanesulfonyl-benzyl)-3-trifluoromethyl-benzamide

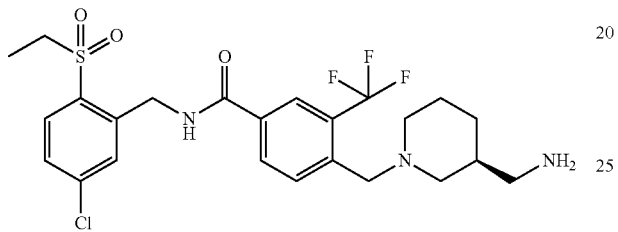

A 4N solution of hydrochloric acid in ethyl acetate (3 ml) was added to a solution of {(S)-1-[4-(5-chloro-2-ethanesulfonyl-benzylcarbamoyl)-2-trifluoromethyl-benzyl]-piperidin-3-ylmethyl}-carbamic acid tert-butyl ester (Compound b38, 267 mg, 0.42 mmol) in ethyl acetate (1 ml), and the mixture was stirred at room temperature for one hour. A 1N aqueous sodium hydroxide solution was added to the reaction mixture, and extraction was performed with ethyl acetate. The organic layer was then washed with saturated saline and dried over anhydrous sodium sulfate. The drying agent was removed by filtration. After concentration under reduced pressure, the resulting residue was purified by amino silica gel column chromatography (methanol/ethyl acetate) to yield the title compound (186 mg, 83%) as a colorless foamy sub stance.

LCMS: m/z 532 [M+H]+

HPLC retention time: 0.42 min (analysis condition A)

Example 133

Compound B-58

N-(5-Chloro-2-ethanesulfonyl-benzyl)-4-((S)-3-dimethylaminomethyl-piperidin-1-ylmethyl)-3-trifluoromethyl-benzamide

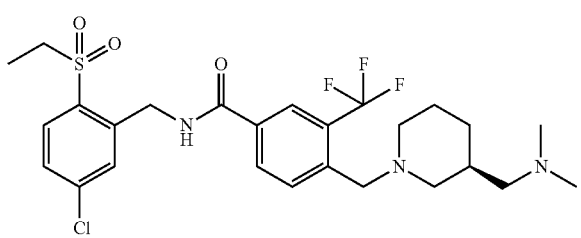 [SMILES: CCS(=O)(=O)c1ccc(Cl)cc1CNC(=O)c1ccc(CN2CCC[C@@H](CN(C)C)C2)c(C(F)(F)F)c1]

The title compound was synthesized from 4-((S)-3-aminomethyl-piperidin-1-ylmethyl)-N-(5-chloro-2-ethanesulfonyl-benzyl)-3-trifluoromethyl-benzamide (Compound B-57) under the same conditions as for Compound B-2.

LCMS: m/z 560 [M+H]+

HPLC retention time: 0.43 min (analysis condition A)

Example 134

Compound B-59

4-[(S)-3-(Acetylamino-methyl)-piperidin-1-ylmethyl]-N-(5-chloro-2-ethanesulfonyl-benzyl)-3-trifluoromethyl-benzamide

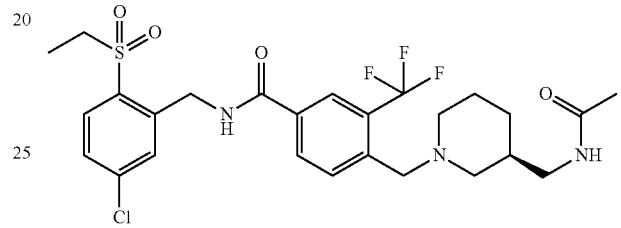

The title compound was synthesized from 4-((S)-3-aminomethyl-piperidin-1-ylmethyl)-N-(5-chloro-2-ethanesulfonyl-benzyl)-3-trifluoromethyl-benzamide (Compound B-57) using DMF in place of DCM under the same conditions as for Compound B-7.

LCMS: m/z 574 [M+H]+

HPLC retention time: 0.51 min (analysis condition A)

Example 135

Compound B-60

N-(5-Chloro-2-ethanesulfonyl-benzyl)-4-[(R)-3-(methanesulfonylamino-methyl)-piperidin-1-ylmethyl]-3-trifluoromethyl-benzamide

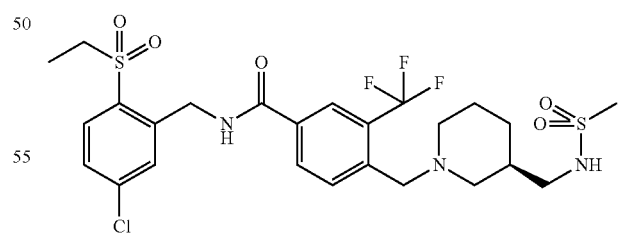

The title compound was synthesized from 4-((S)-3-aminomethyl-piperidin-1-ylmethyl)-N-(5-chloro-2-ethanesulfonyl-benzyl)-3-trifluoromethyl-benzamide (Compound B-57) using DMF in place of DCM under the same conditions as for Compound B-9.

LCMS: m/z 610 [M+H]+

HPLC retention time: 0.53 min (analysis condition A)

Example 136

Compound B-61

4-{(S)-3-[(2-Amino-acetylamino)-methyl]-piperidin-1-ylmethyl}-N-(5-chloro-2-ethanesulfonyl-benzyl)-3-trifluoromethyl-benzamide

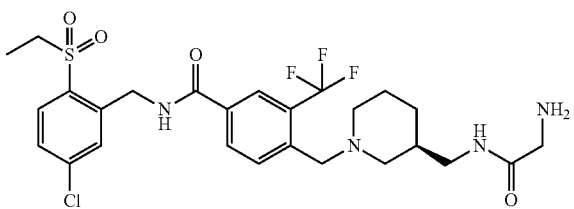 [SMILES: CCS(=O)(=O)c1ccc(Cl)cc1CNC(=O)c1ccc(CN2CCC[C@@H](CNC(=O)CN)C2)c(C(F)(F)F)c1]

The title compound was synthesized from 4-((S)-3-aminomethyl-piperidin-1-ylmethyl)-N-(5-chloro-2-ethanesulfonyl-benzyl)-3-trifluoromethyl-benzamide (Compound B-57) using hydrochloric acid/ethyl acetate in place of TFA/DCM under the same conditions as for Compound B-5.

LCMS: m/z 589 [M+H]$^+$

HPLC retention time: 0.44 min (analysis condition A)

Examples 137 to 139

The compounds of FIG. 7 were synthesized using N-(5-chloro-2-ethanesulfonyl-benzyl)-4-formyl-3-trifluoromethyl-benzamide (Compound b37) and the corresponding cyclic amines under the same conditions as for Compounds b38 and B-57.

Example 140

Compound B-64

N-(5-Chloro-2-ethanesulfonyl-benzyl)-4-((R)-3-dimethylaminomethyl-piperidin-1-ylmethyl)-3-trifluoromethyl-benzamide

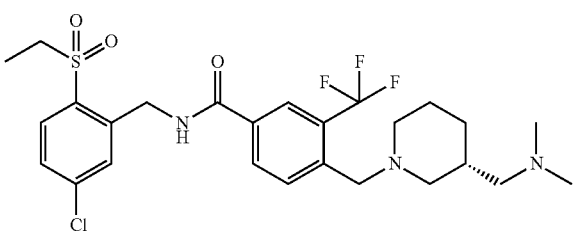 [SMILES: CCS(=O)(=O)c1ccc(Cl)cc1CNC(=O)c1ccc(CN2CCC[C@H](CN(C)C)C2)c(C(F)(F)F)c1]

The title compound was synthesized from 4-((R)-3-aminomethyl-piperidin-1-ylmethyl)-N-(5-chloro-2-ethanesulfonyl-benzyl)-3-trifluoromethyl-benzamide (Compound B-63) under the same conditions as for Compound B-2.

LCMS: m/z 560 [M+H]$^+$

HPLC retention time: 0.44 min (analysis condition A)

Example 141

Compound B-65

4-[(R)-3-(Acetylamino-methyl)-piperidin-1-ylmethyl]-N-(5-chloro-2-ethanesulfonyl-benzyl)-3-trifluoromethyl-benzamide

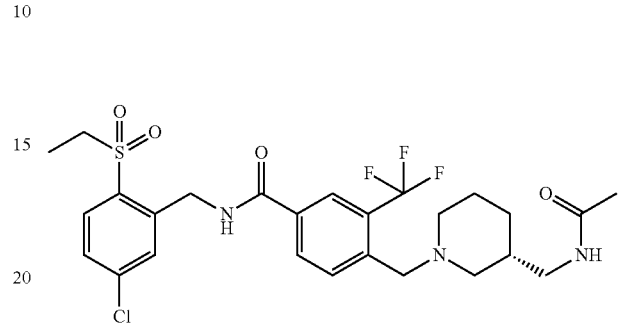

The title compound was synthesized from 4-((R)-3-aminomethyl-piperidin-1-ylmethyl)-N-(5-chloro-2-ethanesulfonyl-benzyl)-3-trifluoromethyl-benzamide (Compound B-63) using DMF in place of DCM under the same conditions as for Compound B-7.

LCMS: m/z 574 [M+H]$^+$

HPLC retention time: 0.52 min (analysis condition A)

Example 142

Compound B-66

N-(5-Chloro-2-ethanesulfonyl-benzyl)-4-[(S)-3-(methanesulfonylamino-methyl)-piperidin-1-ylmethyl]-3-trifluoromethyl-benzamide

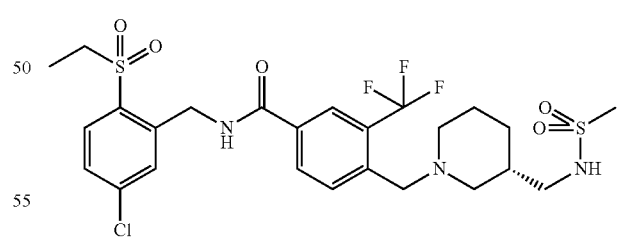

The title compound was synthesized from 4-((R)-3-aminomethyl-piperidin-1-ylmethyl)-N-(5-chloro-2-ethanesulfonyl-benzyl)-3-trifluoromethyl-benzamide (Compound B-63) using DMF in place of DCM under the same conditions as for Compound B-9.

LCMS: m/z 610 [M+H]$^+$

HPLC retention time: 0.54 min (analysis condition A)

Example 143

Compound c1

4-Chloro-3-trifluoromethoxy-benzoic acid ethyl ester

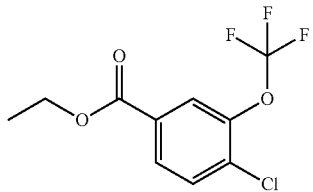 [SMILES: CCOC(=O)c1ccc(Cl)c(OC(F)(F)F)c1]

The title compound was synthesized from 4-chloro-3-trifluoromethoxy-benzoic acid under the same conditions as for Compound b1.

Example 144

Compound c2

4-(4-Ethoxycarbonyl-2-trifluoromethoxy-benzyl)-piperazine-1-carboxylic acid tert-butyl ester

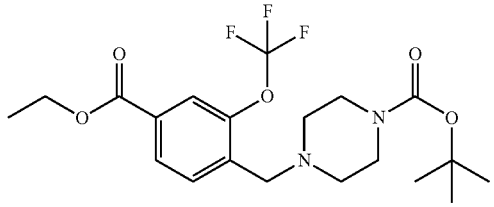 [SMILES: CCOC(=O)c1ccc(CN2CCN(C(=O)OC(C)(C)C)CC2)c(OC(F)(F)F)c1]

The title compound was synthesized from 4-chloro-3-trifluoromethoxy-benzoic acid ethyl ester (Compound c1) under the same conditions as for Compound b2.

Example 145

Compound c3

4-(4-Carboxy-2-trifluoromethoxy-benzyl)-piperazine-1-carboxylic acid tert-butyl ester

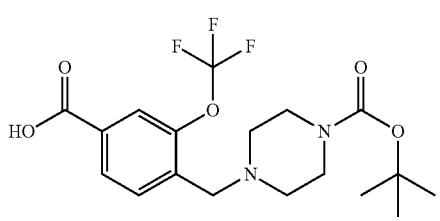 [SMILES: CC(C)(C)OC(=O)N1CCN(Cc2ccc(C(=O)O)cc2OC(F)(F)F)CC1]

The title compound was synthesized from 4-(4-ethoxycarbonyl-2-trifluoromethoxy-benzyl)-piperazine-1-carboxylic acid tert-butyl ester (Compound c2) under the same conditions as for Compound b3.

Example 146

Compound c4

4-[4-(5-Chloro-2-ethanesulfonyl-benzylcarbamoyl)-2-trifluoromethoxy-benzyl]-piperazine-1-carboxylic acid tert-butyl ester

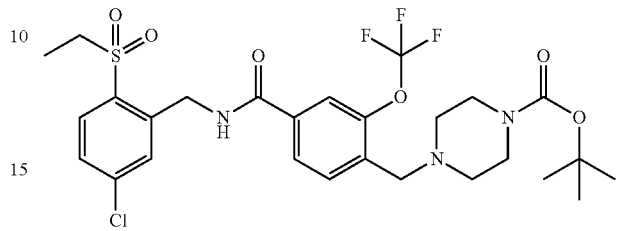

The title compound was synthesized from 4-(4-carboxy-2-trifluoromethoxy-benzyl)-piperazine-1-carboxylic acid tert-butyl ester (Compound c3) under the same conditions as for Compound A-14.

Example 147

Compound C-1

N-(5-Chloro-2-ethanesulfonyl-benzyl)-4-piperazin-1-ylmethyl-3-trifluoromethoxy-benzamide

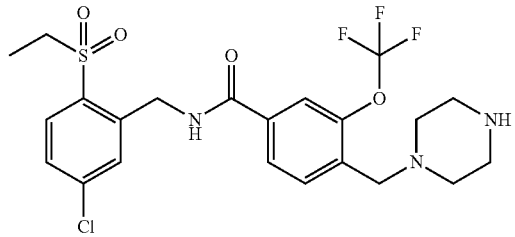 [SMILES: CCS(=O)(=O)c1ccc(Cl)cc1CNC(=O)c1ccc(CN2CCNCC2)c(OC(F)(F)F)c1]

The title compound was synthesized from 4-[4-(5-chloro-2-ethanesulfonyl-benzylcarbamoyl)-2-trifluoromethoxy-benzyl]-piperazine-1-carboxylic acid tert-butyl ester (Compound c4) under the same conditions as for Compound B-1.
LCMS: m/z 520 [M+H]$^+$
HPLC retention time: 0.51 min (analysis condition A)

Example 148

Compound C-2

N-(5-Chloro-2-ethanesulfonyl-benzyl)-4-(4-methyl-piperazin-1-ylmethyl)-3-trifluoromethoxy-benzamide

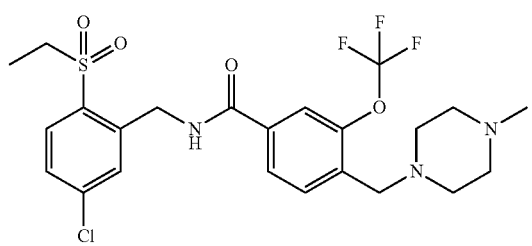 [SMILES: CCS(=O)(=O)c1ccc(Cl)cc1CNC(=O)c1ccc(CN2CCN(C)CC2)c(OC(F)(F)F)c1]

The title compound was synthesized from N-(5-chloro-2-ethanesulfonyl-benzyl)-4-piperazin-1-ylmethyl-3-trifluoromethoxy-benzamide (Compound C-1) under the same conditions as for Compound B-2.

LCMS: m/z 534 [M+H]$^+$

HPLC retention time: 0.54 min (analysis condition A)

Example 149

Compound C-3

N-(5-Chloro-2-ethanesulfonyl-benzyl)-4-(4-isopropyl-piperazin-1-ylmethyl)-3-trifluoromethoxy-benzamide

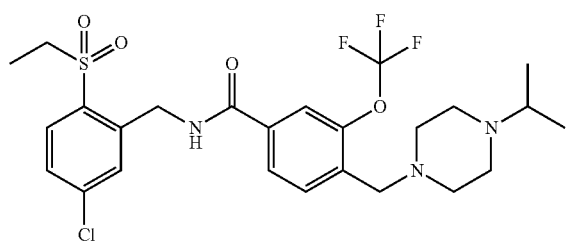 [SMILES: CCS(=O)(=O)c1ccc(Cl)cc1CNC(=O)c1ccc(CN2CCN(C(C)C)CC2)c(OC(F)(F)F)c1]

The title compound was synthesized from N-(5-chloro-2-ethanesulfonyl-benzyl)-4-piperazin-1-ylmethyl-3-trifluoromethoxy-benzamide (Compound C-1) under the same conditions as for Compound B-3.

LCMS: m/z 562 [M+H]$^+$

HPLC retention time: 0.56 min (analysis condition A)

Example 150

Compound C-4

N-(5-Chloro-2-ethanesulfonyl-benzyl)-4-[4-(tetrahydro-pyran-4-yl)-piperazin-1-ylmethyl]-3-trifluoromethoxy-benzamide

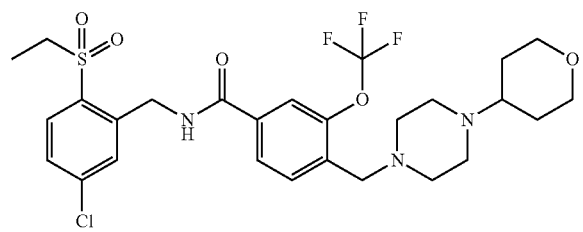 [SMILES: CCS(=O)(=O)c1ccc(Cl)cc1CNC(=O)c1ccc(CN2CCN(C3CCOCC3)CC2)c(OC(F)(F)F)c1]

The title compound was synthesized from N-(5-chloro-2-ethanesulfonyl-benzyl)-4-piperazin-1-ylmethyl-3-trifluoromethoxy-benzamide (Compound C-1) under the same conditions as for Compound B-4.

LCMS: m/z 604 [M+H]$^+$

HPLC retention time: 0.55 min (analysis condition A)

Example 151

Potassium (R)-({3-[(tert-butoxycarbonyl)amino]pyrrolidin-1-yl}methyl)trifluoroborate

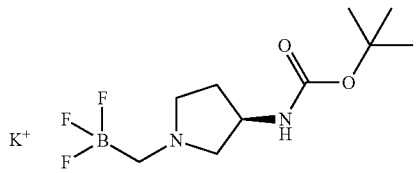

Potassium (bromomethyl)trifluoroborate (1.13 g, 5.64 mmol) was added to a solution of (R)-pyrrolidin-3-yl-carbamic acid tert-butyl ester (1.00 g, 5.37 mmol) in THF (20 ml), followed by refluxing for 17 hours. The reaction mixture was cooled to room temperature and then concentrated under reduced pressure. Acetone (50 ml) and potassium carbonate (742 mg, 5.37 mmol) were then added, and the mixture was stirred at room temperature for one hour. This was filtered through celite, and the filtrate was concentrated under reduced pressure to yield the title compound as a crude product.

Example 152

Potassium (S)-({3-[(tert-butoxycarbonyl)amino]pyrrolidin-1-yl}methyl)trifluoroborate

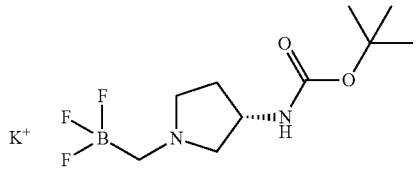

The title compound was synthesized using (S)-pyrrolidin-3-yl-carbamic acid tert-butyl ester under the same conditions as for potassium (R)-({3-[(tert-butoxycarbonyl)amino]pyrrolidin-1-yl}methyl)trifluoroborate.

Example 153

Compound C-5

4-((R)-3-Amino-pyrrolidin-1-ylmethyl)-N-(5-chloro-2-ethanesulfonyl-benzyl)-3-trifluoromethoxy-benzamide

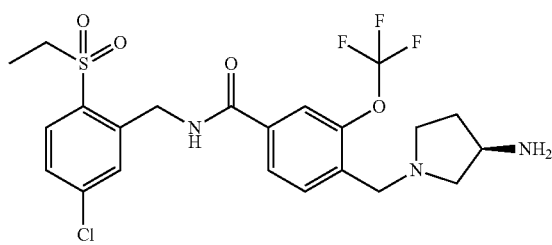 [SMILES: CCS(=O)(=O)c1ccc(Cl)cc1CNC(=O)c1ccc(CN2CC[C@@H](N)C2)c(OC(F)(F)F)c1]

The title compound was synthesized from 4-chloro-3-trifluoromethoxy-benzoic acid ethyl ester (Compound c1) and potassium (R)-({3-[(tert-butoxycarbonyl)amino]pyrrolidin-1-yl}methyl)trifluoroborate under the same conditions as for Compounds c2, c3, c4, and C-1. However, the reaction was performed using S-Phos in place of X-Phos under the conditions for Compound c2.

LCMS: m/z 520 [M+H]$^+$
HPLC retention time: 0.43 min (analysis condition A)

Example 154

Compound C-6

4-((S)-3-Amino-pyrrolidin-1-ylmethyl)-N-(5-chloro-2-ethanesulfonyl-benzyl)-3-trifluoromethoxy-benzamide

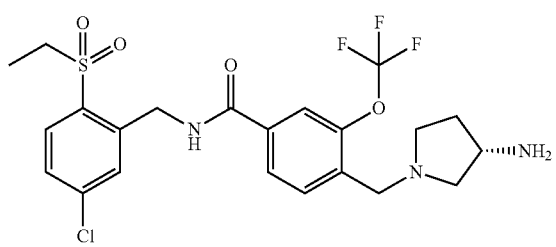 [SMILES: CCS(=O)(=O)c1ccc(Cl)cc1CNC(=O)c1ccc(CN2CC[C@H](N)C2)c(OC(F)(F)F)c1]

The title compound was synthesized from 4-chloro-3-trifluoromethoxy-benzoic acid ethyl ester (Compound c1) and potassium (S)-({3-[(tert-butoxycarbonyl)amino]pyrrolidin-1-yl}methyl)trifluoroborate under the same conditions as for Compounds c2, c3, c4, and C-1. However, the reaction was performed using S-Phos in place of X-Phos under the conditions for Compound c2.

LCMS: m/z 520 [M+H]$^+$
HPLC retention time: 0.43 min (analysis condition A)

Example 155

Compound c5

3-Trifluoromethoxy-4-vinyl-benzoic acid ethyl ester

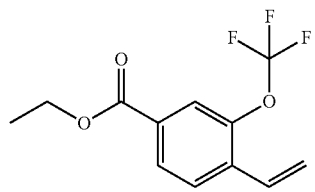 [SMILES: C=Cc1ccc(C(=O)OCC)cc1OC(F)(F)F]

A mixture of 4-chloro-3-trifluoromethoxy-benzoic acid ethyl ester (Compound c1, 1 g, 3.7 mmol), potassium vinyltrifluoroborate (1.5 g, 11 mmol), palladium acetate (167 mg, 0.74 mmol), 2',6'-dimethoxy-2-(dicyclohexylphosphino)biphenyl (611 mg, 1.5 mmol), and cesium carbonate (3.64 g, 11 mmol) in THF (8 mL)/water (4 mL) was stirred at 90° C. for 18 hours. Water was added to the reaction solution, followed by extraction with ethyl acetate. The extract was dried over anhydrous magnesium sulfate. The drying agent was removed by filtration, and the residue obtained after concentration under reduced pressure was purified by silica gel column chromatography (DCM/hexane) to yield the title compound (935 mg, 97%) as an oily substance.

HPLC retention time: 3.13 min (analysis condition E)

Example 156

Compound c6

4-(1,2-Dihydroxy-ethyl)-3-trifluoromethoxy-benzoic acid ethyl ester

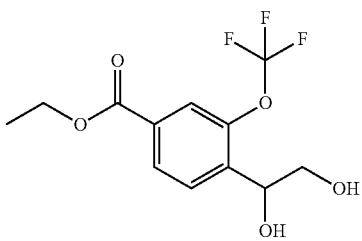 [SMILES: CCOC(=O)c1ccc(C(O)CO)c(OC(F)(F)F)c1]

3-Trifluoromethoxy-4-vinyl-benzoic acid ethyl ester (Compound c5, 55 mg, 0.21 mmol) was added to a mixture of AD-mix-α (manufactured by Aldrich) (330 mg) in t-butyl alcohol (1 mL)/water (1 mL), and the mixture was stirred at room temperature for two hours. Sodium sulfite (211 mg) was added to the reaction solution, followed by stirring for further one hour. The reaction solution was extracted with ethyl acetate, and the organic layer was washed with brine and then dried over anhydrous sodium sulfate. The drying agent was removed by filtration, and the residue obtained after concentration under reduced pressure was purified by silica gel column chromatography (ethyl acetate/hexane) to yield the title compound (56.7 mg, 92%) as a colorless solid.

HPLC retention time: 1.77 min (analysis condition E)

Example 157

Compound c7

4-Formyl-3-trifluoromethoxy-benzoic acid ethyl ester

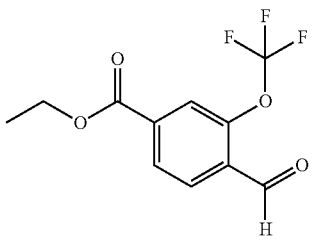 [SMILES: CCOC(=O)c1ccc(C=O)c(OC(F)(F)F)c1]

The title compound was synthesized from 4-(1,2-dihydroxy-ethyl)-3-trifluoromethoxy-benzoic acid ethyl ester (Compound c6) under the same conditions as for Compound b30.

Example 158

Compound c8

4-((S)-3-tert-Butoxycarbonylamino-piperidin-1-ylmethyl)-3-trifluoromethoxy-benzoic acid ethyl ester

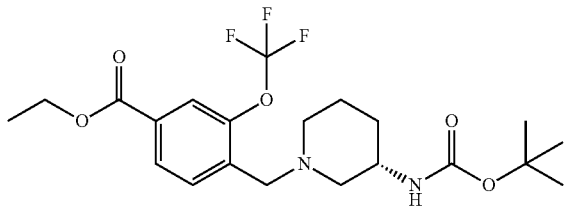 [SMILES: CCOC(=O)c1ccc(CN2CCC[C@H](NC(=O)OC(C)(C)C)C2)c(OC(F)(F)F)c1]

The title compound was synthesized from 4-formyl-3-trifluoromethoxy-benzoic acid ethyl ester (Compound c7) under the same conditions as for Compound b32. However, the reaction was performed using (S)-1-piperidin-3-ylmethyl-carbamic acid tert-butyl ester in place of (S)-1-pyrrolidin-2-ylmethyl-carbamic acid tert-butyl ester.

Example 159

Compound c9

4-((S)-3-tert-Butoxycarbonylamino-piperidin-1-ylmethyl)-3-trifluoromethoxy-benzoic acid

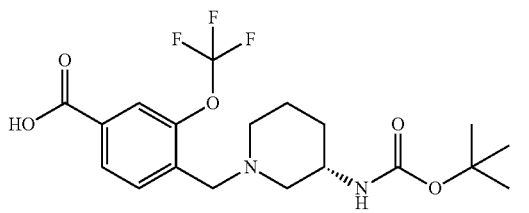 [SMILES: CC(C)(C)OC(=O)N[C@H]1CCCN(Cc2ccc(C(=O)O)cc2OC(F)(F)F)C1]

The title compound was synthesized from 4-((S)-3-tert-butoxycarbonylamino-piperidin-1-ylmethyl)-3-trifluoromethoxy-benzoic acid ethyl ester (Compound c8) under the same conditions as for Compound b3.

Example 160

Compound c10

{(S)-1-[4-(5-Chloro-2-ethanesulfonyl-benzylcarbamoyl)-2-trifluoromethoxy-benzyl]-piperidin-3-yl}-carbamic acid tert-butyl ester

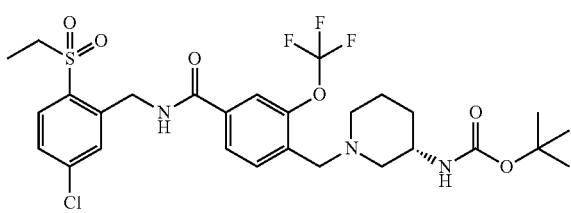 [SMILES: CCS(=O)(=O)c1ccc(Cl)cc1CNC(=O)c1ccc(CN2CCC[C@H](NC(=O)OC(C)(C)C)C2)c(OC(F)(F)F)c1]

The title compound was synthesized from 4-((S)-3-tert-butoxycarbonylamino-piperidin-1-ylmethyl)-3-trifluoromethoxy-benzoic acid (Compound c9) using DCM in place of DMF under the same conditions as for Compound A-14.

Example 161

Compound C-7

4-((S)-3-Amino-piperidin-1-ylmethyl)-N-(5-chloro-2-ethanesulfonyl-benzyl)-3-trifluoromethoxy-benzamide

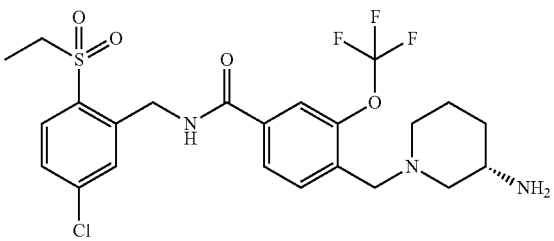 [SMILES: CCS(=O)(=O)c1ccc(Cl)cc1CNC(=O)c1ccc(CN2CCC[C@H](N)C2)c(OC(F)(F)F)c1]

The title compound was synthesized from {(S)-1-[4-(5-chloro-2-ethanesulfonyl-benzylcarbamoyl)-2-trifluoromethoxy-benzyl]-piperidin-3-yl}-carbamic acid tert-butyl ester (Compound c10) under the same conditions as for Compound B-1.

LCMS: m/z 534 [M+H]$^+$

HPLC retention time: 0.48 min (analysis condition A)

Example 162

Compound C-8

N-(5-Chloro-2-ethanesulfonyl-benzyl)-4-((S)-3-dimethylamino-piperidin-1-ylmethyl)-3-trifluoromethoxy-benzamide

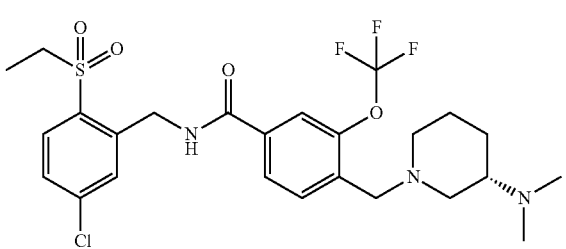 [SMILES: CCS(=O)(=O)c1ccc(Cl)cc1CNC(=O)c1ccc(CN2CCC[C@H](N(C)C)C2)c(OC(F)(F)F)c1]

The title compound was synthesized from 4-((S)-3-amino-piperidin-1-ylmethyl)-N-(5-chloro-2-ethanesulfonyl-benzyl)-3-trifluoromethoxy-benzamide (Compound C-7) under the same conditions as for Compound B-2.

LCMS: m/z 562 [M+H]$^+$

HPLC retention time: 0.51 min (analysis condition A)

Example 163

Compound C-9

4-((S)-3-Acetylamino-piperidin-1-ylmethyl)-N-(5-chloro-2-ethanesulfonyl-benzyl)-3-trifluoromethoxy-benzamide

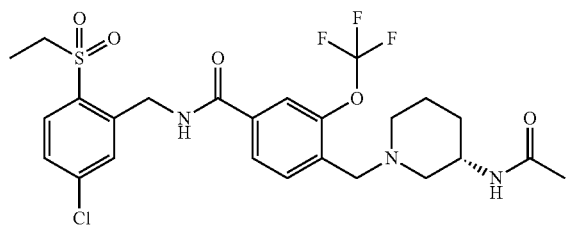 [SMILES: CCS(=O)(=O)c1ccc(Cl)cc1CNC(=O)c1ccc(CN2CCC[C@H](NC(C)=O)C2)c(OC(F)(F)F)c1]

The title compound was synthesized from 4-((S)-3-amino-piperidin-1-ylmethyl)-N-(5-chloro-2-ethanesulfonyl-benzyl)-3-trifluoromethoxy-benzamide (Compound C-7) under the same conditions as for Compound B-7.

LCMS: m/z 576 [M+H]$^+$

HPLC retention time: 0.51 min (analysis condition A)

Example 164

Compound C-10

N-(5-Chloro-2-ethanesulfonyl-benzyl)-4-((S)-3-methanesulfonylamino-piperidin-1-ylmethyl)-3-trifluoromethoxy-benzamide

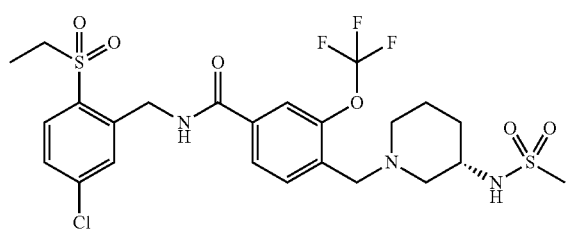 [SMILES: CCS(=O)(=O)c1ccc(Cl)cc1CNC(=O)c1ccc(CN2CCC[C@H](NS(C)(=O)=O)C2)c(OC(F)(F)F)c1]

The title compound was synthesized from 4-((S)-3-amino-piperidin-1-ylmethyl)-N-(5-chloro-2-ethanesulfonyl-benzyl)-3-trifluoromethoxy-benzamide (Compound C-7) under the same conditions as for Compound B-9.

LCMS: m/z 612 [M+H]$^+$

HPLC retention time: 0.53 min (analysis condition A)

Example 165

Compound C-11

N-(5-Chloro-2-ethanesulfonyl-benzyl)-3-trifluoromethoxy-4-((S)-3-ureido-piperidin-1-ylmethyl)-benzamide

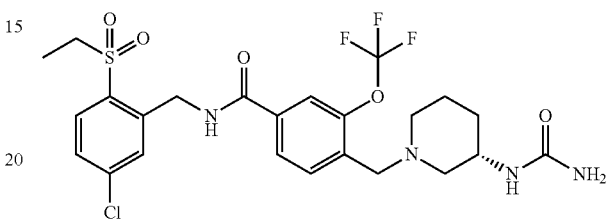

The title compound was synthesized from 4-((S)-3-amino-piperidin-1-ylmethyl)-N-(5-chloro-2-ethanesulfonyl-benzyl)-3-trifluoromethoxy-benzamide (Compound C-7) under the same conditions as for Compound B-11.

LCMS: m/z 577 [M+H]$^+$

HPLC retention time: 0.50 min (analysis condition A)

Example 166

Compound C-12

4-[(S)-3-(2-Amino-acetylamino)-piperidin-1-ylmethyl]-N-(5-chloro-2-ethanesulfonyl-benzyl)-3-trifluoromethoxy-benzamide

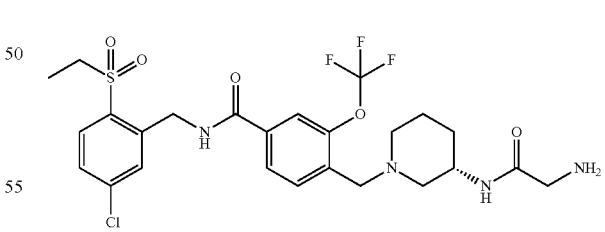

The title compound was synthesized from 4-((S)-3-amino-piperidin-1-ylmethyl)-N-(5-chloro-2-ethanesulfonyl-benzyl)-3-trifluoromethoxy-benzamide (Compound C-7) under the same conditions as for Compound B-5.

LCMS: m/z 591 [M+H]$^+$

HPLC retention time: 0.43 min (analysis condition A)

Example 167

Compound c11

4-[(S)-3-(tert-Butoxycarbonyl-methyl-amino)-piperidin-1-ylmethyl]-3-trifluoromethoxy-benzoic acid ethyl ester

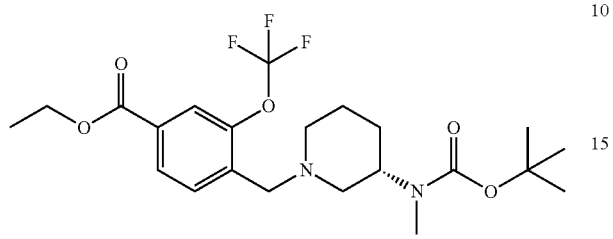

The title compound was synthesized from 4-formyl-3-trifluoromethoxy-benzoic acid ethyl ester (Compound c7) and methyl-(S)-piperidin-3-yl-carbamic acid tert-butyl ester using DCM as a solvent under the same conditions as for Compound b32.

Example 168

Compound c12

4-[(S)-3-(tert-Butoxycarbonyl-methyl-amino)-piperidin-1-ylmethyl]-3-trifluoromethoxy-benzoic acid

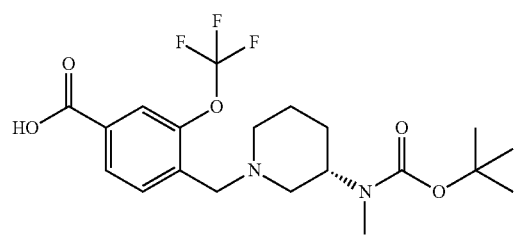 [SMILES: CN(C(=O)OC(C)(C)C)[C@H]1CCCN(Cc2ccc(C(=O)O)cc2OC(F)(F)F)C1]

The title compound was synthesized from 4-[(S)-3-(tert-butoxycarbonyl-methyl-amino)-piperidin-1-ylmethyl]-3-trifluoromethoxy-benzoic acid ethyl ester (Compound c11) under the same conditions as for Compound b8.

Example 169

Compound c13

{(S)-1-[4-(5-Chloro-2-ethanesulfonyl-benzylcarbamoyl)-2-trifluoromethoxy-benzyl]-piperidin-3-yl}-methyl-carbamic acid tert-butyl ester

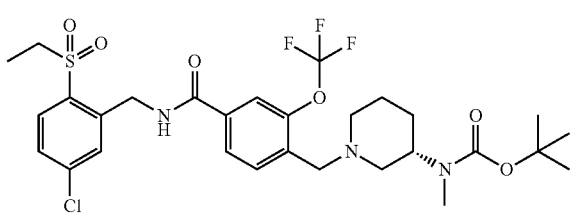 [SMILES: CCS(=O)(=O)c1ccc(Cl)cc1CNC(=O)c1ccc(CN2CCC[C@H](N(C)C(=O)OC(C)(C)C)C2)c(OC(F)(F)F)c1]

The title compound was synthesized from 4-[(S)-3-(tert-butoxycarbonyl-methyl-amino)-piperidin-1-ylmethyl]-3-trifluoromethoxy-benzoic acid (Compound c12) under the same conditions as for Compound A-14.

Example 170

Compound C-13

N-(5-Chloro-2-ethanesulfonyl-benzyl)-4-((S)-3-methylamino-piperidin-1-ylmethyl)-3-trifluoromethoxy-benzamide

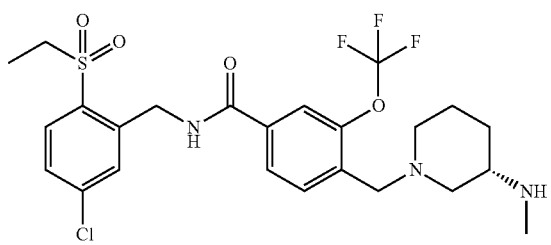 [SMILES: CCS(=O)(=O)c1ccc(Cl)cc1CNC(=O)c1ccc(CN2CCC[C@H](NC)C2)c(OC(F)(F)F)c1]

The title compound was synthesized from {(S)-1-[4-(5-chloro-2-ethanesulfonyl-benzylcarbamoyl)-2-trifluoromethoxy-benzyl]-piperidin-3-yl}-methyl-carbamic acid tert-butyl ester (Compound c13) under the same conditions as for Compound B-1.

LCMS: m/z 548 [M+H]$^+$

HPLC retention time: 0.51 min (analysis condition A)

Example 171

Compound c14

4-((R)-3-tert-Butoxycarbonylamino-piperidin-1-ylmethyl)-3-trifluoromethoxy-benzoic acid ethyl ester

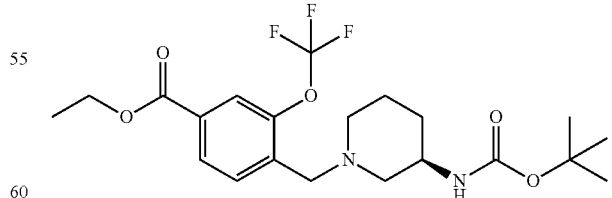

The title compound was synthesized from 4-formyl-3-trifluoromethoxy-benzoic acid ethyl ester (Compound c7) and (R)-piperidin-3-yl-carbamic acid tert-butyl ester under the same conditions as for Compound b32.

Example 172

Compound c15

4-((R)-3-tert-Butoxycarbonylamino-piperidin-1-ylmethyl)-3-trifluoromethoxy-benzoic acid

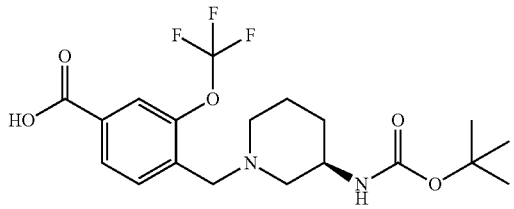 [SMILES: CC(C)(C)OC(=O)N[C@@H]1CCCN(Cc2ccc(C(=O)O)cc2OC(F)(F)F)C1]

The title compound was synthesized from 4-((R)-3-tert-butoxycarbonylamino-piperidin-1-ylmethyl)-3-trifluoromethoxy-benzoic acid ethyl ester (Compound c14) under the same conditions as for Compound b8.

Example 173

Compound c16

{(R)-1-[4-(5-Chloro-2-ethanesulfonyl-benzylcarbamoyl)-2-trifluoromethoxy-benzyl]-piperidin-3-yl}-carbamic acid tert-butyl ester

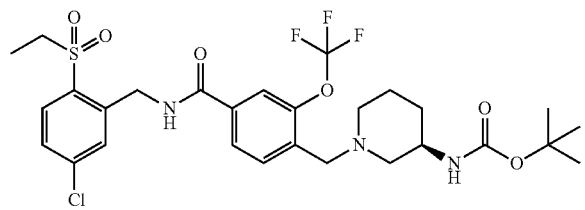 [SMILES: CCS(=O)(=O)c1ccc(Cl)cc1CNC(=O)c1ccc(CN2CCC[C@@H](NC(=O)OC(C)(C)C)C2)c(OC(F)(F)F)c1]

The title compound was synthesized from 4-((R)-3-tert-butoxycarbonylamino-piperidin-1-ylmethyl)-3-trifluoromethoxy-benzoic acid (Compound c15) using DCM in place of DMF under the same conditions as for Compound A-14.

Example 174

Compound C-14

4-((R)-3-Amino-piperidin-1-ylmethyl)-N-(5-chloro-2-ethanesulfonyl-benzyl)-3-trifluoromethoxy-benzamide

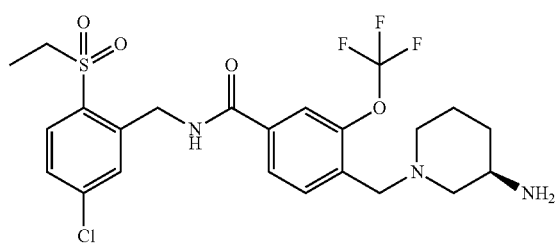 [SMILES: CCS(=O)(=O)c1ccc(Cl)cc1CNC(=O)c1ccc(CN2CCC[C@@H](N)C2)c(OC(F)(F)F)c1]

The title compound was synthesized from {(R)-1-[4-(5-chloro-2-ethanesulfonyl-benzylcarbamoyl)-2-trifluoromethoxy-benzyl]-piperidin-3-yl}-carbamic acid tert-butyl ester (Compound c16) under the same conditions as for Compound B-1.

LCMS: m/z 534 [M+H]⁺

HPLC retention time: 0.47 min (analysis condition A)

Example 175

Compound C-15

4-((S)-3-Aminomethyl-pyrrolidin-1-ylmethyl)-N-(5-chloro-2-ethanesulfonyl-benzyl)-3-trifluoromethoxy-benzamide

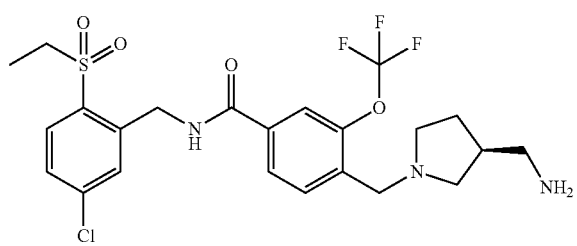 [SMILES: CCS(=O)(=O)c1ccc(Cl)cc1CNC(=O)c1ccc(CN2CC[C@@H](CN)C2)c(OC(F)(F)F)c1]

The title compound was synthesized from 4-formyl-3-trifluoromethoxy-benzoic acid ethyl ester (Compound c7) and (R)-1-pyrrolidin-3-ylmethyl-carbamic acid tert-butyl ester under the same conditions as for Compounds c14, c15, c16, and C-14.

LCMS: m/z 534 [M+H]⁺

HPLC retention time: 0.41 min (analysis condition A)

Example 176

Compound C-16

4-((R)-3-Aminomethyl-pyrrolidin-1-ylmethyl)-N-(5-chloro-2-ethanesulfonyl-benzyl)-3-trifluoromethoxy-benzamide

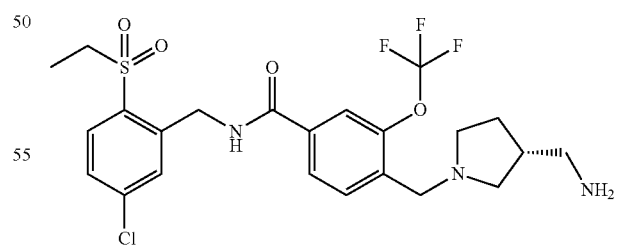

The title compound was synthesized from 4-formyl-3-trifluoromethoxy-benzoic acid ethyl ester (Compound c7) and (S)-1-pyrrolidin-3-ylmethyl-carbamic acid tert-butyl ester under the same conditions as for Compounds c14, c15, c16, and C-14.

LCMS: m/z 534 [M+H]⁺

HPLC retention time: 0.40 min (analysis condition A)

Example 177

Compound d1

4-(5-Amino-4-ethoxycarbonyl-2-trifluoromethyl-benzyl)-piperazine-1-carboxylic acid tert-butyl ester

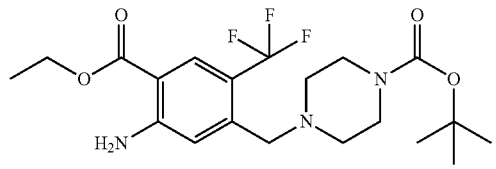 [SMILES: CCOC(=O)c1cc(C(F)(F)F)c(CN2CCN(C(=O)OC(C)(C)C)CC2)cc1N]

A mixture of 2-amino-4-chloro-5-trifluoromethyl-benzoic acid ethyl ester (Compound b27, 1.07 g, 4.0 mmol), potassium (4-tert-butoxycarbonylpiperazin-1-yl)methyltrifluoroborate (1.71 g, 5.6 mmol), palladium acetate (44.9 mg, 0.2 mmol), X-Phos (191 mg, 0.4 mmol), and cesium carbonate (3.91 g, 12 mmol) in THF (40 mL) and water (20 mL) was stirred at 90° C. for three hours. The reaction solution was extracted with ethyl acetate, and the extract was dried over anhydrous sodium sulfate. The drying agent was removed by filtration, and the residue obtained after concentration under reduced pressure was purified by silica gel column chromatography (ethyl acetate/hexane) to yield the title compound (1.49 g, 86%) as a pale yellow solid.

LCMS: m/z 432 [M+H]$^+$

HPLC retention time: 0.75 min (analysis condition A)

Example 178

Compound d2

4-(3-Amino-2-chloro-4-ethoxycarbonyl-6-trifluoromethyl-benzyl)-piperazine-1-carboxylic acid tert-butyl ester

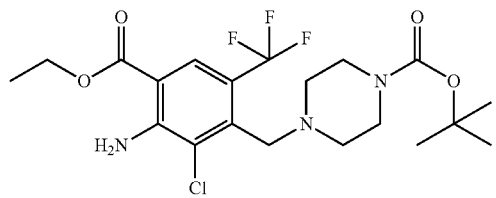 [SMILES: CCOC(=O)c1cc(C(F)(F)F)c(CN2CCN(C(=O)OC(C)(C)C)CC2)c(Cl)c1N]

NCS (1.71 g, 13 mmol) was added to a solution of 4-(5-amino-4-ethoxycarbonyl-2-trifluoromethyl-benzyl)-piperazine-1-carboxylic acid tert-butyl ester (Compound d1, 4.62 g, 11 mmol) in DMF (90 ml), and the mixture was stirred at 65° C. for three hours. Water was added to the reaction mixture, followed by extraction with hexane/ethyl acetate=1/1. The organic layer was then washed with brine and dried over anhydrous sodium sulfate. The drying agent was removed by filtration, and the residue obtained after concentration under reduced pressure was purified by silica gel column chromatography (ethyl acetate/hexane) to yield the title compound (2.70 g, 54%) as a yellow solid.

LCMS: m/z 466 [M+H]$^+$

HPLC retention time: 1.01 min (analysis condition A)

Example 179

Compound d3

4-(2-Chloro-4-ethoxycarbonyl-6-trifluoromethyl-benzyl)-piperazine-1-carboxylic acid tert-butyl ester

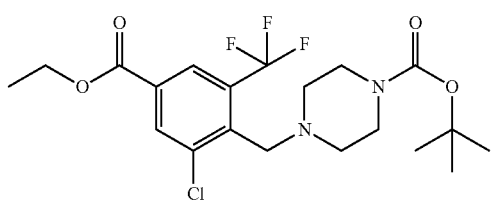 [SMILES: CCOC(=O)c1cc(Cl)c(CN2CCN(C(=O)OC(C)(C)C)CC2)c(C(F)(F)F)c1]

The title compound was synthesized from 4-(3-amino-2-chloro-4-ethoxycarbonyl-6-trifluoromethyl-benzyl)-piperazine-1-carboxylic acid tert-butyl ester (Compound d2) under the same conditions as for Compound b31.

Example 180

Compound d4

4-(4-Carboxy-2-chloro-6-trifluoromethyl-benzyl)-piperazine-1-carboxylic acid tert-butyl ester

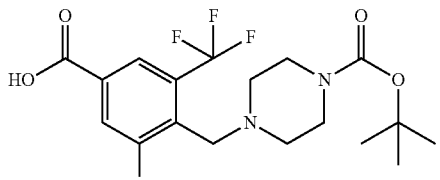

The title compound was synthesized from 4-(2-chloro-4-ethoxycarbonyl-6-trifluoromethyl-benzyl)-piperazine-1-carboxylic acid tert-butyl ester (Compound d3) under the same conditions as for Compound b8.

Example 181

Compound d5

4-[2-Chloro-4-(5-chloro-2-ethanesulfonyl-benzylcarbamoyl)-6-trifluoromethyl-benzyl]-piperazine-1-carboxylic acid tert-butyl ester

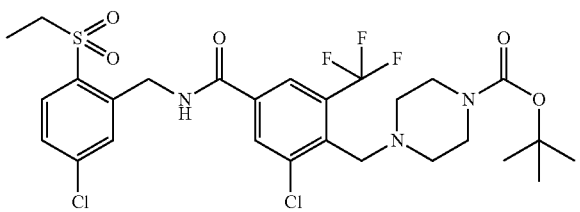 [SMILES: CCS(=O)(=O)c1ccc(Cl)cc1CNC(=O)c1cc(Cl)c(CN2CCN(C(=O)OC(C)(C)C)CC2)c(C(F)(F)F)c1]

The title compound was synthesized from 4-(4-carboxy-2-chloro-6-trifluoromethyl-benzyl)-piperazine-1-carboxylic acid tert-butyl ester (Compound d4) under the same conditions as for Compound A-5.

Example 182

Compound D-1

3-Chloro-N-(5-chloro-2-ethanesulfonyl-benzyl)-4-piperazin-1-ylmethyl-5-trifluoromethyl-benzamide

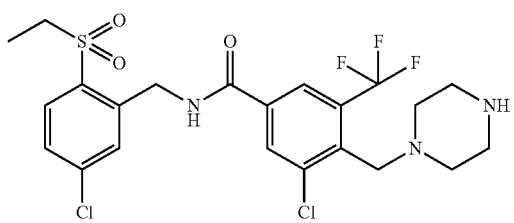 [SMILES: CCS(=O)(=O)c1ccc(Cl)cc1CNC(=O)c1cc(Cl)c(CN2CCNCC2)c(C(F)(F)F)c1]

The title compound was synthesized from 4-[2-chloro-4-(5-chloro-2-ethanesulfonyl-benzylcarbamoyl)-6-trifluoromethyl-benzyl]-piperazine-1-carboxylic acid tert-butyl ester (Compound d5) under the same conditions as for Compound B-57.

LCMS: m/z 538 [M+H]$^+$
HPLC retention time: 0.58 min (analysis condition A)

Example 183

Compound D-2

3-Chloro-N-(5-chloro-2-ethanesulfonyl-benzyl)-4-(4-methyl-piperazin-1-ylmethyl)-5-trifluoromethyl-benzamide

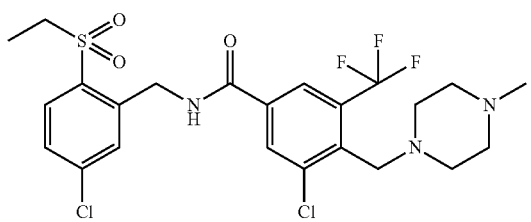 [SMILES: CCS(=O)(=O)c1ccc(Cl)cc1CNC(=O)c1cc(Cl)c(CN2CCN(C)CC2)c(C(F)(F)F)c1]

The title compound was synthesized from 3-chloro-N-(5-chloro-2-ethanesulfonyl-benzyl)-4-piperazin-1-ylmethyl-5-trifluoromethyl-benzamide (Compound D-1) under the same conditions as for Compound B-2.

LCMS: m/z 552 [M+H]$^+$
HPLC retention time: 0.58 min (analysis condition A)

Example 184

Compound D-3

3-Chloro-N-(5-chloro-2-ethanesulfonyl-benzyl)-4-(4-isopropyl-piperazin-1-ylmethyl)-5-trifluoromethyl-benzamide

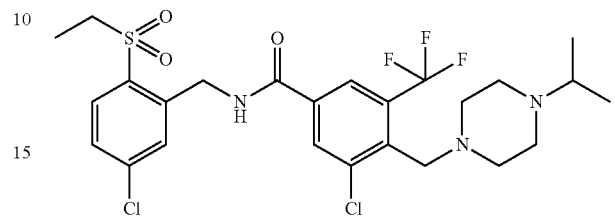

The title compound was synthesized from 3-chloro-N-(5-chloro-2-ethanesulfonyl-benzyl)-4-piperazin-1-ylmethyl-5-trifluoromethyl-benzamide (Compound D-1) under the same conditions as for Compound B-3.

LCMS: m/z 580 [M+H]$^+$
HPLC retention time: 0.60 min (analysis condition A)

Example 185

Compound D-4

3-Chloro-N-(5-chloro-2-ethanesulfonyl-benzyl)-4-[4-(tetrahydro-pyran-4-yl)-piperazin-1-ylmethyl]-5-trifluoromethyl-benzamide

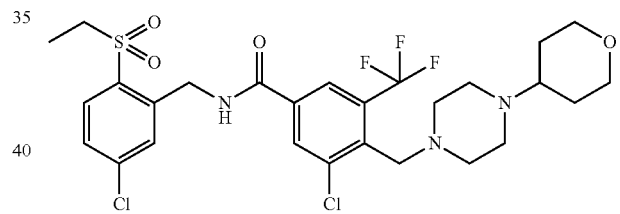

The title compound was synthesized from 3-chloro-N-(5-chloro-2-ethanesulfonyl-benzyl)-4-piperazin-1-ylmethyl-5-trifluoromethyl-benzamide (Compound D-1) under the same conditions as for Compound B-4.

LCMS: m/z 622 [M+H]$^+$
HPLC retention time: 0.59 min (analysis condition A)

Example 186

Compound d6

2-Amino-3-chloro-4-formyl-5-trifluoromethyl-benzoic acid ethyl ester

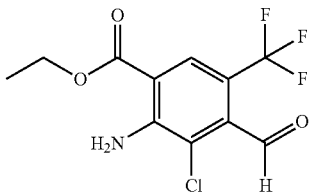 [SMILES: CCOC(=O)c1cc(C(F)(F)F)c(C=O)c(Cl)c1N]

NCS (3.71 g, 14 mmol) was added to a solution of 2-amino-4-formyl-5-trifluoromethyl-benzoic acid ethyl ester (Compound b30, 3.63 g, 14 mmol) in DMF (42 mL), and the mixture was stirred at 70° C. for 0.5 hour. Water (40 mL) was added, followed by extraction with TBME. The extract was dried over anhydrous sodium sulfate. The drying agent was removed by filtration, and the residue obtained after concentration under reduced pressure was purified by silica gel column chromatography (ethyl acetate/hexane) to yield the title compound (3.47 g, 85%) as a yellow solid.

LCMS: m/z 296 [M+H]$^+$

HPLC retention time: 0.89 min (analysis condition A)

Example 187

Compound d7

3-Chloro-4-formyl-5-trifluoromethyl-benzoic acid ethyl ester

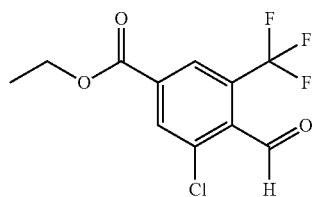 [SMILES: CCOC(=O)c1cc(Cl)c(C=O)c(C(F)(F)F)c1]

The title compound was synthesized from 2-amino-3-chloro-4-formyl-5-trifluoromethyl-benzoic acid ethyl ester (Compound d6) under the same conditions as for Compound b31.

Example 188

Compound d8

4-((R)-3-tert-Butoxycarbonylamino-pyrrolidin-1-ylmethyl)-3-chloro-5-trifluoromethyl-benzoic acid ethyl ester

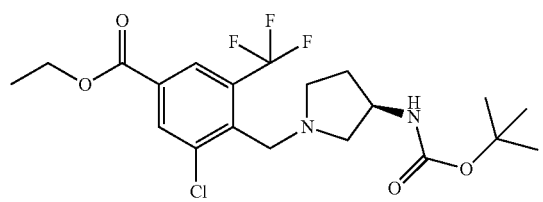 [SMILES: CCOC(=O)c1cc(Cl)c(CN2CC[C@@H](NC(=O)OC(C)(C)C)C2)c(C(F)(F)F)c1]

The title compound was synthesized from 3-chloro-4-formyl-5-trifluoromethyl-benzoic acid ethyl ester (Compound d7) and (R)-pyrrolidin-3-yl-carbamic acid tert-butyl ester under the same conditions as for Compound b32.

Example 189

Compound d9

4-((R)-3-tert-Butoxycarbonylamino-pyrrolidin-1-ylmethyl)-3-chloro-5-trifluoromethyl-benzoic acid

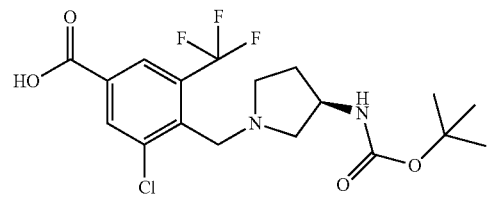 [SMILES: CC(C)(C)OC(=O)N[C@@H]1CCN(Cc2c(Cl)cc(C(=O)O)cc2C(F)(F)F)C1]

The title compound was synthesized from 4-((R)-3-tert-butoxycarbonylamino-pyrrolidin-1-ylmethyl)-3-chloro-5-trifluoromethyl-benzoic acid ethyl ester (Compound d8) under the same conditions as for Compound b8.

Example 190

Compound d10

{(R)-1-[2-Chloro-4-(5-chloro-2-ethanesulfonyl-benzylcarbamoyl)-6-trifluoromethyl-benzyl]-pyrrolidin-3-yl}-carbamic acid tert-butyl ester

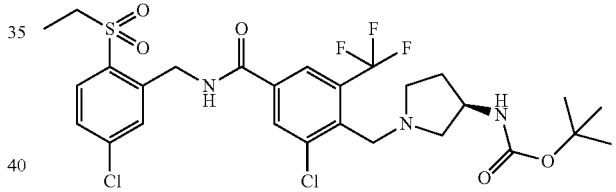

The title compound was synthesized from 4-((R)-3-tert-butoxycarbonylamino-pyrrolidin-1-ylmethyl)-3-chloro-5-trifluoromethyl-benzoic acid (Compound d9) under the same conditions as for Compound A-14.

Example 191

Compound D-5

4-((R)-3-Amino-pyrrolidin-1-ylmethyl)-3-chloro-N-(5-chloro-2-ethanesulfonyl-benzyl)-5-trifluoromethyl-benzamide

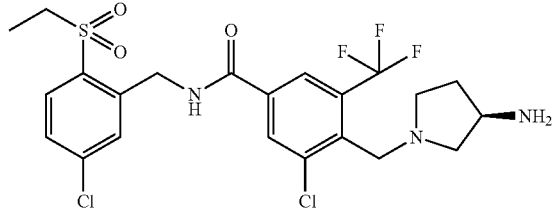 [SMILES: CCS(=O)(=O)c1ccc(Cl)cc1CNC(=O)c1cc(Cl)c(CN2CC[C@@H](N)C2)c(C(F)(F)F)c1]

The title compound was synthesized from {(R)-1-[2-chloro-4-(5-chloro-2-ethanesulfonyl-benzylcarbamoyl)-6-trifluoromethyl-benzyl]-pyrrolidin-3-yl}-carbamic acid tert-butyl ester (Compound d10) under the same conditions as for Compound B-1.

LCMS: m/z 538 [M+H]⁺

HPLC retention time: 0.51 min (analysis condition A)

Example 192

Compound D-6

3-Chloro-N-(5-chloro-2-ethanesulfonyl-benzyl)-4-((R)-3-dimethylamino-pyrrolidin-1-ylmethyl)-5-trifluoromethyl-benzamide

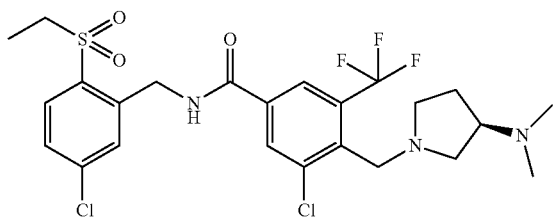 [SMILES: CCS(=O)(=O)c1ccc(Cl)cc1CNC(=O)c1cc(Cl)c(CN2CC[C@@H](N(C)C)C2)c(C(F)(F)F)c1]

The title compound was synthesized from 4-((R)-3-amino-pyrrolidin-1-ylmethyl)-3-chloro-N-(5-chloro-2-ethanesulfonyl-benzyl)-5-trifluoromethyl-benzamide (Compound D-5) under the same conditions as for Compound B-2.

LCMS: m/z 566 [M+H]⁺

HPLC retention time: 0.57 min (analysis condition A)

Example 193

Compound D-7

4-((R)-3-Acetylamino-pyrrolidin-1-ylmethyl)-3-chloro-N-(5-chloro-2-ethanesulfonyl-benzyl)-5-trifluoromethyl-benzamide

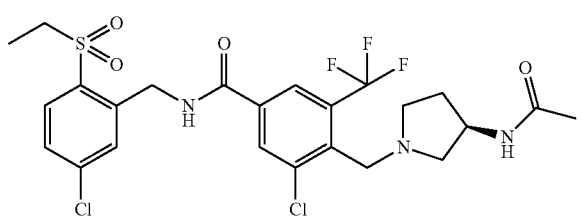 [SMILES: CCS(=O)(=O)c1ccc(Cl)cc1CNC(=O)c1cc(Cl)c(CN2CC[C@@H](NC(C)=O)C2)c(C(F)(F)F)c1]

The title compound was synthesized from 4-((R)-3-amino-pyrrolidin-1-ylmethyl)-3-chloro-N-(5-chloro-2-ethanesulfonyl-benzyl)-5-trifluoromethyl-benzamide (Compound D-5) under the same conditions as for Compound B-7.

LCMS: m/z 580 [M+H]⁺

HPLC retention time: 0.51 min (analysis condition A)

Example 194

Compound D-8

3-Chloro-N-(5-chloro-2-ethanesulfonyl-benzyl)-4-((R)-3-methanesulfonylamino-pyrrolidin-1-ylmethyl)-5-trifluoromethyl-benzamide

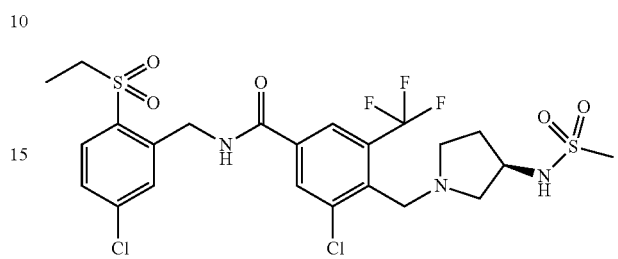

The title compound was synthesized from 4-((R)-3-amino-pyrrolidin-1-ylmethyl)-3-chloro-N-(5-chloro-2-ethanesulfonyl-benzyl)-5-trifluoromethyl-benzamide (Compound D-5) under the same conditions as for Compound B-9. However, the reaction was performed at 0° C. instead of room temperature.

LCMS: m/z 616 [M+H]⁺

HPLC retention time: 0.54 min (analysis condition A)

Example 195

Compound D-9

3-Chloro-N-(5-chloro-2-ethanesulfonyl-benzyl)-5-trifluoromethyl-4-((R)-3-ureido-pyrrolidin-1-ylmethyl)-benzamide

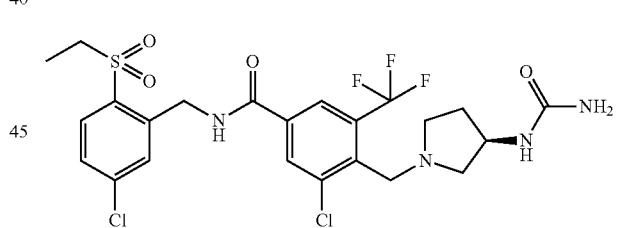

The title compound was synthesized from 4-((R)-3-amino-pyrrolidin-1-ylmethyl)-3-chloro-N-(5-chloro-2-ethanesulfonyl-benzyl)-5-trifluoromethyl-benzamide (Compound D-5) under the same conditions as for Compound B-11.

LCMS: m/z 581 [M+H]⁺

HPLC retention time: 0.49 min (analysis condition A)

Examples 196 to 202

The following compounds of FIGS. 8-9 were synthesized from 3-chloro-4-formyl-5-trifluoromethyl-benzoic acid ethyl ester (Compound d7) and corresponding amines under the same conditions as for Compounds d8, d9, d10, and D-5. However, in the synthesis of D-11, chloroform was used in place of THF as a solvent under the conditions for d8.

Example 203

Compound D-12

3-Chloro-N-(5-chloro-2-ethanesulfonyl-benzyl)-4-((R)-3-dimethylamino-piperidin-1-ylmethyl)-5-trifluoromethyl-benzamide

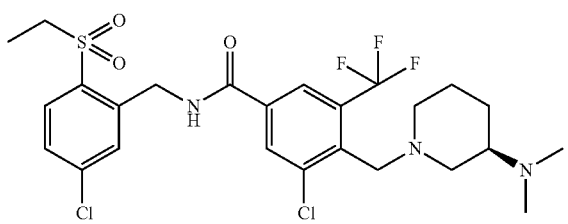 [SMILES: CCS(=O)(=O)c1ccc(Cl)cc1CNC(=O)c1cc(Cl)c(CN2CCC[C@@H](N(C)C)C2)c(C(F)(F)F)c1]

The title compound was synthesized from 4-((R)-3-amino-piperidin-1-ylmethyl)-3-chloro-N-(5-chloro-2-ethanesulfonyl-benzyl)-5-trifluoromethyl-benzamide (Compound D-11) under the same conditions as for Compound B-2.

LCMS: m/z 580 [M+H]$^+$

HPLC retention time: 0.59 min (analysis condition A)

Example 204

Compound D-13

4-((R)-3-Acetylamino-piperidin-1-ylmethyl)-3-chloro-N-(5-chloro-2-ethanesulfonyl-benzyl)-5-trifluoromethyl-benzamide

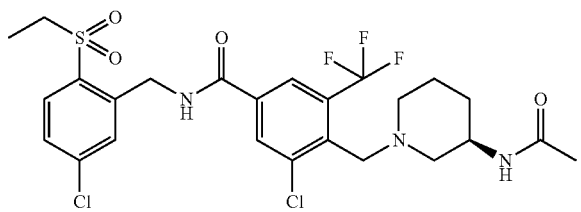 [SMILES: CCS(=O)(=O)c1ccc(Cl)cc1CNC(=O)c1cc(Cl)c(CN2CCC[C@@H](NC(C)=O)C2)c(C(F)(F)F)c1]

The title compound was synthesized from 4-((R)-3-amino-piperidin-1-ylmethyl)-3-chloro-N-(5-chloro-2-ethanesulfonyl-benzyl)-5-trifluoromethyl-benzamide (Compound D-11) under the same conditions as for Compound B-7.

LCMS: m/z 594 [M+H]$^+$

HPLC retention time: 0.55 min (analysis condition A)

Example 205

Compound D-14

3-Chloro-N-(5-chloro-2-ethanesulfonyl-benzyl)-4-((R)-3-methanesulfonylamino-piperidin-1-ylmethyl)-5-trifluoromethyl-benzamide

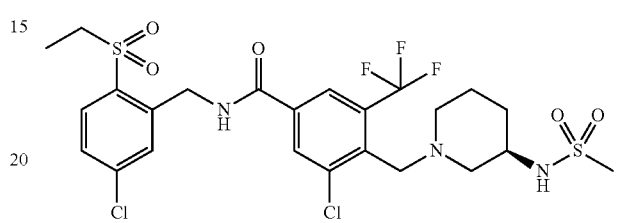

The title compound was synthesized from 4-((R)-3-amino-piperidin-1-ylmethyl)-3-chloro-N-(5-chloro-2-ethanesulfonyl-benzyl)-5-trifluoromethyl-benzamide (Compound D-11) under the same conditions as for Compound B-9.

LCMS: m/z 630 [M+H]$^+$

HPLC retention time: 0.64 min (analysis condition A)

Example 206

Compound D-15

3-Chloro-N-(5-chloro-2-ethanesulfonyl-benzyl)-5-trifluoromethyl-4-((R)-3-ureido-piperidin-1-ylmethyl)-benzamide

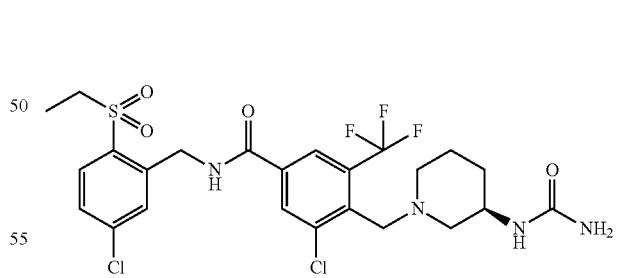

The title compound was synthesized from 4-((R)-3-amino-piperidin-1-ylmethyl)-3-chloro-N-(5-chloro-2-ethanesulfonyl-benzyl)-5-trifluoromethyl-benzamide (Compound D-11) under the same conditions as for Compound B-11.

LCMS: m/z 595 [M+H]$^+$

HPLC retention time: 0.50 min (analysis condition A)

Example 207

Compound D-16

4-[(R)-3-(2-Amino-acetylamino)-piperidin-1-ylmethyl]-3-chloro-N-(5-chloro-2-ethanesulfonyl-benzyl)-5-trifluoromethyl-benzamide

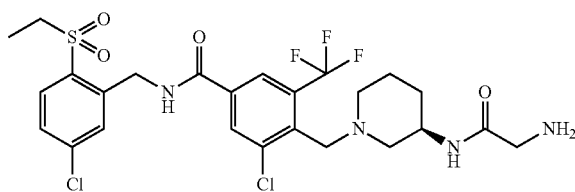 [SMILES: CCS(=O)(=O)c1ccc(Cl)cc1CNC(=O)c1cc(Cl)c(CN2CCC[C@@H](NC(=O)CN)C2)c(C(F)(F)F)c1]

The title compound was synthesized from 4-((R)-3-amino-piperidin-1-ylmethyl)-3-chloro-N-(5-chloro-2-ethanesulfonyl-benzyl)-5-trifluoromethyl-benzamide (Compound D-11) under the same conditions as for Compound B-5.

LCMS: m/z 609 [M+H]+

HPLC retention time: 0.46 min (analysis condition A)

Example 208

Compound D-19

3-Chloro-N-(5-chloro-2-ethanesulfonyl-benzyl)-4-((S)-3-dimethylamino-piperidin-1-ylmethyl)-5-trifluoromethyl-benzamide

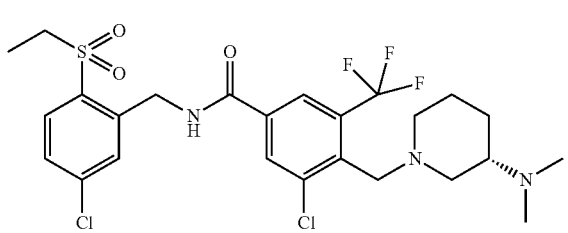 [SMILES: CCS(=O)(=O)c1ccc(Cl)cc1CNC(=O)c1cc(Cl)c(CN2CCC[C@H](N(C)C)C2)c(C(F)(F)F)c1]

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-2.

LCMS: m/z 580 [M+H]+

HPLC retention time: 0.59 min (analysis condition A)

Example 209

Compound D-20

4-((S)-3-Acetylamino-piperidin-1-ylmethyl)-3-chloro-N-(5-chloro-2-ethanesulfonyl-benzyl)-5-trifluoromethyl-benzamide

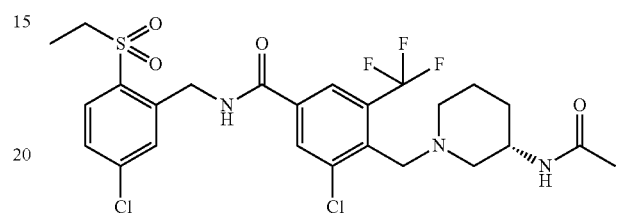

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-7.

LCMS: m/z 594 [M+H]+

HPLC retention time: 0.55 min (analysis condition A)

Example 210

Compound D-21

3-Chloro-N-(5-chloro-2-ethanesulfonyl-benzyl)-4-((S)-3-methanesulfonylamino-piperidin-1-ylmethyl)-5-trifluoromethyl-benzamide

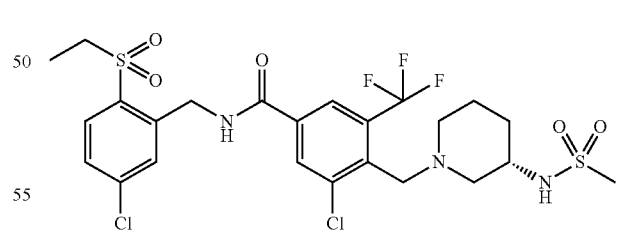

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-9.

LCMS: m/z 630 [M+H]+

HPLC retention time: 0.64 min (analysis condition A)

Example 211

Compound D-22

3-Chloro-N-(5-chloro-2-ethanesulfonyl-benzyl)-5-trifluoromethyl-4-((S)-3-ureido-piperidin-1-ylmethyl)-benzamide

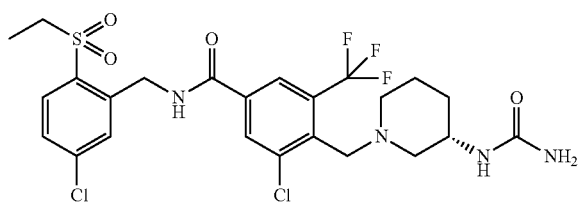 [SMILES: CCS(=O)(=O)c1ccc(Cl)cc1CNC(=O)c1cc(Cl)c(CN2CCC[C@H](NC(N)=O)C2)c(C(F)(F)F)c1]

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-11.

LCMS: m/z 595 [M+H]$^+$

HPLC retention time: 0.52 min (analysis condition A)

Example 212

Compound D-23

4-[(S)-3-(3-Amino-propionylamino)-piperidin-1-ylmethyl]-3-chloro-N-(5-chloro-2-ethanesulfonyl-benzyl)-5-trifluoromethyl-benzamide

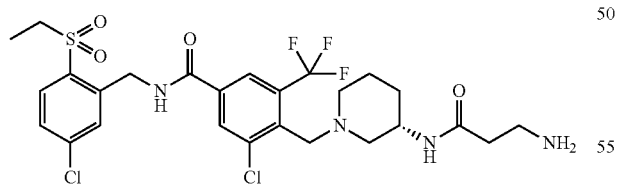

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) and 3-tert-butoxycarbonylamino-propionic acid under the same conditions as for Compound B-5.

LCMS: m/z 623 [M+H]$^+$

HPLC retention time: 0.45 min (analysis condition A)

Example 213

Compound D-24

4-[(S)-3-(2-Amino-2-methyl-propionylamino)-piperidin-1-ylmethyl]-3-chloro-N-(5-chloro-2-ethanesulfonyl-benzyl)-5-trifluoromethyl-benzamide

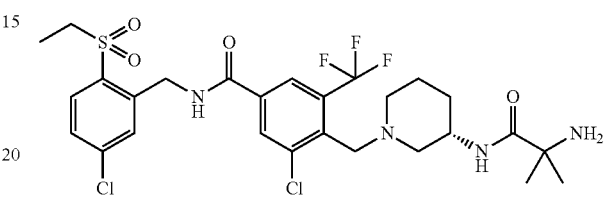

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-33.

LCMS: m/z 637 [M+H]$^+$

HPLC retention time: 0.48 min (analysis condition A)

Example 214

Compound D-25

4-[(S)-3-(2-Amino-acetylamino)-piperidin-1-ylmethyl]-3-chloro-N-(5-chloro-2-ethanesulfonyl-benzyl)-5-trifluoromethyl-benzamide

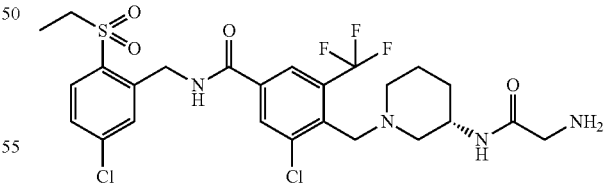

The title compound was synthesized from 4-((S)-3-amino-piperidin-1-ylmethyl)-3-chloro-N-(5-chloro-2-ethanesulfonyl-benzyl)-5-trifluoromethyl-benzamide (Compound D-18) under the same conditions as for Compound B-5.

LCMS: m/z 609 [M+H]$^+$

HPLC retention time: 0.46 min (analysis condition A)

Example 215

Compound e1

2-Amino-3-bromo-4-formyl-5-trifluoromethyl-benzoic acid ethyl ester

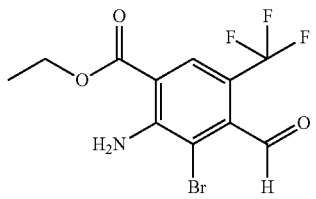 [SMILES: CCOC(=O)c1cc(C(F)(F)F)c(C=O)c(Br)c1N]

NBS (639 mg, 2.29 mmol) was added to a solution of 2-amino-4-formyl-5-trifluoromethyl-benzoic acid ethyl ester (Compound b30, 300 mg, 1.15 mmol) in DMF (3 mL), and the mixture was stirred at 50° C. for one hour. The reaction solution was extracted with ethyl acetate, and the extract was washed with brine and then dried over anhydrous magnesium sulfate. The drying agent was removed by filtration, and the residue obtained after concentration under reduced pressure was purified by silica gel column chromatography (ethyl acetate/hexane) to yield the title compound (342 mg, 87%).

LCMS: m/z 340 [M+H]$^+$

HPLC retention time: 0.87 min (analysis condition A)

Example 216

Compound e2

3-Bromo-4-formyl-5-trifluoromethyl-benzoic acid ethyl ester

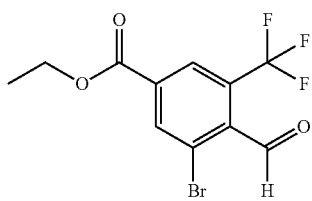 [SMILES: CCOC(=O)c1cc(Br)c(C=O)c(C(F)(F)F)c1]

The title compound was synthesized from 2-amino-3-bromo-4-formyl-5-trifluoromethyl-benzoic acid ethyl ester (Compound e1) under the same conditions as for Compound b31.

Example 217

Compound e3

3-Bromo-4-[(S)-3-(tert-butoxycarbonylamino-methyl)-pyrrolidin-1-ylmethyl]-5-trifluoromethyl-benzoic acid ethyl ester

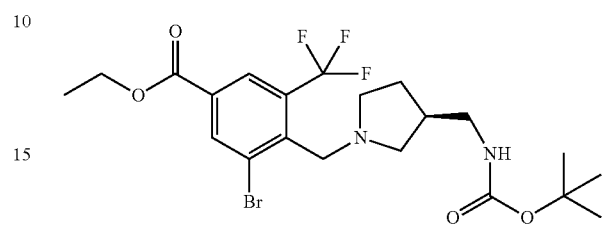

The title compound was synthesized from 3-bromo-4-formyl-5-trifluoromethyl-benzoic acid ethyl ester (Compound e2) and (R)-1-pyrrolidin-3-ylmethyl-carbamic acid tert-butyl ester under the same conditions as for Compound b32.

Example 218

Compound e4

3-Bromo-4-[(S)-3-(tert-butoxycarbonylamino-methyl)-pyrrolidin-1-ylmethyl]-5-trifluoromethyl-benzoic acid

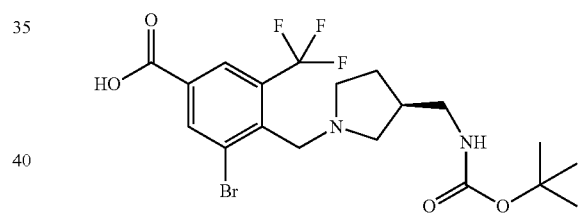

The title compound was synthesized from 3-bromo-4-[(S)-3-(tert-butoxycarbonylamino-methyl)-pyrrolidin-1-ylmethyl]-5-trifluoromethyl-benzoic acid ethyl ester (Compound e3) under the same conditions as for Compound b8.

Example 219

Compound e5

{(S)-1-[2-Bromo-4-(5-chloro-2-ethanesulfonyl-benzylcarbamoyl)-6-trifluoromethyl-benzyl]-pyrrolidin-3-ylmethyl}-carbamic acid tert-butyl ester

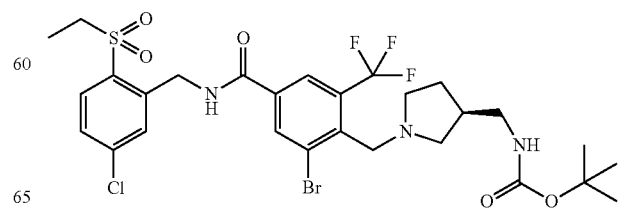

The title compound was synthesized from 3-bromo-4-[(S)-3-(tert-butoxycarbonylamino-methyl)-pyrrolidin-1-yl-methyl]-5-trifluoromethyl-benzoic acid (Compound e4) under the same conditions as for Compound A-14.

Example 220

Compound E-1

4-((S)-3-Aminomethyl-pyrrolidin-1-ylmethyl)-3-bromo-N-(5-chloro-2-ethanesulfonyl-benzyl)-5-trifluoromethyl-benzamide

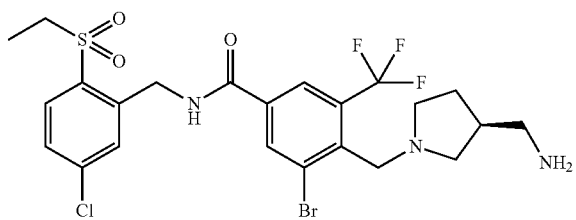 [SMILES: CCS(=O)(=O)c1ccc(Cl)cc1CNC(=O)c1cc(Br)c(CN2CC[C@@H](CN)C2)c(C(F)(F)F)c1]

The title compound was synthesized from {(S)-1-[2-bromo-4-(5-chloro-2-ethanesulfonyl-benzylcarbamoyl)-6-trifluoromethyl-benzyl]-pyrrolidin-3-ylmethyl}-carbamic acid tert-butyl ester (Compound e5) under the same conditions as for Compound B-1.

LCMS: m/z 596 [M+H]$^+$

HPLC retention time: 0.43 min (analysis condition A)

Examples 221 to 223

The following compounds of FIG. 10 were synthesized from 3-bromo-4-formyl-5-trifluoromethyl-benzoic acid ethyl ester (Compound e2) using corresponding cyclic amines under the same conditions as for Compounds e3, e4, e5, and E-1.

Example 224

Compound e6

3-Bromo-4-formyl-5-trifluoromethyl-benzoic acid

Compound 193

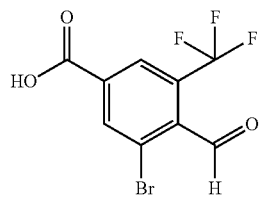

The title compound was synthesized from 3-bromo-4-formyl-5-trifluoromethyl-benzoic acid ethyl ester (Compound e2) under the same conditions as for Compound b8.

Example 225

Compound e7

3-Bromo-N-(5-chloro-2-ethanesulfonyl-benzyl)-4-formyl-5-trifluoromethyl-benzamide

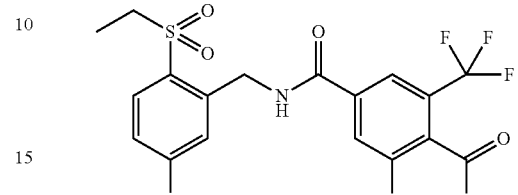

The title compound was synthesized from 3-bromo-4-formyl-5-trifluoromethyl-benzoic acid (Compound e6) under the same conditions as for Compound A-14.

Example 226

Compound e8

{(R)-1-[2-Bromo-4-(5-chloro-2-ethanesulfonyl-benzylcarbamoyl)-6-trifluoromethyl-benzyl]-piperidin-3-yl}-carbamic acid tert-butyl ester

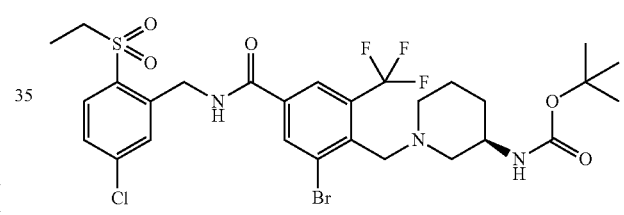

The title compound was synthesized from 3-bromo-N-(5-chloro-2-ethanesulfonyl-benzyl)-4-formyl-5-trifluoromethyl-benzamide (Compound e7) and (R)-piperidin-3-yl-carbamic acid tert-butyl ester under the same conditions as for Compound b32. However, chloroform was used in place of THF as a solvent.

Example 227

Compound E-5

4-((R)-3-Amino-piperidin-1-ylmethyl)-3-bromo-N-(5-chloro-2-ethanesulfonyl-benzyl)-5-trifluoromethyl-benzamide

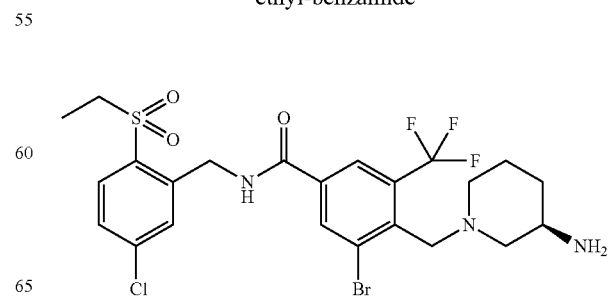

The title compound was synthesized from {(R)-1-[2-bromo-4-(5-chloro-2-ethanesulfonyl-benzylcarbamoyl)-6-trifluoromethyl-benzyl]-piperidin-3-yl}-carbamic acid tert-butyl ester (Compound e8) under the same conditions as for Compound B-57.

LCMS: m/z 596 [M+H]+

HPLC retention time: 0.58 min (analysis condition A)

Examples 228 to 230

The following compounds of FIG. 11 were synthesized from 3-bromo-N-(5-chloro-2-ethanesulfonyl-benzyl)-4-formyl-5-trifluoromethyl-benzamide (Compound e7) using corresponding cyclic amines under the same conditions as for Compounds e8 and E-5.

Example 231

Compound f1

4-Bromo-2-nitro-5-trifluoromethoxy-benzoic acid

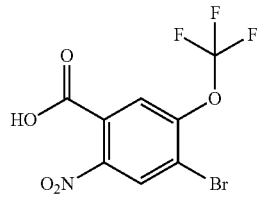 [SMILES: O=C(O)c1cc(OC(F)(F)F)c(Br)cc1[N+](=O)[O-]]

A solution of 2-nitro-5-trifluoromethoxy-benzoic acid (25.3 g, 0.10 mol) in concentrated sulfuric acid (75 ml) was warmed to 80° C., and NBS (18 g, 0.10 mol) was added in three portions at 15 min intervals. After stirring at 80° C. for two hours, NBS (9.0 g, 0.050 mol) and concentrated sulfuric acid (25 ml) were added, and the mixture was stirred at 80° C. for further three hours. The reaction mixture was cooled to room temperature and then added to ice water, and the solid was filtered. This was washed with H₂O and methanol, and H₂O/methanol=5/1 (120 ml) was then added, followed by stirring at 0° C. for 30 minutes. The solid was collected by filtration, washed with H₂O/methanol=5/1, and dried to yield the title compound as a crude product.

Example 232

Compound f2

4-Bromo-2-nitro-5-trifluoromethoxy-benzoic acid ethyl ester

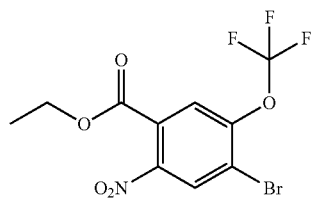 [SMILES: CCOC(=O)c1cc(OC(F)(F)F)c(Br)cc1[N+](=O)[O-]]

The title compound was synthesized from 4-bromo-2-nitro-5-trifluoromethoxy-benzoic acid (Compound f1) under the same conditions as for Compound b1.

Example 233

Compound f3

4-(4-Ethoxycarbonyl-5-nitro-2-trifluoromethoxy-benzyl)-piperazine-1-carboxylic acid tert-butyl ester

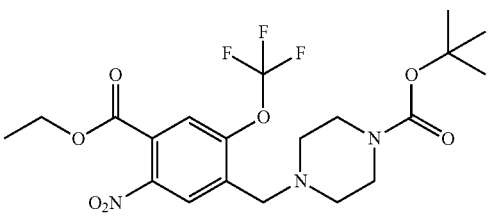

The title compound was synthesized from 4-bromo-2-nitro-5-trifluoromethoxy-benzoic acid ethyl ester (Compound f2) under the same conditions as for Compound b2.

Example 234

Compound f4

4-(5-Amino-4-ethoxycarbonyl-2-trifluoromethoxy-benzyl)-piperazine-1-carboxylic acid tert-butyl ester

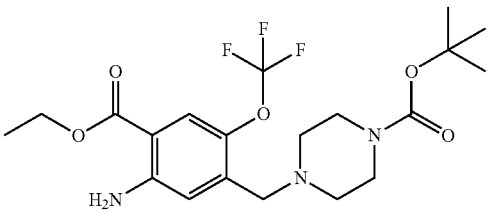 [SMILES: CCOC(=O)c1cc(OC(F)(F)F)c(CN2CCN(C(=O)OC(C)(C)C)CC2)cc1[N+](=O)[O-]]

A saturated aqueous ammonium chloride solution (12 mL) was added to a suspension of 4-(4-ethoxycarbonyl-5-nitro-2-trifluoromethoxy-benzyl)-piperazine-1-carboxylic acid tert-butyl ester (Compound f3, 1.2 g, 2.5 mol) and iron (702 mg, 13 mmol) in 2-PrOH (12 mL), and the mixture was stirred at 100° C. for 1.5 hours. The reaction solution was diluted with ethyl acetate, and the organic layer was washed with water and then dried over anhydrous sodium sulfate. The drying agent was removed by filtration, and the residue obtained after concentration under reduced pressure was purified by silica gel column chromatography (ethyl acetate/hexane) to yield the title compound (760 mg, 68%) as a yellow foamy substance.

LCMS: m/z 448 [M+H]+

HPLC retention time: 2.16 min (analysis condition C)

Example 235

Compound f5

4-(3-Amino-2-chloro-4-ethoxycarbonyl-6-trifluoromethoxy-benzyl)-piperazine-1-carboxylic acid tert-butyl ester

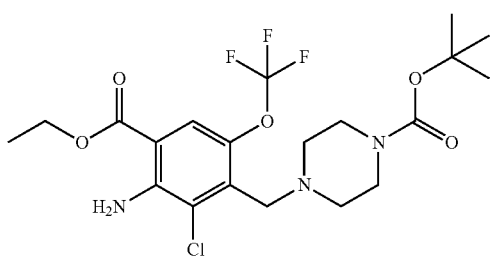 [SMILES: CCOC(=O)c1cc(OC(F)(F)F)c(CN2CCN(C(=O)OC(C)(C)C)CC2)c(Cl)c1N]

The title compound was synthesized from 4-(5-amino-4-ethoxycarbonyl-2-trifluoromethoxy-benzyl)-piperazine-1-carboxylic acid tert-butyl ester (Compound f4) under the same conditions as for Compound d2.

Example 236

Compound f6

4-(2-Chloro-4-ethoxycarbonyl-6-trifluoromethoxy-benzyl)-piperazine-1-carboxylic acid tert-butyl ester

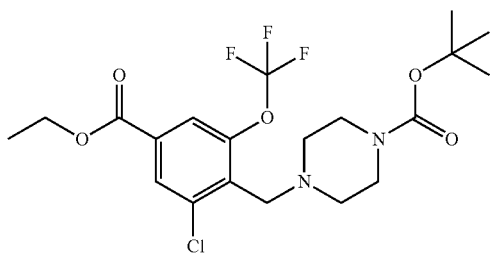 [SMILES: CCOC(=O)c1cc(Cl)c(CN2CCN(C(=O)OC(C)(C)C)CC2)c(OC(F)(F)F)c1]

The title compound was synthesized from 4-(3-amino-2-chloro-4-ethoxycarbonyl-6-trifluoromethoxy-benzyl)-piperazine-1-carboxylic acid tert-butyl ester (Compound f5) under the same conditions as for Compound b31.

Example 237

Compound f7

4-(4-Carboxy-2-chloro-6-trifluoromethoxy-benzyl)-piperazine-1-carboxylic acid tert-butyl ester

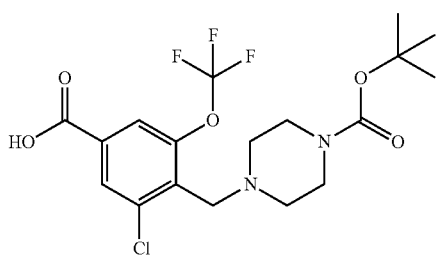 [SMILES: CC(C)(C)OC(=O)N1CCN(Cc2c(Cl)cc(C(=O)O)cc2OC(F)(F)F)CC1]

The title compound was synthesized from 4-(2-chloro-4-ethoxycarbonyl-6-trifluoromethoxy-benzyl)-piperazine-1-carboxylic acid tert-butyl ester (Compound f6) under the same conditions as for Compound b3.

Example 238

Compound f8

4-[2-Chloro-4-(5-chloro-2-ethanesulfonyl-benzylcarbamoyl)-6-trifluoromethoxy-benzyl]-piperazine-1-carboxylic acid tert-butyl ester

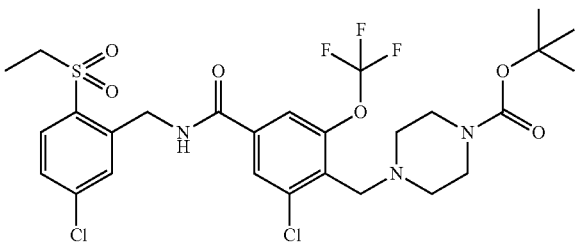 [SMILES: CCS(=O)(=O)c1ccc(Cl)cc1CNC(=O)c1cc(Cl)c(CN2CCN(C(=O)OC(C)(C)C)CC2)c(OC(F)(F)F)c1]

The title compound was synthesized from 4-(4-carboxy-2-chloro-6-trifluoromethoxy-benzyl)-piperazine-1-carboxylic acid tert-butyl ester (Compound f7) under the same conditions as for Compound A-14.

Example 239

Compound F-1

3-Chloro-N-(5-chloro-2-ethanesulfonyl-benzyl)-4-piperazin-1-ylmethyl-5-trifluoromethoxy-benzamide

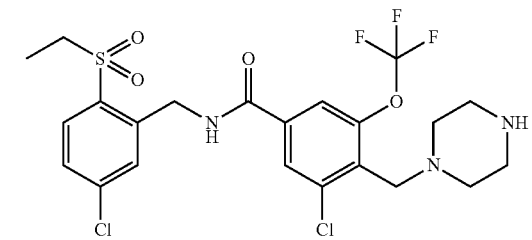 [SMILES: CCS(=O)(=O)c1ccc(Cl)cc1CNC(=O)c1cc(Cl)c(CN2CCNCC2)c(OC(F)(F)F)c1]

The title compound was synthesized from 4-[2-chloro-4-(5-chloro-2-ethanesulfonyl-benzylcarbamoyl)-6-trifluoromethoxy-benzyl]-piperazine-1-carboxylic acid tert-butyl ester (Compound f8) under the same conditions as for Compound B-1.

LCMS: m/z 554 [M+H]$^+$

HPLC retention time: 1.52 min (analysis condition D)

Example 240

Compound F-2

3-Chloro-N-(5-chloro-2-ethanesulfonyl-benzyl)-4-(4-methyl-piperazin-1-ylmethyl)-5-trifluoromethoxy-benzamide

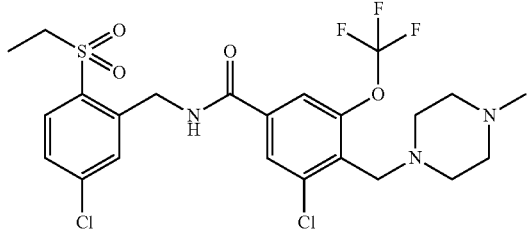 [SMILES: CCS(=O)(=O)c1ccc(Cl)cc1CNC(=O)c1cc(Cl)c(CN2CCN(C)CC2)c(OC(F)(F)F)c1]

The title compound was synthesized from 3-chloro-N-(5-chloro-2-ethanesulfonyl-benzyl)-4-piperazin-1-ylmethyl-5-trifluoromethoxy-benzamide (Compound F-1) under the same conditions as for Compound B-2.

LCMS: m/z 568 [M+H]$^+$

HPLC retention time: 1.55 min (analysis condition D)

Example 241

Compound F-3

3-Chloro-N-(5-chloro-2-ethanesulfonyl-benzyl)-4-(4-isopropyl-piperazin-1-ylmethyl)-5-trifluoromethoxy-benzamide

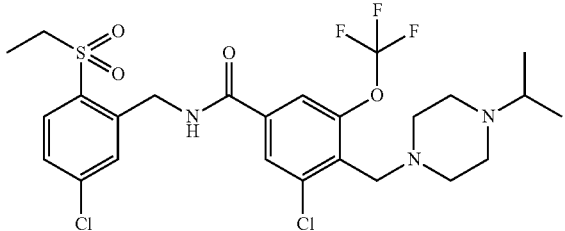 [SMILES: CCS(=O)(=O)c1ccc(Cl)cc1CNC(=O)c1cc(Cl)c(CN2CCN(C(C)C)CC2)c(OC(F)(F)F)c1]

The title compound was synthesized from 3-chloro-N-(5-chloro-2-ethanesulfonyl-benzyl)-4-piperazin-1-ylmethyl-5-trifluoromethoxy-benzamide (Compound F-1) under the same conditions as for Compound B-3.

LCMS: m/z 596 [M+H]$^+$

HPLC retention time: 1.65 min (analysis condition D)

Example 242

Compound F-4

3-Chloro-N-(5-chloro-2-ethanesulfonyl-benzyl)-4-[4-(tetrahydro-pyran-4-yl)-piperazin-1-ylmethyl]-5-trifluoromethoxy-benzamide

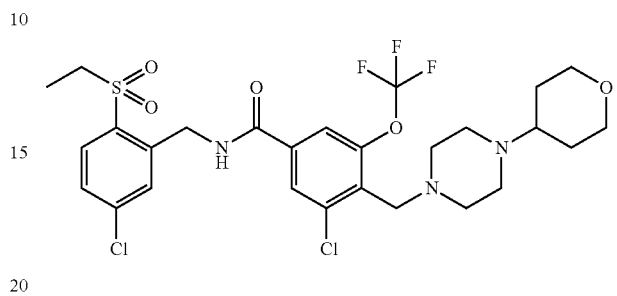

The title compound was synthesized from 3-chloro-N-(5-chloro-2-ethanesulfonyl-benzyl)-4-piperazin-1-ylmethyl-5-trifluoromethoxy-benzamide (Compound F-1) under the same conditions as for Compound B-4.

LCMS: m/z 638 [M+H]$^+$

HPLC retention time: 1.58 min (analysis condition D)

Example 243

Compound f9

4-(3-Amino-2-bromo-4-ethoxycarbonyl-6-trifluoromethoxy-benzyl)-piperazine-1-carboxylic acid tert-butyl ester

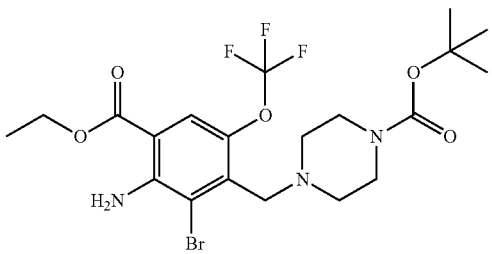

Bromine (505 μL, 9.8 mmol) was added to a suspension of 4-(5-amino-4-ethoxycarbonyl-2-trifluoromethoxy-benzyl)-piperazine-1-carboxylic acid tert-butyl ester (Compound f4, 880 mg, 2.0 mmol) and iron (549 mg, 9.8 mmol) in chloroform, and the mixture was stirred at 60° C. for one hour. The reaction solution was diluted with ethyl acetate, and the organic layer was washed with a saturated aqueous sodium bicarbonate solution, water, and brine, and then dried over anhydrous sodium sulfate. The drying agent was removed by filtration, and the residue obtained after concentration under reduced pressure was dissolved in DCM (10 mL), and Boc$_2$O (430 mg, 2.0 mmol) was added, and the mixture was stirred at room temperature for one hour. The reaction solution was diluted with ethyl acetate, and the organic layer was washed with water and brine, and then dried over anhydrous sodium sulfate. The drying agent was removed by filtration, and the residue obtained after concentration under reduced pressure was purified by silica gel column chromatography (ethyl acetate/n-hexane) to yield the title compound (195 mg, 19%) as an oily substance.

LCMS: m/z 526 [M+H]+

HPLC retention time: 2.26 min (analysis condition C)

Example 244

Compound F-5

3-Bromo-N-(5-chloro-2-ethanesulfonyl-benzyl)-4-piperazin-1-ylmethyl-5-trifluoromethoxy-benzamide

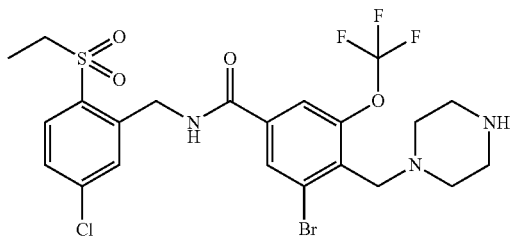 [SMILES: CCS(=O)(=O)c1ccc(Cl)cc1CNC(=O)c1cc(Br)c(CN2CCNCC2)c(OC(F)(F)F)c1]

The title compound was synthesized from 4-(3-amino-2-bromo-4-ethoxycarbonyl-6-trifluoromethoxy-benzyl)-piperazine-1-carboxylic acid tert-butyl ester (Compound f9) under the same conditions as for Compounds f6, f7, f8, and F-1.

LCMS: m/z 598 [M+H]+

HPLC retention time: 0.56 min (analysis condition A)

Example 245

Compound f10

2-Nitro-5-trifluoromethoxy-4-vinyl-benzoic acid ethyl ester

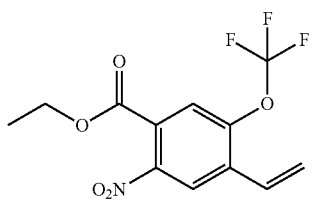 [SMILES: C=Cc1cc([N+](=O)[O-])c(C(=O)OCC)cc1OC(F)(F)F]

The title compound was synthesized from 4-bromo-2-nitro-5-trifluoromethoxy-benzoic acid ethyl ester (Compound f2) under the same conditions as for Compound b28.

Example 246

Compound f11

2-Amino-5-trifluoromethoxy-4-vinyl-benzoic acid ethyl ester

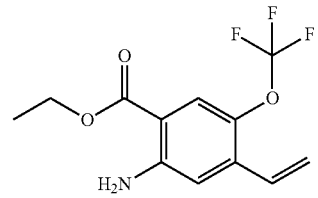

A saturated aqueous ammonium chloride solution (1.5 mL) and powder zinc (167 mg, 2.6 mmol) were added to a solution of 2-nitro-5-trifluoromethoxy-4-vinyl-benzoic acid ethyl ester (Compound f10, 156 mg, 0.51 mmol) in 2-PrOH (1.5 mL), and the mixture was stirred at 80° C. for one hour. The reaction solution was diluted with ethyl acetate, and the organic layer was washed with water and brine, and then dried over anhydrous sodium sulfate. The drying agent was removed by filtration, and the residue obtained after concentration under reduced pressure was purified by silica gel column chromatography (DCM/hexane) to yield the title compound (140 mg, quant.) as a brown solid.

1H-NMR (300 MHz, CDCl$_3$) δ: 7.73 (1H, s), 6.86 (1H, dd, J=17.7, 11.2 Hz), 6.82 (1H, s), 5.81 (1H, d, J=17.7 Hz), 5.76 (2H, brs), 5.45 (1H, d, J=11.2 Hz), 4.34 (2H, q, J=7.1 Hz), 1.39 (3H, t, J=7.1 Hz).

Example 247

Compound f12

2-Amino-4-(1,2-dihydroxy-ethyl)-5-trifluoromethoxy-benzoic acid ethyl ester

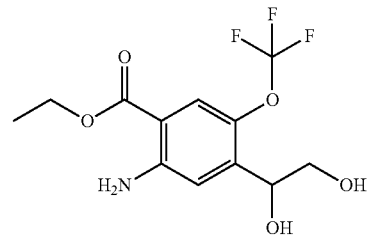 [SMILES: CCOC(=O)c1cc(OC(F)(F)F)c(C(O)CO)cc1N]

The title compound was synthesized from 2-amino-5-trifluoromethoxy-4-vinyl-benzoic acid ethyl ester (Compound f11) under the same conditions as for Compound b29.

Example 248

Compound f13

2-Amino-4-formyl-5-trifluoromethoxy-benzoic acid ethyl ester

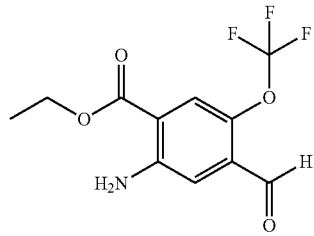 [SMILES: CCOC(=O)c1cc(OC(F)(F)F)c(C=O)cc1N]

The title compound was synthesized from 2-amino-4-(1,2-dihydroxy-ethyl)-5-trifluoromethoxy-benzoic acid ethyl ester (Compound f12) under the same conditions as for Compound b30.

Example 249

Compound f14

2-Amino-3-chloro-4-formyl-5-trifluoromethoxy-benzoic acid ethyl ester

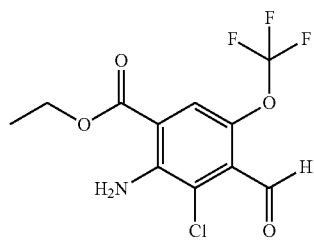 [SMILES: CCOC(=O)c1cc(OC(F)(F)F)c(C=O)c(Cl)c1N]

The title compound was synthesized from 2-amino-4-formyl-5-trifluoromethoxy-benzoic acid ethyl ester (Compound f13) under the same conditions as for Compound d6.

Example 250

Compound f15

3-Chloro-4-formyl-5-trifluoromethoxy-benzoic acid ethyl ester

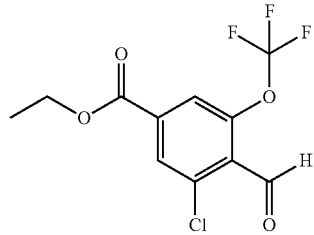 [SMILES: CCOC(=O)c1cc(Cl)c(C=O)c(OC(F)(F)F)c1]

The title compound was synthesized from 2-amino-3-chloro-4-formyl-5-trifluoromethoxy-benzoic acid ethyl ester (Compound f14) under the same conditions as for Compound b31.

Example 251

Compound f16

4-((R)-3-tert-Butoxycarbonylamino-pyrrolidin-1-ylmethyl)-3-chloro-5-trifluoromethoxy-benzoic acid ethyl ester

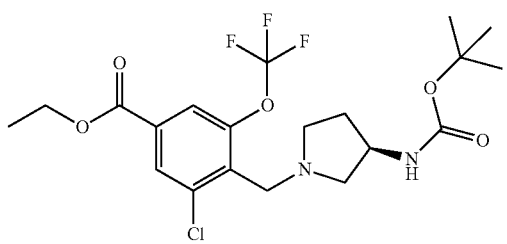 [SMILES: CCOC(=O)c1cc(Cl)c(CN2CC[C@@H](NC(=O)OC(C)(C)C)C2)c(OC(F)(F)F)c1]

The title compound was synthesized from 3-chloro-4-formyl-5-trifluoromethoxy-benzoic acid ethyl ester (Compound f15) and (R)-pyrrolidin-3-yl-carbamic acid tert-butyl ester under the same conditions as for Compound b32.

Example 252

Compound f17

4-((R)-3-tert-Butoxycarbonylamino-pyrrolidin-1-ylmethyl)-3-chloro-5-trifluoromethoxy-benzoic acid

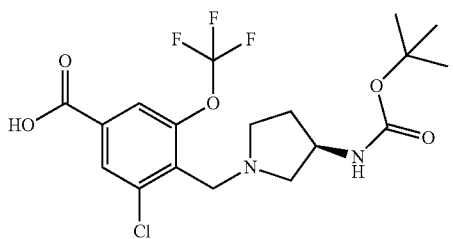 [SMILES: CC(C)(C)OC(=O)N[C@@H]1CCN(Cc2c(Cl)cc(C(=O)O)cc2OC(F)(F)F)C1]

The title compound was synthesized from 4-((R)-3-tert-butoxycarbonylamino-pyrrolidin-1-ylmethyl)-3-chloro-5-trifluoromethoxy-benzoic acid ethyl ester (Compound f16) under the same conditions as for Compound b8.

Example 253

Compound f18

{(R)-1-[2-Chloro-4-(5-chloro-2-ethanesulfonyl-benzylcarbamoyl)-6-trifluoromethoxy-benzyl]-pyrrolidin-3-yl}-carbamic acid tert-butyl ester

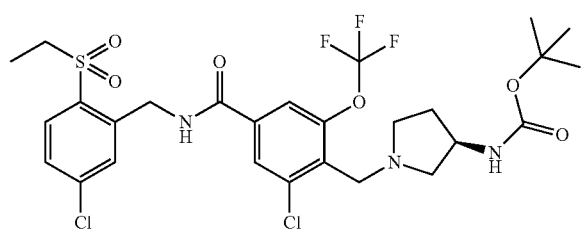 [SMILES: CCS(=O)(=O)c1ccc(Cl)cc1CNC(=O)c1cc(Cl)c(CN2CC[C@@H](NC(=O)OC(C)(C)C)C2)c(OC(F)(F)F)c1]

The title compound was synthesized from 4-((R)-3-tert-butoxycarbonylamino-pyrrolidin-1-ylmethyl)-3-chloro-5-trifluoromethoxy-benzoic acid (Compound f17) under the same conditions as for Compound A-14.

Example 254

Compound F-6

4-((R)-3-Amino-pyrrolidin-1-ylmethyl)-3-chloro-N-(5-chloro-2-ethanesulfonyl-benzyl)-5-trifluoromethoxy-benzamide

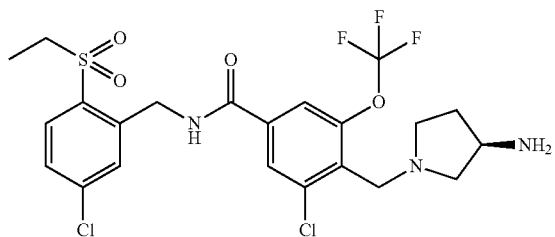 [SMILES: CCS(=O)(=O)c1ccc(Cl)cc1CNC(=O)c1cc(Cl)c(CN2CC[C@@H](N)C2)c(OC(F)(F)F)c1]

The title compound was synthesized from {(R)-1-[2-chloro-4-(5-chloro-2-ethanesulfonyl-benzylcarbamoyl)-6-trifluoromethoxy-benzyl]-pyrrolidin-3-yl}-carbamic acid tert-butyl ester (Compound f18) under the same conditions as for Compound B-1.

LCMS: m/z 554 [M+H]$^+$
HPLC retention time: 0.49 min (analysis condition A)

Examples 255 to 259

The following compounds of FIG. 12 were synthesized from 3-chloro-4-formyl-5-trifluoromethoxy-benzoic acid ethyl ester (Compound f15) and corresponding amines under the same conditions as for Compounds f16, f17, f18, and F-6. However, chloroform was used as a solvent under the conditions for Compound f16 in the synthesis of Compounds F-7 and F-8, and DCM was used as a solvent under the conditions for Compound f16 in the synthesis of Compounds F-9, F-15, and F-16. In addition, DCM was used as a solvent under the conditions for Compound f18 in the synthesis of Compounds F-16.

Example 260

Compound F-10

3-Chloro-N-(5-chloro-2-ethanesulfonyl-benzyl)-4-((S)-3-dimethylamino-piperidin-1-ylmethyl)-5-trifluoromethoxy-benzamide

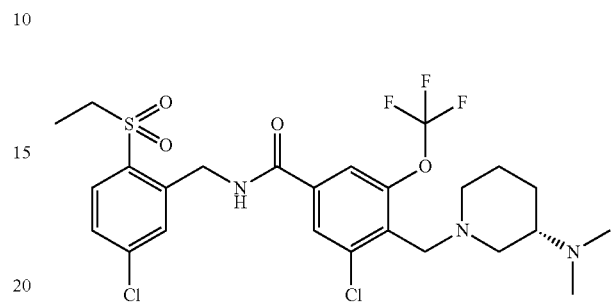

The title compound was synthesized from 4-((S)-3-amino-piperidin-1-ylmethyl)-3-chloro-N-(5-chloro-2-ethanesulfonyl-benzyl)-5-trifluoromethoxy-benzamide (Compound F-9) under the same conditions as for Compound B-2.

LCMS: m/z 596 [M+H]$^+$
HPLC retention time: 0.58 min (analysis condition A)

Example 261

Compound F-12

3-Chloro-N-(5-chloro-2-ethanesulfonyl-benzyl)-4-((S)-3-methanesulfonylamino-piperidin-1-ylmethyl)-5-trifluoromethoxy-benzamide

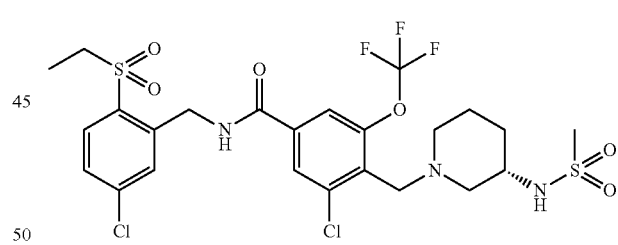

The title compound was synthesized from 4-((S)-3-amino-piperidin-1-ylmethyl)-3-chloro-N-(5-chloro-2-ethanesulfonyl-benzyl)-5-trifluoromethoxy-benzamide (Compound F-9) under the same conditions as for Compound B-9.

LCMS: m/z 646 [M+H]$^+$
HPLC retention time: 0.59 min (analysis condition A)

Example 262

Compounds F-11 and F-13 were synthesized from 4-((S)-3-amino-piperidin-1-ylmethyl)-3-chloro-N-(5-chloro-2-ethanesulfonyl-benzyl)-5-trifluoromethoxy-benzamide (Compound F-9) under the same conditions as for Compound B-11.

Compound F-11

4-((S)-3-Acetylamino-piperidin-1-ylmethyl)-3-chloro-N-(5-chloro-2-ethanesulfonyl-benzyl)-5-trifluoromethoxy-benzamide

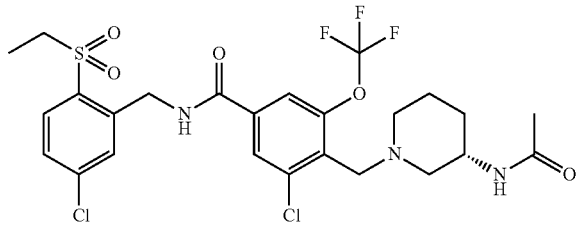 [SMILES: CCS(=O)(=O)c1ccc(Cl)cc1CNC(=O)c1cc(Cl)c(CN2CCC[C@H](NC(C)=O)C2)c(OC(F)(F)F)c1]

LCMS: m/z 610 [M+H]$^+$
HPLC retention time: 0.54 min (analysis condition A)

Compound F-13

3-Chloro-N-(5-chloro-2-ethanesulfonyl-benzyl)-5-trifluoromethoxy-4-((S)-3-ureido-piperidin-1-ylmethyl)-benzamide

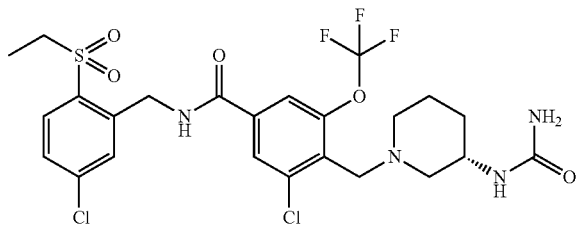 [SMILES: CCS(=O)(=O)c1ccc(Cl)cc1CNC(=O)c1cc(Cl)c(CN2CCC[C@H](NC(N)=O)C2)c(OC(F)(F)F)c1]

LCMS: m/z 611 [M+H]$^+$
HPLC retention time: 0.52 min (analysis condition A)

Example 263

Compound F-14

4-[(S)-3-(2-Amino-acetylamino)-piperidin-1-ylmethyl]-3-chloro-N-(5-chloro-2-ethanesulfonyl-benzyl)-5-trifluoromethoxy-benzamide

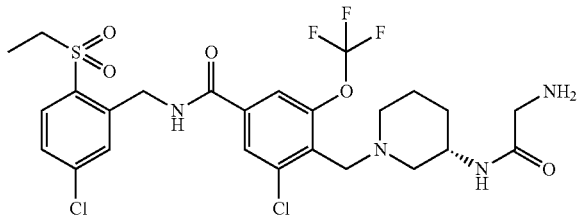 [SMILES: CCS(=O)(=O)c1ccc(Cl)cc1CNC(=O)c1cc(Cl)c(CN2CCC[C@H](NC(=O)CN)C2)c(OC(F)(F)F)c1]

The title compound was synthesized from 4-((S)-3-amino-piperidin-1-ylmethyl)-3-chloro-N-(5-chloro-2-ethanesulfonyl-benzyl)-5-trifluoromethoxy-benzamide (Compound F-9) under the same conditions as for Compound B-5.

LCMS: m/z 625 [M+H]$^+$
HPLC retention time: 0.44 min (analysis condition A)

Example 264

Compound g1

3-Bromo-4-methyl-benzoic acid ethyl ester

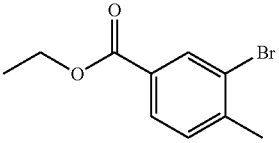

The title compound was synthesized from 3-bromo-4-methyl-benzoic acid under the same conditions as for Compound b1.

Example 265

Compound g2

3-Bromo-4-bromomethyl-benzoic acid ethyl ester

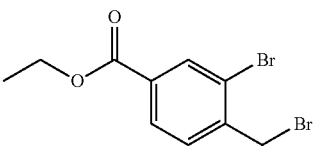

The title compound was synthesized from 3-bromo-4-methyl-benzoic acid ethyl ester (Compound g1) under the same conditions as for Compound b6.

Example 266

Compound g3

4-(2-Bromo-4-ethoxycarbonyl-benzyl)-piperazine-1-carboxylic acid tert-butyl ester

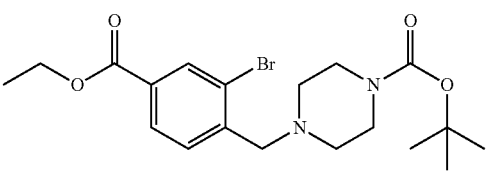 [SMILES: CCOC(=O)c1ccc(CN2CCN(C(=O)OC(C)(C)C)CC2)c(Br)c1]

Piperazine-1-carboxylic acid tert-butyl ester (2.6 g, 14.3 mmol) was added to a mixture of 3-Bromo-4-(bromomethyl)benzoic acid ethyl ester (Compound g2, 2.28 g, 7.08 mmol) in THF, and the mixture was stirred at 75° C. for three hours. After the reaction solution was cooled to room temperature, water was added, followed by extraction with dichloromethane. The organic layer was washed three times with water and then dried over anhydrous magnesium sulfate. The drying agent was removed by filtration, and the residue obtained after concentration under reduced pressure was purified by silica gel column chromatography (ethyl acetate/hexane) to yield the title compound (1.2 g, 40%).

LCMS: m/z 427 [M+H]$^+$

HPLC retention time: 1.13 min (analysis condition E)

Example 267

Compound g4

4-(2-Bromo-4-carboxy-benzyl)-piperazine-1-carboxylic acid tert-butyl ester

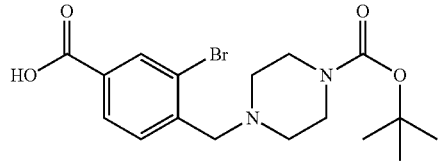 [SMILES: CC(C)(C)OC(=O)N1CCN(Cc2ccc(C(=O)O)cc2Br)CC1]

The title compound was synthesized from 4-(2-bromo-4-ethoxycarbonyl-benzyl)-piperazine-1-carboxylic acid tert-butyl ester (Compound g3) under the same conditions as for Compound b3.

Example 268

Compound g5

4-[2-Bromo-4-(5-chloro-2-ethanesulfonyl-benzylcarbamoyl)-benzyl]-piperazine-1-carboxylic acid tert-butyl ester

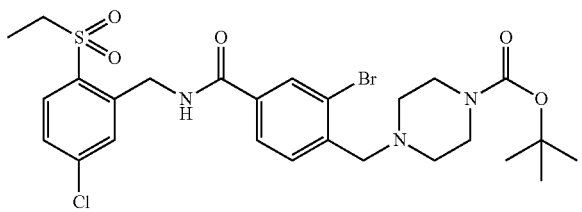 [SMILES: CCS(=O)(=O)c1ccc(Cl)cc1CNC(=O)c1ccc(CN2CCN(C(=O)OC(C)(C)C)CC2)c(Br)c1]

The title compound was synthesized from 4-(2-Bromo-4-carboxy-benzyl)-piperazine-1-carboxylic acid tert-butyl ester (Compound g4) under the same conditions as for Compound A-14.

Example 269

Compound G-1

3-Bromo-N-(5-chloro-2-ethanesulfonyl-benzyl)-4-piperazin-1-ylmethyl-benzamide

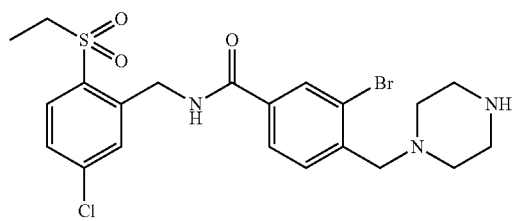 [SMILES: CCS(=O)(=O)c1ccc(Cl)cc1CNC(=O)c1ccc(CN2CCNCC2)c(Br)c1]

The title compound was synthesized from 4-[2-bromo-4-(5-chloro-2-ethanesulfonyl-benzylcarbamoyl)-benzyl]-piperazine-1-carboxylic acid tert-butyl ester (Compound g5) under the same conditions as for Compound B-1.

LCMS: m/z 514 [M+H]$^+$

HPLC retention time: 1.18 min (analysis condition D)

Example 270

Compound G-2

3-Bromo-N-(5-chloro-2-ethanesulfonyl-benzyl)-4-(4-methyl-piperazin-1-ylmethyl)-benzamide

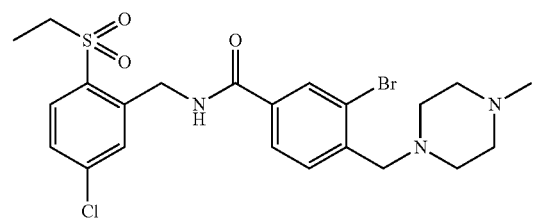

The title compound was synthesized from 3-bromo-N-(5-chloro-2-ethanesulfonyl-benzyl)-4-piperazin-1-ylmethyl-benzamide (Compound G-1) under the same conditions as for Compound B-2.

LCMS: m/z 528 [M+H]$^+$

HPLC retention time: 1.28 min (analysis condition D)

Example 271

Compound G-3

3-Bromo-N-(5-chloro-2-ethanesulfonyl-benzyl)-4-(4-isopropyl-piperazin-1-ylmethyl)-benzamide

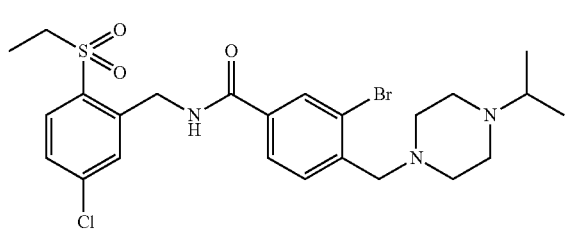

The title compound was synthesized from 3-bromo-N-(5-chloro-2-ethanesulfonyl-benzyl)-4-piperazin-1-ylmethyl-benzamide (Compound G-1) under the same conditions as for Compound B-3.

LCMS: m/z 556 [M+H]$^+$

HPLC retention time: 0.51 min (analysis condition A)

Example 272

Compound G-4

3-Bromo-N-(5-chloro-2-ethanesulfonyl-benzyl)-4-[4-(tetrahydro-pyran-4-yl)-piperazin-1-ylmethyl]-benzamide

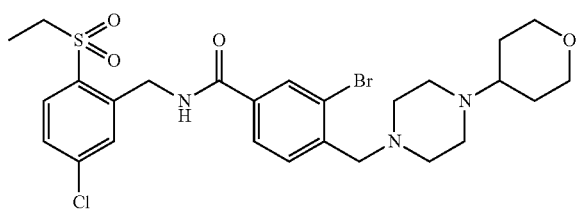

The title compound was synthesized from 3-bromo-N-(5-chloro-2-ethanesulfonyl-benzyl)-4-piperazin-1-ylmethyl-benzamide (Compound G-1) under the same conditions as for Compound B-4.
LCMS: m/z 598 [M+H]$^+$
HPLC retention time: 0.50 min (analysis condition A)

Example 273

Compound g6

3-Bromo-4-((R)-3-tert-butoxycarbonylamino-pyrrolidin-1-ylmethyl)-benzoic acid ethyl ester

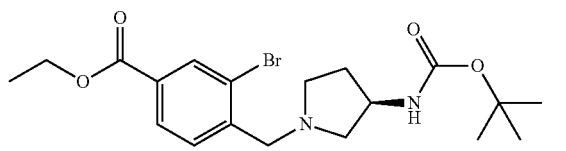 [SMILES: CCOC(=O)c1ccc(CN2CC[C@@H](NC(=O)OC(C)(C)C)C2)c(Br)c1]

The title compound was synthesized from 3-bromo-4-bromomethyl-benzoic acid ethyl ester (Compound g2) and (R)-pyrrolidin-3-yl-carbamic acid tert-butyl ester under the same conditions as for Compound b7.

Example 274

Compound g7

3-Bromo-4-((R)-3-tert-butoxycarbonylamino-pyrrolidin-1-ylmethyl)-benzoic acid

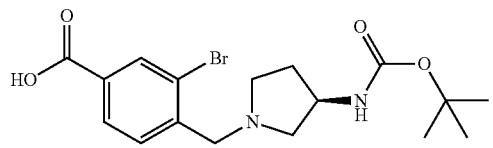 [SMILES: CC(C)(C)OC(=O)N[C@@H]1CCN(Cc2ccc(C(=O)O)cc2Br)C1]

A 6N aqueous sodium hydroxide solution (3 ml) was added to a solution of 3-bromo-4-((R)-3-tert-butoxycarbonylamino-pyrrolidin-1-ylmethyl)-benzoic acid ethyl ester (Compound g6, 1.24 g, 2.9 mmol) in EtOH (14.5 ml), and the mixture was stirred at room temperature overnight. The reaction mixture was neutralized by adding an aqueous hydrochloric acid solution. The aqueous layer was then extracted with ethyl acetate, and the organic layer was collected, washed with saturated saline, and dried over anhydrous sodium sulfate. The drying agent was removed by filtration, and the solvent was then concentrated under reduced pressure to yield a crude product of the title compound.

Example 275

Compound g8

{(R)-1-[2-Bromo-4-(5-chloro-2-ethanesulfonyl-benzylcarbamoyl)-benzyl]-pyrrolidin-3-yl}-carbamic acid tert-butyl ester

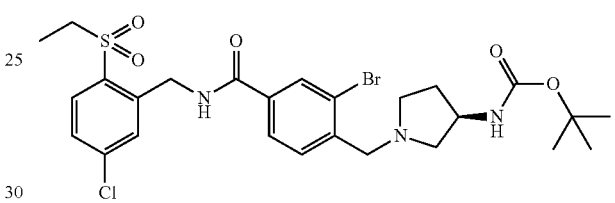

The title compound was synthesized from 3-bromo-4-((R)-3-tert-butoxycarbonylamino-pyrrolidin-1-ylmethyl)-benzoic acid (Crude compound g7) under the same conditions as for Compound A-1.

Example 276

Compound G-5

4-((R)-3-Amino-pyrrolidin-1-ylmethyl)-3-bromo-N-(5-chloro-2-ethanesulfonyl-benzyl)-benzamide

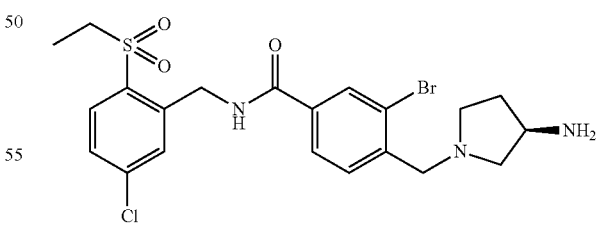

The title compound was synthesized from {(R)-1-[2-bromo-4-(5-chloro-2-ethanesulfonyl-benzylcarbamoyl)-benzyl]-pyrrolidin-3-yl}-carbamic acid tert-butyl ester (Compound g8) under the same conditions as for Compound B-1.
LCMS: m/z 514 [M+H]$^+$
HPLC retention time: 0.39 min (analysis condition A)

Example 277

Compound G-6

3-Bromo-N-(5-chloro-2-ethanesulfonyl-benzyl)-4-((R)-3-dimethylamino-pyrrolidin-1-ylmethyl)-benzamide

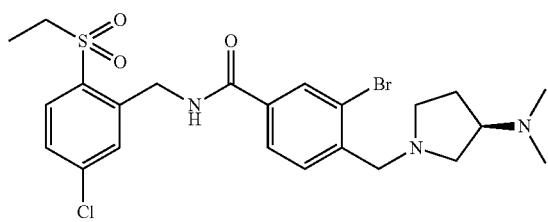 [SMILES: CCS(=O)(=O)c1ccc(Cl)cc1CNC(=O)c1ccc(CN2CC[C@@H](N(C)C)C2)c(Br)c1]

The title compound was synthesized from 4-((R)-3-amino-pyrrolidin-1-ylmethyl)-3-bromo-N-(5-chloro-2-ethanesulfonyl-benzyl)-benzamide (Compound G-5) under the same conditions as for Compound B-2.

LCMS: m/z 542 [M+H]$^+$

HPLC retention time: 0.44 min (analysis condition A)

Example 278

Compound G-7

4-((R)-3-Acetylamino-pyrrolidin-1-ylmethyl)-3-bromo-N-(5-chloro-2-ethanesulfonyl-benzyl)-benzamide

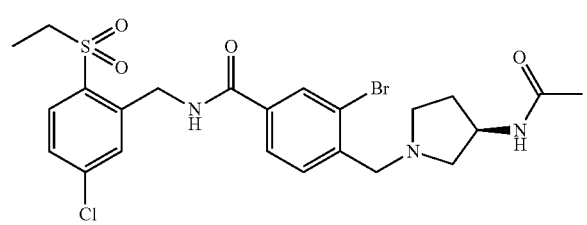 [SMILES: CCS(=O)(=O)c1ccc(Cl)cc1CNC(=O)c1ccc(CN2CC[C@@H](NC(C)=O)C2)c(Br)c1]

The title compound was synthesized from 4-((R)-3-amino-pyrrolidin-1-ylmethyl)-3-bromo-N-(5-chloro-2-ethanesulfonyl-benzyl)-benzamide (Compound G-5) under the same conditions as for Compound B-7.

LCMS: m/z 556 [M+H]$^+$

HPLC retention time: 0.47 min (analysis condition A)

Example 279

Compound G-8

3-Bromo-N-(5-chloro-2-ethanesulfonyl-benzyl)-4-((R)-3-methanesulfonylamino-pyrrolidin-1-ylmethyl)-benzamide

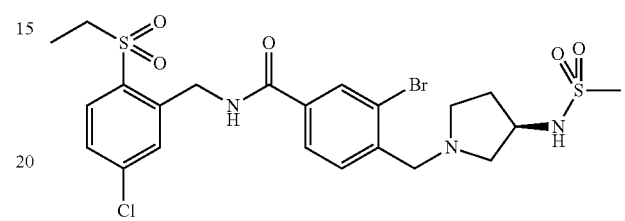

The title compound was synthesized from 4-((R)-3-amino-pyrrolidin-1-ylmethyl)-3-bromo-N-(5-chloro-2-ethanesulfonyl-benzyl)-benzamide (Compound G-5) under the same conditions as for Compound B-9.

LCMS: m/z 592 [M+H]$^+$

HPLC retention time: 0.49 min (analysis condition A)

Example 280

Compound G-9

3-Bromo-N-(5-chloro-2-ethanesulfonyl-benzyl)-4-((R)-3-methylamino-pyrrolidin-1-ylmethyl)-benzamide

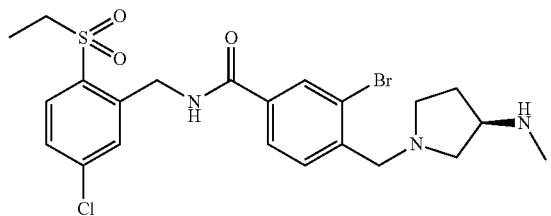

The title compound was synthesized from 3-bromo-4-bromomethyl-benzoic acid ethyl ester (Compound g2) under the same conditions as for Compounds g6, g7, g8, and G-5. However, the reaction was performed using methyl-(R)-pyrrolidin-3-yl-carbamic acid tert-butyl ester in place of (R)-pyrrolidin-3-yl-carbamic acid tert-butyl ester under the conditions for Compound g6.

LCMS: m/z 528 [M+H]$^+$

HPLC retention time: 0.42 min (analysis condition A)

Example 281

Compound G-10

3-Bromo-N-(5-chloro-2-ethanesulfonyl-benzyl)-4-
[(R)-3-(methanesulfonyl-methyl-amino)-pyrrolidin-
1-ylmethyl]-benzamide

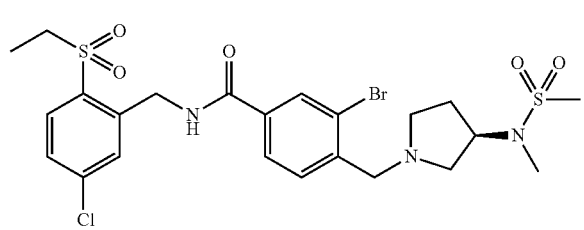 [SMILES: CCS(=O)(=O)c1ccc(Cl)cc1CNC(=O)c1ccc(CN2CC[C@@H](N(C)S(C)(=O)=O)C2)c(Br)c1]

The title compound was synthesized from 3-bromo-N-(5-chloro-2-ethanesulfonyl-benzyl)-4-((R)-3-methylamino-pyrrolidin-1-ylmethyl)-benzamide (Compound G-9) under the same conditions as for Compound B-9.

LCMS: m/z 606 [M+H]$^+$

HPLC retention time: 0.51 min (analysis condition A)

Example 282

Compound G-11

3-Chloro-N-(5-chloro-2-ethanesulfonyl-benzyl)-4-
piperazin-1-ylmethyl-benzamide

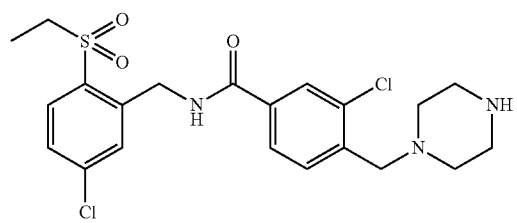

The title compound was synthesized from 3-chloro-4-methyl-benzoic acid ethyl ester under the same conditions as for Compounds g2, g3, g4, g5, and G-1. However, the reaction was performed using a 6N aqueous sodium hydroxide solution in place of potassium hydroxide at room temperature under the conditions for Compound g4.

LCMS: m/z 470 [M+H]$^+$

HPLC retention time: 0.47 min (analysis condition A)

Example 283

Compound G-12

3-Chloro-N-(5-chloro-2-ethanesulfonyl-benzyl)-4-
(4-methyl-piperazin-1-ylmethyl)-benzamide

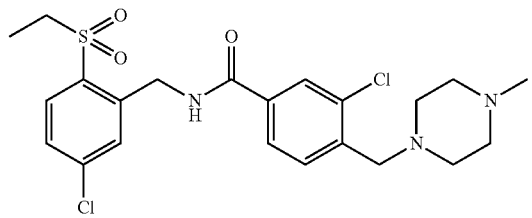 [SMILES: CCS(=O)(=O)c1ccc(Cl)cc1CNC(=O)c1ccc(CN2CCN(C)CC2)c(Cl)c1]

The title compound was synthesized from 3-chloro-N-(5-chloro-2-ethanesulfonyl-benzyl)-4-piperazin-1-ylmethyl-benzamide (Compound G-11) under the same conditions as for Compound B-2.

LCMS: m/z 484 [M+H]$^+$

HPLC retention time: 0.49 min (analysis condition A)

Example 284

Compound G-13

3-Chloro-N-(5-chloro-2-ethanesulfonyl-benzyl)-4-
(4-isopropyl-piperazin-1-ylmethyl)-benzamide

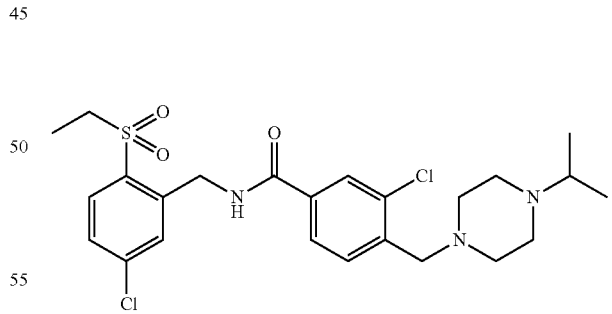

The title compound was synthesized from 3-chloro-N-(5-chloro-2-ethanesulfonyl-benzyl)-4-piperazin-1-ylmethyl-benzamide (Compound G-11) under the same conditions as for Compound B-3.

LCMS: m/z 512 [M+H]$^+$

HPLC retention time: 0.51 min (analysis condition A)

Example 285

Compound G-14

3-Chloro-N-(5-chloro-2-ethanesulfonyl-benzyl)-4-
[4-(tetrahydro-pyran-4-yl)-piperazin-1-ylmethyl]-
benzamide

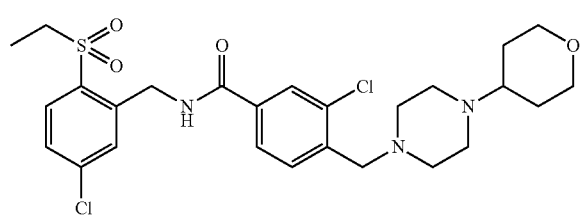

The title compound was synthesized from 3-chloro-N-(5-chloro-2-ethanesulfonyl-benzyl)-4-piperazin-1-ylmethyl-benzamide (Compound G-11) under the same conditions as for Compound B-4.

LCMS: m/z 554 [M+H]$^+$

HPLC retention time: 0.50 min (analysis condition A)

Example 286

Compound G-15

3,5-Dibromo-N-(5-chloro-2-ethanesulfonyl-benzyl)-
4-piperazin-1-ylmethyl-benzamide

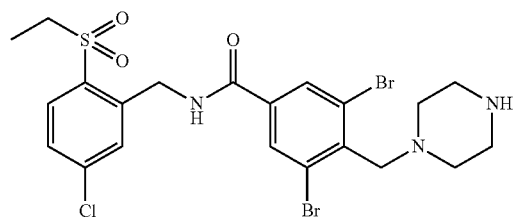 [SMILES: CCS(=O)(=O)c1ccc(Cl)cc1CNC(=O)c1cc(Br)c(CN2CCNCC2)c(Br)c1]

The title compound was synthesized from 3,5-dibromo-4-methyl-benzoic acid methyl ester under the same conditions as for Compounds g2, g3, g4, g5, and G-1. However, the reaction was performed using a 6N aqueous sodium hydroxide solution in place of potassium hydroxide at room temperature under the conditions for Compound g4.

LCMS: m/z 592 [M+H]$^+$

HPLC retention time: 0.54 min (analysis condition A)

Example 287

Compound G-16

3,5-Dibromo-N-(5-chloro-2-ethanesulfonyl-benzyl)-
4-(4-methyl-piperazin-1-ylmethyl)-benzamide

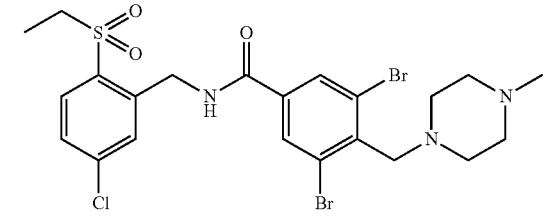 [SMILES: CCS(=O)(=O)c1ccc(Cl)cc1CNC(=O)c1cc(Br)c(CN2CCN(C)CC2)c(Br)c1]

The title compound was synthesized from 3,5-dibromo-N-(5-chloro-2-ethanesulfonyl-benzyl)-4-piperazin-1-ylm-ethyl-benzamide (Compound G-15) under the same conditions as for Compound B-2.

LCMS: m/z 606 [M+H]$^+$

HPLC retention time: 0.54 min (analysis condition A)

Example 288

Compound G-17

3,5-Dibromo-N-(5-chloro-2-ethanesulfonyl-benzyl)-
4-(4-isopropyl-piperazin-1-ylmethyl)-benzamide

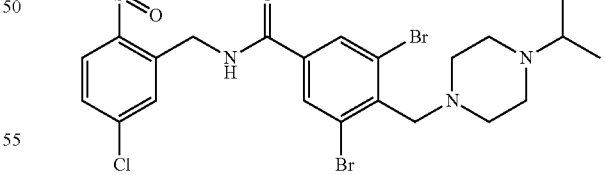

The title compound was synthesized from 3,5-dibromo-N-(5-chloro-2-ethanesulfonyl-benzyl)-4-piperazin-1-ylm-ethyl-benzamide (Compound G-15) under the same conditions as for Compound B-3.

LCMS: m/z 634 [M+H]$^+$

HPLC retention time: 0.56 min (analysis condition A)

Example 289

Compound G-18

3,5-Dibromo-N-(5-chloro-2-ethanesulfonyl-benzyl)-4-[4-(tetrahydro-pyran-4-yl)-piperazin-1-ylmethyl]-benzamide

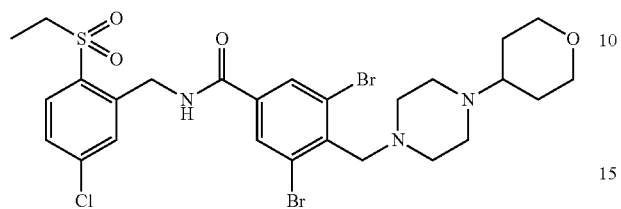

The title compound was synthesized from 3,5-dibromo-N-(5-chloro-2-ethanesulfonyl-benzyl)-4-piperazin-1-ylmethyl-benzamide (Compound G-15) under the same conditions as for Compound B-4.
LCMS: m/z 676 [M+H]⁺
HPLC retention time: 0.54 min (analysis condition A)

Example 290

Compound h1

3-Bromo-5-trifluoromethoxy-benzoic acid ethyl ester

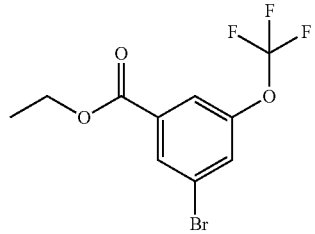 [SMILES: CCOC(=O)c1cc(Br)cc(OC(F)(F)F)c1]

The title compound was synthesized from 3-bromo-5-trifluoromethoxy-benzoic acid under the same conditions as for Compound b1.

Example 291

Compound h2

4-(3-Ethoxycarbonyl-5-trifluoromethoxy-benzyl)-piperazine-1-carboxylic acid tert-butyl ester

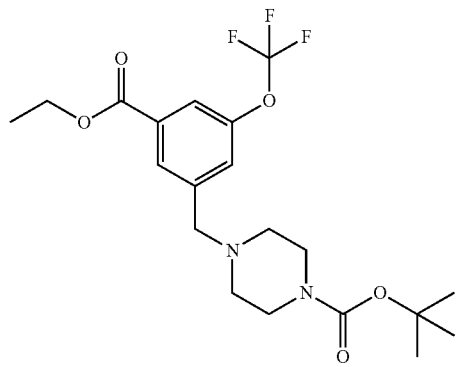 [SMILES: CCOC(=O)c1cc(CN2CCN(C(=O)OC(C)(C)C)CC2)cc(OC(F)(F)F)c1]

The title compound was synthesized from 3-bromo-5-trifluoromethoxy-benzoic acid ethyl ester (Compound h1) under the same conditions as for Compound b2.

Example 292

Compound h3

4-(3-Carboxy-5-trifluoromethoxy-benzyl)-piperazine-1-carboxylic acid tert-butyl ester

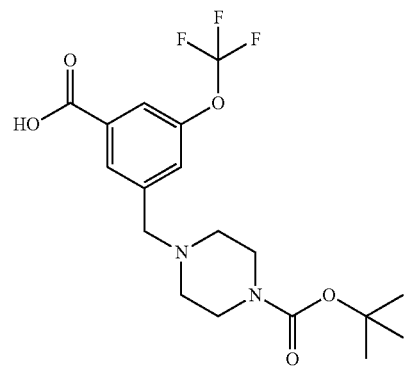 [SMILES: CC(C)(C)OC(=O)N1CCN(Cc2cc(OC(F)(F)F)cc(C(=O)O)c2)CC1]

The title compound was synthesized from 4-(3-ethoxycarbonyl-5-trifluoromethoxy-benzyl)-piperazine-1-carboxylic acid tert-butyl ester (Compound h2) under the same conditions as for Compound b3.

Example 293

Compound h4

4-[3-(5-Chloro-2-ethanesulfonyl-benzylcarbamoyl)-5-trifluoromethoxy-benzyl]-piperazine-1-carboxylic acid tert-butyl ester

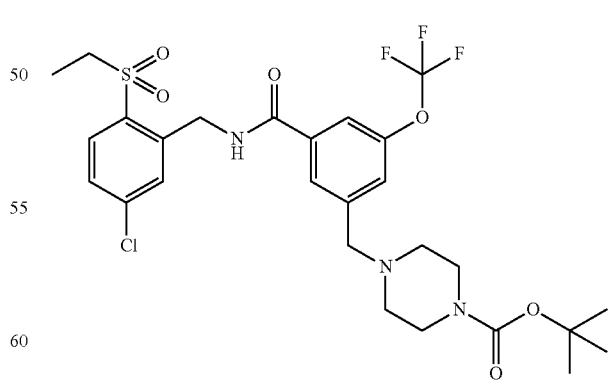

The title compound was synthesized from 4-(3-carboxy-5-trifluoromethoxy-benzyl)-piperazine-1-carboxylic acid tert-butyl ester (Compound h3) under the same conditions as for Compound A-14.

Example 294

Compound H-1

N-(5-Chloro-2-ethanesulfonyl-benzyl)-3-piperazin-1-ylmethyl-5-trifluoromethoxy-benzamide

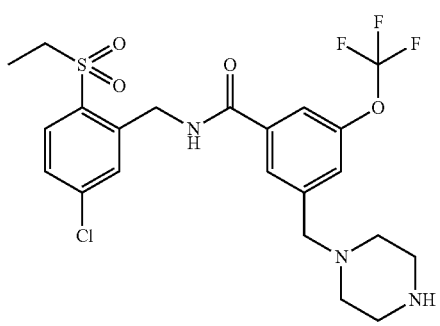 [SMILES: CCS(=O)(=O)c1ccc(Cl)cc1CNC(=O)c1cc(CN2CCNCC2)cc(OC(F)(F)F)c1]

The title compound was synthesized from 4-[3-(5-chloro-2-ethanesulfonyl-benzylcarbamoyl)-5-trifluoromethoxy-benzyl]-piperazine-1-carboxylic acid tert-butyl ester (Compound h4) under the same conditions as for Compound B-1.

LCMS: m/z 520 [M+H]$^+$

HPLC retention time: 0.54 min (analysis condition A)

Example 295

Compound H-2

N-(5-Chloro-2-ethanesulfonyl-benzyl)-3-(4-methyl-piperazin-1-ylmethyl)-5-trifluoromethoxy-benzamide

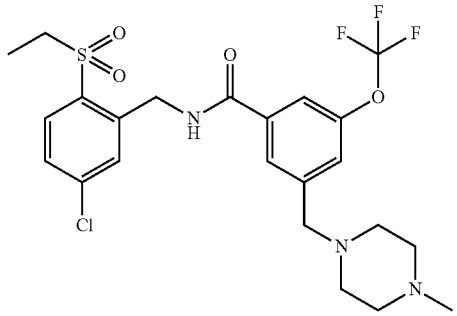 [SMILES: CCS(=O)(=O)c1ccc(Cl)cc1CNC(=O)c1cc(CN2CCN(C)CC2)cc(OC(F)(F)F)c1]

The title compound was synthesized from N-(5-chloro-2-ethanesulfonyl-benzyl)-3-piperazin-1-ylmethyl-5-trifluoromethoxy-benzamide (Compound H-1) under the same conditions as for Compound B-2.

LCMS: m/z 534 [M+H]$^+$

HPLC retention time: 0.55 min (analysis condition A)

Example 296

Compound H-3

N-(5-Chloro-2-ethanesulfonyl-benzyl)-3-(4-isopropyl-piperazin-1-ylmethyl)-5-trifluoromethoxy-benzamide

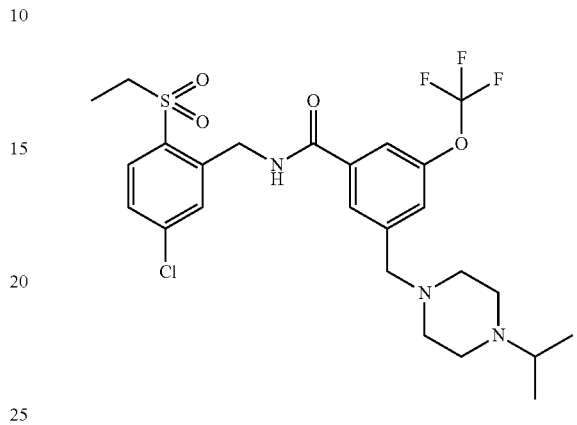

The title compound was synthesized from N-(5-chloro-2-ethanesulfonyl-benzyl)-3-piperazin-1-ylmethyl-5-trifluoromethoxy-benzamide (Compound H-1) under the same conditions as for Compound B-3.

LCMS: m/z 562 [M+H]$^+$

HPLC retention time: 0.56 min (analysis condition A)

Example 297

Compound H-4

N-(5-Chloro-2-ethanesulfonyl-benzyl)-3-[4-(tetrahydro-pyran-4-yl)-piperazin-1-ylmethyl]-5-trifluoromethoxy-benzamide

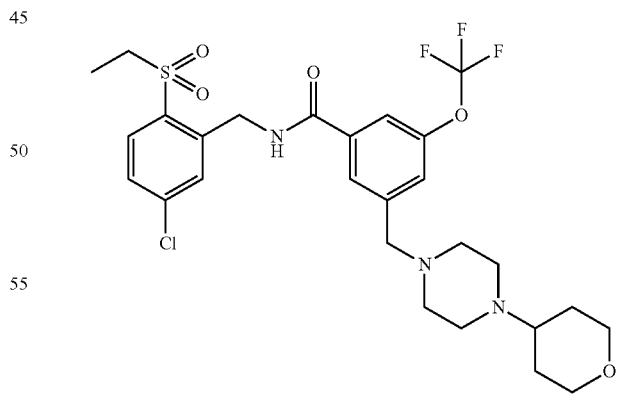

The title compound was synthesized from N-(5-chloro-2-ethanesulfonyl-benzyl)-3-piperazin-1-ylmethyl-5-trifluoromethoxy-benzamide (Compound H-1) under the same conditions as for Compound B-4.

LCMS: m/z 604 [M+H]$^+$

HPLC retention time: 0.55 min (analysis condition A)

Example 298

Compound H-5

N-(5-Chloro-2-ethanesulfonyl-benzyl)-3-(4-ethyl-piperazin-1-ylmethyl)-5-trifluoromethoxy-benzamide

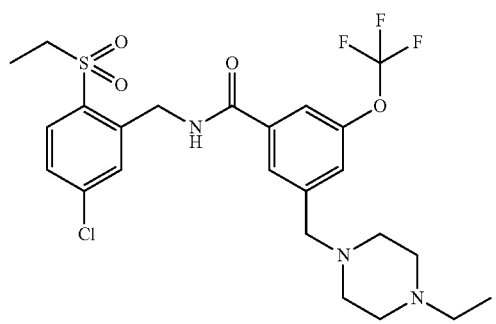 [SMILES: CCN1CCN(Cc2cc(OC(F)(F)F)cc(C(=O)NCc3cc(Cl)ccc3S(=O)(=O)CC)c2)CC1]

Ethyl iodide (11 μL, 0.14 mmol) and potassium carbonate (48 mg, 0.35 mmol) were added to a solution of N-(5-chloro-2-ethanesulfonyl-benzyl)-3-piperazin-1-ylmethyl-5-trifluoromethoxy-benzamide (Compound H-1, 60 mg, 0.12 mmol) in DMF (1 mL), and the mixture was stirred at room temperature for one hour. The reaction solution was diluted with ethyl acetate, washed with water and saturated saline, and then dried over anhydrous sodium sulfate. The drying agent was removed by filtration, and the residue obtained after concentration under reduced pressure was purified by silica gel column chromatography (MeOH/DCM) to yield the title compound (56.9 mg, 90%) as a colorless foamy substance.

LCMS: m/z 548 [M+H]$^+$

HPLC retention time: 0.56 min (analysis condition A)

Example 299

Compound H-6

N-(5-Chloro-2-ethanesulfonyl-benzyl)-3-piperazin-1-ylmethyl-5-trifluoromethyl-benzamide

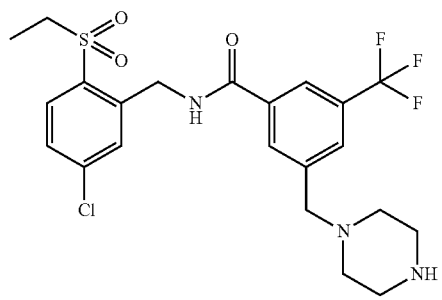 [SMILES: CCS(=O)(=O)c1ccc(Cl)cc1CNC(=O)c1cc(CN2CCNCC2)cc(C(F)(F)F)c1]

The title compound was synthesized from 3-bromo-5-trifluoromethyl-benzoic acid under the same conditions as for Compounds h1, h2, h3, h4, and H-1.

LCMS: m/z 504 [M+H]$^+$

HPLC retention time: 0.52 min (analysis condition A)

Example 300

Compound H-7

N-(5-Chloro-2-ethanesulfonyl-benzyl)-3-(4-methyl-piperazin-1-ylmethyl)-5-trifluoromethyl-benzamide

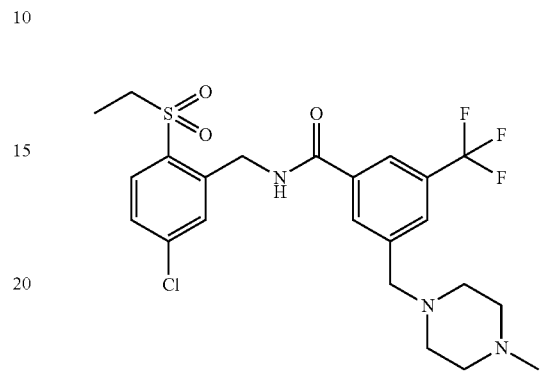

The title compound was synthesized from N-(5-chloro-2-ethanesulfonyl-benzyl)-3-piperazin-1-ylmethyl-5-trifluoromethyl-benzamide (Compound H-6) under the same conditions as for Compound B-2.

LCMS: m/z 518 [M+H]$^+$

HPLC retention time: 0.53 min (analysis condition A)

Example 301

Compound H-8

N-(5-Chloro-2-ethanesulfonyl-benzyl)-3-(4-isopropyl-piperazin-1-ylmethyl)-5-trifluoromethyl-benzamide

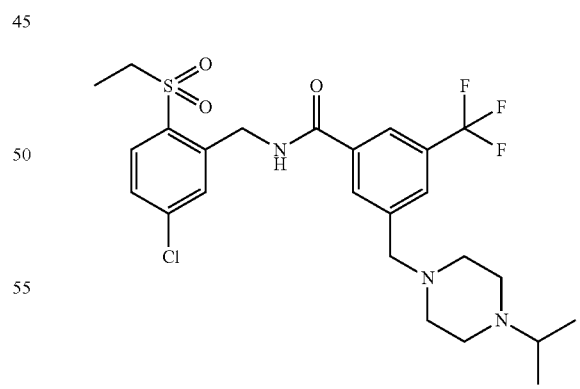

The title compound was synthesized from N-(5-chloro-2-ethanesulfonyl-benzyl)-3-piperazin-1-ylmethyl-5-trifluoromethyl-benzamide (Compound H-6) under the same conditions as for Compound B-3.

LCMS: m/z 546 [M+H]$^+$

HPLC retention time: 0.56 min (analysis condition A)

Example 302

Compound H-9

N-(5-Chloro-2-ethanesulfonyl-benzyl)-3-[4-(tetra-hydro-pyran-4-yl)-piperazin-1-ylmethyl]-5-trifluoromethyl-benzamide

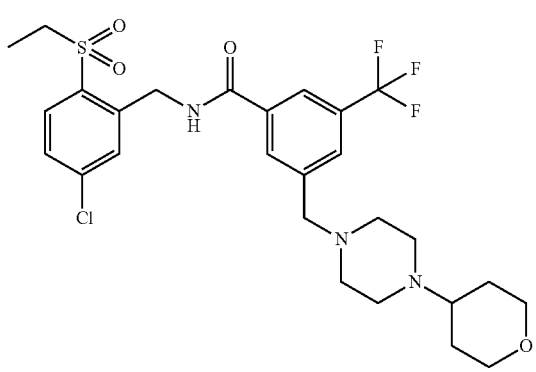 [SMILES: CCS(=O)(=O)c1ccc(Cl)cc1CNC(=O)c1cc(CN2CCN(C3CCOCC3)CC2)cc(C(F)(F)F)c1]

The title compound was synthesized from N-(5-chloro-2-ethanesulfonyl-benzyl)-3-piperazin-1-ylmethyl-5-trifluoromethyl-benzamide (Compound H-6) under the same conditions as for Compound B-4.

LCMS: m/z 588 [M+H]$^+$

HPLC retention time: 1.52 min (analysis condition D)

Example 303

Compound h5

3-Bromo-5-bromomethyl-benzoic acid ethyl ester

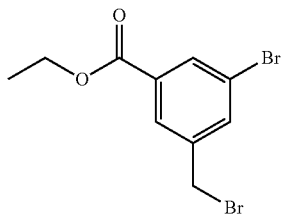

The title compound was synthesized from 3-bromo-5-methyl-benzoic acid ethyl ester under the same conditions as for Compound b6.

Example 304

Compound h6

4-(3-Bromo-5-ethoxycarbonyl-benzyl)-piperazine-1-carboxylic acid tert-butyl ester

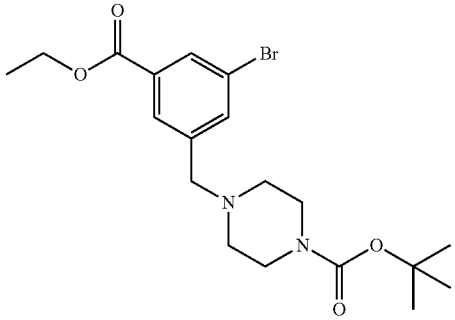 [SMILES: CCOC(=O)c1cc(Br)cc(CN2CCN(C(=O)OC(C)(C)C)CC2)c1]

The title compound was synthesized from 3-bromo-5-bromomethyl-benzoic acid ethyl ester (Compound h5) and piperazine-1-carboxylic acid tert-butyl ester under the same conditions as for Compound g3.

Example 305

Compound h7

4-(3-Bromo-5-carboxy-benzyl)-piperazine-1-carboxylic acid tert-butyl ester

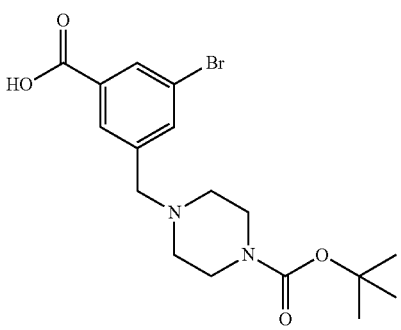 [SMILES: CC(C)(C)OC(=O)N1CCN(Cc2cc(Br)cc(C(=O)O)c2)CC1]

The title compound was synthesized from 4-(3-bromo-5-ethoxycarbonyl-benzyl)-piperazine-1-carboxylic acid tert-butyl ester (Compound h6) under the same conditions as for Compound g7.

Example 306

Compound H-10

3-Bromo-N-(5-chloro-2-ethanesulfonyl-benzyl)-5-piperazin-1-ylmethyl-benzamide

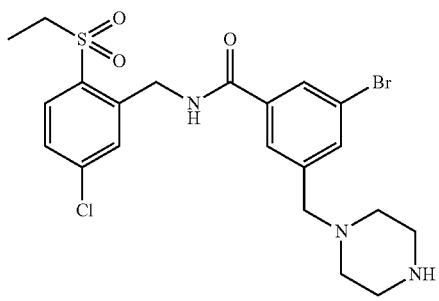

The title compound was synthesized from 4-(3-bromo-5-carboxy-benzyl)-piperazine-1-carboxylic acid tert-butyl ester (Compound h7) under the same conditions as for Compounds h4 and H-1.

LCMS: m/z 514 [M+H]$^+$

HPLC retention time: 0.49 min (analysis condition A)

Example 307

Compound H-11

3-Bromo-N-(5-chloro-2-ethanesulfonyl-benzyl)-5-(4-methyl-piperazin-1-ylmethyl)-benzamide

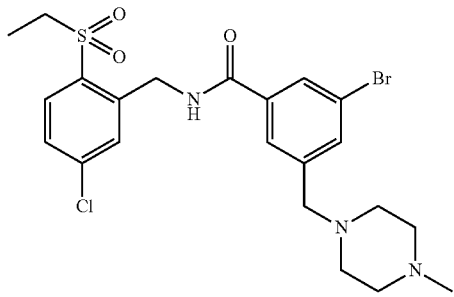

The title compound was synthesized from 3-bromo-N-(5-chloro-2-ethanesulfonyl-benzyl)-5-piperazin-1-ylmethyl-benzamide (Compound H-10) under the same conditions as for Compound B-2.

LCMS: m/z 528 [M+H]$^+$

HPLC retention time: 0.52 min (analysis condition A)

Example 308

Compound H-12

3-Bromo-N-(5-chloro-2-ethanesulfonyl-benzyl)-5-(4-isopropyl-piperazin-1-ylmethyl)-benzamide

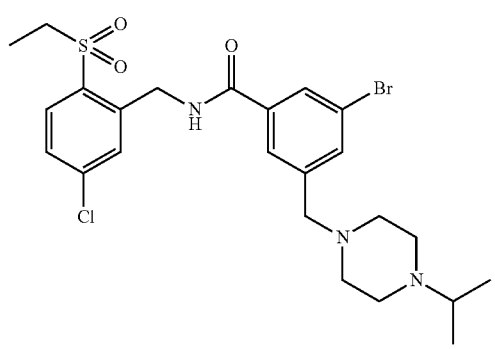

The title compound was synthesized from 3-bromo-N-(5-chloro-2-ethanesulfonyl-benzyl)-5-piperazin-1-ylmethyl-benzamide (Compound H-10) under the same conditions as for Compound B-3.

LCMS: m/z 556 [M+H]$^+$

HPLC retention time: 0.54 min (analysis condition A)

Example 309

Compound H-13

3-Bromo-N-(5-chloro-2-ethanesulfonyl-benzyl)-5-[4-(tetrahydro-pyran-4-yl)-piperazin-1-ylmethyl]-benzamide

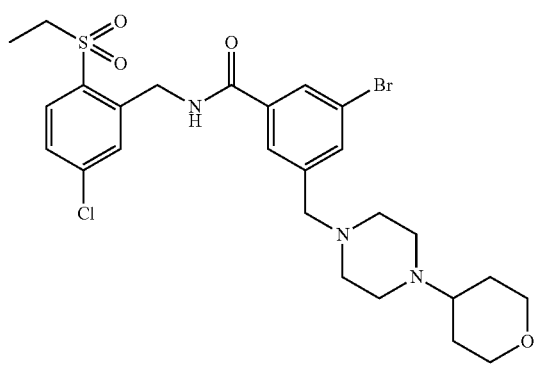 [SMILES: CCS(=O)(=O)c1ccc(Cl)cc1CNC(=O)c1cc(Br)cc(CN2CCN(C3CCOCC3)CC2)c1]

The title compound was synthesized from 3-bromo-N-(5-chloro-2-ethanesulfonyl-benzyl)-5-piperazin-1-ylmethyl-benzamide (Compound H-10) under the same conditions as for Compound B-4.

LCMS: m/z 598 [M+H]$^+$

HPLC retention time: 0.53 min (analysis condition A)

Example 310

Compound h8

3-Chloro-5-methyl-benzoic acid ethyl ester

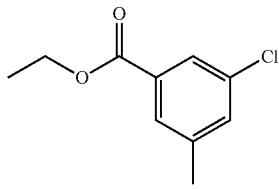

The title compound was synthesized from 3-chloro-5-methyl-benzoic acid under the same conditions as for Compound b1.

Example 311

Compound h9

3-Bromomethyl-5-chloro-benzoic acid ethyl ester

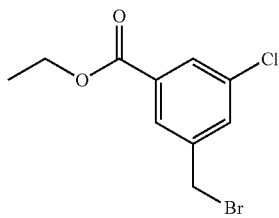

The title compound was synthesized from 3-chloro-5-methyl-benzoic acid ethyl ester (Compound h8) under the same conditions as for Compound b6.

Example 312

Compound h10

4-(3-Carboxy-5-chloro-benzyl)-piperazine-1-carboxylic acid tert-butyl ester

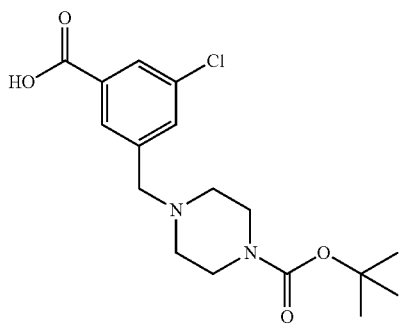 [SMILES: CC(C)(C)OC(=O)N1CCN(Cc2cc(Cl)cc(C(=O)O)c2)CC1]

The title compound was synthesized from 3-bromomethyl-5-chloro-benzoic acid ethyl ester (Compound h9) under the same conditions as for Compounds h6 and h7.

Example 313

Compound H-14

3-Chloro-N-(5-chloro-2-ethanesulfonyl-benzyl)-5-piperazin-1-ylmethyl-benzamide

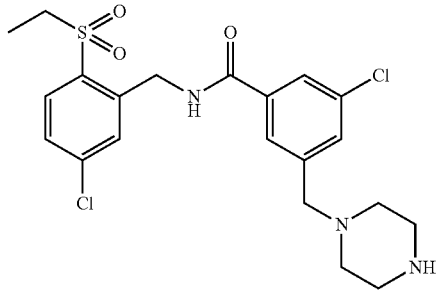

The title compound was synthesized from 4-(3-carboxy-5-chloro-benzyl)-piperazine-1-carboxylic acid tert-butyl ester (Compound h10) under the same conditions as for Compounds h4 and H-1.

LCMS: m/z 470 [M+H]$^+$

HPLC retention time: 1.25 min (analysis condition D)

Example 314

Compound H-15

3-Chloro-N-(5-chloro-2-ethanesulfonyl-benzyl)-5-(4-methyl-piperazin-1-ylmethyl)-benzamide

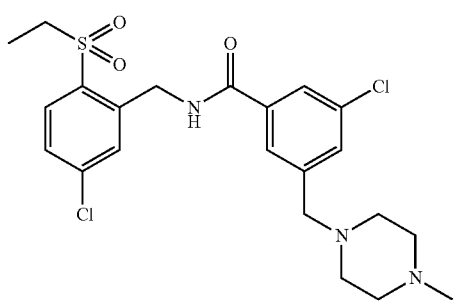 [SMILES: CCS(=O)(=O)c1ccc(Cl)cc1CNC(=O)c1cc(Cl)cc(CN2CCN(C)CC2)c1]

The title compound was synthesized from 3-chloro-N-(5-chloro-2-ethanesulfonyl-benzyl)-5-piperazin-1-ylmethyl-benzamide (Compound H-14) under the same conditions as for Compound B-2.

LCMS: m/z 484 [M+H]$^+$

HPLC retention time: 0.50 min (analysis condition A)

Example 315

Compound H-16

3-Chloro-N-(5-chloro-2-ethanesulfonyl-benzyl)-5-(4-isopropyl-piperazin-1-ylmethyl)-benzamide

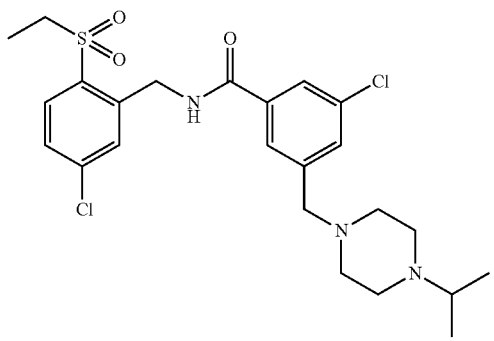 [SMILES: CCS(=O)(=O)c1ccc(Cl)cc1CNC(=O)c1cc(Cl)cc(CN2CCN(C(C)C)CC2)c1]

The title compound was synthesized from 3-chloro-N-(5-chloro-2-ethanesulfonyl-benzyl)-5-piperazin-1-ylmethyl-benzamide (Compound H-14) under the same conditions as for Compound B-3.

LCMS: m/z 512 [M+H]$^+$

HPLC retention time: 1.35 min (analysis condition D)

Example 316

Compound H-17

3-Chloro-N-(5-chloro-2-ethanesulfonyl-benzyl)-5-[4-(tetrahydro-pyran-4-yl)-piperazin-1-ylmethyl]-benzamide

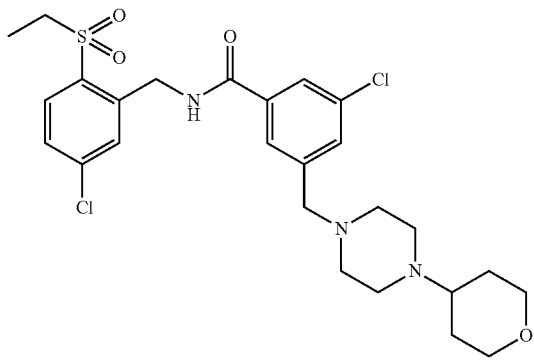 [SMILES: CCS(=O)(=O)c1ccc(Cl)cc1CNC(=O)c1cc(Cl)cc(CN2CCN(C3CCOCC3)CC2)c1]

The title compound was synthesized from 3-chloro-N-(5-chloro-2-ethanesulfonyl-benzyl)-5-piperazin-1-ylmethyl-benzamide (Compound H-14) under the same conditions as for Compound B-4.

LCMS: m/z 554 [M+H]$^+$

HPLC retention time: 1.35 min (analysis condition D)

Example 317

Compound i1

3,5-Dibromo-benzoic acid ethyl ester

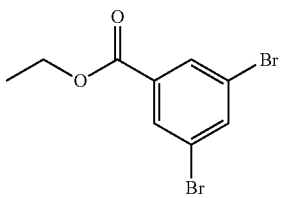

The title compound was synthesized from 3,5-dibromo-benzoic acid under the same conditions as for Compound b1.

Example 318

Compound i2

4-(3-Bromo-5-ethoxycarbonyl-phenyl)-piperazine-1-carboxylic acid tert-butyl ester

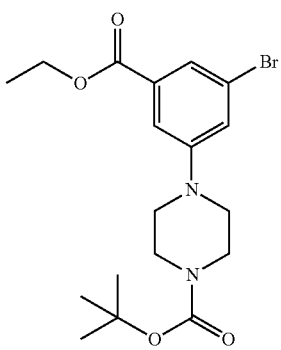 [SMILES: CCOC(=O)c1cc(Br)cc(N2CCN(C(=O)OC(C)(C)C)CC2)c1]

A mixture of 3,5-dibromo-benzoic acid ethyl ester (Compound i1, 1.5 g, 4.9 mmol), piperazine-1-carboxylic acid tert-butyl ester (907 mg, 4.9 mmol), cesium carbonate (4.76 g, 15 mmol), tris(dibenzylideneacetone)dipalladium(0) (504 mg, 0.49 mmol), and BINAP (606 mg, 0.97 mmol) in toluene (25 mL) was stirred at 80° C. overnight. The reaction solution was diluted with ethyl acetate, washed with saturated saline, and then dried over anhydrous sodium sulfate. The drying agent was removed by filtration, and the residue obtained after concentration under reduced pressure was purified by silica gel column chromatography (ethyl acetate/hexane) to yield the title compound (1.05 g, 52%) as a pale yellow solid.

LCMS: m/z 413 [M+H]$^+$

HPLC retention time: 3.25 min (analysis condition C)

Example 319

Compound i3

4-(3-Bromo-5-carboxy-phenyl)-piperazine-1-carboxylic acid tert-butyl ester

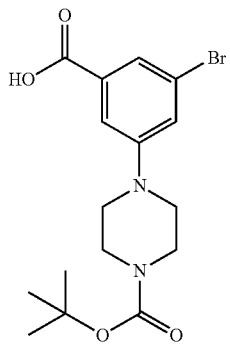

The title compound was synthesized from 4-(3-bromo-5-ethoxycarbonyl-phenyl)-piperazine-1-carboxylic acid tert-butyl ester (Compound i2) under the same conditions as for Compound g7.

Example 320

Compound i4

4-[3-Bromo-5-(5-chloro-2-ethanesulfonyl-benzylcarbamoyl)-phenyl]-piperazine-1-carboxylic acid tert-butyl ester

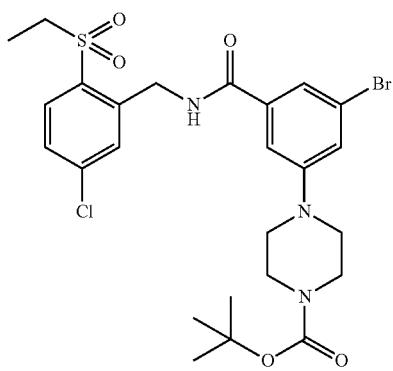 [SMILES: CCS(=O)(=O)c1ccc(Cl)cc1CNC(=O)c1cc(Br)cc(N2CCN(C(=O)OC(C)(C)C)CC2)c1]

The title compound was synthesized from 4-(3-bromo-5-carboxy-phenyl)-piperazine-1-carboxylic acid tert-butyl ester (Compound i3) under the same conditions as for Compound A-14.

Example 321

Compound I-1

3-Bromo-N-(5-chloro-2-ethanesulfonyl-benzyl)-5-piperazin-1-yl-benzamide

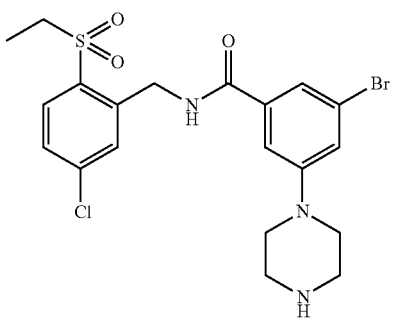 [SMILES: CCS(=O)(=O)c1ccc(Cl)cc1CNC(=O)c1cc(Br)cc(N2CCNCC2)c1]

The title compound was synthesized from 4-[3-bromo-5-(5-chloro-2-ethanesulfonyl-benzylcarbamoyl)-phenyl]-piperazine-1-carboxylic acid tert-butyl ester (Compound i4) under the same conditions as for Compound B-1.

LCMS: m/z 500 [M+H]$^+$

HPLC retention time: 0.51 min (analysis condition A)

Example 322

Compound I-2

3-Bromo-N-(5-chloro-2-ethanesulfonyl-benzyl)-5-(4-methyl-piperazin-1-yl)-benzamide

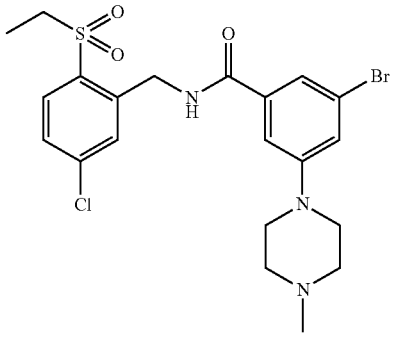 [SMILES: CCS(=O)(=O)c1ccc(Cl)cc1CNC(=O)c1cc(Br)cc(N2CCN(C)CC2)c1]

The title compound was synthesized from 3-bromo-N-(5-chloro-2-ethanesulfonyl-benzyl)-5-piperazin-1-yl-benzamide (Compound I-1) under the same conditions as for Compound B-2.

LCMS: m/z 514 [M+H]$^+$

HPLC retention time: 0.51 min (analysis condition A)

Example 323

Compound I-3

3-Bromo-N-(5-chloro-2-ethanesulfonyl-benzyl)-5-(4-isopropyl-piperazin-1-yl)-benzamide

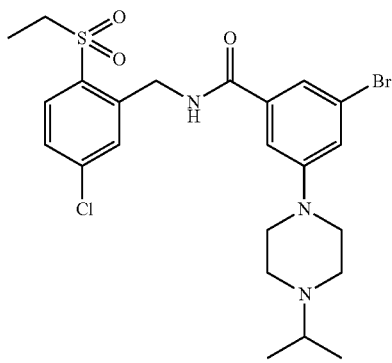 [SMILES: CCS(=O)(=O)c1ccc(Cl)cc1CNC(=O)c1cc(Br)cc(N2CCN(C(C)C)CC2)c1]

The title compound was synthesized from 3-bromo-N-(5-chloro-2-ethanesulfonyl-benzyl)-5-piperazin-1-yl-benzamide (Compound I-1) under the same conditions as for Compound B-3. However, the reaction was performed by using 1,4-dioxane in place of THF as a solvent and heating to 85° C.

LCMS: m/z 542 [M+H]$^+$

HPLC retention time: 0.54 min (analysis condition A)

Example 324

Compound I-4

3-Bromo-N-(5-chloro-2-ethanesulfonyl-benzyl)-5-[4-(tetrahydro-pyran-4-yl)-piperazin-1-yl]-benzamide

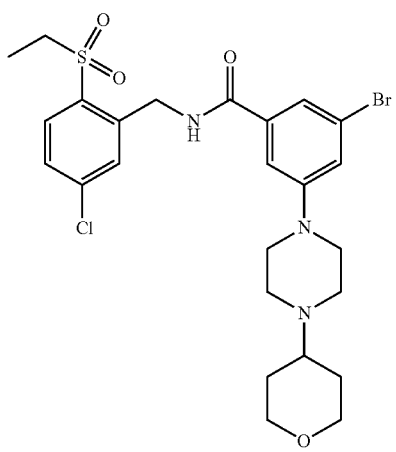 [SMILES: CCS(=O)(=O)c1ccc(Cl)cc1CNC(=O)c1cc(Br)cc(N2CCN(C3CCOCC3)CC2)c1]

The title compound was synthesized from 3-bromo-N-(5-chloro-2-ethanesulfonyl-benzyl)-5-piperazin-1-yl-benzamide (Compound I-1) under the same conditions as for Compound B-4. However, the reaction was performed by using 1,4-dioxane in place of THF as a solvent and heating to 85° C.

LCMS: m/z 584 [M+H]$^+$

HPLC retention time: 0.53 min (analysis condition A)

Example 325

Compound I-5

N-(5-Chloro-2-ethanesulfonyl-benzyl)-3-piperazin-1-yl-5-trifluoromethyl-benzamide

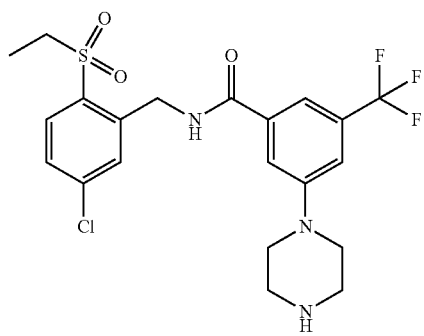 [SMILES: CCS(=O)(=O)c1ccc(Cl)cc1CNC(=O)c1cc(N2CCNCC2)cc(C(F)(F)F)c1]

The title compound was synthesized from 3-chloro-5-trifluoromethyl-benzoic acid under the same conditions as for Compounds i1, i2, i3, i4, and I-1.

LCMS: m/z 490 [M+H]$^+$

HPLC retention time: 0.52 min (analysis condition A)

Example 326

Compound I-6

N-(5-Chloro-2-ethanesulfonyl-benzyl)-3-(4-methyl-piperazin-1-yl)-5-trifluoromethyl-benzamide

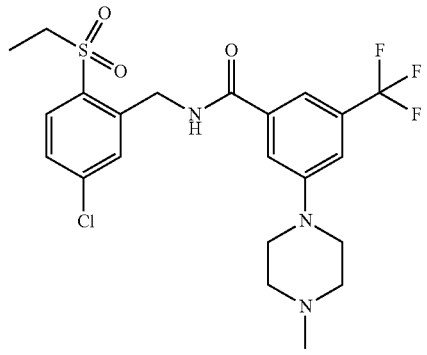 [SMILES: CCS(=O)(=O)c1ccc(Cl)cc1CNC(=O)c1cc(N2CCN(C)CC2)cc(C(F)(F)F)c1]

The title compound was synthesized from N-(5-chloro-2-ethanesulfonyl-benzyl)-3-piperazin-1-yl-5-trifluoromethyl-benzamide (Compound I-5) under the same conditions as for Compound B-2.

LCMS: m/z 504 [M+H]$^+$

HPLC retention time: 0.53 min (analysis condition A)

Example 327

Compound I-7

N-(5-Chloro-2-ethanesulfonyl-benzyl)-3-(4-isopropyl-piperazin-1-yl)-5-trifluoromethyl-benzamide

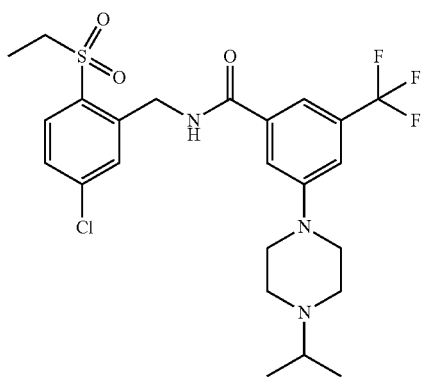 [SMILES: CCS(=O)(=O)c1ccc(Cl)cc1CNC(=O)c1cc(N2CCN(C(C)C)CC2)cc(C(F)(F)F)c1]

The title compound was synthesized from N-(5-chloro-2-ethanesulfonyl-benzyl)-3-piperazin-1-yl-5-trifluoromethyl-benzamide (Compound I-5) under the same conditions as for Compound B-3. However, the reaction was performed by using 1,4-dioxane in place of THF as a solvent and heating to 85° C.

LCMS: m/z 532 [M+H]$^+$

HPLC retention time: 0.55 min (analysis condition A)

Example 328

Compound I-8

N-(5-Chloro-2-ethanesulfonyl-benzyl)-3-[4-(tetrahydro-pyran-4-yl)-piperazin-1-yl]-5-trifluoromethyl-benzamide

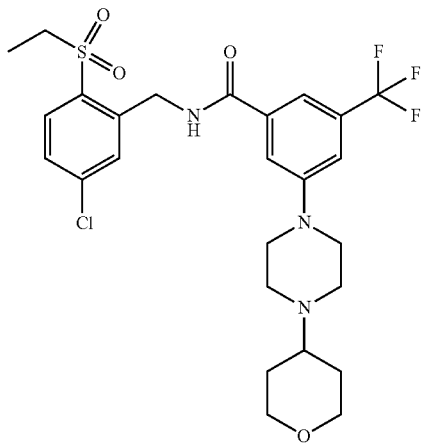 [SMILES: CCS(=O)(=O)c1ccc(Cl)cc1CNC(=O)c1cc(N2CCN(C3CCOCC3)CC2)cc(C(F)(F)F)c1]

The title compound was synthesized from N-(5-chloro-2-ethanesulfonyl-benzyl)-3-piperazin-1-yl-5-trifluoromethyl-benzamide (Compound I-5) under the same conditions as for Compound B-4. However, the reaction was performed by using 1,4-dioxane in place of THF as a solvent and heating to 85° C.

LCMS: m/z 574 [M+H]$^+$

HPLC retention time: 0.54 min (analysis condition A)

Example 329

Compound i5

3-Bromo-5-trifluoromethoxy-benzoic acid ethyl ester

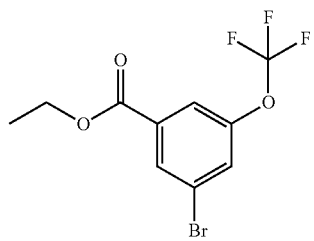 [SMILES: CCOC(=O)c1cc(Br)cc(OC(F)(F)F)c1]

The title compound was synthesized from 3-bromo-5-trifluoromethoxy-benzoic acid under the same conditions as for Compound b1.

Example 330

Compound i6

4-(3-Ethoxycarbonyl-5-trifluoromethoxy-phenyl)-piperazine-1-carboxylic acid tert-butyl ester

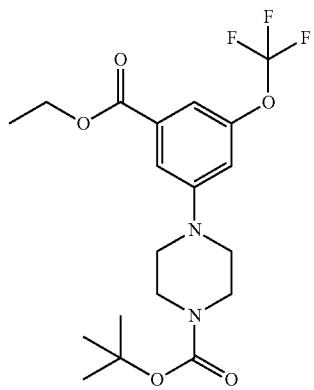 [SMILES: CCOC(=O)c1cc(OC(F)(F)F)cc(N2CCN(C(=O)OC(C)(C)C)CC2)c1]

The title compound was synthesized from 3-bromo-5-trifluoromethoxy-benzoic acid ethyl ester (Compound i5) under the same conditions as for Compound i2.

Example 331

Compound i7

4-(3-Carboxy-5-trifluoromethoxy-phenyl)-piperazine-1-carboxylic acid tert-butyl ester

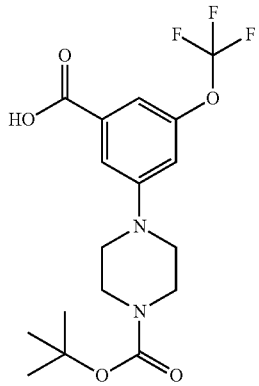 [SMILES: CC(C)(C)OC(=O)N1CCN(c2cc(OC(F)(F)F)cc(C(=O)O)c2)CC1]

The title compound was synthesized from 4-(3-ethoxycarbonyl-5-trifluoromethoxy-phenyl)-piperazine-1-carboxylic acid tert-butyl ester (Compound i6) under the same conditions as for Compound b3.

Example 332

Compound i8

4-[3-(5-Chloro-2-ethanesulfonyl-benzylcarbamoyl)-5-trifluoromethoxy-phenyl]-piperazine-1-carboxylic acid tert-butyl ester

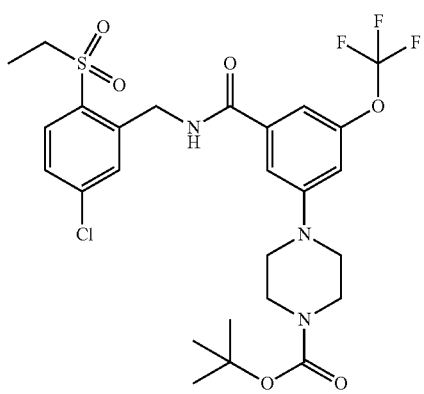 [SMILES: CCS(=O)(=O)c1ccc(Cl)cc1CNC(=O)c1cc(OC(F)(F)F)cc(N2CCN(C(=O)OC(C)(C)C)CC2)c1]

The title compound was synthesized from 4-(3-carboxy-5-trifluoromethoxy-phenyl)-piperazine-1-carboxylic acid tert-butyl ester (Compound i7) under the same conditions as for Compound A-14.

Example 333

Compound I-9

N-(5-Chloro-2-ethanesulfonyl-benzyl)-3-piperazin-1-yl-5-trifluoromethoxy-benzamide

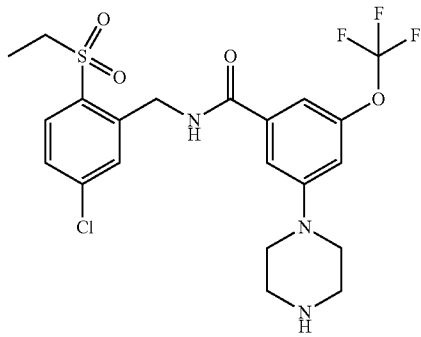 [SMILES: CCS(=O)(=O)c1ccc(Cl)cc1CNC(=O)c1cc(OC(F)(F)F)cc(N2CCNCC2)c1]

The title compound was synthesized from 4-[3-(5-chloro-2-ethanesulfonyl-benzylcarbamoyl)-5-trifluoromethoxy-phenyl]-piperazine-1-carboxylic acid tert-butyl ester (Compound i8) under the same conditions as for Compound B-1.

LCMS: m/z 506 [M+H]$^+$

HPLC retention time: 0.55 min (analysis condition A)

Example 334

Compound I-10

N-(5-Chloro-2-ethanesulfonyl-benzyl)-3-(4-methylpiperazin-1-yl)-5-trifluoromethoxy-benzamide

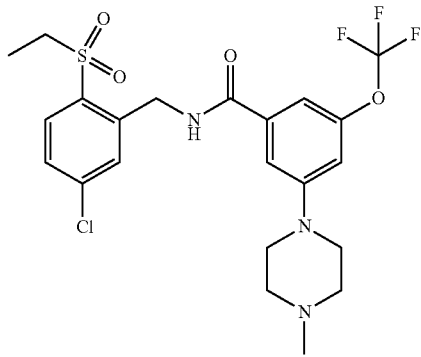 [SMILES: CCS(=O)(=O)c1ccc(Cl)cc1CNC(=O)c1cc(OC(F)(F)F)cc(N2CCN(C)CC2)c1]

The title compound was synthesized from N-(5-chloro-2-ethanesulfonyl-benzyl)-3-piperazin-1-yl-5-trifluoromethoxy-benzamide (Compound I-9) under the same conditions as for Compound B-2.

LCMS: m/z 520 [M+H]$^+$

HPLC retention time: 0.54 min (analysis condition A)

Example 335

Compound I-11

N-(5-Chloro-2-ethanesulfonyl-benzyl)-3-(4-isopropyl-piperazin-1-yl)-5-trifluoromethoxy-benzamide

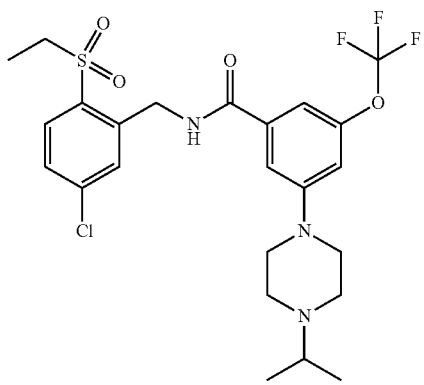 [SMILES: CCS(=O)(=O)c1ccc(Cl)cc1CNC(=O)c1cc(OC(F)(F)F)cc(N2CCN(C(C)C)CC2)c1]

The title compound was synthesized from N-(5-chloro-2-ethanesulfonyl-benzyl)-3-piperazin-1-yl-5-trifluoromethoxy-benzamide (Compound I-9) under the same conditions as for Compound B-3.
LCMS: m/z 548 [M+H]$^+$
HPLC retention time: 0.56 min (analysis condition A)

Example 336

Compound I-12

N-(5-Chloro-2-ethanesulfonyl-benzyl)-3-[4-(tetrahydro-pyran-4-yl)-piperazin-1-yl]-5-trifluoromethoxy-benzamide

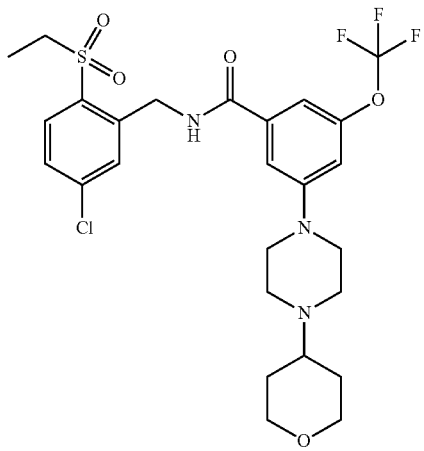 [SMILES: CCS(=O)(=O)c1ccc(Cl)cc1CNC(=O)c1cc(OC(F)(F)F)cc(N2CCN(C3CCOCC3)CC2)c1]

The title compound was synthesized from N-(5-chloro-2-ethanesulfonyl-benzyl)-3-piperazin-1-yl-5-trifluoromethoxy-benzamide (Compound I-9) under the same conditions as for Compound B-4.
LCMS: m/z 590 [M+H]$^+$
HPLC retention time: 0.57 min (analysis condition A)

Example 337

Compound i9

3-((S)-3-tert-Butoxycarbonylamino-pyrrolidin-1-yl)-5-trifluoromethoxy-benzoic acid ethyl ester

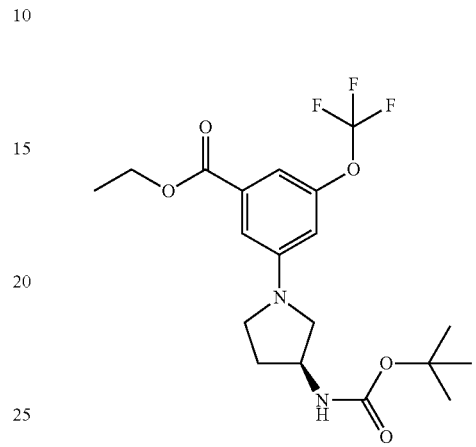

The title compound was synthesized from 3-bromo-5-trifluoromethoxy-benzoic acid ethyl ester (Compound i5) under the same conditions as for Compound i2. However, the reaction was performed using (S)-pyrrolidin-3-yl-carbamic acid tert-butyl ester in place of piperazine-1-carboxylic acid tert-butyl ester.

Example 338

Compound i10

3-((S)-3-tert-Butoxycarbonylamino-pyrrolidin-1-yl)-5-trifluoromethoxy-benzoic acid

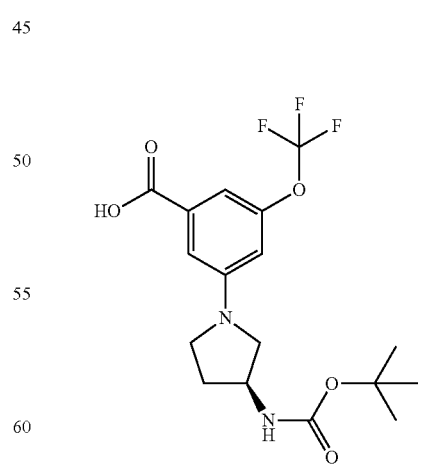

The title compound was synthesized from 3-((S)-3-tert-butoxycarbonylamino-pyrrolidin-1-yl)-5-trifluoromethoxy-benzoic acid ethyl ester (Compound i9) under the same conditions as for Compound g7.

Example 339

Compound i11

{(S)-1-[3-(5-Chloro-2-ethanesulfonyl-benzylcarbamoyl)-5-trifluoromethoxy-phenyl]-pyrrolidin-3-yl}-carbamic acid tert-butyl ester

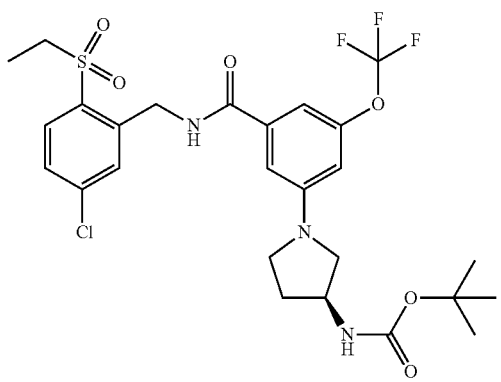 [SMILES: CCS(=O)(=O)c1ccc(Cl)cc1CNC(=O)c1cc(OC(F)(F)F)cc(N2CC[C@H](NC(=O)OC(C)(C)C)C2)c1]

The title compound was synthesized from 3-((S)-3-tert-butoxycarbonylamino-pyrrolidin-1-yl)-5-trifluoromethoxy-benzoic acid (Compound i10) under the same conditions as for Compound A-14.

Example 340

Compound I-13

3-((S)-3-Amino-pyrrolidin-1-yl)-N-(5-chloro-2-ethanesulfonyl-benzyl)-5-trifluoromethoxy-benzamide

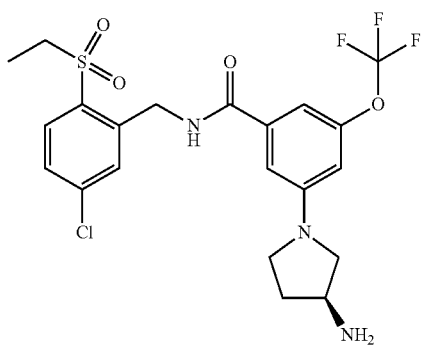 [SMILES: CCS(=O)(=O)c1ccc(Cl)cc1CNC(=O)c1cc(OC(F)(F)F)cc(N2CC[C@H](N)C2)c1]

The title compound was synthesized from {(S)-1-[3-(5-chloro-2-ethanesulfonyl-benzylcarbamoyl)-5-trifluoromethoxy-phenyl]-pyrrolidin-3-yl}-carbamic acid tert-butyl ester (Compound i11) under the same conditions as for Compound B-1.

LCMS: m/z 506 [M+H]$^+$

HPLC retention time: 0.55 min (analysis condition A)

Example 341

Compound I-14

3-((S)-3-Acetylamino-pyrrolidin-1-yl)-N-(5-chloro-2-ethanesulfonyl-benzyl)-5-trifluoromethoxy-benzamide

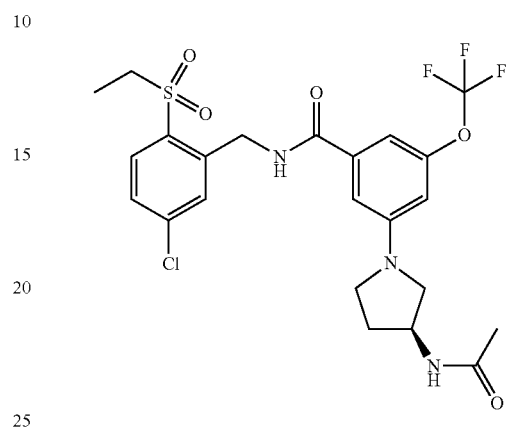

The title compound was synthesized from 3-((S)-3-amino-pyrrolidin-1-yl)-N-(5-chloro-2-ethanesulfonyl-benzyl)-5-trifluoromethoxy-benzamide (Compound I-13) under the same conditions as for Compound B-7.

LCMS: m/z 548 [M+H]$^+$

HPLC retention time: 0.77 min (analysis condition A)

Example 342

Compound I-15

N-(5-Chloro-2-ethanesulfonyl-benzyl)-3-((S)-3-methanesulfonylamino-pyrrolidin-1-yl)-5-trifluoromethoxy-benzamide

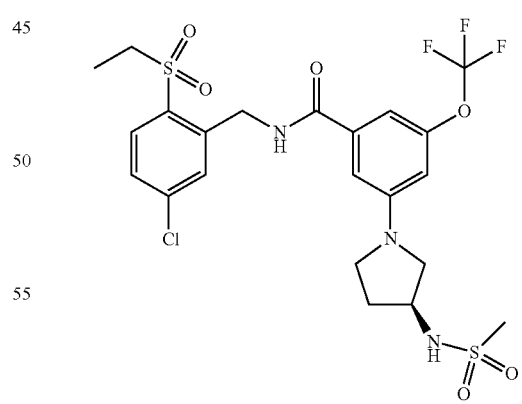

The title compound was synthesized from 3-((S)-3-amino-pyrrolidin-1-yl)-N-(5-chloro-2-ethanesulfonyl-benzyl)-5-trifluoromethoxy-benzamide (Compound I-13) under the same conditions as for Compound B-9.

LCMS: m/z 584 [M+H]$^+$

HPLC retention time: 0.81 min (analysis condition A)

Example 343

Compound I-16

3-((R)-3-Amino-pyrrolidin-1-yl)-N-(5-chloro-2-ethanesulfonyl-benzyl)-5-trifluoromethoxy-benzamide

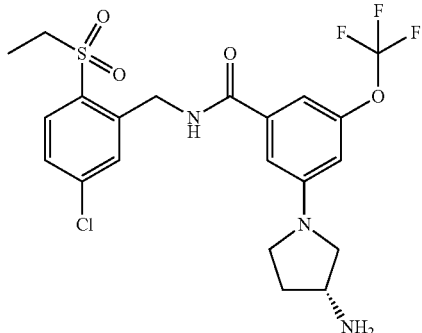

The title compound was synthesized from 3-bromo-5-trifluoromethoxy-benzoic acid ethyl ester (Compound i5) under the same conditions as for Compounds i9, i10, i11, and I-13. However, (R)-pyrrolidin-3-yl-carbamic acid tert-butyl ester was used in place of (S)-pyrrolidin-3-yl-carbamic acid tert-butyl ester under the conditions for Compound i9.

LCMS: m/z 506 [M+H]$^+$

HPLC retention time: 0.54 min (analysis condition A)

Example 344

Compound I-17

3-((R)-3-Acetylamino-pyrrolidin-1-yl)-N-(5-chloro-2-ethanesulfonyl-benzyl)-5-trifluoromethoxy-benzamide

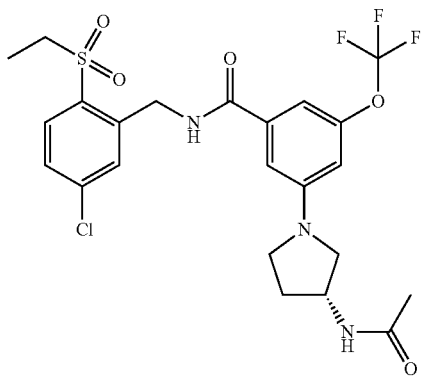 [SMILES: CCS(=O)(=O)c1ccc(Cl)cc1CNC(=O)c1cc(OC(F)(F)F)cc(N2CC[C@@H](NC(C)=O)C2)c1]

The title compound was synthesized from 3-((R)-3-amino-pyrrolidin-1-yl)-N-(5-chloro-2-ethanesulfonyl-benzyl)-5-trifluoromethoxy-benzamide (Compound I-16) under the same conditions as for Compound B-7.

LCMS: m/z 548 [M+H]$^+$

HPLC retention time: 0.77 min (analysis condition A)

Example 345

Compound I-18

N-(5-Chloro-2-ethanesulfonyl-benzyl)-3-((R)-3-methanesulfonylamino-pyrrolidin-1-yl)-5-trifluoromethoxy-benzamide

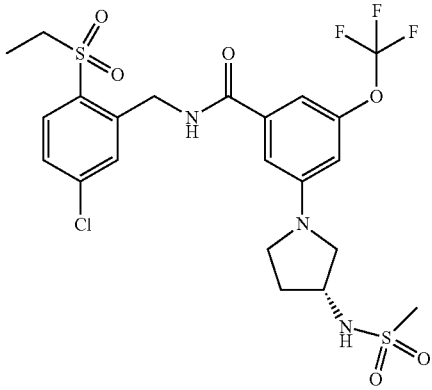 [SMILES: CCS(=O)(=O)c1ccc(Cl)cc1CNC(=O)c1cc(OC(F)(F)F)cc(N2CC[C@@H](NS(C)(=O)=O)C2)c1]

The title compound was synthesized from 3-((R)-3-amino-pyrrolidin-1-yl)-N-(5-chloro-2-ethanesulfonyl-benzyl)-5-trifluoromethoxy-benzamide (Compound I-16) under the same conditions as for Compound B-9.

LCMS: m/z 584 [M+H]$^+$

HPLC retention time: 0.81 min (analysis condition A)

Example 346

Compound I-19

3-(4-Amino-piperidin-1-yl)-N-(5-chloro-2-ethanesulfonyl-benzyl)-5-trifluoromethoxy-benzamide

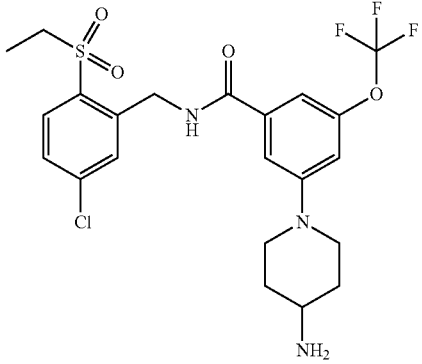 [SMILES: CCS(=O)(=O)c1ccc(Cl)cc1CNC(=O)c1cc(OC(F)(F)F)cc(N2CCC(N)CC2)c1]

The title compound was synthesized from 3-bromo-5-trifluoromethoxy-benzoic acid ethyl ester (Compound i5) under the same conditions as for Compounds i9, i10, i11, and I-13. However, piperidin-4-yl-carbamic acid tert-butyl ester was used in place of (S)-pyrrolidin-3-yl-carbamic acid tert-butyl ester under the conditions for Compound i9.

LCMS: m/z 520 [M+H]$^+$

HPLC retention time: 0.55 min (analysis condition A)

Example 347

Compound I-20

N-(5-Chloro-2-ethanesulfonyl-benzyl)-3-(4-dimethylamino-piperidin-1-yl)-5-trifluoromethoxy-benzamide

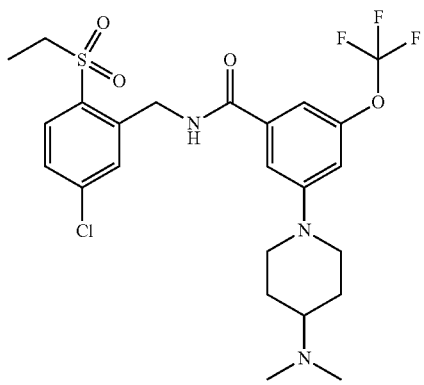

The title compound was synthesized from 3-(4-amino-piperidin-1-yl)-N-(5-chloro-2-ethanesulfonyl-benzyl)-5-trifluoromethoxy-benzamide (Compound I-19) under the same conditions as for Compound B-2. However, sodium triacetoxyborohydride was used in place of formic acid, and 1,2-dichloroethane was used as a solvent.

LCMS: m/z 548 [M+H]$^+$

HPLC retention time: 0.56 min (analysis condition A)

Example 348

Compound I-21

3-(4-Acetylamino-piperidin-1-yl)-N-(5-chloro-2-ethanesulfonyl-benzyl)-5-trifluoromethoxy-benzamide

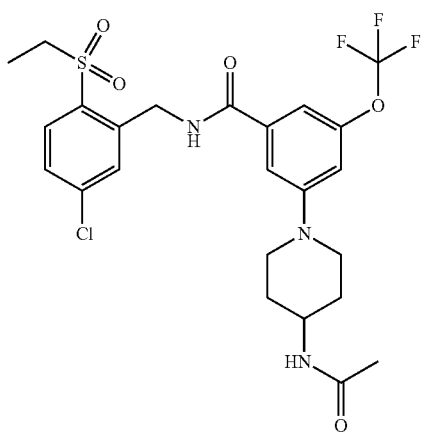 [SMILES: CCS(=O)(=O)c1ccc(Cl)cc1CNC(=O)c1cc(OC(F)(F)F)cc(N2CCC(NC(C)=O)CC2)c1]

The title compound was synthesized from 3-(4-amino-piperidin-1-yl)-N-(5-chloro-2-ethanesulfonyl-benzyl)-5-trifluoromethoxy-benzamide (Compound I-19) under the same conditions as for Compound B-7.

LCMS: m/z 562 [M+H]$^+$

HPLC retention time: 0.76 min (analysis condition A)

Example 349

Compound I-22

N-(5-Chloro-2-ethanesulfonyl-benzyl)-3-(4-methanesulfonylamino-piperidin-1-yl)-5-trifluoromethoxy-benzamide

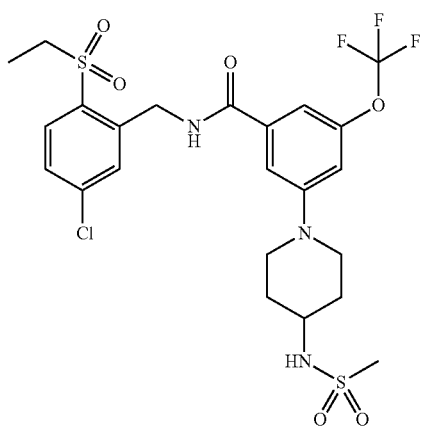 [SMILES: CCS(=O)(=O)c1ccc(Cl)cc1CNC(=O)c1cc(OC(F)(F)F)cc(N2CCC(NS(C)(=O)=O)CC2)c1]

The title compound was synthesized from 3-(4-amino-piperidin-1-yl)-N-(5-chloro-2-ethanesulfonyl-benzyl)-5-trifluoromethoxy-benzamide (Compound I-19) under the same conditions as for Compound B-9.

LCMS: m/z 598 [M+H]$^+$

HPLC retention time: 0.80 min (analysis condition A)

Example 350

Compound I-23

N-(5-Chloro-2-ethanesulfonyl-benzyl)-3-(3,3-dimethyl-piperazin-1-yl)-5-trifluoromethoxy-benzamide

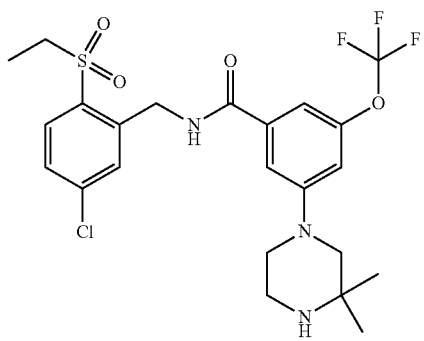 [SMILES: CCS(=O)(=O)c1ccc(Cl)cc1CNC(=O)c1cc(OC(F)(F)F)cc(N2CCNC(C)(C)C2)c1]

The title compound was synthesized from 3-bromo-5-trifluoromethoxy-benzoic acid ethyl ester (Compound i5) under the same conditions as for Compounds i9, i10, i11, and I-13. However, 2,2-dimethyl-piperazine-1-carboxylic acid tert-butyl ester was used in place of (S)-pyrrolidin-3-yl-carbamic acid tert-butyl ester under the conditions for Compound i9.

LCMS: m/z 534 [M+H]$^+$

HPLC retention time: 0.57 min (analysis condition A)

Example 351

Compound I-24

N-(5-Chloro-2-ethanesulfonyl-benzyl)-3-(4-hydroxy-piperidin-1-yl)-5-trifluoromethoxy-benzamide

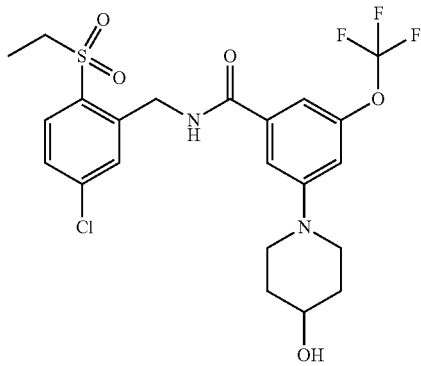 [SMILES: CCS(=O)(=O)c1ccc(Cl)cc1CNC(=O)c1cc(OC(F)(F)F)cc(N2CCC(O)CC2)c1]

The title compound was synthesized from 3-bromo-5-trifluoromethoxy-benzoic acid ethyl ester (Compound i5) under the same conditions as for Compounds i9, i10, and i11. However, the reaction was performed using 4-hydroxy-piperidine in place of (S)-pyrrolidin-3-yl-carbamic acid tert-butyl ester under the conditions for Compound i9; using a 1N aqueous sodium hydroxide solution in place of a 6N aqueous sodium hydroxide solution under the conditions for Compound i10; and using DCM in place of DMF as a solvent under the conditions for Compound i11.

LCMS: m/z 521 [M+H]$^+$

HPLC retention time: 0.78 min (analysis condition A)

Examples 352 to 355

The following compounds of FIG. 13 were synthesized using 3-bromo-N-(5-chloro-2-ethanesulfonyl-benzyl)-5-trifluoromethoxy-benzamide (Compound A-10) and corresponding cyclic amines under the same conditions as for Compound i2.

Example 356

Compound j1

4-Bromo-3-trifluoromethyl-benzoic acid ethyl ester

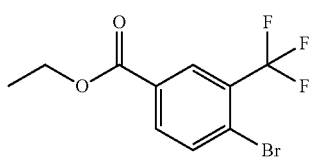 [SMILES: CCOC(=O)c1ccc(Br)c(C(F)(F)F)c1]

The title compound was synthesized from 4-bromo-3-trifluoromethyl-benzoic acid under the same conditions as for Compound b1.

Example 357

Compound j2

4-(4-Ethoxycarbonyl-2-trifluoromethyl-phenyl)-piperazine-1-carboxylic acid tert-butyl ester

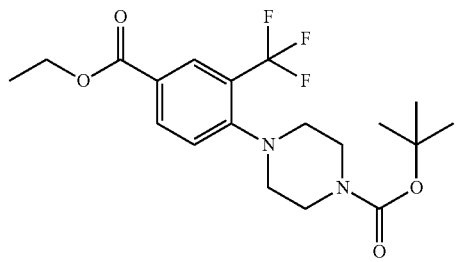 [SMILES: CCOC(=O)c1ccc(N2CCN(C(=O)OC(C)(C)C)CC2)c(C(F)(F)F)c1]

The title compound was synthesized from 4-bromo-3-trifluoromethyl-benzoic acid ethyl ester (Compound j1) under the same conditions as for Compound i2.

Example 358

Compound j3

4-(4-Carboxy-2-trifluoromethyl-phenyl)-piperazine-1-carboxylic acid tert-butyl ester

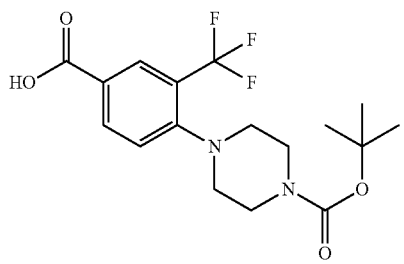 [SMILES: CC(C)(C)OC(=O)N1CCN(c2ccc(C(=O)O)cc2C(F)(F)F)CC1]

The title compound was synthesized from 4-(4-ethoxycarbonyl-2-trifluoromethyl-phenyl)-piperazine-1-carboxylic acid tert-butyl ester (Compound j2) under the same conditions as for Compound g7.

Example 359

Compound j4

4-[4-(5-Chloro-2-ethanesulfonyl-benzylcarbamoyl)-2-trifluoromethyl-phenyl]-piperazine-1-carboxylic acid tert-butyl ester

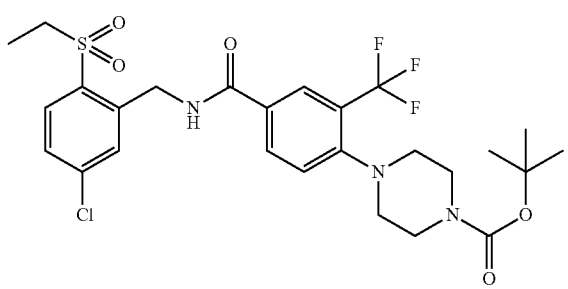 [SMILES: CCS(=O)(=O)c1ccc(Cl)cc1CNC(=O)c1ccc(N2CCN(C(=O)OC(C)(C)C)CC2)c(C(F)(F)F)c1]

The title compound was synthesized from 4-(4-carboxy-2-trifluoromethyl-phenyl)-piperazine-1-carboxylic acid tert-butyl ester (Compound j3) under the same conditions as for Compound A-14.

Example 360

Compound J-1

N-(5-Chloro-2-ethanesulfonyl-benzyl)-4-piperazin-1-yl-3-trifluoromethyl-benzamide

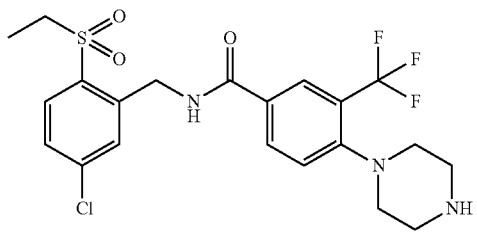 [SMILES: CCS(=O)(=O)c1ccc(Cl)cc1CNC(=O)c1ccc(N2CCNCC2)c(C(F)(F)F)c1]

The title compound was synthesized from 4-[4-(5-chloro-2-ethanesulfonyl-benzylcarbamoyl)-2-trifluoromethyl-phenyl]-piperazine-1-carboxylic acid tert-butyl ester (Compound j4) under the same conditions as for Compound B-1.
LCMS: m/z 490 [M+H]$^+$
HPLC retention time: 1.42 min (analysis condition D)

Example 361

Compound j5

4-(4-Ethoxycarbonyl-2-trifluoromethoxy-phenyl)-piperazine-1-carboxylic acid tert-butyl ester

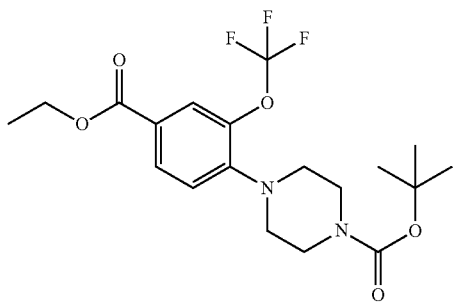 [SMILES: CCOC(=O)c1ccc(N2CCN(C(=O)OC(C)(C)C)CC2)c(OC(F)(F)F)c1]

The title compound was synthesized from 4-chloro-3-trifluoromethoxy-benzoic acid ethyl ester under the same conditions as for Compound i2.

Example 362

Compound j6

4-(2-Chloro-4-ethoxycarbonyl-6-trifluoromethoxy-phenyl)-piperazine-1-carboxylic acid tert-butyl ester

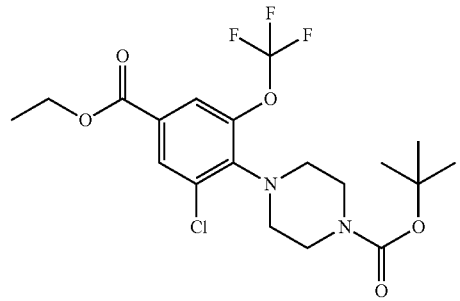 [SMILES: CCOC(=O)c1cc(Cl)c(N2CCN(C(=O)OC(C)(C)C)CC2)c(OC(F)(F)F)c1]

The title compound was synthesized from 4-(4-ethoxycarbonyl-2-trifluoromethoxy-phenyl)-piperazine-1-carboxylic acid tert-butyl ester (Compound j5) under the same conditions as for Compound d2.

Example 363

Compound j7

4-(4-Carboxy-2-chloro-6-trifluoromethoxy-phenyl)-piperazine-1-carboxylic acid tert-butyl ester

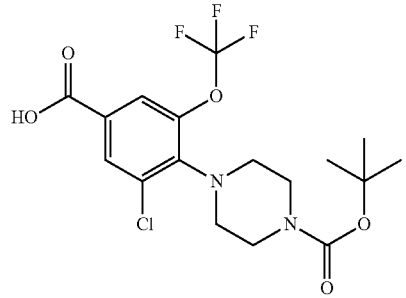 [SMILES: CC(C)(C)OC(=O)N1CCN(c2c(Cl)cc(C(=O)O)cc2OC(F)(F)F)CC1]

The title compound was synthesized from 4-(2-chloro-4-ethoxycarbonyl-6-trifluoromethoxy-phenyl)-piperazine-1-carboxylic acid tert-butyl ester (Compound j6) under the same conditions as for Compound b3.

Example 364

Compound j8

4-[2-Chloro-4-(5-chloro-2-ethanesulfonyl-benzylcarbamoyl)-6-trifluoromethoxy-phenyl]-piperazine-1-carboxylic acid tert-butyl ester

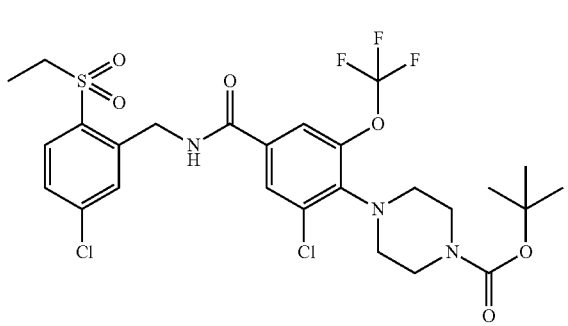 [SMILES: CCS(=O)(=O)c1ccc(Cl)cc1CNC(=O)c1cc(Cl)c(N2CCN(C(=O)OC(C)(C)C)CC2)c(OC(F)(F)F)c1]

The title compound was synthesized from 4-(4-carboxy-2-chloro-6-trifluoromethoxy-phenyl)-piperazine-1-carboxylic acid tert-butyl ester (Compound j7) under the same conditions as for Compound A-14.

Example 365

Compound J-2

3-Chloro-N-(5-chloro-2-ethanesulfonyl-benzyl)-4-piperazin-1-yl-5-trifluoromethoxy-benzamide

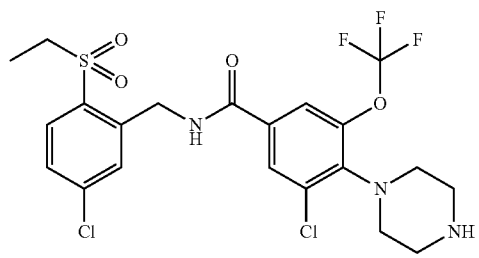 [SMILES: CCS(=O)(=O)c1ccc(Cl)cc1CNC(=O)c1cc(Cl)c(N2CCNCC2)c(OC(F)(F)F)c1]

The title compound was synthesized from 4-[2-chloro-4-(5-chloro-2-ethanesulfonyl-benzylcarbamoyl)-6-trifluoromethoxy-phenyl]-piperazine-1-carboxylic acid tert-butyl ester (Compound j8) under the same conditions as for Compound B-1.

LCMS: m/z 540 [M+H]$^+$

HPLC retention time: 0.54 min (analysis condition A)

Example 366

Compound J-3

3-Chloro-N-(5-chloro-2-ethanesulfonyl-benzyl)-4-(4-methyl-piperazin-1-yl)-5-trifluoromethoxy-benzamide

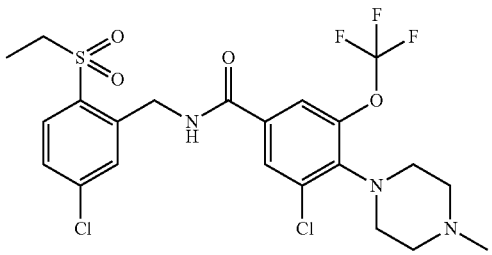 [SMILES: CCS(=O)(=O)c1ccc(Cl)cc1CNC(=O)c1cc(Cl)c(N2CCN(C)CC2)c(OC(F)(F)F)c1]

The title compound was synthesized from 3-chloro-N-(5-chloro-2-ethanesulfonyl-benzyl)-4-piperazin-1-yl-5-trifluoromethoxy-benzamide (Compound J-2) under the same conditions as for Compound B-2.

LCMS: m/z 554 [M+H]$^+$

HPLC retention time: 0.53 min (analysis condition A)

Example 367

Compound bb1

Ethyl 4-[(3-aminophenyl)methyl]-3-(trifluoromethyl)benzoate

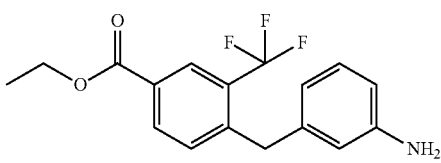 [SMILES: CCOC(=O)c1ccc(Cc2cccc(N)c2)c(C(F)(F)F)c1]

A suspension of ethyl 4-(bromomethyl)-3-(trifluoromethyl)benzoate (Compound b6, 30.0 mg, 0.096 mmol), (3-aminophenyl)boronic acid (18.5 mg, 0.135 mmol), potassium carbonate (40.0 mg, 0.289 mmol) and tetrakis(triphenylphosphine)palladium(0) (11.1 mg, 9.64 µmol) in a mixed solvent of 1,2-dimethoxyethane/water (2/1) (0.9 ml) was stirred at 70° C. for two hours. Water and ethyl acetate were added to the reaction mixture, and the organic layer was washed with brine and then dried over anhydrous magnesium sulfate. The drying agent was removed by filtration, followed by concentration under reduced pressure. The resultant residue was purified by silica gel column chromatography (ethyl acetate/n-hexane) to yield the title compound (20.0 mg, 64%) as a yellow oily substance.

LCMS: m/z 324 [M+H]$^+$

HPLC retention time: 0.80 min (analysis condition F)

Example 368

Compound bb2

4-[(3-Aminophenyl)methyl]-3-(trifluoromethyl)benzoic acid

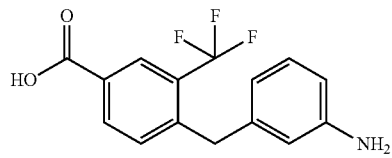 [SMILES: Nc1cccc(Cc2ccc(C(=O)O)cc2C(F)(F)F)c1]

The title compound was synthesized from ethyl 4-[(3-aminophenyl)methyl]-3-(trifluoromethyl)benzoate (Compound bb1) under the same conditions as for Compound b8.

Example 369

Compound BB-1

4-[(3-Aminophenyl)methyl]-N-[(5-chloro-2-ethylsulfonylphenyl)methyl]-3-(trifluoromethyl)benzamide

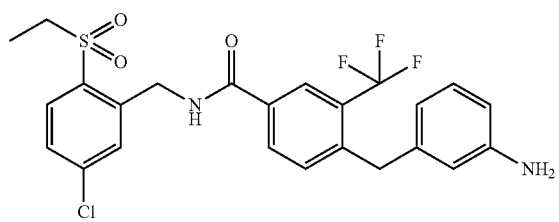 [SMILES: CCS(=O)(=O)c1ccc(Cl)cc1CNC(=O)c1ccc(Cc2cccc(N)c2)c(C(F)(F)F)c1]

The title compound was synthesized from (5-chloro-2-ethylsulfonylphenyl)methanamine hydrochloride (Compound a3) under the same conditions as for Compound A-21. However, 4-[(3-aminophenyl)methyl]-3-(trifluoromethyl)benzoic acid (Compound bb2) was used in place of 3-(trifluoromethyl)benzoic acid.

LCMS: m/z 511 [M+H]$^+$
HPLC retention time: 0.76 min (analysis condition F)

Example 370

Compound BB-2

N-[(5-Chloro-2-ethylsulfonylphenyl)methyl]-4-(pyridin-4-ylmethyl)-3-(trifluoromethyl)benzamide

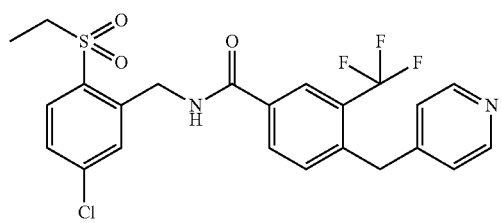 [SMILES: CCS(=O)(=O)c1ccc(Cl)cc1CNC(=O)c1ccc(Cc2ccncc2)c(C(F)(F)F)c1]

The title compound was synthesized from ethyl 4-(bromomethyl)-3-(trifluoromethyl)benzoate (Compound b6) under the same conditions as for bb1, bb2 and BB-1. However, 4-(4,4,5,5-tetramethyl-1,3,2-dioxaborolan-2-yl)pyridine was used in place of (3-aminophenyl)boronic acid under the conditions for Compound bb1, and 4-(pyridin-4-ylmethyl)-3-(trifluoromethyl)benzoic acid was used in place of 4-[(3-aminophenyl)methyl]-3-(trifluoromethyl)benzoic acid (Compound bb2) under the conditions for Compound BB-1.

LCMS: m/z 497 [M+H]$^+$
HPLC retention time: 0.57 min (analysis condition F)

Example 371

Compound bb3 tert-Butyl 4-[[4-ethoxycarbonyl-2-(trifluoromethyl)phenyl]methyl]-3,6-dihydro-2H-pyridine-1-carboxylate

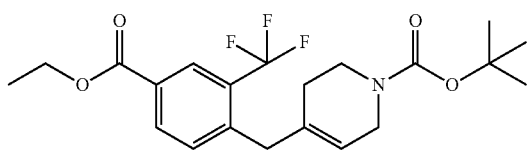 [SMILES: CCOC(=O)c1ccc(CC2=CCN(C(=O)OC(C)(C)C)CC2)c(C(F)(F)F)c1]

The title compound was synthesized from ethyl 4-(bromomethyl)-3-(trifluoromethyl)benzoate (Compound b6) under the same conditions as for Compound bb1. However, tert-butyl 4-(4,4,5,5-tetramethyl-1,3,2-dioxaborolan-2-yl)-3,6-dihydro-2H-pyridine-1-carboxylate was used in place of (3-aminophenyl)boronic acid.

Example 372

Compound bb4 tert-Butyl 4-[[4-ethoxycarbonyl-2-(trifluoromethyl)phenyl]methyl]piperidine-1-carboxylate

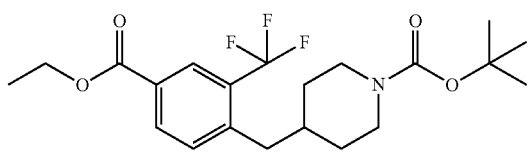 [SMILES: CCOC(=O)c1ccc(CC2CCN(C(=O)OC(C)(C)C)CC2)c(C(F)(F)F)c1]

10% palladium-activated carbon (10 mg) was added to a solution of tert-butyl 4-[[4-ethoxycarbonyl-2-(trifluoromethyl)phenyl]methyl]-3,6-dihydro-2H-pyridine-1-carboxylate (Compound bb3, 34.0 mg, 82.2 μmol) in MeOH (1 ml), and the mixture was stirred at room temperature for 16 hours under a hydrogen atmosphere. DCM was added to the reaction mixture; and after the mixture was filtered through a membrane filter, the title compound (31.0 mg, 91%) was obtained as a colorless oily substance by concentrating the filtrate under reduced pressure.

LCMS: m/z 416 [M+H]$^+$
HPLC retention time: 1.10 min (analysis condition F)

Example 373

Compound bb5

4-[[1-[(2-Methylpropan-2-yl)oxycarbonyl]piperidin-4-yl]methyl]-3-(trifluoromethyl)benzoic acid

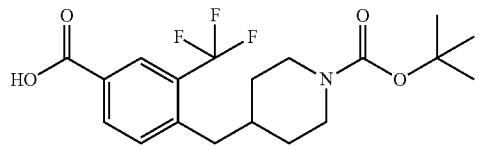 [SMILES: CC(C)(C)OC(=O)N1CCC(Cc2ccc(C(=O)O)cc2C(F)(F)F)CC1]

The title compound was synthesized from tert-butyl 4-[[4-ethoxycarbonyl-2-(trifluoromethyl)phenyl]methyl]piperidine-1-carboxylate (Compound bb4) under the same conditions as for Compound b8.

Example 374

Compound bb6 tert-Butyl 4-[[4-[(5-chloro-2-ethylsulfonylphenyl)methylcarbamoyl]-2-(trifluoromethyl)phenyl]methyl]piperidine-1-carboxylate

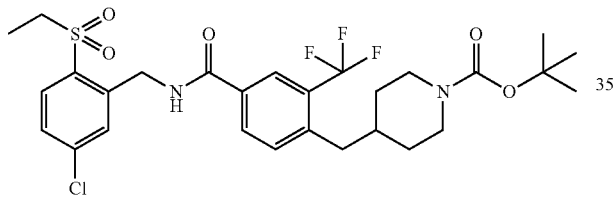

The title compound was synthesized from (5-chloro-2-ethylsulfonylphenyl)methanamine hydrochloride (Compound a3) under the same conditions as for Compound A-21. However, 4-[[1-[(2-methylpropan-2-yl)oxycarbonyl]piperidin-4-yl]methyl]-3-(trifluoromethyl)benzoic acid (Compound bb5) was used in place of 3-(trifluoromethyl)benzoic acid.

Example 375

Compound BB-3

N-[(5-Chloro-2-ethylsulfonylphenyl)methyl]-4-(piperidin-4-ylmethyl)-3-(trifluoromethyl)benzamide

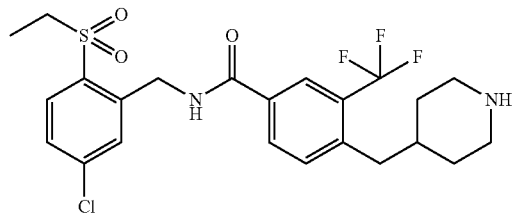 [SMILES: CCS(=O)(=O)c1ccc(Cl)cc1CNC(=O)c1ccc(CC2CCNCC2)c(C(F)(F)F)c1]

The title compound was synthesized from tert-butyl 4-[[4-[(5-chloro-2-ethylsulfonylphenyl)methylcarbamoyl]-2-(trifluoromethyl)phenyl]methyl]piperidine-1-carboxylate (Compound bb6) under the same conditions as for Compound B-1.

LCMS: m/z 503 [M+H]$^+$
HPLC retention time: 0.54 min (analysis condition F)

Example 376

Compound BB-4

N-[(5-Chloro-2-ethylsulfonylphenyl)methyl]-4-[(1-methylpiperidin-4-yl)methyl]-3-(trifluoromethyl)benzamide

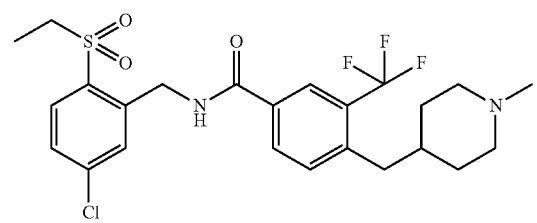 [SMILES: CCS(=O)(=O)c1ccc(Cl)cc1CNC(=O)c1ccc(CC2CCN(C)CC2)c(C(F)(F)F)c1]

The title compound was synthesized from N-[(5-chloro-2-ethylsulfonylphenyl)methyl]-4-(piperidin-4-ylmethyl)-3-(trifluoromethyl)benzamide (Compound BB-3) under the same conditions as for Compound B-2.

LCMS: m/z 517 [M+H]$^+$
HPLC retention time: 0.54 min (analysis condition F)

Example 377

Compound bb1

1,5-Dichloro-2-ethanesulfonyl-3-methyl-benzene

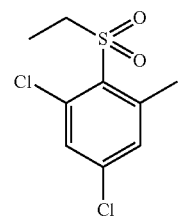

2,4-Dichloro-6-methyl-benzenesulfonyl chloride (1.00 g, 3.90 mmol) was added to an aqueous solution (5 ml) of sodium sulfite (534 mg, 4.24 mmol) and sodium bicarbonate (712 mg, 8.48 mmol), and the mixture was stirred at 75° C. for one hour. Iodoethane (1.98 ml, 19.0 mmol) was added thereto, and the mixture was stirred at 100° C. for 11 hours. Iodoethane (0.988 ml, 9.60 mmol) was added, and the mixture was stirred at 100° C. for three more hours. The reaction solution was extracted by adding DCM; and the organic layer was washed with a saturated aqueous solution of sodium thiosulfate and dried over anhydrous sodium sulfate. The drying agent was removed by filtration, followed by concentration under reduced pressure. The resultant residue was purified by silica gel column chromatography (ethyl acetate/n-hexane) to yield the title compound (664 mg, 68%) as a colorless oily substance.

LCMS: m/z 253 [M+H]$^+$

HPLC retention time: 0.79 min (analysis condition D)

Example 378

Compound bb8

1-(Bromomethyl)-3,5-dichloro-2-ethylsulfonylbenzene

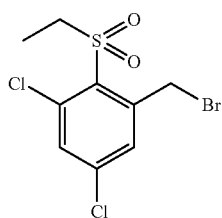

The title compound was synthesized from 1,5-dichloro-2-ethanesulfonyl-3-methyl-benzene (Compound bb1) under the same conditions as for Compound b6. However, acetonitrile was used in place of carbon tetrachloride as a solvent.

Example 379

Compound bb9

(3,5-Dichloro-2-ethylsulfonylphenyl)methanamine

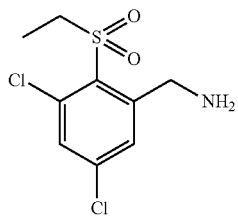

A 25% ammonium aqueous solution (4 ml) was added to a solution of 1-(bromomethyl)-3,5-dichloro-2-ethylsulfonylbenzene (Compound bb8, 140 mg, 0.422 mmol) in EtOH (2 ml) under ice-cooling, and the mixture was warmed to room temperature and stirred for 30 minutes. Further, THF (2 ml) was added to the reaction suspension, and the reaction solution was stirred at room temperature for two hours. After the reaction mixture was extracted with ethyl acetate, the organic layer was dried over anhydrous sodium sulfate. The drying agent was removed by filtration, followed by concentration under reduced pressure. The resultant residue was purified by silica gel column chromatography (methanol/dichloromethane). The resultant mixture was further purified by silica gel column chromatography (ethyl acetate/n-hexane, then methanol/dichloromethane) to yield the title compound (81.9 mg, 72%) as a pale yellow oily substance.

LCMS: m/z 268 [M+H]$^+$

HPLC retention time: 0.36 min (analysis condition A)

Example 380

Compound bb10 tert-Butyl 4-[[4-[(3,5-dichloro-2-ethylsulfonylphenyl)methylcarbamoyl]-2-(trifluoromethyl)phenyl]methyl]piperazine-1-carboxylate

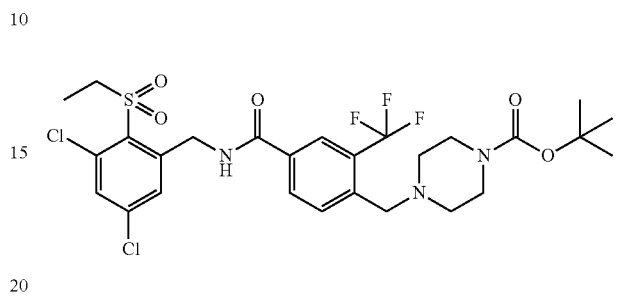

DIPEA (18.0 µl, 0.101 mmol) was added to a solution of (3,5-dichloro-2-ethylsulfonylphenyl)methanamine (Compound bb9, 12.3 mg, 45.8 µmol), 4-[[4-[(2-methylpropan-2-yl)oxycarbonyl]piperazin-1-yl]methyl]-3-(trifluoromethyl)benzoate (Compound b3, 20.1 mg, 47.1 µmol) and HATU (21.4 mg, 56.3 µmol) in DMF (0.5 ml), and the mixture was stirred at room temperature for 30 minutes under a nitrogen atmosphere. Water was added to the reaction mixture, followed by extraction with ethyl acetate. The organic layer was then dried over anhydrous sodium sulfate. The drying agent was removed by filtration, followed by concentration under reduced pressure. The obtained residue was purified by silica gel column chromatography (ethyl acetate/n-hexane) to yield the title compound (20.2 mg, 69%) as a colorless foamy substance.

LCMS: m/z 638 [M+H]$^+$

HPLC retention time: 1.84 min (analysis condition D)

Example 381

Compound bb11

N-[(3,5-Dichloro-2-ethylsulfonylphenyl)methyl]-4-(piperazin-1-ylmethyl)-3-(trifluoromethyl)benzamide

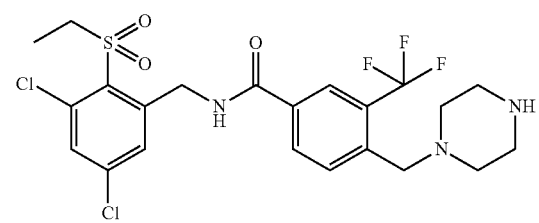 [SMILES: CCS(=O)(=O)c1c(Cl)cc(Cl)cc1CNC(=O)c1ccc(CN2CCNCC2)c(C(F)(F)F)c1]

The title compound was synthesized from tert-butyl 4-[[4-[(3,5-dichloro-2-ethylsulfonylphenyl)methylcarbamoyl]-2-(trifluoromethyl)phenyl]methyl]piperazine-1-carboxylate (Compound bb10) under the same conditions as for Compound B-57.

Example 382

Compound BB-5

N-[(3,5-Dichloro-2-ethylsulfonylphenyl)methyl]-4-[(4-methylpiperazin-1-yl)methyl]-3-(trifluoromethyl)benzamide

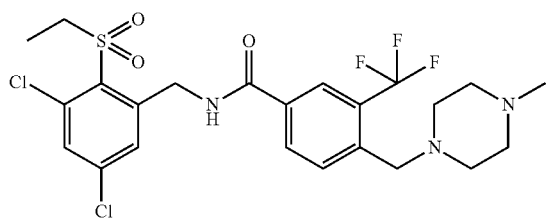 [SMILES: CCS(=O)(=O)c1c(Cl)cc(Cl)cc1CNC(=O)c1ccc(CN2CCN(C)CC2)c(C(F)(F)F)c1]

The title compound was synthesized from N-[(3,5-dichloro-2-ethylsulfonylphenyl)methyl]-4-(piperazin-1-ylmethyl)-3-(trifluoromethyl)benzamide (Compound bb11) under the same conditions as for Compound B-2.

LCMS: m/z 552 [M+H]$^+$

HPLC retention time: 1.53 min (analysis condition D)

Example 383

Compound BB-6

N-[(3,5-Dichloro-2-ethylsulfonylphenyl)methyl]-4-[[(3S)-3-(methylamino)piperidin-1-yl]methyl]-3-(trifluoromethyl)benzamide

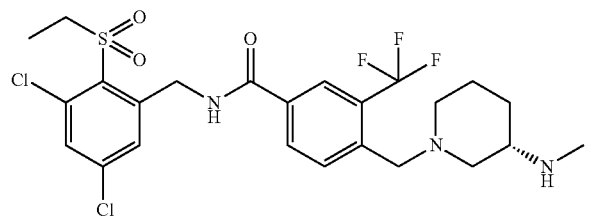 [SMILES: CCS(=O)(=O)c1c(Cl)cc(Cl)cc1CNC(=O)c1ccc(CN2CCC[C@H](NC)C2)c(C(F)(F)F)c1]

The title compound was synthesized from (3,5-dichloro-2-ethylsulfonylphenyl)methanamine (Compound bb9) under the same conditions as for Compounds bb10 and bb11. However, 4-[[(3S)-3-[methyl-[(2-methylpropan-2-yl)oxycarbonyl]amino]piperidin-1-yl]methyl]-3-(trifluoromethyl)benzoate (Compound b17) was used in place of 4-[[4-[(2-methylpropan-2-yl)oxycarbonyl]piperazin-1-yl]methyl]-3-(trifluoromethyl)benzoate (Compound b3) under the conditions for Compound bb10.

LCMS: m/z 566 [M+H]$^+$

HPLC retention time: 1.33 min (analysis condition D)

Example 384

Compound DD-1

N-[(3S)-1-[[2-Chloro-4-[(5-chloro-2-ethylsulfonylphenyl)methylcarbamoyl]-6-(trifluoromethyl)phenyl]methyl]piperidin-3-yl]-1H-pyrrole-2-carboxamide

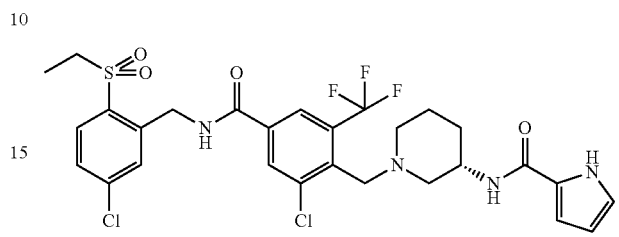

A solution of 4-[[(3S)-3-aminopiperidin-1-yl]methyl]-3-chloro-N-[(5-chloro-2-ethylsulfonylphenyl)methyl]-5-(trifluoromethyl)benzamide (Compound D-18, 30.0 mg, 0.054 mmol), pyrrole-2-carboxylic acid (7.24 mg, 0.065 mmol) and DIPEA (27.0 µl, 0.163 mmol) in DCM (1 ml) was cooled to 0° C. in an ice water bath, HBTU (24.7 mg, 0.065 mmol) was added, and the mixture was then stirred at room temperature for 16 hours. The reaction mixture was concentrated under reduced pressure, and the obtained residue was then purified by preparative HPLC (water/acetonitrile, 0.05% TFA) to yield the title compound (22.0 mg, yield: 62%) as a colorless solid.

LCMS: m/z 645 [M+H]$^+$

HPLC retention time: 0.64 min (analysis condition F)

Examples 385 to 387, Examples 402 to 404

The compounds of FIGS. 14-15 were synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compound DD-1.

Example 388

Compound dd1 tert-Butyl (2S)-2-[[(3S)-1-[[2-chloro-4-[(5-chloro-2-ethylsulfonylphenyl)methylcarbamoyl]-6-(trifluoromethyl)phenyl]methyl]piperidin-3-yl]carbamoyl]pyrrolidine-1-carboxylate

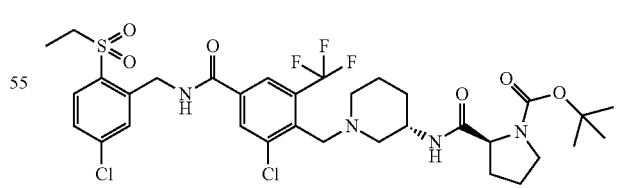

The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compound DD-1. However, as a carboxylic acid, (2S)-1-[(2-methylpropan-2-yl)oxycarbonyl]pyrrolidine-2-carboxylic acid was used in place of 1H-pyrrole-2-carboxylic acid.

Example 389

Compound DD-5

(2S)—N-[(3S)-1-[[2-Chloro-4-[(5-chloro-2-ethylsulfonylphenyl)methylcarbamoyl]-6-(trifluoromethyl)phenyl]methyl]piperidin-3-yl]pyrrolidine-2-carboxamide

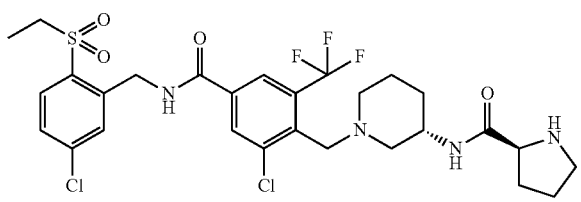 [SMILES: CCS(=O)(=O)c1ccc(Cl)cc1CNC(=O)c1cc(Cl)c(CN2CCC[C@H](NC(=O)[C@@H]3CCCN3)C2)c(C(F)(F)F)c1]

The title compound was synthesized from tert-butyl (2S)-2-[[(3S)-1-[[2-chloro-4-[(5-chloro-2-ethylsulfonylphenyl)methylcarbamoyl]-6-(trifluoromethyl)phenyl]methyl]piperidin-3-yl]carbamoyl]pyrrolidine-1-carboxylate (Compound dd1) under the same conditions as for Compound B-1.

LCMS: m/z 649 [M+H]$^+$
HPLC retention time: 0.48 min (analysis condition F)

Examples 390 to 401

The compounds of FIGS. 16-18 were synthesized using 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) and corresponding carboxylic acids under the same conditions as for Compounds dd1 and DD-5.

Example 405

Compound DD-21

3-Chloro-N-[(5-chloro-2-ethylsulfonylphenyl)methyl]-4-[[(3S)-3-(propan-2-ylamino)piperidin-1-yl]methyl]-5-(trifluoromethyl)benzamide

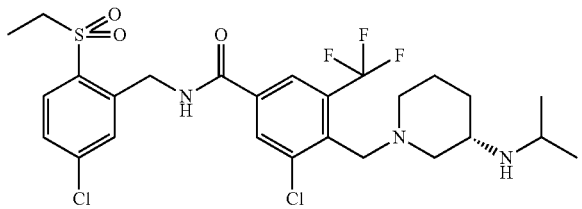 [SMILES: CCS(=O)(=O)c1ccc(Cl)cc1CNC(=O)c1cc(Cl)c(CN2CCC[C@H](NC(C)C)C2)c(C(F)(F)F)c1]

The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compound B-3. However, methanol was used in place of THF as a solvent.

LCMS: m/z 594 [M+H]$^+$
HPLC retention time: 0.59 min (analysis condition F)

Example 406

3-Bromopropyne (16.0 µl, 0.181 mmol) was added to a solution of 4-[[(3S)-3-aminopiperidin-1-yl]methyl]-3-chloro-N-[(5-chloro-2-ethylsulfonylphenyl)methyl]-5-(trifluoromethyl)benzamide (Compound D-18, 50.0 mg, 0.091 mmol) and DIPEA (47.0 µl, 0.272 mmol) in chloroform (1 ml), and the mixture was then stirred at room temperature for 16 hours. The reaction mixture was concentrated under reduced pressure, and the resultant residue was then purified by preparative HPLC (water/acetonitrile, 0.05% TFA) to yield Compound DD-22 (17.5 mg, 32%) and Compound DD-23 (7.1 mg, 12%) independently as yellow solids.

Compound DD-22

3-Chloro-N-[(5-chloro-2-ethylsulfonylphenyl)methyl]-4-[[(3S)-3-(prop-2-ynylamino)piperidin-1-yl]methyl]-5-(trifluoromethyl)benzamide LCMS: m/z 590 [M+H]$^+$
HPLC retention time: 0.59 min (analysis condition F)

Compound DD-23

4-[[(3S)-3-[Bis(prop-2-ynyl)amino]piperidin-1-yl]methyl]-3-chloro-N-[(5-chloro-2-ethylsulfonylphenyl)methyl]-5-(trifluoromethyl)benzamide LCMS: m/z 628 [M+H]$^+$
HPLC retention time: 0.67 min (analysis condition F)

Example 407

Compound DD-24

3-Chloro-N-[(5-chloro-2-ethylsulfonylphenyl)methyl]-4-[[(3S)-3-(cyanomethylamino)piperidin-1-yl]methyl]-5-(trifluoromethyl)benzamide The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compounds DD-22 and DD-23. However, 2-iodoacetonitrile was used in place of 3-bromopropyne.

LCMS: m/z 591 [M+H]$^+$

HPLC retention time: 0.55 min (analysis condition F)

Example 408

Compounds DD-25 and DD-26 were synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compounds DD-22 and DD-23. However, bromoacetamide was used in place of 3-bromopropyne.

Compound DD-25

4-[[(3S)-3-[(2-Amino-2-oxoethyl)amino]piperidin-1-yl]methyl]-3-chloro-N-[(5-chloro-2-ethylsulfonylphenyl)methyl]-5-(trifluoromethyl)benzamide

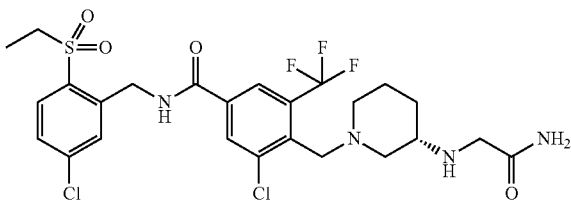 [SMILES: CCS(=O)(=O)c1ccc(Cl)cc1CNC(=O)c1cc(Cl)c(CN2CCC[C@H](NCC(N)=O)C2)c(C(F)(F)F)c1]

LCMS: m/z 609 [M+H]$^+$

HPLC retention time: 0.56 min (analysis condition F)

Compound DD-26

4-[[(3S)-3-[Bis(2-amino-2-oxoethyl)amino]piperidin-1-yl]methyl]-3-chloro-N-[(5-chloro-2-ethylsulfonylphenyl)methyl]-5-(trifluoromethyl)benzamide

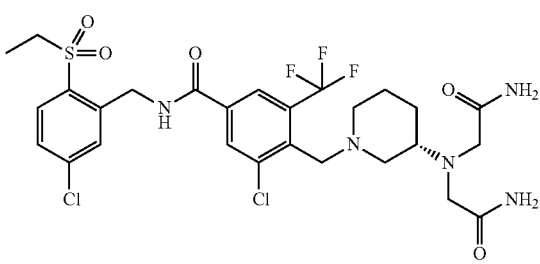 [SMILES: CCS(=O)(=O)c1ccc(Cl)cc1CNC(=O)c1cc(Cl)c(CN2CCC[C@H](N(CC(N)=O)CC(N)=O)C2)c(C(F)(F)F)c1]

LCMS: m/z 666 [M+H]$^+$

HPLC retention time: 0.47 min (analysis condition F)

Example 409

Compound dd2 tert-Butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]amino]ethyl]carbamate

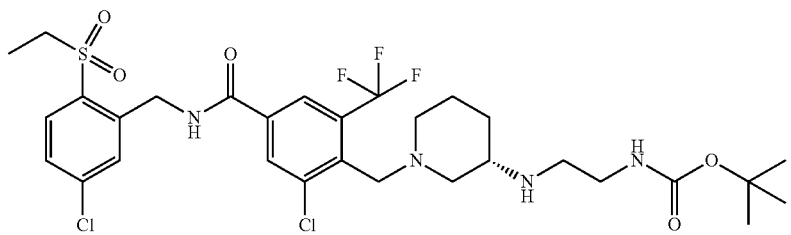 [SMILES: CCS(=O)(=O)c1ccc(Cl)cc1CNC(=O)c1cc(Cl)c(CN2CCC[C@H](NCCNC(=O)OC(C)(C)C)C2)c(C(F)(F)F)c1]

The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compound H-5. However, tert-butyl (2-bromoethyl)carbamate was used in place of iodoethane.

Example 410

Compound DD-27

4-[[(3S)-3-(2-Aminoethylamino)piperidin-1-yl]methyl]-3-chloro-N-[(5-chloro-2-ethylsulfonylphenyl)methyl]-5-(trifluoromethyl)benzamide

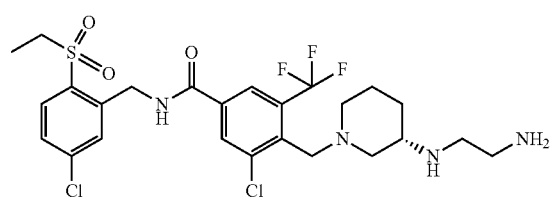 [SMILES: CCS(=O)(=O)c1ccc(Cl)cc1CNC(=O)c1cc(Cl)c(CN2CCC[C@H](NCCN)C2)c(C(F)(F)F)c1]

The title compound was synthesized from tert-butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]amino]ethyl]carbamate (Compound dd2) under the same conditions as for Compound B-1.

LCMS: m/z 595 [M+H]$^+$

HPLC retention time: 0.45 min (analysis condition F)

Example 411

Compound DD-28

3-Chloro-N-[(5-chloro-2-ethylsulfonylphenyl)methyl]-4-[[(3S)-3-(oxetan-3-ylamino)piperidin-1-yl]methyl]-5-(trifluoromethyl)benzamide

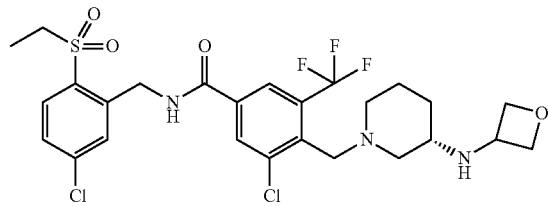 [SMILES: CCS(=O)(=O)c1ccc(Cl)cc1CNC(=O)c1cc(Cl)c(CN2CCC[C@H](NC3COC3)C2)c(C(F)(F)F)c1]

Sodium triacetoxyborohydride (20 mg, 0.095 mmol) was added to a suspension of 4-[[(3S)-3-aminopiperidin-1-yl]methyl]-3-chloro-N-[(5-chloro-2-ethylsulfonylphenyl)methyl]-5-(trifluoromethyl)benzamide (Compound D-18, 35 mg, 0.063 mmol) and 3-oxetanone (6 μl, 0.095 mmol) in chloroform (1 ml); and the mixture was stirred at room temperature. After 20 hours, 3-oxetanone (6 μl, 0.095 mmol) and sodium triacetoxyborohydride (25 mg, 0.118 mmol) were further added; and the mixture was further stirred at room temperature for four hours. Water was added to the reaction mixture, followed by extraction with ethyl acetate. The organic layer was washed with brine and then dried over anhydrous sodium sulfate. The drying agent was removed by filtration, and the solvent was then concentrated under reduced pressure. The resultant residue was purified by preparative HPLC (water/acetonitrile, 0.05% TFA) to yield the title compound (19 mg, 49%) as a colorless solid.

LCMS: m/z 608 [M+H]$^+$

HPLC retention time: 0.56 min (analysis condition F)

Example 412

Compound DD-29

3-Chloro-N-[(5-chloro-2-ethylsulfonylphenyl)methyl]-4-[[(3S)-3-(2,2-difluoroethylamino)piperidin-1-yl]methyl]-5-(trifluoromethyl)benzamide

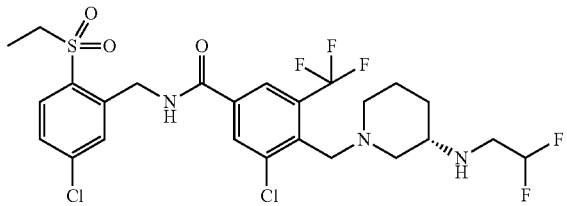 [SMILES: CCS(=O)(=O)c1ccc(Cl)cc1CNC(=O)c1cc(Cl)c(CN2CCC[C@H](NCC(F)F)C2)c(C(F)(F)F)c1]

2,2-Difluoroethyl trifluoromethanesulfonate (25.6 mg, 0.119 mmol) was added to a solution of 4-[[(3S)-3-aminopiperidin-1-yl]methyl]-3-chloro-N-[(5-chloro-2-ethylsulfonylphenyl)methyl]-5-(trifluoromethyl)benzamide (Compound D-18, 55.0 mg, 0.100 mmol) and DIPEA (21.0 μl, 0.119 mmol) in THF (1 ml), and it was stirred at 70° C. for one hour. Water was added to the reaction mixture, followed by extraction with ethyl acetate. The organic layer was washed with brine and then dried over anhydrous sodium sulfate. The drying agent was removed by filtration, and the solvent was then concentrated under reduced pressure. The resultant residue was purified by silica gel column chromatography (ethyl acetate/n-hexane) to yield the title compound (51.0 mg, 83%) as a colorless solid.

LCMS: m/z 616 [M+H]$^+$

HPLC retention time: 0.59 min (analysis condition F)

Example 413

Compound dd3 tert-Butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]-methylamino]-2-oxoethyl]carbamate

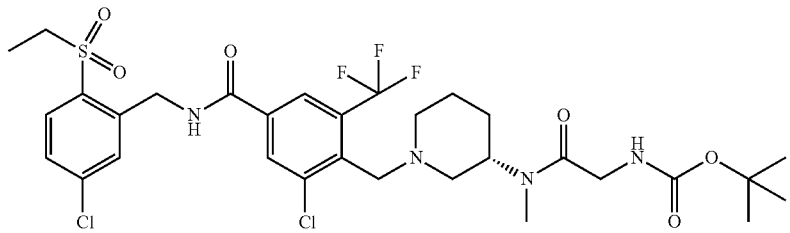 [SMILES: CCS(=O)(=O)c1ccc(Cl)cc1CNC(=O)c1cc(Cl)c(CN2CCC[C@H](N(C)C(=O)CNC(=O)OC(C)(C)C)C2)c(C(F)(F)F)c1]

The title compound was synthesized from 3-chloro-N-(5-chloro-2-ethanesulfonyl-benzyl)-4-((S)-3-methylamino-piperidin-1-ylmethyl)-5-trifluoromethyl-benzamide (Compound D-26) under the same conditions as for Compound DD-1. However, 2-[(2-methylpropan-2-yl)oxycarbonylamino]acetic acid was used in place of 1H-pyrrole-2-carboxylic acid as a carboxylic acid.

Example 414

Compound DD-30

4-[[(3S)-3-[(2-Aminoacetyl)-methylamino]piperidin-1-yl]methyl]-3-chloro-N-[(5-chloro-2-ethylsulfonylphenyl)methyl]-5-(trifluoromethyl)benzamide

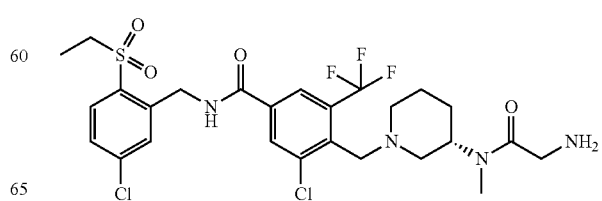

The title compound was synthesized from tert-butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]-methylamino]-2-oxoethyl]carbamate (Compound dd3) under the same conditions as for Compound B-57.

LCMS: m/z 623 [M+H]+

HPLC retention time: 0.45 min (analysis condition F)

Example 415

Compound dd4

4-Amino-3-chloro-5-(trifluoromethyl)benzoic acid

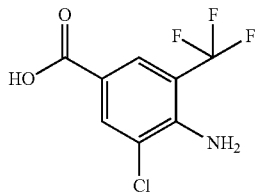 [SMILES: Nc1c(Cl)cc(C(=O)O)cc1C(F)(F)F]

The title compound was synthesized from 4-amino-3-(trifluoromethyl)benzoic acid under the same conditions as for Compound d6.

Example 416

Compound dd5

Methyl 4-amino-3-chloro-5-(trifluoromethyl)benzoate

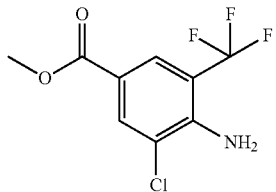 [SMILES: COC(=O)c1cc(Cl)c(N)c(C(F)(F)F)c1]

Sulfuric acid (48 ml) was added to a solution of 4-amino-3-chloro-5-(trifluoromethyl)benzoic acid (Compound dd4, 216 g, 901 mmol) in MeOH (1.08 L) at room temperature, and it was stirred under reflux for 13 hours. The reaction mixture was cooled to room temperature, and the pH was then adjusted to 9 by adding an aqueous solution (2.59 L) of tripotassium phosphate (191 g, 901 mmol). The precipitate was collected by filtration, washed with water, and then dried under reduced pressure to yield the title compound (216 g, 95%) as a pale orange solid.

$^1$H-NMR (400 MHz, DMSO-$d_6$) δ: 7.99 (1H, d, J=2.0 Hz), 7.89 (1H, d, J=2.0 Hz), 6.62 (2H, brs), 3.81 (3H, s).

Example 417

Compound dd6

Methyl 3-chloro-4-iodo-5-(trifluoromethyl)benzoate

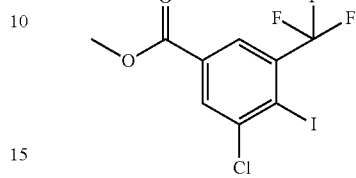

Sulfuric acid (91 ml) was added to a solution (1.73 L) of methyl 4-amino-3-chloro-5-(trifluoromethyl)benzoate (Compound dd5, 216 g, 853 mmol) in trifluoroethanol at room temperature, and it was cooled to −5° C., after which an aqueous solution (324 ml) of sodium nitrite (64.7 g, 938 mmol) was added over 24 minutes, and it was stirred for 30 minutes. An aqueous solution (324 ml) of potassium iodide (149 g, 895 mmol) was added at the same temperature over 30 minutes, and it was stirred at 0° C. for 90 minutes, after which an aqueous solution (2.16 L) of sodium thiosulfate (215 g, 1.71 mol) was added over 25 minutes. The reaction mixture was warmed to 20° C.; and the precipitate was collected by filtration, washed with a mixed solution of ethanol/water (1:1, 2.16 L), and then dried under reduced pressure to yield the title compound (205 g, 66%) as a pale brown solid.

$^1$H-NMR (400 MHz, DMSO-$d_6$) δ: 8.26 (1H, d, J=1.8 Hz), 8.03 (1H, d, J=1.8 Hz), 3.90 (3H, s).

Example 418

Compound dd7

Methyl 3-chloro-4-(hydroxymethyl)-5-(trifluoromethyl)benzoate

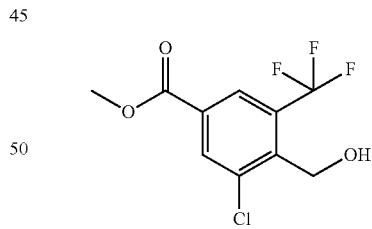

A solution of methyl 3-chloro-4-iodo-5-(trifluoromethyl)benzoate (Compound ddb, 500 mg, 1.37 mmol) in THF (2.7 ml) was cooled to 0° C. in an ice water bath, a 0.74 M isopropylmagnesium bromide/THF solution (2.23 ml, 1.65 mmol) was added dropwise, and it was stirred at the same temperature for 20 minutes. After N-Formylmorpholine (0.277 ml, 2.74 mmol) was added, it was stirred at room temperature for two hours. The reaction mixture was again cooled to 0° C. in an ice water bath, sodium borohydride (78.0 mg, 2.06 mmol) was added, and it was stirred at the same temperature for 20 minutes. Then, sodium borohydride (40.0 mg, 1.06 mmol) was further added, and it was stirred at the same temperature for 10 minutes. A 1N aqueous hydrochloric acid solution was added to the reaction mixture, followed by extraction with ethyl acetate. The organic layer was washed with a saturated aqueous solution of sodium chloride and then dried over anhydrous sodium sulfate. The drying agent was removed by filtration, followed by concentration under reduced pressure. The resultant residue was purified by silica gel column chromatography (ethyl acetate/n-hexane) to yield the title compound (223 mg, 60%) as an orange oily substance.

LCMS: m/z 269 [M+H]$^+$

HPLC retention time: 0.68 min (analysis condition F)

Example 419

Compound dd8

3-Chloro-4-(hydroxymethyl)-5-(trifluoromethyl) benzoic acid

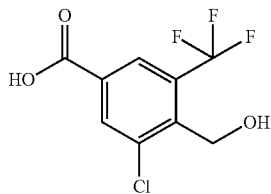 [SMILES: O=C(O)c1cc(Cl)c(CO)c(C(F)(F)F)c1]

The title compound was synthesized from methyl 3-chloro-4-(hydroxymethyl)-5-(trifluoromethyl)benzoate (Compound dd7) under the same conditions as for Compound b8. However, methanol was used in place of ethanol as a solvent.

Example 420

Compound dd9

3-Chloro-N-[(5-chloro-2-ethylsulfonylphenyl) methyl]-4-(hydroxymethyl)-5-(trifluoromethyl)benzamide

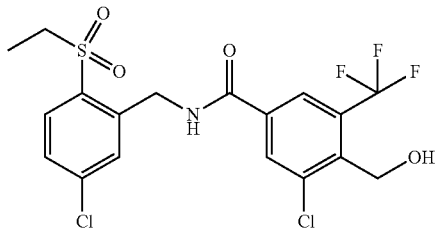 [SMILES: CCS(=O)(=O)c1ccc(Cl)cc1CNC(=O)c1cc(Cl)c(CO)c(C(F)(F)F)c1]

The title compound was synthesized from 5-chloro-2-ethanesulfonyl-benzylamine hydrochloride (Compound a3) under the same conditions as for Compound A-21. However, 3-chloro-4-(hydroxymethyl)-5-(trifluoromethyl)benzoic acid (Compound dd8) was used in place of 3-(trifluoromethyl)benzoic acid as a carboxylic acid.

Example 421

Compound dd10

[2-Chloro-4-[(5-chloro-2-ethylsulfonylphenyl)methylcarbamoyl]-6-(trifluoromethyl)phenyl]methyl methanesulfonate

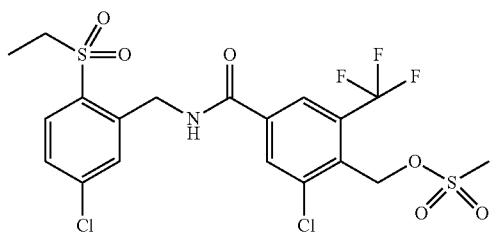 [SMILES: CCS(=O)(=O)c1ccc(Cl)cc1CNC(=O)c1cc(Cl)c(COS(C)(=O)=O)c(C(F)(F)F)c1]

Methanesulfonyl chloride (0.082 ml, 1.06 mmol) was added to a solution of 3-chloro-N-[(5-chloro-2-ethylsulfonylphenyl)methyl]-4-(hydroxymethyl)-5-(trifluoromethyl) benzamide (Compound dd9, 383 mg, 0.814 mmol) and triethylamine (0.340 ml, 2.44 mmol) in DCM (4 ml) while cooling to 0° C. in an ice water bath, and it was stirred at the same temperature for one hour. Water was added to the reaction mixture, followed by extraction with ethyl acetate. The organic layer was washed with a saturated aqueous solution of sodium chloride, and then dried over anhydrous sodium sulfate. The drying agent was removed by filtration, followed by concentration under reduced pressure. The resultant residue was purified by silica gel column chromatography (ethyl acetate/n-hexane) to yield the title compound (305 mg, 68%) as a colorless solid.

LCMS: m/z 548 [M+H]$^+$

HPLC retention time: 0.80 min (analysis condition F)

Example 422

Compound dd11 tert-Butyl N-[(3S)-1-[[2-chloro-4-[(5-chloro-2-ethylsulfonylphenyl)methylcarbamoyl]-6-(trifluoromethyl)phenyl]methyl]piperidin-3-yl]-N-ethylcarbamate

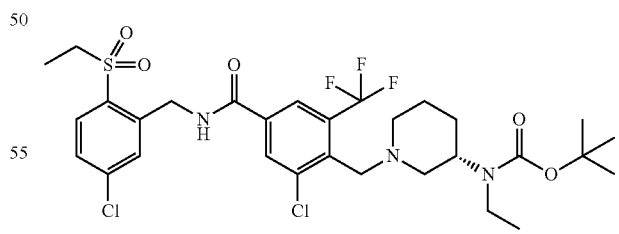

tert-Butyl N-ethyl-N-[(3S)-piperidin-3-yl]carbamate (37.5 mg, 0.164 mmol) was added to a solution of [2-chloro-4-[(5-chloro-2-ethylsulfonylphenyl)methylcarbamoyl]-6-(trifluoromethyl)phenyl]methyl methanesulfonate (Compound dd10, 30.0 mg, 0.055 mmol) in DMF (0.5 ml), and it was stirred at 50° C. for one hour. tert-Butyl N-ethyl-N-[(3S)-piperidin-3-yl]carbamate (6.0 mg, 0.0263 mmol) was further added to the reaction mixture, and it was stirred at the same temperature for one hour. Then, tert-butyl N-ethyl-N-[(3S)-piperidin-3-yl]carbamate (6.0 mg, 0.0263 mmol) was further added, and it was stirred at the same temperature for one hour. The reaction mixture was cooled to room temperature and then water was added, followed by extraction with ethyl acetate. The organic layer was washed with a saturated aqueous solution of sodium chloride, and then dried over anhydrous sodium sulfate. The drying agent was removed by filtration, followed by concentration under reduced pressure. The resultant residue was purified by silica gel column chromatography (ethyl acetate/n-hexane) to yield the title compound (39.0 mg, quant.) as a colorless solid.

LCMS: m/z 680 [M+H]$^+$
HPLC retention time: 0.83 min (analysis condition F)

Example 423

Compound DD-31

3-Chloro-N-[(5-chloro-2-ethylsulfonylphenyl)methyl]-4-[[(3S)-3-(ethyl amino)piperidin-1-yl]methyl]-5-(trifluoromethyl)benzamide

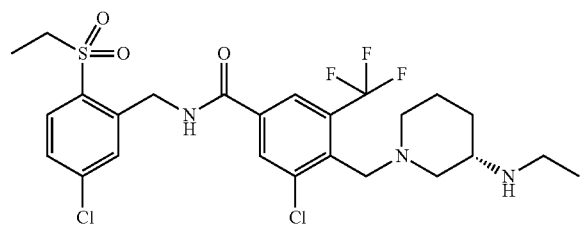 [SMILES: CCN[C@H]1CCCN(Cc2c(Cl)cc(C(=O)NCc3cc(Cl)ccc3S(=O)(=O)CC)cc2C(F)(F)F)C1]

The title compound was synthesized from tert-butyl N-[(3S)-1-[[2-chloro-4-[(5-chloro-2-ethylsulfonylphenyl)methylcarbamoyl]-6-(trifluoromethyl)phenyl]methyl]piperidin-3-yl]-N-ethylcarbamate (Compound dd11) under the same conditions as for Compound B-1.

LCMS: m/z 580 [M+H]$^+$
HPLC retention time: 0.58 min (analysis condition F)

Example 424

Compound DD-32

3-Chloro-N-[(5-chloro-2-ethylsulfonylphenyl)methyl]-4-(3, 6-diazabicyclo[3.1.1]heptan-3-ylmethyl)-5-(trifluoromethyl)benzamide

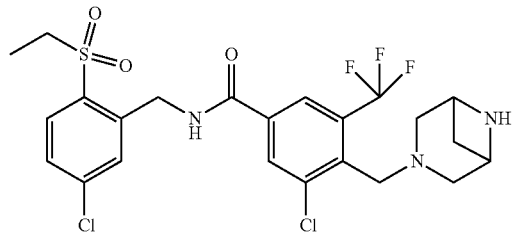 [SMILES: CCS(=O)(=O)c1ccc(Cl)cc1CNC(=O)c1cc(Cl)c(CN2CC3CC(C2)N3)c(C(F)(F)F)c1]

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compounds dd11 and DD-31. However, the reaction was performed using tert-butyl 3,6-diazabicyclo[3.1.1]heptane-6-carboxylate in place of tert-butyl N-ethyl-N-[(3S)-piperidin-3-yl]carbamate and triethylamine was added under the conditions for Compound dd11.

LCMS: m/z 550 [M+H]$^+$
HPLC retention time: 0.55 min (analysis condition F)

Example 425

Compound DD-33

N-[(3S)-1-[[2-Chloro-4-[(5-chloro-2-ethylsulfonylphenyl)methylcarbamoyl]-6-(trifluoromethyl)phenyl]methyl]piperidin-3-yl]pyridine-2-carboxamide

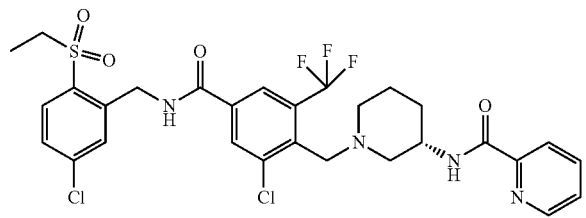 [SMILES: CCS(=O)(=O)c1ccc(Cl)cc1CNC(=O)c1cc(Cl)c(CN2CCC[C@H](NC(=O)c3ccccn3)C2)c(C(F)(F)F)c1]

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, the reaction was performed using N-[(3S)-piperidin-3-yl]pyridine-2-carboxamide dihydrochloride in place of tert-butyl N-ethyl-N-[(3S)-piperidin-3-yl]carbamate and potassium carbonate was added.

LCMS: m/z 657 [M+H]$^+$
HPLC retention time: 0.76 min (analysis condition F)

Examples 426, 432 and 436 to 437

The compounds of FIG. 19 were synthesized using [2-chloro-4-[(5-chloro-2-ethylsulfonylphenyl)methylcarbamoyl]-6-(trifluoromethyl)phenyl]methyl methanesulfonate (Compound dd10) and corresponding amines under the same conditions as for Compounds dd11 and DD-31.

Example 427

Compound dd12 tert-Butyl N-[[(2R)-1-[[2-chloro-4-[(5-chloro-2-ethylsulfonylphenyl)methylcarbamoyl]-6-(trifluoromethyl)phenyl]methyl]piperidin-2-yl]methyl]carbamate

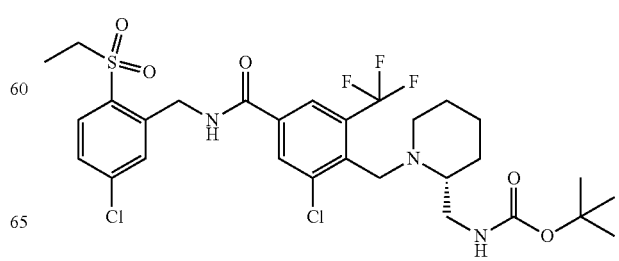

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound b7. However, tert-butyl N-[[(2R)-piperidin-2-yl]methyl]carbamate was used in place of tert-butyl N-[(3R)-pyrrolidin-3-yl]carbamate, and DIPEA was used in place of TEA.

Example 428

Compound DD-35

4-[[(2R)-2-(Aminomethyl)piperidin-1-yl]methyl]-3-chloro-N-[(5-chloro-2-ethylsulfonylphenyl)methyl]-5-(trifluoromethyl)benzamide

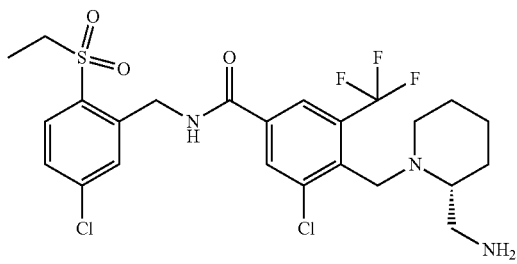 [SMILES: CCS(=O)(=O)c1ccc(Cl)cc1CNC(=O)c1cc(Cl)c(CN2CCCC[C@@H]2CN)c(C(F)(F)F)c1]

The title compound was synthesized from tert-butyl N-[[(2R)-1-[[2-chloro-4-[(5-chloro-2-ethylsulfonylphenyl)methylcarbamoyl]-6-(trifluoromethyl)phenyl]methyl]piperidin-2-yl]methyl]carbamate (Compound dd12) under the same conditions as for Compound B-1.

LCMS: m/z 566 [M+H]$^+$
HPLC retention time: 0.55 min (analysis condition A)

Example 429

Compound dd13 tert-Butyl N-[3-[[(2R)-1-[[2-chloro-4-[(5-chloro-2-ethylsulfonylphenyl)methylcarbamoyl]-6-(trifluoromethyl)phenyl]methyl]piperidin-2-yl]methylamino]-3-oxopropyl]carbamate

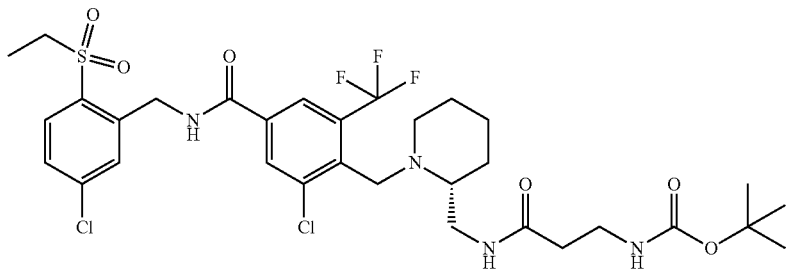 [SMILES: CCS(=O)(=O)c1ccc(Cl)cc1CNC(=O)c1cc(Cl)c(CN2CCCC[C@@H]2CNC(=O)CCNC(=O)OC(C)(C)C)c(C(F)(F)F)c1]

The title compound was synthesized from 4-[[(2R)-2-(aminomethyl)piperidin-1-yl]methyl]-3-chloro-N-[(5-chloro-2-ethylsulfonylphenyl)methyl]-5-(trifluoromethyl)benzamide (Compound DD-35) under the same conditions as for Compound DD-1. However, 3-[(2-methylpropan-2-yl)oxycarbonylamino]propanoic acid was used in place of 1H-pyrrole-2-carboxylic acid, and HATU was used in place of HBTU.

Example 430

Compound DD-36

4-[[(2R)-2-[(3-Aminopropanoylamino)methyl]piperidin-1-yl]methyl]-3-chloro-N-[(5-chloro-2-ethylsulfonylphenyl)methyl]-5-(trifluoromethyl)benzamide

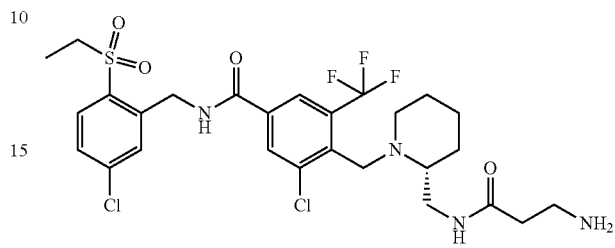

The title compound was synthesized from tert-butyl N-[3-[[(2R)-1-[[2-chloro-4-[(5-chloro-2-ethylsulfonylphenyl)methylcarbamoyl]-6-(trifluoromethyl)phenyl]methyl]piperidin-2-yl]methylamino]-3-oxopropyl]carbamate (Compound dd13) under the same conditions as for Compound B-1.

LCMS: m/z 637 [M+H]$^+$
HPLC retention time: 0.42 min (analysis condition F)

Example 431

Compound DD-37

3-Chloro-N-[(5-chloro-2-ethylsulfonylphenyl)methyl]-4-[[(2R)-2-(methylaminomethyl)piperidin-1-yl]methyl]-5-(trifluoromethyl)benzamide

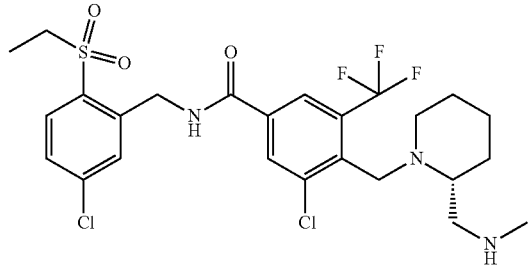 [SMILES: CCS(=O)(=O)c1ccc(Cl)cc1CNC(=O)c1cc(Cl)c(CN2CCCC[C@@H]2CNC)c(C(F)(F)F)c1]

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compounds dd12 and DD-35. However, under the Compound dd12 conditions, tert-butyl N-methyl-N-[[(2R)-piperidin-2-yl]methyl]carbamate was used in place of tert-butyl N-[[(2R)-piperidin-2-yl]methyl]carbamate.

LCMS: m/z 580 [M+H]+
HPLC retention time: 0.60 min (analysis condition F)

Example 433

Compound dd14

Benzyl N-[2-[(3S)-1-[[2-chloro-4-[(5-chloro-2-ethylsulfonylphenyl)methylcarbamoyl]-6-(trifluoromethyl)phenyl]methyl]piperidin-3-yl]oxyethyl]carbamate

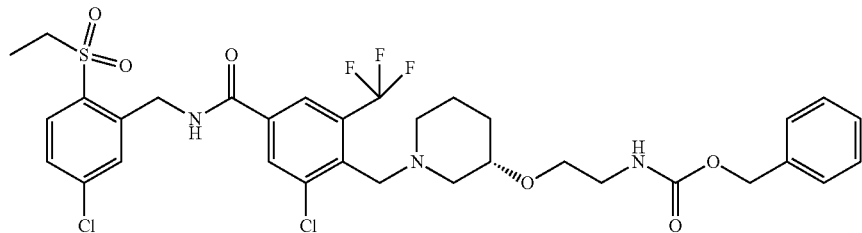 [SMILES: CCS(=O)(=O)c1ccc(Cl)cc1CNC(=O)c1cc(Cl)c(CN2CCC[C@H](OCCNC(=O)OCc3ccccc3)C2)c(C(F)(F)F)c1]

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, benzyl N-[2-[(3S)-piperidin-3-yl]oxyethyl]carbamate was used in place of tert-butyl N-ethyl-N-[(3S)-piperidin-3-yl]carbamate.

Example 434

Compound DD-39

4-[[(3S)-3-(2-Aminoethoxy)piperidin-1-yl]methyl]-3-chloro-N-[(5-chloro-2-ethylsulfonylphenyl)methyl]-5-(trifluoromethyl)benzamide

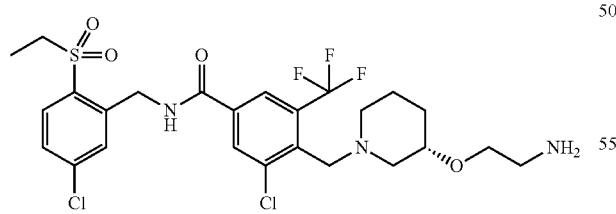

A 25% hydrogen bromide/acetic acid solution (1 ml) was added to benzyl N-[2-[(3S)-1-[[2-chloro-4-[(5-chloro-2-ethylsulfonylphenyl)methylcarbamoyl]-6-(trifluoromethyl)phenyl]methyl]piperidin-3-yl]oxyethyl]carbamate (Compound dd14, 23.0 mg, 0.0310 mmol); and it was stirred at room temperature for two hours. The reaction mixture was made basic by adding a 5N aqueous solution of sodium hydroxide, and the aqueous layer was then extracted three times with DCM. The combined organic layers were dried over anhydrous sodium sulfate. The drying agent was removed by filtration, and the solvent was then concentrated under reduced pressure. The resultant residue was purified by preparative HPLC (water/acetonitrile, 0.05% TFA) to yield the title compound (9.50 mg, 50%) as a colorless solid.

LCMS: m/z 596 [M+H]+
HPLC retention time: 0.41 min (analysis condition F)

Example 435

Compound DD-40

3-Chloro-N-[(5-chloro-2-ethylsulfonylphenyl)methyl]-4-[[(3S)-3-(2-hydroxyethoxy)piperidin-1-yl]methyl]-5-(trifluoromethyl)benzamide

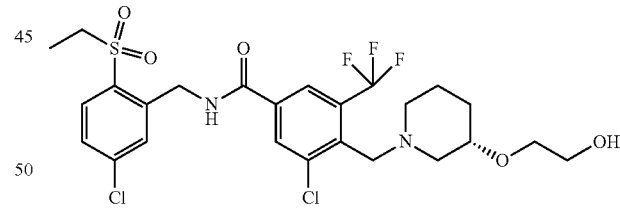

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, the reaction was performed using 2-[(3S)-piperidin-3-yl]oxyethanol in place of tert-butyl N-ethyl-N-[(3S)-piperidin-3-yl]carbamate, and potassium carbonate was added.

LCMS: m/z 597 [M+H]+
HPLC retention time: 0.51 min (analysis condition F)

Example 438

Compound dd15 tert-Butyl N-[3-[[(3S)-1-[[2-chloro-4-[(5-chloro-2-ethylsulfonylphenyl)methylcarbamoyl]-6-(trifluoromethyl)phenyl]methyl]piperidin-3-yl]amino]propyl]carbamate

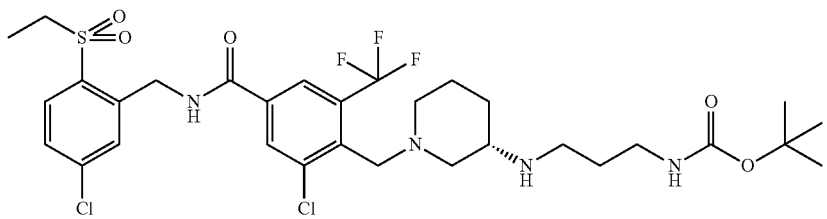 [SMILES: CCS(=O)(=O)c1ccc(Cl)cc1CNC(=O)c1cc(Cl)c(CN2CCC[C@H](NCCCNC(=O)OC(C)(C)C)C2)c(C(F)(F)F)c1]

The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compound H-5. However, tert-butyl (3-bromopropyl)carbamate was used in place of iodoethane.

Example 439

Compound DD-43

4-[[(3S)-3-(3-Aminopropylamino)piperidin-1-yl]methyl]-3-chloro-N-[(5-chloro-2-ethylsulfonylphenyl)methyl]-5-(trifluoromethyl)benzamide

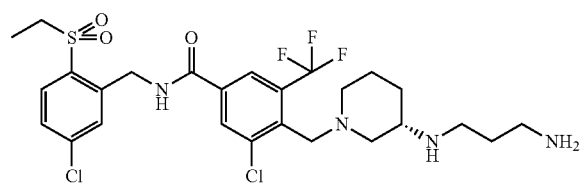 [SMILES: CCS(=O)(=O)c1ccc(Cl)cc1CNC(=O)c1cc(Cl)c(CN2CCC[C@H](NCCCN)C2)c(C(F)(F)F)c1]

The title compound was synthesized from tert-butyl N-[3-[[(3S)-1-[[2-chloro-4-[(5-chloro-2-ethylsulfonylphenyl)methylcarbamoyl]-6-(trifluoromethyl)phenyl]methyl]piperidin-3-yl]amino]propyl]carbamate (Compound dd15) under the same conditions as for Compound B-1.
LCMS: m/z 609 [M+H]+
HPLC retention time: 0.47 min (analysis condition F)

Example 440

Compound DD-44

3-Chloro-N-[(5-chloro-2-ethylsulfonylphenyl)methyl]-4-[[(3R)-3-(3-hydroxypropyl)piperidin-1-yl]methyl]-5-(trifluoromethyl)benzamide

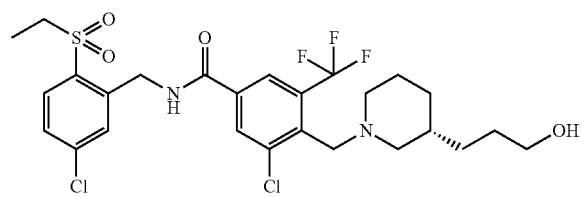 [SMILES: CCS(=O)(=O)c1ccc(Cl)cc1CNC(=O)c1cc(Cl)c(CN2CCC[C@H](CCCO)C2)c(C(F)(F)F)c1]

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, 3-[(3R)-piperidin-3-yl]propan-1-ol was used in place of tert-butyl N-ethyl-N-[(3S)-piperidin-3-yl]carbamate.
LCMS: m/z 595 [M+H]+
HPLC retention time: 0.53 min (analysis condition F)

Example 441

Compound DD-45

4-[(3-Aminopropylamino)methyl]-3-chloro-N-[(5-chloro-2-ethylsulfonylphenyl)methyl]-5-(trifluoromethyl)benzamide

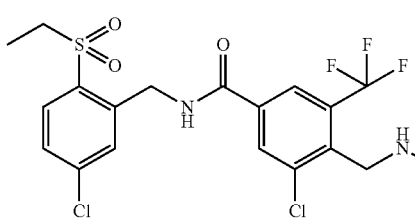

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, the reaction was performed at room temperature using 1,3-propanediamine in place of tert-butyl N-ethyl-N-[(3S)-piperidin-3-yl]carbamate.
LCMS: m/z 526 [M+H]+
HPLC retention time: 0.38 min (analysis condition F)

Example 442

Compound DD-46

3-Chloro-N-[(5-chloro-2-ethylsulfonylphenyl)methyl]-4-[(2-oxo-1,3-diazinan-1-yl)methyl]-5-(trifluoromethyl)benzamide

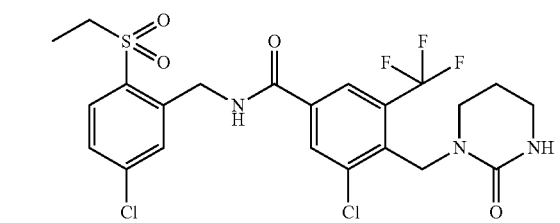 [SMILES: CCS(=O)(=O)c1ccc(Cl)cc1CNC(=O)c1cc(Cl)c(CN2CCCNC2=O)c(C(F)(F)F)c1]

A solution of 4-[(3-aminopropylamino)methyl]-3-chloro-N-[(5-chloro-2-ethylsulfonylphenyl)methyl]-5-(trifluoromethyl)benzamide (Compound DD-45, 15.0 mg, 28.0 μmol) and DIPEA (7.5 μl) in DCM (20 ml) was cooled to 0° C., a solution of 4-nitrophenyl chloroformate (5.90 mg, 29.0 μmol) in DCM (8 ml) was added, and the mixture was stirred for one hour. DIPEA (7.5 μl) was added, and the mixture was stirred at 0° C. for 1.5 hours, at room temperature for three hours and under reflux for one hour. The reaction mixture was cooled to 0° C., a solution of 4-nitrophenyl chloroformate (1.90 mg, 9.00 μmol) in DCM (1 ml) was added, and the mixture was stirred at room temperature for one hour. After adding DMF (20 ml) to the reaction mixture, DCM was removed by concentration under reduced pressure, DIPEA (7.5 μl) was added, and the mixture was stirred at room temperature for 45 minutes and at 60° C. for 40 minutes. The reaction mixture was cooled to room temperature and then concentrated under reduced pressure. The resultant residue was purified by preparative HPLC (water/acetonitrile, 0.05% TFA) to yield the title compound (9.50 mg, 60%) as a colorless foamy substance.

LCMS: m/z 552 [M+H]+

HPLC retention time: 0.71 min (analysis condition F)

Example 443

Compound DD-47

3-Chloro-N-[(5-chloro-2-ethylsulfonylphenyl)methyl]-4-[[3-[3-(dimethylamino)propylamino]propylamino]methyl]-5-(trifluoromethyl)benzamide

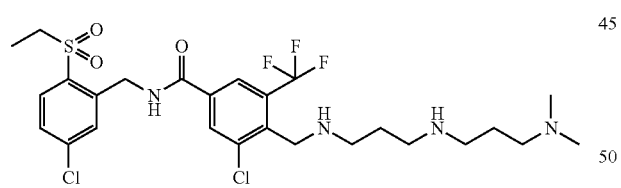

The title compound was synthesized from [2-chloro-4-[(5-chloro-2-ethylsulfonylphenyl)methylcarbamoyl]-6-(trifluoromethyl)phenyl]methyl methanesulfonate (Compound dd10) under the same conditions as for Compound dd11. However, the reaction was performed using N'-(3-aminopropyl)-N,N-dimethyl-1,3-propanediamine in place of tert-butyl N-ethyl-N-[(3S)-piperidin-3-yl]carbamate and at room temperature.

LCMS: m/z 611 [M+H]+

HPLC retention time: 0.34 min (analysis condition F)

Example 444

Compound DD-48

3-Chloro-N-[(5-chloro-2-ethylsulfonylphenyl)methyl]-4-[[3-[3-(dimethyl amino)propyl]-2-oxo-1,3-diazinan-1-yl]methyl]-5-(trifluoromethyl)benzamide

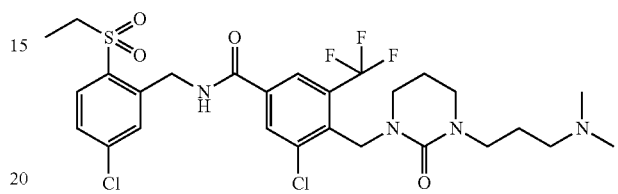

The title compound was synthesized from 3-chloro-N-[(5-chloro-2-ethylsulfonylphenyl)methyl]-4-[[3-[3-(dimethylamino)propylamino]propylamino]methyl]-5-(trifluoromethyl)benzamide (Compound DD-47) under the same conditions as for Compound DD-46.

LCMS: m/z 637 [M+H]+

HPLC retention time: 0.57 min (analysis condition F)

Example 445

Compound dd16

4-(Bromomethyl)-3-chloro-N-[(5-chloro-2-ethylsulfonylphenyl)methyl]-5-(trifluoromethyl)benzamide

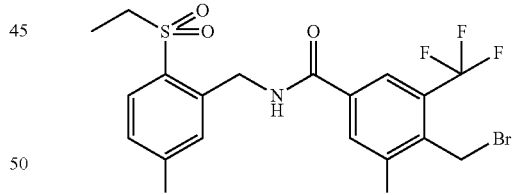

Triphenylphosphine (138 mg, 0.526 mmol) was added to a solution of 3-chloro-N-[(5-chloro-2-ethylsulfonylphenyl)methyl]-4-(hydroxymethyl)-5-(trifluoromethyl)benzamide (Compound dd9, 165 mg, 0.351 mmol) and carbon tetrabromide (175 mg, 0.526 mmol) in THF (2 ml), and the mixture was stirred at room temperature for two hours. The reaction mixture was concentrated under reduced pressure, and the resultant residue was purified by silica gel column chromatography (ethyl acetate/n-hexane) to yield the title compound (152 mg, 81%) as a colorless solid.

LCMS: m/z 532 [M+H]+

HPLC retention time: 0.95 min (analysis condition F)

Example 446

Compound dd17 tert-Butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]sulfamoyl]ethyl]carbamate

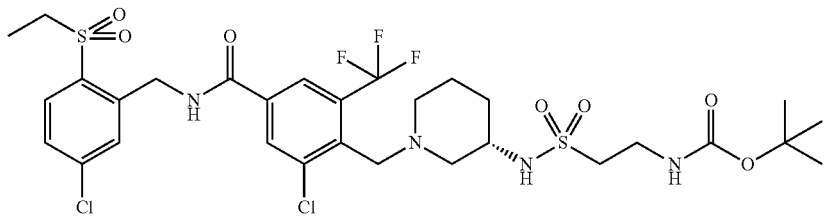 [SMILES: CCS(=O)(=O)c1ccc(Cl)cc1CNC(=O)c1cc(Cl)c(CN2CCC[C@H](NS(=O)(=O)CCNC(=O)OC(C)(C)C)C2)c(C(F)(F)F)c1]

tert-Butyl N-[2-[[(3S)-piperidin-3-yl]sulfamoyl]ethyl]carbamate (25.9 mg, 84.0 μmol) was added to a solution of 4-(bromomethyl)-3-chloro-N-[(5-chloro-2-ethylsulfonylphenyl)methyl]-5-(trifluoromethyl)benzamide (Compound dd16, 30.0 mg, 56.0 μmol) and potassium carbonate (23.3 mg, 0.169 mmol) in DMF (0.5 ml), and the mixture was stirred at 50° C. for two hours. The reaction mixture was cooled to room temperature and then water was added, followed by extraction with ethyl acetate. The organic layer was washed with a saturated aqueous sodium chloride solution and then dried over anhydrous sodium sulfate. The drying agent was removed by filtration, followed by concentration under reduced pressure. The resultant residue was purified by silica gel column chromatography (ethyl acetate/n-hexane) to yield the title compound (39.0 mg, 91%) as a colorless solid.

LCMS: m/z 759 [M+H]$^+$

HPLC retention time: 0.78 min (analysis condition F)

Example 447

Compound DD-49

4-[[(3S)-3-(2-Aminoethylsulfonylamino)piperidin-1-yl]methyl]-3-chloro-N-[(5-chloro-2-ethylsulfonylphenyl)methyl]-5-(trifluoromethyl)benzamide

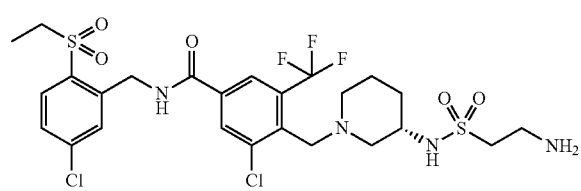 [SMILES: CCS(=O)(=O)c1ccc(Cl)cc1CNC(=O)c1cc(Cl)c(CN2CCC[C@H](NS(=O)(=O)CCN)C2)c(C(F)(F)F)c1]

The title compound was synthesized from tert-butyl N-[2-[[(3S)-1-[[2-chloro-4-[(5-chloro-2-ethylsulfonylphenyl)methylcarbamoyl]-6-(trifluoromethyl)phenyl]methyl]piperidin-3-yl]sulfamoyl]ethyl]carbamate (Compound dd17) under the same conditions as for Compound B-1.

LCMS: m/z 661 [M+H]$^+$

HPLC retention time: 0.49 min (analysis condition F)

Example 448

Compound DD-50

3-Chloro-N-[(5-chloro-2-ethylsulfonylphenyl)methyl]-4-[[(3S)-3-[2-dimethylamino)ethylsulfonylamino]piperidin-1-yl]methyl]-5-(trifluoromethyl)benzamide

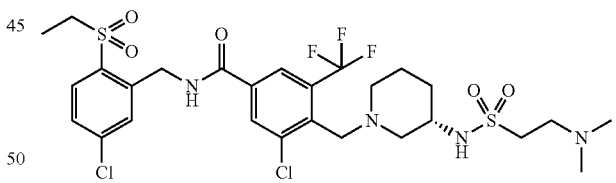

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound dd17. However, 2-(dimethylamino)-N-[(3S)-piperidin-3-yl]ethanesulfonamide was used in place of tert-butyl N-[2-[[(3S)-piperidin-3-yl]sulfamoyl]ethyl]carbamate.

LCMS: m/z 687 [M+H]$^+$

HPLC retention time: 0.50 min (analysis condition F)

Example 449

Compound dd18

Benzyl N-[2-[(3R)-1-[[2-chloro-4-[(5-chloro-2-ethylsulfonylphenyl)methylcarbamoyl]-6-(trifluoromethyl)phenyl]methyl]piperidin-3-yl]ethyl]carbamate

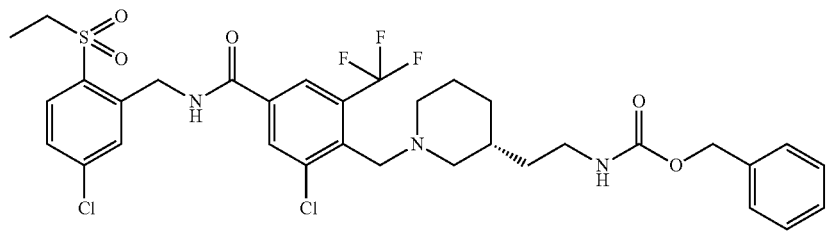 [SMILES: CCS(=O)(=O)c1ccc(Cl)cc1CNC(=O)c1cc(Cl)c(CN2CCC[C@H](CCNC(=O)OCc3ccccc3)C2)c(C(F)(F)F)c1]

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound dd17. However, benzyl N-[2-[(3R)-piperidin-3-yl]ethyl]carbamate was used in place of tert-butyl N-[2-[[(3S)-piperidin-3-yl]sulfamoyl]ethyl]carbamate.

Example 450

Compound DD-51

4-[[(3R)-3-(2-Aminoethyl)piperidin-1-yl]methyl]-3-chloro-N-[(5-chloro-2-ethylsulfonylphenyl)methyl]-5-(trifluoromethyl)benzamide

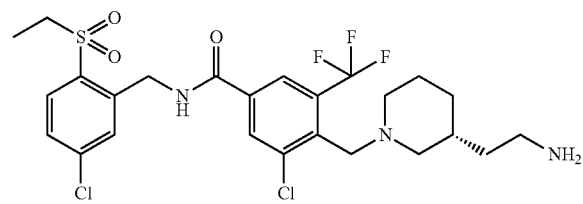 [SMILES: CCS(=O)(=O)c1ccc(Cl)cc1CNC(=O)c1cc(Cl)c(CN2CCC[C@H](CCN)C2)c(C(F)(F)F)c1]

The title compound was synthesized from benzyl N-[2-[(3R)-1-[[2-chloro-4-[(5-chloro-2-ethylsulfonylphenyl)methylcarbamoyl]-6-(trifluoromethyl)phenyl]methyl]piperidin-3-yl]ethyl]carbamate (Compound dd18) under the same conditions as for Compound DD-39.

LCMS: m/z 580 [M+H]$^+$

HPLC retention time: 0.42 min (analysis condition F)

Example 451

Compound dd19 tert-Butyl 5-[[2-chloro-4-[(5-chloro-2-ethylsulfonylphenyl)methylcarbamoyl]-6-(trifluoromethyl)phenyl]methyl]-1,2,5-oxadiazepane-2-carboxylate

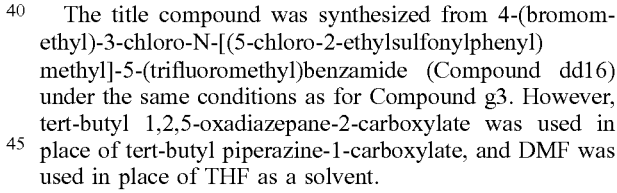

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound g3. However, tert-butyl 1,2,5-oxadiazepane-2-carboxylate was used in place of tert-butyl piperazine-1-carboxylate, and DMF was used in place of THF as a solvent.

Example 452

Compound DD-52

3-Chloro-N-[(5-chloro-2-ethylsulfonylphenyl)methyl]-4-(1,2,5-oxadiazepan-5-ylmethyl)-5-(trifluoromethyl)benzamide

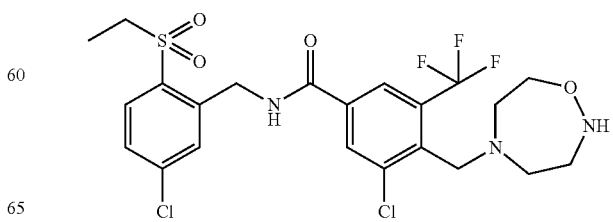

The title compound was synthesized from tert-butyl 5-[[2-chloro-4-[(5-chloro-2-ethylsulfonylphenyl)methylcarbamoyl]-6-(trifluoromethyl)phenyl]methyl]-1,2,5-oxadiazepane-2-carboxylate (Compound dd19) under the same conditions as for Compound B-1.
LCMS: m/z 554 [M+H]$^+$
HPLC retention time: 0.58 min (analysis condition F)

Example 453

Compound dd20 tert-Butyl (2S)-5-[[2-chloro-4-[(5-chloro-2-ethylsulfonylphenyl)methylcarbamoyl]-6-(trifluoromethyl)phenyl]methyl amino]-2-[(2-methylpropan-2-yl)oxycarbonylamino]pentanoate

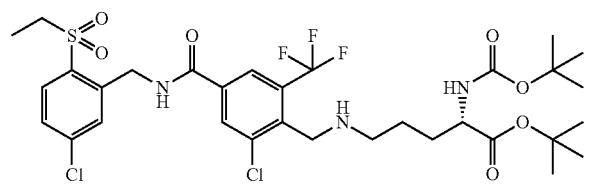 [SMILES: CCS(=O)(=O)c1ccc(Cl)cc1CNC(=O)c1cc(Cl)c(CNCCC[C@H](NC(=O)OC(C)(C)C)C(=O)OC(C)(C)C)c(C(F)(F)F)c1]

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound g3. However, the reaction was performed using tert-butyl (2S)-5-amino-2-[(2-methylpropan-2-yl)oxycarbonylamino]pentanoate in place of tert-butyl piperazine-1-carboxylate and DMF in place of THF as a solvent.

Example 454

Compound DD-53

4-[[(3S)-3-Amino-2-oxopiperidin-1-yl]methyl]-3-chloro-N-[(5-chloro-2-ethylsulfonylphenyl)methyl]-5-(trifluoromethyl)benzamide

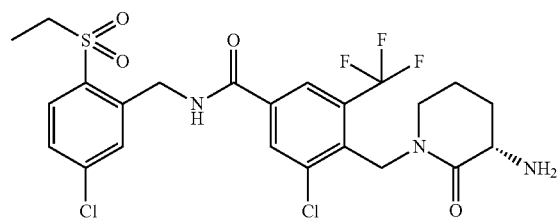 [SMILES: CCS(=O)(=O)c1ccc(Cl)cc1CNC(=O)c1cc(Cl)c(CN2CCC[C@H](N)C2=O)c(C(F)(F)F)c1]

A 36% aqueous hydrochloric acid solution (149 μl) was added to a solution of tert-butyl (2S)-5-[[2-chloro-4-[(5-chloro-2-ethylsulfonylphenyl)methylcarbamoyl]-6-(trifluoromethyl)phenyl]methylamino]-2-[(2-methylpropan-2-yl)oxycarbonylamino]pentanoate (Compound dd20, 29.8 mg, 40.0 μmol) in 2,2,2-trifluoroethanol (750 μl); and it was stirred at room temperature for one hour. The reaction mixture was diluted with 2,2,2-trifluoroethanol (2 ml) and toluene (5 ml), and then concentrated under reduced pressure. The resultant residue was dried by azeotropic distillation with toluene (5 ml×2) to yield a crude product of (S)-2-amino-5-((2-chloro-4-((5-chloro-2-(ethylsulfonyl)benzyl)carbamoyl)-6-(trifluoromethyl)benzyl)amino)pentanoic acid dihydrochloride (32.8 mg) as a pale yellow solid.
LCMS: m/z 584 [M+H]$^+$
HPLC retention time: 0.43 min (analysis condition F)

(Benzotriazol-1-yloxy)tris(dimethylamino)phosphonium hexafluorophosphate (35.7 mg, 0.080 mmol) and DIPEA (35 μl) were sequentially added to a solution of the crude product of (S)-2-amino-5-((2-chloro-4-((5-chloro-2-(ethylsulfonyl)benzyl)carbamoyl)-6-(trifluoromethyl)benzyl)amino)pentanoic acid dihydrochloride obtained above (32.8 mg) in DMF (2 ml); and it was stirred at room temperature for 30 minutes. Water (100 μl) was added to the reaction solution, and the solvent was then concentrated under reduced pressure. The resultant residue was purified by preparative HPLC (water/acetonitrile, 0.05% TFA) and amino silica gel column chromatography (MeOH/DCM) to yield the title compound (9.9 mg, 44%) as a colorless solid.
LCMS: m/z 566 [M+H]$^+$
HPLC retention time: 0.52 min (analysis condition F)

Example 455

Compound dd21 tert-Butyl N-[2-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]ethyl]carbamate

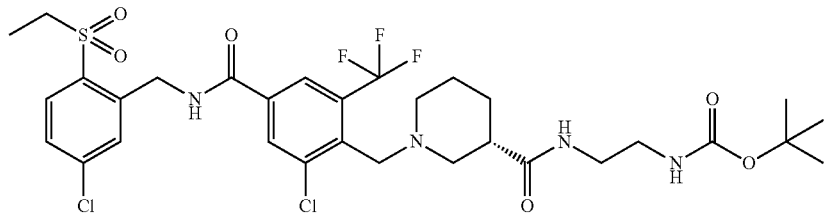 [SMILES: CCS(=O)(=O)c1ccc(Cl)cc1CNC(=O)c1cc(Cl)c(CN2CCC[C@H](C(=O)NCCNC(=O)OC(C)(C)C)C2)c(C(F)(F)F)c1]

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound dd17. However, tert-butyl N-[2-[[(3S)-piperidine-3-carbonyl]amino]ethyl]carbamate was used in place of tert-butyl N-[2-[[(3S)-piperidin-3-yl]sulfamoyl]ethyl]carbamate.

Example 456

Compound DD-54

(3S)—N-(2-Aminoethyl)-1-[[2-chloro-4-[(5-chloro-2-ethylsulfonylphenyl)methylcarbamoyl]-6-(trifluoromethyl)phenyl]methyl]piperidine-3-carboxamide

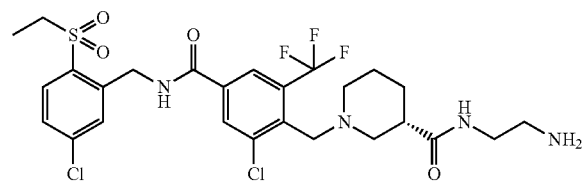 [SMILES: CCS(=O)(=O)c1ccc(Cl)cc1CNC(=O)c1cc(Cl)c(CN2CCC[C@H](C(=O)NCCN)C2)c(C(F)(F)F)c1]

The title compound was synthesized from tert-butyl N-[2-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]ethyl]carbamate (Compound dd21) under the same conditions as for Compound B-1.

LCMS: m/z 623 [M+H]$^+$

HPLC retention time: 0.41 min (analysis condition F)

Example 457

Compound dd22

3-Chloro-4-formyl-5-(trifluoromethyl)benzoic acid

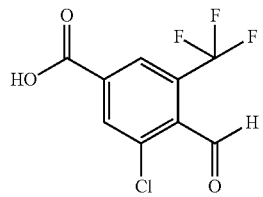 [SMILES: O=Cc1c(Cl)cc(C(=O)O)cc1C(F)(F)F]

The title compound was synthesized from ethyl 3-chloro-4-formyl-5-(trifluoromethyl)benzoate (Compound d7) under the same conditions as for Compound b8. However, a 5N aqueous sodium hydroxide solution was used in place of a 1N aqueous sodium hydroxide solution.

Example 458

Compound dd23

3-Chloro-N-[(5-chloro-2-ethylsulfonylphenyl)methyl]-4-formyl-5-(trifluoromethyl)benzamide

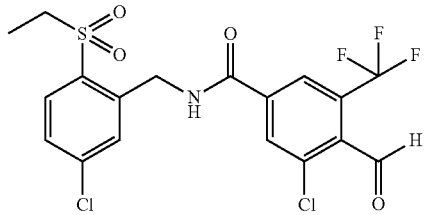 [SMILES: CCS(=O)(=O)c1ccc(Cl)cc1CNC(=O)c1cc(Cl)c(C=O)c(C(F)(F)F)c1]

The title compound was synthesized from 5-chloro-2-ethanesulfonyl-benzylamine hydrochloride (Compound a3) under the same conditions as for Compound bb10. However, the reaction was performed using 3-chloro-4-formyl-5-(trifluoromethyl)benzoic acid (Compound dd22) in place of 4-[[4-[(2-methylpropan-2-yl)oxycarbonyl]piperazin-1-yl]methyl]-3-(trifluoromethyl)benzoic acid (Compound b3) as a carboxylic acid, and acetonitrile in place of DMF as a solvent.

Example 459

Compound dd24 tert-Butyl N-[(3S)-1-[[2-chloro-4-[(5-chloro-2-ethylsulfonylphenyl)methylcarbamoyl]-6-(trifluoromethyl)phenyl]methyl]pyrrolidin-3-yl]carbamate

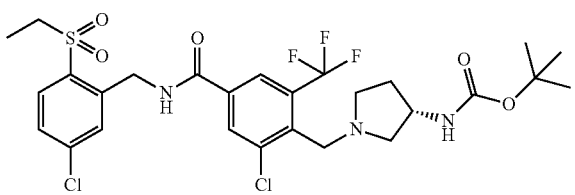 [SMILES: CCS(=O)(=O)c1ccc(Cl)cc1CNC(=O)c1cc(Cl)c(CN2CC[C@H](NC(=O)OC(C)(C)C)C2)c(C(F)(F)F)c1]

The title compound was synthesized from 3-chloro-N-[(5-chloro-2-ethylsulfonylphenyl)methyl]-4-formyl-5-(trifluoromethyl)benzamide (Compound dd23) under the same conditions as for Compound b32. However, tert-butyl N-[(3S)-pyrrolidin-3-yl]carbamate was used in place of tert-butyl N-[[(2S)-pyrrolidin-2-yl]methyl]carbamate, and chloroform was used in place of THF as a solvent. The reaction was performed at a reaction temperature of 0° C.

Example 460

Compound DD-55

4-[[(3S)-3-Aminopyrrolidin-1-yl]methyl]-3-chloro-N-[(5-chloro-2-ethylsulfonylphenyl)methyl]-5-(trifluoromethyl)benzamide

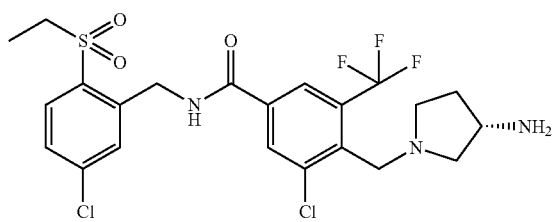 [SMILES: CCS(=O)(=O)c1ccc(Cl)cc1CNC(=O)c1cc(Cl)c(CN2CC[C@H](N)C2)c(C(F)(F)F)c1]

The title compound was synthesized from tert-butyl N-[(3S)-1-[[2-chloro-4-[(5-chloro-2-ethylsulfonylphenyl)methylcarbamoyl]-6-(trifluoromethyl)phenyl]methyl]pyrrolidin-3-yl]carbamate (Compound dd24) under the same conditions as for Compound B-57.

LCMS: m/z 538 [M+H]$^+$

HPLC retention time: 0.49 min (analysis condition F)

Example 461

Compound DD-56

4-[[(3R)-3-(Aminomethyl)piperidin-1-yl]methyl]-3-chloro-N-[(5-chloro-2-ethylsulfonylphenyl)methyl]-5-(trifluoromethyl)benzamide

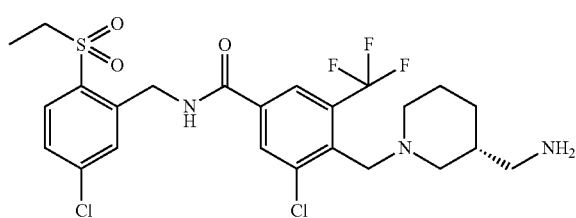 [SMILES: CCS(=O)(=O)c1ccc(Cl)cc1CNC(=O)c1cc(Cl)c(CN2CCC[C@H](CN)C2)c(C(F)(F)F)c1]

The title compound was synthesized from 3-chloro-N-[(5-chloro-2-ethylsulfonylphenyl)methyl]-4-formyl-5-(trifluoromethyl)benzamide (Compound dd23) under the same conditions as for Compounds dd24 and DD-55. However, under the Compound dd24 conditions, tert-butyl N-[[(3S)-piperidin-3-yl]methyl]carbamate was used in place of tert-butyl N-[(3S)-pyrrolidin-3-yl]carbamate.

LCMS: m/z 566 [M+H]$^+$

HPLC retention time: 0.42 min (analysis condition F)

Example 462

Compound dd25

Ethyl 3-chloro-4-[[3-[(2-methylpropan-2-yl)oxycarbonylamino]azetidin-1-yl]methyl]-5-(trifluoromethyl)benzoate

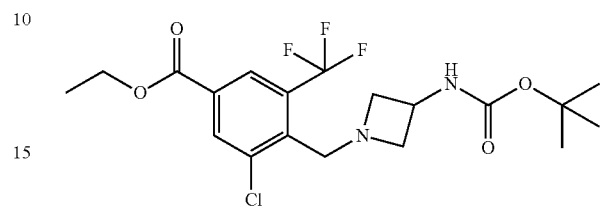

The title compound was synthesized from ethyl 3-chloro-4-formyl-5-(trifluoromethyl)benzoate (Compound d7) under the same conditions as for Compound b32. However, tert-butyl N-(azetidin-3-yl)carbamate was used in place of tert-butyl N-[[(2S)-pyrrolidin-2-yl]methyl]carbamate, and DCM was used in place of THF as a solvent.

Example 463

Compound dd26

3-Chloro-4-[[3-[(2-methylpropan-2-yl)oxycarbonylamino]azetidin-1-yl]methyl]-5-(trifluoromethyl)benzoic acid

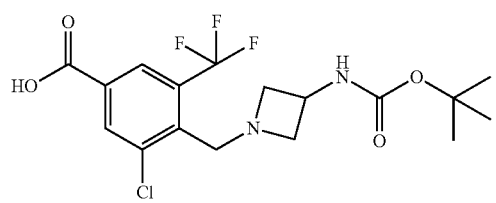 [SMILES: CC(C)(C)OC(=O)NC1CN(Cc2c(Cl)cc(C(=O)O)cc2C(F)(F)F)C1]

The title compound was synthesized from ethyl 3-chloro-4-[[3-[(2-methylpropan-2-yl)oxycarbonylamino]azetidin-1-yl]methyl]-5-(trifluoromethyl)benzoate (Compound dd25) under the same conditions as for Compound b8.

Example 464

Compound dd27 tert-Butyl N-[1-[[2-chloro-4-[(5-chloro-2-ethylsulfonylphenyl)methylcarbamoyl]-6-(trifluoromethyl)phenyl]methyl]azetidin-3-yl]carbamate

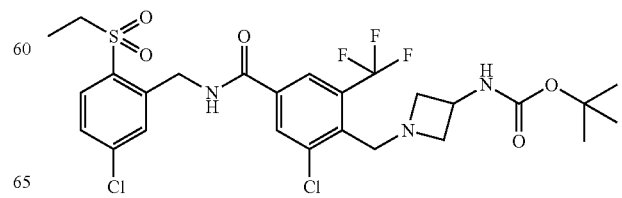

The title compound was synthesized from 5-chloro-2-ethanesulfonyl-benzylamine hydrochloride (Compound a3) under the same conditions as for Compound bb10. However, 3-chloro-4-[[3-[(2-methylpropan-2-yl)oxycarbonylamino]azetidin-1-yl]methyl]-5-(trifluoromethyl)benzoic acid (Compound dd26) was used in place of 4-[[4-[(2-methylpropan-2-yl)oxycarbonyl]piperazin-1-yl]methyl]-3-(trifluoromethyl)benzoic acid (Compound b3) as a carboxylic acid.

Example 465

Compound DD-57

4-[(3-Aminoazetidin-1-yl)methyl]-3-chloro-N-[(5-chloro-2-ethylsulfonylphenyl)methyl]-5-(trifluoromethyl)benzamide

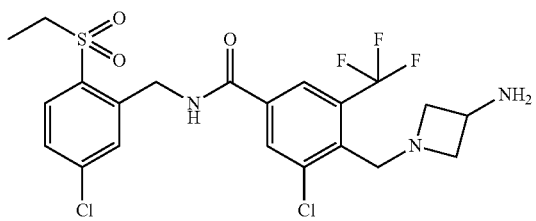 [SMILES: CCS(=O)(=O)c1ccc(Cl)cc1CNC(=O)c1cc(Cl)c(CN2CC(N)C2)c(C(F)(F)F)c1]

The title compound was synthesized from tert-butyl N-[1-[[2-chloro-4-[(5-chloro-2-ethylsulfonylphenyl)methylcarbamoyl]-6-(trifluoromethyl)phenyl]methyl]azetidin-3-yl]carbamate (Compound dd27) under the same conditions as for Compound B-57.
LCMS: m/z 524 [M+H]+
HPLC retention time: 1.10 min (analysis condition D)

Example 466

Compound DD-58

3-Chloro-N-[(5-chloro-2-ethylsulfonylphenyl)methyl]-4-[[3-(methylsulfamoylamino)azetidin-1-yl]methyl]-5-(trifluoromethyl)benzamide

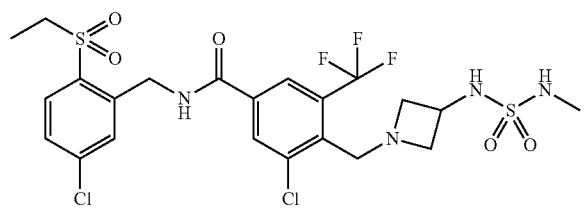 [SMILES: CCS(=O)(=O)c1ccc(Cl)cc1CNC(=O)c1cc(Cl)c(CN2CC(NS(=O)(=O)NC)C2)c(C(F)(F)F)c1]

TEA (23 µl, 0.166 mmol) was added to a solution of 4-[(3-aminoazetidin-1-yl)methyl]-3-chloro-N-[(5-chloro-2-ethylsulfonylphenyl)methyl]-5-(trifluoromethyl)benzamide (Compound DD-57, 28.9 mg, 0.0496 mmol) and N-methyl-2-oxo-1,3-oxazolidine-3-sulfonamide (15.3 mg, 0.0849 mmol) in acetonitrile (1 ml); and it was stirred at 65 to 80° C. for one hour. The reaction solution was cooled to room temperature, followed by addition of water and extraction with ethyl acetate. The organic layer was washed with brine and dried over anhydrous magnesium sulfate. The drying agent was removed by filtration, and the residue obtained by concentration under reduced pressure was purified by silica gel column chromatography (ethyl acetate/n-hexane) to yield the title compound (20.0 mg, 65%) as a colorless solid. However, N-methyl-2-oxo-1,3-oxazolidine-3-sulfonamide was synthesized by following the method described in the WO 2009080638 patent.
LCMS: m/z 617 [M+H]+
HPLC retention time: 1.48 min (analysis condition D)

Example 467

Compound DD-59

3-Chloro-N-[(5-chloro-2-ethylsulfonylphenyl)methyl]-4-[[3-(dimethylsulfamoylamino)azetidin-1-yl]methyl]-5-(trifluoromethyl)benzamide

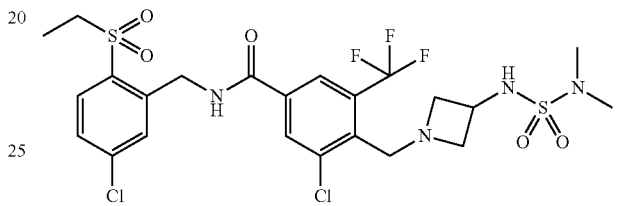

N,N-Dimethylsulfamoyl chloride (17.3 mg, 0.121 mmol) and TEA (34.0 µl, 0.241 mmol) were added to a solution of 4-[(3-aminoazetidin-1-yl)methyl]-3-chloro-N-[(5-chloro-2-ethylsulfonylphenyl)methyl]-5-(trifluoromethyl)benzamide (Compound DD-57, 39.7 mg, 0.0603 mmol) in DMF (0.5 ml) ice-cold; and it was warmed to room temperature and stirred for 2.5 hours under a nitrogen atmosphere. Water was added to the reaction mixture, followed by extraction with ethyl acetate. The organic layer was then washed with brine and dried over anhydrous magnesium sulfate. The drying agent was removed by filtration, and the residue obtained by concentration under reduced pressure was purified by silica gel column chromatography (ethyl acetate/n-hexane) to yield the title compound (22.6 mg, 59%) as a colorless solid.
LCMS: m/z 631 [M+H]+
HPLC retention time: 1.45 min (analysis condition D)

Example 468

Compound dd28 tert-Butyl N-[[1-[[2-chloro-4-[(5-chloro-2-ethylsulfonylphenyl)methylcarbamoyl]-6-(trifluoromethyl)phenyl]methyl]azetidin-3-yl]sulfamoyl]carbamate

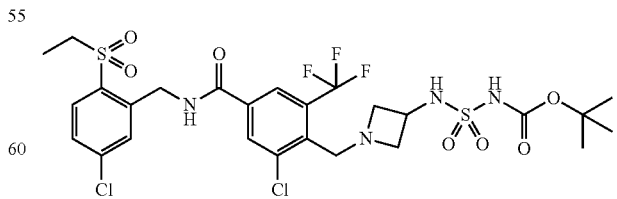

The title compound was synthesized from 4-[(3-aminoazetidin-1-yl)methyl]-3-chloro-N-[(5-chloro-2-ethylsulfonylphenyl)methyl]-5-(trifluoromethyl)benzamide (Compound DD-57) under the same conditions as for Compound

Example 469

Compound DD-60

3-Chloro-N-[(5-chloro-2-ethylsulfonylphenyl)methyl]-4-[[3-(sulfamoylamino)azetidin-1-yl]methyl]-5-(trifluoromethyl)benzamide

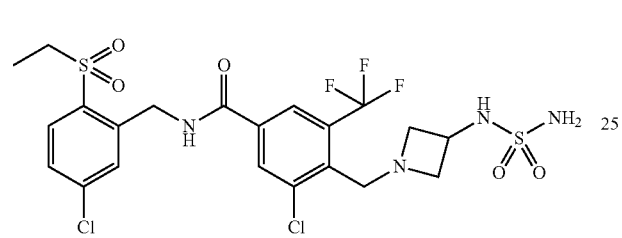

The title compound was synthesized from tert-butyl N-[[1-[[2-chloro-4-[(5-chloro-2-ethylsulfonylphenyl)methylcarbamoyl]-6-(trifluoromethyl)phenyl]methyl]azetidin-3-yl]sulfamoyl]carbamate (Compound dd28) under the same conditions as for Compound B-57.
LCMS: m/z 603 [M+H]+
HPLC retention time: 1.32 min (analysis condition D)

Example 470

Compound dd29

Ethyl 3-chloro-4-[[4-[(2-methylpropan-2-yl)oxycarbonylamino]piperidin-1-yl]methyl]-5-(trifluoromethyl)benzoate

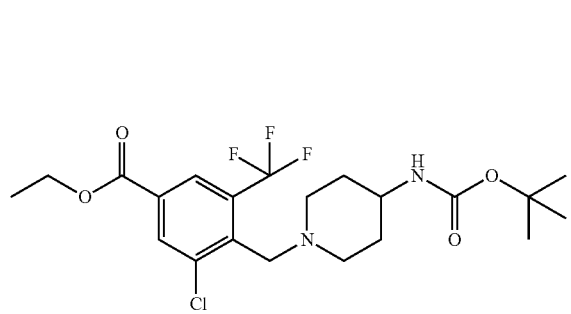 [SMILES: CCOC(=O)c1cc(Cl)c(CN2CCC(NC(=O)OC(C)(C)C)CC2)c(C(F)(F)F)c1]

The title compound was synthesized from ethyl 3-chloro-4-formyl-5-(trifluoromethyl)benzoate (Compound d7) under the same conditions as for Compound b32. However, tert-butyl N-piperidin-4-ylcarbamate was used in place of tert-butyl N-[[(2S)-pyrrolidin-2-yl]methyl]carbamate, and chloroform was used in place of THF as a solvent.

Example 471

Compound dd30

3-Chloro-4-[[4-[(2-methylpropan-2-yl)oxycarbonylamino]piperidin-1-yl]methyl]-5-(trifluoromethyl)benzoic acid

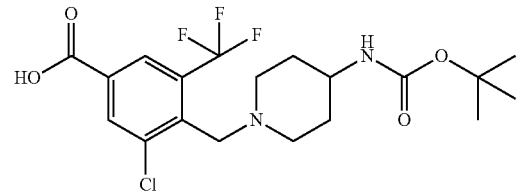 [SMILES: CC(C)(C)OC(=O)NC1CCN(Cc2c(Cl)cc(C(=O)O)cc2C(F)(F)F)CC1]

The title compound was synthesized from ethyl 3-chloro-4-[[4-[(2-methylpropan-2-yl)oxycarbonylamino]piperidin-1-yl]methyl]-5-(trifluoromethyl)benzoate (Compound dd29) under the same conditions as for Compound b8.

Example 472

Compound dd31 tert-Butyl N-[1-[[2-chloro-4-[(5-chloro-2-ethylsulfonylphenyl)methylcarbamoyl]-6-(trifluoromethyl)phenyl]methyl]piperidin-4-yl]carbamate

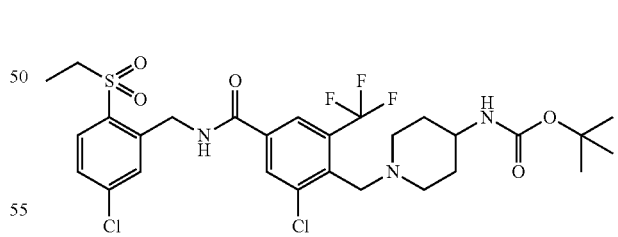

The title compound was synthesized from 5-chloro-2-ethanesulfonyl-benzylamine hydrochloride (Compound a3) under the same conditions as for Compound A-14. However, 3-chloro-4-[[4-[(2-methylpropan-2-yl)oxycarbonylamino]piperidin-1-yl]methyl]-5-(trifluoromethyl)benzoic acid (Compound dd30) was used in place of 4-bromo-3-(trifluoromethyl)benzoic acid as a carboxylic acid, and DCM was used in place of DMF as a solvent.

Example 473

Compound DD-61

4-[(4-Aminopiperidin-1-yl)methyl]-3-chloro-N-[(5-chloro-2-ethylsulfonylphenyl)methyl]-5-(trifluoromethyl)benzamide

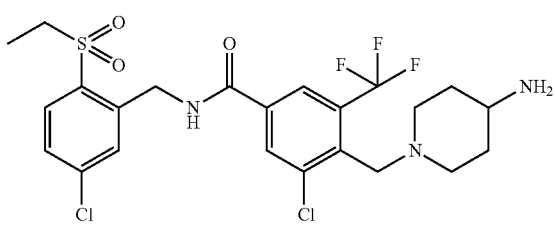 [SMILES: CCS(=O)(=O)c1ccc(Cl)cc1CNC(=O)c1cc(Cl)c(CN2CCC(N)CC2)c(C(F)(F)F)c1]

The title compound was synthesized from tert-butyl N-[1-[[2-chloro-4-[(5-chloro-2-ethylsulfonylphenyl)methylcarbamoyl]-6-(trifluoromethyl)phenyl]methyl]piperidin-4-yl]carbamate (Compound dd31) under the same conditions as for Compound B-57.

LCMS: m/z 552 [M+H]$^+$

HPLC retention time: 0.44 min (analysis condition F)

Example 474

Compound dd32 tert-Butyl N-[2-[4-[[2-chloro-4-[(5-chloro-2-ethylsulfonylphenyl)methylcarbamoyl]-6-(trifluoromethyl)phenyl]methyl]piperazin-1-yl]-2-oxoethyl]carbamate

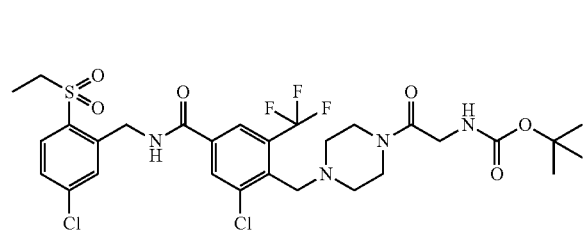 [SMILES: CCS(=O)(=O)c1ccc(Cl)cc1CNC(=O)c1cc(Cl)c(CN2CCN(C(=O)CNC(=O)OC(C)(C)C)CC2)c(C(F)(F)F)c1]

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compound DD-1. However, the reaction was performed using 2-[(2-methylpropan-2-yl)oxycarbonylamino]acetic acid in place of 1H-pyrrole-2-carboxylic acid and using HATU in place of HBTU.

Example 475

Compound DD-62

4-[[4-(2-Aminoacetyl)piperazin-1-yl]methyl]-3-chloro-N-[(5-chloro-2-ethylsulfonylphenyl)methyl]-5-(trifluoromethyl)benzamide

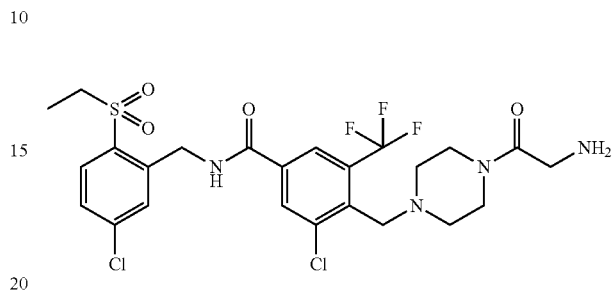

A 4N hydrochloric acid/1,4-dioxane solution (0.9 ml) was added to a solution of tert-butyl N-[2-[4-[[2-chloro-4-[(5-chloro-2-ethylsulfonylphenyl)methylcarbamoyl]-6-(trifluoromethyl)phenyl]methyl]piperazin-1-yl]-2-oxoethyl]carbamate (Compound dd32, 61 mg, 0.088 mmol) in DCM (0.9 ml), and it was stirred at room temperature for 30 minutes. The reaction mixture was concentrated under reduced pressure, and the resultant residue was purified by amino silica gel column chromatography (MeOH/DCM) to yield the title compound (35 mg, 67%) as a colorless solid.

LCMS: m/z 595 [M+H]$^+$

HPLC retention time: 0.53 min (analysis condition F)

Example 476

Compound DD-63

3-Chloro-N-[(5-chloro-2-ethylsulfonylphenyl)methyl]-4-[[4-(2-hydroxyacetyl)piperazin-1-yl]methyl]-5-(trifluoromethyl)benzamide

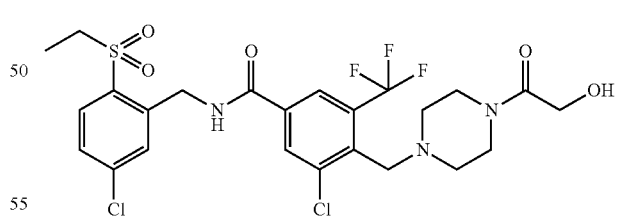

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compound DD-1. However, the reaction was performed using 2-hydroxyacetic acid in place of 1H-pyrrole-2-carboxylic acid and using HATU in place of HBTU.

LCMS: m/z 596 [M+H]$^+$

HPLC retention time: 0.68 min (analysis condition F)

Example 477

Compound DD-64

3-Chloro-N-[(5-chloro-2-ethylsulfonylphenyl)methyl]-4-[[4-(2-hydroxyethyl)piperazin-1-yl]methyl]-5-(trifluoromethyl)benzamide

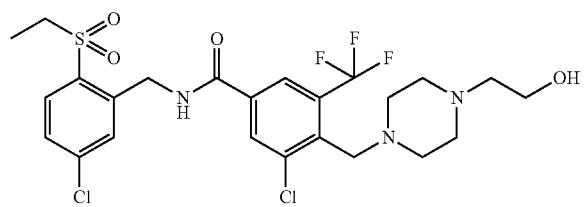 [SMILES: CCS(=O)(=O)c1ccc(Cl)cc1CNC(=O)c1cc(Cl)c(CN2CCN(CCO)CC2)c(C(F)(F)F)c1]

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compound H-5. However, 2-bromoethanol was used in place of iodoethane. The reaction was performed with the addition of triethylamine.

LCMS: m/z 582 [M+H]$^+$

HPLC retention time: 0.54 min (analysis condition F)

Example 478

Compound dd33

Ethyl 3-chloro-4-[[(3S)-3-[methyl-[(2-methylpropan-2-yl)oxycarbonyl]amino]piperidin-1-yl]methyl]-5-(trifluoromethyl)benzoate

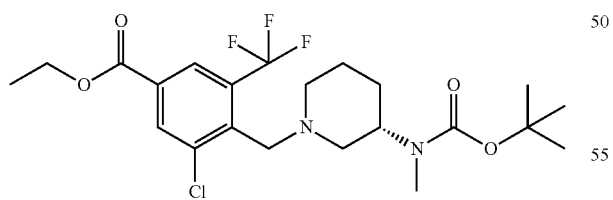

The title compound was synthesized from ethyl 3-chloro-4-formyl-5-(trifluoromethyl)benzoate (Compound d7) under the same conditions as for Compound b32. However, tert-butyl N-methyl-N-[(3S)-piperidin-3-yl]carbamate was used in place of (S)-1-pyrrolidin-2-ylmethyl-carbamic acid tert-butyl ester.

Example 479

Compound dd34

3-Chloro-4-[[(3S)-3-[methyl-[(2-methylpropan-2-yl)oxycarbonyl]amino]piperidin-1-yl]methyl]-5-(trifluoromethyl)benzoic acid

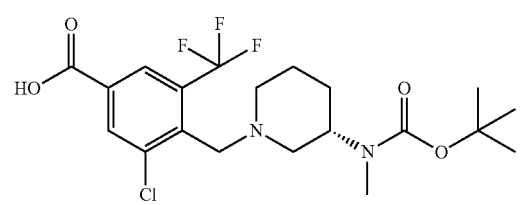 [SMILES: CN(C(=O)OC(C)(C)C)[C@H]1CCCN(Cc2c(Cl)cc(C(=O)O)cc2C(F)(F)F)C1]

The title compound was synthesized from ethyl 3-chloro-4-[[(3S)-3-[methyl-[(2-methylpropan-2-yl)oxycarbonyl]amino]piperidin-1-yl]methyl]-5-(trifluoromethyl)benzoate (Compound dd33) under the same conditions as for Compound b8.

Example 480

Compound dd35

5-Chloro-2-propylsulfanylbenzonitrile

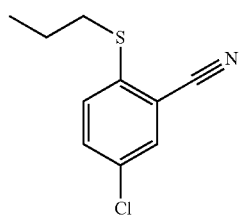

The title compound was synthesized from 5-chloro-2-fluorobenzonitrile under the same conditions as for Compound a1. However, propane-1-thiol was used in place of ethanethiol.

Example 481

Compound dd36

(5-Chloro-2-propyl sulfanylphenyl)methanamine

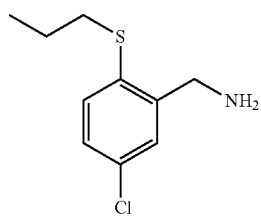

The title compound was synthesized from 5-chloro-2-propylsulfanylbenzonitrile (Compound dd35) under the same conditions as for Compound a2.

Example 482

Compound dd37

(5-Chloro-2-propylsulfonylphenyl)methanamine hydrochloride

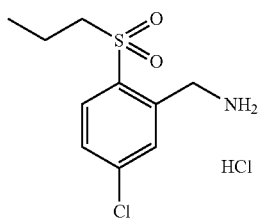

The title compound was synthesized from (5-chloro-2-propylsulfanylphenyl)methanamine (Compound dd36) under the same conditions as for Compound a3.

Example 483

Compound dd38 tert-Butyl N-[(3S)-1-[[2-chloro-4-[(5-chloro-2-propylsulfonylphenyl)methylcarbamoyl]-6-(trifluoromethyl)phenyl]methyl]piperidin-3-yl]-N-methylcarbamate

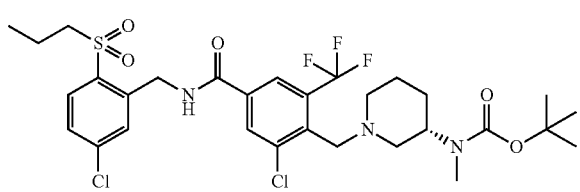 [SMILES: CCCS(=O)(=O)c1ccc(Cl)cc1CNC(=O)c1cc(Cl)c(CN2CCC[C@H](N(C)C(=O)OC(C)(C)C)C2)c(C(F)(F)F)c1]

The title compound was synthesized from (5-chloro-2-propylsulfonylphenyl)methanamine hydrochloride (Compound dd37) under the same conditions as for Compound A-14. However, 3-chloro-4-[[(3S)-3-[methyl-[(2-methylpropan-2-yl)oxycarbonyl]amino]piperidin-1-yl]methyl]-5-(trifluoromethyl)benzoic acid (compound dd34) was used in place of 4-bromo-3-trifluoromethyl-benzoic acid.

Example 484

Compound DD-65

3-Chloro-N-[(5-chloro-2-propylsulfonylphenyl)methyl]-4-[[(3S)-3-(methylamino)piperidin-1-yl]methyl]-5-(trifluoromethyl)benzamide

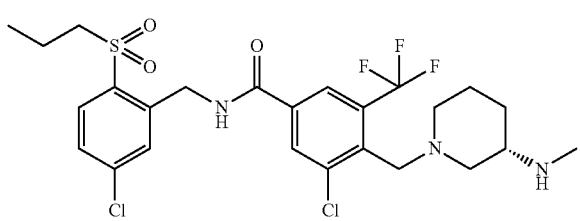 [SMILES: CCCS(=O)(=O)c1ccc(Cl)cc1CNC(=O)c1cc(Cl)c(CN2CCC[C@H](NC)C2)c(C(F)(F)F)c1]

The title compound was synthesized from tert-butyl N-[(3S)-1-[[2-chloro-4-[(5-chloro-2-propylsulfonylphenyl)methylcarbamoyl]-6-(trifluoromethyl)phenyl]methyl]piperidin-3-yl]-N-methylcarbamate (Compound dd38) under the same conditions as for Compound B-1.

LCMS: m/z 580 [M+H]$^+$

HPLC retention time: 0.59 min (analysis condition F)

Example 485

Compound dd39

(5-Chloro-2-phenylsulfanylphenyl)methanamine

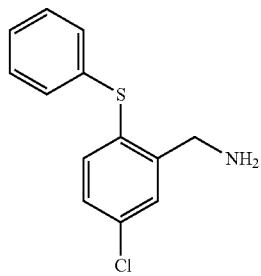 [SMILES: NCc1cc(Cl)ccc1Sc1ccccc1]

The title compound was synthesized from 5-chloro-2-fluorobenzonitrile under the same conditions as for Compounds dd35 and dd36. However, benzenethiol was used in place of propane-1-thiol under the Compound dd35 conditions.

Example 486

Compound dd40

[2-(Benzenesulfonyl)-5-chlorophenyl]methanamine hydrochloride

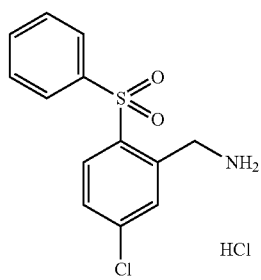 [SMILES: NCc1cc(Cl)ccc1S(=O)(=O)c1ccccc1 ; Cl]

The title compound was synthesized from (5-chloro-2-phenylsulfanylphenyl)methanamine (Compound dd39) under the same conditions as for Compounds a9, a10 and a11. However, the reaction was performed under the Compound a9 conditions with the addition of triethylamine.

Example 487

Compound DD-66

N-[[2-(Benzenesulfonyl)-5-chlorophenyl]methyl]-3-chloro-4-[[(3S)-3-(methylamino)piperidin-1-yl]methyl]-5-(trifluoromethyl)benzamide

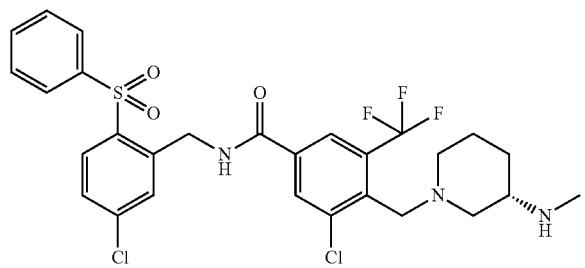 [SMILES: CN[C@H]1CCCN(Cc2c(Cl)cc(C(=O)NCc3cc(Cl)ccc3S(=O)(=O)c3ccccc3)cc2C(F)(F)F)C1]

The title compound was synthesized from [2-(benzenesulfonyl)-5-chlorophenyl]methanamine hydrochloride (Compound dd40) under the same conditions as for Compounds dd38 and DD-65.

LCMS: m/z 614 [M+H]$^+$

HPLC retention time: 0.61 min (analysis condition F)

Example 488

Compound DD-67

3-Chloro-N-[(5-chloro-2-propan-2-ylsulfonylphenyl)methyl]-4-[[(3S)-3-(methylamino)piperidin-1-yl]methyl]-5-(trifluoromethyl)benzamide

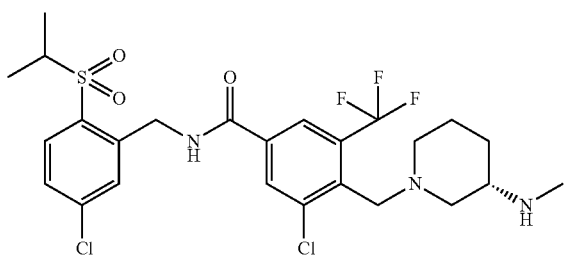 [SMILES: CN[C@H]1CCCN(Cc2c(Cl)cc(C(=O)NCc3cc(Cl)ccc3S(=O)(=O)C(C)C)cc2C(F)(F)F)C1]

The title compound was synthesized from 5-chloro-2-fluorobenzonitrile under the same conditions as for Compounds dd35, dd36, dd37, dd38 and DD-65. However, propane-2-thiol was used in place of propane-1-thiol under the dd35 conditions.

LCMS: m/z 580 [M+H]$^+$

HPLC retention time: 0.60 min (analysis condition F)

Example 489

Compound dd41

(4-Chloro-2-formyl-6-methoxyphenyl)trifluoromethanesulfonate

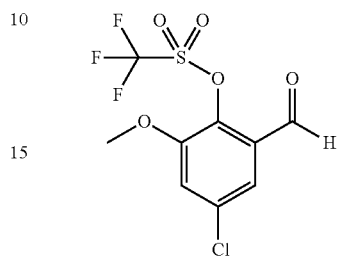

Trifluoromethylsulfonyl trifluoromethanesulfonate (688 mg, 2.44 mmol) was added to a solution of 5-chloro-2-hydroxy-3-methoxybenzaldehyde (403 mg, 2.16 mmol) in pyridine (7 ml), and it was stirred under ice-cooling for 30 minutes under a nitrogen atmosphere. Water was added to the reaction mixture, followed by extraction with ethyl acetate. The organic layer was then dried over anhydrous magnesium sulfate. The drying agent was removed by filtration, and the residue obtained by concentration under reduced pressure was purified by silica gel column chromatography (ethyl acetate/hexane) to yield the title compound (648 mg, 94%) as a pale yellow oily substance.

LCMS: m/z 319 [M+H]$^+$

HPLC retention time: 0.87 min (analysis condition A)

Example 490

Compound dd42

5-Chloro-2-ethylsulfanyl-3-methoxybenzaldehyde

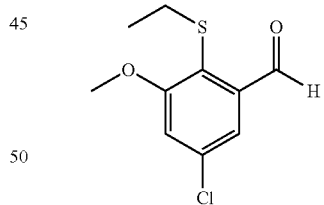

Tris(dibenzylideneacetone)dipalladium(0) (66.8 mg, 0.0729 mmol), (5-diphenylphosphanyl-9,9-dimethylxanthen-4-yl)-diphenylphosphane (83.9 mg, 0.145 mmol), DIPEA (0.362 ml, 2.13 mmol) and ethanethiol (0.210 ml, 2.84 mmol) were added to a solution of (4-chloro-2-formyl-6-methoxyphenyl) trifluoromethanesulfonate (Compound dd41, 319 mg, 0.709 mmol) in 1,4-dioxane (2.5 ml), and it was stirred at 100° C. for 15 minutes. The reaction solution was cooled to room temperature, followed by addition of water and extraction with ethyl acetate. The organic layer was washed with brine and dried over anhydrous magnesium sulfate. The drying agent was removed by filtration, and the residue obtained by concentration under reduced pressure was purified by silica gel column chromatography (ethyl acetate/hexane) to yield the title compound (135 mg, 83%) as a yellow oily substance.
LCMS: m/z 231 [M+H]$^+$
HPLC retention time: 2.64 min (analysis condition D)

Example 491

Compound dd43

(E)-1-(5-Chloro-2-ethylsulfanyl-3-methoxyphenyl)-N-methoxymethanimine

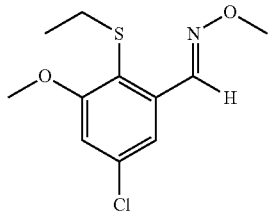

The title compound was synthesized from 5-chloro-2-ethylsulfanyl-3-methoxybenzaldehyde (Compound dd42) under the same conditions as for Compound a7.

Example 492

Compound dd44

(5-Chloro-2-ethylsulfanyl-3-methoxyphenyl)methanamine

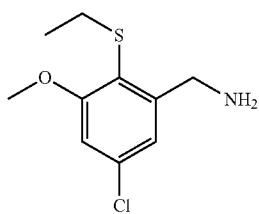

The title compound was synthesized from (E)-1-(5-chloro-2-ethylsulfanyl-3-methoxyphenyl)-N-methoxymethanimine (Compound dd43) under the same conditions as for Compound a8.

Example 493

Compound dd45

(5-Chloro-2-ethylsulfonyl-3-methoxyphenyl)methanamine hydrochloride

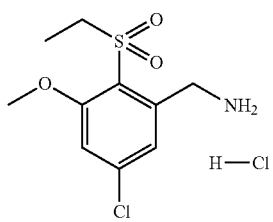

Boc$_2$O (121 mg, 0.553 mmol) was added to a solution of (5-chloro-2-ethylsulfanyl-3-methoxyphenyl)methanamine (Compound dd44, 105 mg, 0.452 mmol) and TEA (94.0 μl, 0.678 mmol) in THF (1.5 ml), and it was stirred at room temperature for 30 minutes under a nitrogen atmosphere. A 10% aqueous citric acid solution was added to the reaction mixture, followed by extraction with ethyl acetate. The organic layer was then washed with brine and dried over anhydrous magnesium sulfate. After the drying agent was removed by filtration, a crude product of tert-butyl N-[(5-chloro-2-ethylsulfanyl-3-methoxyphenyl)methyl]carbamate (182 mg) was obtained as a gray solid by concentration under reduced pressure.

To a solution of the resultant crude product of tert-butyl N-[(5-chloro-2-ethylsulfanyl-3-methoxyphenyl)methyl]carbamate (148 mg) in EtOAc (1.5 ml), m-CPBA (233 mg, 0.876 mmol) was added under ice-cooling, and it was warmed to room temperature and stirred for 30 minutes under a nitrogen atmosphere. A saturated aqueous solution of sodium bicarbonate was added to the reaction mixture, followed by extraction with ethyl acetate. The organic layer was then washed with brine and dried over anhydrous magnesium sulfate. After the drying agent was removed by filtration, a crude product of tert-butyl N-[(5-chloro-2-ethylsulfonyl-3-methoxyphenyl)methyl]carbamate was obtained by concentration under reduced pressure.

A 4N hydrochloric acid/ethyl acetate solution (0.760 ml, 3.04 mmol) was added to the crude product of tert-butyl N-[(5-chloro-2-ethylsulfonyl-3-methoxyphenyl)methyl]carbamate obtained above in MeOH/EtOAc (60 μl/0.75 ml), and it was stirred at 60° C. for three hours. The reaction solution was cooled to room temperature, and the precipitated solid was then washed with ethyl acetate to yield the title compound (99.8 mg, 90%) as a colorless solid.
LCMS: m/z 264 [M+H]$^+$
HPLC retention time: 0.59 min (analysis condition D)

Example 494

Compound dd46 tert-Butyl N-[(3S)-1-[[2-chloro-4-[(5-chloro-2-ethylsulfonyl-3-methoxyphenyl)methylcarbamoyl]-6-(trifluoromethyl)phenyl]methyl]piperidin-3-yl]-N-methylcarbamate

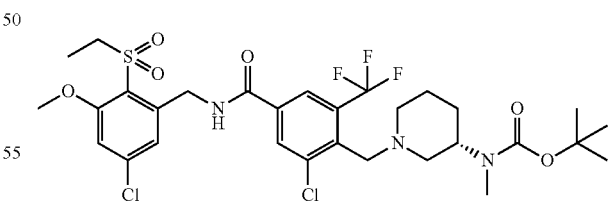

The title compound was synthesized from (5-chloro-2-ethylsulfonyl-3-methoxyphenyl)methanamine hydrochloride (Compound dd45) under the same conditions as for Compound bb10. However, 3-chloro-4-[[(3S)-3-[methyl-[(2-methylpropan-2-yl)oxycarbonyl]amino]piperidin-1-yl]methyl]-5-(trifluoromethyl)benzoic acid (Compound dd34) was used in place of 4-[[4-[(2-methylpropan-2-yl)oxycarbonyl]piperazin-1-yl]methyl]-3-(trifluoromethyl)benzoic acid (Compound b3).

Example 495

Compound DD-68

3-Chloro-N-[(5-chloro-2-ethylsulfonyl-3-methoxy-phenyl)methyl]-4-[[(3S)-3-(methylamino)piperidin-1-yl]methyl]-5-(trifluoromethyl)benzamide

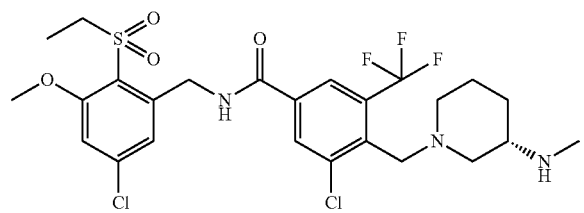

The title compound was synthesized from tert-butyl N-[(3S)-1-[[2-chloro-4-[(5-chloro-2-ethylsulfonyl-3-methoxyphenyl)methylcarbamoyl]-6-(trifluoromethyl)phenyl]methyl]piperidin-3-yl]-N-methylcarbamate (Compound dd46) under the same conditions as for Compound B-57.

LCMS: m/z 596 [M+H]$^+$

HPLC retention time: 1.43 min (analysis condition D)

Example 496

Compound dd47

2-Iodo-4,5-dimethylaniline

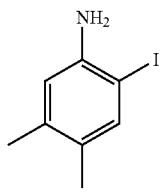

Iodine (2.06 g, 8.11 mmol) was added in 10 parts to a mixed solution of 3,4-dimethylaniline (893 mg, 7.37 mmol) and sodium bicarbonate (683 mg, 8.14 mmol) in MeOH/water (7 ml/7 ml), and it was stirred at room temperature for one hour under a nitrogen atmosphere. Followed by addition of water to the reaction mixture and extraction with dichloromethane, the organic layer was then washed with a saturated aqueous solution of sodium thiosulfate and dried over anhydrous magnesium sulfate. The drying agent was removed by filtration, followed by concentration under reduced pressure. The resultant residue was purified by silica gel column chromatography (ethyl acetate/hexane) to yield the title compound (1.54 g, 85%) as a brown solid.

LCMS: m/z 248 [M+H]$^+$

HPLC retention time: 1.91 min (analysis condition D)

Example 497

Compound dd48

2-Amino-4,5-dimethylbenzonitrile

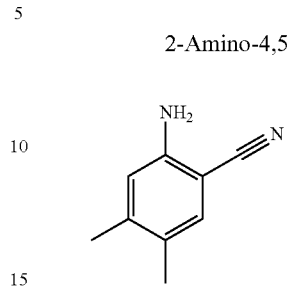

Copper(I) cyanide (1.24 g, 12.4 mmol) was added to a solution of 2-iodo-4,5-dimethylaniline (Compound dd46, 1.53 g, 6.21 mmol) in DMF (20 ml), and it was stirred at 150 to 160° C. for 1.5 hours. After the reaction solution was cooled to room temperature, a 10% aqueous ammonia solution (30 ml) and DCM (30 ml) were added, followed by removal of the insoluble matter by filtration through celite, and it was washed with DCM. The organic layer of the filtrate was concentrated under reduced pressure, and the resultant residue was purified by silica gel column chromatography (ethyl acetate/hexane) to yield the title compound (796 mg, 88%) as a brown solid.

LCMS: m/z 147 [M+H]$^+$

HPLC retention time: 0.66 min (analysis condition A)

Example 498

Compound dd49

2-Iodo-4, 5-dimethylbenzonitrile

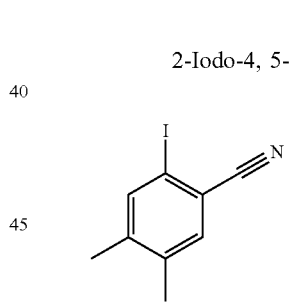

Sodium nitrite (392 mg, 5.68 mmol) dissolved in water (2 ml) was added to a solution of 2-amino-4,5-dimethylbenzonitrile (Compound dd48, 682 mg, 4.67 mmol) in 2,2,2-trifluoroethanol/TFA (27 ml/2.7 ml), and it was stirred at room temperature under a nitrogen atmosphere. After 20 minutes, potassium iodide (2.30 g, 13.9 mmol) was added, and it was further stirred for 1.5 hours. Followed by addition of water to the reaction mixture and extraction with ethyl acetate, the organic layer was then washed with a saturated aqueous solution of sodium thiosulfate and dried over anhydrous magnesium sulfate. The drying agent was removed by filtration, followed by concentration under reduced pressure. The resultant residue was purified by silica gel column chromatography (ethyl acetate/hexane) to yield the title compound (694 mg, 58%) as a pale yellow solid.

LCMS: m/z 258 [M+H]$^+$

HPLC retention time: 0.85 min (analysis condition A)

Example 499

Compound dd50

2-Ethylsulfanyl-4,5-dimethylbenzonitrile

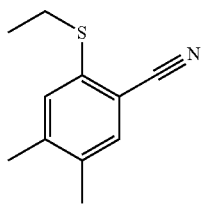

The title compound was synthesized from 2-iodo-4,5-dimethylbenzonitrile (Compound dd49) under the same conditions as for Compound dd42.

Example 500

Compound dd51

(2-Ethylsulfanyl-4,5-dimethylphenyl)methanamine

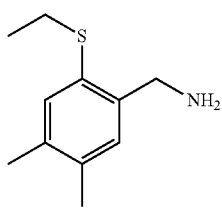

The title compound was synthesized from 2-ethylsulfanyl-4,5-dimethylbenzonitrile (Compound dd50) under the same conditions as for Compound a2.

Example 501

Compound DD-69

3-Chloro-N-[(5-chloro-2-ethylsulfonyl-3-methoxyphenyl)methyl]-4-[[(3S)-3-(methylamino)piperidin-1-yl]methyl]-5-(trifluoromethyl)benzamide

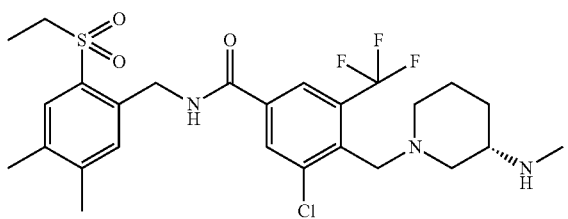 [SMILES: CCS(=O)(=O)c1cc(C)c(C)cc1CNC(=O)c1cc(Cl)c(CN2CCC[C@H](NC)C2)c(C(F)(F)F)c1]

The title compound was synthesized from (2-ethylsulfanyl-4,5-dimethylphenyl)methanamine (Compound dd51) under the same conditions as for Compounds dd44, dd45, dd46 and DD-68.

LCMS: m/z 560 [M+H]$^+$

HPLC retention time: 1.51 min (analysis condition D)

Example 502

Compound DD-70

3-Chloro-N-[(5-chloro-2-ethylsulfonyl-4-methylphenyl)methyl]-4-[[(3S)-3-(methylamino)piperidin-1-yl]methyl]-5-(trifluoromethyl)benzamide

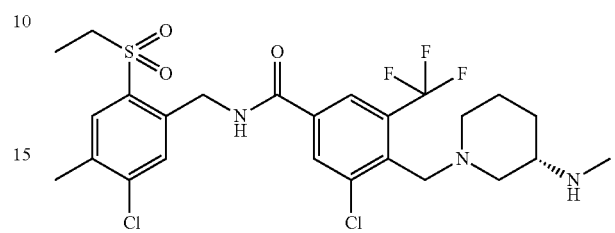

The title compound was synthesized from 5-chloro-2-hydroxy-4-methylbenzaldehyde under the same conditions as for Compounds dd41, dd42, dd43, dd44, dd45, dd46 and DD-68. However, under the Compound dd42 conditions, the reaction was performed at a temperature of 80° C.

LCMS: m/z 580 [M+H]$^+$

HPLC retention time: 0.59 min (analysis condition A)

Example 503

Compound dd52

Methyl 4-(bromomethyl)-3-chloro-5-(trifluoromethyl)benzoate

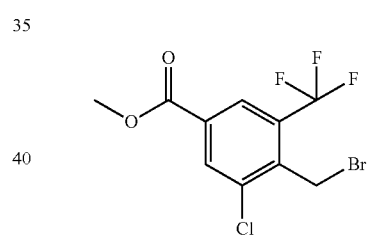

The title compound was synthesized from methyl 3-chloro-4-(hydroxymethyl)-5-(trifluoromethyl)benzoate (Compound dd7) under the same conditions as for Compound dd16.

Example 504

Compound dd53

Methyl 4-[(3-aminophenyl)methyl]-3-chloro-5-(trifluoromethyl)benzoate

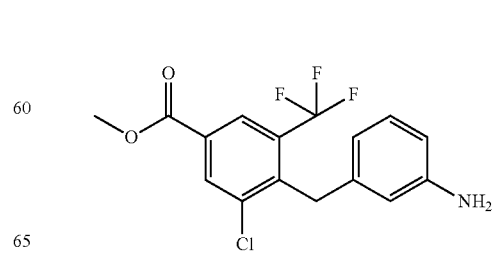

The title compound was synthesized from methyl 4-(bromomethyl)-3-chloro-5-(trifluoromethyl)benzoate (Compound dd52) under the same conditions as for Compound bb1.

Example 505

Compound dd54

4-[(3-Aminophenyl)methyl]-3-chloro-5-(trifluoromethyl)benzoic acid

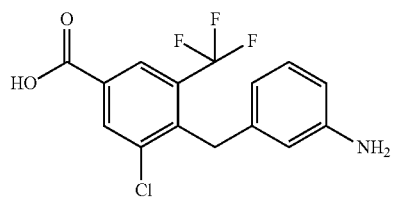 [SMILES: Nc1cccc(Cc2c(Cl)cc(C(=O)O)cc2C(F)(F)F)c1]

The title compound was synthesized from methyl 4-[(3-aminophenyl)methyl]-3-chloro-5-(trifluoromethyl)benzoate (Compound dd53) under the same conditions as for Compound b8. However, methanol was used in place of ethanol as a solvent.

Example 506

Compound DD-71

4-[(3-Aminophenyl)methyl]-3-chloro-N-[(5-chloro-2-ethylsulfonylphenyl)methyl]-5-(trifluoromethyl)benzamide

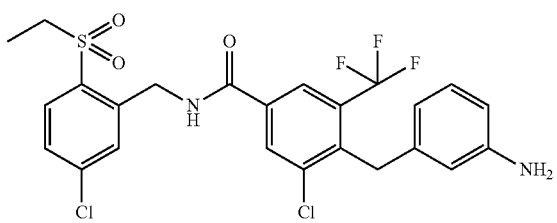 [SMILES: CCS(=O)(=O)c1ccc(Cl)cc1CNC(=O)c1cc(Cl)c(Cc2cccc(N)c2)c(C(F)(F)F)c1]

The title compound was synthesized from (5-chloro-2-ethylsulfonylphenyl)methanamine hydrochloride (Compound a3) under the same conditions as for Compound A-21. However, 4-[(3-aminophenyl)methyl]-3-chloro-5-(trifluoromethyl)benzoic acid (Compound dd54) was used in place of 3-(trifluoromethyl)benzoic acid.

LCMS: m/z 545 [M+H]$^+$

HPLC retention time: 0.81 min (analysis condition F)

Example 507

Compound dd55 tert-Butyl 4-[[2-chloro-4-methoxycarbonyl-6-(trifluoromethyl)phenyl]methyl]-3,6-dihydro-2H-pyridine-1-carboxylate

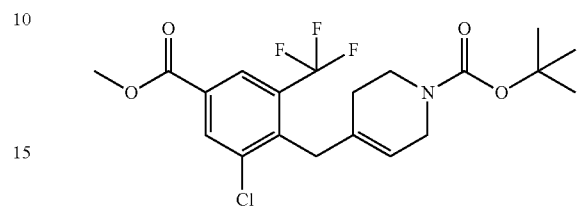

The title compound was synthesized from methyl 4-(bromomethyl)-3-chloro-5-(trifluoromethyl)benzoate (Compound dd52) under the same conditions as for Compound bb1. However, tert-butyl 4-(4,4,5,5-tetramethyl-1,3,2-dioxaborolan-2-yl)-3,6-dihydro-2H-pyridine-1-carboxylate was used in place of (3-aminophenyl)boronic acid.

Example 508

Compound dd56 tert-Butyl 4-[[2-chloro-4-methoxycarbonyl-6-(trifluoromethyl)phenyl]methyl]piperidine-1-carboxylate

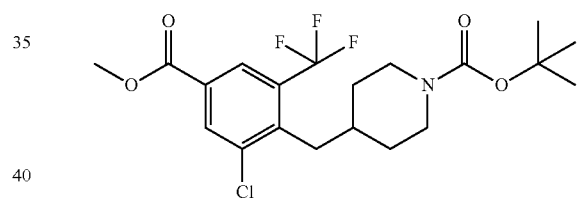

The title compound was synthesized from tert-butyl 4-[[2-chloro-4-methoxycarbonyl-6-(trifluoromethyl)phenyl]methyl]-3,6-dihydro-2H-pyridine-1-carboxylate (Compound dd55) under the same conditions as for Compound bb4.

Example 509

Compound dd57

3-Chloro-4-[[1-[(2-methylpropan-2-yl)oxycarbonyl]piperidin-4-yl]methyl]-5-(trifluoromethyl)benzoic acid

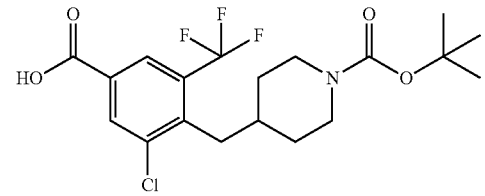 [SMILES: CC(C)(C)OC(=O)N1CCC(Cc2c(Cl)cc(C(=O)O)cc2C(F)(F)F)CC1]

The title compound was synthesized from tert-butyl 4-[[2-chloro-4-methoxycarbonyl-6-(trifluoromethyl)phenyl]methyl]piperidine-1-carboxylate (Compound dd56) under the same conditions as for Compound b8. However, methanol was used in place of ethanol as a solvent.

Example 510

Compound dd58 tert-Butyl 4-[[2-chloro-4-[(5-chloro-2-ethylsulfonylphenyl)methylcarbamoyl]-6-(trifluoromethyl)phenyl]methyl]piperidine-1-carboxylate

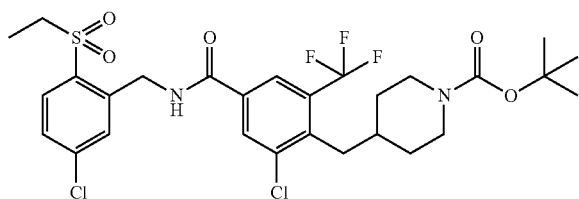 [SMILES: CCS(=O)(=O)c1ccc(Cl)cc1CNC(=O)c1cc(Cl)c(CC2CCN(C(=O)OC(C)(C)C)CC2)c(C(F)(F)F)c1]

The title compound was synthesized from (5-chloro-2-ethylsulfonylphenyl)methanamine hydrochloride (Compound a3) under the same conditions as for Compound A-21. However, 3-chloro-4-[[1-[(2-methylpropan-2-yl)oxycarbonyl]piperidin-4-yl]methyl]-5-(trifluoromethyl)benzoic acid (Compound dd57) was used in place of 3-(trifluoromethyl)benzoic acid.

Example 511

Compound DD-72

3-Chloro-N-[(5-chloro-2-ethylsulfonylphenyl)methyl]-4-(piperidin-4-ylmethyl)-5-(trifluoromethyl)benzamide

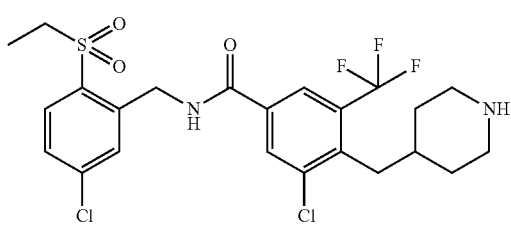

The title compound was synthesized from tert-butyl 4-[[2-Chloro-4-[(5-chloro-2-ethylsulfonylphenyl)methylcarbamoyl]-6-(trifluoromethyl)phenyl]methyl]piperidine-1-carboxylate (Compound dd58) under the same conditions as for Compound B-1.

LCMS: m/z 537 [M+H]+

HPLC retention time: 0.56 min (analysis condition F)

Example 512

Compound ee1 tert-Butyl 4-[[2-bromo-4-[(5-chloro-2-ethylsulfonylphenyl)methylcarbamoyl]-6-(trifluoromethyl)phenyl]methyl]piperazine-1-carboxylate

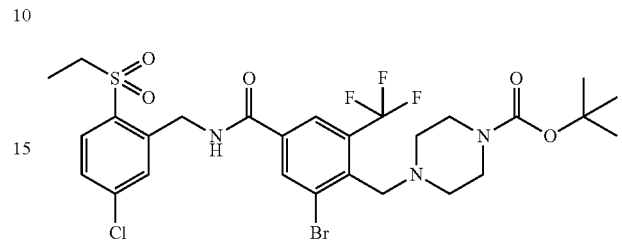

The title compound was synthesized from 3-bromo-N-[(5-chloro-2-ethylsulfonylphenyl)methyl]-4-formyl-5-(trifluoromethyl)benzamide (Compound e7) under the same conditions as for Compound b32. However, tert-butyl piperazine-1-carboxylate was used in place of tert-butyl (S)-1-pyrrolidin-2-ylmethyl-carbamate, and chloroform was used in place of THF as a solvent.

Example 513

Compound EE-1

3-Bromo-N-[(5-chloro-2-ethylsulfonylphenyl)methyl]-4-(piperazin-1-ylmethyl)-5-(trifluoromethyl)benzamide

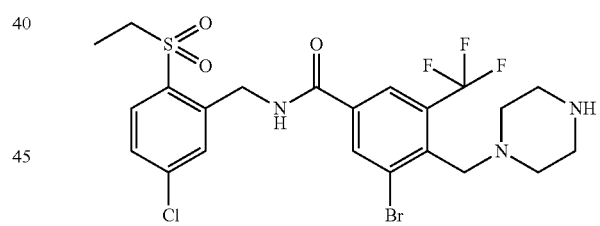

The title compound was synthesized from tert-butyl 4-[[2-bromo-4-[(5-chloro-2-ethylsulfonylphenyl)methylcarbamoyl]-6-(trifluoromethyl)phenyl]methyl]piperazine-1-carboxylate (Compound ee1) under the same conditions as for Compound B-57.

LCMS: m/z 582 [M+H]+

HPLC retention time: 0.53 min (analysis condition A)

Example 514

Compounds EE-2 and EE-3 were synthesized from 3-bromo-N-[(5-chloro-2-ethylsulfonylphenyl)methyl]-4-formyl-5-(trifluoromethyl)benzamide (Compound e7) under the same conditions as for Compound b32. However, 1-methylpiperazine was used in place of tert-butyl (S)-1-pyrrolidin-2-ylmethyl-carbamate, and chloroform was used in place of THF as a solvent.

Compound EE-2

3-Bromo-N-[(5-chloro-2-ethylsulfonylphenyl)methyl]-4-[(4-methylpiperazin-1-yl)methyl]-5-(trifluoromethyl)benzamide

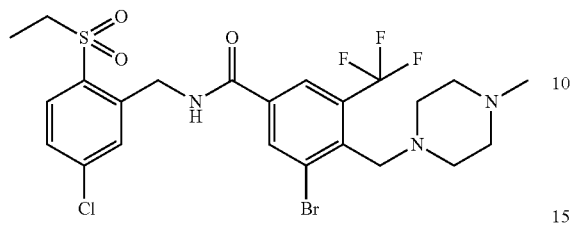

LCMS: m/z 596 [M+H]⁺
HPLC retention time: 0.53 min (analysis condition A)

Compound EE-3

3-Bromo-N-[(5-chloro-2-ethylsulfonylphenyl)methyl]-4-(hydroxymethyl)-5-(trifluoromethyl)benzamide

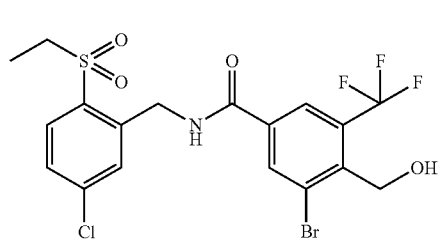 [SMILES: CCS(=O)(=O)c1ccc(Cl)cc1CNC(=O)c1cc(Br)c(CO)c(C(F)(F)F)c1]

LCMS: m/z 514 [M+H]⁺
HPLC retention time: 0.73 min (analysis condition A)

Example 515

Compound EE-4

4-[[(3S)-3-Aminopyrrolidin-1-yl]methyl]-3-bromo-N-[(5-chloro-2-ethylsulfonylphenyl)methyl]-5-(trifluoromethyl)benzamide

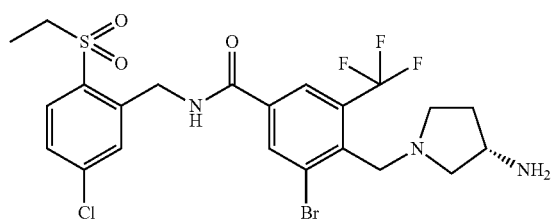 [SMILES: CCS(=O)(=O)c1ccc(Cl)cc1CNC(=O)c1cc(Br)c(CN2CC[C@H](N)C2)c(C(F)(F)F)c1]

The title compound was synthesized from 3-bromo-N-[(5-chloro-2-ethylsulfonylphenyl)methyl]-4-formyl-5-(trifluoromethyl)benzamide (Compound e7) under the same conditions as for Compounds ee1 and EE-1. However, under the Compound ee1 conditions, tert-butyl N-[(3S)-pyrrolidin-3-yl]carbamate was used in place of tert-butyl piperazine-1-carboxylate.

LCMS: m/z 582 [M+H]⁺
HPLC retention time: 0.50 min (analysis condition A)

Example 516

Compound EE-5

3-Bromo-N-[(5-chloro-2-ethylsulfonylphenyl)methyl]-4-[[(3S)-3-(methyl amino)pyrrolidin-1-yl]methyl]-5-(trifluoromethyl)benzamide

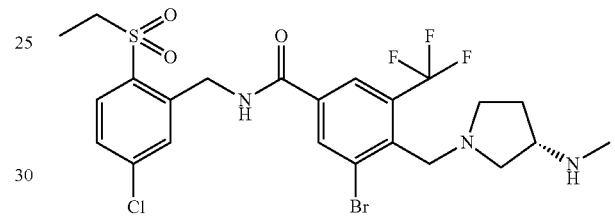

The title compound was synthesized from 3-bromo-N-[(5-chloro-2-ethylsulfonylphenyl)methyl]-4-formyl-5-(trifluoromethyl)benzamide (Compound e7) under the same conditions as for Compounds ee1 and EE-1. However, under the Compound ee1 conditions, tert-butyl N-methyl-N-[(3S)-pyrrolidin-3-yl]carbamate was used in place of tert-butyl piperazine-1-carboxylate.

LCMS: m/z 596 [M+H]⁺
HPLC retention time: 0.53 min (analysis condition A)

Example 517

Compound ee2 tert-Butyl N-[2-[[(3S)-1-[[2-bromo-4-[(5-chloro-2-ethylsulfonylphenyl)methylcarbamoyl]-6-(trifluoromethyl)phenyl]methyl]piperidin-3-yl]amino]-2-oxoethyl]carbamate

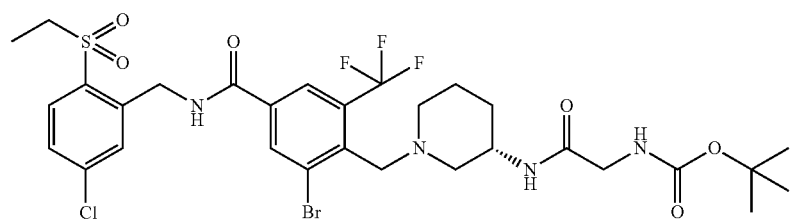 [SMILES: CCS(=O)(=O)c1ccc(Cl)cc1CNC(=O)c1cc(Br)c(CN2CCC[C@H](NC(=O)CNC(=O)OC(C)(C)C)C2)c(C(F)(F)F)c1]

Example 518

Compound EE-6

4-[[(3S)-3-[(2-Aminoacetyl)amino]piperidin-1-yl]methyl]-3-bromo-N-[(5-chloro-2-ethylsulfonylphenyl)methyl]-5-(trifluoromethyl)benzamide

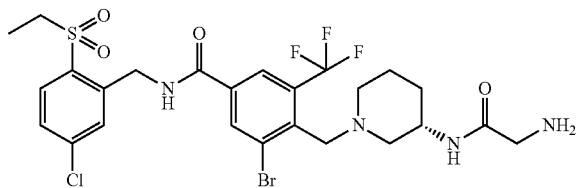 [SMILES: CCS(=O)(=O)c1ccc(Cl)cc1CNC(=O)c1cc(Br)c(CN2CCC[C@H](NC(=O)CN)C2)c(C(F)(F)F)c1]

The title compound was synthesized from tert-butyl N-[2-[[(3S)-1-[[2-bromo-4-[(5-chloro-2-ethylsulfonylphenyl)methylcarbamoyl]-6-(trifluoromethyl)phenyl]methyl]piperidin-3-yl]amino]-2-oxoethyl]carbamate (Compound ee2) under the same conditions as for Compound B-57.

LCMS: m/z 653 [M+H]$^+$

HPLC retention time: 0.45 min (analysis condition A)

Example 519

Compound EE-7

3-Bromo-N-[(5-chloro-2-ethylsulfonylphenyl)methyl]-4-[[(3S)-3-[[2-(methylamino)acetyl]amino]piperidin-1-yl]methyl]-5-(trifluoromethyl)benzamide

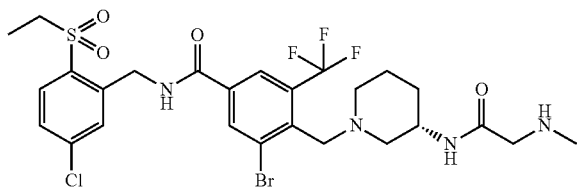 [SMILES: CCS(=O)(=O)c1ccc(Cl)cc1CNC(=O)c1cc(Br)c(CN2CCC[C@H](NC(=O)CNC)C2)c(C(F)(F)F)c1]

The title compound was synthesized from 4-[[(3S)-3-aminopiperidin-1-yl]methyl]-3-bromo-N-[(5-chloro-2-ethylsulfonylphenyl)methyl]-5-(trifluoromethyl)benzamide (Compound E-3) under the same conditions as for Compounds ee2 and EE-6. However, under the Compound ee2 conditions, 2-[methyl-[(2-methylpropan-2-yl)oxycarbonyl]amino]acetic acid was used in place of 2-[(2-methylpropan-2-yl)oxycarbonylamino]acetic acid.

LCMS: m/z 667 [M+H]$^+$

HPLC retention time: 0.46 min (analysis condition A)

The title compound was synthesized from 4-[[(3S)-3-aminopiperidin-1-yl]methyl]-3-bromo-N-[(5-chloro-2-ethylsulfonylphenyl)methyl]-5-(trifluoromethyl)benzamide (Compound E-3) under the same conditions as for Compound DD-1. However, 2-[(2-methylpropan-2-yl)oxycarbonylamino]acetic acid was used in place of 1H-pyrrole-2-carboxylic acid, and HATU was used in place of HBTU as a condensing agent.

Example 520

Compound EE-8

4-[[(3S)-3-(3-Aminopropanoylamino)piperidin-1-yl]methyl]-3-bromo-N-[(5-chloro-2-ethylsulfonylphenyl)methyl]-5-(trifluoromethyl)benzamide

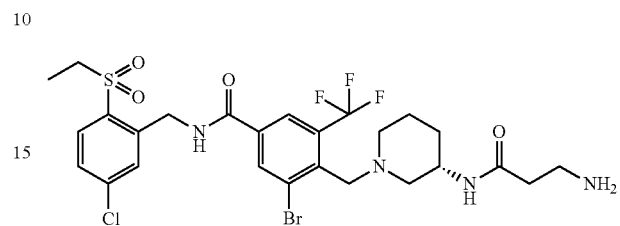

The title compound was synthesized from 4-[[(3S)-3-aminopiperidin-1-yl]methyl]-3-bromo-N-[(5-chloro-2-ethylsulfonylphenyl)methyl]-5-(trifluoromethyl)benzamide (Compound E-3) under the same conditions as for Compounds ee2 and EE-6. However, under the Compound ee2 conditions, 3-[(2-methylpropan-2-yl)oxycarbonylamino]propanoic acid was used in place of 2-[(2-methylpropan-2-yl)oxycarbonylamino]acetic acid.

LCMS: m/z 667 [M+H]$^+$

HPLC retention time: 0.44 min (analysis condition A)

Example 521

Compound gg1

N-(2-Bromo-5-chloro-4-methylphenyl)acetamide

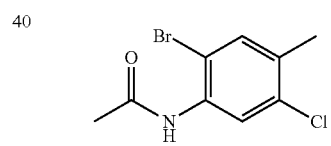

A solution of 3-chloro-4-methylaniline (5.0 g, 35.3 mmol) and pyridine (4.3 ml, 53.0 mmol) in EtOAc (35 ml) was cooled to 0° C., followed by addition of acetic anhydride (5.0 ml, 53.0 mmol), and it was stirred at room temperature for two hours. After addition of ethyl acetate to the reaction mixture and four washes with a 1N aqueous hydrochloric acid solution, the organic layer was dried over anhydrous magnesium sulfate. The drying agent was removed by filtration, followed by concentration under reduced pressure to yield a crude product of N-(3-chloro-4-methylphenyl)acetamide. The resultant crude product in acetic acid solution (35 ml) was cooled to 0° C., followed by addition of a solution of bromine (3.4 ml, 67.1 mmol) in acetic acid (3.4 ml), and it was stirred at room temperature for 20 hours. Followed by addition of DCM to the reaction mixture, and sequential washing with a saturated aqueous solution of sodium bicarbonate, water and a saturated aqueous sodium thiosulfate solution, the organic layer was dried over anhydrous magnesium sulfate. The drying agent was removed by filtration, followed by concentration under reduced pressure. The resultant solid was recrystallized from a mixed solvent of DCM and n-hexane to yield the title compound (7.9 g, 85%, two steps) as a colorless solid.

1H-NMR (400 MHz, CDCl₃) δ: 8.40 (1H, s), 7.49 (1H, brs), 7.39 (1H, s), 2.31 (3H, s), 2.23 (3H, s).

Example 522

Compound gg2

2-Acetamido-4-chloro-5-methylbenzoic acid

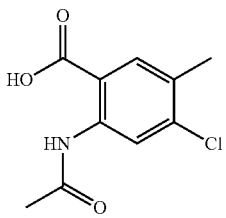

A solution of N-(2-bromo-5-chloro-4-methylphenyl)acetamide (Compound gg1, 7.90 g, 30.1 mmol) in THF (150 ml) was cooled to −78° C., followed by addition of a 1.6 M n-butyllithium/n-hexane solution (41.4 ml, 66.2 mmol), and it was stirred for 30 minutes under a nitrogen atmosphere. The reaction mixture was bubbled with carbon dioxide gas and then stirred at room temperature for 15 hours. After addition of DCM to the reaction solution which was made acidic by adding a 1N aqueous hydrochloric acid solution, the organic layer was separated. The organic layer was concentrated under reduced pressure, and the resultant solid was washed with DCM to yield the title compound (2.55 g, 37%) as a pale brown solid.

LCMS: m/z 228 [M+H]⁺

HPLC retention time: 1.28 min (analysis condition E)

Example 523

Compound gg3

2-Amino-4-chloro-5-methylbenzoic acid

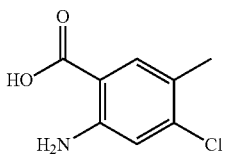

Sodium hydroxide (2.24 g, 56.0 mmol) was added to an aqueous solution (12 ml) of 2-acetamido-4-chloro-5-methylbenzoic acid (Compound gg2, 2.55 g, 11.2 mmol), and it was stirred for 15 hours under reflux. The reaction mixture was cooled to room temperature, and the pH of the solution was then adjusted from 4 to 5 with a 35% aqueous solution of hydrochloric acid. The precipitated solid was collected by filtration and then washed with water to yield the title compound (1.89 g, 91%) as a yellow solid.

1H-NMR (400 MHz, DMSO-d₆) δ: 7.63 (1H, s), 6.83 (1H, s), 2.17 (3H, s).

Example 524

Compound gg4

Ethyl 2-amino-4-chloro-5-methylbenzoate

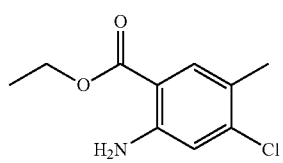

The title compound was synthesized from 2-amino-4-chloro-5-methylbenzoic acid (Compound gg3) under the same conditions as for Compound b1.

Example 525

Compound gg5

Ethyl 2-amino-4-formyl-5-methylbenzoate

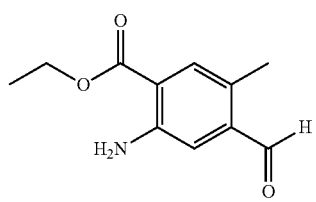

The title compound was synthesized from ethyl 2-amino-4-chloro-5-methylbenzoate (Compound gg4) under the same conditions as for Compounds b28, b29 and b30. However, AD-mix-β was used in place of AD-mix-α.

Example 526

Compound gg6

Ethyl 2-amino-4-(1,3-dioxolan-2-yl)-5-methylbenzoate

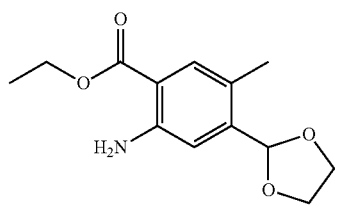 [SMILES: CCOC(=O)c1cc(C)c(C2OCCO2)cc1N]

Ethane-1,2-diol (1.73 ml, 31.1 mmol) and 4-methylbenzenesulfonic acid (118 mg, 0.62 mmol) were added to a solution of ethyl 2-amino-4-formyl-5-methylbenzoate (Compound gg5, 1.32 g, 6.22 mmol) in toluene (62 ml), and it was stirred at 120° C. for 15 hours. The reaction mixture was cooled to room temperature, and the solution was then basified by adding a saturated aqueous solution of sodium bicarbonate. The resultant aqueous solution was extracted with EtOAc, and the organic layer was washed with brine and then dried over anhydrous magnesium sulfate. The drying agent was removed by filtration, and the residue obtained by concentration under reduced pressure was purified by silica gel column chromatography (EtOAc/n-hexane) to yield the title compound (1.25 g, 80%) as a pale brown solid.

LCMS: m/z 252 [M+H]$^+$

HPLC retention time: 1.42 min (analysis condition E)

Example 527

Compound gg7

Ethyl 2-amino-3-chloro-4-(1,3-dioxolan-2-yl)-5-methylbenzoate

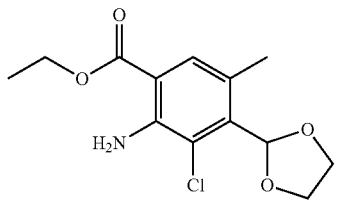 [SMILES: CCOC(=O)c1cc(C)c(C2OCCO2)c(Cl)c1N]

The title compound was synthesized from ethyl 2-amino-4-chloro-5-methylbenzoate (Compound gg6) under the same conditions as for Compound d6.

Example 528

Compound gg8

Ethyl 3-chloro-4-formyl-5-methylbenzoate

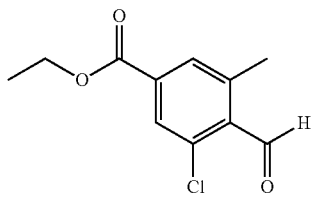

The title compound was synthesized from ethyl 2-amino-3-chloro-4-(1,3-dioxolan-2-yl)-5-methylbenzoate (Compound gg7) under the same conditions as for Compound b31.

Example 529

Compound gg9

Ethyl 3-chloro-5-methyl-4-[[(3S)-3-[methyl-[(2-methylpropan-2-yl)oxycarbonyl]amino]piperidin-1-yl]methyl]benzoate

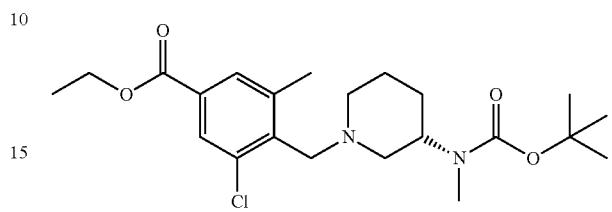

The title compound was synthesized from ethyl 3-chloro-4-formyl-5-methylbenzoate (Compound gg8) under the same conditions as for Compound b32. However, tert-butyl N-methyl-N-[(3S)-piperidin-3-yl]carbamate was used in place of tert-butyl (S)-1-pyrrolidin-2-ylmethyl-carbamate, and chloroform was used in place of THF as a solvent. The reaction was performed at a temperature of 0° C.

Example 530

Compound gg10

3-Chloro-5-methyl-4-[[(3S)-3-[methyl-[(2-methylpropan-2-yl)oxycarbonyl]amino]piperidin-1-yl]methyl]benzoic acid

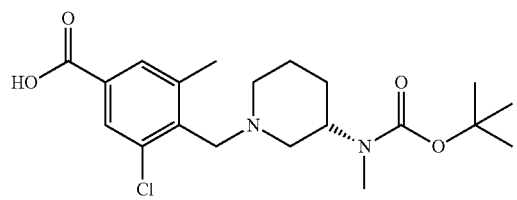

The title compound was synthesized from ethyl 3-chloro-5-methyl-4-[[(3S)-3-[methyl-[(2-methylpropan-2-yl)oxycarbonyl]amino]piperidin-1-yl]methyl]benzoate (Compound gg9) under the same conditions as for Compound b8.

Example 531

Compound gg11 tert-Butyl N-[(3S)-1-[[2-chloro-4-[(5-chloro-2-ethylsulfonylphenyl)methylcarbamoyl]-6-methylphenyl]methyl]piperidin-3-yl]-N-methylcarbamate

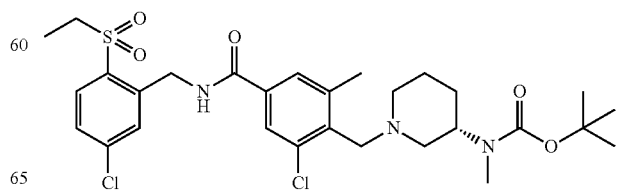

The title compound was synthesized from 5-chloro-2-ethanesulfonyl-benzylamine hydrochloride (Compound a3) under the same conditions as for Compound A-14. However, 3-chloro-5-methyl-4-[[(3S)-3-[methyl-[(2-methylpropan-2-yl)oxycarbonyl]amino]piperidin-1-yl]methyl]benzoic acid (Compound gg10) was used in place of 4-bromo-3-trifluoromethyl-benzoic acid.

Example 532

Compound GG-1

3-Chloro-N-[(5-chloro-2-ethylsulfonylphenyl)methyl]-5-methyl-4-[[(3S)-3-(methylamino)piperidin-1-yl]methyl]benzamide

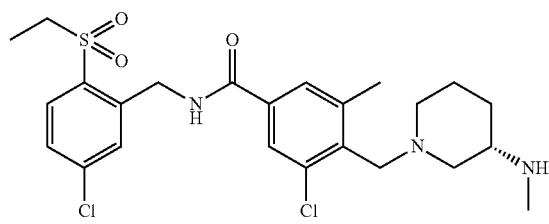 [SMILES: CCS(=O)(=O)c1ccc(Cl)cc1CNC(=O)c1cc(C)c(CN2CCC[C@H](NC)C2)c(Cl)c1]

The title compound was synthesized from tert-butyl N-[(3S)-1-[[2-chloro-4-[(5-chloro-2-ethylsulfonylphenyl)methylcarbamoyl]-6-methylphenyl]methyl]piperidin-3-yl]-N-methylcarbamate (Compound gg11) under the same conditions as for Compound B-1.
LCMS: m/z 512 [M+H]+
HPLC retention time: 0.48 min (analysis condition F)

Example 533

Compound gg12

Ethyl 2-amino-4-methylbenzoate

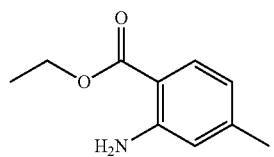

The title compound was synthesized from 2-amino-4-methylbenzoic acid under the same conditions as for Compound b1.

Example 534

Compound gg13

Ethyl 2-amino-5-bromo-4-methylbenzoate

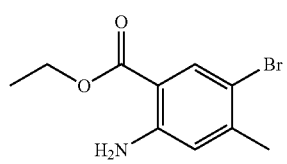

The title compound was synthesized from ethyl 2-amino-4-methylbenzoate (Compound gg12) under the same conditions as for Compound d6. However, NBS was used in place of NCS. The reaction was performed at room temperature.

Example 535

Compound gg14

Ethyl 2-[bis[(2-methylpropan-2-yl)oxycarbonyl]amino]-5-bromo-4-methylbenzoate

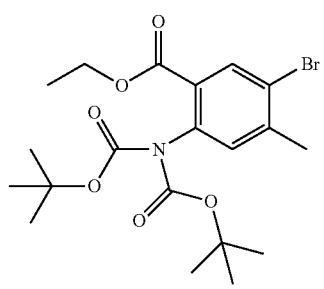 [SMILES: CCOC(=O)c1cc(Br)c(C)cc1N(C(=O)OC(C)(C)C)C(=O)OC(C)(C)C]

4-Dimethylaminopyridine (1.24 g, 10.2 mmol) was added to a solution of ethyl 2-amino-5-bromo-4-methylbenzoate (Compound gg13, 13.1 g, 50.8 mmol) in THF (250 ml), followed by cooling to 0° C. Then, di-tert-butyl dicarbonate (26.6 g, 121.8 mmol) was added, and it was stirred at room temperature for 40 hours. The reaction mixture was concentrated under reduced pressure, and the resultant residue was then purified by silica gel column chromatography (EtOAc/n-hexane) to yield the title compound (21.2 g, 91%) as a colorless solid.
1H-NMR (400 MHz, CDCl$_3$) δ: 8.18 (1H, s), 7.05 (1H, s), 4.31 (2H, q, J=7.2 Hz), 2.43 (3H, s), 1.39 (18H, s), 1.35 (3H, t, J=7.2 Hz).

Example 536

Compound gg15

Ethyl 2-[bis[(2-methylpropan-2-yl)oxycarbonyl]amino]-5-bromo-4-(dibromomethyl)benzoate

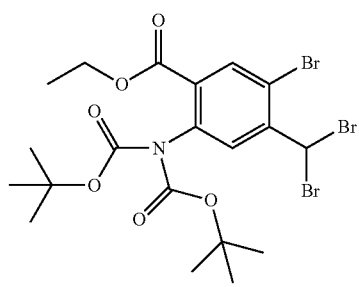 [SMILES: CCOC(=O)c1cc(Br)c(C(Br)Br)cc1N(C(=O)OC(C)(C)C)C(=O)OC(C)(C)C]

The title compound was synthesized from ethyl 2-[bis[(2-methylpropan-2-yl)oxycarbonyl]amino]-5-bromo-4-methylbenzoate (Compound gg14) under the same conditions as for Compound b35.

Example 537

Compound gg16

Ethyl 2-amino-5-bromo-4-(1,3-dioxolan-2-yl)benzoate

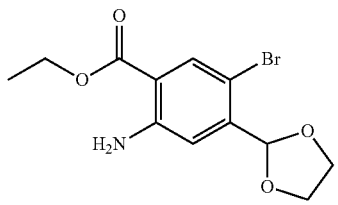 [SMILES: CCOC(=O)c1cc(Br)c(C2OCCO2)cc1N]

Silver(I) nitrate (27.9 g, 164 mmol) was added to a mixed solution of ethyl 2-[bis[(2-methylpropan-2-yl)oxycarbonyl]amino]-5-bromo-4-(dibromomethyl)benzoate (Compound gg15, 20.3 g, 32.9 mmol) in water/acetone (330 ml, 1:2). After one hour of stirring at 65° C., the reaction mixture was extracted with ethyl acetate. The organic layer was sequentially washed with water and brine, and then dried over anhydrous sodium sulfate. The drying agent was removed by filtration, followed by concentration under reduced pressure to yield a mixture of ethyl 2-[bis[(2-methylpropan-2-yl)oxycarbonyl]amino]-5-bromo-4-formylbenzoate and ethyl 2-[(2-methylpropan-2-yl)oxycarbonylamino]-5-bromo-4-formylbenzoate (15.4 g) as a pale yellow solid. Ethylene glycol (0.9 ml, 161 mmol) and p-toluenesulfonic acid (627 mg, 3.29 mmol) were added to a solution of the resultant crude product in toluene (330 ml), followed by stirring under reflux for 15 hours. The reaction mixture was made basic by adding a saturated aqueous solution of sodium bicarbonate, followed by extraction with ethyl acetate. The organic layer was washed with brine, and then dried over anhydrous magnesium sulfate. The drying agent was removed by filtration, followed by concentration under reduced pressure. The resultant residue was purified by silica gel column chromatography (ethyl acetate/n-hexane) to yield the title compound (3.50 g, 34%) as a yellow solid.

1H-NMR (400 MHz, DMSO-$d_6$) δ: 8.03 (1H, s), 6.93 (1H, s), 5.98 (1H, s), 5.78 (2H, brs), 4.33 (2H, q, J=7.1 Hz), 4.05-4.15 (4H, m), 1.39 (3H, t, J=7.1 Hz).

Example 538

Compound gg17

Ethyl 2-amino-4-(1,3-dioxolan-2-yl)-5-ethenylbenzoate

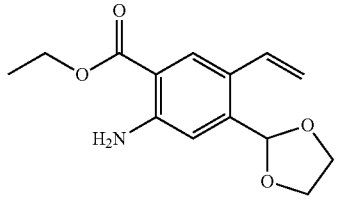 [SMILES: C=Cc1cc(C(=O)OCC)c(N)cc1C1OCCO1]

Tri-n-butyl(ethenyl)tin (1.11 ml, 3.80 mmol) was added to a solution of ethyl 2-amino-5-bromo-4-(1,3-dioxolan-2-yl)benzoate (Compound gg16, 1.00 g, 3.16 mmol), tris(dibenzylideneacetone)dipalladium (145 mg, 0.160 mmol) and tris(2-methylphenyl)phosphine (97.0 mg, 0.320 mmol) in acetonitrile (32 ml), and it was stirred at 90° C. for 15 hours. The reaction mixture was cooled to room temperature, and EtOAc was added. After washing with brine, the organic layer was dried over anhydrous magnesium sulfate. The drying agent was removed by filtration, followed by concentration under reduced pressure. The resultant residue was purified by silica gel column chromatography (EtOAc/n-hexane) to yield the title compound (615 mg, 74%) as a yellow solid.

LCMS: m/z 264 [M+H]$^+$

HPLC retention time: 1.59 min (analysis condition E)

Example 539

Compound gg18

Ethyl 2-amino-4-(1,3-dioxolan-2-yl)-5-ethylbenzoate

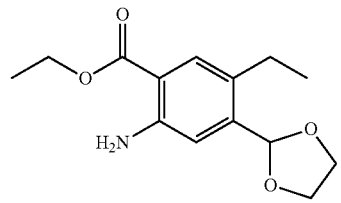 [SMILES: CCOC(=O)c1cc(CC)c(C2OCCO2)cc1N]

The title compound was synthesized from ethyl 2-amino-4-(1,3-dioxolan-2-yl)-5-ethenylbenzoate (Compound gg17) under the same conditions as for Compound bb4.

Example 540

Compound gg19

Ethyl 2-amino-5-ethyl-4-formylbenzoate

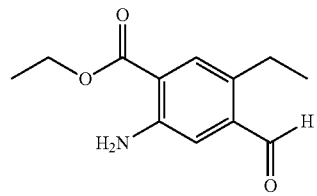 [SMILES: CCOC(=O)c1cc(CC)c(C=O)cc1N]

A mixed solution of N-methylpyrrolidone/water/sulfuric acid (18 ml, 10:1:1) was added to ethyl 2-amino-4-(1,3-dioxolan-2-yl)-5-ethylbenzoate (Compound gg18, 480 mg, 1.81 mmol), and it was stirred at room temperature for 30 minutes. The reaction mixture was diluted with water and then extracted with EtOAc. The organic layer was sequentially washed with a saturated aqueous sodium bicarbonate solution and brine, and dried over anhydrous magnesium sulfate. The drying agent was removed by filtration, followed by concentration under reduced pressure. The resultant residue was purified by silica gel column chromatography (EtOAc/n-hexane) to yield the title compound (370 mg, 92%) as a yellow oily substance.

LCMS: m/z 222 [M+H]$^+$

HPLC retention time: 1.67 min (analysis condition E)

Example 541

Compound gg20

Ethyl 2-amino-3-chloro-5-ethyl-4-formylbenzoate

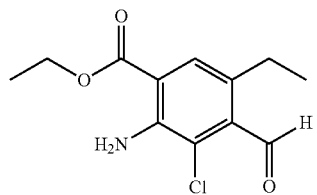 [SMILES: CCOC(=O)c1cc(CC)c(C=O)c(Cl)c1N]

The title compound was synthesized from ethyl 2-amino-5-ethyl-4-formylbenzoate (Compound gg19) under the same conditions as for Compound d6. However, the reaction was performed at room temperature.

Example 542

Compound gg21

Ethyl 3-chloro-5-ethyl-4-formylbenzoate

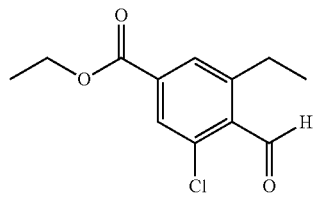 [SMILES: CCOC(=O)c1cc(Cl)c(C=O)c(CC)c1]

The title compound was synthesized from ethyl 2-amino-3-chloro-5-ethyl-4-formylbenzoate (Compound gg20) under the same conditions as for Compound b31.

Example 543

Compound gg22

Ethyl 3-chloro-5-ethyl-4-[[(3S)-3-[methyl-[(2-methylpropan-2-yl)oxycarbonyl]amino]piperidin-1-yl]methyl]benzoate

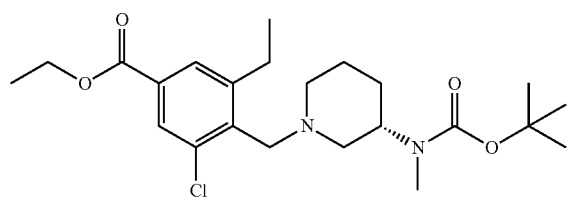

The title compound was synthesized from ethyl 3-chloro-5-ethyl-4-formylbenzoate (Compound gg21) under the same conditions as for Compound b32. However, tert-butyl N-methyl-N-[(3S)-piperidin-3-yl]carbamate was used in place of tert-butyl (S)-1-pyrrolidin-2-ylmethyl-carbamate, and chloroform was used in place of THF as a solvent.

Example 544

Compound gg23

3-Chloro-5-ethyl-4-[[(3S)-3-[methyl-[(2-methylpropan-2-yl)oxycarbonyl]amino]piperidin-1-yl]methyl] benzoic acid

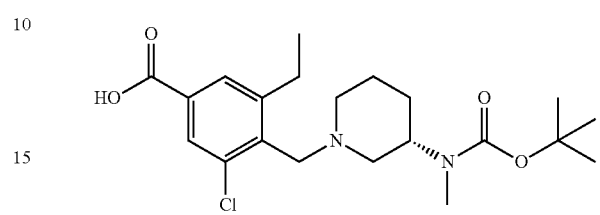

The title compound was synthesized from 3-chloro-5-ethyl-4-[[(3S)-3-[methyl-[(2-methylpropan-2-yl)oxycarbonyl]amino]piperidin-1-yl]methyl]benzoic acid (Compound gg22) under the same conditions as for Compound b8.

Example 545

Compound gg24 tert-Butyl N-[(3S)-1-[[2-chloro-4-[(5-chloro-2-ethylsulfonylphenyl)methylcarbamoyl]-6-ethylphenyl] methyl]piperidin-3-yl]-N-methylcarbamate

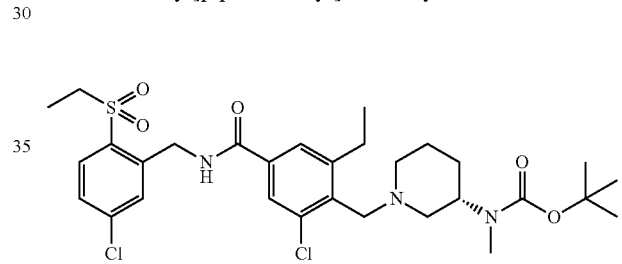

The title compound was synthesized from 5-chloro-2-ethanesulfonyl-benzylamine hydrochloride (Compound a3) under the same conditions as for Compound A-14. However, 3-chloro-5-ethyl-4-[[(3S)-3-[methyl-[(2-methylpropan-2-yl)oxycarbonyl]amino]piperidin-1-yl]methyl]benzoic acid (Compound gg23) was used in place of 4-bromo-3-trifluoromethyl-benzoic acid.

Example 546

Compound GG-2

3-Chloro-N-[(5-chloro-2-ethylsulfonylphenyl)methyl]-5-ethyl-4-[[(3S)-3-(methylamino)piperidin-1-yl]methyl]benzamide

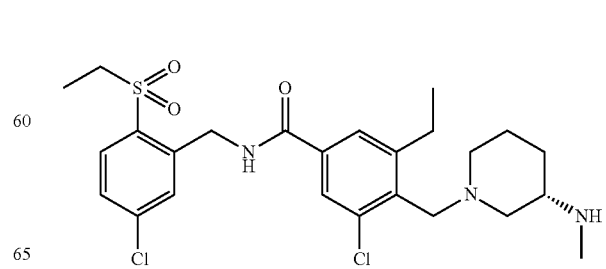

The title compound was synthesized from tert-butyl N-[(3S)-1-[[2-chloro-4-[(5-chloro-2-ethylsulfonylphenyl)methylcarbamoyl]-6-ethylphenyl]methyl]piperidin-3-yl]-N-methylcarbamate (Compound gg24) under the same conditions as for Compound B-1.
LCMS: m/z 526 [M+H]$^+$
HPLC retention time: 0.50 min (analysis condition F)

Example 547

Compound gg25

Ethyl 2-amino-5-bromo-4-formylbenzoate

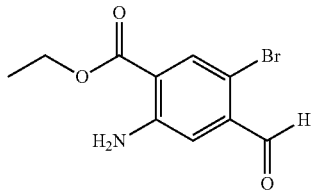

Silver(I) nitrate (9.7 g, 56.8 mmol) was added to a mixed solution of ethyl 2-[bis[(2-methylpropan-2-yl)oxycarbonyl]amino]-5-bromo-4-(dibromomethyl)benzoate (Compound gg15, 7.00 g, 11.4 mmol) in water/acetone (112 ml, 1:2). After one hour of stirring at 65° C., the reaction mixture was extracted with EtOAc. The organic layer was sequentially washed with water and brine, and then dried over anhydrous sodium sulfate. The drying agent was removed by filtration, followed by concentration under reduced pressure to yield a mixture of ethyl 2-[bis[(2-methylpropan-2-yl)oxycarbonyl]amino]-5-bromo-4-formylbenzoate and ethyl 2-[(2-methylpropan-2-yl)oxycarbonylamino]-5-bromo-4-formylbenzoate (3.53 g) as a pale brown solid. A 4 M hydrochloric acid/1,4-dioxane solution (9.4 ml) was added to a solution of the resultant crude product in DCM (94 ml), and it was stirred at room temperature for 1 hour. The reaction mixture was made basic by adding a saturated aqueous solution of sodium bicarbonate, followed by extraction with EtOAc. The organic layer was washed with brine, and then dried over anhydrous magnesium sulfate. The drying agent was removed by filtration, followed by concentration under reduced pressure. The resultant solid was recrystallized from a mixed solvent of DCM and n-hexane to yield the title compound (1.37 g, 51%, two steps) as a yellow solid.
LCMS: m/z 272 [M+H]$^+$
HPLC retention time: 1.79 min (analysis condition E)

Example 548

Compound gg26

Ethyl 2-amino-5-bromo-3-chloro-4-formylbenzoate

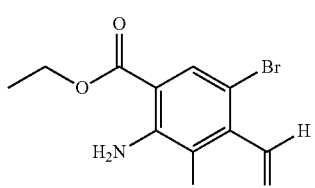

The title compound was synthesized from ethyl 2-amino-5-bromo-4-formylbenzoate (Compound gg25) under the same conditions as for Compound d6. The reaction was performed at room temperature.

Example 549

Compound gg27

Ethyl 3-bromo-5-chloro-4-formylbenzoate

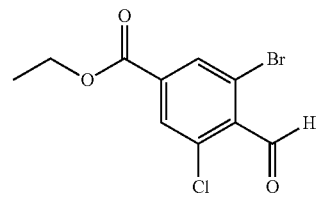

The title compound was synthesized from ethyl 2-amino-5-bromo-3-chloro-4-formylbenzoate (Compound gg26) under the same conditions as for Compound b31.

Example 550

Compound gg28

Ethyl 3-chloro-5-ethenyl-4-formylbenzoate

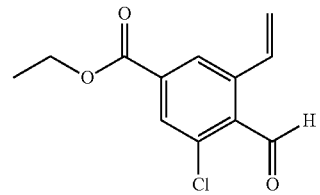 [SMILES: C=Cc1cc(C(=O)OCC)cc(Cl)c1C=O]

The title compound was synthesized from ethyl 3-bromo-5-chloro-4-formylbenzoate (Compound gg27) under the same conditions as for Compound gg17.

Example 551

Compound gg29

Ethyl 3-chloro-5-ethenyl-4-[[(3S)-3-[methyl-[(2-methylpropan-2-yl)oxycarbonyl]amino]piperidin-1-yl]methyl]benzoate

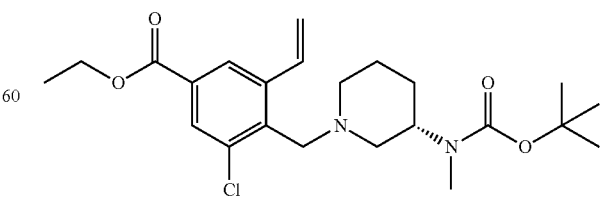

The title compound was synthesized from ethyl 3-chloro-5-ethenyl-4-formylbenzoate (Compound gg28) under the same conditions as for Compound b32. However, tert-butyl N-methyl-N-[(3S)-piperidin-3-yl]carbamate was used in place of tert-butyl (S)-1-pyrrolidin-2-ylmethyl-carbamate, and chloroform was used in place of THF as a solvent.

Example 552

Compound gg30

3-Chloro-5-ethenyl-4-[[(3S)-3-[methyl-[(2-methyl-propan-2-yl)oxycarbonyl]amino]piperidin-1-yl]methyl]benzoic acid

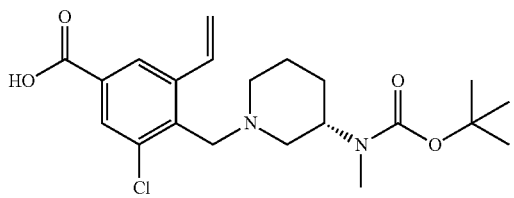 [SMILES: C=Cc1cc(C(=O)O)cc(Cl)c1CN1CCC[C@H](N(C)C(=O)OC(C)(C)C)C1]

The title compound was synthesized from ethyl 3-chloro-5-ethenyl-4-[[(3S)-3-[methyl-[(2-methylpropan-2-yl)oxycarbonyl]amino]piperidin-1-yl]methyl]benzoate (Compound gg29) under the same conditions as for Compound b8.

Example 553

Compound gg31 tert-Butyl N-[(3S)-1-[[2-chloro-4-[(5-chloro-2-ethyl-sulfonylphenyl)methylcarbamoyl]-6-ethenylphenyl]methyl]piperidin-3-yl]-N-methylcarbamate

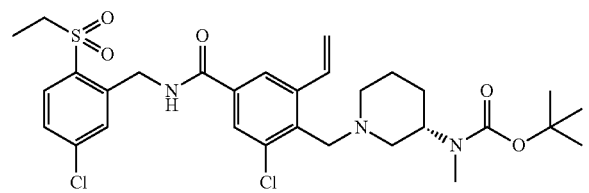 [SMILES: C=Cc1cc(C(=O)NCc2cc(Cl)ccc2S(=O)(=O)CC)cc(Cl)c1CN1CCC[C@H](N(C)C(=O)OC(C)(C)C)C1]

The title compound was synthesized from 5-chloro-2-ethanesulfonyl-benzylamine hydrochloride (Compound a3) under the same conditions as for Compound A-14. However, 3-chloro-5-ethenyl-4-[[(3S)-3-[methyl-[(2-methylpropan-2-yl)oxycarbonyl]amino]piperidin-1-yl]methyl]benzoic acid (Compound gg30) was used in place of 4-bromo-3-trifluoromethyl-benzoic acid.

Example 554

Compound GG-3

3-Chloro-N-[(5-chloro-2-ethylsulfonylphenyl)methyl]-5-ethenyl-4-[[(3S)-3-(methylamino)piperidin-1-yl]methyl]benzamide

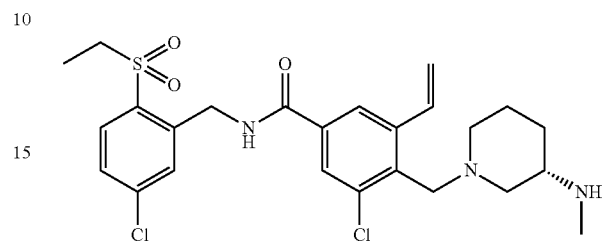

The title compound was synthesized from tert-butyl N-[(3S)-1-[[2-chloro-4-[(5-chloro-2-ethylsulfonylphenyl)methylcarbamoyl]-6-ethenylphenyl]methyl]piperidin-3-yl]-N-methylcarbamate (Compound gg31) under the same conditions as for Compound B-1.
LCMS: m/z 524 [M+H]+
HPLC retention time: 0.51 min (analysis condition F)

Example 555

Compound gg32

N-(2-Bromo-5-chloro-4-methoxyphenyl)acetamide

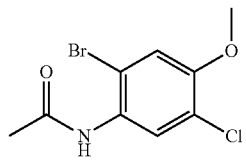

The title compound was synthesized from 3-chloro-4-methoxyaniline under the same conditions as for Compound gg1.

Example 556

Compound gg33

2-Acetamido-4-chloro-5-methoxybenzoic acid

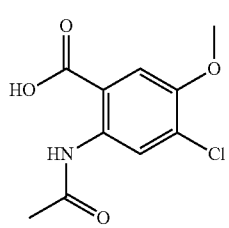 [SMILES: COc1cc(C(=O)O)c(NC(C)=O)cc1Cl]

The title compound was synthesized from N-(2-bromo-5-chloro-4-methoxyphenyl)acetamide (Compound gg32) under the same conditions as for Compound gg2.

Example 557

Compound gg34

2-Amino-4-chloro-5-methoxybenzoic acid

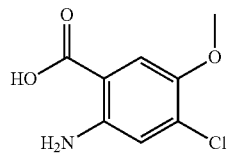

The title compound was synthesized from 2-acetamido-4-chloro-5-methoxybenzoic acid (Compound gg33) under the same conditions as for Compound gg3.

Example 558

Compound gg35

Ethyl 2-amino-4-chloro-5-methoxybenzoate

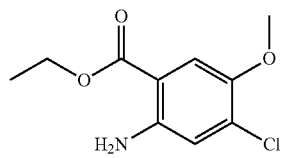

The title compound was synthesized from 2-amino-4-chloro-5-methoxybenzoic acid (Compound gg34) under the same conditions as for Compound b1.

Example 559

Compound gg36

Ethyl 2-amino-4-formyl-5-methoxybenzoate

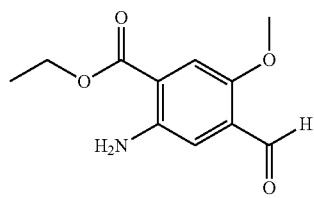 [SMILES: CCOC(=O)c1cc(OC)c(C=O)cc1N]

The title compound was synthesized from ethyl 2-amino-4-chloro-5-methoxybenzoate (Compound gg35) under the same conditions as for Compounds b28, b29 and b30. However, under the b29 conditions, AD-mix-β was used in place of AD-mix-α.

Example 560

Compound gg37

Ethyl 2-amino-4-(1,3-dioxolan-2-yl)-5-methoxybenzoate

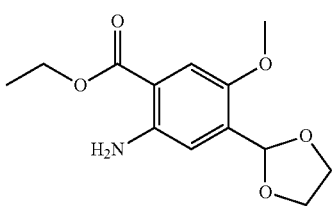 [SMILES: CCOC(=O)c1cc(OC)c(C2OCCO2)cc1N]

The title compound was synthesized from ethyl 2-amino-4-formyl-5-methoxybenzoate (Compound gg36) under the same conditions as for Compound gg6.

Example 561

Compound gg38

Ethyl 2-amino-4-formyl-5-methoxybenzoate

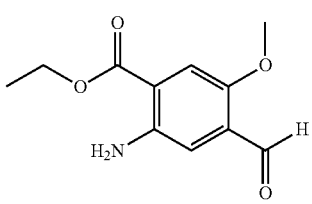

The title compound was synthesized from ethyl 2-amino-4-(1,3-dioxolan-2-yl)-5-methoxybenzoate (Compound gg37) under the same conditions as for Compound gg19. However, the reaction was performed at a temperature of 40° C.

Example 562

Compound gg39

Ethyl 2-amino-3-chloro-4-formyl-5-methoxybenzoate

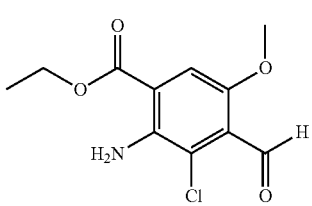 [SMILES: CCOC(=O)c1cc(OC)c(C=O)c(Cl)c1N]

The title compound was synthesized from ethyl 2-amino-4-formyl-5-methoxybenzoate (Compound gg38) under the same conditions as for Compound d6.

Example 563

Compound gg40

Ethyl 3-chloro-4-formyl-5-methoxybenzoate

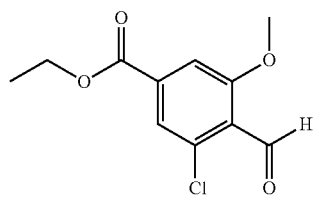 [SMILES: CCOC(=O)c1cc(Cl)c(C=O)c(OC)c1]

The title compound was synthesized from ethyl 2-amino-3-chloro-4-formyl-5-methoxybenzoate (Compound gg39) under the same conditions as for Compound b31.

Example 564

Compound gg41

Ethyl 3-chloro-5-methoxy-4-[[(3S)-3-[methyl-[(2-methylpropan-2-yl)oxycarbonyl]amino]piperidin-1-yl]methyl]benzoate

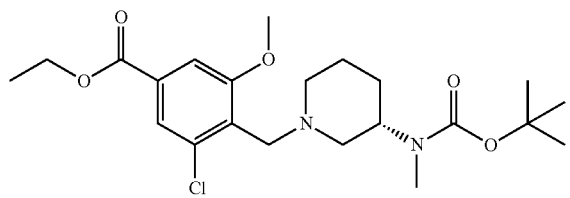 [SMILES: CCOC(=O)c1cc(Cl)c(CN2CCC[C@H](N(C)C(=O)OC(C)(C)C)C2)c(OC)c1]

The title compound was synthesized from ethyl 3-chloro-4-formyl-5-methoxybenzoate (Compound gg40) under the same conditions as for Compound b32. However, tert-butyl N-methyl-N-[(3S)-piperidin-3-yl]carbamate was used in place of tert-butyl (S)-1-pyrrolidin-2-ylmethyl-carbamate, and chloroform was used in place of THF as a solvent.

Example 565

Compound gg42

3-Chloro-5-methoxy-4-[[(3S)-3-[methyl-[(2-methylpropan-2-yl)oxycarbonyl]amino]piperidin-1-yl]methyl]benzoic acid

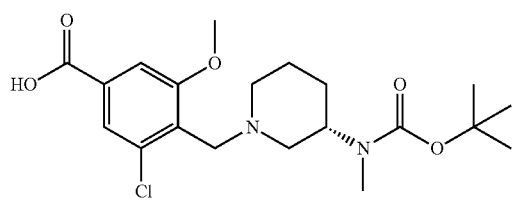 [SMILES: COc1cc(C(=O)O)cc(Cl)c1CN1CCC[C@H](N(C)C(=O)OC(C)(C)C)C1]

The title compound was synthesized from ethyl 3-chloro-5-methoxy-4-[[(3S)-3-[methyl-[(2-methylpropan-2-yl)oxycarbonyl]amino]piperidin-1-yl]methyl]benzoate (Compound gg41) under the same conditions as for Compound b8.

Example 566

Compound gg43 tert-Butyl N-[(3S)-1-[[2-chloro-4-[(5-chloro-2-ethylsulfonylphenyl)methylcarbamoyl]-6-methoxyphenyl]methyl]piperidin-3-yl]-N-methylcarbamate

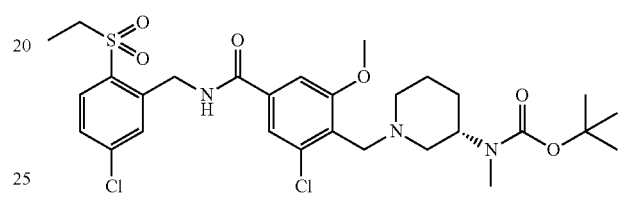

The title compound was synthesized from 5-chloro-2-ethanesulfonyl-benzylamine hydrochloride (Compound a3) under the same conditions as for Compound A-14. However, 3-chloro-5-methoxy-4-[[(3S)-3-[methyl-[(2-methylpropan-2-yl)oxycarbonyl]amino]piperidin-1-yl]methyl]benzoic acid (Compound gg42) was used in place of 4-bromo-3-trifluoromethyl-benzoic acid, and DCM was used in place of DMF as a solvent.

Example 567

Compound GG-4

3-Chloro-N-[(5-chloro-2-ethylsulfonylphenyl)methyl]-5-methoxy-4-[[(3S)-3-(methylamino)piperidin-1-yl]methyl]benzamide

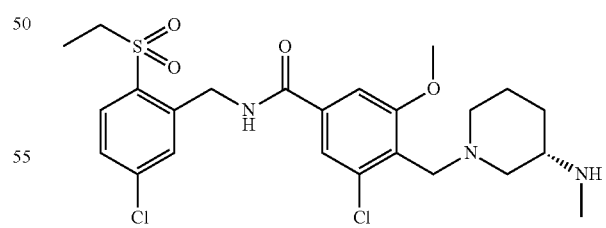

The title compound was synthesized from tert-butyl N-[(3S)-1-[[2-chloro-4-[(5-chloro-2-ethylsulfonylphenyl)methylcarbamoyl]-6-methoxyphenyl]methyl]piperidin-3-yl]-N-methylcarbamate (Compound gg43) under the same conditions as for Compound B-1.

LCMS: m/z 528 [M+H]$^+$

HPLC retention time: 0.41 min (analysis condition F)

Example 568

Compound gg44

3-Chloro-5-methoxy-4-[[4-[(2-methylpropan-2-yl)oxycarbonyl]piperazin-1-yl]methyl]benzoic acid

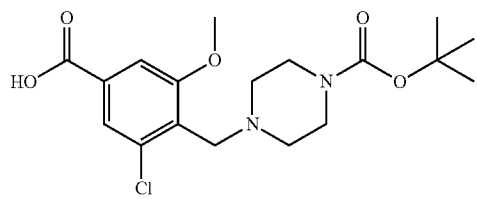 [SMILES: COc1cc(C(=O)O)cc(Cl)c1CN1CCN(C(=O)OC(C)(C)C)CC1]

The title compound was synthesized from ethyl 3-chloro-4-formyl-5-methoxybenzoate (Compound gg40) under the same conditions as for Compounds gg41 and gg42. However, under the gg41 conditions, tert-butyl piperazine-1-carboxylate was used in place of tert-butyl N-methyl-N-[(3S)-piperidin-3-yl]carbamate.

Example 569

Compound GG-5

3-Chloro-N-[(5-chloro-2-ethylsulfonylphenyl)methyl]-5-methoxy-4-(piperazin-1-ylmethyl)benzamide

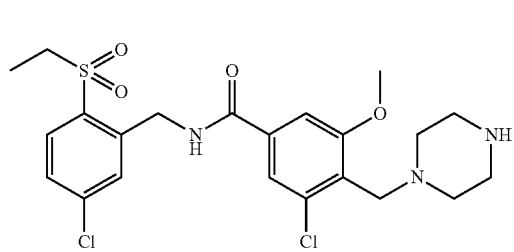 [SMILES: CCS(=O)(=O)c1ccc(Cl)cc1CNC(=O)c1cc(Cl)c(CN2CCNCC2)c(OC)c1]

The title compound was synthesized from 5-chloro-2-ethanesulfonyl-benzylamine hydrochloride (Compound a3) under the same conditions as for Compounds gg43 and GG-4. However, under the gg43 conditions, 3-chloro-5-methoxy-4-[[4-[(2-methylpropan-2-yl)oxycarbonyl]piperazin-1-yl]methyl]benzoic acid (Compound gg44) was used in place of 3-chloro-5-methoxy-4-[[(3S)-3-[methyl-[(2-methylpropan-2-yl)oxycarbonyl]amino]piperidin-1-yl]methyl]benzoic acid (Compound gg42).

LCMS: m/z 500 [M+H]$^+$

HPLC retention time: 0.44 min (analysis condition F)

Example 570

Compound GG-6

3-Chloro-N-[(5-chloro-2-ethylsulfonylphenyl)methyl]-5-methoxy-4-[(4-methylpiperazin-1-yl)methyl]benzamide

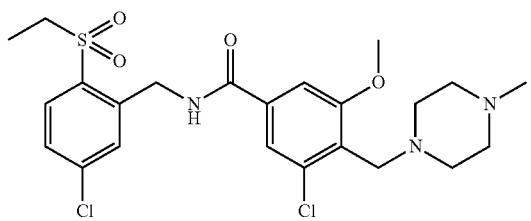 [SMILES: CCS(=O)(=O)c1ccc(Cl)cc1CNC(=O)c1cc(Cl)c(CN2CCN(C)CC2)c(OC)c1]

The title compound was synthesized from 3-chloro-N-[(5-chloro-2-ethylsulfonylphenyl)methyl]-5-methoxy-4-(piperazin-1-ylmethyl)benzamide (Compound GG-5) under the same conditions as for Compound B-2.

LCMS: m/z 514 [M+H]$^+$

HPLC retention time: 0.47 min (analysis condition F)

Example 571

Compound K-1

N-[(5-Chloro-2-ethylsulfonylphenyl)methyl]-3-cyano-4-[[(3S)-3-(methylamino)piperidin-1-yl]methyl]-5-(trifluoromethyl)benzamide

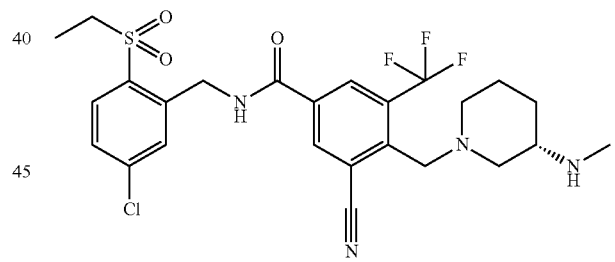

Copper(I) cyanide (12.9 mg, 0.144 mmol) was added to a solution of (S)-3-bromo-N-(5-chloro-2-(ethylsulfonyl)benzyl)-4-((3-(methylamino)piperidin-1-yl)methyl)-5-(trifluoromethyl)benzamide (Compound E-8, 73.1 mg, 0.120 mmol) in DMF (1.0 ml) at room temperature, and it was stirred at 130° C. to 150° C. under microwave irradiation for 30 minutes. After cooling to room temperature, ethyl acetate was added to the reaction mixture, and the organic layer was sequentially washed with a saturated aqueous sodium bicarbonate solution, water and brine, and then dried over anhydrous sodium sulfate. The drying agent was removed by filtration, followed by concentration under reduced pressure. The resultant residue was purified by silica gel column chromatography (MeOH/DCM) to yield the title compound (39.7 mg, 60%) as a colorless foamy substance.

LCMS: m/z 557 [M+H]$^+$

HPLC retention time: 0.54 min (analysis condition A)

Example 572

Compound K-2

N-[(5-Chloro-2-ethylsulfonylphenyl)methyl]-3-methoxy-4-[[(3S)-3-(methylamino)piperidin-1-yl]methyl]-5-(trifluoromethyl)benzamide

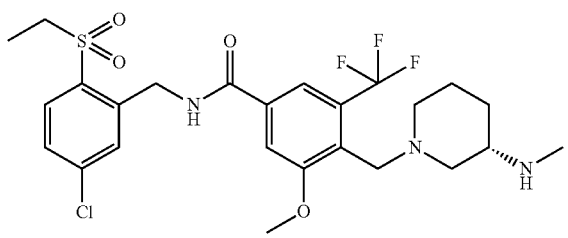

Sodium methoxide (41.5 mg, 0.768 mmol) was added to a solution of (S)-3-bromo-N-(5-chloro-2-(ethylsulfonyl)benzyl)-4-((3-(methylamino)piperidin-1-yl)methyl)-5-(trifluoromethyl)benzamide (Compound E-8, 104 mg, 0.171 mmol) in MeOH (16 ml) at room temperature, and it was stirred for 30 minutes at 110° C. to 130° C. under microwave irradiation. After cooling to room temperature, ethyl acetate was added to the reaction mixture, and the organic layer was sequentially washed with water and brine, and then dried over anhydrous sodium sulfate. The drying agent was removed by filtration, followed by concentration under reduced pressure. The resultant residue was purified by preparative HPLC (water/acetonitrile, 0.05% TFA) to yield the title compound (84.4 mg, 88%) as a colorless foamy substance.

LCMS: m/z 562 [M+H]$^+$

HPLC retention time: 0.43 min (analysis condition A)

Example 573

Compound K-3

N-[(5-Chloro-2-ethylsulfonylphenyl)methyl]-3-cyano-4-(piperazin-1-ylmethyl)-5-(trifluoromethyl)benzamide

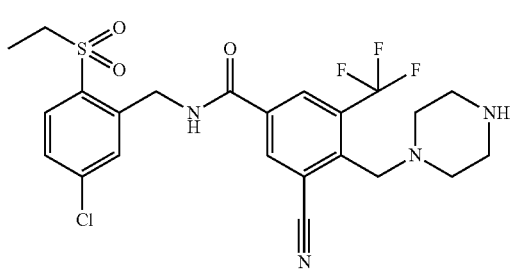 [SMILES: CCS(=O)(=O)c1ccc(Cl)cc1CNC(=O)c1cc(C#N)c(CN2CCNCC2)c(C(F)(F)F)c1]

The title compound was synthesized from 3-bromo-N-[(5-chloro-2-ethylsulfonylphenyl)methyl]-4-(piperazin-1-ylmethyl)-5-(trifluoromethyl)benzamide (Compound EE-1) under the same conditions as for Compound K-1.

LCMS: m/z 529 [M+H]$^+$

HPLC retention time: 0.50 min (analysis condition A)

Example 574

Compound K-4

N-[(5-Chloro-2-ethylsulfonylphenyl)methyl]-3-methoxy-4-(piperazin-1-ylmethyl)-5-(trifluoromethyl)benzamide

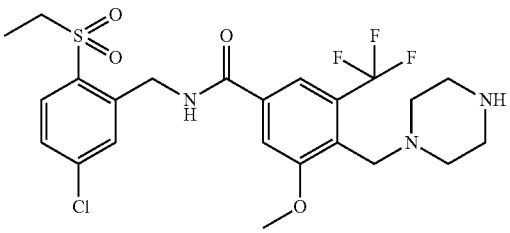 [SMILES: CCS(=O)(=O)c1ccc(Cl)cc1CNC(=O)c1cc(OC)c(CN2CCNCC2)c(C(F)(F)F)c1]

The title compound was synthesized from 3-bromo-N-[(5-chloro-2-ethylsulfonylphenyl)methyl]-4-(piperazin-1-ylmethyl)-5-(trifluoromethyl)benzamide (Compound EE-1) under the same conditions as for Compound K-2. However, the reaction was performed with the addition of copper iodide.

LCMS: m/z 534 [M+H]$^+$

HPLC retention time: 0.47 min (analysis condition A)

Example 575

Compound K-5

N-[(5-Chloro-2-ethylsulfonylphenyl)methyl]-3-cyano-4-[(4-methylpiperazin-1-yl)methyl]-5-(trifluoromethyl)benzamide

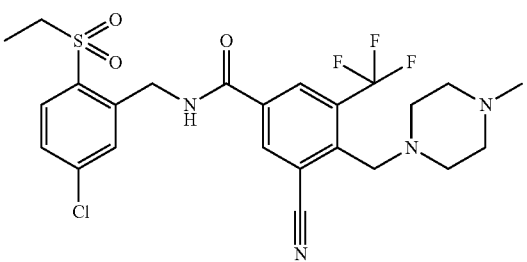 [SMILES: CCS(=O)(=O)c1ccc(Cl)cc1CNC(=O)c1cc(C#N)c(CN2CCN(C)CC2)c(C(F)(F)F)c1]

The title compound was synthesized from 3-bromo-N-[(5-chloro-2-ethylsulfonylphenyl)methyl]-4-[(4-methylpiperazin-1-yl)methyl]-5-(trifluoromethyl)benzamide (Compound EE-2) under the same conditions as for Compound K-1.

LCMS: m/z 543 [M+H]$^+$

HPLC retention time: 0.50 min (analysis condition A)

Example 576

Compound K-6

N-[(5-Chloro-2-ethylsulfonylphenyl)methyl]-3-methoxy-4-[(4-methylpiperazin-1-yl)methyl]-5-(trifluoromethyl)benzamide

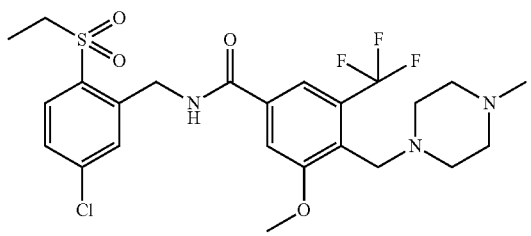 [SMILES: CCS(=O)(=O)c1ccc(Cl)cc1CNC(=O)c1cc(OC)c(CN2CCN(C)CC2)c(C(F)(F)F)c1]

The title compound was synthesized from 3-bromo-N-[(5-chloro-2-ethylsulfonylphenyl)methyl]-4-[(4-methylpiperazin-1-yl)methyl]-5-(trifluoromethyl)benzamide (Compound EE-2) under the same conditions as for Compound K-2. However, the reaction was performed with the addition of copper iodide.

LCMS: m/z 548 [M+H]$^+$

HPLC retention time: 0.50 min (analysis condition A)

Example 577

Compound K-7

4-[[(3R)-3-Aminopyrrolidin-1-yl]methyl]-N-[(5-chloro-2-ethylsulfonylphenyl)methyl]-3-methoxy-5-(trifluoromethyl)benzamide

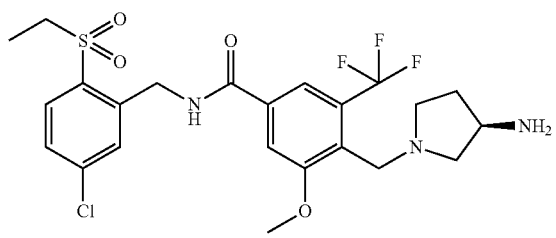 [SMILES: CCS(=O)(=O)c1ccc(Cl)cc1CNC(=O)c1cc(OC)c(CN2CC[C@@H](N)C2)c(C(F)(F)F)c1]

The title compound was synthesized from 4-[[(3R)-3-aminopyrrolidin-1-yl]methyl]-3-bromo-N-[(5-chloro-2-ethylsulfonylphenyl)methyl]-5-(trifluoromethyl)benzamide (Compound E-2) under the same conditions as for Compound K-2. However, the reaction was performed with the addition of copper iodide.

LCMS: m/z 534 [M+H]$^+$

HPLC retention time: 1.08 min (analysis condition D)

Example 578

Compound k1

Ethyl 2-amino-4-formyl-3-methyl-5-(trifluoromethyl)benzoate

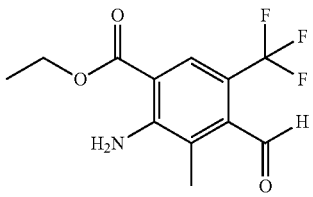 [SMILES: CCOC(=O)c1cc(C(F)(F)F)c(C=O)c(C)c1N]

Potassium trifluoro(methyl)borate (430 mg, 3.53 mmol), butyldi-1-adamanthylphosphine (63.3 mg, 0.176 mmol), potassium carbonate (731 mg, 5.29 mmol) and palladium(II) acetate (19.8 mg, 0.0880 mmol) were added to a mixed solution of ethyl 2-amino-3-bromo-4-formyl-5-(trifluoromethyl)benzoate (Compound e1, 600 mg, 1.76 mmol) in toluene (6.0 ml) and water (2.0 ml) at room temperature, and it was stirred at 90° C. for 15 hours. After cooling to room temperature, water was added to the reaction mixture, followed by extraction with ethyl acetate. The organic layer was washed with brine and then dried over anhydrous sodium sulfate. The drying agent was removed by filtration, followed by concentration under reduced pressure. The resultant residue was purified by silica gel column chromatography (ethyl acetate/n-hexane) to yield the title compound (203 mg, 42%) as a pale yellow solid.

LCMS: m/z 276 [M+H]$^+$

HPLC retention time: 0.87 min (analysis condition A)

Example 579

Compound k2

Ethyl 4-formyl-3-methyl-5-(trifluoromethyl)benzoate

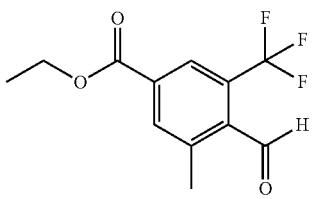 [SMILES: CCOC(=O)c1cc(C)c(C=O)c(C(F)(F)F)c1]

The title compound was synthesized from ethyl 2-amino-4-formyl-3-methyl-5-(trifluoromethyl)benzoate (Compound k1) under the same conditions as for Compound b31.

Example 580

Compound k3

4-Formyl-3-methyl-5-(trifluoromethyl)benzoic acid

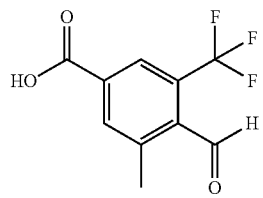 [SMILES: Cc1cc(C(=O)O)cc(C(F)(F)F)c1C=O]

The title compound was synthesized from ethyl 4-formyl-3-methyl-5-(trifluoromethyl)benzoate (Compound k2) under the same conditions as for Compound b8.

Example 581

Compound k4

N-[(5-Chloro-2-ethylsulfonylphenyl)methyl]-4-formyl-3-methyl-5-(trifluoromethyl)benzamide

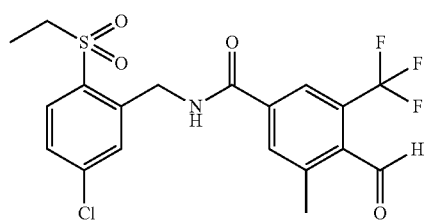 [SMILES: CCS(=O)(=O)c1ccc(Cl)cc1CNC(=O)c1cc(C)c(C=O)c(C(F)(F)F)c1]

The title compound was synthesized from (5-chloro-2-ethylsulfonylphenyl)methanamine hydrochloride (Compound a3) under the same conditions as for Compound bb10. However, 4-formyl-3-methyl-5-(trifluoromethyl)benzoic acid (Compound k3) was used in place of 4-[[4-[(2-methylpropan-2-yl)oxycarbonyl]piperazin-1-yl]methyl]-3-(trifluoromethyl)benzoic acid (Compound b3).

Example 582

Compound k5 tert-Butyl N-[(3S)-1-[[4-[(5-chloro-2-ethylsulfonylphenyl)methylcarbamoyl]-2-methyl-6-(trifluoromethyl)phenyl]methyl]piperidin-3-yl]-N-methylcarbamate

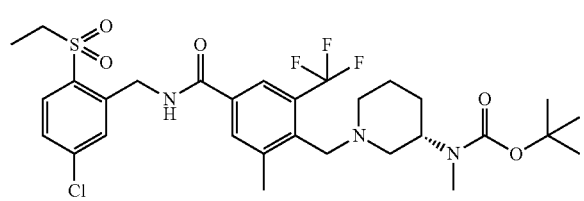 [SMILES: CCS(=O)(=O)c1ccc(Cl)cc1CNC(=O)c1cc(C)c(CN2CCC[C@H](N(C)C(=O)OC(C)(C)C)C2)c(C(F)(F)F)c1]

The title compound was synthesized from N-[(5-chloro-2-ethylsulfonylphenyl)methyl]-4-formyl-3-methyl-5-(trifluoromethyl)benzamide (Compound k4) under the same conditions as for Compound b32. However, tert-butyl N-methyl-N-[(3S)-piperidin-3-yl]carbamate was used in place of tert-butyl (S)-1-pyrrolidin-2-ylmethylcarbamate, and chloroform was used in place of THF as a solvent.

Example 583

Compound K-8

N-[(5-Chloro-2-ethylsulfonylphenyl)methyl]-3-methyl-4-[[(3S)-3-(methylamino)piperidin-1-yl]methyl]-5-(trifluoromethyl)benzamide

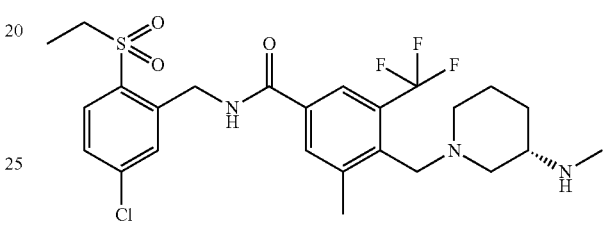

The title compound was synthesized from tert-butyl N-[(3S)-1-[[4-[(5-chloro-2-ethylsulfonylphenyl)methylcarbamoyl]-2-methyl-6-(trifluoromethyl)phenyl]methyl]piperidin-3-yl]-N-methylcarbamate (Compound k5) under the same conditions as for Compound B-57.

LCMS: m/z 546 [M+H]$^+$

HPLC retention time: 0.54 min (analysis condition A)

Example 584

Compound K-9

N-[(5-Chloro-2-ethylsulfonylphenyl)methyl]-3-methyl-4-(piperazin-1-ylmethyl)-5-(trifluoromethyl)benzamide

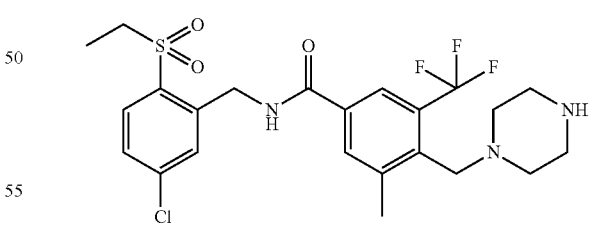

The title compound was synthesized from N-[(5-chloro-2-ethylsulfonylphenyl)methyl]-4-formyl-3-methyl-5-(trifluoromethyl)benzamide (Compound k4) under the same conditions as for Compounds k5 and K-8. However, tert-butyl piperazine-1-carboxylate was used in place of tert-butyl N-methyl-N-[(3S)-piperidin-3-yl]carbamate under the conditions for Compound k5.

LCMS: m/z 518 [M+H]$^+$

HPLC retention time: 0.52 min (analysis condition A)

Example 585

Compound K-10

N-[(5-Chloro-2-ethylsulfonylphenyl)methyl]-3-methyl-4-[(4-methylpiperazin-1-yl)methyl]-5-(trifluoromethyl)benzamide

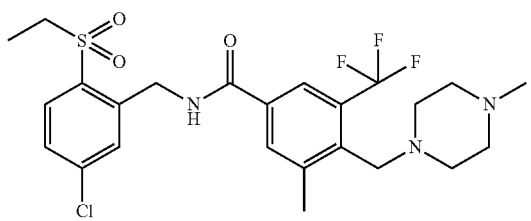

The title compound was synthesized from N-[(5-chloro-2-ethylsulfonylphenyl)methyl]-3-methyl-4-(piperazin-1-ylmethyl)-5-(trifluoromethyl)benzamide (Compound K-9) under the same conditions as for Compound B-2.
LCMS: m/z 532 [M+H]$^+$
HPLC retention time: 0.52 min (analysis condition A)

Example 586

Compound k6

Ethyl 3-bromo-4-[[(3S)-3-[methyl-[(2-methylpropan-2-yl)oxycarbonyl]amino]piperidin-1-yl]methyl]-5-(trifluoromethyl)benzoate

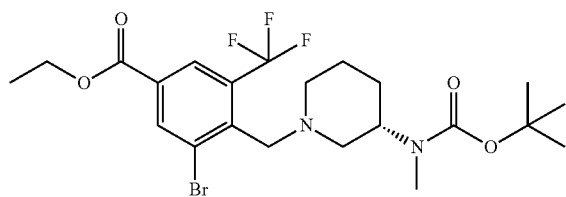 [SMILES: CCOC(=O)c1cc(Br)c(CN2CCC[C@H](N(C)C(=O)OC(C)(C)C)C2)c(C(F)(F)F)c1]

The title compound was synthesized from ethyl 3-bromo-4-formyl-5-(trifluoromethyl)benzoate (Compound e2) under the same conditions as for Compound b32. However, tert-butyl N-methyl-N-[(3S)-piperidin-3-yl]carbamate was used in place of tert-butyl (S)-1-pyrrolidin-2-ylmethyl-carbamate, and chloroform was used in place of THF as a solvent.

Example 587

Compound k7

Ethyl 3-ethenyl-4-[[(3S)-3-[methyl-[(2-methylpropan-2-yl)oxycarbonyl]amino]piperidin-1-yl]methyl]-5-(trifluoromethyl)benzoate

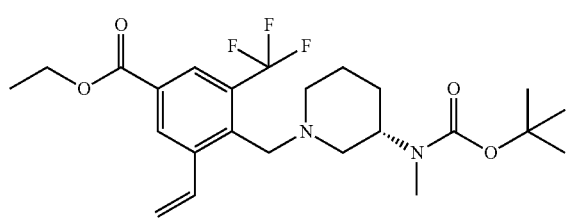 [SMILES: C=Cc1cc(C(=O)OCC)cc(C(F)(F)F)c1CN1CCC[C@H](N(C)C(=O)OC(C)(C)C)C1]

The title compound was synthesized from ethyl 3-bromo-4-[[(3S)-3-[methyl-[(2-methylpropan-2-yl)oxycarbonyl]amino]piperidin-1-yl]methyl]-5-(trifluoromethyl)benzoate (Compound k6) under the same conditions as for Compound k1. However, potassium trifluoro(vinyl)borate was used in place of potassium trifluoro(methyl)borate.

Example 588

Compound k8

3-Ethenyl-4-[[(3S)-3-[methyl-[(2-methylpropan-2-yl)oxycarbonyl]amino]piperidin-1-yl]methyl]-5-(trifluoromethyl)benzoic acid

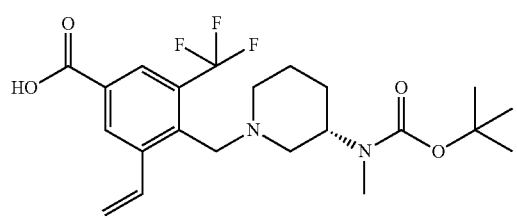 [SMILES: C=Cc1cc(C(=O)O)cc(C(F)(F)F)c1CN1CCC[C@H](N(C)C(=O)OC(C)(C)C)C1]

The title compound was synthesized from ethyl 3-ethenyl-4-[[(3S)-3-[methyl-[(2-methylpropan-2-yl)oxycarbonyl]amino]piperidin-1-yl]methyl]-5-(trifluoromethyl)benzoate (Compound k7) under the same conditions as for Compound b8.

Example 589

Compound k9 tert-Butyl N-[(3S)-1-[[4-[(5-chloro-2-ethylsulfonylphenyl)methylcarbamoyl]-2-ethenyl-6-(trifluoromethyl)phenyl]methyl]piperidin-3-yl]-N-methylcarbamate

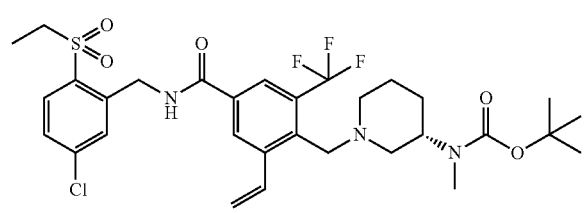 [SMILES: C=Cc1cc(C(=O)NCc2cc(Cl)ccc2S(=O)(=O)CC)cc(C(F)(F)F)c1CN1CCC[C@H](N(C)C(=O)OC(C)(C)C)C1]

The title compound was synthesized from (5-chloro-2-ethylsulfonylphenyl)methanamine hydrochloride (Compound a3) under the same conditions as for Compound bb10. However, 3-ethenyl-4-[[(3S)-3-[methyl-[(2-methylpropan-2-yl)oxycarbonyl]amino]piperidin-1-yl]methyl]-5-(trifluoromethyl)benzoic acid (Compound k8) was used in place of 4-[[4-[(2-methylpropan-2-yl)oxycarbonyl]piperazin-1-yl]methyl]-3-(trifluoromethyl)benzoic acid (Compound b3).

Example 590

Compound K-11

N-[(5-Chloro-2-ethylsulfonylphenyl)methyl]-3-ethenyl-4-[[(3S)-3-(methylamino)piperidin-1-yl]methyl]-5-(trifluoromethyl)benzamide

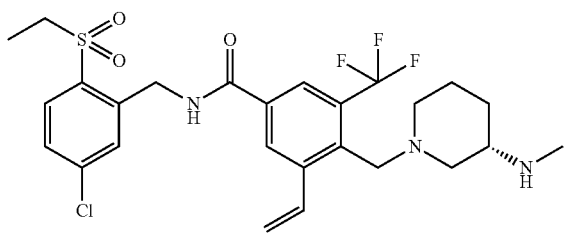 [SMILES: C=Cc1cc(C(=O)NCc2cc(Cl)ccc2S(=O)(=O)CC)cc(C(F)(F)F)c1CN1CCC[C@H](NC)C1]

The title compound was synthesized from tert-butyl N-[(3S)-1-[[4-[(5-chloro-2-ethylsulfonylphenyl)methylcarbamoyl]-2-ethenyl-6-(trifluoromethyl)phenyl]methyl]piperidin-3-yl]-N-methylcarbamate (Compound k9) under the same conditions as for Compound B-57.

LCMS: m/z 558 [M+H]$^+$

HPLC retention time: 0.56 min (analysis condition A)

Example 591

Compound k10

Ethyl 3-ethenyl-4-[[(3S)-3-[methyl-[(2-methylpropan-2-yl)oxycarbonyl]amino]piperidin-1-yl]methyl]-5-(trifluoromethyl)benzoate

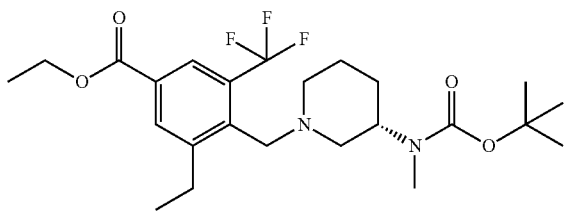 [SMILES: CCOC(=O)c1cc(CC)c(CN2CCC[C@H](N(C)C(=O)OC(C)(C)C)C2)c(C(F)(F)F)c1]

The title compound was synthesized from ethyl 3-ethenyl-4-[[(3S)-3-[methyl-[(2-methylpropan-2-yl)oxycarbonyl]amino]piperidin-1-yl]methyl]-5-(trifluoromethyl)benzoate (Compound k7) under the conditions as for Compound bb4. However, ethyl acetate was used in place of methanol as a solvent.

Example 592

Compound K-12

N-[(5-Chloro-2-ethylsulfonylphenyl)methyl]-3-ethyl-4-[[(3S)-3-(methylamino)piperidin-1-yl]methyl]-5-(trifluoromethyl)benzamide

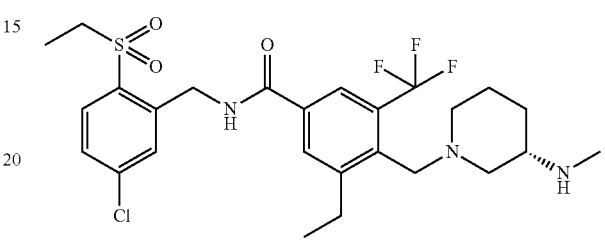

The title compound was synthesized from ethyl 3-ethyl-4-[[(3S)-3-[methyl-[(2-methylpropan-2-yl)oxycarbonyl]amino]piperidin-1-yl]methyl]-5-(trifluoromethyl)benzoate (Compound k10) under the same conditions as for Compounds k8, k9 and K-11.

LCMS: m/z 560 [M+H]$^+$

HPLC retention time: 0.56 min (analysis condition A)

Example 593

Compound k11

Ethyl 2-amino-3-cyclopropyl-4-formyl-5-(trifluoromethyl)benzoate

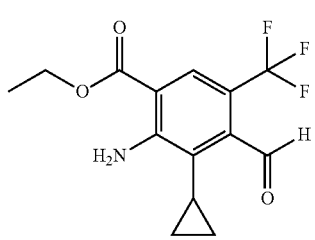 [SMILES: CCOC(=O)c1cc(C(F)(F)F)c(C=O)c(C2CC2)c1N]

The title compound was synthesized from ethyl 2-amino-3-bromo-4-formyl-5-(trifluoromethyl)benzoate (Compound e1) under the same conditions as for Compound k1. However, potassium cyclopropyltrifluoroborate was used in place of potassium trifluoro(methyl)borate.

Example 594

Compound k12

N-[(5-Chloro-2-ethylsulfonylphenyl)methyl]-3-cyclopropyl-4-formyl-5-(trifluoromethyl)benzamide

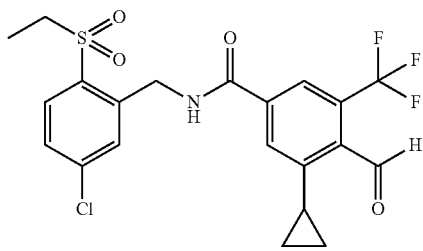 [SMILES: CCS(=O)(=O)c1ccc(Cl)cc1CNC(=O)c1cc(C2CC2)c(C=O)c(C(F)(F)F)c1]

The title compound was synthesized from ethyl 2-amino-3-cyclopropyl-4-formyl-5-(trifluoromethyl)benzoate (Compound k11) under the same conditions as for Compounds k2, k3 and k4.

Example 595

Compound k13 tert-Butyl 4-[[4-[(5-chloro-2-ethylsulfonylphenyl)methylcarbamoyl]-2-cyclopropyl-6-(trifluoromethyl)phenyl]methyl]piperazine-1-carboxylate

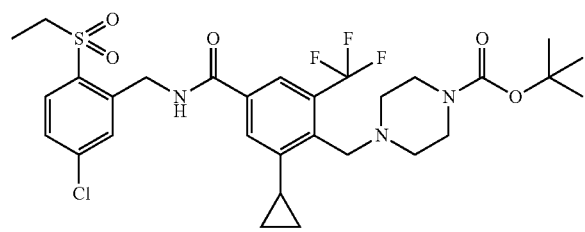 [SMILES: CCS(=O)(=O)c1ccc(Cl)cc1CNC(=O)c1cc(C2CC2)c(CN2CCN(C(=O)OC(C)(C)C)CC2)c(C(F)(F)F)c1]

The title compound was synthesized from N-[(5-chloro-2-ethylsulfonylphenyl)methyl]-3-cyclopropyl-4-formyl-5-(trifluoromethyl)benzamide (Compound k12) under the same conditions as for Compound b32. However, tert-butyl piperazine-1-carboxylate was used in place of tert-butyl (S)-1-pyrrolidin-2-ylmethyl-carbamate, and chloroform was used in place of THF as a solvent.

Example 596

Compound K-13

N-[(5-Chloro-2-ethylsulfonylphenyl)methyl]-3-cyclopropyl-4-(piperazin-1-ylmethyl)-5-(trifluoromethyl)benzamide

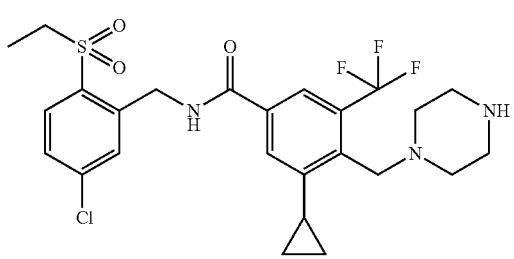 [SMILES: CCS(=O)(=O)c1ccc(Cl)cc1CNC(=O)c1cc(C2CC2)c(CN2CCNCC2)c(C(F)(F)F)c1]

The title compound was synthesized from tert-butyl 4-[[4-[(5-chloro-2-ethylsulfonylphenyl)methylcarbamoyl]-2-cyclopropyl-6-(trifluoromethyl)phenyl]methyl]piperazine-1-carboxylate (Compound k13) under the same conditions as for Compound B-1.

LCMS: m/z 544 [M+H]⁺

HPLC retention time: 0.58 min (analysis condition A)

Example 597

Compound K-14

N-[(5-Chloro-2-ethylsulfonylphenyl)methyl]-3-cyclopropyl-4-[(4-methylpiperazin-1-yl)methyl]-5-(trifluoromethyl)benzamide

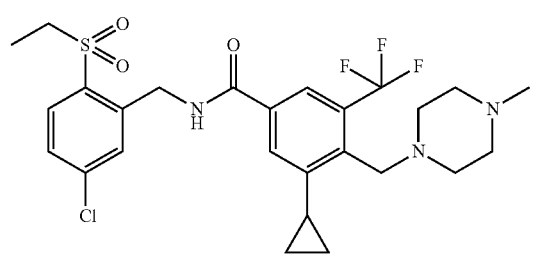 [SMILES: CCS(=O)(=O)c1ccc(Cl)cc1CNC(=O)c1cc(C2CC2)c(CN2CCN(C)CC2)c(C(F)(F)F)c1]

The title compound was synthesized from N-[(5-chloro-2-ethylsulfonylphenyl)methyl]-3-cyclopropyl-4-(piperazin-1-ylmethyl)-5-(trifluoromethyl)benzamide (Compound K-13) under the same conditions as for Compound B-2.

LCMS: m/z 558 [M+H]⁺

HPLC retention time: 0.56 min (analysis condition A)

Example 598

Compound K-15

N-[(5-Chloro-2-ethylsulfonylphenyl)methyl]-3-cyclopropyl-4-[[(3S)-3-(methylamino)piperidin-1-yl]methyl]-5-(trifluoromethyl)benzamide

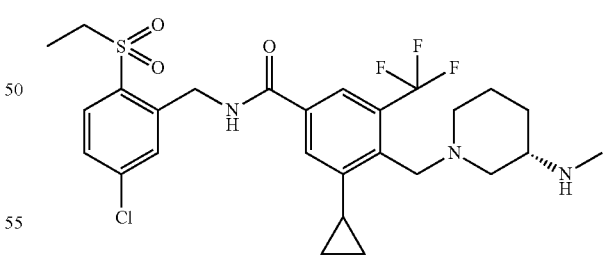

The title compound was synthesized from N-[(5-chloro-2-ethylsulfonylphenyl)methyl]-3-cyclopropyl-4-formyl-5-(trifluoromethyl)benzamide (Compound k12) under the same conditions as for Compounds k13 and K-13. However, under the Compound k13 conditions, tert-butyl N-methyl-N-[(3S)-piperidin-3-yl]carbamate was used in place of tert-butyl piperazine-1-carboxylate.

LCMS: m/z 572 [M+H]⁺

HPLC retention time: 0.61 min (analysis condition A)

Example 599

Compound 11

4-Hydroxy-3-(trifluoromethyl)benzoic acid

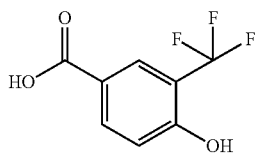 [SMILES: O=C(O)c1ccc(O)c(C(F)(F)F)c1]

Pyridine hydrochloride (262 mg, 2.27 mmol) was added to 4-methoxy-3-(trifluoromethyl)benzoic acid (50.0 mg, 0.227 mmol), and it was heated at 160° C. for eight hours. The reaction mixture was cooled to room temperature, and then a 10% aqueous citric acid solution was added, followed by extraction with ethyl acetate. The organic layer was washed with a saturated aqueous sodium chloride solution, and then dried over anhydrous sodium sulfate. The drying agent was removed by filtration, followed by concentration under reduced pressure. The resultant residue was purified by silica gel column chromatography (methanol/dichloromethane) to yield the title compound (46.0 mg, 98%) as a colorless solid.

LCMS: m/z 205 [M−H]−

HPLC retention time: 0.52 min (analysis condition F)

Example 600

Compound L-1

[2-Chloro-4-[(5-chloro-2-ethylsulfonylphenyl)methylcarbamoyl]-6-(trifluoromethyl)phenyl]acetate

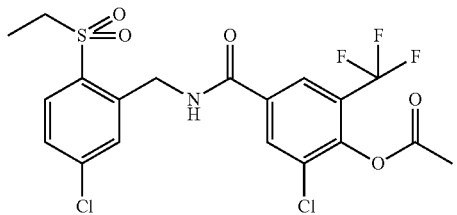 [SMILES: CCS(=O)(=O)c1ccc(Cl)cc1CNC(=O)c1cc(Cl)c(OC(C)=O)c(C(F)(F)F)c1]

Sulfuryl chloride (54.0 μl, 0.670 mmol) was added to a solution of 4-hydroxy-3-(trifluoromethyl)benzoic acid (Compound 11, 46.0 mg, 0.223 mmol) in acetic acid (1 ml), and it was stirred at 60° C. for 16 hours. The reaction mixture was cooled to room temperature, followed by addition of water and extraction with ethyl acetate. The organic layer was washed with a saturated aqueous sodium chloride solution twice, and then dried over anhydrous sodium sulfate. The drying agent was removed by filtration, followed by concentration under reduced pressure. The resultant residue was dissolved in DCM (2.2 ml), to which 5-chloro-2-ethanesulfonyl-benzylamine hydrochloride (Compound a3, 75.0 mg, 0.278 mmol), DIPEA (0.106 ml, 0.642 mmol) and HBTU (97.0 mg, 0.257 mmol) were added while cooling to 0° C. in an ice water bath, and the mixture was stirred at room temperature for one hour. Water was added to the reaction mixture, followed by extraction with ethyl acetate. The organic layer was washed with brine, and then dried over anhydrous sodium sulfate. The drying agent was removed by filtration, followed by concentration under reduced pressure. The resultant residue was purified by silica gel column chromatography (ethyl acetate/n-hexane) to yield the title compound (26.0 mg, 23%) as a yellow solid.

LCMS: m/z 498 [M+H]+

HPLC retention time: 0.88 min (analysis condition F)

Example 601

Compound 12

N-[(5-Chloro-2-ethylsulfonylphenyl)methyl]-4-hydroxy-3-(trifluoromethyl)benzamide

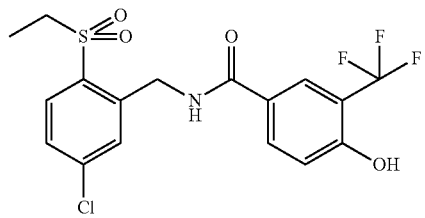 [SMILES: CCS(=O)(=O)c1ccc(Cl)cc1CNC(=O)c1ccc(O)c(C(F)(F)F)c1]

The title compound was synthesized from (5-chloro-2-ethylsulfonylphenyl)methanamine hydrochloride (Compound a3) under the same conditions as for Compound A-21. However, 4-hydroxy-3-(trifluoromethyl)benzoic acid (Compound 11) was used in place of 3-(trifluoromethyl)benzoic acid.

Example 602

Compound 13

4-[4-[(5-Chloro-2-ethylsulfonylphenyl)methylcarbamoyl]-2-(trifluoromethyl)phenoxy]piperidine-1-carboxylic acid tert-butyl ester

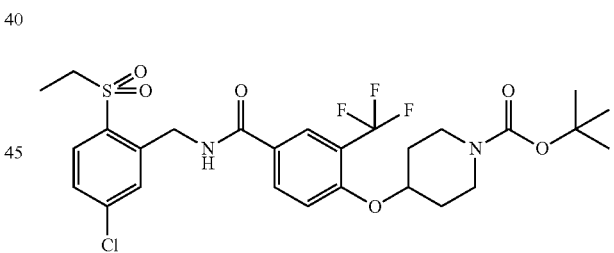

4-Hydroxypiperidine-1-carboxylic acid tert-butyl ester (21.5 mg, 0.107 mmol), diisopropyl azodicarboxylate (21.0 μl, 0.107 mmol) and triphenylphosphine (28.0 mg, 0.107 mmol) were added to a solution of N-[(5-chloro-2-ethylsulfonylphenyl)methyl]-4-hydroxy-3-(trifluoromethyl)benzamide (Compound 12, 30.0 mg, 0.071 mmol) in THF (1 ml), and the mixture was stirred at room temperature. After one hour, 4-hydroxypiperidine-1-carboxylic acid tert-butyl ester (21.5 mg, 0.107 mmol), diisopropyl azodicarboxylate (21.0 μl, 0.107 mmol) and triphenylphosphine (28.0 mg, 0.107 mmol) were further added, and the mixture was stirred at 50° C. for 18 hours. The reaction mixture was cooled to room temperature, followed by addition of water and extraction with ethyl acetate. The organic layer was washed with brine, and then dried over anhydrous sodium sulfate. The drying agent was removed by filtration, followed by concentration under reduced pressure. The resultant residue was purified by silica gel column chromatography (ethyl acetate/n-hexane) to yield the title compound (43.0 mg, quant.) as a colorless oily substance.

LCMS: m/z 605 [M+H]$^+$

HPLC retention time: 0.97 min (analysis condition F)

Example 603

Compound L-2

N-[(5-Chloro-2-ethylsulfonylphenyl)methyl]-4-piperidin-4-yloxy-3-(trifluoromethyl)benzamide

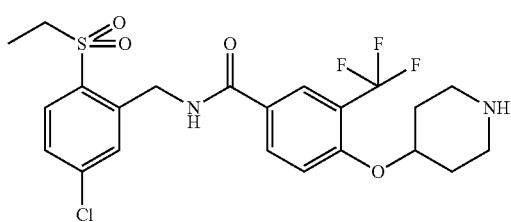 [SMILES: CCS(=O)(=O)c1ccc(Cl)cc1CNC(=O)c1ccc(OC2CCNCC2)c(C(F)(F)F)c1]

The title compound was synthesized from 4-[4-[(5-chloro-2-ethylsulfonylphenyl)methylcarbamoyl]-2-(trifluoromethyl)phenoxy]piperidine-1-carboxylic acid tert-butyl ester (Compound 13) under the same conditions as for Compound B-1.

LCMS: m/z 505 [M+H]$^+$

HPLC retention time: 0.52 min (analysis condition F)

Example 604

Compound L-3

N-[(5-Chloro-2-ethylsulfonylphenyl)methyl]-4-[(3R)-piperidin-3-yl]oxy-3-(trifluoromethyl)benzamide

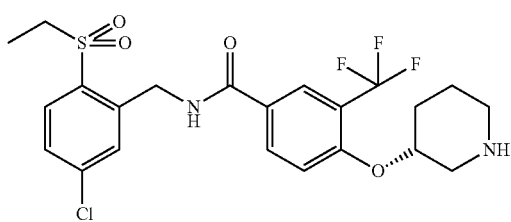

The title compound was synthesized from N-[(5-chloro-2-ethylsulfonylphenyl)methyl]-4-hydroxy-3-(trifluoromethyl)benzamide (Compound 12) under the same conditions as for Compounds 13 and L-2. However, under the Compound 13 conditions, tert-butyl (3S)-3-hydroxypiperidine-1-carboxylate was used in place of tert-butyl 4-hydroxypiperidine-1-carboxylate.

LCMS: m/z 505 [M+H]$^+$

HPLC retention time: 0.51 min (analysis condition F)

Example 605

Compound m1

5-Iodo-3-(trifluoromethyl)pyridin-2-amine

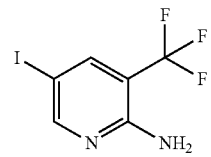

A solution of 3-(trifluoromethyl)pyridin-2-amine (1.50 g, 9.25 mmol) in acetic acid (15 ml) was cooled to 0° C., followed by addition of NIS (2.08 g, 9.25 mmol), and it was warmed to room temperature and stirred for 20 hours. NIS (1.04 g, 4.62 mmol) was then further added at room temperature, and the mixture was stirred for 70 hours. Water was added to the reaction mixture, and the precipitate was filtered off and then washed with a 5% aqueous sodium thiosulfate solution, a 10% aqueous sodium bicarbonate solution, and water to yield the title compound (2.36 g, 89%) as a colorless solid.

LCMS: m/z 289 [M+H]$^+$

HPLC retention time: 0.70 min (analysis condition A)

Example 606

Compound m2

6-Amino-5-(trifluoromethyl)pyridine-3-carbonitrile

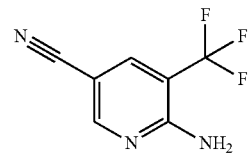

Copper(I) cyanide (805 mg, 8.99 mmol) was added to a solution of 5-iodo-3-(trifluoromethyl)pyridin-2-amine (Compound m1, 1.29 g, 4.49 mmol) in DMF (13 ml), and it was stirred at 130 to 150° C. for four hours. The mixture was cooled to room temperature, followed by removal of the insoluble matter by filtration through celite, and it was washed with ethyl acetate. A saturated aqueous sodium bicarbonate solution was added to the filtrate, followed by extraction. The organic layer was washed with water and brine, and then dried over anhydrous sodium sulfate. The drying agent was removed by filtration, followed by concentration under reduced pressure. The resultant residue was purified by silica gel column chromatography (ethyl acetate/dichloromethane) to yield the title compound (840 mg, quant.) as a pale brown solid.

LCMS: m/z 188 [M+H]$^+$

HPLC retention time: 0.50 min (analysis condition A)

Example 607

Compound m3

Methyl 6-amino-5-(trifluoromethyl)pyridine-3-carboxylate

Sulfuric acid (1 ml) was added to a solution of 6-amino-5-(trifluoromethyl)pyridine-3-carbonitrile (Compound m2, 840 mg, 4.49 mmol) in MeOH (10 ml) at room temperature, and it was heated at 140 to 150° C. and stirred for 30 minutes by microwaves. After the reaction mixture was cooled to room temperature, it was neutralized with a saturated aqueous sodium bicarbonate solution, and ethyl acetate was added thereto. The organic layer was washed with water and brine, and then dried over anhydrous sodium sulfate. The drying agent was removed by filtration, followed by concentration under reduced pressure. The resultant residue was purified by silica gel column chromatography (ethyl acetate/dichloromethane) to yield the title compound (483 mg, 49%) as a pale yellow solid.
LCMS: m/z 221 [M+H]$^+$
HPLC retention time: 0.55 min (analysis condition A)

Example 608

Compound m4

6-Amino-5-(trifluoromethyl)pyridine-3-carboxylic acid

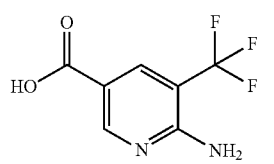

The title compound was synthesized from methyl 6-amino-5-(trifluoromethyl)pyridine-3-carboxylate (Compound m3) under the same conditions as for Compound b8.

Example 609

Compound M-1

6-Amino-N-[(5-chloro-2-ethylsulfonylphenyl)methyl]-5-(trifluoromethyl)pyridine-3-carboxamide

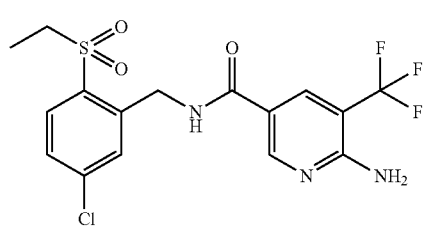 [SMILES: CCS(=O)(=O)c1ccc(Cl)cc1CNC(=O)c1cnc(N)c(C(F)(F)F)c1]

The title compound was synthesized from (5-chloro-2-ethylsulfonylphenyl)methanamine hydrochloride (Compound a3) under the same conditions as for Compound bb10. However, 6-amino-5-(trifluoromethyl)pyridine-3-carboxylic acid (Compound m4) was used in place of 4-[[4-[(2-methylpropan-2-yl)oxycarbonyl]piperazin-1-yl]methyl]-3-(trifluoromethyl)benzoic acid (Compound b3).
LCMS: m/z 422 [M+H]$^+$
HPLC retention time: 0.64 min (analysis condition A)

Example 610

Compound M-2

N-[(5-Chloro-2-ethylsulfonylphenyl)methyl]-2-methyl-5-(trifluoromethyl)-1,3-oxazole-4-carboxamide

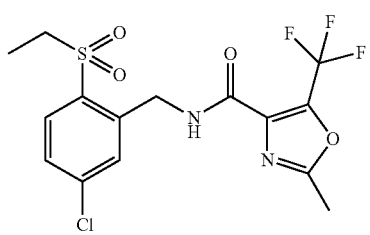 [SMILES: CCS(=O)(=O)c1ccc(Cl)cc1CNC(=O)c1nc(C)oc1C(F)(F)F]

The title compound was synthesized from (5-chloro-2-ethylsulfonylphenyl)methanamine hydrochloride (Compound a3) under the same conditions as for Compound A-5. However, 2-methyl-5-(trifluoromethyl)-1,3-oxazole-4-carboxylic acid was used in place of 3-(trifluoromethyl)benzoic acid.
LCMS: m/z 411 [M+H]$^+$
HPLC retention time: 0.81 min (analysis condition A)

Example 611

Compound N-1

N-[(5-Chloro-2-ethylsulfonylphenyl)methyl]-6-(trifluoromethyl)pyridine-2-carboxamide

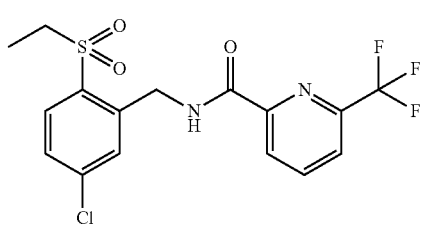 [SMILES: CCS(=O)(=O)c1ccc(Cl)cc1CNC(=O)c1cccc(C(F)(F)F)n1]

The title compound was synthesized from (5-chloro-2-ethylsulfonylphenyl)methanamine hydrochloride (Compound a3) under the same conditions as for Compound bb10. However, 6-(trifluoromethyl)pyridine-2-carboxylic acid was used in place of 4-[[4-[(2-methylpropan-2-yl)oxycarbonyl]piperazin-1-yl]methyl]-3-(trifluoromethyl)benzoic acid (Compound b3).
LCMS: m/z 407 [M+H]$^+$
HPLC retention time: 0.78 min (analysis condition A)

Example 612

Compound N-2

N-[(5-Chloro-2-ethylsulfonylphenyl)methyl]-2-(trifluoromethyl)pyridine-4-carboxamide

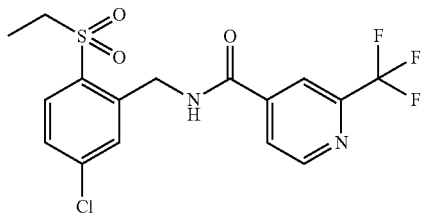 [SMILES: CCS(=O)(=O)c1ccc(Cl)cc1CNC(=O)c1ccnc(C(F)(F)F)c1]

The title compound was synthesized from (5-chloro-2-ethylsulfonylphenyl)methanamine hydrochloride (Compound a3) under the same conditions as for Compound bb10. However, 2-(trifluoromethyl)pyridine-4-carboxylic acid was used in place of 4-[[4-[(2-methylpropan-2-yl)oxycarbonyl]piperazin-1-yl]methyl]-3-(trifluoromethyl)benzoic acid (Compound b3).

LCMS: m/z 407 [M+H]$^+$

HPLC retention time: 0.73 min (analysis condition A)

Example 613

Compound N-3

N-[(5-Chloro-2-ethylsulfonylphenyl)methyl]-4-(trifluoromethyl)pyridine-2-carboxamide

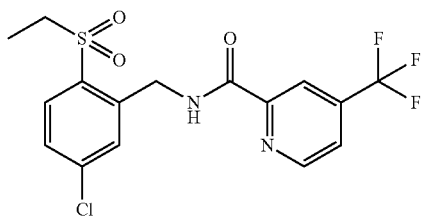 [SMILES: CCS(=O)(=O)c1ccc(Cl)cc1CNC(=O)c1cc(C(F)(F)F)ccn1]

The title compound was synthesized from (5-chloro-2-ethylsulfonylphenyl)methanamine hydrochloride (Compound a3) under the same conditions as for Compound bb10. However, 4-(trifluoromethyl)pyridine-2-carboxylic acid was used in place of 4-[[4-[(2-methylpropan-2-yl)oxycarbonyl]piperazin-1-yl]methyl]-3-(trifluoromethyl)benzoic acid (Compound b3).

LCMS: m/z 407 [M+H]$^+$

HPLC retention time: 0.81 min (analysis condition A)

Example 614

Compound N-4

N-[(5-Chloro-2-ethylsulfonylphenyl)methyl]-1-phenyl-5-pyrrol-1-ylpyrazole-4-carboxamide

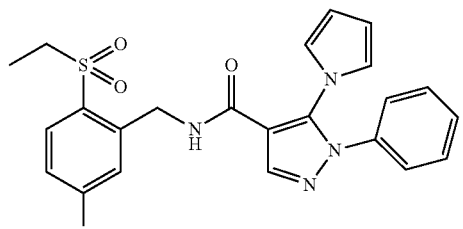

The title compound was synthesized from (5-chloro-2-ethylsulfonylphenyl)methanamine hydrochloride (Compound a3) under the same conditions as for Compound A-21. However, 1-phenyl-5-pyrrol-1-ylpyrazole-4-carboxylic acid was used in place of 3-(trifluoromethyl)benzoic acid, and DMF was used in place of dichloromethane as a solvent.

LCMS: m/z 469 [M+H]$^+$

HPLC retention time: 0.83 min (analysis condition F)

Example 615

Compound N-5

N-[(5-Chloro-2-ethylsulfonylphenyl)methyl]-3,5-bis(trifluoromethyl)benzamide

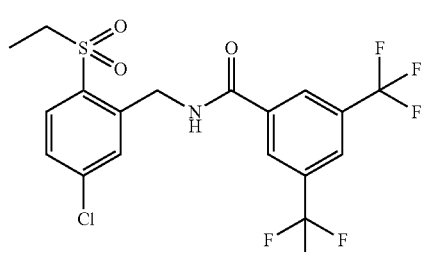

The title compound was synthesized from (5-chloro-2-ethylsulfonylphenyl)methanamine hydrochloride (Compound a3) under the same conditions as for Compound A-21. However, 3,5-bis(trifluoromethyl)benzoic acid was used in place of 3-(trifluoromethyl)benzoic acid.

LCMS: m/z 474 [M+H]$^+$

HPLC retention time: 0.93 min (analysis condition F)

Example 616

Compound N-6

4-Amino-N-[(5-chloro-2-ethylsulfonylphenyl)methyl]-3-(trifluoromethyl)benzamide

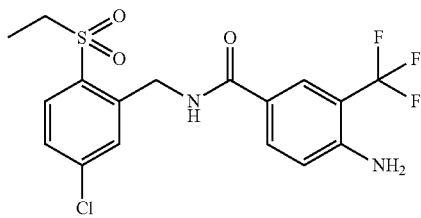 [SMILES: CCS(=O)(=O)c1ccc(Cl)cc1CNC(=O)c1ccc(N)c(C(F)(F)F)c1]

The title compound was synthesized from (5-chloro-2-ethylsulfonylphenyl)methanamine hydrochloride (Compound a3) under the same conditions as for Compound A-21. However, 4-amino-3-(trifluoromethyl)benzoic acid was used in place of 3-(trifluoromethyl)benzoic acid.
LCMS: m/z 421 [M+H]$^+$
HPLC retention time: 0.73 min (analysis condition F)

Example 617

Compound n1

2-Ethylsulfanyl-5-(trifluoromethyl)aniline

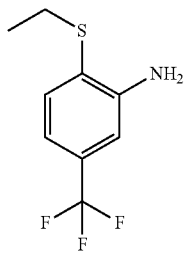

The title compound was synthesized from 2-amino-4-(trifluoromethyl)benzenethiol hydrochloride under the same conditions as for Compound a4.

Example 618

Compound n2

[2-Ethylsulfanyl-5-(trifluoromethyl)phenyl]hydrazine

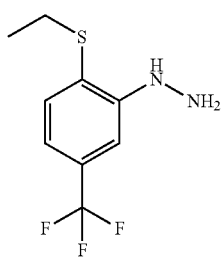

The title compound was synthesized from 2-ethylsulfanyl-5-(trifluoromethyl)aniline (Compound n1) under the same conditions as for Compound a5.

Example 619

Compound n3

3-Chloro-N'-[2-ethylsulfanyl-5-(trifluoromethyl)phenyl]-5-(trifluoromethyl)benzohydrazide

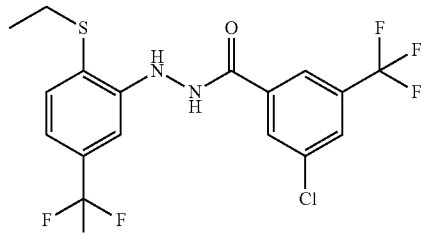

The title compound was synthesized from [2-ethylsulfanyl-5-(trifluoromethyl)phenyl]hydrazine (Compound n2) under the same conditions as for Compound A-1. However, 3-chloro-5-(trifluoromethyl)benzoic acid was used in place of 3-bromo-5-(trifluoromethyl)benzoic acid.

Example 620

Compound N-7

3-Chloro-N'-[2-ethylsulfonyl-5-(trifluoromethyl)phenyl]-5-(trifluoromethyl)benzohydrazide

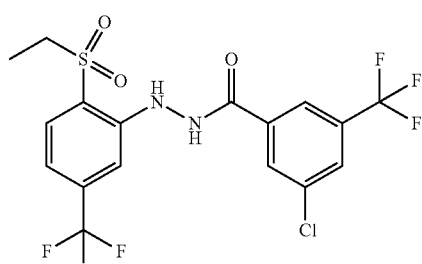

The title compound was synthesized from 3-chloro-N'-[2-ethylsulfanyl-5-(trifluoromethyl)phenyl]-5-(trifluoromethyl)benzohydrazide (Compound n3) under the same conditions as for Compound A-2.
LCMS: m/z 475 [M+H]$^+$
HPLC retention time: 0.97 min (analysis condition F)

Example 621

Compound n4

5-Ethoxy-2-methyl-1,3-benzothiazole

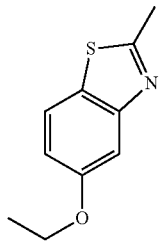

The title compound was synthesized from 2-methyl-1,3-benzothiazol-5-ol under the same conditions as for Compound a4.

Example 622

Compound n5

2-Amino-4-ethoxybenzenethiol

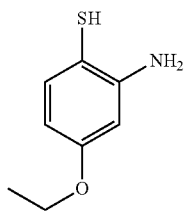

A 30 wt % aqueous sodium hydroxide solution (13 ml) and ethylene glycol (13 ml) were added to 5-ethoxy-2-methyl-1,3-benzothiazole (Compound n4, 858 mg, 4.44 mmol) at room temperature under a nitrogen atmosphere, and the reaction suspension mixture was stirred under reflux for 5.5 hours. After cooling to room temperature, the organic layer was washed with diethyl ether three times (20 ml×3); and the aqueous layer was cooled to 0° C., then adjusted to pH 2 or 3 by adding a 36% aqueous hydrochloric acid solution, and extracted with diethyl ether. The combined organic layers were sequentially washed with brine and water, and dried over anhydrous sodium sulfate. The drying agent was removed by filtration, followed by concentration under reduced pressure to yield the title compound as a crude product.

1H-NMR (400 MHz, DMSO-$d_6$) δ: 7.28 (1H, d, J=7.9 Hz), 6.24-6.29 (2H, m), 4.29 (2H, brs), 3.97 (2H, q, J=6.9 Hz), 2.76 (1H, s), 1.38 (3H, t, J=6.9 Hz).

Example 623

Compound N-8

3-Chloro-N'-(5-ethoxy-2-ethylsulfonylphenyl)-5-(trifluoromethyl)benzohydrazide

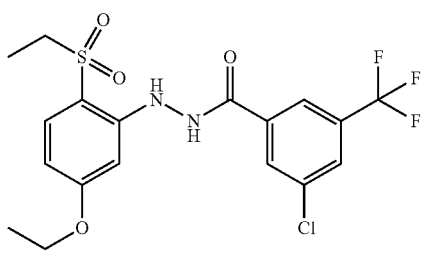 [SMILES: CCOc1ccc(S(=O)(=O)CC)c(NNC(=O)c2cc(Cl)cc(C(F)(F)F)c2)c1]

The title compound was synthesized from 2-amino-4-ethoxybenzenethiol (Compound n5) under the same conditions as for Compounds n1, n2, n3 and N-7.

LCMS: m/z 451 [M+H]$^+$

HPLC retention time: 0.93 min (analysis condition F)

Example 624

Compound n6 tert-Butyl N-[(3R)-1-[[4-[(3,5-dichloro-2-ethylsulfonylphenyl)methylcarbamoyl]-2-(trifluoromethyl)phenyl]methyl]pyrrolidin-3-yl]-N-methylcarbamate

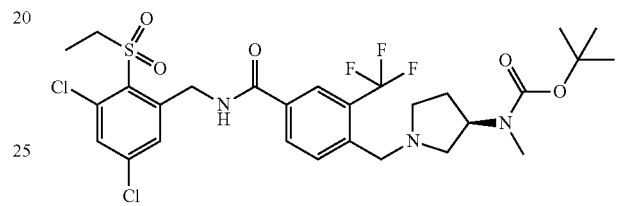

The title compound was synthesized from (3,5-dichloro-2-ethylsulfonylphenyl)methanamine (Compound bb9) under the same conditions as for Compound bb10. However, 4-[[(3R)-3-[methyl-[(2-methylpropan-2-yl)oxycarbonyl]amino]pyrrolidin-1-yl]methyl]-3-(trifluoromethyl)benzoic acid (Compound b11) was used in place of 4-[[4-[(2-methylpropan-2-yl)oxycarbonyl]piperazin-1-yl]methyl]-3-(trifluoromethyl)benzoic acid (Compound b3).

Example 625

Compound N-9

N-[(3,5-Dichloro-2-ethylsulfonylphenyl)methyl]-4-[[(3R)-3-(methylamino)pyrrolidin-1-yl]methyl]-3-(trifluoromethyl)benzamide

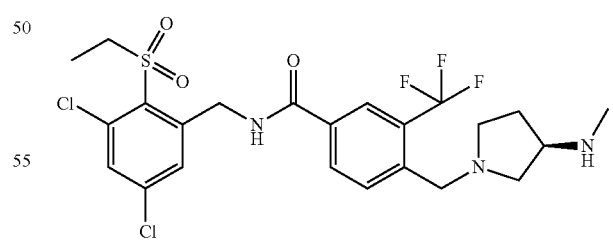

The title compound was synthesized from tert-butyl N-[(3R)-1-[[4-[(3,5-dichloro-2-ethylsulfonylphenyl)methylcarbamoyl]-2-(trifluoromethyl)phenyl]methyl]pyrrolidin-3-yl]-N-methylcarbamate (Compound n6) under the same conditions as for Compound B-57.

LCMS: m/z 552 [M+H]$^+$

HPLC retention time: 0.49 min (analysis condition A)

Example 626

Compound n7

4-Chloro-2-iodo-6-methylaniline

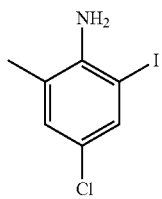

NIS (2.95 g, 13.1 mmol) was added to a solution of 4-chloro-2-methylaniline (1.69 g, 12.0 mmol) in DMF (27 ml), and it was stirred at room temperature for 1.5 hours under a nitrogen atmosphere. NIS (738 mg, 3.28 mmol) was added, followed by another 1.5 hours of stirring. Water was added to the reaction mixture, followed by extraction with ethyl acetate. The organic layer was then washed with a saturated aqueous sodium thiosulfate solution, and dried over anhydrous magnesium sulfate. The drying agent was removed by filtration, followed by concentration under reduced pressure. The resultant residue was purified by silica gel column chromatography (ethyl acetate/hexane) to yield the title compound (1.51 g, 47%) as a pale brown solid.

LCMS: m/z 268 [M+H]$^+$

HPLC retention time: 2.68 min (analysis condition D)

Example 627

Compound n8

2-Amino-5-chloro-3-methylbenzonitrile

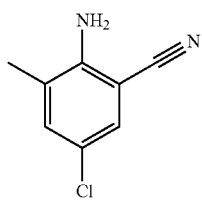

The title compound was synthesized from 4-chloro-2-iodo-6-methylaniline (Compound n7) under the same conditions as for Compound dd48. However, the reaction was performed at a temperature of 140 to 150° C.

Example 628

Compound n9

5-Chloro-2-iodo-3-methylbenzonitrile

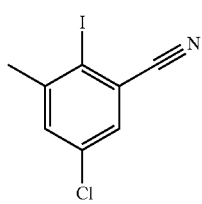

The title compound was synthesized from 2-amino-5-chloro-3-methylbenzonitrile (Compound n8) under the same conditions as for Compound dd49.

Example 629

Compound n10

5-Chloro-2-ethylsulfanyl-3-methylbenzonitrile

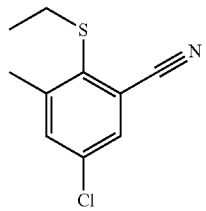

The title compound was synthesized from 5-chloro-2-iodo-3-methylbenzonitrile (Compound n9) under the same conditions as for Compound dd42. However, the reaction was performed at a temperature of 80° C.

Example 630

Compound n11

(5-Chloro-2-ethylsulfanyl-3-methylphenyl)methanamine 2,2,2-trifluoroacetate

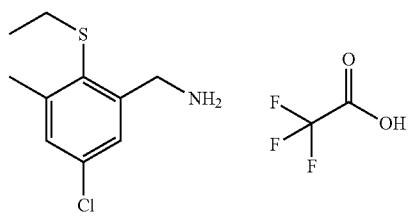

A solution of 5-chloro-2-ethylsulfanyl-3-methylbenzonitrile (Compound n10, 95.4 mg, 0.450 mmol) in THF (2 ml) was added to a solution of lithium aluminum hydride (27.5 mg, 0.579 mmol) in THF (4.5 ml) under ice-cooling, and it was warmed to room temperature and stirred for five hours under a nitrogen atmosphere. Lithium aluminum hydride (35.8 mg, 0.754 mmol) was further added under ice-cooling, and the mixture was warmed to room temperature and stirred for 2.5 hours under a nitrogen atmosphere. Water (25 µl), a 5N aqueous sodium hydroxide solution (25 µl), THF (600 µl) and water (60 µl) were added to the reaction suspension under ice-cooling, followed by 30 minutes of stirring and removal of the insoluble matter by filtration through celite, and it was washed with THF. The filtrate was concentrated under reduced pressure, and the resultant residue was purified by preparative HPLC (water/acetonitrile, 0.05% TFA) to yield the title compound (69.3 mg, 47%) as a colorless solid.

LCMS: m/z 216 [M+H]$^+$

HPLC retention time: 0.44 min (analysis condition F)

Example 631

Compound n12

(5-Chloro-2-ethylsulfonyl-3-methylphenyl)methanamine hydrochloride

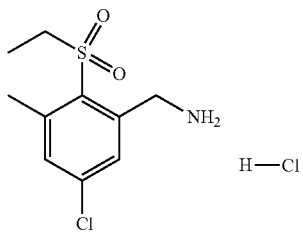

The title compound was synthesized from (5-chloro-2-ethylsulfanyl-3-methylphenyl)methanamine 2,2,2-trifluoroacetate (Compound n11) under the same conditions as for Compound dd45.

Example 632

Compound N-10

N-[(5-Chloro-2-ethylsulfonyl-3-methylphenyl)methyl]-4-[[(3S)-3-(methylamino)piperidin-1-yl]methyl]-3-(trifluoromethyl)benzamide

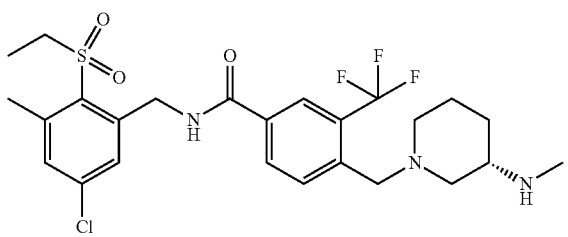

The title compound was synthesized from (5-chloro-2-ethylsulfonyl-3-methylphenyl)methanamine hydrochloride (Compound n12) under the same conditions as for Compounds n6 and N-9. However, 4-[[(3S)-3-[methyl-[(2-methylpropan-2-yl)oxycarbonyl]amino]piperidin-1-yl]methyl]-3-(trifluoromethyl)benzoic acid (Compound b17) was used in place of 4-[[(3R)-3-[methyl-[(2-methylpropan-2-yl)oxycarbonyl]amino]pyrrolidin-1-yl]methyl]-3-(trifluoromethyl)benzoic acid (Compound b11) under the conditions for Compound n6.

LCMS: m/z 546 [M+H]$^+$

HPLC retention time: 0.56 min (analysis condition F)

Example 633

Compound N-11

3-Chloro-N-[(5-chloro-2-ethylsulfonyl-3-methylphenyl)methyl]-4-[[(3S)-3-(methylamino)piperidin-1-yl]methyl]-5-(trifluoromethyl)benzamide

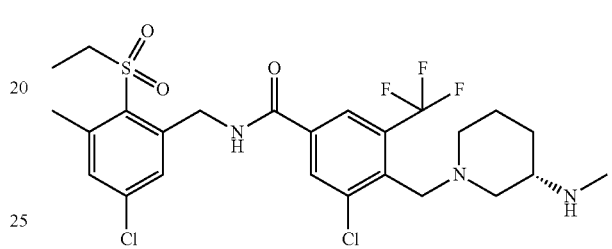

The title compound was synthesized from (5-chloro-2-ethylsulfonyl-3-methylphenyl)methanamine hydrochloride (Compound n12) under the same conditions as for Compounds n6 and N-9. However, under the Compound n6 conditions, 3-chloro-4-[[(3S)-3-[methyl-[(2-methylpropan-2-yl)oxycarbonyl]amino]piperidin-1-yl]methyl]-5-(trifluoromethyl)benzoic acid (Compound dd34) was used in place of 4-[[(3R)-3-[methyl-[(2-methylpropan-2-yl)oxycarbonyl]amino]pyrrolidin-1-yl]methyl]-3-(trifluoromethyl)benzoic acid (Compound b11).

LCMS: m/z 580 [M+H]$^+$

HPLC retention time: 0.60 min (analysis condition F)

Example 634

Compound n13 tert-Butyl N-[3-[4-[[2-chloro-4-[(5-chloro-2-ethylsulfonylphenyl)methylcarbamoyl]-6-(trifluoromethyl)phenyl]methyl]piperazin-1-yl]-3-oxopropyl]carbamate

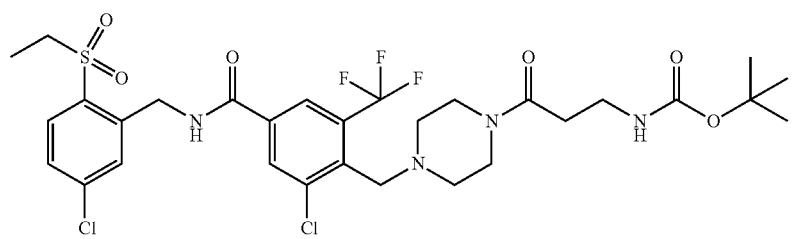 [SMILES: CCS(=O)(=O)c1ccc(Cl)cc1CNC(=O)c1cc(Cl)c(CN2CCN(C(=O)CCNC(=O)OC(C)(C)C)CC2)c(C(F)(F)F)c1]

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compound DD-1. However, 3-[(2-methylpropan-2-yl)oxycarbonylamino]propanoic acid was used in place of 1H-pyrrole-2-carboxylic acid, and HATU was used in place of HBTU.

Example 635

Compound N-12

4-[[4-(3-Aminopropanoyl)piperazin-1-yl]methyl]-3-chloro-N-[(5-chloro-2-ethylsulfonylphenyl)methyl]-5-(trifluoromethyl)benzamide

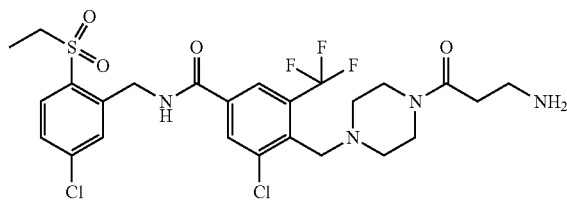 [SMILES: CCS(=O)(=O)c1ccc(Cl)cc1CNC(=O)c1cc(Cl)c(CN2CCN(C(=O)CCN)CC2)c(C(F)(F)F)c1]

The title compound was synthesized from tert-butyl N-[3-[4-[[2-chloro-4-[(5-chloro-2-ethylsulfonylphenyl)methylcarbamoyl]-6-(trifluoromethyl)phenyl]methyl]piperazin-1-yl]-3-oxopropyl]carbamate (Compound n13) under the same conditions as for Compound DD-62.

LCMS: m/z 609 [M+H]$^+$

HPLC retention time: 0.48 min (analysis condition A)

Example 636

Compound N-13

3-Chloro-N-[(5-chloro-2-ethylsulfonylphenyl)methyl]-4-[[4-(piperidine-4-carbonyl)piperazin-1-yl]methyl]-5-(trifluoromethyl)benzamide

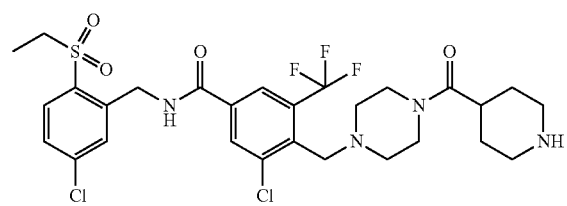 [SMILES: CCS(=O)(=O)c1ccc(Cl)cc1CNC(=O)c1cc(Cl)c(CN2CCN(C(=O)C3CCNCC3)CC2)c(C(F)(F)F)c1]

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compounds n13 and N-12. However, under the Compound n13 conditions, 1-[(2-methylpropan-2-yl)oxycarbonyl]piperidine-4-carboxylic acid was used in place of 3-[(2-methylpropan-2-yl)oxycarbonylamino]propanoic acid.

LCMS: m/z 649 [M+H]$^+$

HPLC retention time: 0.50 min (analysis condition A)

Example 637

Compound N-14

3-Chloro-N-[(5-chloro-2-ethylsulfonylphenyl)methyl]-4-[[4-[(3R)-pyrrolidine-3-carbonyl]piperazin-1-yl]methyl]-5-(trifluoromethyl)benzamide

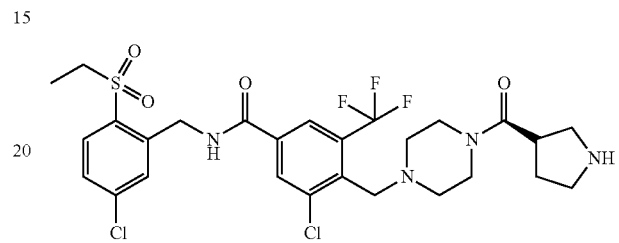

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compounds n13 and N-12. However, under the Compound n13 conditions, (3R)-1-[(2-methylpropan-2-yl)oxycarbonyl]pyrrolidine-3-carboxylic acid was used in place of 3-[(2-methylpropan-2-yl)oxycarbonylamino]propanoic acid.

LCMS: m/z 635 [M+H]$^+$

HPLC retention time: 0.52 min (analysis condition A)

Example 638

Compound n14 tert-Butyl N-[2-[4-[[2-chloro-4-[(5-chloro-2-ethylsulfonylphenyl)methylcarbamoyl]-6-(trifluoromethyl)phenyl]methyl]piperazin-1-yl]ethyl]carbamate

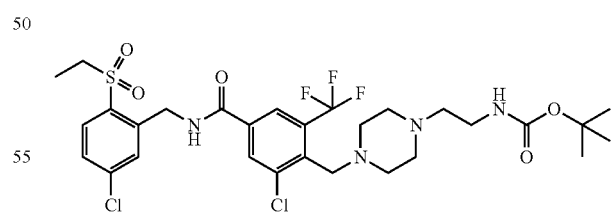

The title compound was synthesized from 3-chloro-N-[(5-chloro-2-ethylsulfonylphenyl)methyl]-4-(piperazin-1-ylmethyl)-5-(trifluoromethyl)benzamide (Compound D-1) under the same conditions as for Compound H-5. However, the reaction was performed using tert-butyl N-(2-bromoethyl)carbamate in place of ethyl iodide and with the addition of TEA.

Example 639

Compound N-15

4-[[4-(2-Aminoethyl)piperazin-1-yl]methyl]-3-chloro-N-[(5-chloro-2-ethylsulfonylphenyl)methyl]-5-(trifluoromethyl)benzamide

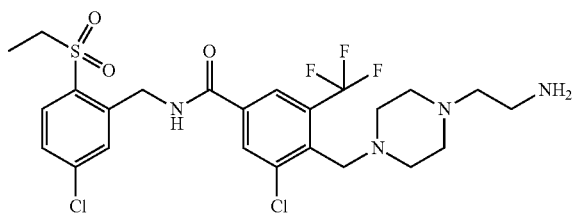 [SMILES: CCS(=O)(=O)c1ccc(Cl)cc1CNC(=O)c1cc(Cl)c(CN2CCN(CCN)CC2)c(C(F)(F)F)c1]

The title compound was synthesized from tert-butyl N-[2-[4-[[2-chloro-4-[(5-chloro-2-ethylsulfonylphenyl)methylcarbamoyl]-6-(trifluoromethyl)phenyl]methyl]piperazin-1-yl]ethyl]carbamate (Compound n14) under the same conditions as for Compound B-1.

LCMS: m/z 581 [M+H]$^+$

HPLC retention time: 0.44 min (analysis condition F)

Example 640

Compound N-16

3-Chloro-N-[(5-chloro-2-ethylsulfonylphenyl)methyl]-4-[[(3S)-3-(methylsulfamoylamino)pyrrolidin-1-yl]methyl]-5-(trifluoromethyl)benzamide

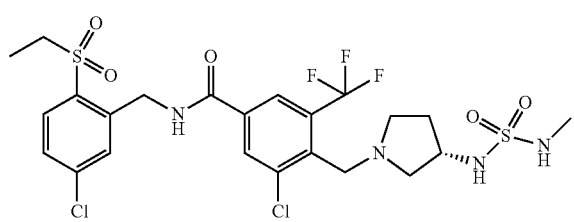 [SMILES: CCS(=O)(=O)c1ccc(Cl)cc1CNC(=O)c1cc(Cl)c(CN2CC[C@H](NS(=O)(=O)NC)C2)c(C(F)(F)F)c1]

The title compound was synthesized from 4-[[(3S)-3-aminopyrrolidin-1-yl]methyl]-3-chloro-N-[(5-chloro-2-ethylsulfonylphenyl)methyl]-5-(trifluoromethyl)benzamide (Compound DD-55) under the same conditions as for Compound DD-58.

LCMS: m/z 631 [M+H]$^+$

HPLC retention time: 0.53 min (analysis condition F)

Example 641

Compound N-17

3-Chloro-N-[(5-chloro-2-ethylsulfonylphenyl)methyl]-4-[[(3S)-3-(propan-2-ylamino)pyrrolidin-1-yl]methyl]-5-(trifluoromethyl)benzamide

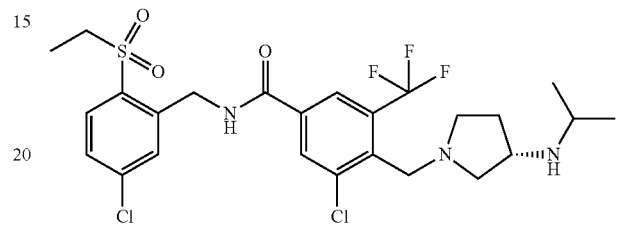

The title compound was synthesized from 4-[[(3S)-3-aminopyrrolidin-1-yl]methyl]-3-chloro-N-[(5-chloro-2-ethylsulfonylphenyl)methyl]-5-(trifluoromethyl)benzamide (Compound DD-55) under the same conditions as for Compound B-3. However, MeOH was used in place of THF as a reaction solvent.

LCMS: m/z 580 [M+H]$^+$

HPLC retention time: 0.55 min (analysis condition F)

Example 642

Compound N-18

3-Bromo-N-[(5-chloro-2-ethylsulfonylphenyl)methyl]-4-[[(3R)-3-(methylsulfamoylamino)pyrrolidin-1-yl]methyl]-5-(trifluoromethyl)benzamide

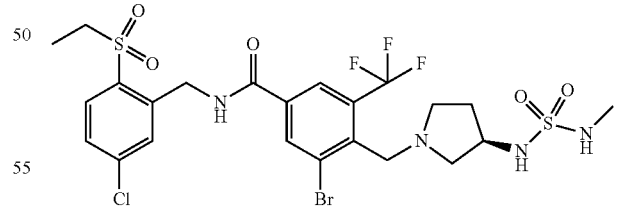

The title compound was synthesized from 4-[[(3R)-3-aminopyrrolidin-1-yl]methyl]-3-bromo-N-[(5-chloro-2-ethylsulfonylphenyl)methyl]-5-(trifluoromethyl)benzamide (Compound E-2) under the same conditions as for Compound DD-58.

LCMS: m/z 675 [M+H]$^+$

HPLC retention time: 0.54 min (analysis condition F)

Example 643

Compound N-19

3-Chloro-N-[(5-chloro-2-ethylsulfonylphenyl)methyl]-4-[[(3S)-3-(cyclobutylamino)piperidin-1-yl]methyl]-5-(trifluoromethyl)benzamide

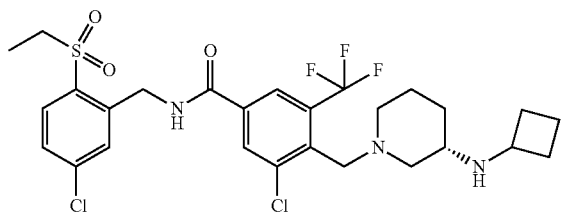 [SMILES: CCS(=O)(=O)c1ccc(Cl)cc1CNC(=O)c1cc(Cl)c(CN2CCC[C@H](NC3CCC3)C2)c(C(F)(F)F)c1]

The title compound was synthesized from 4-[[(3S)-3-aminopiperidin-1-yl]methyl]-3-chloro-N-[(5-chloro-2-ethylsulfonylphenyl)methyl]-5-(trifluoromethyl)benzamide (Compound D-18) under the same conditions as for Compound DD-28. However, cyclobutanone was used in place of 3-oxetanone as a solvent.

LCMS: m/z 606 [M+H]$^+$
HPLC retention time: 0.61 min (analysis condition F)

Example 644

Compound n15 tert-Butyl N-[(3S)-1-[[2-chloro-4-[(5-chloro-2-ethylsulfonylphenyl)methylcarbamoyl]-6-(trifluoromethyl)phenyl]methyl]piperidin-3-yl]-N-[2-[methyl-[(2-methylpropan-2-yl)oxycarbonyl]amino]ethyl]carbamate

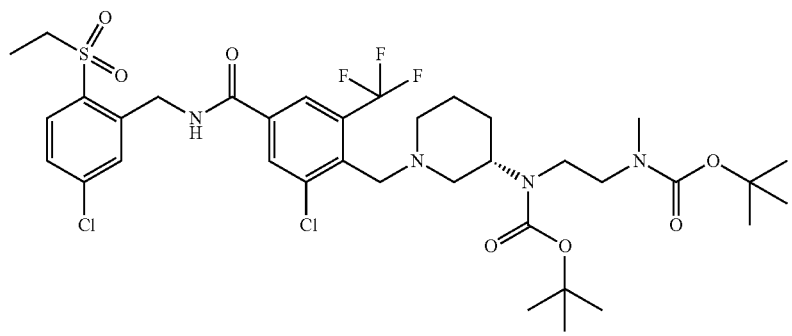 [SMILES: CCS(=O)(=O)c1ccc(Cl)cc1CNC(=O)c1cc(Cl)c(CN2CCC[C@H](N(CCN(C)C(=O)OC(C)(C)C)C(=O)OC(C)(C)C)C2)c(C(F)(F)F)c1]

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound dd17. However, tert-butyl N-methyl-N-[2-[(2-methylpropan-2-yl)oxycarbonyl-[(3S)-piperidin-3-yl]amino]ethyl]carbamate was used in place of tert-butyl N-[2-[[(3S)-piperidin-3-yl]sulfamoyl]ethyl]carbamate.

Example 645

Compound N-20

3-Chloro-N-[(5-chloro-2-ethylsulfonylphenyl)methyl]-4-[[(3S)-3-[2-(methylamino)ethylamino]piperidin-1-yl]methyl]-5-(trifluoromethyl)benzamide

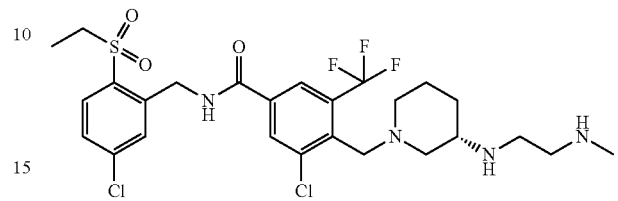

The title compound was synthesized from tert-butyl N-[(3S)-1-[[2-chloro-4-[(5-chloro-2-ethylsulfonylphenyl)methylcarbamoyl]-6-(trifluoromethyl)phenyl]methyl]piperidin-3-yl]-N-[2-[methyl-[(2-methylpropan-2-yl)oxycarbonyl]amino]ethyl]carbamate (Compound n15) under the same conditions as for Compound B-1.

LCMS: m/z 609 [M+H]$^+$
HPLC retention time: 0.46 min (analysis condition F)

Example 646

Compound N-21

4-[[(3S)-3-(3-Aminopropyl)piperidin-1-yl]methyl]-3-chloro-N-[(5-chloro-2-ethylsulfonylphenyl)methyl]-5-(trifluoromethyl)benzamide

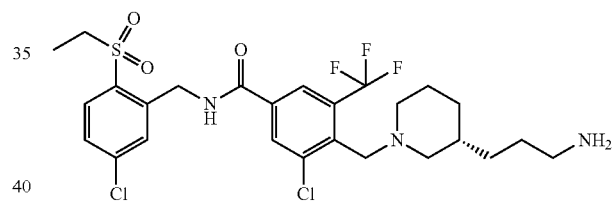

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compounds n15 and N-20. However, under the Compound n15 conditions, tert-butyl N-[3-[(3R)-piperidin-3-yl]propyl]carbamate was used in place of tert-butyl N-methyl-N-[2-[(2-methylpropan-2-yl)oxycarbonyl-[(3S)-piperidin-3-yl]amino]ethyl]carbamate.

LCMS: m/z 594 [M+H]⁺
HPLC retention time: 0.43 min (analysis condition F)

Example 647

Compound n16

5-Chloro-2-cyclopentylsulfanylbenzonitrile

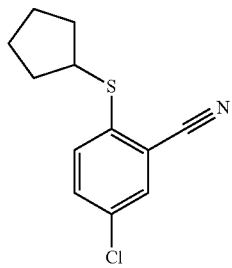 [SMILES: N#Cc1cc(Cl)ccc1SC1CCCC1]

The title compound was synthesized from 5-chloro-2-fluorobenzonitrile under the same conditions as for Compound a1. However, cyclopentanethiol was used in place of ethanethiol.

Example 648

Compound n17

(5-Chloro-2-cyclopentylsulfanylphenyl)methanamine

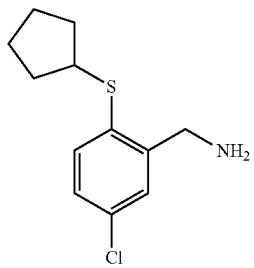 [SMILES: NCc1cc(Cl)ccc1SC1CCCC1]

The title compound was synthesized from 5-chloro-2-cyclopentylsulfanylbenzonitrile (Compound n16) under the same conditions as for Compound a2.

Example 649

Compound n18

(5-Chloro-2-cyclopentylsulfonylphenyl)methanamine hydrochloride

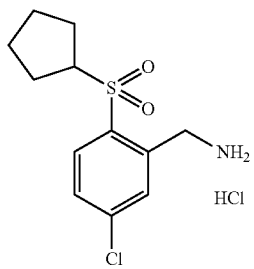 [SMILES: NCc1cc(Cl)ccc1S(=O)(=O)C1CCCC1 ; Cl]

The title compound was synthesized from (5-chloro-2-cyclopentylsulfanylphenyl)methanamine (Compound n17) under the same conditions as for Compound a3.

Example 650

Compound n19 tert-Butyl N-[(3S)-1-[[2-chloro-4-[(5-chloro-2-cyclopentylsulfonylphenyl)methylcarbamoyl]-6-(trifluoromethyl)phenyl]methyl]piperidin-3-yl]-N-methylcarbamate

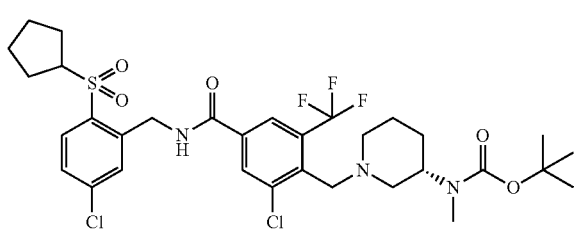 [SMILES: CN(C(=O)OC(C)(C)C)[C@H]1CCCN(Cc2c(Cl)cc(C(=O)NCc3cc(Cl)ccc3S(=O)(=O)C3CCCC3)cc2C(F)(F)F)C1]

The title compound was synthesized from (5-chloro-2-cyclopentylsulfonylphenyl)methanamine hydrochloride (Compound n18) under the same conditions as for Compound A-14. However, 3-chloro-4-[[(3S)-3-[methyl-[(2-methylpropan-2-yl)oxycarbonyl]amino]piperidin-1-yl]methyl]-5-(trifluoromethyl)benzoic acid (compound dd34) was used in place of 4-bromo-3-trifluoromethyl-benzoic acid.

Example 651

Compound N-22

3-Chloro-N-[(5-chloro-2-cyclopentylsulfonylphenyl)methyl]-4-[[(3S)-3-(methylamino)piperidin-1-yl]methyl]-5-(trifluoromethyl)benzamide

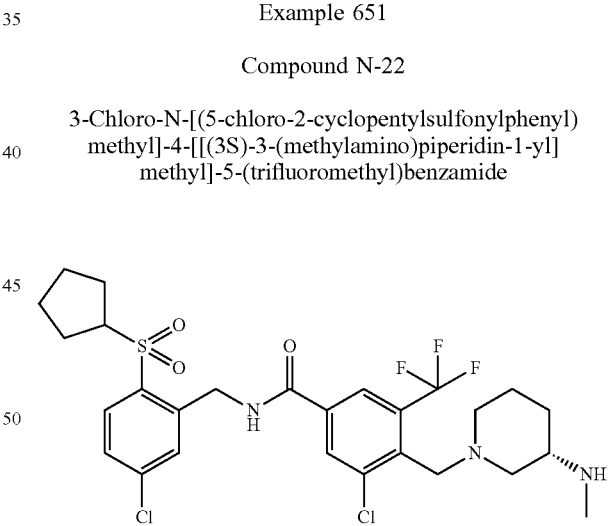

The title compound was synthesized from tert-butyl N-[(3S)-1-[[2-chloro-4-[(5-chloro-2-cyclopentylsulfonylphenyl)methylcarbamoyl]-6-(trifluoromethyl)phenyl]methyl]piperidin-3-yl]-N-methylcarbamate (Compound n19) under the same conditions as for Compound B-1.
LCMS: m/z 606 [M+H]⁺
HPLC retention time: 0.64 min (analysis condition F)

Example 652

Compounds N-23 and N-24 were synthesized from 4-[(4-aminopiperidin-1-yl)methyl]-3-chloro-N-[(5-chloro-2-eth- Compound N-23

3-Chloro-N-[(5-chloro-2-ethylsulfonylphenyl)methyl]-4-[[4-(dimethylamino)piperidin-1-yl]methyl]-5-(trifluoromethyl)benzamide

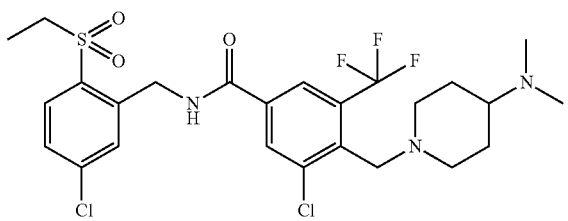 [SMILES: CCS(=O)(=O)c1ccc(Cl)cc1CNC(=O)c1cc(Cl)c(CN2CCC(N(C)C)CC2)c(C(F)(F)F)c1]

LCMS: m/z 580 [M+H]$^+$
HPLC retention time: 0.46 min (analysis condition A)

Compound N-24

1-[[2-Chloro-4-[(5-chloro-2-ethylsulfonylphenyl)methylcarbamoyl]-6-trifluoromethyl)phenyl]methyl]-N,N-dimethylpiperidine-4-amine oxide

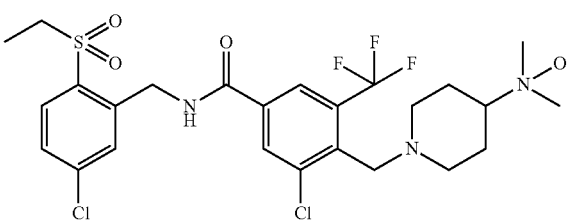

LCMS: m/z 596 [M+H]$^+$
HPLC retention time: 0.49 min (analysis condition A)

Example 653

Compound n20

Ethyl (3S)-1-[[2-chloro-4-[(5-chloro-2-ethylsulfonylphenyl)methylcarbamoyl]-6-(trifluoromethyl)phenyl]methyl]piperidine-3-carboxylate

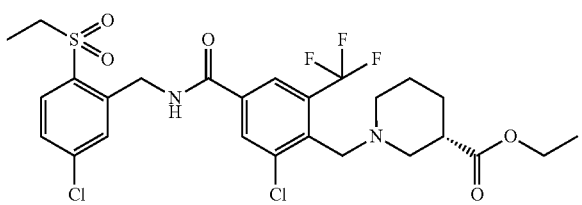 [SMILES: CCOC(=O)[C@H]1CCCN(Cc2c(Cl)cc(C(=O)NCc3cc(Cl)ccc3S(=O)(=O)CC)cc2C(F)(F)F)C1]

The title compound was synthesized from 3-chloro-N-[(5-chloro-2-ethylsulfonylphenyl)methyl]-4-formyl-5-(trifluoromethyl)benzamide (Compound dd23) under the same conditions as for Compound b32. However, ethyl (3S)-piperidine-3-carboxylate was used in place of tert-butyl N-[[(2S)-pyrrolidin-2-yl]methyl]carbamate, and chloroform was used in place of THF as a solvent.

Example 654

Compound N-25

(3S)-1-[[2-Chloro-4-[(5-chloro-2-ethylsulfonylphenyl)methylcarbamoyl]-6-(trifluoromethyl)phenyl]methyl]piperidine-3-carboxylic acid

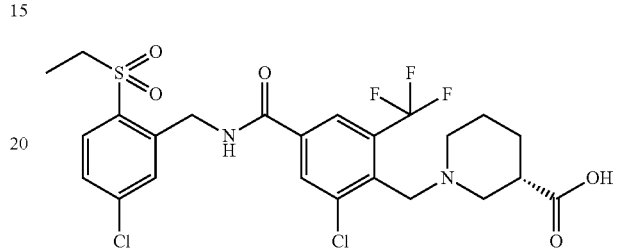

The title compound was synthesized from ethyl (3S)-1-[[2-chloro-4-[(5-chloro-2-ethylsulfonylphenyl)methylcarbamoyl]-6-(trifluoromethyl)phenyl]methyl]piperidine-3-carboxylate (Compound n20) under the same conditions as for Compound b8.
LCMS: m/z 581 [M+H]$^+$
HPLC retention time: 0.55 min (analysis condition F)

Example 655

Compound N-26

(3S)-1-[[2-Chloro-4-[(5-chloro-2-ethylsulfonylphenyl)methylcarbamoyl]-6-(trifluoromethyl)phenyl]methyl]-N,N-dimethylpiperidine-3-carboxamide

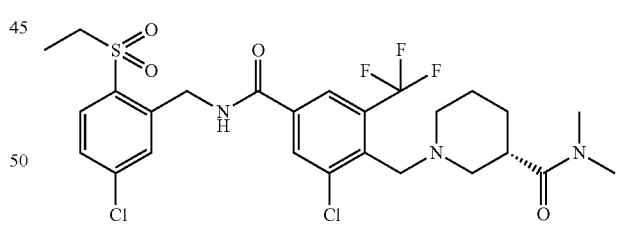

N,N-Dimethylamine (57 µl, 0.114 mmol) and DIPEA (36 µl, 0.206 mmol) were added to a solution of (3S)-1-[[2-chloro-4-[(5-chloro-2-ethylsulfonylphenyl)methylcarbamoyl]-6-(trifluoromethyl)phenyl]methyl]piperidine-3-carboxylic acid (Compound N-25, 60 mg, 0.102 mmol) and HATU (51 mg, 0.134 mmol) in acetonitrile (1 ml), and it was stirred at room temperature for 30 minutes. The reaction mixture was concentrated under reduced pressure, and the resultant residue was purified by amino silica gel column chromatography (DCM/n-hexane) to yield the title compound (49 mg, 79%) as a colorless solid.
LCMS: m/z 608 [M+H]$^+$
HPLC retention time: 0.52 min (analysis condition F)

Example 656

Compound N-27

(3S)-1-[[2-Chloro-4-[(5-chloro-2-ethylsulfonylphenyl)methylcarbamoyl]-6-(trifluoromethyl)phenyl]methyl]-N-methylpiperidine-3-carboxamide

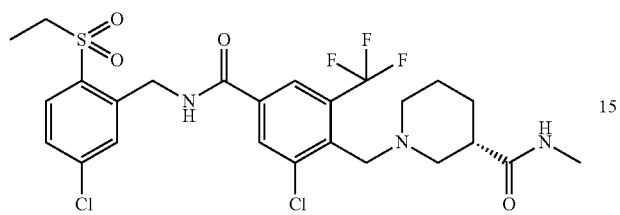

The title compound was synthesized from (3S)-1-[[2-chloro-4-[(5-chloro-2-ethylsulfonylphenyl)methylcarbamoyl]-6-(trifluoromethyl)phenyl]methyl]piperidine-3-carboxylic acid (Compound N-25) under the same conditions as for Compound N-26. However, methanamine hydrochloride was used in place of N,N-dimethylamine.

LCMS: m/z 594 [M+H]+
HPLC retention time: 0.52 min (analysis condition F)

Example 657

Compound N-28

(3S)-1-[[2-Chloro-4-[(5-chloro-2-ethylsulfonylphenyl)methylcarbamoyl]-6-(trifluoromethyl)phenyl]methyl]-N-[2-(dimethylamino)ethyl]piperidine-3-carboxamide

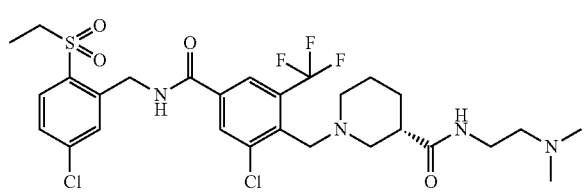 [SMILES: CCS(=O)(=O)c1ccc(Cl)cc1CNC(=O)c1cc(Cl)c(CN2CCC[C@H](C(=O)NCCN(C)C)C2)c(C(F)(F)F)c1]

The title compound was synthesized from (3S)-1-[[2-chloro-4-[(5-chloro-2-ethylsulfonylphenyl)methylcarbamoyl]-6-(trifluoromethyl)phenyl]methyl]piperidine-3-carboxylic acid (Compound N-25) under the same conditions as for Compound N-26. However, N',N'-dimethylethane-1,2-diamine was used in place of N,N-dimethylamine.

LCMS: m/z 651 [M+H]+
HPLC retention time: 0.42 min (analysis condition F)

Example 658

Compound n21 tert-Butyl 4-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]piperidine-1-carboxylate

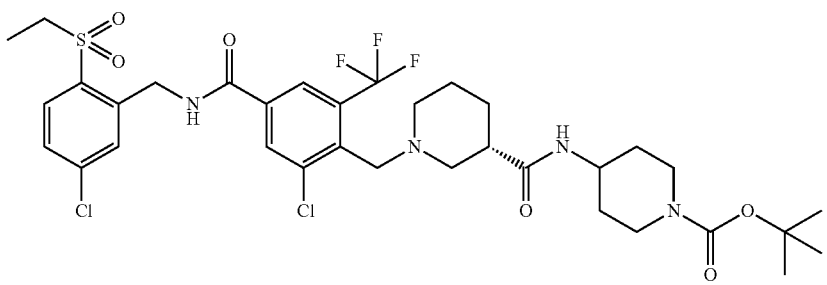 [SMILES: CCS(=O)(=O)c1ccc(Cl)cc1CNC(=O)c1cc(Cl)c(CN2CCC[C@H](C(=O)NC3CCN(C(=O)OC(C)(C)C)CC3)C2)c(C(F)(F)F)c1]

The title compound was synthesized from (3S)-1-[[2-chloro-4-[(5-chloro-2-ethylsulfonylphenyl)methylcarbamoyl]-6-(trifluoromethyl)phenyl]methyl]piperidine-3-carboxylic acid (Compound N-25) under the same conditions as for Compound N-26. However, tert-butyl 4-aminopiperidine-1-carboxylate was used in place of N,N-dimethylamine.

Example 659

Compound N-29

(3S)-1-[[2-Chloro-4-[(5-chloro-2-ethylsulfonylphenyl)methylcarbamoyl]-6-(trifluoromethyl)phenyl]methyl]-N-piperidin-4-ylpiperidine-3-carboxamide

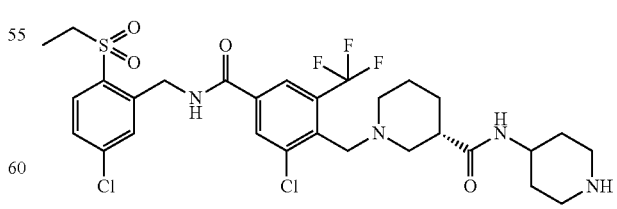

The title compound was synthesized from tert-butyl 4-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]piperidine-1-carboxylate (Compound n21) under the same conditions as for Compound B-1.

LCMS: m/z 663 [M+H]+
HPLC retention time: 0.42 min (analysis condition F)

Example 660

Compound o1

5-Chloro-2-ethylsulfanylaniline

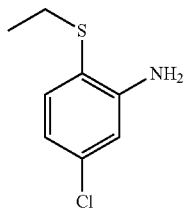

The title compound was synthesized from 2-amino-4-chlorobenzenethiol under the same conditions as for Compound a4.

Example 661

Compound o2

5-Chloro-2-ethylsulfonylaniline

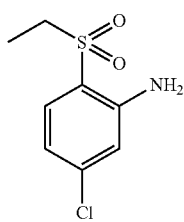

The title compound was synthesized from 5-chloro-2-ethylsulfanylaniline (Compound o1) under the same conditions as for Compound A-2.

Example 662

Compound o3

(5-Chloro-2-ethylsulfonylphenyl)hydrazine

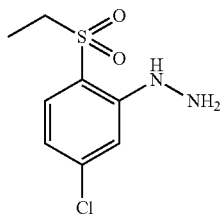

The title compound was synthesized from 5-chloro-2-ethylsulfonylaniline (Compound o2) under the same conditions as for Compound a5.

Example 663

Compound O-1

N'-(5-Chloro-2-ethylsulfonylphenyl)-2-phenyl-5-(trifluoromethyl)-1,3-oxazole-4-carbohydrazide

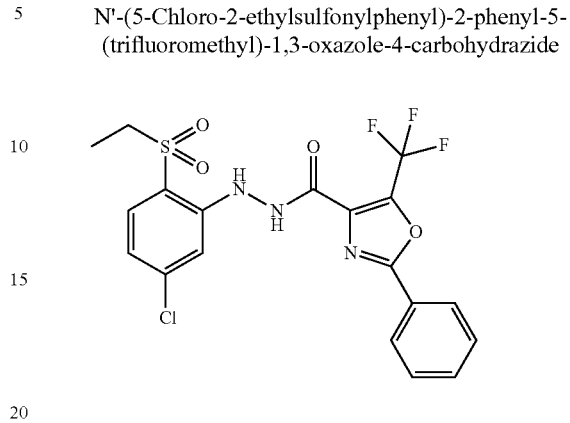

The title compound was synthesized from (5-chloro-2-ethylsulfonylphenyl)hydrazine (Compound o3) under the same conditions as for Compound A-14. However, 2-phenyl-5-(trifluoromethyl)-1,3-oxazole-4-carboxylic acid was used in place of 4-bromo-3-(trifluoromethyl)benzoic acid.

LCMS: m/z 474 [M+H]+
HPLC retention time: 0.96 min (analysis condition F)

Example 664

Compound o4

1,2-Dichloro-4-ethylsulfanyl-5-nitrobenzene

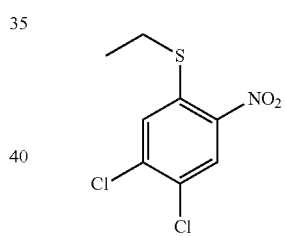

The title compound was synthesized from 1,2-dichloro-4-fluoro-5-nitrobenzene under the same conditions as for Compound a1. However, triethylamine was used in place of potassium carbonate.

Example 665

Compound o5

4,5-Dichloro-2-ethylsulfanylaniline

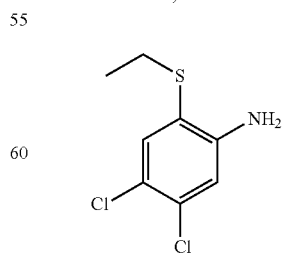

The title compound was synthesized from 1,2-dichloro-4-ethylsulfanyl-5-nitrobenzene (Compound o4) under the

319 same conditions as for Compound f4. However, the reaction was performed using ethanol in place of 2-propanol as a solvent and at a temperature of 80° C.

Example 666

Compound o6

(4,5-Dichloro-2-ethylsulfanylphenyl)hydrazine

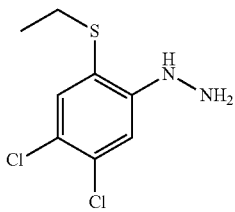

The title compound was synthesized from 4,5-dichloro-2-ethylsulfanylaniline (Compound o5) under the same conditions as for Compound a5.

Example 667

Compound o7

3-Chloro-N'-(4,5-dichloro-2-ethylsulfanylphenyl)-5-(trifluoromethyl)benzohydrazide

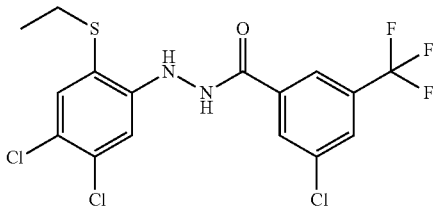 [SMILES: CCSc1cc(Cl)c(Cl)cc1NNC(=O)c1cc(Cl)cc(C(F)(F)F)c1]

The title compound was synthesized from (4,5-dichloro-2-ethylsulfanylphenyl)hydrazine (Compound o6) under the same conditions as for Compound A-1. However, 3-chloro-5-(trifluoromethyl)benzoic acid was used in place of 3-bromo-5-(trifluoromethyl)benzoic acid.

Example 668

Compound O-2

3-Chloro-N'-(4,5-dichloro-2-ethylsulfonylphenyl)-5-(trifluoromethyl)benzohydrazide

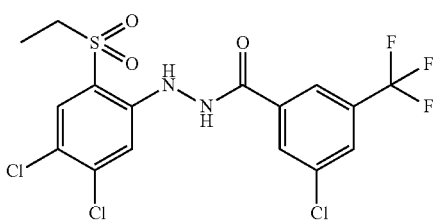 [SMILES: CCS(=O)(=O)c1cc(Cl)c(Cl)cc1NNC(=O)c1cc(Cl)cc(C(F)(F)F)c1]

320

The title compound was synthesized from 3-chloro-N'-(4,5-dichloro-2-ethylsulfanyl phenyl)-5-(trifluoromethyl)benzohydrazide (Compound o7) under the same conditions as for Compound A-2.

LCMS: m/z 475 [M+H]$^+$
HPLC retention time: 0.97 min (analysis condition F)

Example 669

Compound o8

3-Amino-4-ethylsulfanylbenzonitrile

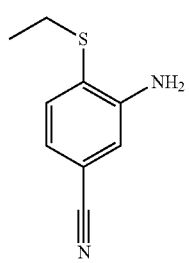

Sodium ethanethiolate (1.62 g, 19.27 mmol) was added to a solution of 3-amino-4-chlorobenzonitrile (1.96 g, 12.85 mmol) in DMF (12 ml), and it was stirred at 80° C. for 50 minutes using a microwave reactor. The reaction solution was cooled to room temperature, and then diluted with EtOAc (250 ml). The resultant solution was washed with 13% saline (100 ml×3), and the organic layer was then dried over anhydrous sodium sulfate. The drying agent was removed by filtration, followed by concentration under reduced pressure. The resultant residue was purified by amino silica gel column chromatography (EtOAc/n-hexane) to yield the title compound (2.13 g, 93%) as a pale yellow solid.

LCMS: m/z 179 [M+H]$^+$
HPLC retention time: 2.00 min (analysis condition D)

Example 670

Compound O-3

3-Chloro-N'-(5-cyano-2-ethylsulfonylphenyl)-5-(trifluoromethyl)benzohydrazide

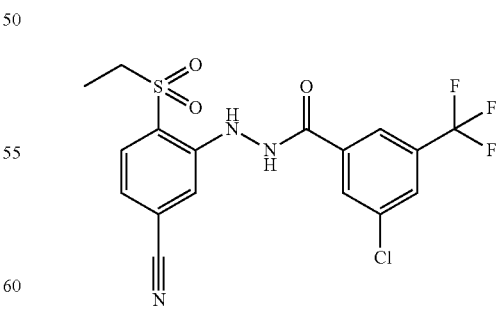

The title compound was synthesized from 3-amino-4-ethylsulfanylbenzonitrile (Compound o8) under the same conditions as for Compounds o6, o7 and O-2. However, under the Compound O-2 conditions, the reaction was performed with the addition of THF.

LCMS: m/z 432 [M+H]⁺
HPLC retention time: 0.85 min (analysis condition F)

Example 671

Compound o9

4-Ethylsulfanyl-3-methylbenzonitrile

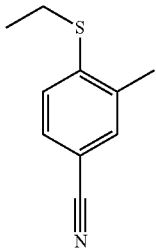

The title compound was synthesized from 4-fluoro-3-methylbenzonitrile under the same conditions as for Compound a1.

Example 672

Compound o10

4-Ethylsulfonyl-3-methylbenzonitrile

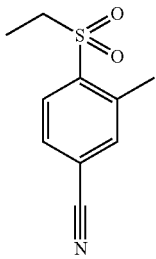

The title compound was synthesized from 4-ethylsulfanyl-3-methylbenzonitrile (Compound o9) under the same conditions as for Compound A-2.

Example 673

Compound o11

3-(Bromomethyl)-4-ethylsulfonylbenzonitrile

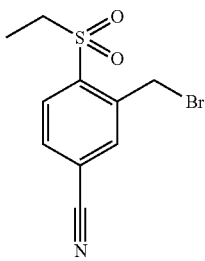

The title compound was synthesized from 4-ethylsulfonyl-3-methylbenzonitrile (Compound o10) under the same conditions as for Compound b6.

Example 674

Compound o12

3-(Aminomethyl)-4-ethylsulfonylbenzonitrile

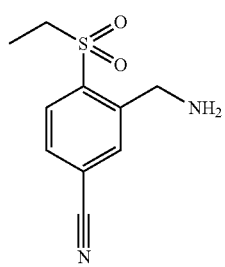

The title compound was synthesized from 3-(bromomethyl)-4-ethylsulfonylbenzonitrile (Compound o11) under the same conditions as for Compound bb9.

Example 675

Compound O-4

3-Chloro-N-[(5-cyano-2-ethylsulfonylphenyl)methyl]-5-(trifluoromethyl)benzamide

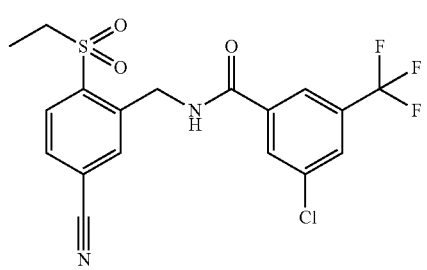 [SMILES: CCS(=O)(=O)c1ccc(C#N)cc1CNC(=O)c1cc(Cl)cc(C(F)(F)F)c1]

The title compound was synthesized from 3-(aminomethyl)-4-ethylsulfonylbenzonitrile (Compound o12) under the same conditions as for Compound bb10. However, 3-chloro-5-(trifluoromethyl)benzoic acid was used in place of 4-[[4-[(2-methylpropan-2-yl)oxycarbonyl]piperazin-1-yl]methyl]-3-(trifluoromethyl)benzoic acid (Compound b3).
LCMS: m/z 431 [M+H]⁺
HPLC retention time: 0.84 min (analysis condition F)

Example 676

Compound o13 tert-Butyl N-[(5-chloro-2-phenylsulfanylphenyl)methyl]carbamate

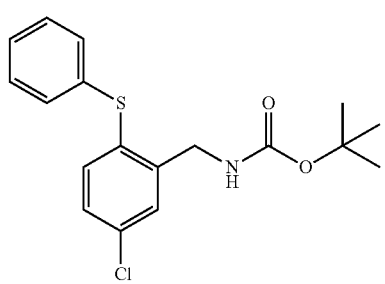 [SMILES: CC(C)(C)OC(=O)NCc1cc(Cl)ccc1Sc1ccccc1]

Boc₂O (454 mg, 2.08 mmol) and TEA (483 μl, 3.48 mmol) were added to a solution of (5-chloro-2-phenylsulfanylphenyl)methanamine (Compound dd39, 435 mg, 1.74 mmol) in THF (17 ml), and it was stirred at room temperature for 30 minutes. The reaction mixture was concentrated under reduced pressure, and the resultant residue was purified by silica gel column chromatography (ethyl acetate/hexane) to yield the title compound (510 mg, 84%).

¹H-NMR (300 MHz, CDCl₃) δ: 7.17-7.42 (8H, m), 4.91 (1H, brs), 4.39 (2H, d, J=4.5 Hz), 1.44 (9H, s).

Example 677

Compound o14

(5-Chloro-2-phenylsulfanylphenyl)methanamine hydrochloride

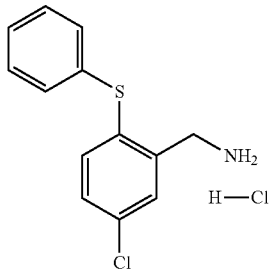

The title compound was synthesized from tert-butyl N-[(5-chloro-2-phenylsulfanylphenyl)methyl]carbamate (Compound o13) under the same conditions as for Compound B-57. However, the reaction was performed at a temperature of 40° C.

Example 678

Compound O-5

3-Chloro-N-[(5-chloro-2-phenylsulfanylphenyl)methyl]-5-(trifluoromethyl)benzamide

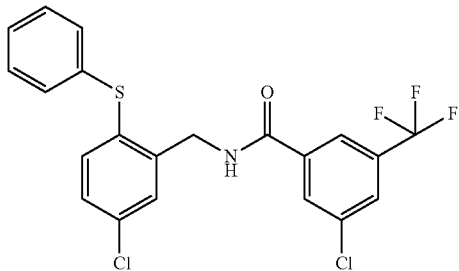 [SMILES: O=C(NCc1cc(Cl)ccc1Sc1ccccc1)c1cc(Cl)cc(C(F)(F)F)c1]

The title compound was synthesized from (5-chloro-2-phenylsulfanylphenyl)methanamine hydrochloride (Compound o14) under the same conditions as for Compound bb10. However, 3-chloro-5-(trifluoromethyl)benzoic acid was used in place of 4-[[4-[(2-methylpropan-2-yl)oxycarbonyl]piperazin-1-yl]methyl]-3-(trifluoromethyl)benzoic acid (Compound b3).

LCMS: m/z 456 [M+H]⁺

HPLC retention time: 1.09 min (analysis condition F)

Example 679

Compound O-6

N-[[2-(Benzenesulfinyl)-5-chlorophenyl]methyl]-3-chloro-5-(trifluoromethyl)benzamide

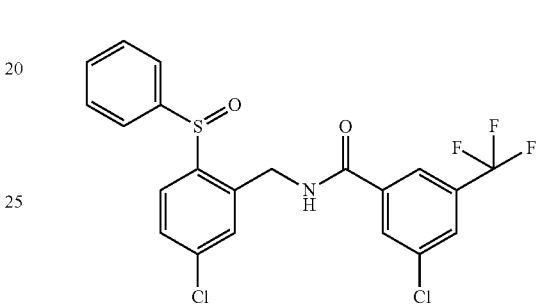

m-CPBA (6.9 mg, 0.031 mmol) was added to a solution of 3-chloro-N-[(5-chloro-2-phenylsulfanylphenyl)methyl]-5-(trifluoromethyl)benzamide (Compound O-5, 47 mg, 0.10 mmol) in EtOAc (2 ml) under ice-cooling. After two hours, m-CPBA (6.9 mg, 0.031 mmol) was further added. Two hours later, m-CPBA (8.1 mg, 0.036 mmol) was added once again, and the mixture was stirred under ice-cooling for two hours. The reaction mixture was allowed to pass through an amino silica gel and then concentrated under reduced pressure, and the resultant residue was purified by silica gel column chromatography (ethyl acetate/n-hexane) to yield the title compound (28 mg, 59%).

LCMS: m/z 472 [M+H]⁺

HPLC retention time: 0.92 min (analysis condition F)

Example 680

Compound o15 tert-Butyl N-[2-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]ethyl]-N-methylcarbamate

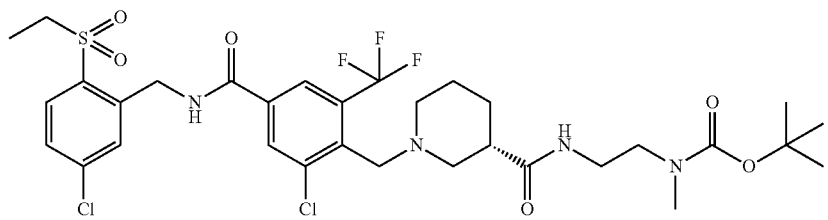 [SMILES: CCS(=O)(=O)c1ccc(Cl)cc1CNC(=O)c1cc(Cl)c(CN2CCC[C@H](C(=O)NCCN(C)C(=O)OC(C)(C)C)C2)c(C(F)(F)F)c1]

325

The title compound was synthesized from (3S)-1-[[2-chloro-4-[(5-chloro-2-ethylsulfonylphenyl)methylcarbamoyl]-6-(trifluoromethyl)phenyl]methyl]piperidine-3-carboxylic acid (Compound N-25) under the same conditions as for Compound N-26. However, tert-butyl N-(2-aminoethyl)-N-methylcarbamate was used in place of N,N-dimethylamine.

Example 681

Compound O-7

(3S)-1-[[2-Chloro-4-[(5-chloro-2-ethylsulfonylphenyl)methylcarbamoyl]-6-(trifluoromethyl)phenyl]methyl]-N-[2-(methylamino)ethyl]piperidine-3-carboxamide

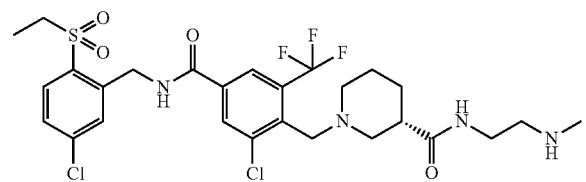 [SMILES: CCS(=O)(=O)c1ccc(Cl)cc1CNC(=O)c1cc(Cl)c(CN2CCC[C@H](C(=O)NCCNC)C2)c(C(F)(F)F)c1]

The title compound was synthesized from tert-butyl N-[2-[[(3S)-1-[[2-chloro-4-[(5-chloro-2-ethylsulfonylphenyl)methylcarbamoyl]-6-(trifluoromethyl)phenyl]methyl]piperidine-3-carbonyl]amino]ethyl]-N-methylcarbamate (Compound o15) under the same conditions as for Compound B-1.

LCMS: m/z 637 [M+H]+

HPLC retention time: 0.41 min (analysis condition F)

Example 682

Compound o16

4-[(2-Benzhydryl-5-oxa-2,8-diazaspiro[3.5]nonan-8-yl)methyl]-3-chloro-N-[(5-chloro-2-ethylsulfonylphenyl)methyl]-5-(trifluoromethyl)benzamide

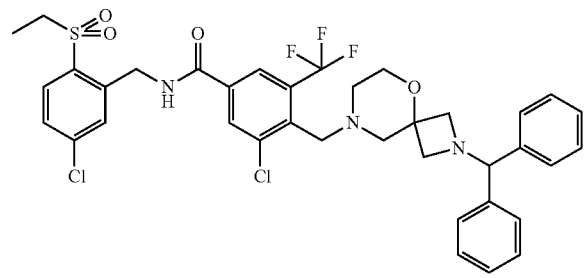 [SMILES: CCS(=O)(=O)c1ccc(Cl)cc1CNC(=O)c1cc(Cl)c(CN2CCOC3(C2)CN(C(c2ccccc2)c2ccccc2)C3)c(C(F)(F)F)c1]

The title compound was synthesized from (4-(bromomethyl)-3-chloro-N-[(5-chloro-2-ethylsulfonylphenyl)methyl]-5-(trifluoromethyl)benzamide (Compound dd16) under the same conditions as for Compound g3. However, 2-benzhydryl-5-oxa-2,8-diazaspiro[3.5]nonane was used in place of tert-butyl piperazine-1-carboxylate, and DIPEA was added. DMF was used in place of THF as a solvent.

326

Example 683

Compound O-8

3-Chloro-N-[(5-chloro-2-ethylsulfonylphenyl)methyl]-4-(5-oxa-2,8-diazaspiro[3.5]nonan-8-ylmethyl)-5-(trifluoromethyl)benzamide

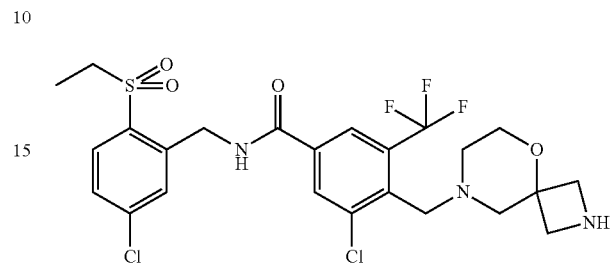

1-Chloroethyl chloroformate (3.2 µl, 0.029 mol) was added to a solution of 4-[(2-benzhydryl-5-oxa-2,8-diazaspiro[3.5]nonan-8-yl)methyl]-3-chloro-N-[(5-chloro-2-ethylsulfonylphenyl)methyl]-5-(trifluoromethyl)benzamide (Compound o16, 18 mg, 0.025 mmol) in DCM (2 ml), and it was stirred at room temperature for 27 hours. 1-Chloroethyl chloroformate (1.6 µl, 0.015 mol) was further added to the reaction solution, and it was stirred at room temperature for 22 hours. The reaction solution was concentrated under reduced pressure, and the resultant residue was diluted with methanol (2 ml). The resultant solution was stirred under reflux for one hour. The reaction solution was concentrated under reduced pressure, and the resultant residue was purified by preparative HPLC (water/acetonitrile, 0.05% TFA) to yield the title compound (9 mg, 66%) as a colorless solid.

LCMS: m/z 580 [M+H]+

HPLC retention time: 0.57 min (analysis condition F)

Example 684

Compound P-1

N'-(5-Chloro-2-ethylsulfonylphenyl)-2-methyl-6-oxo-1H-pyridine-4-carbohydrazide

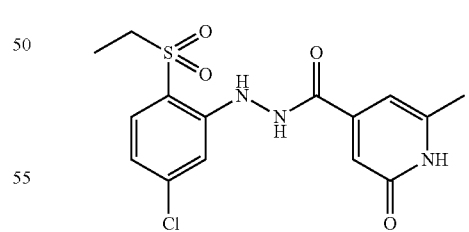

The title compound was synthesized from (5-chloro-2-ethylsulfonylphenyl)hydrazine (Compound o3) under the same conditions as for Compound A-14. However, 2-methyl-6-oxo-1H-pyridine-4-carboxylic acid was used in place of 4-bromo-3-(trifluoromethyl)benzoic acid as a carboxylic acid.

LCMS: m/z 370 [M+H]+

HPLC retention time: 0.50 min (analysis condition A)

Example 685

Compound p1

5-Iodo-3-(trifluoromethyl)-1H-pyridin-2-one

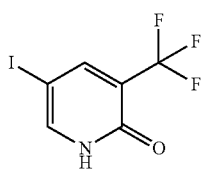 [SMILES: O=c1[nH]cc(I)cc1C(F)(F)F]

The title compound was synthesized from 3-(trifluoromethyl)-1H-pyridin-2-one under the same conditions as for Compound n7. However, the reaction was performed with the addition of potassium carbonate.

Example 686

Compound p2

6-Oxo-5-(trifluoromethyl)-1H-pyridine-3-carbonitrile

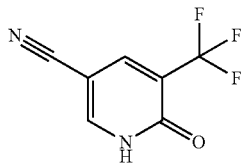

The title compound was synthesized from 5-iodo-3-(trifluoromethyl)-1H-pyridin-2-one (Compound p1) under the same conditions as for Compound m2.

Example 687

Compound p3

Methyl 6-oxo-5-(trifluoromethyl)-1H-pyridine-3-carboxylate

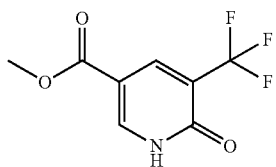

The title compound was synthesized from 6-oxo-5-(trifluoromethyl)-1H-pyridine-3-carbonitrile (Compound p2) under the same conditions as for Compound m3.

Example 688

Compound p4

6-Oxo-5-(trifluoromethyl)-1H-pyridine-3-carboxylic acid

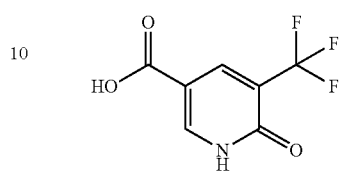

The title compound was synthesized from methyl 6-oxo-5-(trifluoromethyl)-1H-pyridine-3-carboxylate (Compound p3) under the same conditions as for Compound b8. However, MeOH was used in place of EtOH as a solvent.

Example 689

Compound P-2

N-[(5-Chloro-2-ethylsulfonylphenyl)methyl]-6-oxo-5-(trifluoromethyl)-1H-pyridine-3-carboxamide

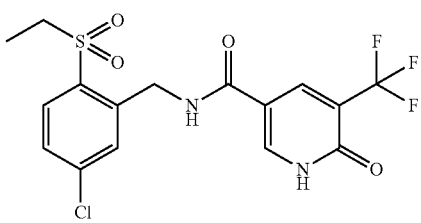 [SMILES: CCS(=O)(=O)c1ccc(Cl)cc1CNC(=O)c1c[nH]c(=O)c(C(F)(F)F)c1]

The title compound was synthesized from 5-chloro-2-ethanesulfonyl-benzylamine hydrochloride (Compound a3) under the same conditions as for Compound bb10. However, 6-oxo-5-(trifluoromethyl)-1H-pyridine-3-carboxylic acid (Compound p4) was used in place of 4-[[4-[(2-methylpropan-2-yl)oxycarbonyl]piperazin-1-yl]methyl]-3-(trifluoromethyl)benzoic acid (Compound b3) as a carboxylic acid.

LCMS: m/z 423 [M+H]$^+$
HPLC retention time: 0.59 min (analysis condition A)

Example 690

Compound p5 tert-Butyl N-[(5-chloro-2-ethylsulfanylphenyl)methyl]carbamate

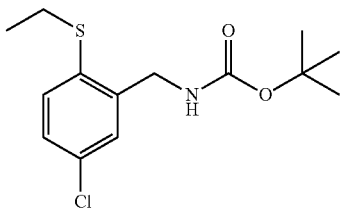

The title compound was synthesized from (5-chloro-2-ethylsulfanylphenyl)methanamine (Compound a2) under the same conditions as for Compound o15.

Example 691

Compound p6

(5-Chloro-2-ethylsulfanylphenyl)methanamine hydrochloride

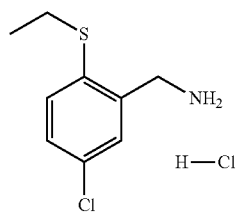

The title compound was synthesized from tert-butyl N-[(5-chloro-2-ethylsulfanylphenyl)methyl]carbamate (Compound p5) under the same conditions as for Compound B-57. However, the reaction was performed at a temperature of 40° C.

Example 692

Compound p7

3-Chloro-N-[(5-chloro-2-ethylsulfanylphenyl)methyl]-5-(trifluoromethyl)benzamide

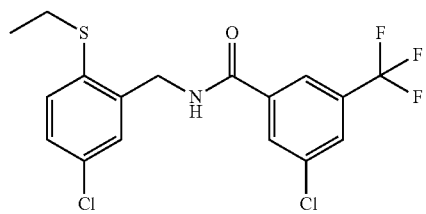 [SMILES: CCSc1ccc(Cl)cc1CNC(=O)c1cc(Cl)cc(C(F)(F)F)c1]

The title compound was synthesized from (5-chloro-2-ethylsulfanylphenyl)methanamine hydrochloride (Compound p6) under the same conditions as for Compound bb10. However, 3-chloro-5-(trifluoromethyl)benzoic acid was used in place of 4-[[4-[(2-methylpropan-2-yl)oxycarbonyl]piperazin-1-yl]methyl]-3-(trifluoromethyl)benzoic acid (Compound b3) as a carboxylic acid.

Example 693

Compound P-3

3-Chloro-N-[(5-chloro-2-ethylsulfinylphenyl)methyl]-5-(trifluoromethyl)benzamide

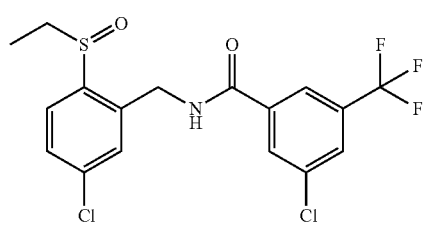 [SMILES: CCS(=O)c1ccc(Cl)cc1CNC(=O)c1cc(Cl)cc(C(F)(F)F)c1]

The title compound was synthesized from 3-chloro-N-[(5-chloro-2-ethylsulfanylphenyl)methyl]-5-(trifluoromethyl)benzamide (Compound p7) under the same conditions as for Compound O-6.

LCMS: m/z 424 [M+H]$^+$

HPLC retention time: 0.82 min (analysis condition F)

Example 694

Compound p8

3-Ethyl sulfanylpyridine-4-carbonitrile

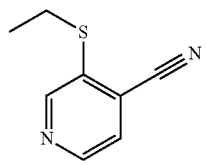

The title compound was synthesized from 3-chloropyridine-4-carbonitrile under the same conditions as for Compound a6. However, the reaction was performed with the addition of potassium carbonate and at room temperature.

Example 695

Compound p9

(3-Ethylsulfanylpyridin-4-yl)methanamine

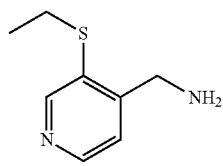

A solution of 2 M ammonia in methanol (1 ml) and a 50% aqueous Raney nickel suspension (1 ml) were added to a solution of 3-ethylsulfanylpyridine-4-carbonitrile (Compound p8, 82 mg, 0.5 mmol) in methanol (10 ml), and it was stirred at room temperature for four hours under a hydrogen atmosphere, followed by removal of the insoluble matter by filtration through celite, and then it was washed with methanol. The filtrate and the washings were combined, followed by concentration under reduced pressure. The resultant residue was purified by silica gel column chromatography (ethyl acetate/n-hexane) to yield the title compound (66 mg, 80%) as a yellow oily substance.

1H-NMR (300 MHz, CDCl$_3$) δ: 8.51 (1H, s), 8.43 (1H, d, J=3.6 Hz), 7.32 (1H, d, J=3.6 Hz), 3.95 (2H, s), 2.99 (2H, q, J=5.4 Hz), 1.34 (3H, t, J=5.4 Hz).

Example 696

Compound p10

3-Chloro-N-[(3-ethylsulfanylpyridin-4-yl)methyl]-5-(trifluoromethyl)benzamide

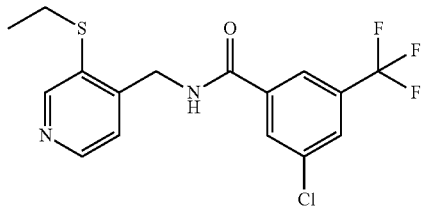 [SMILES: CCSc1cnccc1CNC(=O)c1cc(Cl)cc(C(F)(F)F)c1]

The title compound was synthesized from (3-ethylsulfanylpyridin-4-yl)methanamine (Compound p9) under the same conditions as for Compound bb10. However, 3-chloro-5-(trifluoromethyl)benzoic acid was used in place of 4-[[4-[(2-methylpropan-2-yl)oxycarbonyl]piperazin-1-yl]methyl]-3-(trifluoromethyl)benzoic acid (Compound b3) as a carboxylic acid.

Example 697

Compound P-4

3-Chloro-N-[(3-ethylsulfanylpyridin-4-yl)methyl]-5-(trifluoromethyl)benzamide

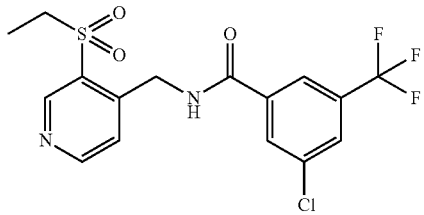 [SMILES: CCS(=O)(=O)c1cnccc1CNC(=O)c1cc(Cl)cc(C(F)(F)F)c1]

The title compound was synthesized from 3-chloro-N-[(3-ethylsulfanylpyridin-4-yl)methyl]-5-(trifluoromethyl)benzamide (Compound p10) under the same conditions as for Compound A-2. However, the reaction was performed using EtOAc in place of DCM as a solvent, and at a temperature of −20° C. to 0° C.

LCMS: m/z 407 [M+H]$^+$
HPLC retention time: 0.74 min (analysis condition F)

Example 698

Compound p11

2-Ethylsulfanyl-5-methylbenzonitrile

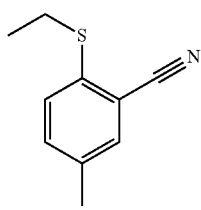

The title compound was synthesized from 2-fluoro-5-methylbenzonitrile under the same conditions as for Compound a1.

Example 699

Compound p12

(2-Ethylsulfanyl-5-methylphenyl)methanamine

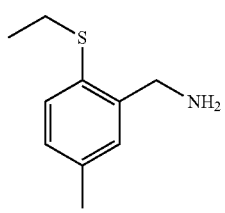

The title compound was synthesized from 2-ethylsulfanyl-5-methylbenzonitrile (Compound p11) under the same conditions as for Compound a2.

Example 700

Compound p13

(2-Ethylsulfonyl-5-methylphenyl)methanamine hydrochloride

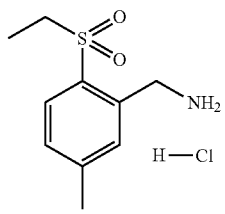

The title compound was synthesized from (2-ethylsulfanyl-5-methylphenyl)methanamine (Compound p12) under the same conditions as for Compound dd45.

Example 701

Compound p14 tert-Butyl N-[(3S)-1-[[2-chloro-4-[(2-ethylsulfonyl-5-methylphenyl)methylcarbamoyl]-6-(trifluoromethyl)phenyl]methyl]piperidin-3-yl]-N-methylcarbamate

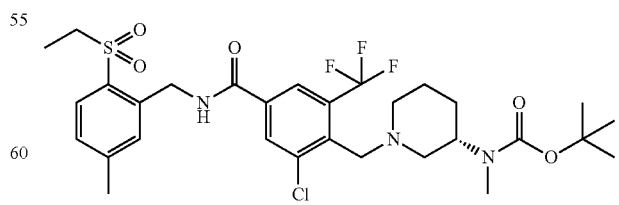

The title compound was synthesized from (2-ethylsulfonyl-5-methylphenyl)methanamine hydrochloride (Compound p13) under the same conditions as for Compound bb10. However, 3-chloro-4-[[(3S)-3-[methyl-[(2-methylpropan-2-yl)oxycarbonyl]amino]piperidin-1-yl]methyl]-5-(trifluoromethyl)benzoic acid (Compound dd34) was used in place of 4-[[4-[(2-methylpropan-2-yl)oxycarbonyl]piperazin-1-yl]methyl]-3-(trifluoromethyl)benzoic acid (Compound b3) as a carboxylic acid.

Example 702

Compound P-5

3-Chloro-N-[(2-ethylsulfonyl-5-methylphenyl)methyl]-4-[[(3S)-3-(methylamino)piperidin-1-yl]methyl]-5-(trifluoromethyl)benzamide

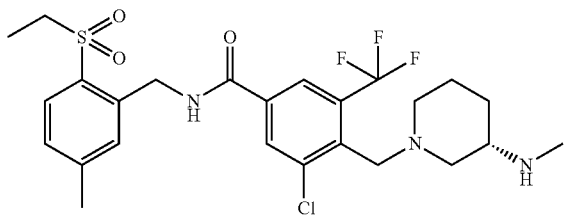 [SMILES: CCS(=O)(=O)c1ccc(C)cc1CNC(=O)c1cc(Cl)c(CN2CCC[C@H](NC)C2)c(C(F)(F)F)c1]

The title compound was synthesized from tert-butyl N-[(3S)-1-[[2-chloro-4-[(2-ethylsulfonyl-5-methylphenyl)methylcarbamoyl]-6-(trifluoromethyl)phenyl]methyl]piperidin-3-yl]-N-methylcarbamate (Compound p14) under the same conditions as for Compound B-57.

LCMS: m/z 546 [M+H]$^+$

HPLC retention time: 0.54 min (analysis condition F)

Example 703

Compound P-6

N'-(5-Chloro-2-ethylsulfonylphenyl)-3-(trifluoromethyl)-1H-pyrazole-4-carbohydrazide

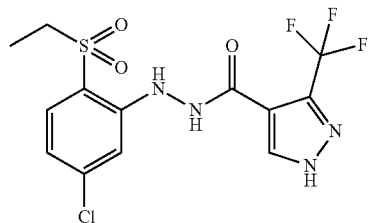 [SMILES: CCS(=O)(=O)c1ccc(Cl)cc1NNC(=O)c1c[nH]nc1C(F)(F)F]

The title compound was synthesized from (5-chloro-2-ethylsulfonylphenyl)hydrazine (Compound o3) under the same conditions as for Compound A-14. However, 3-(trifluoromethyl)-1H-pyrazole-4-carboxylic acid was used in place of 4-bromo-3-(trifluoromethyl)benzoic acid as a carboxylic acid.

LCMS: m/z 397 [M+H]$^+$

HPLC retention time: 0.65 min (analysis condition F)

Example 704

Compound P-8

N'-(5-Chloro-2-ethylsulfonylphenyl)-2-ethyl-4-methyl-1,3-oxazole-5-carbohydrazide

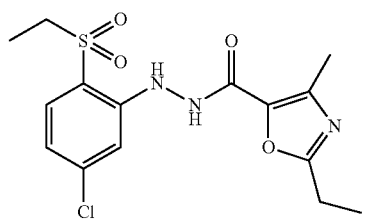 [SMILES: CCc1nc(C)c(C(=O)NNc2cc(Cl)ccc2S(=O)(=O)CC)o1]

The title compound was synthesized from (5-chloro-2-ethylsulfonylphenyl)hydrazine (Compound o3) under the same conditions as for Compound A-14. However, 2-ethyl-4-methyl-1,3-oxazole-5-carboxylic acid was used in place of 4-bromo-3-(trifluoromethyl)benzoic acid as a carboxylic acid.

LCMS: m/z 372 [M+H]$^+$

HPLC retention time: 0.69 min (analysis condition F)

Example 705

Compound p15 tert-Butyl 2-[[2-chloro-4-[(5-chloro-2-ethylsulfonylphenyl)methylcarbamoyl]-6-(trifluoromethyl)phenyl]methyl]-5-oxa-2,8-diazaspiro[3.5]nonane-8-carboxylate

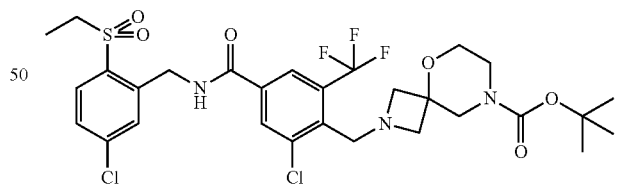

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compound dd17. However, the reaction was performed using tert-butyl 5-oxa-2,8-diazaspiro[3.5]nonane-8-carboxylate and DIPEA in place of tert-butyl N-[2-[[(3S)-piperidin-3-yl]sulfamoyl]ethyl]carbamate and potassium carbonate, respectively, and at a temperature of 80° C.

Example 706

Compound P-9

3-Chloro-N-[(5-chloro-2-ethylsulfonylphenyl)methyl]-4-(5-oxa-2,8-diazaspiro[3.5]nonan-2-ylmethyl)-5-(trifluoromethyl)benzamide

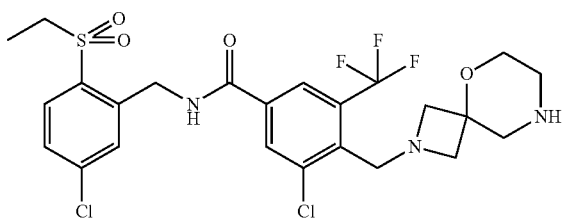 [SMILES: CCS(=O)(=O)c1ccc(Cl)cc1CNC(=O)c1cc(Cl)c(CN2CC3(CNCCO3)C2)c(C(F)(F)F)c1]

The title compound was synthesized from tert-butyl 2-[[2-chloro-4-[(5-chloro-2-ethylsulfonylphenyl)methylcarbamoyl]-6-(trifluoromethyl)phenyl]methyl]-5-oxa-2,8-diazaspiro[3.5]nonane-8-carboxylate (Compound p15) under the same conditions as for Compound B-1.

LCMS: m/z 580 [M+H]$^+$

HPLC retention time: 0.45 min (analysis condition F)

Example 707

Compound P-10

3-Chloro-N-[(5-chloro-2-ethylsulfonylphenyl)methyl]-4-(1,8-diazaspiro[5.5]undecan-8-ylmethyl)-5-(trifluoromethyl)benzamide

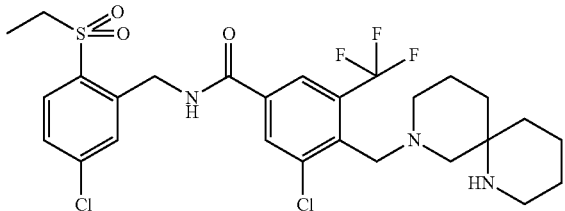 [SMILES: CCS(=O)(=O)c1ccc(Cl)cc1CNC(=O)c1cc(Cl)c(CN2CCCC3(CCCCN3)C2)c(C(F)(F)F)c1]

The title compound was synthesized from 4-(bromomethyl)-3-chloro-N-[(5-chloro-2-ethylsulfonylphenyl)methyl]-5-(trifluoromethyl)benzamide (Compound dd16) under the same conditions as for Compounds p15 and P-9. However, under the Compound p15 conditions, tert-butyl 1,8-diazaspiro[5.5]undecane-1-carboxylate was used in place of tert-butyl 5-oxa-2,8-diazaspiro[3.5]nonane-8-carboxylate.

LCMS: m/z 606 [M+H]$^+$

HPLC retention time: 0.59 min (analysis condition F)

Example 708

Compound p16

1-Ethylsulfonylpyrrole-2-carbonitrile

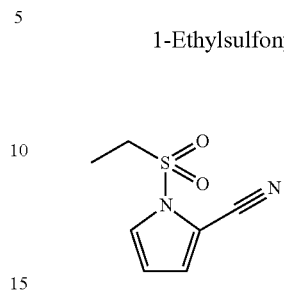

Ethanesulfonyl chloride (0.98 g, 7.60 mmol) was added to a mixed solution of 1H-pyrrole-2-carbonitrile (500 mg, 5.43 mmol) and TEA (1.51 ml, 10.9 mmol) in THF (5 ml) and DCM (5 ml), followed by stirring for three hours. A saturated aqueous solution of sodium chloride was added to the reaction mixture, followed by extraction with DCM. The organic layer was then dried over anhydrous sodium sulfate. The drying agent was removed by filtration, followed by concentration under reduced pressure. The resultant residue was purified by silica gel column chromatography (ethyl acetate/n-hexane) to yield the title compound (694 mg, 69%) as a colorless oily substance.

LCMS: m/z 185 [M+H]$^+$

HPLC retention time: 0.55 min (analysis condition A)

Example 709

Compound p17 tert-Butyl N-[(1-ethylsulfonylpyrrol-2-yl)methyl]carbamate

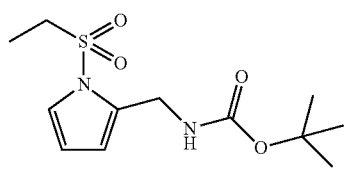 [SMILES: CCS(=O)(=O)n1cccc1CNC(=O)OC(C)(C)C]

Sodium borohydride (1.13 g, 29.8 mmol) was added in five portions at five-minute intervals to a solution of 1-ethylsulfonylpyrrole-2-carbonitrile (Compound p16, 686 mg, 3.72 mmol), Boc$_2$O (1.71 ml, 7.44 mmol) and nickel(II) chloride hexahydrate (221 mg, 0.93 mmol) in methanol (15 ml) while cooling to 0° C., and the mixture was maintained at 0° C. and stirred for one hour. A saturated aqueous solution of sodium bicarbonate was added to the reaction mixture, followed by extraction with ethyl acetate. The organic layer was then dried over anhydrous sodium sulfate. The drying agent was removed by filtration, followed by concentration under reduced pressure. The resultant residue was purified by silica gel column chromatography (ethyl acetate/n-hexane) to yield the title compound (629 mg, 59%) as a colorless solid.

LCMS: m/z 172 [M-Boc-NH$_2$]$^+$

HPLC retention time: 0.72 min (analysis condition A)

Example 710

Compound p18 tert-Butyl N-[(3S)-1-[[2-chloro-4-[(1-ethylsulfonylpyrrol-2-yl)methylcarbamoyl]-6-(trifluoromethyl)phenyl]methyl]piperidin-3-yl]-N-methylcarbamate

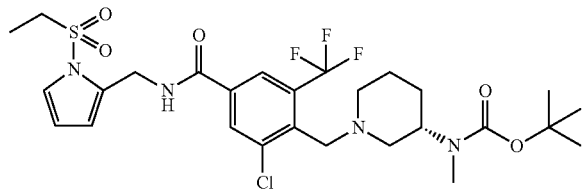 [SMILES: CCS(=O)(=O)n1cccc1CNC(=O)c1cc(Cl)c(CN2CCC[C@H](N(C)C(=O)OC(C)(C)C)C2)c(C(F)(F)F)c1]

The title compound was synthesized from tert-butyl N-[(1-ethylsulfonylpyrrol-2-yl)methyl]carbamate (Compound p17) under the same conditions as for Compounds p6 and p7. However, the reaction was performed at room temperature under the p6 conditions, and using 3-chloro-4-[[(3S)-3-[methyl-[(2-methylpropan-2-yl)oxycarbonyl]amino]piperidin-1-yl]methyl]-5-(trifluoromethyl)benzoic acid (Compound dd34) in place of 3-chloro-5-(trifluoromethyl)benzoic acid under the p7 conditions.

Example 711

Compound P-11

3-Chloro-N-[(1-ethylsulfonylpyrrol-2-yl)methyl]-4-[[(3S)-3-(methylamino)piperidin-1-yl]methyl]-5-(trifluoromethyl)benzamide

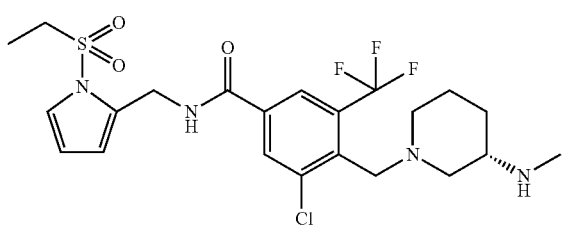 [SMILES: CCS(=O)(=O)n1cccc1CNC(=O)c1cc(Cl)c(CN2CCC[C@H](NC)C2)c(C(F)(F)F)c1]

The title compound was synthesized from tert-butyl N-[(3S)-1-[[2-chloro-4-[(1-ethylsulfonylpyrrol-2-yl)methylcarbamoyl]-6-(trifluoromethyl)phenyl]methyl]piperidin-3-yl]-N-methylcarbamate (Compound p18) under the same conditions as for Compound B-1.

LCMS: m/z 521 [M+H]$^+$

HPLC retention time: 0.55 min (analysis condition A)

Example 712

Compound p19

3-Bromo-5-chloro-4-methylbenzoic acid

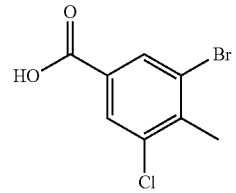

The title compound was synthesized from 3-chloro-4-methylbenzoic acid under the same conditions as for Compound f9. However, the reaction was performed undiluted without using chloroform.

Example 713

Compound p20

Ethyl 3-bromo-5-chloro-4-methylbenzoate

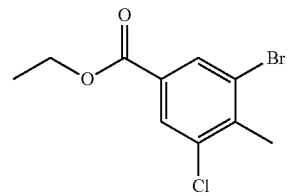

The title compound was synthesized from 3-bromo-5-chloro-4-methylbenzoic acid (Compound p19) under the same conditions as for Compound b1.

Example 714

Compound p21

Ethyl 3-chloro-5-cyano-4-methylbenzoate

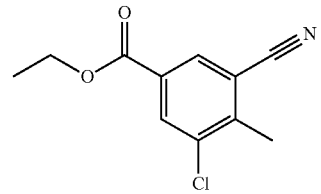

The title compound was synthesized from ethyl 3-bromo-5-chloro-4-methylbenzoate (Compound p20) under the same conditions as for Compound K-1. However, the reaction was performed using NMP in place of DMF as a solvent, and at a temperature of 200° C.

Example 715

Compound p22

Ethyl 4-(bromomethyl)-3-chloro-5-cyanobenzoate

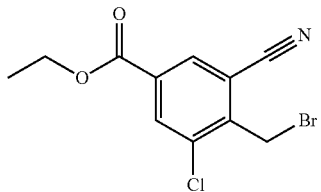 [SMILES: CCOC(=O)c1cc(Cl)c(CBr)c(C#N)c1]

The title compound was synthesized from ethyl 3-chloro-5-cyano-4-methylbenzoate (Compound p21) under the same conditions as for Compound b6. However, the reaction was performed at a temperature of 75° C.

Example 716

Compound p23

Ethyl 3-chloro-5-cyano-4-[(4-methylpiperazin-1-yl)methyl]benzoate

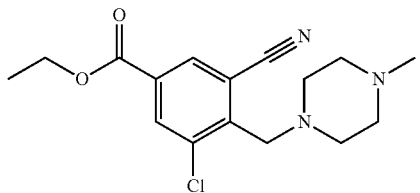 [SMILES: CCOC(=O)c1cc(Cl)c(CN2CCN(C)CC2)c(C#N)c1]

The title compound was synthesized from ethyl 4-(bromomethyl)-3-chloro-5-cyanobenzoate (Compound p22) under the same conditions as for Compound g3. However, 1-methylpiperazine was used in place of tert-butyl piperazine-1-carboxylate.

Example 717

Compound p24

3-Chloro-5-cyano-4-[(4-methylpiperazin-1-yl)methyl]benzoic acid

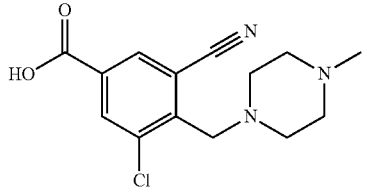 [SMILES: CN1CCN(Cc2c(Cl)cc(C(=O)O)cc2C#N)CC1]

The title compound was synthesized from ethyl 3-chloro-5-cyano-4-[(4-methylpiperazin-1-yl)methyl]benzoate (Compound p23) under the same conditions as for Compound b8.

Example 718

Compound P-12

3-Chloro-N-[(5-chloro-2-ethylsulfonylphenyl)methyl]-5-cyano-4-[(4-methylpiperazin-1-yl)methyl]benzamide

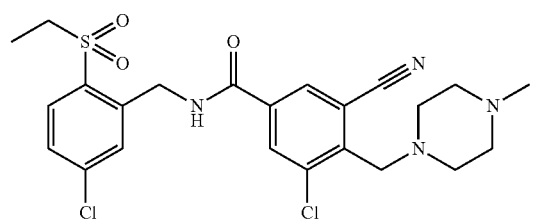 [SMILES: CCS(=O)(=O)c1ccc(Cl)cc1CNC(=O)c1cc(Cl)c(CN2CCN(C)CC2)c(C#N)c1]

The title compound was synthesized from (5-chloro-2-ethylsulfonylphenyl)methanamine hydrochloride (Compound a3) under the same conditions as for Compound bb10. However, 3-chloro-5-cyano-4-[(4-methylpiperazin-1-yl)methyl]benzoic acid (Compound p24) was used in place of 4-[[4-[(2-methylpropan-2-yl)oxycarbonyl]piperazin-1-yl]methyl]-3-(trifluoromethyl)benzoic acid (Compound b3) as a carboxylic acid.
LCMS: m/z 509 [M+H]$^+$
HPLC retention time: 0.51 min (analysis condition A)

Example 719

Compound q1

4-Chloropyridine-3-carbonitrile

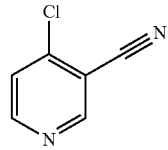

A 48% aqueous tetrafluoroboric acid solution (10 ml) was added to a solution of 4-chloropyridin-3-amine (1.29 g, 10.0 mmol) in ethanol (10 ml) at 0° C. An aqueous solution (10 ml) of sodium nitrite (725 mg, 10.5 mmol) was added to the resultant mixed solution at the same temperature, and it was stirred at the same temperature for 30 minutes. The precipitate was collected by filtration and washed with ethanol, and the resultant brown solid (1.94 g) was then dissolved in acetonitrile (10 ml). A mixed solution of sodium cyanide (980 mg, 20.0 mmol) and copper(I) cyanide (896 mg, 10.0 mmol) in water (10 ml) and acetonitrile (1 ml) was added to the resultant solution at 0° C., and it was stirred while gradually warming to room temperature for 10 hours. The reaction mixture was cooled to 0° C., after which a saturated aqueous solution of sodium bicarbonate was added, and it was stirred for five minutes. The resultant solution was extracted with ethyl acetate, and the organic layer was then washed with a saturated aqueous solution of sodium chloride and dried over anhydrous magnesium sulfate. The drying agent was removed by filtration, followed by concentration under reduced pressure. The resultant residue was purified by silica gel column chromatography (ethyl acetate/n-hexane) to yield the title compound (605 mg, 44%) as a pale yellow solid.

1H-NMR (300 MHz, CDCl$_3$) δ: 8.87 (1H, s), 8.72 (1H, d, J=3.9 Hz), 7.51 (1H, d, J=3.9 Hz).

Example 720

Compound q2

4-Ethylsulfanylpyridine-3-carbonitrile

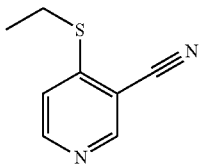

The title compound was synthesized from 4-chloropyridine-3-carbonitrile (Compound q1) under the same conditions as for Compound a1. However, sodium ethanethiolate was used in place of ethanethiol.

Example 721

Compound q3

(4-Ethylsulfanylpyridin-3-yl)methanamine

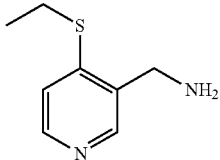

The title compound was synthesized from 4-ethylsulfanylpyridine-3-carbonitrile (Compound q2) under the same conditions as for Compound p9. However, the reaction was performed at a temperature of 50° C.

Example 722

Compound q4

3-Chloro-N-[(4-ethylsulfanyl pyri din-3-yl)methyl]-5-(trifluoromethyl)benzamide

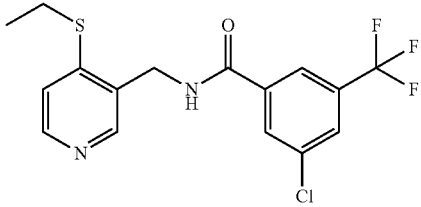 [SMILES: CCSc1ccncc1CNC(=O)c1cc(Cl)cc(C(F)(F)F)c1]

The title compound was synthesized from (4-ethylsulfanylpyridin-3-yl)methanamine (Compound q3) under the same conditions as for Compound A-14. However, 3-chloro-5-(trifluoromethyl)benzoic acid was used in place of 4-bromo-3-(trifluoromethyl)benzoic acid, and dichloromethane was used as a solvent.

Example 723

Compound Q-2

3-Chloro-N-[(4-ethylsulfonylpyridin-3-yl)methyl]-5-(trifluoromethyl)benzamide

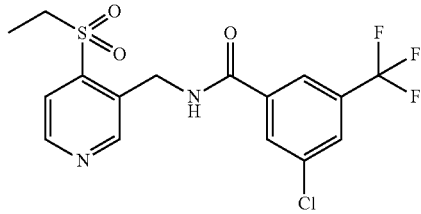 [SMILES: CCS(=O)(=O)c1ccncc1CNC(=O)c1cc(Cl)cc(C(F)(F)F)c1]

The title compound was synthesized from 3-chloro-N-[(4-ethylsulfanylpyridin-3-yl)methyl]-5-(trifluoromethyl) benzamide (Compound q4) under the same conditions as for Compound A-2. However, the reaction was performed using EtOAc as a solvent, and at a temperature of 0° C.

LCMS: m/z 407 [M+H]$^+$

HPLC retention time: 0.75 min (analysis condition F)

Example 724

Compound q5

(1-Ethylsulfonylpyrrol-2-yl)methanamine hydrochloride

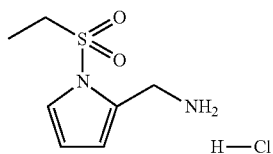

The title compound was synthesized from tert-butyl N-[(1-ethylsulfonylpyrrol-2-yl)methyl]carbamate (Compound p17) under the same conditions as for Compound B-57.

Example 725

Compound Q-9

N-[(1-Ethylsulfonylpyrrol-2-yl)methyl]-3-(trifluoromethyl)benzamide

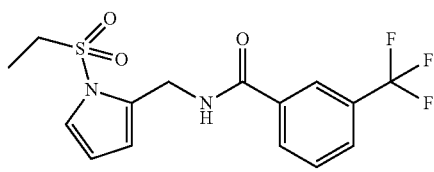 [SMILES: CCS(=O)(=O)n1cccc1CNC(=O)c1cccc(C(F)(F)F)c1]

The title compound was synthesized from (1-ethylsulfonylpyrrol-2-yl)methanamine hydrochloride (Compound q5) under the same conditions as for Compound A-14. However, 3-(trifluoromethyl)benzoic acid was used in place of 4-bromo-3-(trifluoromethyl)benzoic acid, and dichloromethane was used as a solvent.

LCMS: m/z 361 [M+H]+
HPLC retention time: 0.80 min (analysis condition A)

Example 726

Compound q6

4-Amino-N-[(5-chloro-2-ethylsulfonylphenyl)methyl]-3-methoxybenzamide

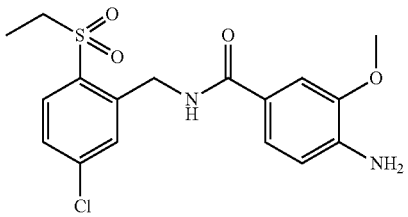 [SMILES: CCS(=O)(=O)c1ccc(Cl)cc1CNC(=O)c1ccc(N)c(OC)c1]

The title compound was synthesized from (5-chloro-2-ethylsulfonylphenyl)methanamine hydrochloride (Compound a3) under the same conditions as for Compound A-21. However, 4-amino-3-methoxybenzoic acid was used in place of 3-(trifluoromethyl)benzoic acid.

Example 727

Compound q7 tert-Butyl 4-[4-[(5-chloro-2-ethylsulfonylphenyl)methylcarbamoyl]-2-methoxyanilino]piperidine-1-carboxylate

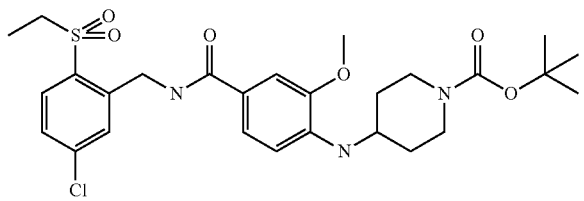 [SMILES: CCS(=O)(=O)c1ccc(Cl)cc1CNC(=O)c1ccc(NC2CCN(C(=O)OC(C)(C)C)CC2)c(OC)c1]

Sodium triacetoxyborohydride (49.8 mg, 0.235 mmol) was added to a solution of 4-amino-N-[(5-chloro-2-ethylsulfonylphenyl)methyl]-3-methoxybenzamide (Compound q6, 30.0 mg, 0.078 mmol) and tert-butyl 4-oxopiperidin-1-carboxylate (23.4 mg, 0.118 mmol) in chloroform (1 ml), and it was stirred at room temperature for two hours. The reaction temperature was raised to 50° C., followed by two hours of further stirring. tert-Butyl 4-oxopiperidine-1-carboxylate (23.4 mg, 0.118 mmol) and sodium triacetoxyborohydride (49.8 mg, 0.235 mmol) were added, followed by 16 hours of further stirring. The reaction mixture was cooled to room temperature, followed by addition of water and extraction with ethyl acetate. The organic layer was washed with brine, and then dried over anhydrous sodium sulfate. The drying agent was removed by filtration, followed by concentration under reduced pressure. The resultant residue was purified by silica gel column chromatography (ethyl acetate/n-hexane) to yield the title compound (28.0 mg, 63%) as a colorless solid.

LCMS: m/z 566 [M+H]+
HPLC retention time: 0.89 min (analysis condition F)

Example 728

Compound Q-10

N-[(5-Chloro-2-ethylsulfonylphenyl)methyl]-3-methoxy-4-(piperidin-4-ylamino)benzamide

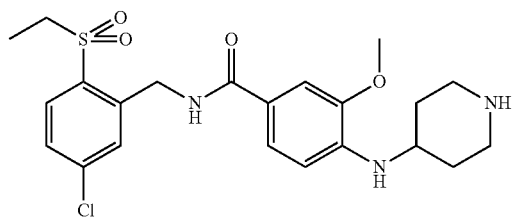 [SMILES: CCS(=O)(=O)c1ccc(Cl)cc1CNC(=O)c1ccc(NC2CCNCC2)c(OC)c1]

The title compound was synthesized from tert-butyl 4-[4-[(5-chloro-2-ethylsulfonylphenyl)methylcarbamoyl]-2-methoxyanilino]piperidine-1-carboxylate (Compound q7) under the same conditions as for Compound B-1.

LCMS: m/z 466 [M+H]+
HPLC retention time: 0.47 min (analysis condition F)

Example 729

Compound q8

Methyl 4-amino-3-methoxybenzoate

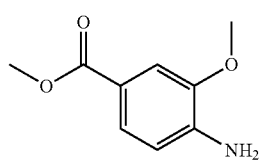

The title compound was synthesized from 4-amino-3-methoxybenzoic acid under the same conditions as for Compound dd5. However, the reaction was performed at a temperature of 65° C.

Example 730

Compound q9 tert-Butyl 4-(2-methoxy-4-methoxycarbonylanilino)piperidine-1-carboxylate

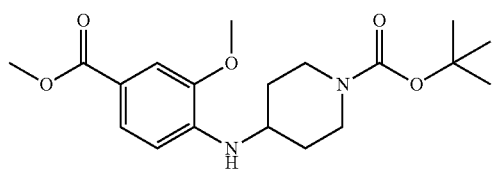 [SMILES: COC(=O)c1ccc(NC2CCN(C(=O)OC(C)(C)C)CC2)c(OC)c1]

The title compound was synthesized from methyl 4-amino-3-methoxybenzoate (Compound q8) under the same conditions as for Compound q7.

Example 731

Compound q10

3-Methoxy-4-[[1-[(2-methylpropan-2-yl)oxycarbonyl]piperidin-4-yl]amino]benzoic acid

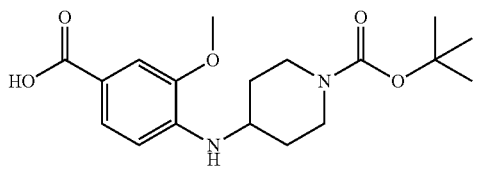 [SMILES: COc1cc(C(=O)O)ccc1NC1CCN(C(=O)OC(C)(C)C)CC1]

The title compound was synthesized from tert-butyl 4-(2-methoxy-4-methoxycarbonylanilino)piperidine-1-carboxylate (Compound q9) under the same conditions as for Compound b8. However, methanol was used as a solvent.

Example 732

Compound q11 tert-Butyl 4-[4-[(5-chloro-2-ethylsulfonylanilino)carbamoyl]-2-methoxyanilino]piperidine-1-carboxylate

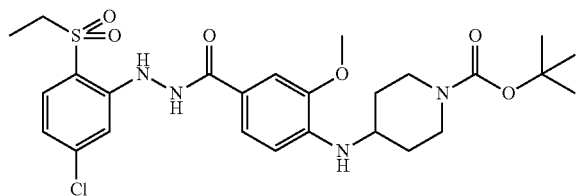 [SMILES: CCS(=O)(=O)c1ccc(Cl)cc1NNC(=O)c1ccc(NC2CCN(C(=O)OC(C)(C)C)CC2)c(OC)c1]

The title compound was synthesized from (5-chloro-2-ethylsulfonylphenyl)hydrazine (Compound o3) under the same conditions as for Compound A-14. However, 3-methoxy-4-[[1-[(2-methylpropan-2-yl)oxycarbonyl]piperidin-4-yl]amino]benzoic acid (compound q10) was used in place of 4-bromo-3-(trifluoromethyl)benzoic acid.

Example 733

Compound Q-11

N'-(5-Chloro-2-ethylsulfonylphenyl)-3-methoxy-4-(piperidin-4-ylamino)benzohydrazide hydrochloride

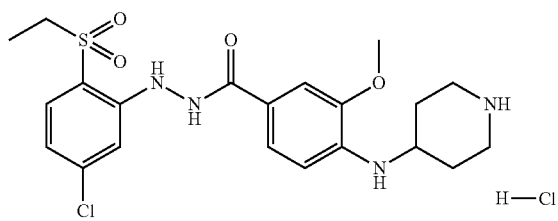

TFA (0.4 ml) was added to a solution of tert-butyl 4-[4-[(5-chloro-2-ethylsulfonylanilino)carbamoyl]-2-methoxyanilino]piperidine-1-carboxylate (Compound q11, 35.9 mg, 0.063 mmol) in DCM (0.6 ml), and it was stirred at room temperature. After one hour, the reaction mixture was concentrated under reduced pressure, and the resultant residue was purified by preparative HPLC (water/acetonitrile, 0.05% TFA). The fractions containing the substance of interest were collected and concentrated under reduced pressure, after which the resultant residue was dissolved by adding EtOH and a 1N aqueous hydrochloric acid solution; and the resultant solution was concentrated under reduced pressure to yield the title compound (20.0 mg, 63%) as a colorless solid.

LCMS: m/z 467 [M+H]$^+$

HPLC retention time: 0.46 min (analysis condition F)

Example 734

Compound q12

1-Iodo-2-nitro-4-(trifluoromethoxy)benzene

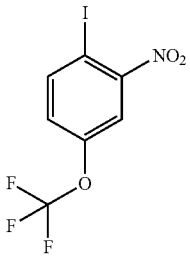

Ice (8 g) and sodium nitrite (378 mg, 5.48 mmol) were added to a mixture of 2-nitro-4-(trifluoromethoxy)aniline (1.11 g, 4.98 mmol), a 35% aqueous hydrochloric acid solution (7.2 ml) and water (7.2 ml) under ice-cooling. After 20 minutes of stirring, acetic acid (5 ml) was added, and the mixture was stirred at room temperature for 20 minutes. Sodium nitrite (80.7 mg, 1.17 mmol) was added, and the mixture was stirred for 20 minutes under ice-cooling, after which potassium iodide (1.22 g, 7.38 mmol) dissolved in water (1.5 ml) was added, followed by 30 minutes of stirring. Water was added to the reaction mixture, followed by extraction with ethyl acetate. The organic layer was then washed with a saturated aqueous sodium thiosulfate solution, and dried over anhydrous magnesium sulfate. The drying agent was removed by filtration, followed by concentration under reduced pressure. The resultant residue was purified by silica gel column chromatography (ethyl acetate/n-hexane) to yield the title compound (1.07 g, 65%) as an orange oily substance.

LCMS: m/z 334 [M+H]$^+$

HPLC retention time: 0.90 min (analysis condition F)

Example 735

Compound q13

1-Ethylsulfanyl-2-nitro-4-(trifluoromethoxy)benzene

The title compound was synthesized from 1-iodo-2-nitro-4-(trifluoromethoxy)benzene (Compound q12) under the same conditions as for Compound dd42. However, the reaction was performed at 80° C.

Example 736

Compound q14

1-Ethylsulfonyl-2-nitro-4-(trifluoromethoxy)benzene

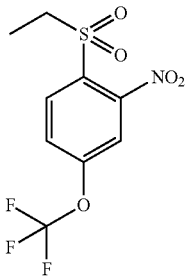 [SMILES: CCS(=O)(=O)c1ccc(OC(F)(F)F)cc1[N+](=O)[O-]]

The title compound was synthesized from 1-ethylsulfanyl-2-nitro-4-(trifluoromethoxy)benzene (Compound q13) under the same conditions as for Compound A-2. However, ethyl acetate was used in place of dichloromethane as a solvent.

Example 737

Compound q15

2-Ethylsulfonyl-5-(trifluoromethoxy)aniline

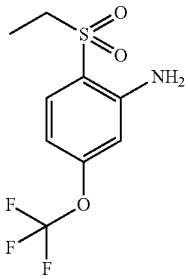 [SMILES: CCS(=O)(=O)c1ccc(OC(F)(F)F)cc1N]

The title compound was synthesized from 1-ethylsulfonyl-2-nitro-4-(trifluoromethoxy)benzene (Compound q14) under the same conditions as for Compound f11. However, the reaction was performed at room temperature using a mixed solvent of acetic acid and methanol in place of a mixed solvent of a saturated aqueous ammonium chloride solution and 2-propanol as a solvent.

Example 738

Compound q16

[2-Ethylsulfonyl-5-(trifluoromethoxy)phenyl]hydrazine

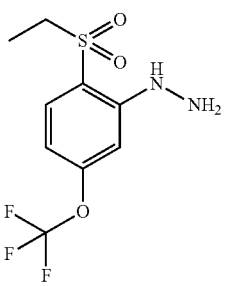 [SMILES: CCS(=O)(=O)c1ccc(OC(F)(F)F)cc1NN]

The title compound was synthesized from 2-ethylsulfonyl-5-(trifluoromethoxy)aniline (Compound q15) under the same conditions as for Compound a5.

Example 739

Compound q17 tert-Butyl N-[(3S)-1-[[4-[[2-ethylsulfonyl-5-(trifluoromethoxy)anilino]carbamoyl]-2-(trifluoromethyl)phenyl]methyl]piperidin-3-yl]-N-methylcarbamate

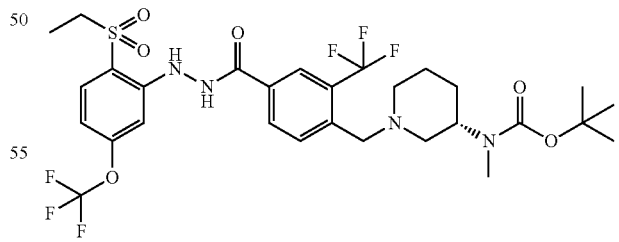

The title compound was synthesized from [2-ethylsulfonyl-5-(trifluoromethoxy)phenyl]hydrazine (Compound q16) under the same conditions as for Compound A-1. However, 4-[[(3S)-3-[methyl-[(2-methylpropan-2-yl)oxycarbonyl]amino]piperidin-1-yl]methyl]-3-(trifluoromethyl)benzoic acid (Compound b17) was used in place of 3-bromo-5-(trifluoromethyl)benzoic acid.

Example 740

Compound Q-12

N'-[2-Ethyl sulfonyl-5-(trifluoromethoxy)phenyl]-4-[[(3S)-3-(methylamino)piperidin-1-yl]methyl]-3-(trifluoromethyl)benzohydrazide hydrochloride

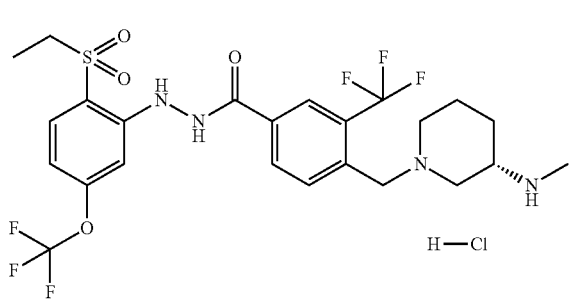 [SMILES: CCS(=O)(=O)c1ccc(OC(F)(F)F)cc1NNC(=O)c1ccc(CN2CCC[C@H](NC)C2)c(C(F)(F)F)c1 ; Cl]

The title compound was synthesized from tert-butyl N-[(3S)-1-[[4-[[2-ethylsulfonyl-5-(trifluoromethoxy)anilino]carbamoyl]-2-(trifluoromethyl)phenyl]methyl]piperidin-3-yl]-N-methylcarbamate (Compound q17) under the same conditions as for Compound B-57.

LCMS: m/z 583 [M+H]$^+$

HPLC retention time: 0.56 min (analysis condition F)

Example 741

Compound q18 tert-Butyl N-[(3S)-1-[[4-[[2-ethylsulfanyl-5-(trifluoromethoxy)anilino]carbamoyl]-2-(trifluoromethyl)phenyl]methyl]piperidin-3-yl]-N-methylcarbamate

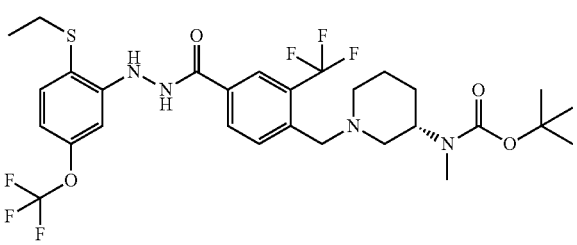 [SMILES: CCSc1ccc(OC(F)(F)F)cc1NNC(=O)c1ccc(CN2CCC[C@H](N(C)C(=O)OC(C)(C)C)C2)c(C(F)(F)F)c1]

The title compound was synthesized from (1-ethylsulfanyl-2-nitro-4-(trifluoromethoxy)benzene (Compound q13) under the same conditions as for Compounds q15, q16 and q17.

Example 742

Compound Q-13

N'-[2-Ethyl sulfanyl-5-(trifluoromethoxy)phenyl]-4-[[(3S)-3-(methylamino)piperidin-1-yl]methyl]-3-(trifluoromethyl)benzohydrazide 2,2,2-trifluoroacetate

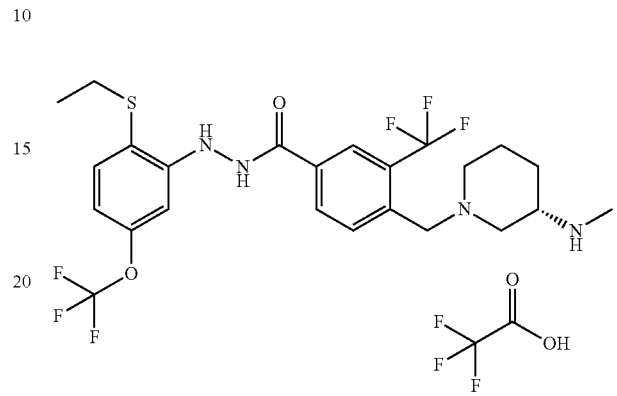

The title compound was synthesized from tert-butyl N-[(3S)-1-[[4-[[2-ethylsulfanyl-5-(trifluoromethoxy)anilino]carbamoyl]-2-(trifluoromethyl)phenyl]methyl]piperidin-3-yl]-N-methylcarbamate (Compound q18) under the same conditions as for Compound B-1.

LCMS: m/z 551 [M+H]$^+$

HPLC retention time: 0.62 min (analysis condition F)

Example 743

Compound q19

1,4-Dichloro-2-methoxy-5-nitrobenzene

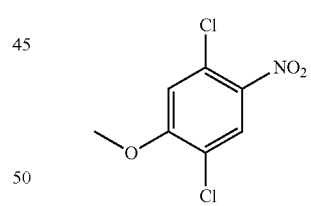

Sulfuric acid (0.520 ml) and nitric acid (0.520 ml) were added to a mixture of 1,4-dichloro-2-methoxybenzene (1.01 g, 5.73 mmol) and sulfuric acid (0.235 ml) under ice-cooling, followed by four hours of stirring. Water was added to the reaction mixture, followed by extraction with ethyl acetate. The organic layer was then washed with a saturated aqueous sodium bicarbonate solution and brine, and dried over anhydrous sodium sulfate. The drying agent was removed by filtration, followed by concentration under reduced pressure. The resultant residue was purified by silica gel column chromatography (ethyl acetate/n-hexane) to yield the title compound (331 mg, 26%) as an orange solid.

LCMS: m/z 222 [M+H]$^+$

HPLC retention time: 0.83 min (analysis condition F)

Example 744

Compound q20

1-Chloro-4-ethylsulfanyl-2-methoxy-5-nitrobenzene

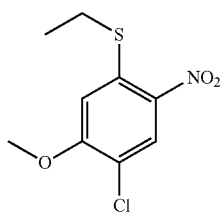

The title compound was synthesized from 1,4-dichloro-2-methoxy-5-nitrobenzene (Compound q19) under the same conditions as for Compound a1.

Example 745

Compound Q-14

3-Chloro-N'-(5-chloro-2-ethylsulfonyl-4-methoxyphenyl)-4-[[(3S)-3-(methyl amino)piperidin-1-yl]methyl]-5-(trifluoromethyl)benzohydrazide hydrochloride

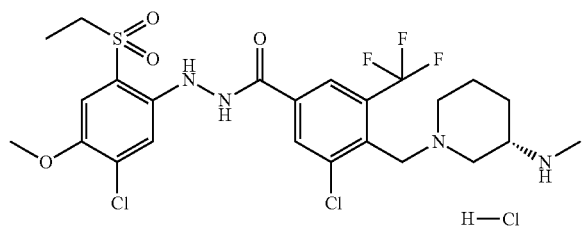

The title compound was synthesized from 1-chloro-4-ethylsulfanyl-2-methoxy-5-nitrobenzene (Compound q20) under the same conditions as for Compounds q14, q15, q16, q17 and Q-12. However, under the Compound q17 conditions, 3-chloro-4-[[(3S)-3-[methyl-[(2-methylpropan-2-yl)oxycarbonyl]amino]piperidin-1-yl]methyl]-5-(trifluoromethyl)benzoic acid (Compound dd34) was used in place of 4-[[(3S)-3-[methyl-[(2-methylpropan-2-yl)oxycarbonyl]amino]piperidin-1-yl]methyl]-3-(trifluoromethyl)benzoic acid (Compound b17).

LCMS: m/z 597 [M+H]$^+$
HPLC retention time: 0.54 min (analysis condition F)

Example 746

Amine 1 tert-Butyl N-methyl-N-[[(2R)-pyrrolidin-2-yl]methyl]carbamate

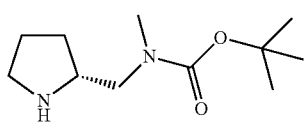

A solution of tert-butyl N-[[(2R)-pyrrolidin-2-yl]methyl]carbamate (302 mg, 1.46 mmol) and triethylamine (0.815 ml, 5.85 mmol) in DCM (3 mL) was cooled to 0° C., after which a solution of benzyl chloroformate (0.272 ml, 1.91 mmol) in DCM (1.5 ml) was added dropwise over five minutes, and the mixture was stirred at 0° C. for 2.5 hours. Water was added to the reaction mixture, followed by extraction with ethyl acetate. The organic layer was washed with a saturated aqueous solution of sodium bicarbonate, and then dried over anhydrous sodium sulfate. The drying agent was removed by filtration, followed by concentration under reduced pressure. The resultant residue was purified by silica gel column chromatography (ethyl acetate/hexane) to yield benzyl (2R)-2-[[(2-methylpropan-2-yl)oxycarbonylamino]methyl]pyrrolidine-1-carboxylate (410 mg, 81%) as a colorless solid.

LCMS: m/z 335 [M+H]$^+$
HPLC retention time: 0.83 min (analysis condition A)

A solution of benzyl (2R)-2-[[(2-methylpropan-2-yl)oxycarbonylamino]methyl]pyrrolidine-1-carboxylate (407 mg, 1.22 mmol) and methyl iodide (0.379 ml, 6.09 mmol) in DMF (2.4 ml) was cooled to 0° C., followed by addition of sodium hydride (>61% oil, 96.5 mg, 2.45 mmol), and it was stirred at room temperature for 16 hours. Water was added to the reaction mixture, followed by extraction with a mixed solvent of ethyl acetate and hexane. The organic layer was washed with a saturated aqueous solution of sodium chloride, and then dried over anhydrous sodium sulfate. The drying agent was removed by filtration, followed by concentration under reduced pressure. The resultant residue was purified by silica gel column chromatography (ethyl acetate/hexane) to yield benzyl (2R)-2-[[methyl-[(2-methylpropan-2-yl)oxycarbonyl]amino]methyl]pyrrolidine-1-carboxylate (414 mg, 97%) as a colorless oily substance.

LCMS: m/z 349 [M+H]$^+$
HPLC retention time: 0.90 min (analysis condition A)

10% palladium on carbon (43.5 mg) was added to a solution of benzyl (2R)-2-[[methyl-[(2-methylpropan-2-yl)oxycarbonyl]amino]methyl]pyrrolidine-1-carboxylate (410 mg, 1.18 mmol) in MeOH (4.1 ml) under an argon atmosphere, and the mixture was stirred at room temperature for 15 hours under a hydrogen atmosphere. The reaction mixture was filtered through celite, and the filtrate was then concentrated under reduced pressure to yield the title compound (253 mg, quant.) as a colorless oily substance.

1H-NMR (270 MHz, CDCl$_3$) δ: 2.73-3.51 (5H, m), 2.91 (3H, s), 1.26-1.99 (4H, m), 1.46 (9H, s).

Example 747

Amine 2 tert-Butyl N-methyl-N-[[(2S)-pyrrolidin-2-yl]methyl]carbamate

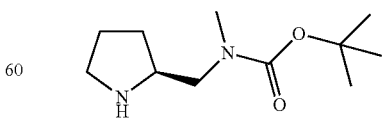

The title compound was synthesized from tert-butyl N-[[(2S)-pyrrolidin-2-yl]methyl]carbamate under the same conditions as for tert-butyl N-methyl-N-[[(2R)-pyrrolidin-2-yl]methyl]carbamate (Amine 1).

1H-NMR (270 MHz, CDCl₃) δ: 2.76-3.46 (5H, m), 2.91 (3H, s), 1.26-1.97 (4H, m), 1.46 (9H, s).

Example 748

Amine 3 tert-Butyl N-methyl-N-[[(3S)-piperidin-3-yl]methyl]carbamate

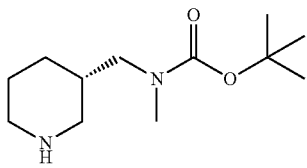 [SMILES: CN(C[C@H]1CCCNC1)C(=O)OC(C)(C)C]

The title compound was synthesized from tert-butyl N-[[(3S)-piperidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl₃) δ: 2.74-3.28 (4H, m), 2.85 (3H, s), 2.50-2.63 (1H, m), 2.23-2.41 (1H, m), 1.36-1.86 (4H, m), 1.45 (9H, s), 1.00-1.19 (1H, m).

Example 749

Amine 4 tert-Butyl N-methyl-N-[[(3R)-piperidin-3-yl]methyl]carbamate

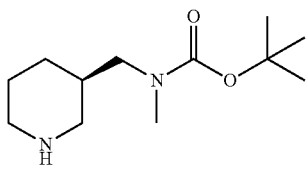 [SMILES: CN(C[C@@H]1CCCNC1)C(=O)OC(C)(C)C]

The title compound was synthesized from tert-butyl N-[[(3R)-piperidin-3-yl]methyl]carbamate under the same conditions as for tert-butyl N-methyl-N-[[(2R)-pyrrolidin-2-yl]methyl]carbamate (Amine 1).

1H-NMR (400 MHz, CDCl₃) δ: 2.67-3.31 (4H, m), 2.84 (3H, s), 2.48-2.64 (1H, m), 2.22-2.40 (1H, m), 1.31-1.92 (4H, m), 1.45 (9H, s), 0.97-1.20 (1H, m).

Example 750

Amine 5 tert-Butyl N-ethyl-N-[(3S)-piperidin-3-yl]carbamate

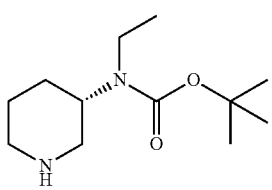 [SMILES: CCN(C(=O)OC(C)(C)C)[C@H]1CCCNC1]

The title compound was synthesized from tert-butyl N-[(3S)-piperidin-3-yl]carbamate under the same conditions as for tert-butyl N-methyl-N-[[(2R)-pyrrolidin-2-yl]methyl] carbamate (Amine 1). However, ethyl iodide was used in place of methyl iodide in the N-alkylation step.

1H-NMR (400 MHz, CDCl₃, 60° C.) δ: 3.08-3.83 (5H, m), 2.87-2.98 (1H, m), 2.50-2.62 (1H, m), 1.59-1.93 (4H, m), 1.46 (9H, s), 1.10 (3H, t, J=7.04 Hz).

Example 751

Amine 6 tert-Butyl N-methyl-N-[[(2R)-piperidin-2-yl]methyl]carbamate

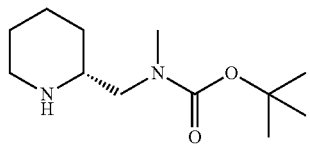 [SMILES: CN(C[C@H]1CCCCN1)C(=O)OC(C)(C)C]

The title compound was synthesized from tert-butyl N-[[(2R)-piperidin-2-yl]methyl]carbamate under the same conditions as for tert-butyl N-methyl-N-[[(2R)-pyrrolidin-2-yl]methyl]carbamate (Amine 1).

1H-NMR (400 MHz, CDCl₃, 60° C.) δ: 3.14-3.20 (1H, m), 3.03-3.13 (2H, m), 2.89 (3H, s), 2.71-2.80 (1H, m), 2.57-2.65 (1H, m), 1.75-1.82 (1H, m), 1.54-1.64 (2H, m), 1.46 (9H, s), 1.26-1.48 (3H, m).

Example 752

Amine 7

Benzyl N-[2-[(3S)-piperidin-3-yl]oxyethyl]carbamate

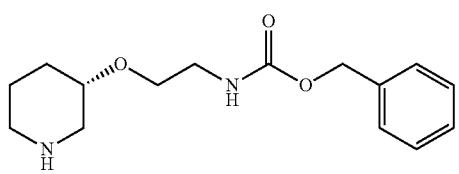 [SMILES: O=C(NCCO[C@H]1CCCNC1)OCc1ccccc1]

A solution of tert-butyl (3S)-3-hydroxypiperidine-1-carboxylate (100 mg, 0.497 mmol) in THF (0.5 ml) was cooled to 0° C., followed by addition of sodium hydride (>60% oil, 23.0 mg, 0.600 mmol), and it was stirred for 10 minutes. Sodium hydride (>60% oil, 24.0 mg, 0.626 mmol) and 2-bromoethanamine bromate (122 mg, 0.596 mmol) were added, and the mixture was stirred at room temperature for three days. Water was added to the reaction mixture, followed by extraction with ethyl acetate. The organic layer was washed with a saturated aqueous solution of sodium chloride, and then dried over anhydrous sodium sulfate. After the drying agent was removed by filtration, a crude product of tert-butyl (3S)-3-(2-aminoethoxy)piperidine-1-carboxylate (124 mg) was obtained as a yellow oily substance by concentration under reduced pressure.

Benzyl chloroformate (0.140 ml, 0.827 mmol) was added to a mixed solution of the crude product of tert-butyl (3S)-3-(2-aminoethoxy)piperidine-1-carboxylate (124 mg) and sodium bicarbonate (99.0 mg, 1.18 mmol) in ethanol/ water (1/1, 2 ml), and it was stirred at room temperature for 16 hours. The reaction mixture was concentrated under reduced pressure, and water was added to the resultant residue, followed by extraction with ethyl acetate. The organic layer was washed with a saturated aqueous solution of sodium chloride, and then dried over anhydrous sodium sulfate. After the drying agent was removed by filtration, a crude product of tert-butyl (3S)-3-[2-(phenylmethoxycarbonylamino)ethoxy]piperidine-1-carboxylate (178 mg) was obtained as a yellow oily substance by concentration under reduced pressure.

A 4N hydrochloric acid/ethyl acetate solution was added to the crude product of tert-butyl (3S)-3-[2-(phenylmethoxycarbonylamino)ethoxy]piperidine-1-carboxylate (178 mg), and it was stirred at room temperature for one hour. 1N hydrochloric acid was added to the reaction mixture, followed by washing with ethyl acetate. The aqueous layer was made basic with a 1N aqueous sodium hydroxide solution, followed by extraction with ethyl acetate three times. The combined organic layers were dried over anhydrous sodium sulfate. The drying agent was removed by filtration, and the title compound (23 mg, yield in three steps: 16%) was obtained as a yellow oily substance by concentration under reduced pressure.

1H-NMR (400 MHz, CDCl$_3$) δ: 7.27-7.40 (5H, m), 5.53-5.65 (1H, m), 5.10 (2H, s), 3.29-3.61 (4H, m), 2.65-3.05 (5H, m), 1.69-1.86 (2H, m), 1.51-1.63 (1H, m), 1.37-1.49 (1H, m).

Example 753

Amine 8 tert-Butyl N-(2-hydroxyethyl)-N-[(3S)-piperidin-3-yl]carbamate

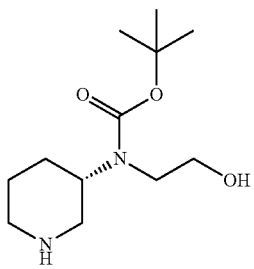 [SMILES: CC(C)(C)OC(=O)N(CCO)[C@H]1CCCNC1]

Amine 9 tert-Butyl N-(2-phenylmethoxyethyl)-N-[(3S)-piperidin-3-yl]carbamate

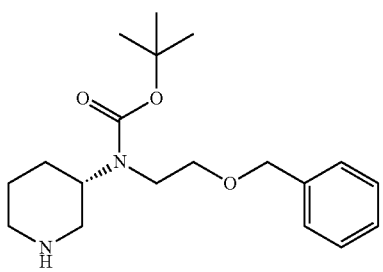 [SMILES: CC(C)(C)OC(=O)N(CCOCc1ccccc1)[C@H]1CCCNC1]

A solution of tert-butyl N-[(3S)-piperidin-3-yl]carbamate (100 mg, 0.499 mmol) and triethylamine (0.104 ml, 0.749 mmol) in DCM (2.5 ml) was cooled to 0° C., followed by addition of benzyl chloroformate (0.101 ml, 0.599 mmol), and it was stirred for one hour. Water was added to the reaction mixture, followed by extraction with ethyl acetate. The organic layer was washed with a saturated aqueous solution of sodium chloride, and then dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[(2-methylpropan-2-yl)oxycarbonylamino]piperidine-1-carboxylate (159 mg, 95%) as a colorless solid.

LCMS: m/z 335 [M+H]$^+$

HPLC retention time: 0.82 min (analysis condition F)

A solution of benzyl (3S)-3-[(2-methylpropan-2-yl)oxycarbonylamino]piperidine-1-carboxylate (150 mg, 0.449 mmol) in DMF (0.9 ml) was cooled to 0° C., followed by addition of sodium hydride (>60% oil, 26.9 mg, 0.673 mmol), and it was stirred for 15 minutes. 2-Bromoethoxymethylbenzene (0.213 ml, 1.35 mmol) was added, and the mixture was stirred at room temperature for two hours. Sodium hydride (>60% oil, 27 mg, 0.675 mmol) was added, followed by two hours of further stirring. Water was added to the reaction mixture, followed by extraction with a mixed solvent of ethyl acetate and hexane. The organic layer was washed three times with a saturated aqueous solution of sodium chloride, and then dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[(2-methylpropan-2-yl)oxycarbonyl-(2-phenylmethoxyethyl)amino]piperidine-1-carboxylate (123 mg, 58%) as a colorless oily substance.

LCMS: m/z 469 [M+H]$^+$

HPLC retention time: 1.05 min (analysis condition F)

10% palladium on carbon (20 mg) was added to a solution of benzyl (3S)-3-[(2-methylpropan-2-yl)oxycarbonyl-(2-phenylmethoxyethyl)amino]piperidine-1-carboxylate (123 mg, 0.262 mmol) in MeOH (1 ml) under an argon atmosphere, and it was stirred at room temperature for 16 hours under a hydrogen atmosphere. The reaction mixture was filtered through celite, and a crude product of a mixture of Amines 8 and 9 (80 mg) was obtained as a yellow oily substance by concentrating the filtrate under reduced pressure.

Example 754

Amine 10

3-[(3R)-Piperidin-3-yl]propan-1-ol

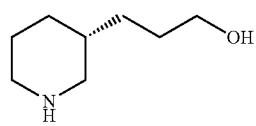

A solution of tert-butyl (3S)-3-(hydroxymethyl)piperidine-1-carboxylate (200 mg, 0.929 mmol) and triethylamine (0.646 ml, 4.64 mmol) in DCM (3 ml) was cooled to 0° C., and a solution of sulfur trioxide-pyridine complex (482 mg, 2.79 mmol) in DMSO (1.5 ml) was added dropwise, followed by one hour of stirring at 0° C. A saturated aqueous solution of ammonium chloride was added to the reaction mixture, followed by extraction with ethyl acetate. The organic layer was washed with a saturated aqueous solution of sodium chloride, and then dried over anhydrous sodium sulfate. After the drying agent was removed by filtration, a crude product of tert-butyl (3S)-3-formylpiperidine-1-carboxylate (200 mg) was obtained as a yellow oily substance by concentration under reduced pressure.

(Carbomethoxymethylene)triphenylphosphorane (466 mg, 1.39 mmol) was added to a solution of the crude product of tert-butyl (3S)-3-formylpiperidine-1-carboxylate (198 mg) in toluene (4 ml), and it was stirred at 90° C. for 16 hours. The reaction mixture was cooled to room temperature, and then purified by silica gel column chromatography (ethyl acetate/hexane) to yield tert-butyl (3R)-3-[(E)-3-methoxy-3-oxoprop-1-enyl]piperidine-1-carboxylate (242 mg, yield in two steps: 97%) as a colorless oily substance.

1H-NMR (400 MHz, CDCl$_3$) δ: 6.85 (1H, dd, J=7.1, 15.9 Hz), 5.86 (1H, dd, J=1.8, 15.9 Hz), 3.95-4.04 (1H, m), 3.87-3.95 (1H, m), 3.73 (3H, s), 2.76-2.86 (1H, m), 2.65-2.75 (1H, m), 2.27-2.39 (1H, m), 1.83-1.93 (1H, m), 1.62-1.73 (1H, m), 1.28-1.56 (2H, m), 1.45 (9H, s).

10% palladium on carbon (25 mg) was added to a solution of tert-butyl (3R)-3-[(E)-3-methoxy-3-oxoprop-1-enyl]piperidine-1-carboxylate (242 mg, 0.899 mmol) in MeOH (4 ml) under an argon atmosphere, and the mixture was stirred at room temperature for 16 hours under a hydrogen atmosphere. The reaction mixture was filtered through celite, and tert-butyl (3R)-3-(3-methoxy-3-oxopropyl)piperidine-1-carboxylate (222 mg, 91%) was obtained as a colorless oily substance by concentrating the filtrate under reduced pressure.

1H-NMR (400 MHz, CDCl$_3$) δ: 3.82-3.95 (2H, m), 3.66 (3H, s), 2.73-2.83 (1H, m), 2.44-2.54 (1H, m), 2.31-2.38 (2H, m), 1.76-1.86 (1H, m), 1.34-1.73 (5H, m), 1.45 (9H, s), 1.01-1.15 (1H, m).

A suspension of lithium aluminum hydride (31.9 mg, 0.840 mmol) in THF (0.8 ml) was cooled to 0° C., and a solution of tert-butyl (3R)-3-(3-methoxy-3-oxopropyl)piperidine-1-carboxylate (152 mg, 0.560 mmol) in THF (2 mL) was added dropwise, followed by one hour of stirring at 0° C. Water and a 1N aqueous sodium hydroxide solution were sequentially added to the reaction mixture, followed by filtration. The filtrate was concentrated under reduced pressure, and the resultant residue was purified by silica gel column chromatography (ethyl acetate/hexane) to yield tert-butyl (3R)-3-(3-hydroxypropyl)piperidine-1-carboxylate (115 mg, 84%) as a colorless oily substance.

1H-NMR (400 MHz, CDCl$_3$) δ: 3.85-3.96 (2H, m), 3.61-3.68 (2H, m), 2.74-2.83 (1H, m), 2.45-2.53 (1H, m), 1.80-1.87 (1H, m), 1.54-1.68 (3H, m), 1.36-1.50 (2H, m), 1.45 (9H, s), 1.19-1.36 (2H, m), 1.03-1.14 (1H, m).

TFA (0.4 ml) was added to a solution of tert-butyl (3R)-3-(3-hydroxypropyl)piperidine-1-carboxylate (31.0 mg, 0.127 mmol) in DCM (0.6 ml), and it was stirred at room temperature for one hour. A crude product of the TFA salt of the title compound (143 mg) was obtained as a yellow oily substance by concentrating the reaction mixture under reduced pressure. The crude product was dissolved in MeOH, and the TFA was removed using an anion exchange resin (manufactured by Biotage Japan Ltd., MP-Carbonate). A crude product of the title compound (20 mg) was obtained as a yellow oily substance by concentrating the eluate under reduced pressure.

LCMS: m/z 144 [M+H]$^+$

Example 755

Amine 11

Benzyl N-[2-[(3R)-piperidin-3-yl]ethyl]carbamate

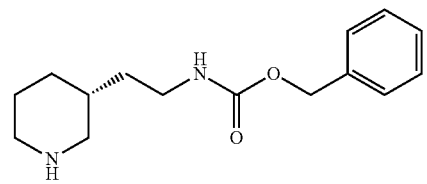 [SMILES: O=C(NCC[C@H]1CCCNC1)OCc1ccccc1]

A 1N aqueous sodium hydroxide solution (0.516 ml) was added to a solution of tert-butyl (3R)-3-(3-methoxy-3-oxopropyl)piperidine-1-carboxylate (70.0 mg, 0.258 mmol) in MeOH (2 ml), and it was stirred at room temperature for 0.5 hour. The reaction mixture was concentrated under reduced pressure, and water was added to the resultant residue, followed by extraction with ethyl acetate. The organic layer was sequentially washed with a 1N aqueous hydrochloric acid solution and a saturated aqueous sodium chloride solution, and dried over anhydrous sodium sulfate. After the drying agent was removed by filtration, a crude product of (3-[(3R)-1-[(2-methylpropan-2-yl)oxycarbonyl]piperidin-3-yl]propanoic acid (66.1 mg) was obtained as a colorless solid by concentration under reduced pressure.

Diphenylphosphoryl azide (77.0 μl, 0.359 mmol) was added to a solution of the crude product of (3-[(3R)-1-[(2-methylpropan-2-yl)oxycarbonyl]piperidin-3-yl]propanoic acid (66.0 mg) and triethylamine (53.0 μl, 0.385 mmol) in toluene (1.3 ml), and it was stirred at 85° C. for one hour. Benzyl alcohol (53.0 μl, 0.513 mmol) was added, and the mixture was further stirred at 85° C. for 16 hours. The reaction mixture was concentrated under reduced pressure, and the resultant residue was purified by silica gel column chromatography (ethyl acetate/hexane) to yield tert-butyl (3R)-3-[2-(phenylmethoxycarbonylamino)ethyl]piperidine-1-carboxylate (84.0 mg) as a colorless solid.

TFA (0.4 ml) was added to a solution of tert-butyl (3R)-3-[2-(phenylmethoxycarbonylamino)ethyl]piperidine-1-carboxylate (84.0 mg) in DCM (0.6 ml), and it was stirred at room temperature for one hour. The reaction mixture was concentrated under reduced pressure, and a saturated aqueous solution of sodium bicarbonate was added to the resultant residue, followed by extraction with ethyl acetate. The organic layer was washed with a saturated aqueous solution of sodium chloride, and dried over anhydrous sodium sulfate. The drying agent was removed by filtration, and a crude product of the title compound (43.0 mg) was obtained as a yellow oily substance by concentration under reduced pressure.

LCMS: m/z 263 [M+H]$^+$

HPLC retention time: 0.40 min (analysis condition F)

Example 756

Amine 12 tert-Butyl N-[3-[(3R)-piperidin-3-yl]propyl]carbamate

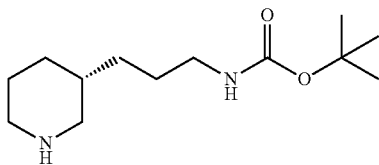 [SMILES: CC(C)(C)OC(=O)NCCC[C@H]1CCCNC1]

Diisopropyl azodicarboxylate (0.104 ml, 0.524 mmol) was added to a solution of tert-butyl (3R)-3-(3-hydroxypropyl)piperidine-1-carboxylate (85 mg, 0.349 mmol), triphenylphosphine (137 mg, 0.524 mmol) and phthalimide (77.0 mg, 0.524 mmol) in THF (1.7 ml), and it was stirred at room temperature for 1.5 hours. The reaction mixture was concentrated under reduced pressure, and the resultant residue was purified by silica gel column chromatography (ethyl acetate/hexane) to yield tert-butyl (3S)-3-[3-(1,3-dioxoisoindol-2-yl)propyl]piperidine-1-carboxylate (126 mg, 97%) as a yellow oily substance.

LCMS: m/z 373 [M+H]$^+$

HPLC retention time: 0.94 min (analysis condition F)

TFA (0.8 ml) was added to a solution of tert-butyl (3S)-3-[3-(1,3-dioxoisoindol-2-yl)propyl]piperidine-1-carboxylate (126 mg, 0.338 mmol) in DCM (1.2 ml), and it was stirred at room temperature for one hour. The reaction mixture was concentrated under reduced pressure, and a saturated aqueous sodium bicarbonate solution was added, followed by extraction with ethyl acetate. The organic layer was washed with a saturated aqueous sodium chloride solution, and dried over anhydrous sodium sulfate. After the drying agent was removed by filtration, a crude product of 2-[3-[(3R)-piperidin-3-yl]propyl]isoindole-1,3-dione (78.0 mg) was obtained as a yellow oily substance by concentration under reduced pressure.

LCMS: m/z 273 [M+H]$^+$

HPLC retention time: 0.40 min (analysis condition F)

A solution of the crude product of 2-[3-[(3R)-piperidin-3-yl]propyl]isoindole-1,3-dione (78.0 mg) and triethylamine (60.0 µl, 0.429 mmol) in DCM (1.4 ml) was cooled to 0° C., and benzyl chloroformate (58.0 µl, 0.343 mmol) was added, followed by one hour of stirring at 0° C. Water was added to the reaction mixture, followed by extraction with ethyl acetate. The organic layer was washed with a saturated aqueous sodium chloride solution, and dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[3-(1,3-dioxoisoindol-2-yl)propyl]piperidine-1-carboxylate (65.0 mg, yield in two steps: 42%) as a colorless oily substance.

LCMS: m/z 407 [M+H]$^+$

HPLC retention time: 0.93 min (analysis condition F)

Hydrazine monohydrate (80.0 mg, 1.60 mmol) was added to a solution of benzyl (3S)-3-[3-(1,3-dioxoisoindol-2-yl)propyl]piperidine-1-carboxylate (65.0 mg, 0.160 mmol) in EtOH (1.6 ml), and it was stirred at 60° C. for one hour. The reaction mixture was cooled to room temperature and filtered. The filtrate was concentrated under reduced pressure, and water was added to the resultant residue, followed by three times of extraction with ethyl acetate. The combined organic layers were dried over anhydrous sodium sulfate. After the drying agent was removed by filtration, a crude product of benzyl (3S)-3-(3-aminopropyl)piperidine-1-carboxylate (78.0 mg) was obtained as a yellow oily substance by concentration under reduced pressure.

LCMS: m/z 277 [M+H]$^+$

HPLC retention time: 0.46 min (analysis condition F)

Boc$_2$O (69.8 mg, 0.320 mmol) was added to a mixed solution of the crude product of benzyl (3S)-3-(3-aminopropyl)piperidine-1-carboxylate (44.2 mg) and sodium bicarbonate (53.8 mg, 0.640 mmol) in ethanol/water (1/1, 1 ml), and the mixture was stirred at room temperature for two hours. The reaction mixture was concentrated to approximately half its volume under reduced pressure, and water was then added, followed by extraction with ethyl acetate. The organic layer was washed with a saturated aqueous sodium chloride solution, and dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[3-[(2-methylpropan-2-yl)oxycarbonylamino]propyl]piperidine-1-carboxylate (39.0 mg, yield in two steps: 65%) as a colorless oily substance.

LCMS: m/z 377 [M+H]$^+$

HPLC retention time: 0.92 min (analysis condition F)

10% palladium on carbon (10 mg) was added to a solution of benzyl (3S)-3-[3-[(2-methylpropan-2-yl)oxycarbonylamino]propyl]piperidine-1-carboxylate (39.0 mg, 0.104 mmol) in MeOH (2 ml) under an argon atmosphere, and the mixture was stirred at room temperature for 16 hours under a hydrogen atmosphere. The reaction mixture was filtered through celite, and a crude product of the title compound (23.0 mg) was obtained as a yellow oily substance by concentrating the filtrate under reduced pressure.

LCMS: m/z 243 [M+H]$^+$

Example 757

Amine 13 tert-Butyl N-[2-[[(3S)-piperidin-3-yl]sulfamoyl]ethyl]carbamate

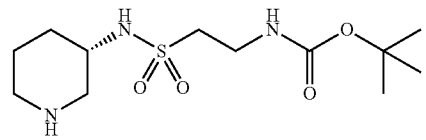 [SMILES: CC(C)(C)OC(=O)NCCS(=O)(=O)N[C@H]1CCCNC1]

TFA (2 ml) was added to a solution of benzyl (3S)-3-[(2-methylpropan-2-yl)oxycarbonylamino]piperidine-1-carboxylate (364 mg, 1.09 mmol) in DCM (3 ml), and the mixture was stirred at room temperature for one hour. The reaction mixture was concentrated under reduced pressure, and the resultant residue was dissolved in ethyl acetate. The solution was sequentially washed with a saturated aqueous sodium bicarbonate solution and a saturated aqueous sodium chloride solution, followed by drying over anhydrous sodium sulfate. After the drying agent was removed by filtration, a crude product of benzyl (3S)-3-aminopiperidine- 1-carboxylate (302 mg) was obtained as a colorless oily substance by concentration under reduced pressure.

LCMS: m/z 235 [M+H]$^+$

HPLC retention time: 0.38 min (analysis condition F)

2-(1,3-Dioxoisoindol-2-yl)ethanesulfonyl chloride (140 mg, 0.512 mmol) was added to a solution of the crude product of benzyl (3S)-3-aminopiperidine-1-carboxylate (100 mg) and DIPEA (0.149 ml, 0.854 mmol) in DCM (2 ml), and it was stirred at room temperature for two hours. Water was added to the reaction mixture, followed by extraction with ethyl acetate. The organic layer was washed with a saturated aqueous sodium chloride solution, and then dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[2-(1,3-dioxoisoindol-2-yl)ethylsulfonylamino]piperidine-1-carboxylate (213 mg) as a yellow foamy substance.

LCMS: m/z 472 [M+H]$^+$

HPLC retention time: 0.75 min (analysis condition F)

Hydrazine monohydrate (214 mg, 4.27 mmol) was added to a solution of benzyl (3S)-3-[2-(1,3-dioxoisoindol-2-yl)ethylsulfonylamino]piperidine-1-carboxylate (201 mg, 0.427 mmol) in EtOH (3 ml), and it was stirred at 60° C. for one hour. The reaction mixture was cooled to room temperature and filtered. The filtrate was concentrated under reduced pressure, and water was added to the resultant residue, followed by three times of extraction with ethyl acetate. The combined organic layers were dried over anhydrous sodium sulfate. After the drying agent was removed by filtration, a crude product of benzyl (3S)-3-(2-aminoethylsulfonylamino)piperidine-1-carboxylate (168 mg) was obtained concentration under reduced pressure.

LCMS: m/z 342 [M+H]$^+$

HPLC retention time: 0.43 min (analysis condition F)

Boc$_2$O (186 mg, 0.854 mmol) was added to a mixed solution of the crude product of benzyl (3S)-3-(2-aminoethylsulfonylamino)piperidine-1-carboxylate (146 mg) and sodium bicarbonate (143 mg, 1.71 mmol) in ethanol/water (1/1, 2 ml), and it was stirred at room temperature for two hours. The reaction mixture was concentrated to approximately half its volume under reduced pressure, and water was then added, followed by extraction with ethyl acetate. The organic layer was washed with a saturated aqueous sodium chloride solution, and dried over anhydrous sodium sulfate. The drying agent was removed by filtration, followed by concentration under reduced pressure. The resultant residue was purified by silica gel column chromatography (ethyl acetate/hexane) to yield benzyl (3S)-3-[2-[(2-methylpropan-2-yl)oxycarbonylamino]ethylsulfonylamino]piperidine-1-carboxylate (166 mg, yield in two steps: 88%) as a yellow oily substance.

LCMS: m/z 442 [M+H]$^+$

HPLC retention time: 0.76 min (analysis condition F)

10% palladium on carbon (10 mg) was added to a solution of benzyl (3S)-3-[2-[(2-methylpropan-2-yl)oxycarbonylamino]ethylsulfonylamino]piperidine-1-carboxylate (92.0 mg, 0.208 mmol) in MeOH (2 ml) under an argon atmosphere, and the mixture was stirred at room temperature for 16 hours under a hydrogen atmosphere. The reaction mixture was filtered through celite, and a crude product of the title compound (65 mg) was obtained as a colorless oily substance by concentrating the filtrate under reduced pressure.

LCMS: m/z 308 [M+H]$^+$

Example 758

Amine 14

2-(Dimethylamino)-N-[(3S)-piperidin-3-yl]ethanesulfonamide

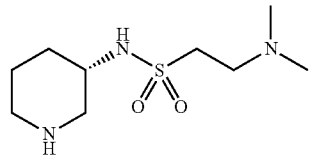

Paraformaldehyde (17.6 mg, 0.586 mmol) was added to a solution of benzyl (3S)-3-(2-aminoethylsulfonylamino)piperidine-1-carboxylate (50.0 mg, 0.146 mmol) in formic acid (1 ml), and the mixture was stirred at 80° C. for four hours. Paraformaldehyde (17.6 mg, 0.586 mmol) was further added, and the mixture was stirred at 80° C. for two more hours. The reaction mixture was concentrated under reduced pressure, and the resultant residue was dissolved in ethyl acetate. This product was sequentially washed with a saturated aqueous sodium bicarbonate solution and a saturated aqueous sodium chloride solution, and dried over anhydrous sodium sulfate. The drying agent was removed by filtration, followed by concentration under reduced pressure. The resultant residue was purified by silica gel column chromatography (methanol/dichloromethane) to yield benzyl (3S)-3-[2-(dimethylamino)ethylsulfonylamino]piperidine-1-carboxylate (27.7 mg, 51%) as a brown oily substance.

LCMS: m/z 370 [M+H]$^+$

HPLC retention time: 0.45 min (analysis condition F)

10% palladium on carbon (15 mg) was added to a solution of benzyl (3S)-3-[2-(dimethylamino)ethylsulfonylamino]piperidine-1-carboxylate (27.0 mg, 0.0731 mmol) in MeOH (2 ml) under an argon atmosphere, and the mixture was stirred at room temperature for 16 hours under a hydrogen atmosphere. The reaction mixture was filtered through celite, and a crude product of the title compound (21 mg) was obtained as a yellow oily substance by concentrating the filtrate under reduced pressure.

LCMS: m/z 236 [M+H]$^+$

Example 759

Amine 15 tert-Butyl N-methyl-N-[2-[(2-methylpropan-2-yl)oxycarbonyl-[(3S)-piperidin-3-yl]amino]ethyl]carbamate

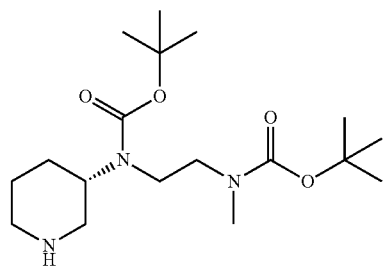 [SMILES: CN(CCN(C(=O)OC(C)(C)C)[C@H]1CCCNC1)C(=O)OC(C)(C)C]

TFA (4 ml) was added to a solution of benzyl (3S)-3-[(2-methylpropan-2-yl)oxycarbonylamino]piperidine-1-carboxylate (487 mg, 1.46 mmol) in DCM (6 ml), and the mixture was stirred at room temperature for one hour. The reaction mixture was concentrated under reduced pressure, and the resultant residue was dissolved in ethyl acetate and a saturated aqueous sodium bicarbonate solution. The separated organic layer was washed with a saturated aqueous sodium chloride solution, and dried over anhydrous sodium sulfate. After the drying agent was removed by filtration, a crude product of benzyl (3S)-3-aminopiperidine-1-carboxylate was obtained by concentration under reduced pressure.

LCMS: m/z 235 [M+H]+

HPLC retention time: 0.37 min (analysis condition F)

tert-Butyl N-methyl-N-(2-oxoethyl)carbamate was synthesized from tert-butyl N-(2-hydroxyethyl)-N-methylcarbamate by following the method described in the literature (Bioorganic and Medicinal Chemistry, vol. 12, pp. 5147-5160, 2004).

A solution of the crude product of benzyl (3S)-3-aminopiperidine-1-carboxylate (107 mg) and tert-butyl N-methyl-N-(2-oxoethyl)carbamate (59.3 mg, 0.343 mmol) in chloroform (2.1 ml) was cooled to 0° C., followed by addition of sodium triacetoxyborohydride (145 mg, 0.685 mmol), and it was stirred at 0° C. After 30 minutes, tert-butyl N-methyl-N-(2-oxoethyl)carbamate (6.0 mg, 0.035 mmol) was added, and the mixture was stirred at 0° C. for 30 more minutes. Water was added to the reaction mixture, followed by extraction with ethyl acetate. The organic layer was washed with a saturated aqueous sodium chloride solution, and then dried over anhydrous sodium sulfate. After the drying agent was removed by filtration, a crude product of benzyl (3S)-3-[2-[methyl-[(2-methylpropan-2-yl)oxycarbonyl]amino]ethylamino]piperidine-1-carboxylate (169 mg) was obtained as a yellow oily substance by concentration under reduced pressure.

LCMS: m/z 392 [M+H]+

HPLC retention time: 0.51 min (analysis condition F)

Boc2O (188 mg, 0.863 mmol) was added to a solution of the crude product of benzyl (3S)-3-[2-[methyl-[(2-methylpropan-2-yl)oxycarbonyl]amino]ethyl amino]piperidine-1-carboxylate (169 mg) and triethylamine (0.180 ml, 1.30 mmol) in THF (2.2 ml), and the mixture was stirred at room temperature for three hours. The reaction mixture was concentrated under reduced pressure, and the resultant residue was purified by silica gel column chromatography (ethyl acetate/hexane) to yield benzyl (3S)-3-[2-[methyl-[(2-methylpropan-2-yl)oxycarbonyl]amino]ethyl-[(2-methylpropan-2-yl)oxycarbonyl]amino]piperidine-1-carboxylate (139 mg, yield in two steps: 62%) as a yellow oily substance.

LCMS: m/z 492 [M+H]+

HPLC retention time: 1.04 min (analysis condition F)

10% palladium on carbon (20.0 mg) was added to a solution of benzyl (3S)-3-[2-[methyl-[(2-methylpropan-2-yl)oxycarbonyl]amino]ethyl-[(2-methylpropan-2-yl)oxycarbonyl]amino]piperidine-1-carboxylate (112 mg, 0.228 mmol) in MeOH (2.2 ml) under an argon atmosphere, and the mixture was stirred at room temperature for 16 hours under a hydrogen atmosphere. The reaction mixture was filtered through celite, and a crude product of the title compound (112 mg) was obtained as a yellow oily substance by concentrating the filtrate under reduced pressure.

LCMS: m/z 358 [M+H]+

Example 760

Amine 16 tert-Butyl N-[2-[[(3S)-piperidine-3-carbonyl]amino]ethyl]carbamate

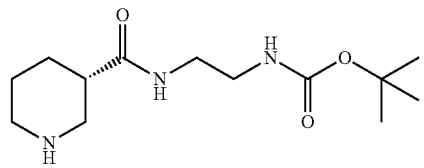 [SMILES: CC(C)(C)OC(=O)NCCNC(=O)[C@H]1CCCNC1]

A solution of (3S)-1-phenylmethoxycarbonylpiperidine-3-carboxylic acid (72.0 mg, 0.273 mmol), tert-butyl N-(2-aminoethyl)carbamate (52.6 mg, 0.328 mmol) and HBTU (124 mg, 0.328 mmol) in DCM (1.3 ml) was cooled to 0° C., followed by addition of DIPEA (0.136 ml, 0.820 mmol), and it was stirred at room temperature for two hours. The reaction mixture was concentrated under reduced pressure, and the resultant residue was purified by silica gel column chromatography (ethyl acetate/hexane) to yield benzyl (3S)-3-[2-[(2-methylpropan-2-yl)oxycarbonylamino]ethylcarbamoyl]piperidine-1-carboxylate (81.0 mg, 73%) as a colorless oily substance.

LCMS: m/z 406 [M+H]+

HPLC retention time: 0.71 min (analysis condition F)

10% palladium on carbon (15.0 mg) was added to a solution of benzyl (3S)-3-[2-[(2-methylpropan-2-yl)oxycarbonylamino]ethylcarbamoyl]piperidine-1-carboxylate (81.0 mg, 0.200 mmol) in MeOH (2.2 ml) under an argon atmosphere, and the mixture was stirred at room temperature for 16 hours under a hydrogen atmosphere. The reaction mixture was filtered through celite, and a crude product of the title compound (58.0 mg) was obtained as a colorless solid by concentrating the filtrate under reduced pressure.

LCMS: m/z 272 [M+H]+

Pharmacological Study

1. Measurement of DDR1 Binding Activity

DDR1 binding activity was measured by the LanthaScreen (Registered trademark) Eu Kinase Binding Assay (manufactured by Life Technologies Corporation). A test compound and the Alexa Fluor (Registered trademark) 647-labeled Kinase Tracer 178 (manufactured by Life Technologies Corporation) were added to a mixture of DDR1 and the LanthaScreen (Registered trademark) Eu-anti-GST antibody. After reacting at room temperature for one hour, the fluorescence resonance energy transfer was measured. The 50% inhibitory concentration (IC50) was calculated from the inhibition rate relative to the test compound-free control.

2. Path-Hunter DDR1 Functional Assay

The human osteosarcoma cell line U2OS (manufactured by DiscoveRX Corporation) in which DDR1 and SHC1 were overexpressed was suspended in a medium (MEM Eagle Medium; manufactured by Life Technologies Corporation) supplemented with 10% fetal bovine serum and antibiotics (500 μg/mL Geneticin (G418): manufactured by Life Technologies Corporation and 250 μg/mL hygromycin) to prepare a cell suspension at a concentration of 10,000 cells/100 μL. This cell suspension was added to a 96-well plate, and the cells were cultured at 37° C. in a 5% carbon dioxide incubator for one hour. The medium was then removed after confirming that the cells were attached to the plate. The test compound was serially diluted with dimethyl sulfoxide and then added to 50 μL of the Cell Planting 16 Reagent (manufactured by DiscoveRX Corporation), and the mixture was aliquoted to the 96-well plate. After incubating at 37° C. in the 5% carbon dioxide incubator for one hour, 50 μL of 100 μg/mL collagen for tissue culture (Collagen Type I-C; manufactured by Nitta Gelatin Inc.) was dispensed, and the plate was incubated at 37° C. in the 5% carbon dioxide incubator for 24 hours. The incubated plate was returned to normal temperature, and 25 μL of the prepared Path-Hunter Detection Kit (manufactured by DiscoveRX Corporation) was dispensed to the plate. The plate was incubated at normal temperature for two hours in the dark. Measurement was performed at 1 sec/well using a fluorescence plate reader. The 50% inhibitory concentration (IC50) of the test compound was calculated from the value when the test compound was added relative to the test compound-free control.

The results are shown in Tables 14 to 24.

TABLE 14

| Example | Compound No. | DDR1 binding activity IC50 (μM) | Path Hunter IC50 (uM) |
| --- | --- | --- | --- |
| 43 | B-2 | 0.0097 | 0.44 |
| 52 | B-6 | 0.013 | 2.82 |
| 54 | B-8 | 0.023 | 3.59 |
| 55 | B-9 | 0.017 | 1.43 |
| 62 | B-13 | 0.039 | 1.68 |
| 78 | B-25 | 0.019 | 0.84 |
| 92 | B-37 | 0.012 | 0.033 |
| 196 | D-10 | 0.011 | 0.16 |
| 197 | D-11 | 0.0099 | 0.34 |
| 198 | D-17 | 0.0099 | 0.52 |
| 199 | D-18 | 0.0074 | 0.11 |
| 208 | D-19 | 0.010 | 1.43 |
| 209 | D-20 | 0.014 | 3.68 |
| 210 | D-21 | 0.030 | 1.19 |
| 200 | D-26 | 0.0067 | 0.089 |
| 202 | D-28 | 0.0046 | 0.17 |
| 221 | E-2 | 0.010 | 0.27 |
| 222 | E-3 | 0.0092 | 0.078 |
| 227 | E-5 | 0.027 | 0.42 |
| 228 | E-6 | 0.029 | 0.087 |
| 229 | E-7 | 0.023 | 0.22 |
| 230 | E-8 | 0.024 | 0.19 |
| 257 | F-9 | 0.019 | 0.21 |
| 258 | F-15 | 0.014 | 0.54 |

TABLE 15

| Example | Compound No. | DDR1 binding activity IC50 (μM) |
| --- | --- | --- |
| 3 | A-1 | 0.13 |
| 4 | A-2 | 0.029 |
| 5 | A-3 | 0.11 |
| 6 | A-4 | 0.030 |
| 8 | A-5 | 0.14 |
| 9 | A-6 | 0.68 |
| 10 | A-7 | 0.11 |
| 11 | A-8 | 0.42 |
| 12 | A-9 | 0.031 |
| 13 | A-10 | 0.050 |
| 14 | A-11 | 0.049 |
| 15 | A-12 | 4.17 |
| 16 | A-13 | 0.12 |
| 19 | A-14 | 0.21 |
| 17 | A-15 | 0.060 |
| 18 | A-16 | 0.055 |
| 22 | A-17 | 0.0090 |
| 23 | A-18 | 0.028 |
| 24 | A-19 | 2.53 |
| 25 | A-20 | 1.11 |
| 32 | A-21 | 0.80 |

TABLE 15-continued

| Example | Compound No. | DDR1 binding activity IC50 (μM) |
| --- | --- | --- |
| 33 | A-22 | 0.071 |
| 34 | A-23 | 0.11 |
| 35 | A-24 | 0.37 |
| 36 | A-25 | 66.0 |
| 37 | A-26 | 21.2 |
| 42 | B-1 | 0.016 |
| 44 | B-3 | 0.012 |
| 45 | B-4 | 0.024 |
| 46 | B-5 | 1.69 |
| 53 | B-7 | 0.029 |
| 56 | B-10 | 0.025 |
| 57 | B-11 | 0.086 |
| 58 | B-12 | 0.25 |
| 66 | B-14 | 0.16 |
| 67 | B-15 | 0.018 |
| 68 | B-16 | 0.037 |
| 69 | B-17 | 0.050 |
| 70 | B-18 | 0.040 |

TABLE 16

| Example | Compound No. | DDR1 binding activity IC50 (μM) |
| --- | --- | --- |
| 71 | B-19 | 0.022 |
| 72 | B-20 | 0.075 |
| 73 | B-21 | 0.13 |
| 74 | B-22 | 0.025 |
| 75 | B-23 | 0.19 |
| 76 | B-24 | 0.025 |
| 79 | B-26 | 0.045 |
| 80 | B-27 | 0.12 |
| 81 | B-28 | 0.13 |
| 82 | B-29 | 0.072 |
| 83 | B-30 | 0.093 |
| 84 | B-31 | 0.035 |
| 85 | B-32 | 0.055 |
| 89 | B-33 | 0.024 |
| 86 | B-34 | 0.012 |
| 87 | B-35 | 0.025 |
| 88 | B-36 | 0.056 |
| 94 | B-38 | 0.018 |
| 95 | B-39 | 0.024 |
| 96 | B-40 | 0.22 |
| 97 | B-41 | 0.094 |
| 101 | B-42 | 0.050 |
| 103 | B-43 | 0.047 |
| 104 | B-44 | 0.099 |
| 105 | B-45 | 0.14 |
| 106 | B-46 | 0.054 |
| 110 | B-47 | 0.054 |
| 111 | B-48 | 0.066 |
| 112 | B-49 | 0.21 |
| 113 | B-50 | 0.50 |
| 122 | B-51 | 0.027 |
| 126 | B-52 | 0.13 |
| 123 | B-53 | 0.066 |
| 124 | B-54 | 0.023 |
| 127 | B-55 | 0.25 |
| 125 | B-56 | 0.13 |
| 132 | B-57 | 0.065 |
| 133 | B-58 | 0.046 |
| 134 | B-59 | 0.46 |

TABLE 17

| Example | Compound No. | DDR1 binding activity IC50 (μM) |
| --- | --- | --- |
| 135 | B-60 | 0.20 |
| 136 | B-61 | 0.044 |
| 137 | B-62 | 0.042 |

TABLE 17-continued

| Example | Compound No. | DDR1 binding activity IC50 (μM) |
|---|---|---|
| 138 | B-63 | 0.082 |
| 140 | B-64 | 0.041 |
| 141 | B-65 | 0.40 |
| 142 | B-66 | 0.33 |
| 139 | B-67 | 0.050 |
| 147 | C-1 | 0.055 |
| 148 | C-2 | 0.062 |
| 149 | C-3 | 0.070 |
| 150 | C-4 | 0.23 |
| 153 | C-5 | 0.066 |
| 154 | C-6 | 0.19 |
| 161 | C-7 | 0.0065 |
| 162 | C-8 | 0.26 |
| 163 | C-9 | 0.94 |
| 164 | C-10 | 1.35 |
| 165 | C-11 | 0.78 |
| 166 | C-12 | 0.18 |
| 170 | C-13 | 0.015 |
| 174 | C-14 | 0.035 |
| 175 | C-15 | 0.026 |
| 176 | C-16 | 0.10 |
| 182 | D-1 | 0.018 |
| 183 | D-2 | 0.022 |
| 184 | D-3 | 0.031 |
| 185 | D-4 | 0.046 |
| 191 | D-5 | 0.010 |
| 192 | D-6 | 0.0099 |
| 193 | D-7 | 0.050 |
| 194 | D-8 | 0.018 |
| 195 | D-9 | 0.025 |
| 203 | D-12 | 0.014 |
| 204 | D-13 | 0.041 |
| 205 | D-14 | 0.029 |
| 206 | D-15 | 0.043 |
| 207 | D-16 | 0.15 |
| 211 | D-22 | 0.048 |

TABLE 18

| Example | Compound No. | DDR1 binding activity IC50 (μM) |
|---|---|---|
| 212 | D-23 | 0.072 |
| 213 | D-24 | 0.028 |
| 214 | D-25 | 0.020 |
| 201 | D-27 | 0.010 |
| 220 | E-1 | 0.016 |
| 223 | E-4 | 0.010 |
| 239 | F-1 | 0.057 |
| 240 | F-2 | 0.045 |
| 241 | F-3 | 0.11 |
| 242 | F-4 | 0.33 |
| 244 | F-5 | 0.029 |
| 254 | F-6 | 0.021 |
| 255 | F-7 | 0.068 |
| 256 | F-8 | 0.092 |
| 260 | F-10 | 0.038 |
| 260 | F-11 | 0.14 |
| 261 | F-12 | 0.26 |
| 262 | F-13 | 0.068 |
| 263 | F-14 | 0.16 |
| 259 | F-16 | 0.036 |
| 269 | G-1 | 0.067 |
| 270 | G-2 | 0.077 |
| 271 | G-3 | 0.034 |
| 272 | G-4 | 0.19 |
| 276 | G-5 | 0.11 |
| 277 | G-6 | 0.082 |
| 278 | G-7 | 0.16 |
| 279 | G-8 | 0.076 |
| 280 | G-9 | 0.058 |
| 281 | G-10 | 0.31 |
| 282 | G-11 | 0.10 |
| 283 | G-12 | 0.15 |

TABLE 18-continued

| Example | Compound No. | DDR1 binding activity IC50 (μM) |
|---|---|---|
| 284 | G-13 | 0.30 |
| 285 | G-14 | 1.05 |
| 286 | G-15 | 0.034 |
| 287 | G-16 | 0.020 |
| 288 | G-17 | 0.043 |
| 289 | G-18 | 0.13 |
| 294 | H-1 | 0.032 |

TABLE 19

| Example | Compound No. | DDR1 binding activity IC50 (μM) |
|---|---|---|
| 295 | H-2 | 0.044 |
| 296 | H-3 | 0.052 |
| 297 | H-4 | 0.061 |
| 298 | H-5 | 0.052 |
| 299 | H-6 | 0.053 |
| 300 | H-7 | 0.056 |
| 301 | H-8 | 0.058 |
| 302 | H-9 | 0.11 |
| 306 | H-10 | 0.36 |
| 307 | H-11 | 0.58 |
| 308 | H-12 | 0.63 |
| 309 | H-13 | 1.15 |
| 313 | H-14 | 0.64 |
| 314 | H-15 | 0.45 |
| 315 | H-16 | 0.92 |
| 316 | H-17 | 1.24 |
| 321 | I-1 | 1.67 |
| 322 | I-2 | 2.54 |
| 323 | I-3 | 1.01 |
| 324 | I-4 | 0.69 |
| 325 | I-5 | 0.34 |
| 326 | I-6 | 0.37 |
| 327 | I-7 | 0.14 |
| 328 | I-8 | 0.17 |
| 333 | I-9 | 0.084 |
| 334 | I-10 | 0.12 |
| 335 | I-11 | 0.049 |
| 336 | I-12 | 0.045 |
| 340 | I-13 | 0.075 |
| 341 | I-14 | 0.13 |
| 342 | I-15 | 0.18 |
| 343 | I-16 | 0.12 |
| 344 | I-17 | 0.15 |
| 345 | I-18 | 0.081 |
| 346 | I-19 | 0.050 |
| 347 | I-20 | 0.052 |
| 348 | I-21 | 0.098 |
| 349 | I-22 | 0.036 |
| 350 | I-23 | 0.25 |

TABLE 20

| Example | Compound No. | DDR1 binding activity IC50 (μM) |
|---|---|---|
| 351 | I-24 | 0.11 |
| 352 | I-25 | 0.056 |
| 353 | I-26 | 0.16 |
| 354 | I-27 | 0.046 |
| 355 | I-28 | 0.085 |
| 360 | J-1 | 4.49 |
| 365 | J-2 | 1.94 |
| 366 | J-3 | 3.90 |

TABLE 21

| Example | Compound No. | DDR1 binding activity IC50 (uM) |
|---|---|---|
| 369 | BB-1 | 0.90 |
| 370 | BB-2 | 0.62 |
| 375 | BB-3 | 0.060 |
| 376 | BB-4 | 0.047 |
| 382 | BB-5 | 0.028 |
| 383 | BB-6 | 0.027 |
| 384 | DD-1 | 0.087 |
| 385 | DD-2 | 0.052 |
| 386 | DD-3 | 0.058 |
| 387 | DD-4 | 0.048 |
| 389 | DD-5 | 0.020 |
| 390 | DD-6 | 0.025 |
| 391 | DD-7 | 0.021 |
| 392 | DD-8 | 0.019 |
| 393 | DD-9 | 0.021 |
| 394 | DD-10 | 0.023 |
| 395 | DD-11 | 0.035 |
| 396 | DD-12 | 0.023 |
| 397 | DD-13 | 0.017 |
| 398 | DD-14 | 0.021 |
| 399 | DD-15 | 0.025 |
| 400 | DD-16 | 0.016 |
| 401 | DD-17 | 0.033 |
| 402 | DD-18 | 0.025 |
| 403 | DD-19 | 0.038 |
| 404 | DD-20 | 0.020 |
| 405 | DD-21 | 0.026 |
| 406 | DD-22 | 0.024 |
| 406 | DD-23 | 0.80 |
| 407 | DD-24 | 0.077 |
| 408 | DD-25 | 0.021 |
| 408 | DD-26 | 0.48 |
| 410 | DD-27 | 0.011 |
| 411 | DD-28 | 0.025 |
| 412 | DD-29 | 0.035 |
| 414 | DD-30 | 0.10 |
| 423 | DD-31 | 0.013 |
| 424 | DD-32 | 0.11 |
| 425 | DD-33 | 0.13 |

TABLE 22

| Example | Compound No. | DDR1 binding activity IC50 (uM) |
|---|---|---|
| 426 | DD-34 | 0.080 |
| 428 | DD-35 | 0.012 |
| 430 | DD-36 | 0.10 |
| 431 | DD-37 | 0.044 |
| 432 | DD-38 | 0.029 |
| 434 | DD-39 | 0.069 |
| 435 | DD-40 | 0.083 |
| 436 | DD-41 | 0.022 |
| 437 | DD-42 | 0.019 |
| 439 | DD-43 | 0.025 |
| 440 | DD-44 | 0.39 |
| 441 | DD-45 | 0.067 |
| 442 | DD-46 | 1.98 |
| 443 | DD-47 | 0.042 |
| 444 | DD-48 | 1.91 |
| 447 | DD-49 | 0.064 |
| 448 | DD-50 | 0.033 |
| 450 | DD-51 | 0.034 |
| 452 | DD-52 | 0.068 |
| 454 | DD-53 | 0.068 |
| 456 | DD-54 | 0.034 |
| 460 | DD-55 | 0.017 |
| 461 | DD-56 | 0.026 |
| 465 | DD-57 | 0.041 |
| 466 | DD-58 | 0.043 |
| 467 | DD-59 | 0.034 |
| 469 | DD-60 | 0.034 |
| 473 | DD-61 | 0.032 |
| 475 | DD-62 | 0.12 |

TABLE 22-continued

| Example | Compound No. | DDR1 binding activity IC50 (uM) |
|---|---|---|
| 476 | DD-63 | 0.045 |
| 477 | DD-64 | 0.020 |
| 484 | DD-65 | 0.019 |
| 487 | DD-66 | 0.024 |
| 488 | DD-67 | 0.020 |
| 495 | DD-68 | 0.47 |
| 501 | DD-69 | 0.26 |
| 502 | DD-70 | 0.12 |
| 506 | DD-71 | 0.14 |
| 511 | DD-72 | 0.033 |

TABLE 23

| Example | Compound No. | DDR1 binding activity IC50 (uM) |
|---|---|---|
| 513 | EE-1 | 0.017 |
| 514 | EE-2 | 0.021 |
| 514 | EE-3 | 0.69 |
| 515 | EE-4 | 0.046 |
| 516 | EE-5 | 0.036 |
| 518 | EE-6 | 0.045 |
| 519 | EE-7 | 0.040 |
| 520 | EE-8 | 0.031 |
| 532 | GG-1 | 0.041 |
| 546 | GG-2 | 0.021 |
| 554 | GG-3 | 0.034 |
| 567 | GG-4 | 0.25 |
| 569 | GG-5 | 2.10 |
| 570 | GG-6 | 0.50 |
| 571 | K-1 | 0.014 |
| 572 | K-2 | 0.036 |
| 573 | K-3 | 0.026 |
| 574 | K-4 | 0.14 |
| 575 | K-5 | 0.016 |
| 576 | K-6 | 0.064 |
| 577 | K-7 | 0.083 |
| 583 | K-8 | 0.018 |
| 584 | K-9 | 0.038 |
| 585 | K-10 | 0.030 |
| 590 | K-11 | 0.020 |
| 592 | K-12 | 0.024 |
| 596 | K-13 | 0.057 |
| 597 | K-14 | 0.019 |
| 598 | K-15 | 0.023 |
| 600 | L-1 | 0.14 |
| 603 | L-2 | 0.073 |
| 604 | L-3 | 0.14 |
| 609 | M-1 | 5.44 |
| 610 | M-2 | 2.95 |
| 611 | N-1 | 9.26 |
| 612 | N-2 | 0.81 |
| 613 | N-3 | 0.78 |
| 614 | N-4 | 1.69 |
| 615 | N-5 | 0.090 |

TABLE 24

| Example | Compound No. | DDR1 binding activity IC50 (uM) |
|---|---|---|
| 616 | N-6 | 3.21 |
| 620 | N-7 | 0.17 |
| 623 | N-8 | 0.38 |
| 625 | N-9 | 0.064 |
| 632 | N-10 | 0.014 |
| 633 | N-11 | 0.0091 |
| 635 | N-12 | 0.29 |
| 636 | N-13 | 0.43 |
| 637 | N-14 | 0.30 |
| 639 | N-15 | 0.29 |
| 640 | N-16 | 0.027 |
| 641 | N-17 | 0.039 |
| 642 | N-18 | 0.024 |

TABLE 24-continued

| Example | Compound No. | DDR1 binding activity IC50 (uM) |
|---|---|---|
| 643 | N-19 | 0.017 |
| 645 | N-20 | 0.021 |
| 646 | N-21 | 0.099 |
| 651 | N-22 | 0.015 |
| 652 | N-23 | 0.041 |
| 652 | N-24 | 0.076 |
| 654 | N-25 | 9.53 |
| 655 | N-26 | 2.19 |
| 656 | N-27 | 0.018 |
| 657 | N-28 | 0.048 |
| 659 | N-29 | 0.038 |
| 663 | O-1 | 0.46 |
| 668 | O-2 | 0.045 |
| 670 | O-3 | 0.021 |
| 675 | O-4 | 0.21 |
| 678 | O-5 | 0.32 |
| 679 | O-6 | 1.08 |
| 681 | O-7 | 0.023 |
| 683 | O-8 | 0.010 |
| 684 | P-1 | 118.8 |
| 689 | P-2 | 139.8 |
| 693 | P-3 | 2.54 |
| 697 | P-4 | 13.3 |
| 702 | P-5 | 0.011 |
| 703 | P-6 | 3.87 |
| 704 | P-8 | 4.22 |
| 706 | P-9 | 0.13 |
| 707 | P-10 | 0.010 |
| 711 | P-11 | 0.087 |
| 718 | P-12 | 0.039 |
| 723 | Q-2 | 0.33 |
| 725 | Q-9 | 26.1 |
| 728 | Q-10 | 61.3 |
| 733 | Q-11 | 0.51 |
| 740 | Q-12 | 0.098 |
| 742 | Q-13 | 0.066 |
| 745 | Q-14 | 0.018 |

3. Measurement of Antitumor Effect

The antitumor effect was measured for representative examples of the compounds of the present invention.

The antitumor effect was measured using cancer-bearing mice in which the human endometrial cancer cell line MFE-280 (manufactured by DSMZ) was subcutaneously transplanted to the flank of BALB/c nude mice (manufactured by Charles River Laboratories Japan, Inc.).

About $1 \times 10^7$ MFE-280 cells were subcutaneously transplanted to the flank of the purchased nude mice after a one-week quarantine period. The tumor size was measured with calipers, and the tumor volume was calculated (tumor volume=length×breadth$^2$/2 (mm$^3$)). The mice were subjected to the experiment when the tumor volume was about 200 mm$^3$.

The test compound was suspended in the administration solution, and 0.4 mL of the suspension was orally administered once daily. The antitumor effect was calculated as inhibition of tumor growth by comparing the tumor growth between the drug-treated group and the administration solution-administered control group on the 11th day after the start of administration.

Tumor volume growth inhibition (TGI)=(1−tumor volume growth in drug-treated group/tumor volume growth in control group)×100(%)

The results are shown in Table 25 and FIG. 1.

TABLE 25

| Compound No. | Antitumor effect | |
|---|---|---|
| | Dose (mg/kg) | TGI after 11 days passed (%) |
| B-2 | 200 | 61 |

4. Measurement of Inhibition of DDR1 Phosphorylation in Tumors

Inhibition of DDR1 by the test compound in MFE-280 tumors was measured using Western blotting.

Four hours after the final administration, tumors were homogenized and solubilized, subjected to SDS-PAGE, and then transferred to PVDF membrane. After blocking, the membrane was treated with an anti-phosphorylated Y796-DDR1 antibody (manufactured by Sigma-Aldrich Co. LLC.), an anti-DDR1 antibody (manufactured by Santa Cruz Biotechnology, Inc.), and an anti-actin antibody (manufactured by Santa Cruz Biotechnology, Inc.). After washing off the primary antibodies, the membrane was treated with an HRP-labeled secondary antibody. After washing, signals were detected by a chemiluminescence method using ECL Plus or ECL (manufactured by GE Healthcare).

The results are shown in FIG. 2.

From these results, it was observed that the compounds of the present invention have high DDR1 inhibitory activity and a high antitumor effect.

INDUSTRIAL APPLICABILITY

Compounds that have a DDR1 inhibitory effect are provided by the present invention. Pharmaceuticals for prevention and/or treatment of cancer, prevention and/or treatment of cancer invasion and metastasis, and prevention and/or treatment of fibrosis and inflammation are also provided by the present invention.

The invention claimed is:
1. A compound represented by general formula (I) below:

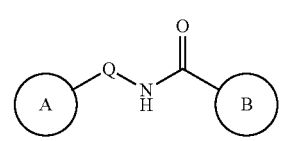

(I)

wherein
Q represents CH$_2$ or NH;
Ring A represents formula (1) or (2) below:

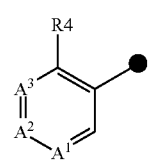

(1)

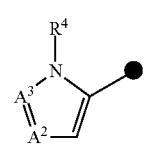

(2)

wherein A¹ represents N or CR¹;
R¹ represents a halogen atom, cyano group, $C_{1-3}$ alkyl group, or $C_{1-3}$ alkoxy group, wherein the $C_{1-3}$ alkyl group and $C_{1-3}$ alkoxy group can be substituted with 1 to 5 halogen atoms;
A² represents N or CR²;
R² represents a hydrogen atom, halogen atom, $C_{1-3}$ alkyl group, or $C_{1-3}$ alkoxy group, wherein the $C_{1-3}$ alkyl group and $C_{1-3}$ alkoxy group can be substituted with 1 to 5 halogen atoms;
A³ represents N or CR³;
R³ represents a hydrogen atom, a halogen atom, a $C_{1-3}$ alkyl group, or a $C_{1-3}$ alkoxy group, wherein the $C_{1-3}$ alkyl group and $C_{1-3}$ alkoxy group can be substituted with 1 to 5 halogen atoms; and
R⁴ represents a $C_{1-6}$ alkylsulfonyl group, $C_{1-6}$ alkylsulfanyl group, $C_{1-6}$ alkylsulfinyl group, $C_{3-8}$ cycloalkylsulfonyl group, $C_{3-8}$ cycloalkylsulfanyl group, $C_{3-8}$ cycloalkylsulfinyl group, $C_{6-10}$ arylsulfonyl group, $C_{6-10}$ arylsulfanyl group, or $C_{6-10}$ arylsulfinyl group; and
Ring B represents any one of formulas (3) to (9) below:

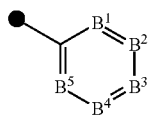  (3)

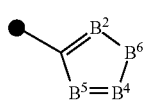  (4)

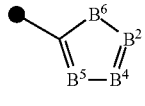  (5)

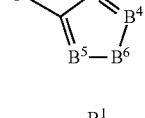  (6)

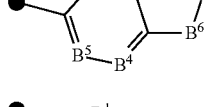  (7)

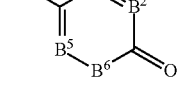  (8)

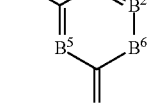  (9)

wherein B¹ represents N or CH;
B² represents N or CR⁵;
R⁵ represents a halogen atom, $C_{1-6}$ alkyl group, $C_{1-6}$ alkoxy group, $C_{2-6}$ alkenyl group, cyano group, nitro group, $C_{3-8}$ cycloalkyl group, 6- to 10-membered aromatic ring, 5- to 10-membered aromatic heterocycle, 3- to 12-membered heterocycle, or $C_{1-6}$ alkylsulfanyl group, wherein the $C_{1-6}$ alkyl group, $C_{1-6}$ alkoxy group, $C_{2-6}$ alkenyl group, or $C_{1-6}$ alkylsulfanyl group can be substituted with 1 to 5 halogen atoms;
B³ represents N or CR⁶;
B⁶ represents O, S, or NR⁶;
R⁶ represents a hydrogen atom, $C_{1-3}$ alkyl group, halogen atom, amino group or OCOCH₃ group, wherein the $C_{1-3}$ alkyl group is optionally substituted with a hydroxyl group, or
R⁶ represents a group represented by following formula (i) below:

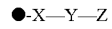  (i)

wherein in the formula (i),
X represents $-(CH_2)_n-$, $-NH-$, or $-O-$;
Y represents a $C_{3-8}$ cycloalkyl group, 6- to 10-membered aromatic ring, 3- to 12-membered heterocycle, 5- to 10-membered aromatic heterocycle, or $-(NH(CH_2)_q)_r-$, wherein the $C_{3-8}$ cycloalkyl group, 6- to 10-membered aromatic ring, 3- to 12-membered heterocycle, or 5- to 10-membered aromatic heterocycle may be substituted with 1 to 5 $C_{1-6}$ alkyl groups;
Z represents a hydrogen atom, a $C_{1-6}$ alkyl group, dimethylamine oxide, $-(CH_2)_m NRaRb$, $-NRiCOCH_2Rc$, $-(CH_2)_m NRiCORc$, $-(CH_2)_m ORd$, $-(CH_2)_m CORe$, $-(CH_2)_m NRjSO_2Rk$, $-(CH_2)_m SO_2Rk$, $-(CH_2)_m CONRlRm$, $C_{3-8}$ cycloalkyl group, 5- to 10-membered aromatic heterocycle, or 4- to 12-membered heterocycle, wherein the 5- to 10-membered aromatic heterocycle or 4- to 12-membered heterocycle may be substituted with 1 to 5 $C_{1-6}$ alkyl groups;
n represents 0, 1, 2, or 3;
m represents 0, 1, 2, or 3;
q represents 0, 1, 2, or 3;
r represents 0, 1, 2, or 3;
Ra and Rb are identical or different, each representing a hydrogen atom, $C_{1-6}$ alkyl group, $C_{2-6}$ alkynyl group, $C_{3-8}$ cycloalkyl group, 3- to 12-membered heterocycle, or $-SO_2CH_3$, wherein the $C_{1-6}$ alkyl group, $C_{3-8}$ cycloalkyl group, 3- to 12-membered heterocycle, or $C_{2-6}$ alkynyl group can be substituted with 1 to 5 halogen atoms, hydroxyl groups, $C_{1-6}$ alkoxy groups, amino groups, $-CONH_2$, mono-$C_{1-6}$ alkylamino groups, di-$C_{1-6}$ alkylamino groups, cyano groups, OCH₂Ph, and/or 3- to 12-membered heterocycles;
Rc represents a $C_{1-6}$ alkyl group, $C_{1-6}$ alkoxy group, $C_{3-8}$ cycloalkyl group, hydroxyl group, cyano group, 3- to 12-membered heterocycle, 5- to 10-membered aromatic heterocycle, or amino group, wherein the $C_{1-6}$ alkyl group may be independently substituted with 1 to 3 hydroxyl, amino, mono-$C_{1-6}$ alkylamino, and/or di-$C_{1-6}$ alkylamino groups;
Rd represents a hydrogen atom or a $C_{1-6}$ alkyl group, wherein the $C_{1-6}$ alkyl group can be substituted with 1 to 3 hydroxyl and/or amino groups;
Re represents a $C_{1-6}$ alkyl group, hydroxyl group, 3- to 12-membered heterocycle, or 5- to 10-membered aromatic heterocycle, wherein the $C_{1-6}$ alkyl group may be substituted with 1 to 3 hydroxyl and/or amino groups;

Ri represents a hydrogen atom or a $C_{1-6}$ alkyl group, wherein the $C_{1-6}$ alkyl group can be substituted with 1 to 5 halogen atoms;

Rj represents a hydrogen atom or a $C_{1-6}$ alkyl group, wherein the $C_{1-6}$ alkyl group can be substituted with 1 to 5 halogen atoms;

Rk represents a hydrogen atom, $C_{1-6}$ alkyl group, amino group, mono-$C_{1-6}$ alkylamino group, or di-$C_{1-6}$ alkylamino group, wherein the $C_{1-6}$ alkyl group can be substituted with 1 to 3 hydroxyl, amino, mono-$C_{1-6}$ alkylamino, and/or di-$C_{1-6}$ alkylamino groups; and Rl and Rm are identical or different, each representing a hydrogen atom, $C_{1-6}$ alkyl group, or 3- to 12-membered heterocycle, wherein the $C_{1-6}$ alkyl group can be independently substituted with 1 to 3 amino, mono-$C_{1-6}$ alkylamino, and/or di-$C_{1-6}$ alkylamino groups;

$B^4$ represents N or $CR^7$;

$R^7$ represents a hydrogen atom, halogen atom, cyano group, $C_{1-6}$ alkyl group, $C_{1-6}$ alkoxy group, $C_{2-6}$ alkenyl group, or $C_{3-8}$ cycloalkyl group, wherein the $C_{1-6}$ alkyl group, $C_{1-6}$ alkoxy group, $C_{2-6}$ alkenyl group, or $C_{3-8}$ cycloalkyl group can be substituted with 1 to 5 halogen atoms, or $R^7$ represents a group represented by formula (ii) below:

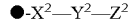

●-$X^2$—$Y^2$—$Z^2$     (ii)

wherein $X^2$ represents —$(CH_2)_p$—;

p represents 0, 1, 2, or 3;

$Y^2$ represents a 6- to 10-membered aromatic ring, 3- to 12-membered heterocycle, or 5- to 10-membered aromatic heterocycle, wherein the 6- to 10-membered aromatic ring, 3- to 12-membered heterocycle, or 5- to 10-membered aromatic heterocycle can be substituted with 1 to 5 $C_{1-6}$ alkyl groups;

$Z^2$ represents a hydrogen atom, a $C_{1-6}$ alkyl group, hydroxyl group, —NRfRg, 3- to 12-membered heterocycle, or 5- to 10-membered aromatic heterocycle, wherein the $C_{1-6}$ alkyl group can be substituted with 1 to 5 halogen atoms, and the 3- to 12-membered heterocycle or 5- to 10-membered aromatic heterocycle can be substituted with 1 to 5 $C_{1-6}$ alkyl groups; and Rf and Rg are identical or different, each representing a hydrogen atom, $C_{1-6}$ alkyl group, —$COCH_3$, or —$SO_2CH_3$;

$B^5$ represents N or $CR^8$; and $R^8$ represents a hydrogen atom, a $C_{1-6}$ alkyl group, or halogen atom, wherein the $C_{1-6}$ alkyl group can be substituted with 1 to 5 halogen atoms, or a pharmaceutically acceptable salt thereof.

2. The compound or a pharmaceutically acceptable salt thereof according to claim 1, represented by formula (II):

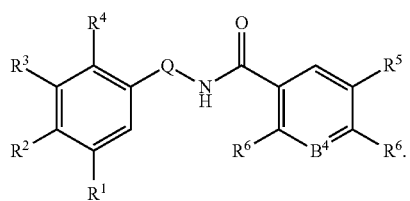

(II)

3. The compound or a pharmaceutically acceptable salt thereof according to claim 1, wherein Q is $CH_2$.

4. The compound or a pharmaceutically acceptable salt thereof according to claim 1, wherein $R^2$ represents a hydrogen atom or $C_{1-3}$ alkyl group, wherein the $C_{1-3}$ alkyl group can be substituted with 1 to 5 halogen atoms.

5. The compound or a pharmaceutically acceptable salt thereof according to claim 1, wherein $R^3$ represents a hydrogen atom, chlorine atom, or $C_{1-3}$ alkyl group, wherein the $C_{1-3}$ alkyl group can be substituted with 1 to 5 halogen atoms.

6. The compound or a pharmaceutically acceptable salt thereof according to claim 1, wherein $R^5$ represents a halogen atom, $C_{1-3}$ alkyl group, $C_{2-3}$ alkenyl group, or $C_{1-3}$ alkoxy group, wherein the $C_{1-3}$ alkyl group, $C_{2-3}$ alkenyl group, or $C_{1-3}$ alkoxy group can be substituted with 1 to 5 halogen atoms.

7. The compound or a pharmaceutically acceptable salt thereof according to claim 1, wherein $R^6$ represents a hydrogen atom or a group represented by formula (i) below:

●-X—Y—Z     (i)

wherein X represents $CH_2$;

Y represents piperazine, pyrrolidine, piperidine, morpholine, 3,3-dimethylpiperazine, 3,6-diazabicyclo[3.1.1]heptane, azaspiro[2.4]heptane, 2-oxo-1,3-diazinane, 1,2,5-oxadiazepane, 2-oxopiperidine, azetidine, 5-oxa-2,8-diazaspiro[3.5]nonane, 1,8-diazaspiro[5.5]undecane, imidazole, or benzene;

Z represents a hydrogen atom, —$(CH_2)_m$NRaRb, —$NHCOCH_2$Rc, —$(CH_2)_m$NHCORc, —$(CH_2)_m$ORd, —$(CH_2)_m$CORe, —$(CH_2)_m$CONRlRm, piperazine, pyrrolidine, piperidine, or tetrahydropyran;

m represents 0, 1, 2, or 3;

Ra and Rb are identical or different, each representing a hydrogen atom, $C_{1-6}$ alkyl group, $C_{3-6}$ cycloalkyl group, or —$SO_2CH_3$, wherein the $C_{1-6}$ alkyl group or $C_{3-6}$ cycloalkyl group can be substituted with 1 to 5 halogen atoms, hydroxyl groups, $C_{1-6}$ alkoxy groups, amino groups, —$CONH_2$, mono-$C_{1-6}$ alkylamino groups, di-$C_{1-6}$ alkylamino groups, or cyano groups;

Rc represents a $C_{1-4}$ alkyl group, $C_{1-4}$ alkoxy group, 4- to 6-membered heterocycle, 5- to 6-membered aromatic heterocycle, or amino group, wherein the $C_{1-4}$ alkyl group can be independently substituted with 1 to 2 amino, mono-$C_{1-2}$ alkylamino, and/or di-$C_{1-2}$ alkylamino groups;

Rd represents a hydrogen atom or $C_{1-2}$ alkyl group, wherein the $C_{1-2}$ alkyl group can be substituted with an amino group or hydroxyl group;

Re represents a $C_{1-2}$ alkyl group or 4- to 6-membered heterocycle, wherein the $C_{1-2}$ alkyl group can be substituted with an amino group or hydroxyl group; and Rl and Rm are identical or different, each representing a hydrogen atom, $C_{1-3}$ alkyl group, or 4- to 6-membered heterocycle, wherein the $C_{1-3}$ alkyl group can be independently substituted with 1 to 3 amino, mono-$C_{1-3}$ alkylamino, and/or di-$C_{1-3}$ alkylamino groups.

8. The compound or a pharmaceutically acceptable salt thereof according to claim 1, wherein $B^4$ represents $CR^7$, and $R^7$ represents a chlorine atom, bromine atom, hydrogen atom, cyano group, $C_{1-3}$ alkyl group, $C_{1-3}$ alkoxy group, $C_{2-3}$ alkenyl group, or $C_{3-6}$ cycloalkyl group, wherein the $C_{1-3}$ alkyl group, $C_{1-3}$ alkoxy group, $C_{2-3}$ alkenyl group, or $C_{3-6}$ cycloalkyl group can be substituted with 1 to 3 halogen atoms, or $R^7$ represents a group represented by formula (ii) below:

 (ii)

wherein
- $X^2$ represents —$(CH_2)_p$—, p represents 0 or 1;
- $Y^2$ represents piperazine, pyrrolidine, piperidine, morpholine, or 3,3-dimethylpiperazine;
- $Z^2$ represents a hydrogen atom, a $C_{1-3}$ alkyl group, —NRfRg, pyrrolidine, morpholine, or tetrahydropyran, wherein the $C_{1-3}$ alkyl group may be substituted with 1 to 3 halogen atoms; and
- Rf and Rg are identical or different, each representing a hydrogen atom, $C_{1-3}$ alkyl group, —$COCH_3$, or —$SO_2CH_3$.

9. The compound or a pharmaceutically acceptable salt thereof according to claim 1, wherein $R^8$ represents a hydrogen atom.

10. A pharmaceutical composition comprising the compound or a pharmaceutically acceptable salt thereof according to claim 1 as an active ingredient.

11. A method for inhibiting DDR1, comprising administering a pharmaceutically effective amount of a composition comprising the compound or a pharmaceutically acceptable salt thereof according to claim 1 to a patient in need thereof.

* * * * *

UNITED STATES PATENT AND TRADEMARK OFFICE
CERTIFICATE OF CORRECTION

PATENT NO. : 9,695,118 B2
APPLICATION NO. : 14/396678
DATED : July 4, 2017
INVENTOR(S) : Murata et al.

Page 1 of 1

It is certified that error appears in the above-identified patent and that said Letters Patent is hereby corrected as shown below:

In the Claims

Column 374
Claim 1, Lines 26, 36, 57 and 66, each occurrence of "may be" should read -- can be --.

Column 375
Claim 2, Lines 57-65, the structure of formula (II)

" 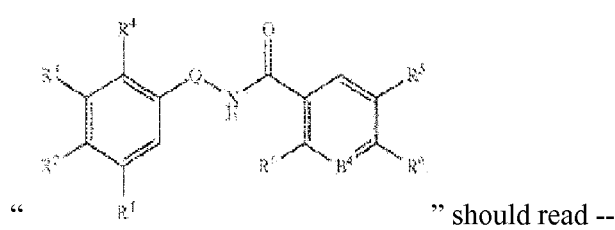 " should read -- 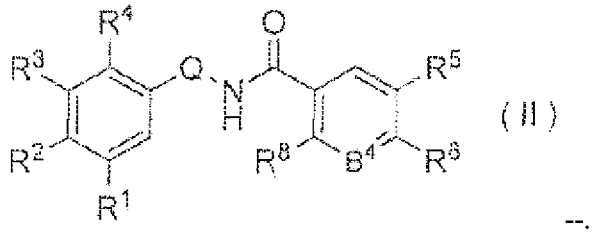 --.

Column 377
Claim 8, Line 10, "may be" should read -- can be --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*